US007785780B2

(12) United States Patent
Gala et al.

(10) Patent No.: US 7,785,780 B2
(45) Date of Patent: Aug. 31, 2010

(54) ASSAY FOR DETECTING AND IDENTIFYING MICRO-ORGANISMS

(75) Inventors: Jean-Luc Gala, Sint-Stevens-Woluwe (BE); Léonid Irenge, Woluwe-St-Lambert (BE)

(73) Assignees: Universite Catholique de Louvain, Louvain-la-Neuve (BE); La Defense Nationale, Brussels (BE)

( * ) Notice: Subject to any disclaimer, the term of this patent is extended or adjusted under 35 U.S.C. 154(b) by 681 days.

(21) Appl. No.: 10/591,791

(22) PCT Filed: Mar. 18, 2005

(86) PCT No.: PCT/EP2005/002927

§ 371 (c)(1), (2), (4) Date: Sep. 6, 2006

(87) PCT Pub. No.: WO2005/090596

PCT Pub. Date: Sep. 29, 2005

(65) Prior Publication Data

US 2008/0026953 A1 Jan. 31, 2008

(30) Foreign Application Priority Data

Mar. 19, 2004 (BE) ................................ 2004/0152

(51) Int. Cl.
*C12Q 1/68* (2006.01)
*C07H 21/02* (2006.01)
*C07H 21/04* (2006.01)

(52) U.S. Cl. ......................... 435/6; 536/23.1; 536/23.7; 536/24.3; 536/24.32

(58) Field of Classification Search ....................... None
See application file for complete search history.

(56) References Cited

U.S. PATENT DOCUMENTS 6,617,156 B1 9/2003 Doucette-Stamm et al.

FOREIGN PATENT DOCUMENTS

WO WO 90/11370 10/1990
WO WO 98/20160 5/1998

OTHER PUBLICATIONS

Carroll, et al. "Detection of and Discrimination between Gram-Positive and Gram-Negative Bacteria in Intraocular Samples by Using Nested PCR," *Journal of Clinical Microbiology*, vol. 38, No. 5, pp. 1753-1757, May 2000.
Klaschik, et al. "Real-Time PCR for Detection and Differentiation of Gram-Positive and Gram-Negative Bacteria," *Journal of Clinical Microbiology*, vol. 40, No. 11, pp. 4304-4307, Nov. 2002.
van Leeuwen, et al. "Multilocus Sequence Typing of *Staphylococcus aureus* with DNA Array Technology," *Journal of Clinical Microbiology*, vol. 41, No. 7, pp. 3323-3326, Jul. 2003.
International Search Report dated Jul. 13, 2005.

*Primary Examiner*—Carla Myers
(74) *Attorney, Agent, or Firm*—Knobbe, Martens, Olson & Bear, LLP

(57) ABSTRACT

An assay for detecting and identifying micro-organisms, particularly bacteria, is disclosed. In particular, an assay for detecting bacteria in a sample is disclosed. Bacteria are identified according to Gram-, genus- species- and strain-specificity based on multigenotypic testing of bacterial DNA from human, animal or environmental samples.

6 Claims, 26 Drawing Sheets

Figure 1 Amplification of molecular marker I (pur A) in Gram-positive bacteria

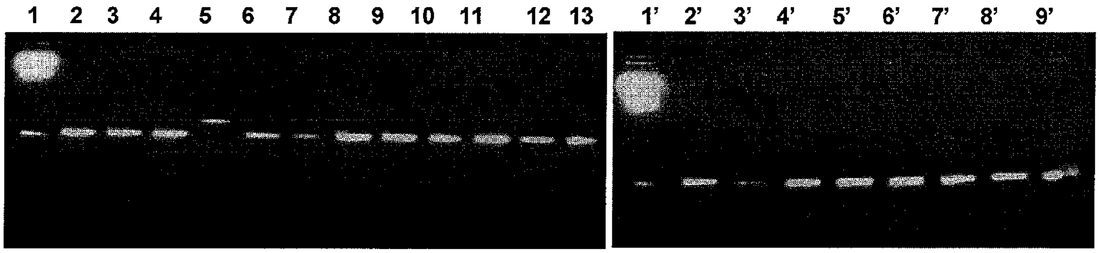

1 = DNA Ladder (λ/Hind III)
*2 : Streptococcus pyogenes*
*3. Streptococcus penumoniae*
*4. Streptococcus oralis*
*5. Enterococcus hirae*
*6. Enterococcus casseliflavus*
*7. Streptococcus agalactiae*
*8. Streptococcus sanguis*
*9. Enterococcus faecalis*
*10. Enterococcus gallinarum*
*11. Enterococcus faecium*
*12. Enterococcus flavescens*
*13. Enterococcus durans*

1' : DNA Ladder (λ/Hind III)
*2' : Enterococcus raffinosus*
*3' : Enterococcus villorum*
*4' : Staphylococcus aureus*
*5' : Staph. epidermidis*
*6' : Staphylococcus hominis*
*7' : Bacillus anthracis*
*8' : Bacillus cereus*
*9' : Bacillus megatherium*

Figure 2. Amplification of molecular marker II (ptsI) in Gram-positive bacteria

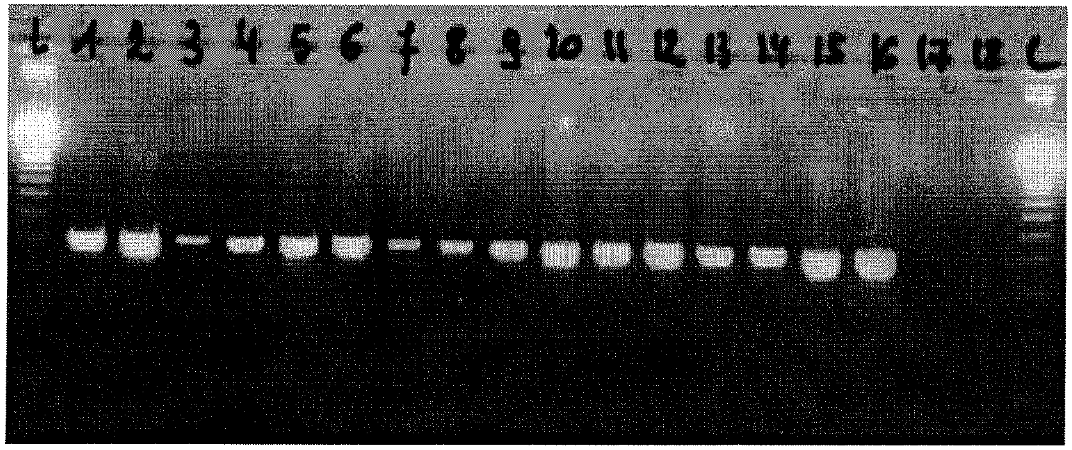

L = DNA ladder (123 bp)

1. *Bacillus anthracis*
2. *Bacillus cereus*
3. *Listeria moniocytogenes*
4. *Bacillus subtilis*
5. *Streptococcus peneumoniae*
6. *Streptococcus pyogenes*
7. *Streptococcus agalactiae*
8. *Streptococcus mutans*
9. *Enterococcus faecalis*
10. *Staphylococcus aureus*
11. *Staphylococcus epidermidis*
12. *Bacillus thuringensis*
13. *Staphylococcus hominis*
14. *Enteococcus faecium*
15. *Clostridium perfringens*
16. *Bacillus mycoides*
17. *Negative control*
18. *Negative control*

Figure 3. Amplification of molecular marker III (SpyM3_0902- SpyM3_0903) in Gram-positive bacteria

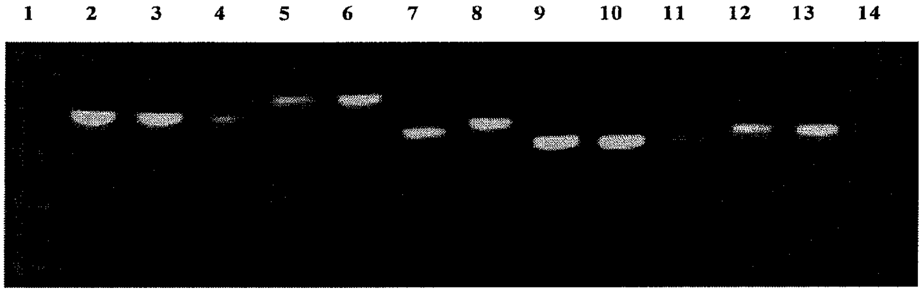

1. DNA Ladder
*2 : Streptococcus pyogenes*
*3. Streptococcus pneumoniae*
*4. Enterococcus faecalis*
*5. Streptococcus agalactiae*
*6. Streptococcus sanguis*
*7. Enterococcus casseliflavus*
*8. Streptococcus oralis*
*9. Bacillus anthracis*
*10.Bacillus cereus*
*11. Enterococcus raffinosus*
*12. Enterococcus gallinarum*
*13. Enterococcus flavescens*
*14. Negative control of PCR.*

Figure 4A: Marker I (PurA) sequences amplified from different Gram positive bacteria (SEQ ID NOs 1-62), and from a Gram-negative bacterium (SEQ ID NO: 63)

| | | |
|---|---|---|
| 1. | *Enterococcus faecalis* (SEQ ID NO. 1) | EFCL |
| 2. | *Enterococcus gallinarum* (SEQ ID NO. 2) | EGAL |
| 3. | *Enterococcus flavescens* (SEQ ID NO. 3) | EFLA |
| 4. | *Streptococcus agalactiae* (SEQ ID NO. 4) | SAGA |
| 5. | *Streptococcus sanguis* (SEQ ID NO. 5) | SSAN |
| 6. | *Enterococcus faecium* (SEQ ID NO. 6) | EFCM |
| 7. | *Enterococcus durans* (SEQ ID NO. 7) | EDUR |
| 8. | *Streptococcus pyogenes* (SEQ ID NO. 8) | SPYO |
| 9. | *Streptococcus pneumoniae* (SEQ ID NO. 9) | SPNE |
| 10. | *Streptococcus oralis (SEQ ID NO. 10)* | *SORA* |
| 11. | *Staphylococcus hominis* (SEQ ID NO. 11) | SHOM |
| 12. | *Bacillus anthracis 1978* (SEQ ID NO. 12) | |
| 13. | *Bacillus anthracis Butare* (SEQ ID NO. 13) | |
| 14. | *Bacillus anthracis Sterne* (SEQ ID NO. 14) | |
| 15. | *Bacillus anthracis 1655H85* (SEQ ID NO. 15) | |
| 16. | *Bacillus anthracis Coda-cerva* (SEQ ID NO. 16) | |
| 17. | *Bacillus anthracis* 2054H82 (SEQ ID NO. 17) | |
| 18. | *Bacillus cereus ATCC 10987* (SEQ ID NO. 18) | BCER10987 |
| 19. | *Bacillus cereus ATCC 14579* (SEQ ID NO. 19) | BCER14579 |
| 20. | *Bacillus megatherium* (SEQ ID NO. 20) | BMEG |
| 21. | *Enterococcus casseliflavus* (SEQ ID NO. 21) | ECAS |
| 22. | *Enterococcus raffinosus* (SEQ ID NO. 22) | ERAF |
| 23. | *Staphylococcus aureus* (SEQ ID NO. 23) | SAUR |
| 24. | *Staphylococcus epidermidis* (SEQ ID NO. 24) | SEPI |
| 25. | *Streptococcus mitis* (SEQ ID NO. 25) | SMIT |
| 26. | *Streptococcus species* (SEQ ID NO. 26) | SSPE |
| 27. | *Streptococcus canis* (SEQ ID NO. 27) | SCAN |
| 28. | *Streptococcus mutans* (SEQ ID NO. 28) | SMUT |
| 29. | *Streptococcus gordonii* (SEQ ID NO. 29) | SGOR |
| 30. | *Bacillus species* (SEQ ID NO. 30) | BSPE |
| 31. | *Bacillus pumilus* (SEQ ID NO. 31) | BPUM |
| 32. | *Enterococcus villorum* (SEQ ID NO. 32) | EVIL |
| 33. | *Bacillus thuringiensis serovar israelensis* (SEQ ID NO. 33) | BTHUISR |

Figure 4B: Marker I (PurA) sequences amplified from different Gram positive bacteria (SEQ ID NOs 1-62), and from a Gram-negative bacterium (SEQ ID NO: 63)

| | | |
|---|---|---|
| 34. | *Bacillus thuringiensis* serovar *kurstaki* (SEQ ID NO. 34) | BTHUKUR |
| 35. | *Bacillus mycoïdes MYC003* (SEQ ID NO. 35) | BMYC003 |
| 36. | *Bacillus mycoïdes NRS306* (SEQ ID NO. 36) | BMYC306 |
| 37. | *Bacillus weihenstephanensis* (SEQ ID NO. 37) | BWEI |
| 38. | *Staphylococcus haemolyticus* (SEQ ID NO. 38) | SHAE |
| 39. | *Staphylococcus saprophyticus* (SEQ ID NO. 39) | SSAP |
| 40. | *Bacillus subtilis* (SEQ ID NO. 40) | BSUB |
| 41. | *Listeria monocytogenes* (SEQ ID NO. 41) | LMON |
| 42. | *Lactococcus lactis* (SEQ ID NO. 42) | LLAC |
| 43. | *Enterococcus hirae* (SEQ ID NO. 43) | EHIR |
| 44. | *Enterococcus avium* (SEQ ID NO. 44) | EAVI |
| 45. | *Streptococcus bovis* (SEQ ID NO. 45) | SBOV |
| 46. | *Streptococcus thermophilus* (SEQ ID NO. 46) | STHE |
| 47. | *Streptococcus suis* (SEQ ID NO. 47) | SSUI |
| 48. | *Bacillus pseudomycoïdes* (SEQ ID NO. 48) | BPMS |
| 49. | *Staphylococcus capitis capitis* (SEQ ID NO. 49) | SCAPCAP |
| 50. | *Staphylococcus sciuri* (SEQ ID NO. 50) | SSCI |
| 51. | *Staphylococcus warneri* (SEQ ID NO. 51) | SWAR |
| 52. | *Staphylococcus lugdunensis* (SEQ ID NO. 52) | SLUG |
| 53. | *Staphylococcus gallinarum* (SEQ ID NO. 53) | SGAL |
| 54. | *Staphylococcus schleiferi schleiferi* (SEQ ID NO. 54) | SSCH |
| 55. | *Staphylococcus capitis ureolyticus* (SEQ ID NO. 55) | SCAPURE |
| 56. | *Staphylococcus cohnii urealyticum* (SEQ ID NO. 56) | SCAPURE |
| 57. | *Staphylococcus xylosus* (SEQ ID NO. 57) | SXYL |
| 58. | *Staphylococcus simulans* (SEQ ID NO. 58) | SSIM |
| 59. | *Staphylococcus cohnii cohnii* (SEQ ID NO. 59) | SCOHCOH |
| 60. | *Staphylococcus auricularis* (SEQ ID NO. 60) | SAURICU |
| 61. | *Staphylococcus caseolyticus* (SEQ ID NO. 61) | SCAS |
| 62. | *Listeria innocua* (SEQ ID NO. 62) | LINN |
| 63. | *Escherichia coli* K12 (SEQ ID NO. 63) | ECOK12 |

Figure 5A. Molecular marker II (ptsI) sequences amplified from Gram positive bacteria (SEQ ID NOs: 64-107; SEQ ID NOs: 109-111, SEQ ID NOs: 117-129, SEQ ID NO: 137, SEQ ID NOs 145-148), from some Gram-negative bacteria (SEQ ID NOs 108, 112-116, 130-136, 138-144) and from the fungi Cryptococcus neoformans (SEQ ID NO: 149).

| | | |
|---|---|---|
| 64. | *Bacillus anthracis 1978 (SEQ ID NO. 64)* | |
| 65. | *Bacillus anthracis butare (SEQ ID NO. 65)* | |
| 66. | *Bacillus anthracis sterne (SEQ ID NO. 66)* | |
| 67. | *Bacillus anthracis 1655H85 (SEQ ID NO. 67)* | |
| 68. | *Bacillus anthracis* Coda-Cerva (SEQ ID NO. 68) | |
| 69. | *Bacillus anthracis* 2054H82 (SEQ ID NO. 69) | |
| 70. | *Bacillus cereus* ATCC 10987 (SEQ ID NO. 70) | |
| 71. | *Bacillus cereus* ATCC 14579 (SEQ ID NO. 71) | |
| 72. | *Listeria monocytogenes* (SEQ ID NO. 72) | |
| 73. | *Streptococcus pneumoniae* (SEQ ID NO. 73) | |
| 74. | *Streptococcus pyogenes* (SEQ ID NO. 74) | |
| 75. | *Streptococcus agalactiae* (SEQ ID NO. 75) | |
| 76. | *Streptococcus mutans* (SEQ ID NO. 76) | |
| 77. | *Enterococcus faecalis* (SEQ ID NO. 77) | |
| 78. | *Staphylococcus aureus* (SEQ ID NO. 78) | SAUR |
| 79. | *Staphylococcus epidermidis* (SEQ ID NO. 79) | SEPI |
| 80. | *Bacillus thuringiensis* serovar *israelensis* (SEQ ID NO. 80) | BTHUISR |
| 81. | *Bacillus thuringiensis* serovar *kurstaki* (SEQ ID NO. 81) | BTHUKUR |
| 82. | *Staphylococcus hominis* (SEQ ID NO. 82) | SHOM |
| 83. | *Enterococcus faecium* (SEQ ID NO. 83) | EFCM |
| 84. | *Clostridium perfringens* (SEQ ID NO. 84) | CPER |
| 85. | *Bacillus mycoïdes* MYC003 (SEQ ID NO. 85) | BMYC003 |
| 86. | *Bacillus mycoïdes* NRS306 (SEQ ID NO. 86) | BMYC306 |
| 87. | *Streptococcus oralis* (SEQ ID NO. 87) | SORA |
| 88. | *Enterococcus hirae* (SEQ ID NO. 88) | EHIR |
| 89. | *Enterococcus avium* (SEQ ID NO. 89) | EAVI |
| 90. | *Staphylococcus saprophyticus* (SEQ ID NO. 90) | SSAP |
| 91. | *Staphylococcus haemolyticus* (SEQ ID NO. 91) | SHAE |
| 92. | *Enterococcus flavescens* (SEQ ID NO. 92) | EFLA |
| 93. | *Enterococcus casseliflavus* (SEQ ID NO. 93) | ECAS |
| 94. | *Enterococcus gallinarum* (SEQ ID NO. 94) | EGAL |

Figure 5B. Molecular marker II (ptsI) sequences amplified from Gram positive bacteria (SEQ ID NOs: 64-107; SEQ ID NOs: 109-111, SEQ ID NOs: 117-129, SEQ ID NO: 137, SEQ ID NOs 145-148), from some Gram-negative bacteria (SEQ ID NOs 108, 112-116, 130-136, 138-144) and from the fungi Cryptococcus neoformans (SEQ ID NO: 149).

| | | |
|---|---|---|
| 95. | *Enterococcus raffinosus* (SEQ ID NO. 95) | ERAF |
| 96. | *Enterococcus villorum* (SEQ ID NO. 96) | EVIL |
| 97. | *Clostridium difficile* (SEQ ID NO. 97) | CDIF |
| 98. | *Streptococcus mitis* (SEQ ID NO. 98) | SMIT |
| 99. | *Bacillus halodurans* (SEQ ID NO. 99) | BHAL |
| 100. | *Bacillus weihenstephanensis* (SEQ ID NO. 100) | BWEI |
| 101. | *Streptococcus species* (SEQ ID NO. 101) | SSPE |
| 102. | *Streptococcus gordonii* (SEQ ID NO. 102) | SGOR |
| 103. | *Streptococcus canis* (SEQ ID NO. 103) | SCAN |
| 104. | *Bacillus pumilus* (SEQ ID NO. 104) | BPUM |
| 105. | *Bacillus species* (SEQ ID NO. 105) | BSPE |
| 106. | *Lactococcus lactis* (SEQ ID NO. 106) | LLAC |
| 107. | *Bacillus firmus* (SEQ ID NO. 107) | BFIR |
| 108. | *Haemophilus influenzae* (SEQ ID NO. 108) | HINF |
| 109. | *Streptococcus bovis* (SEQ ID NO. 109) | SBOV |
| 110. | *Enterococcus durans* (SEQ ID NO. 110) | EDUR |
| 111. | *Streptococcus sanguis* (SEQ ID NO. 111) | SSAN |
| 112. | *Enterobacter cloaceae* (SEQ ID NO. 112) | ECLO |
| 113. | *Serratia liquefasciens* (SEQ ID NO. 113) | SLIQ |
| 114. | *Proteus mirabis* (SEQ ID NO. 114) | PMIR |
| 115. | *Providencia stuartii* (SEQ ID NO. 115) | PSTU |
| 116. | *Proteus vulgaris* (SEQ ID NO. 116) | PVUL |
| 117. | *Staphylococcus simulans* (SEQ ID NO. 117) | SSIM |
| 118. | *Staphylococcus sciuri* (SEQ ID NO. 118) | SSCI |
| 119. | *Staphylococcus capitis capitis* (SEQ ID NO. 119) | SCAPCA |
| 120. | *Staphylococcus warneri* (SEQ ID NO. 120) | SWAR |
| 121. | *Staphylococcus cohnii urealyticus* (SEQ ID NO. 121) | SCOHURE |
| 122. | *Staphylococcus schleiferi scheiferi* (SEQ ID NO. 122) | SSCH |
| 123. | *Staphylococcus intermedius* (SEQ ID NO. 123) | SINT |
| 124. | *Staphylococcus cohnii cohnii* (SEQ ID NO. 124) | SCOHCOH |
| 125. | *Staphylococcus capitis uralyticus* (SEQ ID NO. 125) | SCAPURA |
| 126. | *Staphylococcus gallinarum* (SEQ ID NO. 126) | SGAL |
| 127. | *Staphylococcus auricularis* (SEQ ID NO. 127) | SAURICU |

Figure 5C. Molecular marker II (ptsI) sequences amplified from Gram positive bacteria (SEQ ID NOs: 64-107; SEQ ID NOs: 109-111, SEQ ID NOs: 117-129, SEQ ID NO: 137, SEQ ID NOs 145-148), from some Gram-negative bacteria (SEQ ID NOs 108, 112-116, 130-136, 138-144) and from the fungi Cryptococcus neoformans (SEQ ID NO: 149).

| | | |
|---|---|---|
| *128.* | *Staphylococcus caseolyticus (SEQ ID NO. 128)* | SCAS |
| 129. | *Staphylococcus xylosus* (SEQ ID NO. 129) | SXYL |
| 130. | *Klebsiella pneumoniae* (SEQ ID NO. 130) | KPNE |
| *131.* | *Salmonella typhymurium* (SEQ ID NO. 131) | STPMM |
| *132.* | *Escherichia coli* O157 :H7 (SEQ ID NO. 132) | ECO157 |
| *133.* | *Escherichia coli* K12 (SEQ ID NO. 133) | ECOK12 |
| *134.* | *Citrobacter freundii* (SEQ ID NO. 134) | CFRE |
| *135.* | *Pseudomonas putida* (SEQ ID NO. 135) | PPUT |
| *136.* | *Shigella sonnei* (SEQ ID NO. 136) | SSON |
| *137.* | *Listeria innocua* (SEQ ID NO. 137) | LINN |
| *138.* | *Serratia marcescens* (SEQ ID NO. 138) | SMAR |
| *139.* | *Salmonella enterica* hadar (SEQ ID NO. 139) | SHAD |
| *140.* | *Salmonella enteritidis* (SEQ ID NO. 140) | SENT |
| *141.* | *Salmonella enterica* Brandenburg (SEQ ID NO. 141) | SBRA |
| *142.* | *Salmonella enterica* derby (SEQ ID NO. 142) | SDER |
| *143.* | *Salmonella enterica* virschow (SEQ ID NO. 143) | SVIR |
| *144.* | *Salmonella enterica paratyphi B* (SEQ ID NO. 144) | SPTB |
| 145. | *Streptococcus thermophilus* (SEQ ID NO. 145) | STHE |
| 146. | *Streptococcus suis* (SEQ ID NO. 146) | SSUI |
| 147. | Bacillus pseudomycoïdes (SEQ ID NO. 147) | BPMS |
| 148. | Staphylococcus lugdunensis (SEQ ID NO. 148) | SLUG |
| *149.* | *Cryptococcus neoformans* (SEQ ID NO. 149) | CNEO |

Figure 6. Molecular marker III (SpyM_0902 &SpyM_0903) sequences amplified from Gram positive bacteria (SEQ ID NOs 150-180).

| | | |
|---|---|---|
| 150. | *Streptococcus thermophilus* (SEQ ID NO. 150) | STHE |
| 151. | *Enterococcus villorum* (SEQ ID NO. 151) | SVIL |
| 152. | *Streptococcus pyogenes* (SEQ ID NO. 152) | SPYO |
| 153. | *Streptococcus mutans* (SEQ ID NO. 153) | SMUT |
| 154. | *Streptococcus agalactiae* (SEQ ID NO. 154) | SAGA |
| 155. | *Streptococcus sanguis* (SEQ ID NO. 155) | SSAN |
| 156. | *Streptococcus oralis* (SEQ ID NO. 156) | SORA |
| 157. | *Streptococcus suis* (SEQ ID NO. 157) | SSUI |
| 158. | *Staphylococcus simulans* (SEQ ID NO. 158) | SSIM |
| 159. | *Enterococcus faecalis* (SEQ ID NO. 159) | EFLS |
| 160. | *Streptococcus pneumoniae* (SEQ ID NO. 160) | SPNE |
| 161. | *Enterococcus durans* (SEQ ID NO. 161) | EDUR |
| 162. | *Bacillus anthracis* 1978 (SEQ ID NO. 162) | |
| 163. | *Bacillus anthracis* Sterne (SEQ ID NO. 163) | |
| 164. | *Bacillus anthracis* Butare (SEQ ID NO. 164) | |
| 165. | *Bacillus anthracis* 1655H85 (SEQ ID NO. 165) | |
| 166. | *Bacillus anthracis* Coda-Cerva (SEQ ID NO. 166) | |
| 167. | *Bacillus anthracis* 2054H82 (SEQ ID NO. 167) | |
| 168. | *Bacillus cereus* ATCC 10987 (SEQ ID NO. 168) | BCER10987 |
| 169. | *Bacillus cereus* ATCC 14579 (SEQ ID NO. 169) | BCER14579 |
| 170. | *Bacillus thuringiensis* serovar *israelensis* (SEQ ID NO. 170) | BTHUISR |
| 171. | *Bacillus mycoïdes* serovar MYC003 (SEQ ID NO. 171) | BMYC003 |
| 172. | *Bacillus mycoïdes* serovar NRS306 (SEQ ID NO. 172) | BMYC306 |
| 173. | *Bacillus thuringiensis* serovar *Kurstaki* (SEQ ID NO. 173) | BTHUKUR |
| 174. | Enterococcus faecium (SEQ ID NO. 174) | FCM |
| 175. | *Enterococcus casseliflavus* (SEQ ID NO. 175) | ECAS |
| 176. | *Enterococcus flavescens* (SEQ ID NO. 176) | EFLA |
| 177. | *Enterococcus gallinarum* (SEQ ID NO. 177) | EGAL |
| 178. | *Enterococcus raffinosus* (SEQ ID NO. 178) | ERAF |
| 179. | *Streptococcus mitis* (SEQ ID NO. 179) | SMIT |
| 180. | *Streptococcus canis* (SEQ ID NO. 180) | SCAN |

Figure 7: Molecular marker IV (putative GTP-binding factor plus 160 nt downstream this ORF) sequences amplified from Gram-positive bacteria (SEQ ID NOs 181-193)

181. *Listeria monocytogenes* (SEQ ID NO. 181)
182. *Listeria innocua* (SEQ ID NO. 182)
183. *Bacillus cereus* (SEQ ID NO. 183)
184. *Bacillus anthracis* (SEQ ID NO. 184)
185. *Staphylococcus aureus* (SEQ ID NO. 185)
186. *Staphylococcus epidermidis* (SEQ ID NO. 186)
187. *Bacillus subtilis* (SEQ ID NO. 187)
188. *Streptococcus mutans* (SEQ ID NO. 188)
189. *Streptococcus pneumoniae* (SEQ ID NO. 189)
190. *Streptococcus agalactiae* (SEQ ID NO. 190)
191. *Streptococcus pyogenes* (SEQ ID NO. 191)
192. *Enterococcus faecalis* (SEQ ID NO. 192)
193. *Lactococcus lactis* (SEQ ID NO. 193)

Figure 8. Amplification of molecular marker V (carB) in Gram-negative bacteria

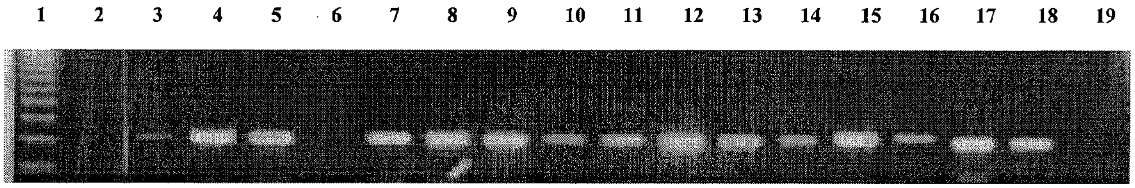

1. DNA Ladder (123 bp)
2. Pseudomonas aeruginosa
3. Pseudomonas pseudoalacaligenes
4. Stenotrophomonas maltophilia
5. Citrobacter freundii
6. Serratia liquefasciens
7. Providencia stuartii
8. Klebsiella pneumoniae
9. Klebsiella oxytoca
10. Pseudomonas syringae
11. Pseudomonas putida
12. Enterobacter aerogenes
13. Pseudomonas diminuta
14. Proteus mirabilis
15. Burkholderia cepacia
16. Burkholderia picketti
17. Proteus vulgaris
18. Serratia marcescens
19. Negative control Figure 9A. Molecular marker V (carB) sequences amplified from different Gram-negative bacteria (SEQ ID NOs 194-232, 238-239, 242-254) and from various Gram-positive bacteria (SEQ ID NOs 233-237, 240-241, 255)

| | | |
|---|---|---|
| *194.* | *Neisseria meningitidis groupe B* (SEQ ID NO. 194) | NMENB |
| *195.* | *Neisseria meningitidis groupe C* (SEQ ID NO. 195) | NMENC |
| *196.* | *Enterobacter cloaceae* (SEQ ID NO. 196) | ECLO |
| *197.* | *Klebsiella pneumoniae* (SEQ ID NO. 197) | KPNE |
| *198.* | *Shigella sonnei* (SEQ ID NO. 198) | SSON |
| *199.* | *Escherichia coli K12* (SEQ ID NO. 199) | ECOK12 |
| *200.* | *Pseudomonas aeruginosa* (SEQ ID NO. 200) | PAER |
| *201.* | *Escherichia coli O157 :H7* (SEQ ID NO. 201) | ECO157 |
| *202.* | *Salmonella typhimurium* (SEQ ID NO. 202) | STPMM |
| *203.* | *Salmonella enterica hadar* (SEQ ID NO. 203) | SHAD |
| *204.* | *Salmonella enteritidis* (SEQ ID NO. 204) | SENT |
| *205.* | *Salmonella enterica Brandenburg* (SEQ ID NO. 205) | SBRA |
| *206.* | *Salmonella enterica derby* (SEQ ID NO. 206) | SDER |
| *207.* | *Salmonella enterica virschow* (SEQ ID NO. 207) | SVIR |
| *208.* | *Salmonella paratyphi B* (SEQ ID NO. 208) | SPTB |
| *209.* | *Proteus vulgaris* (SEQ ID NO. 209) | PVUL |
| *210.* | *Enterobacter aerogenes* (SEQ ID NO. 210) | EAER |
| 211. | *Burkholderia cepacia* (SEQ ID NO. 211) | BCEP |
| *212.* | *Burkholderia mallei* (SEQ ID NO. 212) | |
| *213.* | *Burkholderia pseudomallei* (SEQ ID NO. 213) | |
| *214.* | *Legionella pneumophila* (SEQ ID NO. 214) | |
| *215.* | *Citrobacter freundii* (SEQ ID NO. 215) | |
| *216.* | *Acinetobacter baumanii* (SEQ ID NO. 216) | ABAU |
| *217.* | *Serratia marcescens* (SEQ ID NO. 217) | SMAR |
| *218.* | *Pseudomonas putida* (SEQ ID NO. 218) | PPUT |
| *219.* | *Morganella morganii* (SEQ ID NO. 219) | MMOR |
| *220.* | *Klebsiella oxytoca* (SEQ ID NO. 220) | KOXY |
| *221.* | *Moraxella catarrhalis* (SEQ ID NO. 221) | MCAT |
| 222. | *Brucella melitensis biovar 1* (SEQ ID NO. 222) | BMEL1 |
| *223.* | *Brucella melitensis biovar 2* (SEQ ID NO. 223) | BMEL2 |
| *224.* | *Brucella abortus biovar 1* (SEQ ID NO. 224) | BABO1 |

Figure 9B. Molecular marker V (carB) sequences amplified from different Gram-negative bacteria (SEQ ID NOs 194-232, 238-239, 242-254) and from various Gram-positive bacteria (SEQ ID NOs 233-237, 240-241, 255)

| | | |
|---|---|---|
| 225. | *Brucella abortus biovar 2* (SEQ ID NO. 225) | BABO2 |
| 226. | *Brucella suis biovar 1* (SEQ ID NO. 226) | BSUI1 |
| 227. | *Brucella suis biovar 3* (SEQ ID NO. 227) | BSUI3 |
| 228. | *Brucella canis* (SEQ ID NO. 228) | BCAN |
| 229. | *Brucella ovis 69/290* (SEQ ID NO. 229) | BOVI |
| 230. | *Francisella tularensis strain 4/j7* (SEQ ID NO. 230) | |
| 231. | *Francisella tularensis strain sva/t7* (SEQ ID NO.231) | |
| 232. | *Acinetobacter calcoaceticus* (SEQ ID NO. 232) | ACAL |
| 233. | *Mycobacterium tuberculosis* (SEQ ID NO. 233) | |
| 234. | *Mycobacterium bovis subspecies bovis* (SEQ ID NO. 234) | |
| 235. | *Mycobacterium avium subspecies paratuberculosis* (SEQ ID NO. 235) | |
| 236. | *Mycobacterium leprae* (SEQ ID NO. 236) | |
| 237. | *Nocardia farcinica* (SEQ ID NO. 237) | |
| 238. | *Streptomyces coelicolor* (SEQ ID NO. 238) | |
| 239. | *Streptomyces avermitilis* (SEQ ID NO. 239) | |
| 240. | *Corynebacterium efficiens* (SEQ ID NO. 240) | |
| 241. | *Corynebacterium glutamicum* (SEQ ID NO. 241) | |
| 242. | *Bordetella parapertussis* (SEQ ID NO. 242) | |
| 243. | Bordetella *bronchiseptica* (SEQ ID NO. 243) | |
| 244. | *Bordetella pertussis* (SEQ ID NO. 244) | |
| 245. | *Burkholderia mallei* (SEQ ID NO. 245) | |
| 246. | *Burkholderia pseudomallei* (SEQ ID NO. 246) | |
| 247. | *Pseudomonas putida* (SEQ ID NO. 247) | |
| 248. | *Yersinia pseudotuberculosis* (SEQ ID NO. 248) | |
| 249. | *Yersinia pestis* (SEQ ID NO. 249) | |
| 250. | *Vibrio cholerae* (SEQ ID NO. 250) | |
| 251. | *Vibrio vulnificus* (SEQ ID NO. 251) | |
| 252. | *Vibrio parahaemolyticus* (SEQ ID NO. 252) | |
| 253. | *Vibrio fischeri* (SEQ ID NO. 253) | |
| 254. | *Campylobacter jejuni* (SEQ ID NO. 254) | |
| 255. | *Corynebacterium diphtheriae* (SEQ ID NO. 255) | |

Figure 10. Amplification of molecular marker VI (pgi) in Gram-negative bacteria

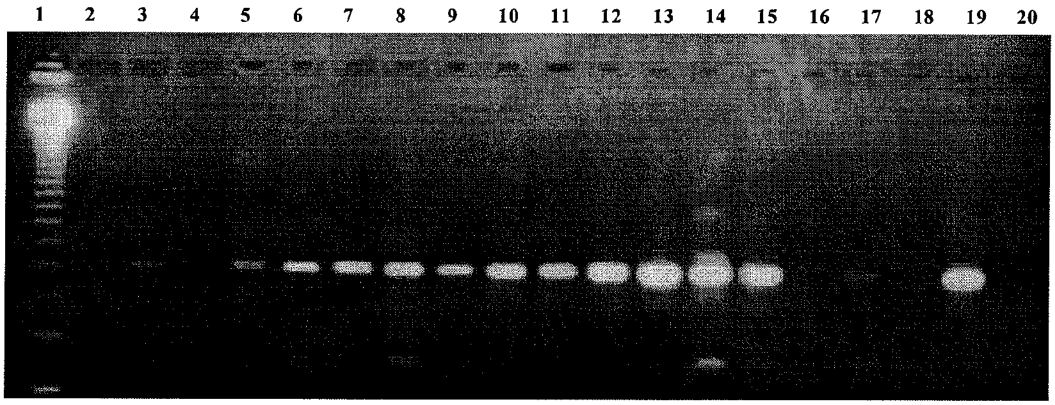

1. DNA Ladder (123 bp)
2. Pseudomonas aeruginosa
3. Pseudomonas diminuta
4. Stenotraophomas maltophilia
5. Pseudomonas pseudoalcaligenes
6. Burkholderia cepacia
7. Pseudomonas putida
8. Pseudomonas syringae
9. Providencia stuartii
10. Proteus mirabilis
11. Proteus vulgaris
12. Citrobacter freundii
13. Enterobacter aerogenes
14. Klebsiella oxytoca
15. Klebsiella pneumoniae
16. Haemophilus influenzae
17. Leigonella pneumophila
18. Serratia liquefasciens
19. Serratia marcescens
20. Negative control

Figure 11. Molecular marker VI (pgi) sequences amplified from different Gram negative bacteria (SEQ ID NOs 256-277).

| | | | |
|---|---|---|---|
| 256. | *Providencia stuartii* | (SEQ ID NO. 256) | PSTU |
| 257. | *Enterobacter cloaceae* | (SEQ ID NO. 257) | ECLO |
| 258. | *Proteus mirabilis* | (SEQ ID NO. 258) | PMIR |
| 259. | *Proteus vulgaris* | (SEQ ID NO. 259) | PVUL |
| 260. | *Enterobacter aerogenes* | (SEQ ID NO. 260) | EAER |
| 261. | *Klebsiella pneumoniae* | (SEQ ID NO. 261) | KPNE |
| 262. | *Escherichia coli* 0157 :H7 | (SEQ ID NO. 262) | ECO157 |
| 263. | *Escherichia coli* K12 | (SEQ ID NO. 263) | ECOK12 |
| 264. | *Citrobacter freundii* | (SEQ ID NO. 264) | CFRE |
| 265. | *Haemophilus influenzae* | (SEQ ID NO. 265) | HINF |
| 266. | *Serratia marcescens* | (SEQ ID NO. 266) | SMAR |
| 267. | *Morganella morganii* | (SEQ ID NO. 267) | MMOR |
| 268. | *Klebsiella oxytoca* | (SEQ ID NO. 268) | KOXY |
| 269. | *Shigella sonnei* | (SEQ ID NO. 269) | SSON |
| 270. | *Salmonella enteritidis* | (SEQ ID NO. 270) | SENT |
| 271. | *Salmonella enterica hadar* | (SEQ ID NO. 271) | SHAD |
| 272. | *Salmonella enterica brandenburg* | (SEQ ID NO. 272) | SBRA |
| 273. | *Salmonella enterica* derby | (SEQ ID NO. 273) | SDER |
| 274. | *Salmonella enterica* virschow | (SEQ ID NO. 274) | SVIR |
| 275. | *Salmonella enterica typhimurium* | (SEQ ID NO. 275) | STPMM |
| 276. | *Salmonella enterica paratyphi* B | (SEQ ID NO. 276) | SPTB |
| 277. | *Serratia liquefasciens* | (SEQ ID NO. 277) | SLIQ |

Figure 12. Molecular marker VII (EG10839 & EG11396 or sfrB & yigC) in Gram-negative bacteria (SEQ ID NOs 278-303).

278. *Neisseria meningitidis serogroup A strain Z2491* (SEQ ID NO. 278)

279. *Klebsiella oxytoca* (SEQ ID NO. 279)

280. *Salmonella enterica subsp. enterica serovar Paratyphi A* (SEQ ID NO. 280)

281. *Salmonella typhimurium LT2* (SEQ ID NO. 281)

282. *Escherichia coli* CFT073 (SEQ ID NO. 282)

283. *Escherichia coli K12* (SEQ ID NO. 283)

284. *Salmonella enterica subsp. enterica serovar Typhi* (SEQ ID NO. 284)

285. *Escherichia coli O157:H7 EDL933* (SEQ ID NO. 285)

286. *Shigella flexneri 2a str. 301* (SEQ ID NO. 286)

287. *Pseudomonas aeruginosa PAO1* (SEQ ID NO. 287)

288. *Pseudomonas syringae pv. tomato str. DC3000* (SEQ ID NO. 288)

289. *Yersinia pseudotuberculosis IP 32953* (SEQ ID NO. 289)

290. *Neisseria meningitidis serogroup B strain MC58* SEQ ID NO. 290)

291. *Neisseria gonorrhoeae FA 1090* (SEQ ID NO. 291)

292. *Yersinia pestis CO92* (SEQ ID NO. 292)

293. *Pseudomonas putida KT2440* (SEQ ID NO. 293)

294. *Serratia marcescens ATCC 13880* (SEQ ID NO. 294)

295. *Burkholderia mallei ATCC 23344* (SEQ ID NO. 295)

296. *Burkholderia pseudomallei K96243* (SEQ ID NO. 296)

297. *Bordetella parapertussis* (SEQ ID NO. 297)

298. *Bordetella bronchiseptica RB50* (SEQ ID NO. 298)

299. *Bordetella pertussis Tohama I* (SEQ ID NO. 299)

300. *Legionella pneumophila subsp. pneumophila str. Philadelphia 1* (SEQ ID NO. 300)

301. *Klebsiella pneumoniae ATCC 13883* (SEQ ID NO. 301)

302. *Serratia liquefasciens ATCC 27592* (SEQ ID NO. 302)

303. *Brucella melitensis* (SEQ ID NO. 303)

Figure 13. Molecular marker VIII (hypothetical protein yleA) in Gram-negative bacteria (SEQ ID NOs 304-325).

304. *Haemophilus influenzae* (SEQ ID NO. 304)
305. *Pasteurella multocida* (SEQ ID NO. 305)
306. *Haemophilus ducrei* (SEQ ID NO. 306)
307. *Vibrio parahaemolyticus* (SEQ ID NO. 307)
308. *Yersinia pestis* (SEQ ID NO. 308)
309. *Vibrio cholerae* (SEQ ID NO. 309)
310. *Escherichia coli souche K12* (SEQ ID NO. 310)
311. *Escherichia coli souche 0157:H7* (SEQ ID NO. 311)
312. *Pseudomonas aeruginosa* (SEQ ID NO. 312)
313. *Bordetella pertussis* (SEQ ID NO. 313)
314. *Bordetella parapertussis* (SEQ ID NO. 314)
315. *Burkholderia pseudomallei* (SEQ ID NO. 315)
316. *Vibrio vulnificus* (SEQ ID NO. 316)
317. *Vibrio fischeri* (SEQ ID NO. 317)
318. *Yersinia pseudotuberculosis* (SEQ ID NO. 318)
319. *Salmonella enterica subspecies paratyphi A* (SEQ ID NO. 319)
320. *Salmonella typhimurium* (SEQ ID NO. 320)
321. *Shigella flexneri* (SEQ ID NO. 321)
322. *Pseudomonas syringae* (SEQ ID NO. 322)
323. *Burkholderia mallei* (SEQ ID NO. 323)
324. *Legionella pneumophila* (SEQ ID NO. 324)
325. *Bordetella bronchiseptica* (SEQ ID NO. 325)

Figure 14 represents marker I (purA) sequences amplified from different Gram-positive bacteria (SEQ ID NOs 326-359)

326 *Enterococcus faecalis* (SEQ ID NO. 326)
327 *Enterococcus gallinarum* (SEQ ID NO. 327)
328 *Enterococcus flavescens* (SEQ ID NO. 328)
329 *Streptococcus agalactiae* (SEQ ID NO. 329)
330 *Streptococcus sanguis* (SEQ ID NO. 330)
331 *Enterococcus faecium* (SEQ ID NO. 331)
332 *Enterococcus durans* (SEQ ID NO. 332)
333 *Streptococcus pyogenes* (SEQ ID NO. 333)
334 *Streptococcus pneumoniae* (SEQ ID NO. 334)
335 *Streptococcus oralis* (SEQ ID NO. 335)
336 *Staphylococcus hominis* (SEQ ID NO. 336)
337 *Bacillus anthracis* (SEQ ID NO. 337)
338 *Bacillus cereus* (SEQ ID NO. 338)
339 *Bacillus megatherium* (SEQ ID NO. 339)
340 *Enterococcus casseliflavus* (SEQ ID NO. 340)
341 *Enterococcus raffinosus* (SEQ ID NO. 341)
342 *Staphylococcus aureus* (SEQ ID NO. 342)
343 *Staphylococcus epidermidis* (SEQ ID NO. 343)
344 *Stretpococcus mitis* (SEQ ID NO. 344)
345 *Streptococcus species* (SEQ ID NO. 345)
346 *Streptococcus canis* (SEQ ID NO. 346)
347 *Streptococcus mutans* (SEQ ID NO. 347)
348 *Streptococcus gordonii* (SEQ ID NO. 348)
349 *Bacillus species* (SEQ ID NO. 349)
350 *Bacillus pumilus* (SEQ ID NO. 350)
351 *Enterococcus villorum* (SEQ ID NO. 351)
352 *Bacillus thuringensis* (SEQ ID NO. 352)
353 *Bacillus mycoides* (SEQ ID NO. 353)
354 *Bacillus weihennstephanensis* (SEQ ID NO. 354)
355 *Staphylococcus haemolyticus* (SEQ ID NO. 355)
356 *Staphylococcus saprophyticus* (SEQ ID NO. 356)
357 *Bacillus subtilis* (SEQ ID NO. 357)
358 *Listeria monocytogenes* (SEQ ID NO. 358)
359 *Lactococcus lactis* (SEQ ID NO. 359)

Figure 15A represents marker II (pstI) sequences amplified from Gram-positive bacteria (SEQ ID NOs: 360-395; SEQ ID NOs: 397-399), and some Gram-negative bacteria (SEQ ID NOs 396, 400-403).

| | |
|---|---|
| *SEQ ID NO. 360* | *Bacillus anthracis* |
| *SEQ ID NO. 361* | *Bacillus cereus* |
| *SEQ ID NO. 362* | *Listeria monocytogenes* |
| *SEQ ID NO. 363* | *Streptococcus pneumoniae* |
| *SEQ ID NO. 364* | *Streptococcus pyogenes* |
| *SEQ ID NO. 365* | *Streptococcus agalactiae* |
| *SEQ ID NO. 366* | *Streptococcus mutans* |
| *SEQ ID NO. 367* | *Enterococcus flavescens* |
| *SEQ ID NO. 368* | *Staphylococcus aureus* |
| *SEQ ID NO. 369* | *Staphylococcus epidermidis* |
| *SEQ ID NO. 370* | *Bacillus thuringensis* |
| *SEQ ID NO. 371* | *Staphylococcus hominis* |
| *SEQ ID NO. 372* | *Enterococcus faecium* |
| *SEQ ID NO. 373* | *Clostridium perfringens* |
| *SEQ ID NO. 374* | *Bacillus mycoides* |
| *SEQ ID NO. 375* | *Streptococcus oralis* |
| *SEQ ID NO. 376* | *Enterococcus hirae* |
| *SEQ ID NO. 377* | *Enterococcus avium* |
| *SEQ ID NO. 378* | *Staphylococcus saprophyticus* |
| *SEQ ID NO. 379* | *Staphylococcus haemolyticus* |
| *SEQ ID NO. 380* | *Enterococcus flavescens* |
| *SEQ ID NO. 381* | *Enterococcus casseliflavus* |
| *SEQ ID NO. 382* | *Enterococcus gallinarum* |
| *SEQ ID NO. 383* | *Enterococcus raffinosus* |
| *SEQ ID NO. 384* | *Enterococcus villorum* |
| *SEQ ID NO. 385* | *Clostridium difficile* |
| *SEQ ID NO. 386* | *Streptococcus mitis* |
| *SEQ ID NO. 387* | *Bacillus halodurans* |
| *SEQ ID NO. 388* | *Bacillus weihenstephanensis* |
| *SEQ ID NO. 389* | *Streptococcus species* |
| *SEQ ID NO. 390* | *Streptococcus gordonii* |
| *SEQ ID NO. 391* | *Streptococcus canis* |
| *SEQ ID NO. 392* | *Bacillus pumilus* |
| *SEQ ID NO. 393* | *Bacillus species* |

Figure 15B represents marker II (pstI) sequences amplified from Gram-positive bacteria (SEQ ID NOs: 360-395; SEQ ID NOs: 397-399), and some Gram-negative bacteria (SEQ ID NOs 396, 400-403).

| | |
|---|---|
| *SEQ ID NO. 394* | *Lactococcus lactis* |
| *SEQ ID NO. 395* | *Bacillus firmus* |
| *SEQ ID NO. 396* | *Haemophilus influenzae* |
| *SEQ ID NO. 397* | *Streptococcus bovis* |
| *SEQ ID NO. 398* | *Enterococcus durans* |
| *SEQ ID NO. 399* | *Streptococcus sanguis* |
| *SEQ ID NO. 400* | *Escherichia coli* |
| *SEQ ID NO. 401* | *Serratia liquefasciens* |
| *SEQ ID NO. 402* | *Proteus mirabilis* |
| *SEQ ID NO. 403* | *Proteus vulgaris* |

Figure 16 represents marker III (SpyM_0902 & SpyM_0903) sequences amplified from Gram-positive bacteria (SEQ ID NOs 404-412).

| | |
|---|---|
| *SEQ ID NO. 404* | *Streptococcus pyogenes* |
| *SEQ ID NO. 405* | *Streptococcus oralis* |
| *SEQ ID NO.* 406 | Streptococcus *faecalis* |
| *SEQ ID NO. 407* | *Streptococcus agalactiae* |
| *SEQ ID NO. 408* | *Streptococcus pneumoniae* |
| *SEQ ID NO. 409* | *Enterococcus durans* |
| *SEQ ID NO. 410* | *Streptococcus anthracis* |
| *SEQ ID NO. 411* | *Bacillus cereus* |
| *SEQ ID NO. 412* | *Streptococcus mutans* |

Figure 17 represents marker IV (Spy1527, a putative GTP-binding factor plus 160 nt downstream) sequences amplified from Gram-positive bacteria (SEQ ID NOs 413-425).

*SEQ ID NO. 413 Listeria monocytogenes*

*SEQ ID NO. 414 Listeria innocua*

*SEQ ID NO. 415 Bacillus cereus*
*SEQ ID NO. 416 Bacillus anthracis*

*SEQ ID NO. 417 Staphylococcus aureus*

*SEQ ID NO. 418 Staphylococcus epidermidis*

*SEQ ID NO. 419 Bacillus subtilis*

*SEQ ID NO. 420 Streptococcus mutans*

*SEQ ID NO. 421 Streptococcus pneumoniae*

*SEQ ID NO. 422 Streptococcus agalactiae*

*SEQ ID NO. 423 Streptococcus pyogenes*

*SEQ ID NO. 424 Enterococcus faecalis*

*SEQ ID NO. 425 Lactococcus lactis*

Figure 18 represents sequences amplified with molecular marker VI (pgi) from various Gram-negative bacteria (SEQ ID NOs 426-430).

| | |
|---|---|
| *SEQ ID NO. 426* | *Citrobacter freundii* |
| *SEQ ID NO. 427* | *Klebsiella pneumoniae* |
| *SEQ ID NO. 428* | *Klebsiella oxytoca* |
| *SEQ ID NO. 429* | *Escherichia coli* |
| *SEQ ID NO. 430* | *Serratia marcescens* |

Figure 19 represents sequences amplified with molecular marker V (carB) from various Gram-negative bacteria (SEQ ID NOs 431-442).

| | |
|---|---|
| *SEQ ID NO. 431* | *Neisseria gonorrhoeae* |
| *SEQ ID NO. 432* | *Serratia marcescens* |
| *SEQ ID NO. 433* | *Citrobacter freundii* |
| *SEQ ID NO. 434* | *Enterobacter aerogenes* |
| *SEQ ID NO. 435* | *Enterobacter cloacae* |
| *SEQ ID NO. 436* | *Morganella morganii* |
| *SEQ ID NO. 437* | *Escherichia coli* |
| *SEQ ID NO. 438* | *Proteus mirabilis* |
| *SEQ ID NO. 439* | *Proteus vulgaris* |
| *SEQ ID NO. 440* | *Neisseria meningitidis* |
| *SEQ ID NO. 441* | *Klebsiella oxytoca* |
| *SEQ ID NO. 442* | *Legionella pneumophila* |

Figure 20 represents sequences amplified with molecular marker VII ((EG10839 & EG11396 or sfrB & yigC) in Gram-negative bacteria (SEQ ID NOs 443-451).

| | |
|---|---|
| *SEQ ID NO. 443* | *Pseudomonas aeruginosa* |
| *SEQ ID NO. 444* | *Pseudomonas syringae* |
| *SEQ ID NO. 445* | *Bordetella parapertussis* |
| *SEQ ID NO. 446* | *Neisseria meningitidis* |
| *SEQ ID NO. 447* | *Shigella flexneri* |
| *SEQ ID NO. 448* | *Escherichia coli K12* |
| *SEQ ID NO. 449* | *Escherichia coli O157:H7* |
| *SEQ ID NO. 450* | *Bordetella bronchiseptica* |
| *SEQ ID NO. 451* | *Bordetella pertussis* |

Figure 21 represents sequences amplified with molecular marker VIII (hypothetic yleA protein) in Gram-negative bacteria (SEQ ID NOs 452-461).

| | |
|---|---|
| *SEQ ID NO. 452* | *Haemophilus influenzae* |
| *SEQ ID NO. 453* | *Pasteurella multocida* |
| SEQ ID NO. 454 | Haemophilus ducreyi |
| *SEQ ID NO. 455* | *Vibrio parahaemolyticus* |
| *SEQ ID NO. 456* | *Yersinia pestis* |
| *SEQ ID NO. 457* | *Salmonella typhimurium* |
| *SEQ ID NO. 458* | *Vibrio cholerae* |
| *SEQ ID NO. 459* | *Escherichia coli K12* |
| *SEQ ID NO. 460* | *Escherichia coli O157:H7* |
| *SEQ ID NO. 461* | *Pseudomonas aeruginosa* |

SEQUENCE LISTING

```
<160> NUMBER OF SEQ ID NOS: 479

<210> SEQ ID NO 1
<211> LENGTH: 597
<212> TYPE: DNA
<213> ORGANISM: Enterococcus Faecalis

<400> SEQUENCE: 1

ctatttgaag ggcgcaaggt gtcatgttgg atatcgatca aggaacctat ccatttgtta      60

cttcctctaa tccagtagct ggtggcgtaa ctatcggtag tggcgttggt ccatcaaaaa     120

ttaataaagt ggttggtgtc tgcaaagcgt acacttcacg tgtcggtgac ggcccattcc     180

caacagaatt atttgatgaa acaggagaaa ccattcgtcg tgtcggtaaa gaatacggaa     240

caacaacagg acgtccgcgt cgtgtcggtt ggtttgattc agtagtcatg cgtcattcaa     300

aacgtgtatc agggattaca aacttgtcat taaactcgat tgacgtgtta agtggtttag     360

aaacggtgaa aatttgtaca gcttatgaac ttgatggtga attaatttat cattatccag     420

caagcttgaa agaattaagc cgctgtaaac cagtttatga agaattacca ggttggtctg     480

aagatatcac tggttgcaaa actttagccg atttaccagc taatgctcgt aactatgtgc     540

atcggatttc agaattagtt ggtgtgcgca tttcaacatt ctcagtaggg ccagacc        597

<210> SEQ ID NO 2
<211> LENGTH: 597
<212> TYPE: DNA
<213> ORGANISM: Enterococcus gallinarum
```

-continued

<400> SEQUENCE: 2

```
ctcttcgagg tgcgcaagga gttatgctag atattgatca aggaacatat ccgttcgtaa      60
catcctcaaa tccagtagct ggtggagtaa ccattggtag tggagtgggt ccttctaaaa     120
tcaataaagt agttggtgtt tgtaaagcat atacttcaag agttggtgac ggcccattcc     180
caacagaact ttttgatgaa acaggcaatc aaattcgtga agttggccgt gaatatggta     240
cgacaactgg tcgtccacgt cgtgttggtt ggtttgactc tgttgtcatg cgtcattcaa     300
aacgtgtttc tggtatcacg aatctgtctt taaattcaat tgatgttttg agcggcttgg     360
aaactgtaaa aatttgtact gcttatgaat tagatggaga attgatttat cattatcctg     420
caagtctaaa agaattgaat cgttgtaaac cagtctatga agagttacca ggctggtcag     480
aagatattac tggatgcaaa acattagctg atcttcctga aaatgcacgt aactatgtac     540
atcgtatctc tgaattagtt ggggttcgta tctcaacatt ctcagtaggt cctgacc        597
```

<210> SEQ ID NO 3
<211> LENGTH: 598
<212> TYPE: DNA
<213> ORGANISM: Enterococcus flavescens
<220> FEATURE:
<221> NAME/KEY: misc_feature
<222> LOCATION: (594)..(594)
<223> OTHER INFORMATION: n is a, c, g, or t

<400> SEQUENCE: 3

```
ctttttgaag gtgctcaagg cgtgatgctg gatatcgacc aaggaaccta tcctttcgtg      60
acatcatcca accccgttgc tgggggagtc actattggta gtggtgtggg tccttcaaaa     120
atcaacaaag tcgttggtgt ctgcaaagct tacacctctc gggtaggaga tggtcctttc     180
ccaacggaac tgtttgatga aacaggtgaa caaatccgta agatcggtcg tgaatacgga     240
acaacgacag gacgtcctcg ccgtgtgggc tggtttgata ccgtcgtgat gcgccattca     300
aaacgtgttt cagggattac aaacctatcc cttaactcga tcgatgtctt gagcggctta     360
gaaaccgtga agatctgtac ggcttatgaa ctagacggcg aattgatcta tcattaccca     420
gcaagcttga aagagttgaa ccgctgcaaa ccagtctacg aagaacttcc tggctggtct     480
gaagacatta ctggctgcaa aacattagca gatctgccag aaaatgcacg caattacgtt     540
caccgcatct ctgaattagt cggtgtccgc atttcgacct tctcagtagg gccngacc       598
```

<210> SEQ ID NO 4
<211> LENGTH: 598
<212> TYPE: DNA
<213> ORGANISM: Streptococcus agalactiae
<220> FEATURE:
<221> NAME/KEY: misc_feature
<222> LOCATION: (581)..(581)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t

<400> SEQUENCE: 4

```
ctctttgaag ggcgcaagga gttatgctcg acattgatca aggaacatac ccatttgtaa      60
catcttccaa tccagtagca ggtggtgtca caattggttc gggagttgga ccaagtaaaa     120
ttaataaagt agtaggtgta tgtaaagctt acactagccg tgttggtgat ggaccattcc     180
caacagaact ttttgatgag gttggtgacc gtattcgtga gattggtaaa gagtatggta     240
```

-continued caacgaccgg tcgtcctcgt cgcgttggat ggtttgattc tgttgttatg cgtcacagcc 300
gtcgagtatc aggtattact aacctctctc tgaattcaat tgatgttctt tcagggcttg 360
atacggtgaa aatttgtgtg gcttatgacc ttgatgggaa acgtattgac tattacccag 420
caagccttga acagctaaaa cgttgtaaac caatctatga agaattaccg ggctggtctg 480
aagatattac agcttgtcgt agcttagatg atcttccaga aaatgcacgt aattacgttc 540
gccgtgttgg cgaattggtt ggtgttcgta tttctacttt nctcagtagg nccaggtc 598

<210> SEQ ID NO 5
<211> LENGTH: 599
<212> TYPE: DNA
<213> ORGANISM: Streptococcus sanguis

<400> SEQUENCE: 5
ctttttgaag gggctcaagg agttatgctc gacattgatc aaggaacata cccatttgta 60
acatcttcca atccagtagc aggtggtgtc acaattggtt cgggagttgg accaagtaaa 120
attaataaag tagtaggtgt atgtaaagct tacactagcc gtgttggtga tggaccattc 180
ccaacagaac tttttgatga ggttggtgac cgtattcgtg agattggtaa agagtatggt 240
acaacgaccg gtcgtcctcg tcgcgttgga tggtttgatt ctgttgttat gcgtcacagc 300
cgtcgagtat caggtattac taacctctct ctgaattcaa ttgatgttct ttcagggctt 360
gatacggtga aaatttgtgt ggcttatgac cttgatggga aacgtattga ctattaccca 420
gcaagccttg aacagctaaa acgttgtaaa ccaatctatg aagaattacc gggctggtct 480
gaagatatta cagcttgtcg tagcttagat gatcttccag aaaatgcacg taattacgtt 540
cgccgtgttg gcgaattggt tggtgttcgt atttctactt tctcagttgg gtccagacc 599

<210> SEQ ID NO 6
<211> LENGTH: 598
<212> TYPE: DNA
<213> ORGANISM: Enterococcus faecium
<220> FEATURE:
<221> NAME/KEY: misc_feature
<222> LOCATION: (581)..(581)
<223> OTHER INFORMATION: n is a, c, g, or t

<400> SEQUENCE: 6
ttcttcgaag gggcgcaagg ggttatgctg gatattgacc aagggactta tccatttgta 60
acttcttcta atccagttgc aggggagtca ccatcggttc cggtgttggt ccgagcaaaa 120
ttgacaaggt agttggtgtc tgcaaggcct acaccagtcg ggtcggagat ggaccattcc 180
caacagagct ttttgatgaa gttggtgacc gcattcgtga tatcggccac gaatatggca 240
ctaccactgg tcgcccacgt cgggtaggtt ggtttgactc ggttgttatg cgccatagcc 300
gccgtgtatc agggattacc aatctttcgc ttaactccat cgatgtcttg agtggtctgg 360
atacagtgaa aatctgtgta gcttatgact tggatggcca aagaatcgac cactacccag 420
ctagtctgga acagctcaag cgctgcaagc cgatttacga agagctgcca ggctggtcag 480
aggacatcac tggagtccgc agtctggaag acttgccaga aaatgcccgt aactatgttc 540
gccgagtgag tgagctggtt ggcgttcgca tttctacctt nctcagtagg gccagacc 598

<210> SEQ ID NO 7
<211> LENGTH: 598
<212> TYPE: DNA
<213> ORGANISM: Enterococcus durans

<400> SEQUENCE: 7

-continued

```
ctctttgaag gggcacaagg tgtgatgttg gatatcgatc aaggaacgta tccatttgtg     60

acttcttcta atccggtagc tggtggtgta acgatcggta gtggcgttgg cccttcaaag    120

atcaataaag tcgttggtgt atgtaaagct tatacttctc gtgtaggaga tggcccattc    180

ccaacagaac tatttgacga aacaggtcaa caaatccgtg aagtcggtcg tgaatatggt    240

acgacaacag gtcgacctcg tcgtgtcggt tggtttgata cagtcgtggt gcgccattca    300

aaacgtgtat caggaatcac taacctatca ttgaattcaa tcgatgtatt aagcggacta    360

gaaacagtaa aaatctgtac agcgtatgaa ttagatggag aattgatcta tcattaccca    420

gcaagcctga aagaattgaa acgttgcaaa ccagtatacg aagaacttcc tggttggtct    480

gaagatatta cagcatgtaa aacacttgct gaactaccag aaaacgcccg taactatgtt    540

agacgtatct cagagcctgt aggagtccgt atttcaacat tctcagtagg tccagacc      598
```

<210> SEQ ID NO 8
<211> LENGTH: 597
<212> TYPE: DNA
<213> ORGANISM: Streptococcus pyogenes

<400> SEQUENCE: 8

```
ctatttgaag gggcacaagg ggttatgctt gatattgacc aggaacgtac ccatttgtaa     60

cgtcttcaaa cccagttgct ggtggtgtaa ccattggttc tggtgttggc ccaaataaaa    120

tcaacaaagt agttggtgtc tgtaaagcct acacaagccg tgtcggtgat gggccattcc    180

ctacagaact ctttgatgaa gtgggtgagc gcattcgtga agtgggtcat gagtacggga    240

caacgaccgg ccgtccacgt cgtgtcggtt ggtttgattc ggttgtcatg cgccacagtc    300

gtcgtgtatc aggtattact aacctctctc tgaattcaat tgatgttctt tcagggcttg    360

atacggttaa gatttgtgtg gcttatgacc ttgatgggaa acgtattgac tattacccag    420

caaaccttga acaactcaaa cgttgcaaac caatctatga agaattacca ggctggcaag    480

aggacatcac aggtgttcgt agccttgatg agcttcctga aaatgcccgc aactacgttc    540

gtcgtgttgg agaattggtt ggcgttcgca tttcaacctt ctcagttggg ccagacc       597
```

<210> SEQ ID NO 9
<211> LENGTH: 599
<212> TYPE: DNA
<213> ORGANISM: Streptococcus pneumoniae

<400> SEQUENCE: 9

```
ctatttgaag gggctcaagg tgttatgcta gatatcgacc aaggtactta tccatttgtt     60

acgtcatcaa accctgtagc tggtggtgtg acaattggtt ctggtgtcgg tccaagcaag    120

attgacaagg ttgtaggtgt atgtaaagct tatacgagtc gtgtaggaga tggtcctttc    180

ccaactgagt tgtttgatga agtgggagaa cgtatccgtg aagtgggtca tgaatatggt    240

acaacaactg gtcgtccacg tcgtgtaggt tggtttgact cagttgtgat gcgtcatagc    300

cgtcgtgttt ctggtattac taacctttct ttgaactcta ttgatgtttt gagcggtttg    360

gatactgtga aaatctgtgt ggcctatgat cttgacggtc aacgtattga ctactatcca    420

gctagtcttg agcaattgaa acgttgcaag cctatctatg aagagttgcc aggttggtca    480

gaagatatta ccggagttcg caatttggaa gatcttcctg agaatgcgcg taactatgtt    540

cgtcgtgtga gtgaattggt tggcgttcgt atttctactt ttctcagtag gtccaggcc      599
```

<210> SEQ ID NO 10

-continued

<211> LENGTH: 598
<212> TYPE: DNA
<213> ORGANISM: Streptococcus oralis

<400> SEQUENCE: 10

```
cttttcgaag gtgcgcaagg tgtcatgttg gacattgatc aagggactta tccatttgtt     60

acttcttcaa accctgtcgc tggtggtgtg acgattgggt ctggtgttgg tccaagtaag    120

attgacaagg ttgtaggtgt ctgtaaagcc tacacaagtc gtgtaggaga tggaccgttc    180

ccaactgaat tatttgatga agtgggagat cgcatccgtg aagtaggtca tgaatatggt    240

acaacaactg gtcgtccacg tcgtgtgggt tggtttgact cagttgtgat gcgtcacagc    300

cgccgtgtat ctgggattac caatctttca ttgaactcta tagatgtttt gagtggtttg    360

gatactgtga aaatctgtgt cgcctatgat cttgatggtc aacgtattga ttactatcct    420

gctagtcttg agcagttgaa acgttgtaag ccaatctacg aggaattgcc aggttggtca    480

gaagacatca ctggagtccg taatttggaa gaccttcctg agaatgcacg caactatgtt    540

cgtcgtgtaa gcgagttggt tggtgttcgt atctcaactt tctcagttgg gccagatc      598
```

<210> SEQ ID NO 11
<211> LENGTH: 598
<212> TYPE: DNA
<213> ORGANISM: Staphylococcus hominis

<400> SEQUENCE: 11

```
ctctttgaag gagcgcaagg agttatgtta gatatcgacc atggtacata tccttttgta     60

acgtcaagta atcctgtggc aggtaatgtg acagtaggaa ctggcgtggg tccaaccttc    120

gtatctaaag tgattggggt atgtaaatcc tatacatctc gtgtaggtga cggcccattc    180

cctactgaat tattcgacga agatggtcat catattagag aagtaggtcg tgaatatgga    240

acgacaacag gacgtcctcg tcgtgtaggt tggttcgact cagttgtatt acgtcactct    300

cgtcgtgtaa gtggtattac agacttatct attaactcaa ttgacgtttt aacaggttta    360

gatacggtta aaatttgtac agcttatgag ttagatggtg aaacaatcac agaatatcca    420

gcaaacttag accaattacg tcgttgtaaa ccaattttcg aagagttacc tggttggacg    480

gaagacatta caggttgtcg tacattagaa gaattacctg aaaacgcacg taaatactta    540

gaacgtattt ctgaattatg tggcgttcat atttcaatct tctcagtagg tccaggcc      598
```

<210> SEQ ID NO 12
<211> LENGTH: 560
<212> TYPE: DNA
<213> ORGANISM: Bacillus anthracis
<220> FEATURE:
<221> NAME/KEY: misc_feature
<222> LOCATION: (7)..(7)
<223> OTHER INFORMATION: n is a, c, g, or t

<400> SEQUENCE: 12

```
gcttcantcg acccggtacg tacccgttcg ttacatcttc taacccaatt gctggtggtg     60

taacagttgg aactggagtt ggtcctgcga aagttactcg cgttgtaggt gtatgtaaag    120

catatacaag ccgcgttggt gatggtccat tccctactga gcttcatgac gaaattggtc    180

atcaaattcg tgaagttggt cgtgagtatg gaacgacaac tggtcgtcca cgccgcgtag    240

gttggttcga tagcgttgtt gtaagacatg cacgtcgtgt tagtggttta acagatttat    300

cattaaactc tatcgacgtt ctaactggta ttccaacact taaaatttgt gttgcttaca    360

aatgcgatgg gaaagttatc gatgaagttc cagcaaactt aaacatttta gcgaaatgtg    420
```

-continued

```
agcctgtata cgaagagctt ccaggttgga cagaagatat tactggtgta agatcattag    480

atgagcttcc tgaaaatgca cgaaaatacg tagaacgtgt ttctgagtta acaggaattc    540

aattatctat gttctcagtg                                                560


<210> SEQ ID NO 13
<211> LENGTH: 560
<212> TYPE: DNA
<213> ORGANISM: Bacillus anthracis Butare

<400> SEQUENCE: 13

gcttgctatc gacccggtac gtacccgttc gttacatctt ctaacccaat tgctggtggt     60

gtaacagttg gaactggagt tggtcctgcg aaagttactc gcgttgtagg tgtatgtaaa    120

gcatatacaa gccgcgttgg tgatggtcca ttccctactg agcttcatga cgaaattggt    180

catcaaattc gtgaagttgg tcgtgagtat ggaacgacaa ctggtcgtcc acgccgcgta    240

ggttggttcg atagcgttgt tgtaagacat gcacgtcgtg ttagtggttt aacagattta    300

tcattaaact ctatcgacgt tctaactggt attccaacac ttaaaatttg tgttgcttac    360

aaatgcgatg ggaaagttat cgatgaagtt ccagcaaact taaacatttt agcgaaatgt    420

gagcctgtat acgaagagct tccaggttgg acagaagata ttactggtgt aagatcatta    480

gatgagcttc ctgaaaatgc acgaaaatac gtagaacgtg tttctgagtt aacaggaatt    540

caattatcta tgttctcgtg                                                560


<210> SEQ ID NO 14
<211> LENGTH: 560
<212> TYPE: DNA
<213> ORGANISM: Bacillus anthracis Sterne
<220> FEATURE:
<221> NAME/KEY: misc_feature
<222> LOCATION: (8)..(8)
<223> OTHER INFORMATION: n is a, c, g, or t

<400> SEQUENCE: 14

cttcgacncg gtacgtaccc gttcgttaca tcttctaacc caattgctgg tggtgtaaca     60

gttggaactg gagttggtcc tgcgaaagtt actcgcgttg taggtgtatg taaagcatat    120

acaagccgcg ttggtgatgg tccattccct actgagcttc atgacgaaat tggtcatcaa    180

attcgtgaag ttggtcgtga gtatggaacg acaactggtc gtccacgccg cgtaggttgg    240

ttcgatagcg ttgttgtaag acatgcacgt cgtgttagtg gtttaacaga tttatcatta    300

aactctatcg acgttctaac tggtattcca acacttaaaa tttgtgttgc ttacaaatgc    360

gatgggaaag ttatcgatga agttccagca aacttaaaca ttttagcgaa atgtgagcct    420

gtatacgaag agcttccagg ttggacagaa gatattactg gtgtaagatc attagatgag    480

cttcctgaaa atgcacgaaa atacgtagaa cgtgtttctg agttaacagg aattcaatta    540

tctatgttct cagtggcccc                                                560


<210> SEQ ID NO 15
<211> LENGTH: 560
<212> TYPE: DNA
<213> ORGANISM: Bacillus anthracis
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (552)..(552)
```

-continued

<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (560)..(560)
<223> OTHER INFORMATION: n is a, c, g, or t

<400> SEQUENCE: 15

```
ggtncgtacc cgttcgttac atcttctaac ccaattgctg gtggtgtaac agttggaact     60

ggagttggtc ctgcgaaagt tactcgcgtt gtaggtgtat gtaaagcata tacaagccgc    120

gttggtgatg gtccattccc tactgagctt catgacgaaa ttggtcatca aattcgtgaa    180

gttggtcgtg agtatggaac gacaactggt cgtccacgcc gcgtaggttg gttcgatagc    240

gttgttgtaa gacatgcacg tcgtgttagt ggtttaacag atttatcatt aaactctatc    300

gacgttctaa ctggtattcc aacacttaaa atttgtgttg cttacaaatg cgatgggaaa    360

gttatcgatg aagttccagc aaacttaaac attttagcga aatgtgagcc tgtatacgaa    420

gagcttccag gttggacaga agatattact ggtgtaagat cattagatga gcttcctgaa    480

aatgcacgaa aatacgtaga acgtgtttct gagttaacag gaattcaatt atctatgttc    540

tcagtggccc cnggnccnan                                                560
```

<210> SEQ ID NO 16
<211> LENGTH: 560
<212> TYPE: DNA
<213> ORGANISM: Bacillus anthracis
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (552)..(553)
<223> OTHER INFORMATION: n is a, c, g, or t
<220> FEATURE:
<221> NAME/KEY: misc_feature
<222> LOCATION: (556)..(556)
<223> OTHER INFORMATION: n is a, c, g, or t

<400> SEQUENCE: 16

```
ggtncgtacc cgtncgttac atcttctaac ccaattgctg gtggtgtaac agttggaact     60

ggagttggtc ctgcgaaagt tactcgcgtt gtaggtgtat gtaaagcata tacaagccgc    120

gttggtgatg gtccattccc tactgagctt catgacgaaa ttggtcatca aattcgtgaa    180

gttggtcgtg agtatggaac gacaactggt cgtccacgcc gcgtaggttg gttcgatagc    240

gttgttgtaa gacatgcacg tcgtgttagt ggtttaacag atttatcatt aaactctatc    300

gacgttctaa ctggtattcc aacacttaaa atttgtgttg cttacaaatg cgatgggaaa    360

gttatcgatg aagttccagc aaacttaaac attttagcga aatgtgagcc tgtatacgaa    420

gagcttccag gttggacaga agatattact ggtgtaagat cattagatga gcttcctgaa    480

aatgcacgaa aatacgtaga acgtgtttct gagttaacag gaattcaatt atctatgttc    540

tcagtggccc cnnggnccca                                                560
```

-continued

<210> SEQ ID NO 17
<211> LENGTH: 560
<212> TYPE: DNA
<213> ORGANISM: Bacillus anthracis
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 17
ngcttnaatc gacccggtac gtacccgttc gttacatctt ctaacccaat tgctggtggt 60
gtaacagttg gaactggagt tggtcctgcg aaagttactc gcgttgtagg tgtatgtaaa 120
gcatatacaa gccgcgttgg tgatggtcca ttccctactg agcttcatga cgaaattggt 180
catcaaattc gtgaagttgg tcgtgagtat ggaacgacaa ctggtcgtcc acgccgcgta 240
ggttggttcg atagcgttgt tgtaagacat gcacgtcgtg ttagtggttt aacagattta 300
tcattaaact ctatcgacgt tctaactggt attccaacac ttaaaatttg tgttgcttac 360
aaatgcgatg ggaaagttat cgatgaagtt ccagcaaact taaacatttt agcgaaatgt 420
gagcctgtat acgaagagct tccaggttgg acagaagata ttactggtgt aagatcatta 480
gatgagcttc ctgaaaatgc acgaaaatac gtagaacgtg tttctgagtt aacaggaatt 540
caattatcta tgttctcagt 560

<210> SEQ ID NO 18
<211> LENGTH: 557
<212> TYPE: DNA
<213> ORGANISM: Bacillus cereus
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (553)..(553)
<223> OTHER INFORMATION: n is a, c, g, or t

<400> SEQUENCE: 18
gncncggtac gtacccgttc gttacatctt ctaacccaat tgctggcggt gtaacagttg 60
gaactggagt tggtcctgcg aaagttactc gcgttgtagg tgtatgtaaa gcatatacaa 120
gccgcgttgg tgatggtcca ttccctactg agcttcatga tgaaattggt catcaaattc 180
gtgaagttgg tcgcgagtat ggaacgacaa ctggtcgtcc acgccgcgta ggttggttcg 240
atagcgttgt tgtaagacat gcacgtcgtg ttagtggttt aacggatcta tcattaaatt 300
ctatcgacgt tttaacaggt attccaactc ttaaaatttg tgtagcttac aaatacaatg 360
gcgaagttat tgatgaagtt ccagctaact taaacatttt agcgaaatgt gagcctgtat 420
atgaagagct tccaggttgg gaagaagata ttactggtgt aaaatcatta gatgaacttc 480
ctgaaaatgc acgaaaatac gtagaacgtg tttctgagtt aacaggaatt caaatatcta 540
tgttctcagt agncccc 557

<210> SEQ ID NO 19

-continued

<211> LENGTH: 551
<212> TYPE: DNA
<213> ORGANISM: Bacillus cereus
<220> FEATURE:
<221> NAME/KEY: misc_feature
<222> LOCATION: (545)..(545)
<223> OTHER INFORMATION: n is a, c, g, or t

<400> SEQUENCE: 19
ggtcgtaccc gttcgttaca tcttctaacc caattgctgg tggtgtaaca gttggaactg 60
gagttggtcc tgcgaaagtt actcgcgttg taggtgtatg taaagcatat acaagccgcg 120
ttggtgatgg tccattccct actgagcttc atgatgaaat tggtcatcaa attcgtgaag 180
ttggtcgcga gtatggaacg acaactggtc gtccacgccg cgtaggttgg ttcgatagcg 240
ttgttgtaag acatgcacgt cgtgttagtg gtttaacgga tctatcatta aattctatcg 300
acgttttaac aggtattcca actcttaaaa tttgtgtagc ttacaaatac aatggcgaag 360
ttattgatga agttccagct aacttaaaca ttttagcgaa atgtgagcct gtatatgaag 420
agcttccagg ttgggaagaa gatattactg gtgtaaaatc attagatgaa cttcctgaaa 480
atgcacgaaa atacgtagaa cgtgtttctg agttaacagg aattcaaata tctatgttct 540
cagtnggccc c 551

<210> SEQ ID NO 20
<211> LENGTH: 598
<212> TYPE: DNA
<213> ORGANISM: Bacillus megatherium

<400> SEQUENCE: 20
ctattcgaag gggcacaagg tgttatgtta gatatcgatc aaggaacata tccatttgtt 60
acatcttcaa acccagtagc gggtggagta acaattggtt ctggggtagg tccatctaaa 120
atcaaacacg ttgtaggtgt atcaaaagcg tatacaactc gtgttggtga cggccctttc 180
ccaactgaat taacaaacga aatcggtgat caaatccgtg aagtaggacg tgaatatggt 240
acaacaactg gtcgtcctcg ccgtgtaggt tggttcgaca gtgtagttgt acgtcatgct 300
cgtcgcgtta gtggaatcac agatctatct ttaaactcaa ttgatgtatt aacgggaatt 360
gagacattaa agatttgcgt agcttatcgt tataaagggg aagttatgga agaattccct 420
gctagcttaa aaacacttgc agagtgcgaa cctgtatatg aagagcttcc aggttggaca 480
gaagatatta cgggtgtgaa aacattagat gagttacctg ataacgctcg ccactactta 540
gagcgcgtgt ctcaattaac aggtattcct ttatctattt tctcagtagg tccaggcc 598

<210> SEQ ID NO 21
<211> LENGTH: 598
<212> TYPE: DNA
<213> ORGANISM: Enterococcus casseliflavus
<220> FEATURE:
<221> NAME/KEY: misc_feature
<222> LOCATION: (11)..(11)
<223> OTHER INFORMATION: n is a, c, g, or t

<400> SEQUENCE: 21
tattcgaagg nagctcaagg cgtgatgctg gatatcgacc aaggaaccta tcctttcgtg 60
acatcatcca accccgttgc tggaggtgtc accatcggta gtggtgtggg tccttcaaaa 120
atcaacaaag tcgttggtgt ctgcaaagct tacacctctc gggtaggaga tggtcctttc 180
ccaacggaac tgtttgatga aacaggtgaa caaattcgta agatcggtcg tgaatacgga 240
acaacgacag gacgtcctcg ccgtgtgggc tggtttgata ccgtcgtgat gcgccattca 300

-continued

```
aaacgggtct cagggatcac gaatctatcc cttaactcga tcgatgtctt gagcggctta    360

gaaaccgtga agatctgtac ggcttatgaa ctagacggcg aattgatcta tcattaccca    420

gcaagcttga aagagttgaa ccgctgcaaa ccagtctacg aagaacttcc tggctggtct    480

gaagacatta ctggctgcaa aacattagca gatctgccag aaaatgcacg caattacgtt    540

caccgcatct ctgaattagt cggtgtccgc atttcgacct tctcagtagg tccagacc      598
```

<210> SEQ ID NO 22
<211> LENGTH: 598
<212> TYPE: DNA
<213> ORGANISM: Enterococcus raffinosus

<400> SEQUENCE: 22

```
ctatttgaag gtgctcaagg cgttatgctg gatattgatc aaggaaccta tccatttgtt     60

acttcttcga acccagttgc cggtggggta actatcggta gtggtgtagg acctgctaaa    120

atcgacaaag ttgtcggtgt ttgtaaagcc tatacttcac gcgtaggtga tggacctttc    180

ccaactgaat tgtttgatga agttggagat cagattcgtg aagtcggtcg tgaatatgga    240

acgactactg gtcgtccacg tcgtgtgggc tggtttgact cggttgtgat gcgtcattca    300

aaacgtgttt ctgggattac gaatctttct ttaaactcga ttgatgtctt gagcggtctg    360

gatacagtga aaatttgtac agcgtatgag ctggacggag aactaattta ccattatcca    420

gcaagcctaa aagaattaaa tcgttgtaag cccgtttatg aagaactacc tggttggagc    480

gaagatatta caggctgccg tgatttagct gatctaccgg aaaatgcgcg taattatgta    540

cgtcgcgttt ctgaacttgt gggtgtgcgt atctcgacct tctcagttgg tcctggtc      598
```

<210> SEQ ID NO 23
<211> LENGTH: 598
<212> TYPE: DNA
<213> ORGANISM: Staphylococcus aureus

<400> SEQUENCE: 23

```
ctatttgaag gggcacaagg tgtaatgtta gatatcgacc atggtacata tccattcgtt     60

acatcaagta atccaattgc aggtaacgtt actgttggta caggtgtagg tcctacattc    120

gtttcaaagg taattggtgt atgtaaagct tatacatcac gtgttggtga tggtccattc    180

cctactgaat tattcgatga agatggacat catattagag aagttggtcg tgaatatggt    240

acaacaacag gacgtccacg tcgtgtaggt tggtttgatt cagttgtatt acgtcactct    300

cgtcgtgtaa gtggtattac agatttatct attaactcaa tcgatgtttt aacaggccta    360

gacacagtga aaatctgtac agcttatgaa ttagacggta aagaaattac tgagtaccca    420

gcaaacttag atcaattaaa acgttgtaaa ccaatctttg aagagttacc aggttggaca    480

gaagacgtaa caagtgtgcg tactttagaa gaattacctg aaaatgcacg taaatattta    540

gagcgtattt cagaattatg taatgtacaa atttctatct tctcagtagg tccaggcc      598
```

<210> SEQ ID NO 24
<211> LENGTH: 598
<212> TYPE: DNA
<213> ORGANISM: Staphylococcus epidermidis

<400> SEQUENCE: 24

```
ctcttcgaag gtgctcaagg tgtcatgtta gatatcgacc atggtacata tccattcgtt     60

acatctagta atccagttgc aggtaacgtt acagtaggta caggtgttgg ccctacatca    120
```

-continued

```
gtgtctaaag tgattggtgt atgtaaatca tatacatctc gtgtaggtga cggtccattc    180

ccaactgaac tttttgatga agatggccac catattagag aagtgggtcg tgaatatggt    240

acaactactg gacgtccacg tcgtgtaggt tggttcgact cagttgtatt acgtcattca    300

cgtcgtgtaa gtggtatcac agatctttca attaactcaa tcgacgtttt aacaggatta    360

gacacagtta aaatttgtac tgcttacgaa ttagatggtg aaaaaattac tgaataccca    420

gcaaacttag atcaattaag acgttgtaaa cctatcttcg aagagcttcc aggttggact    480

gaagacatta caggttgtcg tagtttagat gaacttcctg agaatgcacg taattactta    540

gagcgtattt cagaattatg cggtgtccat atttcaatct tctcagtagg tcctggtc      598
```

```
<210> SEQ ID NO 25
<211> LENGTH: 567
<212> TYPE: DNA
<213> ORGANISM: Streptococcus mitis
<220> FEATURE:
<221> NAME/KEY: misc_feature
<222> LOCATION: (11)..(11)
<223> OTHER INFORMATION: n is a, c, g, or t

<400> SEQUENCE: 25

tatggctagc natagaccaa ggtacgtatc catttgttac gtcatcaaac cctgtggctg     60

gtggtgttac gattggttct ggtgttggtc caagtaagat tgacaaggtt gtaggtttat    120

gtaaagccta tacgagtcga gtaggagacg gtcctttccc aactgaattg tttgatgaag    180

tgggagaacg tatccgtgaa gttggtcatg aatatggtac aacaactggt cgtccacgtc    240

gtgtgggttg gtttgactca gttgtgatgc gtcatagtcg tcgtgtttct ggtattacta    300

atctttcatt gaactctatc gatgttttga gtggtttaga tacagtgaaa atctgtgtgg    360

cctatgatct tgatggtcaa cgtattgact actatccagc tagtcttgag caattgaaac    420

gttgcaagcc tatctatgaa gagttgccag gttggtcaga agatattact ggagttcgta    480

atttggaaga tcttcctgag aatgcgcgta actatgttcg tcgtgtgagt gaattggttg    540

gcgttcgtat ttctactttc tcagtag                                        567
```

```
<210> SEQ ID NO 26
<211> LENGTH: 572
<212> TYPE: DNA
<213> ORGANISM: Streptococcus species

<400> SEQUENCE: 26

atggcttgct attgaccaag ggtacatacc catttgtaac atcatctaac ccagtcgctg     60

gtggtgtaac aatcggttct ggtgttggtc caagtaaaat caacaaagtt gtcggtgtat    120

gtaaagccta cacaagccgt gttggtgacg gaccattccc aactgaactt ttagacgaag    180

ttggtgaccg catccgtgaa gtgggtcacg aatatgggac aacaactgga cgtccacgtc    240

gtgttggttg gtttgactca gttgttatgc gtcacagccg ccgcgtatca ggtatcacaa    300

acttgtcact taactcaatt gacgttcttt caggtcttga tacggtcaaa atctgtgtgg    360

catacgacct tgacggtcaa cgtatcgacc actacccagc aagccttgaa caattgaaac    420

gttgtaaacc aatctacgaa gaattgccag gttggtcaga agacatcaca ggttgccgta    480

gcctagatga acttcccgaa aatgctcgtg actacgttcg ccgtgttggt gaactcgttg    540

gtgttcgcat ttcaacattc tcagttggcc cc                                   572
```

```
<210> SEQ ID NO 27
<211> LENGTH: 571
```

-continued

<212> TYPE: DNA
<213> ORGANISM: Streptococcus canis
<220> FEATURE:
<221> NAME/KEY: misc_feature
<222> LOCATION: (9)..(9)
<223> OTHER INFORMATION: n is a, c, g, or t

<400> SEQUENCE: 27
tggcttgcna tcgaccaagg taacttaccc atttgttact tcttcaaacc cagttgctgg 60
tggggtaaca atcggttcag gtgttggtcc aagcaagatc aataaagttg tcggtgtatg 120
taaagcttac acaagccgtg ttggtgacgg tccgttccca acagaacttc tagatgaagt 180
tggagatcgt atccgtgaaa ttggtcacga atatggtaca acaactggac gtccacgtcg 240
tgttggttgg tttgactcag ttgttatgcg tcacagccgc cgcgtatcag gtatcacaaa 300
cttgtcactt aactcaatcg atgttctttc aggacttgat actgttaaaa tctgtgtggc 360
atacgacctt gacggtcaac gtatcgacca ctacccagca agtcttgaac aattgaaacg 420
ttgtaaacca atctacgaag aattgccagg ttggtcagaa gacatcacag gttgccgtag 480
cctagatgaa cttcccgaaa atgctcgtga ctacgttcgc cgtgttggtg aactcgttgg 540
tgttcgcatt tcaacattct cagttggccc c 571

<210> SEQ ID NO 28
<211> LENGTH: 573
<212> TYPE: DNA
<213> ORGANISM: Streptococcus mutans
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t

<400> SEQUENCE: 28
tatggcttgc nattgaccaa ggtaacctat ccatttgtaa cttcatcaaa tccagttgca 60
ggtggcgtta ccatcggatc tggtgttgga ccaagtaaaa tcaataaggt tgttggtgtc 120
tgcaaagcct ataccagccg tgtaggtgat ggtcctttcc ccacagaact ttttgaccaa 180
acgggagagc gcattcgtga agttgggcat gaatacggga caacaacagg gcgtccgcgt 240
cgagttggtt ggtttgactc agttgttatg cgtcacagcc gccgtgtatc aggcattacc 300
aatttatctc ttaactgtat tgatgtactt tcaggtcttg atatcgtaaa aatctgtgta 360
gcctatgatt tggatggaaa acggattgat cactaccctg ccagtctcga acaactcaaa 420
cgctgtaaac ctatttatga agaattgccg ggctggtctg aagatattac aggggttcgc 480
agtttagaag atcttcctga aaatgctcgt aattatgtcc gccgtgtaag tgaattagtt 540
ggtgttcgta tttctacttt ctcagtngtc ccc 573

<210> SEQ ID NO 29
<211> LENGTH: 572
<212> TYPE: DNA
<213> ORGANISM: Streptococcus gordonii

<400> SEQUENCE: 29
taatgctagc aattgaccaa ggtacctatc catttgtaac ctcatctaat ccagttgctg 60
gtggtgtaac gatcggttct ggtgtgggtc ctagcaagat tgacaaagta gtgggtgttt 120
gtaaagccta tacaagtcgt gttggtgatg gtcctttccc aacagagctt ttcgatgaag 180

-continued

```
taggtgaccg cattcgtgag gttggtcatg agtatggtac aacaacagga cgtccgcgtc    240

gagttggttg gtttgactct gttgttatgc gccatagccg ccgtgtatct gggattacca    300

atctttcgct taactctatc gatgttttga gcggtctgga tacagtcaag atctgtgtag    360

cctatgattt ggatggccaa agaatcgacc actatccagc tagtttggaa cagcttaaac    420

gttgtaagcc gatttacgaa gagcttcctg gatggtctga agatattact ggcgttcgta    480

agttagaaga tcttccagaa aatgctcgca actatgttcg gcgagtaagc gagttggttg    540

gtgtacgtat ttccaccttc tcagttggcc cc                                  572
```

<210> SEQ ID NO 30
<211> LENGTH: 571
<212> TYPE: DNA
<213> ORGANISM: Bacillus species
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (565)..(565)
<223> OTHER INFORMATION: n is a, c, g, or t

<400> SEQUENCE: 30

```
tatggcttgc aattgacncg gtacgtaccc attcgttaca tcttctaacc cgattgcggg     60

tggtgtaaca gttggaactg gagttggtcc tgcgaaagtt actcgcgttg taggtgtatg    120

taaagcatat acaagccgtg ttggtgacgg tccattccct actgaactta atgatgaaat    180

tggtcatcaa attcgtgaag ttggtcgtga gtacggaaca acaactggtc gtccgcgccg    240

cgtaggttgg ttcgatagcg ttgttgtaag acatgcgcgt cgtgttagtg gtttaacgga    300

tctatcatta aattctatcg acgttttaac agatattccg actcttaaaa tttgtgttgc    360

ttacaaatac aatggcgaag ttatcgatga agttccagca aacttaaaca ttttagcaaa    420

atgtgagcct gtatatgaag agcttccagg ttggacagaa gatattactg gtgtaaaatc    480

attagacgag cttcctgaaa atgcacgaaa atacgtagaa cgtgtttctg agttaacagg    540

aattcaatta tctatgttct cagtngtccc c                                   571
```

<210> SEQ ID NO 31
<211> LENGTH: 574
<212> TYPE: DNA
<213> ORGANISM: Bacillus pumilus
<220> FEATURE:
<221> NAME/KEY: misc_feature
<222> LOCATION: (570)..(570)
<223> OTHER INFORMATION: n is a, c, g, or t

<400> SEQUENCE: 31

```
gttatggctt gctattgatc aagggacata tccatttgtc acgtcatcta acccagtagc     60

tggaggagtg acgattggtt ctggcgtagg accaacaaaa attcaacatg tggtcggcgt    120

gtcaaaagcg tacacaacac gtgttggaga tggcccattc ccgacagaac tccatgatga    180

aattggcgat caaatccgtg aggttggccg tgaatacggt acaacaactg gacgtccgcg    240

ccgtgttggc tggtttgaca gtgtcgttgt ccgtcatgct cgacgtgtga gcgggattac    300

agatctatct cttaactcaa ttgatgtact gacagggatt gaaacattga aaatctgtgt    360

cgcttataaa ttgaacggag aaatcacaga ggaattccca gcaagtctaa atgaactagc    420

gaaatgtgag cctgtctacg aagaaatgcc aggatggaca gaggatatta caggcgtgaa    480

gaatttaagc gaactgcctg aaaatgcccg tcattattta gagcgcattt cacaattaac    540
```

-continued

```
aggtattcca ctttccattt tctcagttgn cccc                              574


<210> SEQ ID NO 32
<211> LENGTH: 560
<212> TYPE: DNA
<213> ORGANISM: Enterococcus villorum
<220> FEATURE:
<221> NAME/KEY: misc_feature
<222> LOCATION: (557)..(557)
<223> OTHER INFORMATION: n is a, c, g, or t

<400> SEQUENCE: 32

tatcgaccag ggacatatcc atttgttact tcttccatcc agtagcaggt ggtgtaacaa   60

ttggtagtgg cgttggtcca tctaaaatta ataaagtcgt cggagtatgt aaagcttata  120

cttctcgtgt tggagatggc ccgttcccta cagaattatt tgatgaaaca gggcaacaaa  180

tacgtgaagt aggtcgtgaa tatggcacaa caacaggtcg tccacgacga gttggatggt  240

ttgatacggt tgttatgcgc cattcaaaac gtgtatcagg tattacaaat ttatctctta  300

attcgattga tgtattaagc ggattagaaa cagtaaaaat ttgtacggcc tatgaactag  360

atggtgagct gatttatcat tacccagcaa gtttgaaaga attgaaacgt tgtaaaccag  420

tatatgaaga actacctgga tggtctgaag atattacgaa atgcaagaca ctttctgaat  480

tgccagaaaa tgcacgtaac tatgtaagac gtatttctga gcttgtaggt gtacgcatct  540

ccacatttct cagtggnccc                                              560


<210> SEQ ID NO 33
<211> LENGTH: 554
<212> TYPE: DNA
<213> ORGANISM: Bacillus thuringiensis serovar israelensis
<220> FEATURE:
<221> NAME/KEY: misc_feature
<222> LOCATION: (2)..(2)
<223> OTHER INFORMATION: n is a, c, g, or t

<400> SEQUENCE: 33

cncggtacgt acccgttcgt tacatcttct aacccgattg cgggtggtgt aacagttgga   60

actggagttg gccctgcgaa agttactcgc gttgtaggtg tatgtaaagc atatacaagc  120

cgtgttggtg acggtccatt ccctactgaa cttaatgatg aaattggtca tcaaattcgt  180

gaagttggtc gtgagtacgg aacaacaact ggtcgtccgc gccgcgtagg ttggttcgat  240

agcgttgttg taagacatgc gcgtcgtgtt agtggtttaa cggatctatc attaaattct  300

atcgacgttc taacagatat tccaactctt aaaatttgtg ttgcttacaa atacaatggc  360

gaagttatcg atgaagttcc agcaaactta aacattttag cgaaatgtga gcctgtatat  420

gaagagcttc caggttggac agaagatatt actggtgtaa aatcattaga cgagcttcct  480

gaaaatgcaa gaaaatacgt agaacgtgtt tctgagttaa caggaattca attatctatg  540

ttctcagtgg cccc                                                    554


<210> SEQ ID NO 34
<211> LENGTH: 552
<212> TYPE: DNA
<213> ORGANISM: Bacillus thuringiensis serovar kurstaki
<220> FEATURE:
<221> NAME/KEY: misc_feature
<222> LOCATION: (547)..(547)
<223> OTHER INFORMATION: n is a, c, g, or t

<400> SEQUENCE: 34
```

-continued ggtcgtatcc attcgttaca tcttctaacc cagttgctgg tggtgtaaca atcggttctg 60
gagttggtcc ttctaaaatc aatcgtgtag taggcgtatg taaagcatat acaagccgtg 120
ttggtgacgg tccattccct actgaactta atgatgaaat tggccatcaa attcgtgaag 180
ttggtcgtga atatggtaca acaacaggtc gtccacgtcg cgtaggttgg tttgacagcg 240
ttgttgtaag acatgcacgc cgtgtgagtg gtttaacaga tttatcttta aactctatcg 300
acgtattaac aggtattcca actgtgaaaa tctgtattgc atataagtat aatggagaag 360
ttctggatga agttccagca aacttaaaca ttttagcaaa atgtgagcct gtatatgaag 420
agcttccagg ttggacagaa gatattactg gtgtaaaatc attagaggag cttcctgaaa 480
atgcaagaca ttatgtagag cgtgtgtctc aattaacagg tatccaatta tctatgttct 540
cagttgnccc cc 552

<210> SEQ ID NO 35
<211> LENGTH: 555
<212> TYPE: DNA
<213> ORGANISM: Bacillus myco?es
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (548)..(548)
<223> OTHER INFORMATION: n is a, c, g, or t

<400> SEQUENCE: 35
ggtncgtacc cattcgttac atcttctaac ccgattgctg gtggtgtaac agttggaact 60
ggagttggtc ctgcgaaagt tactcgcgtt gtaggtgtat gtaaagcata tacaagccgt 120
gtaggtgatg gtccgttccc tactgagctt catgatgaaa ttggtcatca aattcgtgaa 180
gttggtcgtg aatacggaac aacaactggt cgtccacgcc gcgtaggttg gttcgatagc 240
gttgttgtaa gacatgcacg tcgtgttagt ggtttaacag atctatcatt aaattctatc 300
gacgttctaa caggtattcc aactcttaaa atttgtgttg cttacaaata caatggcgaa 360
gttatcgatg aagttccagc aaacttaaac attttagcga aatgtgagcc tgtatatgaa 420
gagcttccag gttggacaga agatattact ggtgtaagag cattagacga gcttcctgaa 480
aatgcacgaa aatacgtaga acgtgtttct gagttaacag gaattcaatt atctatgttc 540
tcagtggncc cccgg 555

<210> SEQ ID NO 36
<211> LENGTH: 546
<212> TYPE: DNA
<213> ORGANISM: Bacillus myco?es
<220> FEATURE:
<221> NAME/KEY: misc_feature
<222> LOCATION: (5)..(5)
<223> OTHER INFORMATION: n is a, c, g, or t

<400> SEQUENCE: 36
cggtncgtac ccgttcgtta catcttctaa cccgattgct ggtggtgtaa cagttggaac 60
tggagttggt cctgcgaaag ttactcgcgt tgtaggtgtg tgtaaagcat atacaagccg 120
tgtaggtgat ggtccattcc ctactgagct tcatgatgaa attggtcatc aaattcgtga 180
agttggtcgt gagtatggaa cgacaactgg tcgtccacgc cgcgtaggtt ggttcgatag 240
cgttgttgta agacatgcac gtcgtgttag tggtttaaca gatttatcat taaattctat 300
cgacgttcta acaggtattc caactcttaa aatttgtgtt gcttacaaat acaatggcga 360

-continued

```
agttatcgat gaagttccag caaacttaaa catcttagcg aaatgtgagc ctgtatatga    420

agagcttcca ggttgggaag aagatattac tggtgtaaaa tcattagacg aacttcctga    480

aaatgcaaga aaatacgtag agcgtgtttc tgaattaaca ggaatccaat tatctatgtt    540

ctcagt                                                               546


<210> SEQ ID NO 37
<211> LENGTH: 581
<212> TYPE: DNA
<213> ORGANISM: Bacillus weihenstephanensis
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (473)..(473)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (576)..(577)
<223> OTHER INFORMATION: n is a, c, g, or t

<400> SEQUENCE: 37

tttttttngg aagngcgcaa ggtgttatgc ttgatatcga ccacggtacg tacccgttcg     60

ttacatcttc taacccaatt gctggtggtg taacagttgg aactggagtt ggtcctgcga    120

aagttactcg cgttgtaggt gtatgtaaag catatacaag ccgtgttggt gatggtccat    180

tccctactga acttaatgat gaaatcggtc accaaattcg tgaagttggt cgtgaatacg    240

gaacaacaac gggtcgtcca cgccgtgtag gttggttcga tagcgttgtt gtaagacatg    300

cacgtcgtgt tagtggttta acagatttat cattaaactc tatcgatgta ttaacaggta    360

ttccaactgt taaaatttgt gttgcttaca aatgcaatgg cgaagttatc gatgaagttc    420

cagctaactt aaacatttta gcgaaatgtg agcctgtata tgaagagctt ccnggttgga    480

cagaagatgt tactgctgtg aaatcattgg atgagcttcc tgaaaatgca agaaaatacg    540

tagagcgtgt tttctgaatt aacnggaagc caattnncaa g                        581


<210> SEQ ID NO 38
<211> LENGTH: 572
<212> TYPE: DNA
<213> ORGANISM: Staphylococcus haemolyticus

<400> SEQUENCE: 38

caaggtgtca tgttagatat cgaccatggt acatatcctt tcgtaacttc aagtaaccct     60

gttgcaggta atgtaacagt tggtacaggt gtaggcccaa ctttcgtatc taaagtgatt    120

ggtgtatgta aagcatatac atctcgtgta ggcgatggtc cattccctac agaattattt    180

gatgaaaatg gacatcatat tagagaagtt ggtcgtgaat acggtacaac aacaggacgt    240

ccacgtcgtg taggttggtt tgactcagtt gtattacgtc actctcgtcg tgttagtggt    300

attacagact tatctattaa ctctatcgac gtacttacag gtcttgatac agtgaagatt    360

tgtactgctt acgaattaga tggagaagaa attacagaat atcctgctaa cttagatcaa    420
```

-continued

```
ttacgtcgtt gtaaaccaat ctttgaagag ttaccaggat gggaagaaga tatcactggt    480

tgccgtacat tagaagaatt accagataac gcacgtaaat acttagaacg catttctgaa    540

ttatgtaatg tacgtatttc aatcttctca gt                                  572
```

<210> SEQ ID NO 39
<211> LENGTH: 578
<212> TYPE: DNA
<213> ORGANISM: Staphylococcus saprophyticus

<400> SEQUENCE: 39

```
gcaaggtgtg atgttagata tcgaccatgg tacatatcca ttcgttcatc aagtaaccca     60

gttgcaggta atgtgactgt cggtggcggt gtaggtccaa cattcgtctc taaagttatc    120

ggtgtgtgta aagcctatac atcacgtgtc ggcgatggtc cattcccaac agaactattt    180

gacgaagatg ggcaccacat ccgtgaagta ggtcgtgaat acggtacaac aacaggacgt    240

ccacgtcgtg taggttggtt cgactcagtt gtattacgtc attctcgtcg tgcaagtggt    300

attacagatt tatctattaa ctcaattgat gtattaacag gccttaaaga agttaaaatc    360

tgtactgctt atgagttaga cggtaaagaa attacggaat acccagctaa cttgaaagac    420

ttacaacgtt gtaagccaat ttttgaaaca ttaccaggtt ggacagaaga tgtgacaggt    480

tgtcgttcat tagaagaatt acctaataat gcgcgtagat acttagaacg tatttctgaa    540

ttatgtgacg tgaagatttc aatcttctca gttggccc                            578
```

<210> SEQ ID NO 40
<211> LENGTH: 583
<212> TYPE: DNA
<213> ORGANISM: Bacillus subtilis
<220> FEATURE:
<221> NAME/KEY: misc_feature
<222> LOCATION: (542)..(542)
<223> OTHER INFORMATION: n is a, c, g, or t

<400> SEQUENCE: 40

```
ctcaaggggt tatgcttgat attgaccaag ggacataccc gtttgtcact tcatccaacc     60

cggtcgccgg aggggtgacg atcggttcag gcgtaggccc gacaaaaatc cagcacgtcg    120

tcggtgtatc taaagcgtac acaacccgtg tcggtgacgg tcctttcccg actgagctga    180

aagatgaaac cggggatcaa atccgtgaag tcggacgcga atacggcaca acgacaggcc    240

gtccgcgccg tgtcggctgg tttgacagcg ttgttgtccg ccatgcccgc cgcgtcagcg    300

gaatcacaga tctttctctg aactcaatcg atgtgctgac tggcattgaa acattgaaaa    360

tctgtgtcgc ttaccgctac aaaggtgaag tgattgaaga attcccggca agtctgaaag    420

ctctcgcaga gtgtgaaccg gtatatgaag aaatgcctgg ctggacggaa gatatcacag    480

gcgcaaaaac attaagcgat cttcctgaaa atgcgcgcca ttatctggaa cgcgtgtctc    540

anctgacagg tattccgctt tctattttct cagtaggtcc aga                      583
```

<210> SEQ ID NO 41
<211> LENGTH: 598
<212> TYPE: DNA
<213> ORGANISM: Listeria monocytogenes

<400> SEQUENCE: 41

```
tttggaaggg gcgcaagggg ttatgcttga tattgatcaa ggaacatatc catttgtaac     60

ttcaagtaac ccgattgctg gtggcgtaac tatcggtagt ggtgttggtc cttcaaaaat    120

caatcatgtt gttggtgtgg cgaaagctta tacaacacgt gttggtgatg gtcctttccc    180
```

aacagaatta tttgattcta ttggtgacac tattcgtgaa gtcggtcatg aatatggtac 240
aacgactggt cgtccgcgtc gtgtaggttg gtttgatagc gtagtggttc gtcatgcgcg 300
tcgtgttagt ggattaacag atttatcgtt aacactactt gatgttttga caggaattga 360
gacacttaaa atctgtgtag cttacaaatt agacggaaaa acaattacag agttcccagc 420
aagtttgaaa gatttagctc gttgcgaacc tgtttatgaa gaacttccag gctggacgga 480
agatattact ggagttacat cactagatga tcttccagtg aactgccgcc attacatgga 540
gcgtatcgcc caacttacgg gagtgcaagt ttctatgttc tcagtaggtc ccagacca 598

<210> SEQ ID NO 42
<211> LENGTH: 573
<212> TYPE: DNA
<213> ORGANISM: Lactococcus lactis
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t

<400> SEQUENCE: 42
tnatgcttga tattgacnag gaacataccc atttgtaact tctcaaaccc agtagctggt 60
ggggtaacga ttggctctgg tgtgggtcca tcaaaaattt caaaagttgt tggtgtttgt 120
aaagcctata cttcacgtgt gggtgatggt ccattcccaa cagaactttt tgatgaagtt 180
ggacatcaaa ttcgtgaagt aggacatgaa tatggaacaa caacaggacg tccacgtcgt 240
gttggttggt ttgactcagt cgtaatgcgt catgcaaaac gtgtttctgg cttgacaaat 300
cttagcttga attcaattga cgttctctca ggacttgaaa cagtaaaaat ttgtgttgct 360
tacgaacgta gtaatggtga acaaattact cattatccag catcacttaa ggaattagca 420
gattgcaaac caatctatga agaattgcca ggatggtctg aagatattac ttcatgccga 480
actttagaag agttaccaga agctgctcgt aactatgttc gtcgggttgg tgaactagtt 540
ggcgtacgta tctcgacttt ctcagtngtc ccc 573

<210> SEQ ID NO 43
<211> LENGTH: 599
<212> TYPE: DNA
<213> ORGANISM: Enterococcus hirae
<220> FEATURE:
<221> NAME/KEY: misc_feature
<222> LOCATION: (551)..(551)
<223> OTHER INFORMATION: n is a, c, g, or t

<400> SEQUENCE: 43
ctttttgaag gggcgcaagg ggtaatgcta gatattgacc aaggtaccta tccatttgta 60
acctcatcta atccagttgc tggtggtgta acgatcggtt ctggtgtggg tcctagcaag 120
attgacaaag tagtgggtgt ttgtaaagcc tatacaagtc gtgttggtga tggtcctttc 180
ccaacagagc ttttcgatga agtaggtgac cgcattcgtg aggttggtca tgagtatggt 240
acaacaacag gacgtccgcg tcgagttggt tggtttgact ctgttgttat gcgccatagc 300
cgccgtgtat ctgggattac caatctttcg cttaactcta tcgatgtgtt gagcggtctg 360

-continued gatacagtca agatctgtgt agcctatgat ttggatggcc aaagaatcga ccactatcca 420
gctagtttgg aacagcttaa acgttgtaag ccgatttacg aagagcttcc tggatggtct 480
gaagatatta ctggcgttcg taagttagaa gatcttccag aaaatgctcg caactatgtt 540
cggcgagtaa ncgagttggt tggtgtacgt atttccacct tctcagtagg tccagacca 599

<210> SEQ ID NO 44
<211> LENGTH: 505
<212> TYPE: DNA
<213> ORGANISM: Enterococcus avium

<400> SEQUENCE: 44
cttttcgaag gtgcgcaagg tgtaatgctg gatattgatc aagggactta tccatttgtt 60
acctcttcta atccggttgc cggcggtgtc acgatcggta gcggtgttgg accatcgaag 120
attgataaag tcgtaggggt atgtaaagct tatacatcac gcgttggtga tggacctttt 180
ccaacggaat tatttgacga agtcggcgat cagatccgcg aagttggtcg tgaatatgga 240
acaacaactg gccgtccacg tcgagttggc tggtttgact ctgtggttat gcggcactca 300
aaacgcgctt ctgggattac caatctatct ttgaactcaa tcgatgtgtt gagcggcttg 360
gaaacggtca agatttgtac cgcttatgag ttagacggag aattaatcta tcattatcca 420
gcaagcttaa aggaattgaa tcgctgcaaa ccagtttatg aagagctacc tggctggagt 480
aaggatatta ctggctgtcg tgatt 505

<210> SEQ ID NO 45
<211> LENGTH: 598
<212> TYPE: DNA
<213> ORGANISM: Streptococcus bovis

<400> SEQUENCE: 45
tttttgaagg ggctcaaggt gtcatgcttg atattgacca aggtacatac ccatttgtta 60
catcttcaaa cccagttgct ggtggtgtaa ctatcggttc aggtgttggt ccaagcaaga 120
tcaacaaagt tgttggtgta tgtaaagcct acacaagtcg tgttggtgat ggtccattcc 180
caacagaact tctagacgaa gttggagatc gtatccgtga aatcggtcac gaatatggta 240
caacaacagg acgtccacgt cgtgttggat ggtttgactc agttgtaatg cgtcacagcc 300
gtcgcgtatc aggtatcaca aacttgtcac ttaactcaat cgacgttctt tcaggacttg 360
atactgttaa ggtctgtgtg gcttacgacc ttgatggcca acgtatcgac cactatccag 420
caagtcttga acaattgaaa cgttgtaaac caatctacga agaattgcca ggttggtcag 480
aagacatcac aggctgccgt agcctagatg agcttccaga aaatgctcgt aactatgttc 540
gtcgtgttgg tgaacttgtt ggtgttcgca tttcaacatt ctcagttggt ccaggcca 598

<210> SEQ ID NO 46
<211> LENGTH: 598
<212> TYPE: DNA
<213> ORGANISM: Streptococcus thermophilus
<220> FEATURE:
<221> NAME/KEY: misc_feature
<222> LOCATION: (508)..(508)
<223> OTHER INFORMATION: n is a, c, g, or t
<220> FEATURE:
<221> NAME/KEY: misc_feature
<222> LOCATION: (569)..(569)
<223> OTHER INFORMATION: n is a, c, g, or t
<220> FEATURE:
<221> NAME/KEY: misc_feature
<222> LOCATION: (593)..(594)
<223> OTHER INFORMATION: n is a, c, g, or t -continued

<400> SEQUENCE: 46
ctatttgaag gtgcgcaagg agttatgctt gatattgacc aaggaacata cccatttgta 60
acgtcatcaa acccagttgc tggtggtgtt acaattggtt ctggtgttgg gccatctaaa 120
attaataagg ttgtgggtgt atgtaaggcc tatacaagtc gtgtcggcga tggtcctttc 180
ccaactgagt tgtttgatga agtgggtgaa cgtatccgtg aagttggcca tgaatatgga 240
acaacaactg gacgtccacg tcgtgtggga tggtttgact cagtggtaat gcgtcatagc 300
cgtcgtgtat caggtattac aaaccttagc ttgaactgta tcgacgttct ttctggtctt 360
gatactgtga aaatttgtgt agcctacgat cttgatggtg agcgcattga ttactatccg 420
gctagccttg agcaattgaa acgttgtaaa ccaatttatg aagaattgcc aggttgggaa 480
gaggatatta caggttgccg tagtttanat gagcttcctg aaaatgcccg taattatgtt 540
cgtcgtattg gtgagttggt cggtatacnt atctctacct tctcagtagg ccnnacca 598

<210> SEQ ID NO 47
<211> LENGTH: 591
<212> TYPE: DNA
<213> ORGANISM: Streptococcus suis

<400> SEQUENCE: 47
cgaaggacgc aaggagttat gttggatatg accaaggtac ctatccattc gttacttctt 60
caaacccagt tgctggtggt gtgacgatcg gtagcggtgt cggcccaagc aagattgaca 120
aggttgttgg tgtatgtaag gcctacacta gccgtgttgg tgacggacca tttccgactg 180
aattgcacga tgaaatcgga gaccgtatcc gcgaaatcgg taaagagtac ggtacgacaa 240
ctggccgtcc acgccgtgtc ggttggtttg actcagtggt gatgcgccat agccgccgtg 300
tgtcaggtat taccaacttg tccctcaact cgattgacgt cttgtcaggt cttgggacct 360
tgaaaatctg cgtggcttat gacttggatg gtgagcgtat tgaccactac ccagcaagtt 420
tggagcaact caaacgttgc aaaccaatct acgaagaaat gccaggttgg tctgaagaca 480
tcacaggtgt acgtagcctg gatgaattgc cagaagcggc tcgcaactat gttcgtcgta 540
tcagcgaatt ggtaggcgtt cgtatctcaa ccttctcagt aggtccagac c 591

<210> SEQ ID NO 48
<211> LENGTH: 599
<212> TYPE: DNA
<213> ORGANISM: Bacillus pseudomyco?es
<220> FEATURE:
<221> NAME/KEY: misc_feature
<222> LOCATION: (594)..(594)
<223> OTHER INFORMATION: n is a, c, g, or t

<400> SEQUENCE: 48
ctatttgaag gggcgcaagg cgtaatgctt gatattgatc aaggtacgta tccattcgtt 60
acatcttcta acccagttgc tggtggtgta acaatcggtt ctggagttgg tccttctaaa 120
atcaatcgtg tagtaggcgt atgtaaagca tatacaagcc gtgttggtga cggtccattc 180
cctactgaac ttaatgatga aattggccat caaattcgtg aagttggtcg tgaatatggt 240
acaacaacag gtcgtccacg tcgcgtaggt tggtttgaca gcgttgttgt aagacatgca 300
cgccgtgtga gtggtttaac agatttatct ttaaactcta tcgacgtatt aacaggtatt 360
ccaactgtga aaatctgtat tgcatataag tataatggag aagttctgga tgaagttcca 420
gcaaacttaa acattttagc aaaatgtgag cctgtatatg aagagcttcc aggttggaca 480

-continued

```
gaagatatta ctggtgtaaa atcattagag gagcttcctg aaaatgcaag acattatgta    540

gagcgtgtgt ctcaattaac aggtatccaa ttatctatgt tctcagtagg gccngacca     599


<210> SEQ ID NO 49
<211> LENGTH: 604
<212> TYPE: DNA
<213> ORGANISM: Staphylococcus capitis capitis
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (530)..(530)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t

<400> SEQUENCE: 49

ctcttcgagg agctcaaggt gtcatgttag acatcgacca tggtacttac ccattcgtta     60

cgtcaagtaa cccagttgct ggtaatgtca cagtaggtac aggtgtaggt cctacatcag    120

tttctaaagt catcggtgta tgtaaatcat atacgtcacg tgtaggtgat ggtccattcc    180

ccacagaatt attcgatgaa gatggtcatc acattagaga agtaggtcgt gaatatggta    240

caacaacagg acgtccacgc cgtgtaggtt ggtttgactc agtggtacta cgtcattcac    300

gtcgcgtaag tggtatcaca gatctttcaa tcaactctat cgacgtttta acaggtttag    360

atacagttaa aatttgtaca gcatatgagt tagatggcga agaaatcact gaatacccag    420

ctaacttaga tcaattaaga cgctgtaaac caatcttcga agaacttcca ggttggacag    480

aagatatcac agggctgccg cagtttagaa gaactccctg aaaatgcncn ccaaatacct    540

agagcgtatt tcaaaattat gtggcgtacn catttcaatc cttctcagta ggggccctga    600

cccc                                                                 604


<210> SEQ ID NO 50
<211> LENGTH: 597
<212> TYPE: DNA
<213> ORGANISM: Staphylococcus sciuri
<220> FEATURE:
<221> NAME/KEY: misc_feature
<222> LOCATION: (563)..(563)
<223> OTHER INFORMATION: n is a, c, g, or t
<220> FEATURE:
<221> NAME/KEY: misc_feature
<222> LOCATION: (571)..(571)
<223> OTHER INFORMATION: n is a, c, g, or t

<400> SEQUENCE: 50

ctttttgaag gtgcgcaagg tgttatgtta gatatcgacc acggtacata tccattcgtt     60

acttcaagta atccaattgc aggtaacgtt acagtaggtg gcggtgttgg tccaacatac    120

gtatctaaag taattggtgt atgtaaagct tatacatctc gtgtaggaga cggtccattc    180

ccaacagaat tatttgatga agatggtcac catatccgtg aagtaggtcg tgaatacggt    240

acaacaactg gaagaccacg tcgtgtaggt tggtttgact cagtagttct acgtcactca    300

cgccgtgtaa gtggtattac agatttatca atcaactcaa ttgacgtatt aacaggatta    360

aaaacagtta aaatctgtac agcatacgaa attgatggtg ttgaaatcac tgaatatcca    420

gcaaacttaa acgaattaga acgttgtaaa ccaatctttg aagaactacc aggttgggaa    480

gaagacatta caggatgccg ttcactagaa gaattaccag ataacgcacg tcgtttttta    540
```

-continued aaacgcatct ctgaattatg tancgttaaa nttctatctt ctcagtaggt ccaggtc 597

<210> SEQ ID NO 51
<211> LENGTH: 605
<212> TYPE: DNA
<213> ORGANISM: Staphylococcus warneri

<400> SEQUENCE: 51 cttttgaag gagcgcaagg tgtgatgtta gacatcgacc acggtacata tccattcgtc 60
acttcaagta acccagtagc aggtaacgtt actgtaggta ctggtgtagg tccaacatac 120
gtatcaaaag tcattggtgt atgtaaagct tatacatcac gtgttggtga tggtccattc 180
cctacagaat tatttgatga agatggtcat cacattagag aagttggtcg tgaatacggt 240
acaacaactg gtcgtccacg tcgtgtaggt tggttcgact cagtagtatt acgtcattca 300
cgccgtgtaa gtggtattac agacttatca atcaactcaa ttgatgtgtt aactggctta 360
gatacagtta aaatctgtac agcatatgaa ttagatggta aagaaattac tgaatatcca 420
gctaacctag atcaattaca acgttgtaaa ccaatcttcg aagaattacc tggttggaca 480
gaagatatta caggttgccg tactttagaa gagcttcctg aaaatgcacg caaatattta 540
gaacgtattt ctgaattatg tggcgtacgt atttcaatct tctcagttgg tcctggccag 600
ggcga 605

<210> SEQ ID NO 52
<211> LENGTH: 599
<212> TYPE: DNA
<213> ORGANISM: Staphylococcus lugdunensis

<400> SEQUENCE: 52
ttctttgaag gagctcaagg tgttatgtta gatattgatc atggtacata tcctttcgtc 60
acatcaagca atcctgtagc cggcaatgtc actgttggta caggtgtagg tccaaccttc 120
gtttctaaag taattggtgt gtgtaaagca tacacatctc gcgtaggcga tggtcctttc 180
ccaactgaac tatttgatga agatgggcac catattagag aggttggtcg tgaatatggt 240
acgacgacag gacgtccacg tcgcgtgggt tggtttgatt cagtcgtgct acgtcactca 300
cgtcgtgtta gtggtattac agacttatct attaactcta ttgatgtact aacaggttta 360
gatacggtaa aaatttgtac agcttatgag ttagatggag aagaaattac ggagtatcca 420
gctaaccttg atcaattaaa acgttgtaaa ccaatctttg aagaattacc tggttggaca 480
gaagatatta caggctgtcg ttcattagaa gcattgcctg ataatgcacg tcgctattta 540
gaacgtattt cagaattatg cggcgttcat atttcaattt tctcagtagg gccagacca 599

<210> SEQ ID NO 53
<211> LENGTH: 599
<212> TYPE: DNA
<213> ORGANISM: Staphylococcus gallinarum

<400> SEQUENCE: 53
ctttttgaag gtgcgcaagg cgttatgtta gatatcgacc atggtacata cccatttgtt 60
acttctagta atccagttgc aggtaacgta actgtaggtg gcggtgttgg accaacattc 120
gtatcaaaag taattggcgt atgtaaagcc tatacatcac gtgttggtga cggcccattc 180
ccaactgaat tatttgatga agatggacat catatccgtg aagttggccg cgaatatggt 240
acaacaacag gacgtccacg tcgtgtgggt tggtttgact ctgttgtatt acgtcattca 300

-continued

```
cgccgtgcaa gtggtatcac agatttatct atcaactcta ttgacgtatt aacaggtctt    360

gaaaatgtta agatttgtac tgcatacgaa ttagatggag aagaaatcac tgaataccca    420

gcaaacttaa aggacttaca acgttgtaaa ccaatctttg aaacattacc aggttggaca    480

gaagatgtca caagctgtcg ttcactagat gaattaccag ataatgcacg cagatattta    540

gagcgcattt ctgaaccatg taacgtgaag atttcaatct tctcagtagg gccagacca     599
```

<210> SEQ ID NO 54
<211> LENGTH: 600
<212> TYPE: DNA
<213> ORGANISM: Staphylococcus schleiferi schleiferi

<400> SEQUENCE: 54

```
gacctggacc aactgagaag atagaaatat ggacgttaca taattctgaa atacgctcta     60

agtaacggcg tgcattttgt ggtagttcgt ctaaactacg tacacctgta atatcttcag    120

tccaacctgg taatgtttca aagataggtt tacaacgttt taagtcgttt aagtttgctg    180

ggtattccgt aatctctttt ccatctaatt cataagctgt acagatttta acctcttcta    240

agccagttaa gacgtcgata gagttgattg ataaatctgt aatcccactt acacgacgag    300

agtgacgtaa tacaacggag tcaaaccaac ctacacggcg tggacgacct gttgttgtgc    360

catattcacg tccgatttca cgaatatggt gcccttgttc atcaaataat tctgttggga    420

atggcccatc acctacacgt gaagtgtatg ctttacatac gccaactact tttgatacat    480

ttgttggccc tacaccagca ccaactgtca cgttacccgc tacagggtta cttgatgtta    540

caaaaggata tgttccgtga tcgatgtctg acatcacccc cttgagcccc ttcaaagaga    600
```

<210> SEQ ID NO 55
<211> LENGTH: 599
<212> TYPE: DNA
<213> ORGANISM: Staphylococcus capitis ureolyticus

<400> SEQUENCE: 55

```
gaccaggccc aactgagaag attgaaatgt gtacgccaca taattctgaa atacgctcta     60

ggtatttgcg tgcattttca gggagttctt ctagactgcg acaacctgtg atatcttctg    120

tccaacctgg aagttcttcg aagattggtt tacagcgtct taattgatct aagttagctg    180

ggtattcagt gatttcttcg ccatctaact catatgctgt acaaatttta actgtatcta    240

aacctgttaa aacgtcgata gagttgattg aaagatctgt gataccactt acgcgacgtg    300

aatgacgtaa tactactgag tcgaaccaac ctacacggcg tggacgtcct gttgttgtac    360

catattcacg acctacttct ctaatgtgat gaccatcttc atcgaataat tctgtaggga    420

atggaccatc acctacacgt gacgtatatg atttacatac accgatgact ttagaaactg    480

atgtaggacc tacacctgta cctactgtga cattaccagc aactgggtta cttgacgtaa    540

cgaatggata tgtaccgtgg tcgatgtcta acatgacacc ttgcgcacct tcaaataaa     599
```

<210> SEQ ID NO 56
<211> LENGTH: 599
<212> TYPE: DNA
<213> ORGANISM: Staphylococcus cohnii urealyticum

<400> SEQUENCE: 56

```
ctcgttgaag gtgcacaagg cgttatgtta gatatcgacc acggtacata cccattcgtt     60

acgtcaagta acccagttgc aggtaatgtc actgtcggtg gtggtgttgg tccaacatac    120

gtatctaaag tcattggcgt atgtaaagct tatacatcac gtgtcggtga tggcccattc    180
```

-continued ccaacagaac tatttgatga tgatggacac cacatccgtg aaattggccg tgagtacggt 240
acaactactg gacgtccacg tcgtgtaggt tggttcgatt cagttgtatt acgtcactct 300
cgtcgtgcga gtggtattac tgatttatca atcaactcta tcgatgtctt aacaggcctt 360
aaagaagtga agatttgtac ggcgtatgaa ttggacggta aagaaattac tgaatatcca 420
gcgaatttaa aagacttaca acgttgtaag ccaatctttg aaacattacc tggttggaca 480
gaagatgtta caggttgtcg ctcattagat gagctgccag acaatgcacg tagatattta 540
gaacgtatct ctgaattatg tgacgttcaa atttcaatct tctcagtagg gcctgacca 599

<210> SEQ ID NO 57
<211> LENGTH: 599
<212> TYPE: DNA
<213> ORGANISM: Staphylococcus xylosus

<400> SEQUENCE: 57
ctttttgaag gtgctcaagg tgtaatgcta gatatcgatc atggtactta cccattcgtt 60
acttcaagta acccagttgc cggtaacgtt actgttggtg gcggtgtagg tccaacattc 120
gtatctaaag tcattggtgt atgtaaggca tatacatcac gtgtaggcga tggtcctttc 180
ccaactgaac tatttgatga tgacgggcac catatccgtg aagtaggtcg tgaatacggt 240
acaactacag gtcgtccacg ccgtgtaggt tggttcgatt cagttgtatt acgtcactct 300
cgccgtgcga gtggtattac agacctatca atcaactcta ttgatgtgtt aacaggtcta 360
aaagaagtta aaatctgtac tgcctatgag ttagacggta aagaaatcac tgaatatcca 420
gcaaacttga aagacttaca acgttgtaag ccaatctttg aaacattgcc tggttggaca 480
gaagatgtaa ctggttgtca atcattagat gaattacctg ataatgcacg tagatactta 540
gaacgtatat ctgaactaag tgatgttaag atttctatct tctcagtagg gccagatca 599

<210> SEQ ID NO 58
<211> LENGTH: 599
<212> TYPE: DNA
<213> ORGANISM: Staphylococcus simulans

<400> SEQUENCE: 58
ctatttgaag gagcgcaagg ggttatgtta gacatcgacc atggtacata cccattcgtt 60
acatcaagta acccgattgc tggtaacgtt actgtcggcg gcggtatcgg accaacatca 120
gtatctaaag taatcggtgt atgtaaagcg tatacgtcac gtgtaggtga tggtccattc 180
cctactgaat tattcgatga agatggtcat catatccgtg aagtaggtcg tgaatatggt 240
acaactacag gacgcccacg tcgtgtcggc tggttcgact cagtggtatt acgtcattca 300
cgtcgtgtaa gtggtattac tgacttatct atcaactcaa tcgacgtttt aactggttta 360
gatacagtta aaatctgtgt tgcgtatgag ttagatggtg aagaaatcac tgaataccca 420
gcaaacttaa acgcgttgaa ccgttgtaaa ccaatttacg aagaattacc aggttggtct 480
gaagatatta caggcgtaca atcattagaa gaattaccag ataacgcacg tcgttactta 540
gaacgtattt ctgagttatg taacgtaggt atctcaatct tctcagttgg tccaggtca 599

<210> SEQ ID NO 59
<211> LENGTH: 598
<212> TYPE: DNA
<213> ORGANISM: Staphylococcus cohnii cohnii

<400> SEQUENCE: 59

-continued

```
tatttgaagg tgcacaagga gtaatgcttg atatcgatca tggtacttat ccgttcgtca     60

cttcaagtaa cccgattgcc ggtaacgtaa cagttggtac tggtgtaggt ccaacgtttg    120

tagataaagt tgttggtgta tgtaaagctt acacatcacg tgtaggggat ggaccattcc    180

caactgaatt atttgatgaa gatggtcatc atattcgtga agtgggtcgt gaatatggaa    240

cgactacagg acgtccacgt cgtgtaggtt ggtttgactc tgttgtatta cgccattctc    300

gccgtgcaag tggtattacg gacttgtcaa ttaactctat tgacgtatta actggtttag    360

aaactgttaa gatttgtaca gcatatgaat tggatggaaa agagattaca gaatatccag    420

cgaatttaaa tgaactaaat cgttgtaaac cgattttcga agaattacca ggatggactg    480

aagatgtgac ttcatgtaag tcattagacg agctacctga taacgcacgc cgttacttag    540

agcgtatttc ggagttatgt aatgttaaga tttctatctt ctcagtaggt ccagacca      598
```

```
<210> SEQ ID NO 60
<211> LENGTH: 599
<212> TYPE: DNA
<213> ORGANISM: Staphylococcus auricularis
<220> FEATURE:
<221> NAME/KEY: misc_feature
<222> LOCATION: (361)..(361)
<223> OTHER INFORMATION: n is a, c, g, or t
<220> FEATURE:
<221> NAME/KEY: misc_feature
<222> LOCATION: (484)..(484)
<223> OTHER INFORMATION: n is a, c, g, or t
<220> FEATURE:
<221> NAME/KEY: misc_feature
<222> LOCATION: (541)..(541)
<223> OTHER INFORMATION: n is a, c, g, or t
<220> FEATURE:
<221> NAME/KEY: misc_feature
<222> LOCATION: (553)..(553)
<223> OTHER INFORMATION: n is a, c, g, or t

<400> SEQUENCE: 60

ctatttgaag gagctcaagg tgtgatgtta gatatcgacc atggtacgta cccatttgtt     60

acatctagta accctgttgc tggtaacgtg acagtgggtg caggtgtagg tccaacgttt    120

gtctctaaag tgattggtgt atgtaaagcc tatacatcac gtgtcggtga tggtccattc    180

ccaactgaat tatttgatga tgatggtcac cacatccgtg aagtcggaca tgaatacggt    240

acaacaacag gacgcccaag acgtgtcggt tggttcgact ctgtggtatt acgtcactct    300

cgccgtgtga gcggtattac agacctttct attaactcta ttgatgtgtt aactggttta    360

natacagtta aaatttgtac cgcatacgaa ttagatgggg aagaaattac agagtaccca    420

gcaaacttaa acgatctaaa acgctgcaaa ccaatctttg aagaacttcc aggttggaac    480

gaanatatta caggttgccg cagcttagaa gaattacctg acaatgcacg tcactactta    540

naacgcattg canaactttg tgacgtaaac atttcaatct tctcagttgg gccagacca     599
```

```
<210> SEQ ID NO 61
<211> LENGTH: 599
<212> TYPE: DNA
<213> ORGANISM: Staphylococcus caseolyticus

<400> SEQUENCE: 61

cttttcgaag gggcgcaagg agtaatgctt gatatcgatc atggtactta tccgttcgtc     60

acttcaagta acccgattgc cggtaacgta acagttggta ctggtgtagg tccaacgttt    120

gtagataaag ttgttggtgt atgtaaagct tacacatcac gtgtaggaga tggaccattc    180

ccaactgaat tatttgatga agatggtcat catattcgtg aagtgggtcg tgaatatgga    240
```

-continued

```
acgactacag gacgtccacg tcgtgtaggt tggtttgact ctgttgtatt acgccattct    300

cgccgtgcaa gtggtattac ggacttgtca attaactcta ttgacgtatt aactggttta    360

gaaactgtta agatttgtac agcatatgaa ttggatggaa aagagattac agaatatcta    420

gcgaatttaa atgaactaaa tcgttgtaaa ccgattttcg aagaattacc aggatggact    480

gaagatgtga cttcatgtaa gtcattagac gagctacctg ataacgcacg ccgttactta    540

gagcgtattt cggagttatg taatgttaag atttctatct tctcagttgg tccagacca     599
```

<210> SEQ ID NO 62
<211> LENGTH: 599
<212> TYPE: DNA
<213> ORGANISM: Listeria innocua

<400> SEQUENCE: 62

```
cttttcgaag gagcacaagg ggttatgctt gatattgatc aaggaacata tccatttgta     60

acttcaagta atccgattgc tggtggcgta acaattggta gcggtgttgg cccatcgaaa    120

atcaatcatg ttgttggtgt tgcaaaagca tatacaactc gtgttggaga tggtcctttc    180

ccaactgaat tatttgattc tattggtgac actatccgtg aagttggcca tgaatatggt    240

acaactactg gtcgtccgcg tcgtgtaggt tggtttgata gcgtggttgt tcgtcatgct    300

cgtcgtgtga gcggactaac aggtttatcc ttaacgctac tggacgtttt gacagggatt    360

gaaacactta aaatctgtgt agcgtacaag ttagacggaa aaacaattac agaattcccg    420

gcaagcttga aagacttagc tcgttgtgaa cctgtttatg aagaactgcc tggttggaca    480

gaagatatta ctgaagtgca atcattagat gacctaccag taagttgtcg tcattacatg    540

gaacgcattg ctcaacttac aggtgtgcaa gtttctatgt tctcagtagg gcctgatca     599
```

<210> SEQ ID NO 63
<211> LENGTH: 469
<212> TYPE: DNA
<213> ORGANISM: Escherichia coli

<400> SEQUENCE: 63

```
ctatttgaag gggcgcaagg aaaaaggatt gtcgatgcat aacgcctccg gattgactct     60

ggcttaaagc gtagtcagtg gaggagataa caaattcatt tttacaaaaa cttaaacatg    120

aagggggaga cgctttctcc cccttagttt tcaggccttc tcaagcatgg cgtgcttctg    180

caggctctgg atactcagcg ttaagctcat cagacaattt tcaagcttat cggcgttgac    240

ggtaataaca gtcgggcaat catggtgccc actcatcaaa catactgcgg ctgtcgctaa    300

tgcttcttca gcatgatgaa gagcactcca ctcttcctga tccagatgaa gattcaaccg    360

cagcgattta tcgtgcagtt cgcgattcag tttaaaaaag ttatctcgta gatgattgct    420

ttcgctgacg gacatgtatc cttttgcctt tctcagttgg gccagacca                469
```

<210> SEQ ID NO 64
<211> LENGTH: 460
<212> TYPE: DNA
<213> ORGANISM: Bacillus anthracis
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:

-continued

<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (440)..(440)
<223> OTHER INFORMATION: n is a, c, g, or t
<220> FEATURE:
<221> NAME/KEY: misc_feature
<222> LOCATION: (449)..(449)
<223> OTHER INFORMATION: n is a, c, g, or t

<400> SEQUENCE: 64
anttngggca tgggnccntc tttatnagca gcatcgataa ccatttttac aagacgtaaa 60
atagataggt tatatggttg gtataagtaa gatacttgtt cgttcatacg gtctgcagcc 120
attgtgtatt gaattaagtc atttgttccg atagagaaga aatcaacttc ttttgcgaat 180
tgatctgcta atactgctga agctgggatt tcaaccatca taccaacttc aatagaatca 240
gaaacagttg tacccacttc tacaagtttc gctttttctt ctaataagat cgcttttgct 300
tgacggaact catcaagagt tgcaatcatt gggaacataa tttttaagtt accgtatacg 360
ctagcacgaa gtaatgcacg aagttgtgta cggaacacat cttgctcatc aagacataag 420
cgaattgcac ggtagcccan gaacggatnt ttttctttaa 460

<210> SEQ ID NO 65
<211> LENGTH: 444
<212> TYPE: DNA
<213> ORGANISM: Bacillus anthracis butare
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 65
ncttggcagg gccntcttna tnagcagcat cgataaccat ttttacaaga cgtaaaatag 60
ataggttata tggttggtat aagtaagata cttgttcgtt catacggtct gcagccattg 120
tgtattgaat taagtcattt gttccgatag agaagaaatc aacttctttt gcgaattgat 180
ctgctaatac tgctgaagct gggatttcaa ccatcatacc aacttcaata gaatcagaaa 240
cagttgtacc cacttctaca agtttcgctt tttcttctaa taagatcgct tttgcttgac 300
ggaactcatc aagagttgca atcattggga acataatttt taagttaccg tatacgctag 360
cacgaagtaa tgcacgaagt tgtgtacgga acacatcttg ctcatcaaga cataagcgaa 420
ttgcacggta gcccaagaac ggat 444

-continued

<210> SEQ ID NO 66
<211> LENGTH: 457
<212> TYPE: DNA
<213> ORGANISM: Bacillus anthracis sterne
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (437)..(437)
<223> OTHER INFORMATION: n is a, c, g, or t
<220> FEATURE:
<221> NAME/KEY: misc_feature
<222> LOCATION: (446)..(447)
<223> OTHER INFORMATION: n is a, c, g, or t
<220> FEATURE:
<221> NAME/KEY: misc_feature
<222> LOCATION: (451)..(451)
<223> OTHER INFORMATION: n is a, c, g, or t

<400> SEQUENCE: 66
actgcgcatn ngccttcttt atgagcagca tcgataacca tttttacaag acgtaaaata 60
gataggttat atggttggta taagtaagat acttgttcgt tcatacggtc tgcagccatt 120
gtgtattgaa ttaagtcatt tgttccgata gagaagaaat caacttcttt tgcgaattga 180
tctgctaata ctgctgaagc tgggatttca accatcatac caacttcaat agaatcagaa 240
acagttgtac ccacttctac aagtttcgct ttttcttcta ataagatcgc ttttgcttga 300
cggaactcat caagagttgc aatcattggg aacataattt ttaagttacc gtatacgcta 360
gcacgaagta atgcacgaag ttgtgtacgg aacacatctt gctcatcaag acataagcga 420
attgcacggt agcccangaa cggatnnttt ntcttaa 457

<210> SEQ ID NO 67
<211> LENGTH: 457
<212> TYPE: DNA
<213> ORGANISM: Bacillus anthracis
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (437)..(437)
<223> OTHER INFORMATION: n is a, c, g, or t
<220> FEATURE:
<221> NAME/KEY: misc_feature
<222> LOCATION: (445)..(445)
<223> OTHER INFORMATION: n is a, c, g, or t

<400> SEQUENCE: 67
nncnngcatg ggccntcttt atnagcagca tcgataacca tttttacaag acgtaaaata 60
gataggttat atggttggta taagtaagat acttgttcgt tcatacggtc tgcagccatt 120
gtgtattgaa ttaagtcatt tgttccgata gagaagaaat caacttcttt tgcgaattga 180
tctgctaata ctgctgaagc tgggatttca accatcatac caacttcaat agaatcagaa 240

-continued

```
acagttgtac ccacttctac aagtttcgct ttttcttcta ataagatcgc ttttgcttga    300

cggaactcat caagagttgc aatcattggg aacataattt ttaagttacc gtatacgcta    360

gcacgaagta atgcacgaag ttgtgtacgg aacacatctt gctcatcaag acataagcga    420

attgcacggt agcccangaa cgganctttt ttcttta                             457
```

<210> SEQ ID NO 68
<211> LENGTH: 455
<212> TYPE: DNA
<213> ORGANISM: Bacillus anthracis Coda-Cerva
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (437)..(437)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (451)..(451)
<223> OTHER INFORMATION: n is a, c, g, or t

<400> SEQUENCE: 68

```
anntggcatn ggncttcttt atgagcagca tcgataacca tttttacaag acgtaaaata     60

gataggttat atggttggta taagtaagat acttgttcgt tcatacggtc tgcagccatt    120

gtgtattgaa ttaagtcatt tgttccgata gagaagaaat caacttcttt tgcgaattga    180

tctgctaata ctgctgaagc tgggatttca accatcatac caacttcaat agaatcagaa    240

acagttgtac ccacttctac aagtttcgct ttttcttcta ataagatcgc ttttgcttga    300

cggaactcat caagagttgc aatcattggg aacataattt ttaagttacc gtatacgcta    360

gcacgaagta atgcacgaag ttgtgtacgg aacacatctt gctcatcaag acataagcga    420

attgcacggt agcccangaa cggatcnttt ntctt                               455
```

<210> SEQ ID NO 69
<211> LENGTH: 458
<212> TYPE: DNA
<213> ORGANISM: Bacillus anthracis
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 69

-continued

```
tttnnggcat ggcgccntct tnatnagcag catcgataac catttttaca agacgtaaaa     60

tagataggtt atatggttgg tataagtaag atacttgttc gttcatacgg tctgcagcca    120

ttgtgtattg aattaagtca tttgttccga tagagaagaa atcaacttct tttgcgaatt    180

gatctgctaa tactgctgaa gctgggattt caaccatcat accaacttca atagaatcag    240

aaacagttgt acccacttct acaagtttcg ctttttcttc taataagatc gcttttgctt    300

gacggaactc atcaagagtt gcaatcattg ggaacataat ttttaagtta ccgtatacgc    360

tagcacgaag taatgcacga agttgtgtac ggaacacatc ttgctcatca agacataagc    420

gaattgcacg gtagcccaag aacggatctt tttcttta                            458
```

<210> SEQ ID NO 70
<211> LENGTH: 445
<212> TYPE: DNA
<213> ORGANISM: Bacillus cereus

<400> SEQUENCE: 70

```
gccttcttta tgagcagcat cgataaccat ttttacaaga cgtaaaatag atgggttata     60

tggttggtat aagtatgata cttgttcgtt catacggtct gcagccattg tgtattggat    120

taaatcattt gttccgatag agaagaagtc aacttctttc gcgaattgat ctgctaatac    180

tgctgaagct gggatttcaa ccatcatacc aacttcaata gaatcagaaa cagttgtacc    240

cgcttctaca agtttcgctt tctcttctaa taaaatcgct ttcgcttgac ggaactcatc    300

aagagttgca atcattggga acataatttt taagttaccg tatacgctag cacgaagtaa    360

tgcacgaagt tgtgtacgga acacatcttg ctcatcaaga cataagcgaa ttgcacggta    420

tcccaagaac ggatcattct cgtta                                          445
```

<210> SEQ ID NO 71
<211> LENGTH: 438
<212> TYPE: DNA
<213> ORGANISM: Bacillus cereus

<400> SEQUENCE: 71

```
ccatttcctt ctttatgagc agcatcgata accattttta caagacgtaa aatagatggg     60

ttatatggtt ggtataagta tgatacttgt tcgttcatac ggtctgcagc cattgtgtat    120

tggattaaat catttgttcc gatagagaag aagtcaactt ctttcgcgaa ttgatctgct    180

aatactgctg aagctgggat ttcaaccatc ataccaactt caatagaatc agaaacagtt    240

gtacccgctt ctacaagttt cgctttctct tctaataaaa ttgctttcgc ttgacggaac    300

tcatcaagag ttgcaatcat tgggaacata atttttaagt taccgtatac gctagcacga    360

agtaatgcac gaagttgtgt acggaacaca tcttgctcat caagacataa gcgaattgca    420

cgatatccca agaacgga                                                  438
```

<210> SEQ ID NO 72
<211> LENGTH: 445
<212> TYPE: DNA
<213> ORGANISM: Listeria monocytogenes
<220> FEATURE:
<221> NAME/KEY: misc_feature
<222> LOCATION: (436)..(436)
<223> OTHER INFORMATION: n is a, c, g, or t

<400> SEQUENCE: 72

```
gccctcttta tgagaagcat caattaccat ttttactaaa cgtaagatgg atggattgta     60
```

-continued tggttggtaa aggtaagaaa cgcgttcgtt catacggtcc gcagccattg tatactgaat 120
taagtcattt gttccgatag agaagaaatc aacttctttt gcaaattgat cagcaagaac 180
tgcagcggca ggaatttcaa tcataattcc aagttcgatg gaatcagata cttctgttcc 240
agcagctttt agttttgctt tctcatctag taaaatatca cgtgcttgac ggaattcatt 300
tactgttgca atcatcggga acataatttt taagttacca tatacacttg cgcgaagtaa 360
ggcgcgaagt tgcgtacgga ataattcttc attcgcaaaa caaagacgaa ttgcgcggaa 420
tcccaagaac ggatcnttct cctta 445

<210> SEQ ID NO 73
<211> LENGTH: 444
<212> TYPE: DNA
<213> ORGANISM: Streptococcus pneumoniae
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (425)..(425)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t

<400> SEQUENCE: 73
cgcgtgagct gctttgatcc attgttaatc aagcgtagga ttgatgggtt gtatggttgg 60
taaaggtatg aaacttgttc gttcatacgg tctgctgcca ttgtatattg gatcaagtca 120
tttgtaccaa ttgagaagaa gtcaacttct ttagcaaatt ggtctgcaag catagccgct 180
gcaggaatct cgatcatgat accaacttga atgttatccg caactgcaac accttcagca 240
agaaggtttg ctttttcttc atcaaagact gctttcgctg cacggaattc tttcaagagc 300
gcaaccattg ggaacatgat acgcaattga ccgtgaacag acgcacgaag aagagcacgg 360
atttgtgtgc ggaacatagc atctccagtc tcagagatag agatacgaag agcacggaat 420
ccnangaacg gatccttttt cnta 444

<210> SEQ ID NO 74
<211> LENGTH: 441
<212> TYPE: DNA
<213> ORGANISM: Streptococcus pyogenes
<220> FEATURE:
<221> NAME/KEY: misc_feature
<222> LOCATION: (419)..(419)
<223> OTHER INFORMATION: n is a, c, g, or t
<220> FEATURE:
<221> NAME/KEY: misc_feature
<222> LOCATION: (431)..(431)
<223> OTHER INFORMATION: n is a, c, g, or t
<220> FEATURE:
<221> NAME/KEY: misc_feature
<222> LOCATION: (436)..(436)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t

<400> SEQUENCE: 74
tgcgctgctt tgatacattg ttgatcaaac gtaatattga tgggttgtat ggttggtaaa 60
ggtatgatac ttgttcgttc atacggtctg ctgccatagt gtattggata aggtcgtttg 120
ttccaattga gaagaaatca acttccttag caaattggtc tgcaagcata gcagctgcag 180

-continued

```
gaatctcaat catgatacca acttggatgt catcagcaac cgcaacgcct tctgcaagca    240

agtttgcttt ttcttcgtca aagactgctt ttgcagcacg gaattcttta agaagcgcaa    300

ccattgggaa cataatacga agttgtccgt gaacagaggc acgaagaagc gcacgcattt    360

gtgtgcggaa catggcatcc ccagtttcag agatggaaat acgaagagca cggaaaccna    420

agaacggatc nttttnccnt a                                              441
```

```
<210> SEQ ID NO 75
<211> LENGTH: 440
<212> TYPE: DNA
<213> ORGANISM: Streptococcus agalactiae
<220> FEATURE:
<221> NAME/KEY: misc_feature
<222> LOCATION: (431)..(431)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t

<400> SEQUENCE: 75

gagcagcttt gataacgttg ttaatcaaac gaaggattga tggattgtat ggttgataga     60

ggtatgaaac ttgctcattc atacggtccg cagccattgt gtattggata agatcattag    120

taccaattga gaagaaatca acttcttttg caaattggtc tgcaagcata gctgccgctg    180

ggatttcaat cataatacca acttcaatgc cttcagctac tgctacaccg tcagctaaca    240

agttcgcttt ctcttcttca aatatagctt tagcagcacg gaattcttta agcaaagcaa    300

ccattgggaa catgatgcgt agctgtccat gaactgaagc acgaagaagt gctcggattt    360

gtgtgcggaa cattgcatca ccagtttcag aaattgaaat acgcaatgca cggaatccca    420

agaacggatc ntttttcnta                                                440
```

```
<210> SEQ ID NO 76
<211> LENGTH: 439
<212> TYPE: DNA
<213> ORGANISM: Streptococcus mutans

<400> SEQUENCE: 76

tgagcagcct taacccatga tcaaccaagc gaagaatgga tggattataa ggttggtaga     60

ggtatgatac ttgttcattc atacggtcag cagccatggt gtattgaata aggtcatttg    120

taccgattga gaagaaatca acttccttag caaattggtc agccaacatt gcagctgcag    180

gaatttcaat catgatacca acttggatat catctgaaac agcaacgcct tcagctttaa    240

gattagcctt ttcttcttcc agaatacctt tagctttacg gaactcattg agcaaagcta    300

ccattgggaa catgatacgc aactgaccat gaacagaagc acgcaaaagg gcacgcaact    360

gtgtgcggaa catctgattg cctgtttctg agattgaaat acgaagtgca cgaaaaccaa    420

agaacggatc attctctta                                                 439
```

```
<210> SEQ ID NO 77
<211> LENGTH: 445
<212> TYPE: DNA
<213> ORGANISM: Enterococcus faecalis
<220> FEATURE:
<221> NAME/KEY: misc_feature
<222> LOCATION: (436)..(436)
<223> OTHER INFORMATION: n is a, c, g, or t

<400> SEQUENCE: 77
```

-continued

```
cgtcgtgtgc tgcatcaatt acatttttaa ttaaacgtaa gattgatggg ttgtatggtt     60

ggtataagta agaaacgcgt tcgttcatac ggtctgccgc cattgtgtat tggattaagt    120

cgttggttcc aacactaaag aagtctactt ctttggcaaa tttatcagct aatacggcag    180

ctgctggaat ttcaatcata atacctactt ggatatcgtt tgaaacttca acaccttcgt    240

tgactaattt ttgtttttcg tcttcaaaga ttgctttcgc tgctctaaat tctttcaaag    300

tagcaaccat tgggaacatg atacgtaagt taccatgaac agacgcacgt aataatgcac    360

gcatttgtgt acggaacatg ccgtcaccta gttctgataa gctaatacgt aatgcacggt    420

aacccaagaa cggatnattc tcgta                                          445
```

<210> SEQ ID NO 78
<211> LENGTH: 448
<212> TYPE: DNA
<213> ORGANISM: Staphylococcus aureus
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t

<400> SEQUENCE: 78

```
nncccntctt atgtgacgct tcaataactt gtttaactaa acgtaagatt gaagggttat     60

atggttggta tagatatgat acacgctctg acatacggtc agcagctaat gtgtattgaa    120

ttaaatcatt tgtaccgata ctgaagaaat ctacttcttt agcaaagaca tcagctaatg    180

ctgctgttgc aggtatctct accatgattc ctaattctat atcatccgaa atgtcatgac    240

cttcattttt aaggttttct ttttcttcta ataatatagc ttttgcttct ctaaattcgt    300

taattgttgc aaccattggg aacatgatat ttaacttacc ataaactgat gcacgtaata    360

atgcacgtag ctgtggtctg aaaatatctt gttgcgcaag gcataaacga atcgcacggt    420

aacccaagaa cggatccntt ntccttaa                                       448
```

<210> SEQ ID NO 79
<211> LENGTH: 443
<212> TYPE: DNA
<213> ORGANISM: Staphylococcus epidermidis
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t

<400> SEQUENCE: 79

```
cttctttatg agaagcttca ataacttgtt taactaatcg taaaattgaa ggattatatg     60

gttgatataa gtatgaaact cgttcagaca tacggtcagc agctaatgtg tattgaatta    120

agtcattcgt tcctatacta aagaaatcta cttctttagc aaatacatca gcaagtgccg    180

cggtagctgg aatttcaacc ataataccta attcaatatc atctgaaact tcgtaacctt    240
```

-continued

```
cgcgaagaag attttctttc tcttcaagaa gcattgattt agcgtcacgg aattctttaa    300

ttgttgctac cattgggaac ataatattca atttcccata gactgaagca cgtagtaatg    360

cacgtaattg tggtctaaag atttccggct gtgctaaaca taaacgtatc gcacgataac    420

ccaagaacgg atcnttctnc gta                                             443
```

<210> SEQ ID NO 80
<211> LENGTH: 440
<212> TYPE: DNA
<213> ORGANISM: Bacillus thuringiensis serovar israelensis
<220> FEATURE:
<221> NAME/KEY: misc_feature
<222> LOCATION: (437)..(437)
<223> OTHER INFORMATION: n is a, c, g, or t

<400> SEQUENCE: 80

```
ctttatgagc agcatcgata accattttta caagacgtaa aatagatggg ttatatggtt     60

ggtataagta tgatacttgt tcgttcatac ggtctgcagc cattgtgtat tggattaaat    120

cattcgttcc gatagagaag aaatcaactt ctttcgcgaa ttgatctgct aatactgctg    180

aagctgggat ttcaaccatc ataccaactt caatagaatc agaaacagtt gtacccgctt    240

ctacaagttt cgctttctct tctaataaaa tcgctttcgc ttgacggaac tcatcaagag    300

ttgcaatcat tgggaacata atttttaagt tgccgtatac gctagcacga agtaatgcac    360

gaagttgtgt acggaacaca tcttgctcat caagacataa gcgaattgca cggtatccca    420

agaacggatc attctcntta                                                 440
```

<210> SEQ ID NO 81
<211> LENGTH: 440
<212> TYPE: DNA
<213> ORGANISM: Bacillus thuringiensis serovar kurstaki

<400> SEQUENCE: 81

```
gccattttcc ttctttatga gcagcatcga taaccatttt tacaaggcgt aaaatagatg     60

gattatacgg ttggtataag taagatacac gttcattcat acggtctgca gccattgtgt    120

attggattag gtcgtttgtt ccgatagaga agaaatcaac ttcttttgca aactgatctg    180

ctaatactgc agaagcggga atttctacca tcatacctac ctcaatagca tcagaaacag    240

ttgtaccagc ttgaacaagt ctttctttct cttctaataa aattgctttt gcttgacgga    300

attcatcaag agttgcaatc attgggaaca taatttttaa attaccatat acgcttgcac    360

gaagcaatgc acgaagttgt gtacggaaca catcttgttc ttcaaggcat aagcgaatcg    420

cacggtaacc caagaacgga                                                 440
```

<210> SEQ ID NO 82
<211> LENGTH: 446
<212> TYPE: DNA
<213> ORGANISM: Staphylococcus hominis
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (428)..(428)
<223> OTHER INFORMATION: n is a, c, g, or t
<220> FEATURE:

<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t

<400> SEQUENCE: 82
cnccnncctt atgaggaagc ttcaataacc tgtttaacta aacgtaaaat tgctggatta 60
tatggttgat ataaatatga aacacgttca gacatacgat cagctgccat agtatattga 120
attaagtcat tagttcctat actaaagaaa tctacttctt tagcaaagat atcagctaac 180
gcagcagtag aaggaatctc taccatgata cctacttcga tatcatcagc aacttcttgt 240
ccttcgctag ttaatttatc tttttcttct aaaagaatag ctttagcatc tctaaactct 300
ttaatagtag ctaccattgg gaacataata tttaatttac cataagcaga tgcgcgtaat 360
aacgcacgta attgtgttct gaagatgtct tgttgatcta agcacaaacg aattgcacga 420
taacccanga acggattcat ntcnta 446

<210> SEQ ID NO 83
<211> LENGTH: 445
<212> TYPE: DNA
<213> ORGANISM: Enterococcus faecium

<400> SEQUENCE: 83
cgcgtgtgct gcatcaatta catttttgat caaacgtaaa attgatgggt tatatggttg 60
gtacaagtaa gaaacgcgtt cgttcatacg gtctgctgcc attgtgtatt gaatcaaatc 120
gttcgtacct acagagaaga aatctacttc ttttgcaaac ttgtctgcta agactgctgc 180
tgctggaatc tcgatcatga tgccgacttg gatcgtatca gatacttcct tgccttcact 240
gatcaatttt tgtttttctt cttcaaagat cgcttttgct gcgcggaatt ctttgagtgt 300
agctaccata gggaacatga tacgtaagtt accatgaaca gatgcacgaa gcaatgcacg 360
catttgtgta cggaacattt cgtcgccttg ttcagataaa ctgatacgca atgcacgata 420
tcccaagaac ggatcattct cctta 445

<210> SEQ ID NO 84
<211> LENGTH: 445
<212> TYPE: DNA
<213> ORGANISM: Clostridium perfringens
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (434)..(435)
<223> OTHER INFORMATION: n is a, c, g, or t
<220> FEATURE:
<221> NAME/KEY: misc_feature
<222> LOCATION: (437)..(438)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t

<400> SEQUENCE: 84
cntgtttgtg agctccatct attgtcattt tgattaatct taatacagct ggatgcattg 60
gattgtaaag gtatgatacc ttttcactca ttctgtcagc agctaatgta tattgtatta 120
aatcgttagt tcctattgag aagaaatcaa catgcttagc taattcatca gcataaactg 180

-continued

```
ctgcagctgg gatttcaacc atgatacccc attgaattga atctgagtat gctatacctt    240

ctgcttttaa ctcagctttg cattcttcaa caaatgcttt agcttgttgg aattcttcta    300

atcctgaaat cattgggaac attactgcaa gatttccata aacagaagct cttaataaag    360

ctcttatttg aactctaaag atatcttttc tgtctaagca taatcttata gctctgtatc    420

ccaagaacgg atcnntnntc nttaa                                          445
```

<210> SEQ ID NO 85
<211> LENGTH: 440
<212> TYPE: DNA
<213> ORGANISM: Bacillus myco?es
<220> FEATURE:
<221> NAME/KEY: misc_feature
<222> LOCATION: (431)..(431)
<223> OTHER INFORMATION: n is a, c, g, or t
<220> FEATURE:
<221> NAME/KEY: misc_feature
<222> LOCATION: (437)..(437)
<223> OTHER INFORMATION: n is a, c, g, or t

<400> SEQUENCE: 85

```
ctttatgagc agcatcgatc accattttta caagacgtaa aattgatggg ttatatggtt     60

ggtataagta agatacacgt tcgttcatac ggtctgcagc cattgtgtat tggattaagt    120

catttgttcc gatagagaag aaatcgactt cttttgcgaa ttgatctgct aatactgctg    180

aagctggaat ttcaaccatc ataccaactt caatagaatc agaaacagtt gtacccgctt    240

ggacaagtct ttctttctct tctaataaaa tcgctttcgc ttgacggaat tcatcaagag    300

ttgcaatcat cgggaacata atttttaagt taccgtatac gctagcacga agtaatgcac    360

gaagttgtgt acggaacaca tcttgttctt caaggcataa gcgaattgca cggtatccca    420

agaacggatc nttctcntta                                                440
```

<210> SEQ ID NO 86
<211> LENGTH: 451
<212> TYPE: DNA
<213> ORGANISM: Bacillus myco?es

<400> SEQUENCE: 86

```
gccattttcc ttctttatga gcagcatcga taaccatttt tacaagacgt aaaatagatg     60

ggttatatgg ttggtataag taagctactt gttcgttcat acggtccgca gccattgtgt    120

attggattaa atcatttgtt ccgatagaga agaaatcaac ttcttttgcg aattgatctg    180

ctaatactgc agaagctgga atttcaacca tcataccaac ttcaatagaa tcagaaacag    240

ttgtacccgc ttctacaagt tttgctttct cttctaataa gattgctttc gcttgacgga    300

actcatcaag agttgcaatc attgggaaca taatttttaa gttaccgtat acgctagcac    360

gaagtaatgc acgaagttgt gtacggaaca catcttgctc atcaagacat aagcgaattg    420

cacggtatcc caagaacgga tcattctctt a                                   451
```

<210> SEQ ID NO 87
<211> LENGTH: 455
<212> TYPE: DNA
<213> ORGANISM: Streptococcus oralis
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (434)..(434)

-continued

<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t

<400> SEQUENCE: 87
cnntttccct tcgcgtgagc tgctttgata acgttgttga tcagcgtagg attgatgggt 60
tgtatggttg gtaaaggtat gaaacttgct cgttcatacg gtctgctgcc attgtgtatt 120
ggatcaagtc gtttgtacca attgagaaga agtcaacttc tttagcaaat tggtctgcaa 180
gcattgctgc tgcaggaatt tcgatcatga taccaacttg gatattatcc gcaactgcaa 240
caccttcagc aagaaggttt gctttttctt cgtcaaagac tgctttcgct gcacggaatt 300
ctttcaagag cgcaaccatt gggaacatga tacgtaattg accgtgaaca gacgcacgaa 360
gaagagcacg gatttgtgtg cggaacatag catctccagt ctcagagata gagatacgaa 420
gagcacggaa tccnaagaac ggatcntttc tctta 455

<210> SEQ ID NO 88
<211> LENGTH: 456
<212> TYPE: DNA
<213> ORGANISM: Enterococcus hirae
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t

<400> SEQUENCE: 88
cnatttacct tcgcatgcgc tgcatcgatc acgtttttaa tcaaacgtag gattgatggg 60
ttgtaaggtt gatacaagta tgaaacacgt tcgttcatac ggtcagctgc catagtgtat 120
tggatcaagt cattcgttcc tactgagaag aagtcaactt ccttagcaaa cttgtcagct 180
aagacagctg ctgctggaat ttcgatcatg atgccgactt ggatcgtatc agatacttcc 240
acgccttcat tcaataattt ttgtttttcg tcttcaaaga ttgcttttgc agcacggaat 300
tctttaagag tcgctaccat tgggaacatg atacgtaagt ttccatgaac agatgcacgt 360
aataatgcgc gcatttgcgt acggaacatt tcgtcacctt gttctgacaa gctgattcgt 420
aatgcacgat agcccaagaa cggatcnttn tcctta 456

<210> SEQ ID NO 89
<211> LENGTH: 457
<212> TYPE: DNA
<213> ORGANISM: Enterococcus avium
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t

<400> SEQUENCE: 89

-continued

```
cnatttncct tcgcgtgcgc tgcatcaatc acgtttttga ttaagcgtag aattgatggg     60

ttatatggtt ggtaaaggta agaaacgcgt tcgttcatac ggtcagctgc catcgtgtat    120

tgaattaagt catttgttcc gatactgaag aaatcaactt ctttggcaaa cttgtcagct    180

agtacagctg cagctggaat ttcgatcatg attccgactt ggatcgtatc agaaacttcc    240

acgccttctt taaccaattt ttctttttct tcgttgaaca ttttcttcgc tgcacggaat    300

tcttttaatg tcgcaaccat tgggaacatg atgcgtaagt taccatgaac agaagcgcgc    360

aacaatgcac gtaattgtgt acggaacatg tcatcgccta gttcggatag actaatacgc    420

aatgcacgat aacccaagaa cggatcnttt ttcttaa                             457
```

<210> SEQ ID NO 90
<211> LENGTH: 437
<212> TYPE: DNA
<213> ORGANISM: Staphylococcus saprophyticus

<400> SEQUENCE: 90

```
tcgtaagaag cttctattac ttgttttact aaacgtaata ttgaaggatt atatggttga     60

tacaagtaag aaacacgttc tgacattcta tcagcagcca ttgtatattg aattaaatca    120

ttcgttccta tactgaagaa atcaacttct ttagcaaata catctgccaa cgcagcagta    180

gaaggaattt ctaccataat accaagttcg atatcatcag aaacttcaat gccttcattt    240

gttaagttat ctttttcttc aagtaacaat gctttagcat cacggaactc ttggattgta    300

gctaccatag ggaacatgat attcaattta ccaaaagcag atgcacgtaa taatgcacgc    360

aactgtggtc tgaaaatatc aggttgatct aggcataaac ggatagcacg gtaacccaag    420

aacggatcat tctctta                                                   437
```

<210> SEQ ID NO 91
<211> LENGTH: 430
<212> TYPE: DNA
<213> ORGANISM: Staphylococcus haemolyticus
<220> FEATURE:
<221> NAME/KEY: misc_feature
<222> LOCATION: (419)..(419)
<223> OTHER INFORMATION: n is a, c, g, or t
<220> FEATURE:
<221> NAME/KEY: misc_feature
<222> LOCATION: (422)..(422)
<223> OTHER INFORMATION: n is a, c, g, or t

<400> SEQUENCE: 91

```
gaagcttcat gacttgttta accaagcgta aaatagctgg gttataaggt tggtataagt     60

atgaaacgcg ttctgacata cggtcagctg ccatagtata ttgaattaaa tcattagtac    120

caatactgaa gaaatccatt tctttagcaa agatatcagc taaagcagct gtagatggaa    180

tctcaaccat gatacctaac tcaatttcat cagaaacgtc atgaccatca tttttaagat    240

tttctttttc ttctaacaga atggctttag catcacggaa ttcattgatt gtagctacca    300

ttgggaacat aatgtttaat ttaccgtaag ctgacgcgcg taataatgca cgtaattgtg    360

ttctgaaaat atcttgttga tctaagcata gacgaattgc tctgtaaccc aagaacggnt    420

cnttctctta                                                           430
```

<210> SEQ ID NO 92
<211> LENGTH: 444
<212> TYPE: DNA
<213> ORGANISM: Enterococcus flavescens
<220> FEATURE:

-continued

<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (438)..(439)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t

<400> SEQUENCE: 92
ngcatgcgct gagtcgatca cgtttttgat caaacgtaaa attgatgggt tgtatggttg 60
gtacaagtaa gacacgcgct cgttcatgcg gtctgcagcc attgtgtatt ggatcaagtc 120
attggtacca atactgaaga agtcaacttc cttcgcaaac ttgtctgcta agacagcagc 180
tgctggaatt tcgatcatga ttccgacttg gatctcgtta gaaacctcaa cgccttcgtc 240
aatcaatttt tgacgctctt cttcatacat tttcttcgca gtacggaact ctttcaatgt 300
tgccaccatt gggaacatga tacgtaagtt gccgtgagca gaagcacgta acaacgcacg 360
aagttgggta cggaacatgt catccccaag ttcagataag ctgatacgca atgcacgata 420
gcccaagaac ggatattnnt cnta 444

<210> SEQ ID NO 93
<211> LENGTH: 439
<212> TYPE: DNA
<213> ORGANISM: Enterococcus casseliflavus
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t

<400> SEQUENCE: 93
gcgctgagtc gatacgtttt tgatcaaacg taaaattgat gggttgtatg gttggtacaa 60
gtaagacacg cgctcgttca tgcggtctgc agccatggtg tattggatca agtcattggt 120
accaatactg aagaagtcaa cttccttcgc aaacttgtct gctaagacag cagctgctgg 180
aatttcgatc atgattccga cttggatctc gttagaaacc tcaacgcctt cgtcaatcaa 240
tttttgacgc tcttcttcat acattttctt cgcagtacgg aactctttca atgttgccac 300
cattgggaac atgatacgta agttgccgtg agcagaagca cgtaacaacg cacgaagttg 360
ggtacggaac atgtcatccc caagttcaga taagctgata cgcaatgcac gatagcccaa 420
gaacggatna tttntctta 439

<210> SEQ ID NO 94
<211> LENGTH: 450
<212> TYPE: DNA
<213> ORGANISM: Enterococcus gallinarum
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (443)..(443)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t -continued

<400> SEQUENCE: 94
accttngcat gtgctgaatc gattacgttt ttgatcaacg tagaatagat gggttatatg 60
gttggtaaag atatgaaact tgttcattca tacggtctgc agccattgtg tattggatca 120
agtcattggt accaatactg aagaagtcta cttccttggc aaatttgtca gctaagacag 180
ctgctgcagg aatttcgatc atgataccta cttgaatatc ttcagagacg gttacgcctt 240
catcgatcaa tttttgacgt tcttcttcgt acattttttt cgcagcacgg aactctttca 300
atgttgccac cattgggaac ataatccgca agtttccgtg agcagaagca cgtaacagcg 360
cacgaagttg tgtacggaac atgccgtcac ccaactcaga caaactgata cgcaatgcac 420
gatagcccaa gaacggatct ttntccntta 450

<210> SEQ ID NO 95
<211> LENGTH: 443
<212> TYPE: DNA
<213> ORGANISM: Enterococcus raffinosus
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (432)..(433)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t

<400> SEQUENCE: 95
ntgtgctgca tcaatgacgt ttttaatcaa acgtaagatt gatgggttat atggttgata 60
caggtatgaa acgcgttcgt tcatacggtc agcagccatt gtgtattgaa tcaagtcgtt 120
tgttccgata ctaaagaagt caacttcttt tgcaaacttg tcagctagaa cagctgcggc 180
agggatctcg atcatgattc cgacttgaat cgtatcagaa accttcacgc cttcgttaac 240
aagcttttct ttttcttcgt tgaacatttt cttcgctgca cggaactctt ttaatgttgc 300
aaccattggg aacatgatgc gtaaattgcc atgaactgaa gcgcgtaaca atgcacgtaa 360
ctgtgtacgg aacatatcgt cgcctaattc agataaactg atacgcaatg cacgataacc 420
caagaacgga tnnttctncg taa 443

<210> SEQ ID NO 96
<211> LENGTH: 453
<212> TYPE: DNA
<213> ORGANISM: Enterococcus villorum
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (441)..(441)

-continued

<223> OTHER INFORMATION: n is a, c, g, or t
<220> FEATURE:
<221> NAME/KEY: misc_feature
<222> LOCATION: (451)..(451)
<223> OTHER INFORMATION: n is a, c, g, or t

<400> SEQUENCE: 96

```
ggnctctcgt cgtnagctgc atcaatcacg tttttgatta aacgtaaaat tgatgggtta     60

taaggttggt ataagtatga aacgcgttcg ttcatacggt cagctgccat agtgtattga    120

atcaaatcat ttgttcctac tgagaagaag tcaacttcct tcgcaaactt gtcagctaaa    180

acagcagctg caggaatttc aatcataatg ccgacttgga tcgtatcaga tacttccacg    240

ccttcattca ataacttttg tttttcatct tcaaagattg cttttgcccc acggaattct    300

ttaagtgtcg ccaccattgg gaacatgata cgtaagttac cgtgaacgga tgcacgcaat    360

aacgcacgca tttgtgtacg gaacatttcg tctccttgtt cagaaagact gatacgtaat    420

gcacgatatc cnangaacgg nttatttttc nta                                 453
```

<210> SEQ ID NO 97
<211> LENGTH: 442
<212> TYPE: DNA
<213> ORGANISM: Clostridium difficile
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t

<400> SEQUENCE: 97

```
tttnnggang gcntctntcg tangcattgt ctatancagt ctttataagt cttaaaacag     60

ctggatnaaa ttgattgtaa agntaactta tcttttgatt cattctatca actgcacaag    120

tgtattgaat taaatcatta gttcctatag agaagaaatc tacgtgttta gccaatacat    180

cagatatcac agcagcagat ggaacttcta tcatcatacc aatttctaca tctttagcat    240

aagccacacc ttcagaatca agttctgcta aaacttcttt tacaacttct ttagcttgta    300

acaactcttc taaagatgaa atcattggga acatgattct taatcttcca tgaacactag    360

ctctatataa agctctcaat tgagtcttaa atatatcttt tctatctagg caaagtctta    420

ttgctctgta acccaagaac gg                                             442
```

-continued

<210> SEQ ID NO 98
<211> LENGTH: 444
<212> TYPE: DNA
<213> ORGANISM: Streptococcus mitis
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (424)..(424)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t

<400> SEQUENCE: 98
ngcgtgagct gccttgataa cgttgttgat caagcgaagg attgatgggt tatatggttg 60
gtaaaggtat gaaacttgct cgttcatacg gtctgctgcc attgagtatt ggatcaagtc 120
gtttgttcca attgacatga agtctacttc ttttgcaaat tggtctgcaa gcatcgctgc 180
tgcagggatt tcaatcatga taccaacttg gatatcatcc gcaactgcaa caccttcagc 240
aagaaggttt gccttttctt cttcataaac tgctttggct gcacggaatt ctttcaaaag 300
agcaaccatt gggaacatga tacgcaattg accatgaaca gaagcacgaa gaagagcacg 360
gatttgtgta cggaacattg catctccagt ttcagaaata gagatacgaa gggcacggaa 420
tccnaagaac ggatattttt cnta 444

<210> SEQ ID NO 99
<211> LENGTH: 446
<212> TYPE: DNA
<213> ORGANISM: Bacillus halodurans
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (424)..(424)
<223> OTHER INFORMATION: n is a, c, g, or t
<220> FEATURE:
<221> NAME/KEY: misc_feature
<222> LOCATION: (435)..(436)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (443)..(443)
<223> OTHER INFORMATION: n is a, c, g, or t

<400> SEQUENCE: 99
nccttcgcta tgagctgctt taataaccat atcgacgagg cgtaaaatcg cagggtggta 60
tggctgatac aggtaggaga ctcgctcatt catgcggtca gcagccatcg tatattgaat 120
taagtcgttc gttccgatac tgaaaaagtc tacttctttt gcaaaaagat tagccgctac 180
cgccgtcgat gggatttcta ccatgattcc cacttcaatt gaatcggata cgtccactcc 240
ttcactaaga agcttgtctt tttcctcttg catgatcgct tttgcttggc gaagctcttc 300
aagggtggcg atcattggaa acatcacctt taagttaccg tatgtgcttg cgcgaagcaa 360
ggcacggagt tgggtccgga aaatatcttg tttttcaagg cacagacgaa tcgcccggaa 420

-continued

```
accnaagaac ggatnnttnt tcntaa                                        446


<210> SEQ ID NO 100
<211> LENGTH: 436
<212> TYPE: DNA
<213> ORGANISM: Bacillus weihenstephanensis
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (427)..(427)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t

<400> SEQUENCE: 100

ntgagcagca tcgataacca tttttacaag acgtaaaata gatgggttat atggttggta     60

taagtaagct acttgttcgt tcatacggtc tgcagccatt gtgtattgga ttaagtcatt    120

tgttccaata gagaagaaat caacttcttt tgcgaactga tcagctaata ctgctgaagc    180

tggaatttca accatcatac caacttcaat agaatcagaa acagttgtac ccgctttaac    240

aagtctttct ttctcttcta ataagattgc tttcgcttga cggaactcat caagagttgc    300

aatcattggg aacataattt ttaagttacc gtatacgcta gcacgaagta atgcacgaag    360

ttgtgtacgg aacacatctt gctcatcaag acataagcga attgcacggt atcccaagaa    420

cggatcnttc tcntta                                                   436


<210> SEQ ID NO 101
<211> LENGTH: 458
<212> TYPE: DNA
<213> ORGANISM: Streptococcus species
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t

<400> SEQUENCE: 101

cnnanttncc ttcgcgtgag ctgctttgat aacgttgtta atcaacgaag gattgatggg     60

ttgtatggtt ggtaaaggta tgaaacttgt tcgttcatac ggtcagcagc cattgtgtat    120

tggataaggt cgtttgttcc gattgagaag aagtcaactt ctttcgcaaa ttggtcagca    180

agcatagctg cagctgggat ttcaatcatg ataccaactt ggatatcatc tgaaacggca    240

acaccttcag ctttaaggtt tgctttttct tcatcaaaga ttgctttagc agcacggaat    300

tctttaagaa gagcaaccat tgggaacatg atacgaagtt gtccgtgtac agatgcacga    360

agaagtgcac ggatttgtgt acggaacatt gcatttcctg tttctgagat agaaatacga    420

agtgcacgga atccnaagaa cggatccttt ttccttaa                           458
```

-continued

<210> SEQ ID NO 102
<211> LENGTH: 446
<212> TYPE: DNA
<213> ORGANISM: Streptococcus gordonii
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (431)..(431)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t

<400> SEQUENCE: 102
ntgccttcgc atgagccgcc ttgataacat tgttgatcaa gcgaaggata gatgggttat 60
aaggttgata gaggtaagag acttgttcat tcatccggtc agctgccata gtgtactgga 120
tcaagtcgtt ggtaccaatt gagaagaagt caacttcctt ggcaaattga tccgccaaca 180
tagctgctgc tggaatttca atcatgatac ccacttgaat gttatccgct acagcaacac 240
cttcagcttg caatttcgct ttttcttctt cgtaaactgc tttagcctta cggaattctg 300
ttagaagggc taccattggg aacatgatac gtaattgtcc atgtacagac gcacgtaaga 360
gagcgcggat ttgtgtacgg aacatagcat taccagtttc agagatagag atacgcaaag 420
cacggaagcc naagaacggt cntttt 446

<210> SEQ ID NO 103
<211> LENGTH: 446
<212> TYPE: DNA
<213> ORGANISM: Streptococcus canis
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (424)..(424)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t

<400> SEQUENCE: 103
cncgtgagct gctttgataa cgttgttaat caaacgaagg attgatgggt tgtatggttg 60
gtaaaggtat gaaacttgtt cgttcatacg gtcagcagcc attgtgtatt ggataaggtc 120
gtttgttccg attgagaaga agtcaacttc tttcgcaaat tggtcagcaa gcatagctgc 180
agctgggatt tcaatcatga taccaacttc gatatcatct gaaacggcaa caccttcagc 240
tttaaggttt gctttttctt catcaaagat tgctttagca gcacggaatt ctttaagaag 300
agcaaccatt gggaacatga tacgaagttg tccgtgtaca gatgcacgaa gaagtgcacg 360
gatttgtgta cggaacattg catttcctgt ttctgagata gaaatacgaa gtgcacggaa 420
tccnaagaac ggtcnttttt ctctaa 446

<210> SEQ ID NO 104
<211> LENGTH: 437
<212> TYPE: DNA
<213> ORGANISM: Bacillus pumilus
<220> FEATURE:
<221> NAME/KEY: misc_feature
<222> LOCATION: (2)..(2)

-continued

<223> OTHER INFORMATION: n is a, c, g, or t
<220> FEATURE:
<221> NAME/KEY: misc_feature
<222> LOCATION: (415)..(415)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t

<400> SEQUENCE: 104
cntacgctgc ttcataacaa gcgtaatcaa acgtaaaatc gctggattgt aaggctggta 60
aagataagac actcgttcgt tcattcgatc agcagccatt gtgtattgaa tcaaatcatt 120
tgttccaata ctgaagaaat caacttcttt tgcgaattgg tctgcgatga cagcggttga 180
tggaatttct accattatac cgatttcaat ggaatcggat acgtctgtac cagcggcaac 240
caatgcttct ttttcttcaa gtaaaatggc ttttgcttct ctaaattctg ataatgtcgc 300
gatcataggg aacatgattt tcaagtttcc atatgtactt gcacgaagta aggcgcgtag 360
ttgtgttctg aaaatctcct gttcttcgag gcaaaggcgg atcgctctaa agccnaagaa 420
cggatntttt tcnttaa 437

<210> SEQ ID NO 105
<211> LENGTH: 437
<212> TYPE: DNA
<213> ORGANISM: Bacillus species
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (431)..(431)
<223> OTHER INFORMATION: n is a, c, g, or t

<400> SEQUENCE: 105
tgagcgcatc gataaccatt tttacaagac gtaaaataga tgggttatat ggttggtata 60
agtatgatac ttgttcgttc atacggtctg cagccattgt gtattggatt aaatcatttg 120
ttccgataga gaagaagtca acttctttcg cgaattgatc tgctaatact gctgaagctg 180
ggatttcaac catcatacca acttcaatag aatcagaaac agttgtaccc gcttctacaa 240
gtttcgcttt ctcttctaat aaaattgctt ttgcttgacg gaactcatca agagttgcaa 300
tcattgggaa cataattttt aagttaccgt atacgctagc acgaagtaat gcacgaagtt 360
gtgtacggaa cacatcttgc tcatcaagac ataagcgaat tgcacggtat cccaagaacg 420
gatccnttnt nctttaa 437

<210> SEQ ID NO 106
<211> LENGTH: 443
<212> TYPE: DNA
<213> ORGANISM: Lactococcus lactis
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature -continued
<222> LOCATION: (422)..(422)
<223> OTHER INFORMATION: n is a, c, g, or t
<220> FEATURE:
<221> NAME/KEY: misc_feature
<222> LOCATION: (430)..(431)
<223> OTHER INFORMATION: n is a, c, g, or t
<220> FEATURE:
<221> NAME/KEY: misc_feature
<222> LOCATION: (437)..(437)
<223> OTHER INFORMATION: n is a, c, g, or t

<400> SEQUENCE: 106
gtgagctgct ttgatncatt gttaatcaaa cgaaggattg atggattgta aggttggtaa 60
aggtaagaaa cttgttcatt catacggtct gcagccattg tatattggat gaggtcgttt 120
gtaccaattg agaagaaatc aacttcctta gcaaattggt ctgcaagcat tgctgctgct 180
ggaatttcaa tcatgatacc tacttcgata ccatctgcaa ctggaacacc ttcagcaatc 240
aattttgctt tttcttcgtc ataaatcttc ttagctgcac ggaactcagt tacgagagca 300
accattggga acatgatacg aagttgtccg tgtacagaag cacgcaagag tgcacgcaat 360
tgtgtacgga acattccgtc accagctgtt gaaaggctga tacgaagtgc acgccatccc 420
angaacggtn ntttttnttt taa 443

<210> SEQ ID NO 107
<211> LENGTH: 454
<212> TYPE: DNA
<213> ORGANISM: Bacillus firmus
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (449)..(449)
<223> OTHER INFORMATION: n is a, c, g, or t

<400> SEQUENCE: 107
tccaggangg gttctntcnt angctgcgtc aattaccatt ttaactaaac gcaggattgc 60
aggattatac ggctggtaaa ggtaagaaac acgctcattc atgcggtctg cagccattgt 120
gtactgaatt agatcattag tgccaacact gaagaaatcg acttctttag caaactgatc 180
agccataaca gcagttgaag gaatttcaac cataattcca atttcaatgt tgtcggcaac 240
ctctgctcct tcgctcacaa gcttttgttt ttcttcttca aggattgctt tgccctgacg 300
gaattcttca agagtggcaa tcatagggaa catgatttta aggtttccat aggtgcttgc 360
tcttaataaa gcccttaatt gcgtcctgaa catatcctgt tcttccagac acagacgaat 420
cgcccggaag cccaagaacg gattcattnt ctta 454

<210> SEQ ID NO 108
<211> LENGTH: 434
<212> TYPE: DNA
<213> ORGANISM: Haemophilus influenzae
<220> FEATURE:

-continued

<221> NAME/KEY: misc_feature
<222> LOCATION: (425)..(426)
<223> OTHER INFORMATION: n is a, c, g, or t

<400> SEQUENCE: 108
tgagaggcat caatcacttg tttaattaaa ccaagcacag aggggtgcat cggattataa 60
agatgggaaa taaactcatt accgcgatct acagccaaag tatattgagt taaatcgtta 120
gtaccgatac taaagaaatc cacttctttt gctaaaaatt ttgcatttac tgcggcagag 180
ggggtttcga ccattacacc aacttggata ttattatcaa acagtctccc ctcttcacgt 240
aattccgctt ttaatgtttc aataaccgct tttaattccc gaatttcttc tacagaaata 300
atcatcggga acattaccgc caatttacca aaagctgaag cacgtaacac cgcgcgtaat 360
tgtgcattta aaatttcacg acgatctaat gcaatgcgaa tcgcacgcca tcccaagaac 420
ggatnntttt tctt 434

<210> SEQ ID NO 109
<211> LENGTH: 442
<212> TYPE: DNA
<213> ORGANISM: Streptococcus bovis
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t

<400> SEQUENCE: 109
tgagctgctt tgataacgtt gttaatcaaa cgaaggattg atgggttata tggttggtaa 60
aggtatgaaa cttgttcatt catacggtca gcagccattg tgtattggat aaggtcgttt 120
gttccgattg agaagaagtc aacttctttt gcaaattggt cagcaagcat agctgcagct 180
gggatttcaa tcatgatacc aacttggata tcatctgaaa cggcaacacc ttcagcttta 240
aggttagctt tttcttcatc aaagattgct ttagcagcac ggaattcttt aagaagtgca 300
accattggga acatgatacg aagttgtccg tgtacagatg cacgaagaag tgcacggatt 360
tgtgtacgga acattgcatt tcctgtttct gagatagaaa tacgaagtgc acggaatccn 420
aagaacggtc cntttttnct ta 442

<210> SEQ ID NO 110
<211> LENGTH: 443
<212> TYPE: DNA
<213> ORGANISM: Enterococcus durans
<220> FEATURE:
<221> NAME/KEY: misc_feature
<222> LOCATION: (431)..(432)
<223> OTHER INFORMATION: n is a, c, g, or t

<400> SEQUENCE: 110
tgtgctgcat caatcacgtt tttgatcaaa cgtaaaattg aagggttata aggttgatac 60
aagtaagata cacgttcgtt catgcggtca gctgccattg tgtattgaat caagtcattc 120
gtacctactg agaagaagtc aacttccttc gcaaacttat ctgctaagac agctgctgca 180
gggatttcaa tcatgatgcc gacttggatc gtatcagata cttccacgcc ttcgctcact 240
aatttttgtt tttcttcttc aaagattgct ttcgctgcac ggaattcttt aagagtcgct 300

-continued

```
accattggga acatgatgcg taagtttcca tgaacagatg cacgtaacaa tgcgcgcatt    360

tgtgtacgga acatttcgtc acctaattca gacaagctga tacgtagcgc acgatagccc    420

aagaacggat nnttttccct taa                                            443
```

<210> SEQ ID NO 111
<211> LENGTH: 450
<212> TYPE: DNA
<213> ORGANISM: Streptococcus sanguis
<220> FEATURE:
<221> NAME/KEY: misc_feature
<222> LOCATION: (434)..(435)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t

<400> SEQUENCE: 111

```
cgcatgagct gccttgataa cattgttaat caagcgaagg atagatggat tgtaaggttg     60

atagaggtaa gagacttgct cattcatccg gtcagccgcc atagtgtact gaatcaagtc    120

gttagtacca attgagaaga agtctacttc cttggcaaat tgatccgcca acatagctgc    180

tgctgggatt tcaatcatga tacccacttg gatattatct gctactgcaa cgccttcagc    240

ttgcagctta gctttttctt cgtcataaac cgctttagct ttgcggaatt ctgtcagaag    300

ggccaccatt gggaacatga tacgcaattg tccatgtaca gaagcacgca agagagcgcg    360

gatttgtgta cggaacatag catcgccagt ttcagagata gagatacgca aagcacggaa    420

accaaagaac ggtnnttttt ntctttaaaa                                     450
```

<210> SEQ ID NO 112
<211> LENGTH: 453
<212> TYPE: DNA
<213> ORGANISM: Enterobacter cloaceae
<220> FEATURE:
<221> NAME/KEY: misc_feature
<222> LOCATION: (440)..(441)
<223> OTHER INFORMATION: n is a, c, g, or t

<400> SEQUENCE: 112

```
tcctttacct tctgcatgag agcatcaata acttgcttga tcaagttcag tacggacggt     60

gacattggct ggtagagatg tgaaatcata tcattaccac ggtcaactgc cagggtgtac    120

tgcgttaaat cattggtgcc gatactaaag aaatcaactt ctttggctaa atgacgcgca    180

atggtcgcgg ctgctggtgt ttccaccatt acgccgatct caattgactc gtcaaatgct    240

ttaccttcgt cacgcaattc ctgtttgtag atctcgatct ctttcttcag tgcacgcact    300

tcttcaacag agatgatcat cgggaacata atgcgcagct taccgaaagc agaggcacgc    360

agaatcgcac gcacctggtc acgcaggatt tctttacgat ccatggcgat acgcactgca    420

cgccagccca agaacggatn nttttttctt taa                                 453
```

<210> SEQ ID NO 113
<211> LENGTH: 449
<212> TYPE: DNA
<213> ORGANISM: Serratia liquefasciens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)

-continued

<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (427)..(427)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (445)..(445)
<223> OTHER INFORMATION: n is a, c, g, or t

<400> SEQUENCE: 113
ntgncttctg catgagnatg catcaataac ctgtttgatc aggccaagca ctgatgggga 60
catcgggtta tagagatgag aaatcagctc attgccgcga tctaccgcca gagtatactg 120
ggttagatcg tttgtcccaa tactaaagaa gtcgacttct ttcgccaggt gatgagcaat 180
cactgccgcg gccggtgttt ccaccattac gcccacttca atggtctcgt caaaggcctt 240
ggattcttca cgcagctgcg ccttcagcgt ctcgatttca cctttcagat cgcggacttc 300
ttccacggaa atgatcatcg ggaacatgat gcgcagtttg ccgaacgcgg aagcgcgcag 360
gatggcgcgc agttgcgcgt gcaggatttc tctgcggtcc atggcgatac gaatcgcgcg 420
ccagccnaag aacgnttntt tttanttta 449

<210> SEQ ID NO 114
<211> LENGTH: 436
<212> TYPE: DNA
<213> ORGANISM: Proteus mirabis
<220> FEATURE:
<221> NAME/KEY: misc_feature
<222> LOCATION: (427)..(427)
<223> OTHER INFORMATION: n is a, c, g, or t
<220> FEATURE:
<221> NAME/KEY: misc_feature
<222> LOCATION: (431)..(431)
<223> OTHER INFORMATION: n is a, c, g, or t

<400> SEQUENCE: 114
gtgtgatgca tcaatcacct gtttaatcag attaagtaca gcaggtgaca ttggattata 60
tagatgagat atcagctcat ttccacggtc tacagccaga gtatattgtg ttagatcgtt 120
agtcccaata ctgaaaaagt caacttcttt tgccatatgg cgagccataa cagccgctgc 180
tggcgtttca accataacac cgacttcgat agattcatca aaaggcttat tttcttcacg 240
aagctggctt ttcagtattt caagttccgc tttcaatgct cggatctctt caacagagat 300
aatcattgga aacataatac gtagtttacc aaaagcagac gctcttaaga tagcacgtaa 360
ttgtggatga aggatctctt tgcggtcaag acaaatacga attgcacgcc aacccaagaa 420
cggatcnttt ntcctt 436

<210> SEQ ID NO 115
<211> LENGTH: 431
<212> TYPE: DNA
<213> ORGANISM: Providencia stuartii

<400> SEQUENCE: 115

-continued

```
gcctctgcat gtgatgcatc aatgacttgc ttaatcagtt caatacagca ggcgacattg     60

gattgtagag gtgagaaatc agctcattac cacggtcaac agctagagta tattgagtga    120

gatcgttcgt cccaatactg aaaaagtcaa cttcttttgc taaatgatga gcaataaccg    180

ctgcggcagg ggtttccacc atgacaccaa cttcgattga ttcatcaaag gctttgcctt    240

cttcacgtaa ttgacctttt agcatctcaa gttctgcttt tagttcgcga acttcctcaa    300

cggaaataat catcgggaac ataatacgca gtttaccaaa acttgaggct cttaaaatag    360

ctcttaactg agaatgtaga atttctttgc gatcaaggca aatacgaatt gcccgccagc    420

ccaagaacgg t                                                         431
```

```
<210> SEQ ID NO 116
<211> LENGTH: 446
<212> TYPE: DNA
<213> ORGANISM: Proteus vulgaris
<220> FEATURE:
<221> NAME/KEY: misc_feature
<222> LOCATION: (434)..(435)
<223> OTHER INFORMATION: n is a, c, g, or t

<400> SEQUENCE: 116

ccttctgcat gtgatgcatc aataacctgt tttatcaggt taagtactgc tggtgacatt     60

ggattataca gatgagatat cagctcattt ccacggtcta cagccagagt atattgtgtt    120

agatcgttag tcccaatact gaaaaagtca acttcttttg ccatgagacg tgccattacg    180

gccgccgcag gggtttcaac catgacaccg acttcgatag actcatcgaa agttttgttt    240

tctgcacgaa gctggctttt cagtatttca agttctgctt tcaatgcgcg aatctcttca    300

atagagataa tcattggaaa cataatgcgt agtttaccaa aagcagatgc tcttaagata    360

gcacgtaatt gcgaatgaag gatctcttta cggtcaagac aaatacgaat tgctctccaa    420

cccaagaacg gtcnnttttt ttctta                                         446
```

```
<210> SEQ ID NO 117
<211> LENGTH: 458
<212> TYPE: DNA
<213> ORGANISM: Staphylococcus simulans

<400> SEQUENCE: 117

ttctccgcac atacctgtcc atttaccttc agcatgagac gcttcgataa cacgttgtac     60

caagcgtaaa atagctgggt tatatggttg gtataaataa gacacacgtt ctgacatacg    120

gtcagctgcc attgtatatt ggattaagtc atttgttccg atactgaaga agtctacttc    180

tttcgcaaag acatcagcaa gtgctgctgt cgatggaatt tcaaccatga taccgacttc    240

gatatcatct gaaacttcaa caccttcatt tttaaggttt tgacgttctt cttctaataa    300

tgctttcgca tcacggaatt cttgaattgt cgcaaccatt gggaacataa tgtttaattt    360

tccgtatact gaagcacgta ataacgcgcg taattgcgga cggaaaattt ctggttgtgc    420

taagcacaag cggattgcac gataacccaa gaacggat                            458
```

```
<210> SEQ ID NO 118
<211> LENGTH: 454
<212> TYPE: DNA
<213> ORGANISM: Staphylococcus sciuri

<400> SEQUENCE: 118

ctccgcacat accagtccat ttaccttctt tatgagaagc ttcaattact tgcttaacta     60
```

-continued

```
agcgaagaat tgcagggtta tatggttggt ataagtaaga aacacgctca gacatacggt    120

cagcagccat tgtatattgg attaaatcat tcgtaccaat actgaagaaa tcaacttctt    180

tagcaaagat gtctgcaagt gctgcagtag atggaatttc taccataata ccgatttcga    240

tatcatccgc aacgttaaca ccttcagaaa ctaatttttc tttttcctca agtaagattg    300

ctttagcatc tctaaattct ttaatagttg caatcatagg gaacatgata tttaacttac    360

caaattcaga tgcgcgtaat aaagctctta attgtgttct aaagatttca gtttgatcta    420

aacataaacg aatcgctcta tatcccaaga acgg                                454
```

```
<210> SEQ ID NO 119
<211> LENGTH: 454
<212> TYPE: DNA
<213> ORGANISM: Staphylococcus capitis capitis

<400> SEQUENCE: 119

tccgcacata ccagtccatt taccttcttt atgagaagct tcaatgactt gcttaacaag     60

acgtaatata gatgggttat atggttgata taaataagat acacgctctg acatacgatc    120

agcagctagt gtatattgaa ttaaatcatt tgtaccaata ctaaagaaat ctacttcctt    180

cgcaaagaca tctgctaatg cagcagttgc tggaatttca accatgatac ctaattcaat    240

atcatcagaa atgtcataac cttcattttc aaggtttttc ttttcctcta aaagaattgc    300

tttggcatca cggaattctt taatagtagc aaccattggg aacatgatat ttaatttacc    360

gtaagcagat gcacgtaata atgcacgtaa ttgcggtcta aaaatatctt gttgagctaa    420

acataaacga attgctctat aacccaagaa cgga                                454
```

```
<210> SEQ ID NO 120
<211> LENGTH: 464
<212> TYPE: DNA
<213> ORGANISM: Staphylococcus warneri

<400> SEQUENCE: 120

ccgcacatac cagtccattt accttctttg tgagaagctt caatgacttg ttttactaag     60

cgtaaaattg aagggttgta tggttgatat aagtaagata cacgttcaga catacggtca    120

gctgctaatg tgtattggat taagtcattt gtaccaatac taaagaaatc tacttcttta    180

gcaaatacat cagctaatgc tgctgtcgct ggtatttcaa ccatgatacc taactcaata    240

tcttcagaaa cttcataacc ttcattttga agattttctt tttcttctaa taacattgct    300

ttagcatcac ggaattcctt gatagttgct accattggga acatgatatt taatttacca    360

taaactgatg cacgtaataa cgcgcgtaat tgtggtctga aaatatcagg ttgagctaag    420

caaagacgaa tcgctctgta tcccaagaac ggatcattct ctta                      464
```

```
<210> SEQ ID NO 121
<211> LENGTH: 454
<212> TYPE: DNA
<213> ORGANISM: Staphylococcus cohnii urealyticus
<220> FEATURE:
<221> NAME/KEY: misc_feature
<222> LOCATION: (453)..(453)
<223> OTHER INFORMATION: n is a, c, g, or t

<400> SEQUENCE: 121

ccgcacattc cagtccattt gccttcttta tgagaagcat caatcacttg ttgcactaaa     60

cgtaaaattg ctggattgta tggttgatac aagtaagata ctcgctctga catacgatcc    120

gcggccattg tatattgaat taaatcgttc gttccgatgc tgaagaaatc tacttcttta    180
```

-continued

```
gcaaaaacat ctgctaatgc tgcagttgaa ggaatttcta ccatgatacc aacttctata    240

tcatcagata cttcaatacc ttcatttgtt aaattttctt tttcctctaa taacaatgct    300

ttcgcatcac ggaattcttt aattgtcgct accattggga acataatatt taaattccca    360

taagctgacg cacgtaataa agcacgcaat tgcggtctga aaatgtcagg ttgatctaaa    420

cataaacgaa tcgcacggta tcccaagaac ggnt                                454
```

<210> SEQ ID NO 122
<211> LENGTH: 443
<212> TYPE: DNA
<213> ORGANISM: Staphylococcus schleiferi scheiferi

<400> SEQUENCE: 122

```
ccgcacatac ctgtccattt accttcttta tgagatgctt caattacttg cttaactaag     60

cgtaaaattg aaggattgta aggttggtaa agatatgata cacgttctga catacggtca    120

gctgccatcg tatattgaat taagtcattc gttccaatac taaagaagtc aacttcttta    180

gcaaaaacat cagctaaagc tgctgtagat ggaatttcca ccataatacc taactcaata    240

tcatcgctaa cttcaacgcc ttcttgtttt aagttttctt tttcttcaag aagaagcgct    300

tttgcatcgc ggaattcttt aatcgtcgca accattggga acataatgtt cagttttccg    360

taagttgaag cgcgtaataa cgctcttaat tgtggacgga aaatttcagg ttgatctaaa    420

caaagacgaa ttgcacggta tcc                                            443
```

<210> SEQ ID NO 123
<211> LENGTH: 459
<212> TYPE: DNA
<213> ORGANISM: Staphylococcus intermedius
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t

<400> SEQUENCE: 123

```
ccgcacatac ctgtccattt gccctcttgg tgagaagcgt caatcacttg tttaattaaa     60

cgtaagnatt gatggattat atggttggta aagataagat acacgttctg acatacggtc    120

tgcagccatt gtgtattgaa ttaaatcgtt tgtaccgata ctgaagaaat ccacttcttt    180

cgcaaataca tctgcaagtg cggctgttgc agggatttca accatgatac ctanttcgat    240

atcgtcgctc acttctacgc cttcttgttt caagttttcc ttttcttcaa gaagtaacgc    300

tttcgcatca cggaattctt gaatcgttgc caccattggg aacataatat tcaatttacc    360

gtatgctgaa gctcttaata atgcacgtaa ttgtggacgg aaaatttcag gttgatctaa    420

acataaacga atcgcacggt aacccaagaa cggattcat                           459
```

<210> SEQ ID NO 124
<211> LENGTH: 458
<212> TYPE: DNA
<213> ORGANISM: Staphylococcus cohnii cohnii
<220> FEATURE:
<221> NAME/KEY: misc_feature
<222> LOCATION: (446)..(446)
<223> OTHER INFORMATION: n is a, c, g, or t
<220> FEATURE:
<221> NAME/KEY: misc_feature
<222> LOCATION: (453)..(453)

-continued

```
<223> OTHER INFORMATION: n is a, c, g, or t

<400> SEQUENCE: 124

ccgcacatcc ctgtccattt accttcttta tgactggcat caataacttg tttcatcagt     60

ctaagaatcg ctgggttata aggctggtaa agataagaga cgcgttcact catacggtct    120

gcagccatcg tatattgaat aagatcattc gtaccgatac taaagaaatc aacctctttc    180

gcaaagatat cggccattgc tgctgtagaa ggaatctcta ccatgatgcc aagctcgata    240

tcgtcagcaa ctttaacttt atctgcaatt aaattggctt tctcttcttc taagattgct    300

ttcgcatcac ggaattcgtt gatagtcgca atcatcggga acatgatgct cagtttaccg    360

tggatggatg cacgtaataa cgcacgaagc tgtgttctaa agatatcctg ctgatccaga    420

caaagtcgaa tcgcacggta tccaangaac ggnttcat                            458


<210> SEQ ID NO 125
<211> LENGTH: 464
<212> TYPE: DNA
<213> ORGANISM: Staphylococcus capitis uralyticus
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t

<400> SEQUENCE: 125

ccgcacatac cagtccattt accttcttta tgagaagcct ctattacttg cttaacaaga     60

cgtaaaatag aaggattata tggttgatat aaataagata cacgttctga catacgatca    120

gcagctagtg tgtattgaat taagtcatta gtaccgatac taaagaagtc tacttccttc    180

gcaaagacat ctgctaatgc agcagttgct ggaatttcaa ccatgatacc taattcgata    240

tcgtcagaaa tgtcataacc ttcattttca aggtttttct tttcttctaa aagaatcgct    300

ttagcatcac ggaattcttt gatagtagca accattggga acatgatatt taatttaccg    360

taagcagatg cacgtaataa tgcacgtaat tgcggtctga aaatatcttg ttgcgctaaa    420

cataaacgaa ttgctctata acccaagaac ggnttcatnt ctta                     464


<210> SEQ ID NO 126
<211> LENGTH: 440
<212> TYPE: DNA
<213> ORGANISM: Staphylococcus gallinarum
<220> FEATURE:
<221> NAME/KEY: misc_feature
<222> LOCATION: (435)..(435)
<223> OTHER INFORMATION: n is a, c, g, or t

<400> SEQUENCE: 126

ccgcacatac ctgtccattt accttgttta actaaacgta aaattgaagg attatatggt     60

tgatacaagt atgatacacg ttctgacatt ctatctgcag ccatagtgta ttgaattaaa    120

tcatttgtac cgatactaaa gaagtcaacc tctttagcaa atacatcagc taaagctgct    180

gtagaaggaa tttctaccat gatacctaat tcgatatcat cagatacttc aacaccttct    240

tgtgttaaat tgtccttctc ttcaagaagt aatgctttgg catcacggaa ctcttgaatt    300

gtagcaacca ttgggaacat gatatttaac ttaccgaatg cagatgcgcg taataatgca    360

cgcaattgcg gtctgaaaat atcaggttga tccaagcata aacgtatcgc acgatatccc    420

aagaacggat tcatntctta                                                440
```

-continued

<210> SEQ ID NO 127
<211> LENGTH: 462
<212> TYPE: DNA
<213> ORGANISM: Staphylococcus auricularis

<400> SEQUENCE: 127
ccgcacatgc cagtccattt accttcttta tgagaagctt cgatgacttg tttgctcaac 60
caagcgtaaa atagctggat tatatggttg ataaaggtat gatacgcgtt ctgacatgcg 120
gtctgcagcc attgtatatt gaattaagtc gtttgtaccg atactaaaga agtcgacttc 180
tttcgcaaag acatctgcta aagcagctgt tgatggaatt tcgaccataa tacctaattc 240
aatatcatct gagacttcaa ctccctcttg ttctaagttt gctttttctt cttccaacaa 300
tgctttagca tcacggaatt cttgaattgt cgcaaccatt gggaacatga tattgagttt 360
tccgtacgta gatgcacgta ataatgcacg taattgtgga cggaaaatat caggttgatc 420
taagcataaa cgaatcgcac gataacccaa gaacggattc at 462

<210> SEQ ID NO 128
<211> LENGTH: 457
<212> TYPE: DNA
<213> ORGANISM: Staphylococcus caseolyticus

<400> SEQUENCE: 128
ccgcacatcc ctgtccattt accttcttta tgactggcat caataacttg tttgatcagt 60
ctaagaatcg ctgggttata gggctggtaa agataagaga cgcgttcact catacggtct 120
gcagccatcg tatattgaat aagatcattc gtaccgatac taaagaaatc aacctctttc 180
gcaaagatat cggccattgc tgctgtagaa ggaatctcta ccatgatgcc aagctcgata 240
tcgtcagcaa ctttaacttt atctgcaatt aaattggctt tctcttcttc taagattgct 300
ttcgcatcac ggaattcgtt gatagtcgca atcattggga acatgatgct cagtttaccg 360
tggatggatg cacgtaataa cgcacgaagc tgtgttctaa agatatcctg ctgatccaga 420
caaagtcgaa tcgcacggta tccaaagaac ggattca 457

<210> SEQ ID NO 129
<211> LENGTH: 436
<212> TYPE: DNA
<213> ORGANISM: Staphylococcus xylosus

<400> SEQUENCE: 129
tgtgaagctt taatcacttg ttttactaaa cgtaaaattg aaggattgta tggttgatac 60
aagtaagaaa cacgctcaga catacgatca gcagccattg tatattgaat caaatcattt 120
gtaccaatac taaagaaatc aacttcttta gcaaatacat ctgctaaagc agcagttgat 180
ggtatctcta ccataatacc taattcaata tcgtcagata cttcaatgcc ttcgtttgtt 240
aaattctctt tttcttccaa taataatgct tttgcatctc gaaactcttt aattgtggca 300
accattggga acatgatatt taatttaccg taagtagacg cacgtaacaa tgctcttaat 360
tgtggtctga aaatatcagg ttgatctaag cataaacgaa ttgcacgata tcccaagaac 420
ggatcatttt tcgtaa 436

<210> SEQ ID NO 130
<211> LENGTH: 454
<212> TYPE: DNA
<213> ORGANISM: Klebsiella pneumoniae
<220> FEATURE:

-continued

<221> NAME/KEY: misc_feature
<222> LOCATION: (444)..(444)
<223> OTHER INFORMATION: n is a, c, g, or t

<400> SEQUENCE: 130
ccgcacatgc cagtccattt accttcagcg tgagaagcat caataacttg cttaatcaga 60
ttcagtacag acggtgacat cggctggtaa agatgtgaaa tcatatcatt accacggtca 120
actgccagag tatattgcgt taaatcattg gtgccgatac taaagaaatc aacttctttg 180
gccagatgac gagcaatagt cgccgcagcc ggtgtttcca ccatcacgcc gatctcaatg 240
gattcgtcaa atgctttacc ttcgtcacgc agttcctgtt tgtagatttc gatctctttc 300
ttcagcgcac gcacttcttc aacagagatg atcatcggga acataatgcg cagcttaccg 360
aaagcggagg cgcgcaggat ggcgcgaacc tggtcgcgca ggatctcttt acgatccatc 420
gcaatacgca cggcacgcca gccnaagaac ggat 454

<210> SEQ ID NO 131
<211> LENGTH: 454
<212> TYPE: DNA
<213> ORGANISM: Salmonella typhymurium
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t

<400> SEQUENCE: 131
ccgcacatgc cagtccattt accttctgca tgagaagcat caataacttg cttgatcaag 60
ttcagtacgg acggtgacat tggctggtaa aggtgtgaaa tcatatcatt accacggtca 120
actgccaggg tgtactgcgt taaatcattg gtgccgatac taaagaaatc aacttctttg 180
gctaaatgac gcgcaattgt cgccgcagcc ggtgtttcca ccatcacgcc aatctcaatg 240
ctttcgtcaa atgctttacc ttcgtcacgc agttcctgtt tgtagatttc aatctctttg 300
cgcagcgcgc gaacttcttc aacagagatg atcatcggga acataatgcg caatttaccg 360
aaagcggagg cacgcagaat cgcgcgaacc tggtcacgca ggatctcttt gcgatccatg 420
gcgatacgca cggcgcgcca gccnangaac ggat 454

<210> SEQ ID NO 132
<211> LENGTH: 476
<212> TYPE: DNA
<213> ORGANISM: Escherichia coli

<400> SEQUENCE: 132
cctgccattt caccgcacat gccagtccat ttgccttcag catgagaagc atcaataact 60
tgcttgatca agttcagcac ggacggtgac attggctggt aaaggtgtga aatcatatca 120
ttaccacggt caactgccag agtgtactgc gttaaatcat tggtgccgat actaaagaaa 180
tcaacttctt tggctaaatg acgtgcaatt gttgcggcag ccggtgtttc caccattacg 240
ccgacttcaa ttgactcgtc aaacgcttta ccttcgtcgc gcagttcctg tttgtagatt 300
tcgatctctt tgcgcagtgc acgcacttct tcaacagaga tgatcatcgg gaacataatg 360
cgcaatttac cgaaagccga ggcacgcagg atagcgcgga gctgatcgcg caggatctct 420
ttacgatcca ttgcgatacg gatagcgcgc cagccaaaga acgggttcat ttctta 476

-continued

<210> SEQ ID NO 133
<211> LENGTH: 476
<212> TYPE: DNA
<213> ORGANISM: Escherichia coli

<400> SEQUENCE: 133
tcctgccatt tctccgcaca tgccagtcca tttgccttca gcatgagaag catcaataac 60
ttgcttgatc aagttcagca cggacggtga cattggctgg taaaggtgtg aaatcatatc 120
attaccacgg tcaactgcca gagtgtactg cgttaaatca ttggtgccga tactaaagaa 180
atcaacttct ttggctaaat gacgtgcgat tgttgcggca gccggtgttt ccaccattac 240
gccgatttca attgactcgt caaacgcttt accttcgtcg cgcagttcct gtttgtagat 300
ttcgatctct ttgcgcagtg cacgcacttc ttcaacagag atgatcatcg ggaacataat 360
gcgcaattta ccgaaagccg aggcacgcag gatagcgcgg agctgatcgc gcaggatctc 420
tctacgatcc atcgcgatac ggatagcgcg ccagcccaag aacggattca tttctt 476

<210> SEQ ID NO 134
<211> LENGTH: 476
<212> TYPE: DNA
<213> ORGANISM: Citrobacter freundii

<400> SEQUENCE: 134
tcccgccatt tctccgcaca tgccagtcca tttgccttca gcatgagaag catcaataac 60
ttgcttgatc agcgtcagca cagatggcga catcggttgg taaaggtgtg aaatcatatc 120
attaccacgg tcaactgcca gggtgtactg cgttaaatca ttggtgccga tactaaagaa 180
atcaacttct ttggctaaat gacgcgcaat tgttgccgca gccggtgttt ccaccatcac 240
gccaatctca atgctctcgt caaatgcttt accttcgtcg cgcagttcct gtttgtagat 300
ttcaatctct ttgcgcagtg cacgcacttc ttcaacagag atgatcattg ggaacataat 360
gcgcagttta ccgaaagcag aggcgcgcag aatcgcgcga acctggtcac gcaggatctc 420
tttacgatcc atggcgatac gcacggcacg tcagcccagg aatgggttca tctctt 476

<210> SEQ ID NO 135
<211> LENGTH: 476
<212> TYPE: DNA
<213> ORGANISM: Pseudomonas putida

<400> SEQUENCE: 135
tcccgccatt tctccgcaca tgctcactgg cttgccttca ccatgggcat cgcgcaccac 60
cgtgctcaag gcttgcagct ccgccgggtg caggtagtcg tacaggtcgg caacccgcgg 120
gttgttgcgg tccaccgcca gcaggtactg ggtcaggtcg ttggagccga ccgacaggaa 180
atccacctgc cgcgccagtt ccttggtctg gtacaccgcc gcaggtattt ccaccatcac 240
gcccaccggc ggcatcggca catcggtgcc ttcgtcacgc acctcgcccc aggcgcggtg 300
gatcaggtgc agcgcttctt ccagctcgtg gatgccggaa atcatcggca gcaggatgcg 360
caggttgttc aggccctcgc tggccttgag catggcgcga gtctgcacca ggaagatttc 420
cgggtggtcg agggtgacgc ggatgccgcg ccagcctaag aatggattca tctcgt 476

<210> SEQ ID NO 136
<211> LENGTH: 476
<212> TYPE: DNA
<213> ORGANISM: Shigella sonnei

<400> SEQUENCE: 136

-continued

```
ccggccattt caccacacat gccagtccat ttgccttcag catgagaagc atcaataact     60

tgcttgatca agttcagcac ggacggtgac attggctggt aaaggtgtga aatcatatca    120

ttaccacggt caactgccag agtgtactgc gttaaatcat tggtgccgat actaaagaaa    180

tcaacttctt tggctaaatg acgtgcaatt gttgcggcag ccggtgtttc caccattacg    240

ccgatttcaa ttgactcgtc aaacgcttta ccttcgtcgc gcagttcctg tttgtagatt    300

tcgatctctt tgcgcagtgc acgcacttct tcaacagaga tgatcatcgg gaacataatg    360

cgcaatttac cgaaagccga ggcacgcagg atagcgcgga gctgatcgcg caggatctct    420

ttacgatcca tcgcgatacg gatagcgcgc cagcccagga acggattcat ctctta        476
```

```
<210> SEQ ID NO 137
<211> LENGTH: 476
<212> TYPE: DNA
<213> ORGANISM: Listeria innocua

<400> SEQUENCE: 137

tcctgccatt tctccgcaca taccagtcca tttgccctct ttatgagaag catcaattac     60

catttttact aagcgtaaaa tagatggatt gtatggttgg taaaggtaag aaacgcgttc    120

attcatacgg tcagcagcca ttgtatactg aatcaagtca tttgttccga ttgagaagaa    180

atcaacttct tttgcaaatt gatcagctaa aactgcagca gcaggaattt caatcataat    240

tccaagttcg atggaatcag atacttctgt tccagcagct tttagtttcg ctttttcatc    300

tagtaaaata tcgcgcgctt ggcggaattc atttactgtt gcaatcatcg ggaacataat    360

ttttaagtta ccatatacac ttgcgcgaag tagagcgcga agttgtgtac ggaataattc    420

ttcattcgca aaacaaagac gaatcgcacg gaatcctaag aacgggttca tttcgt        476
```

```
<210> SEQ ID NO 138
<211> LENGTH: 455
<212> TYPE: DNA
<213> ORGANISM: Serratia marcescens
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t

<400> SEQUENCE: 138

ttctnngang gactctntcn taaanagcat caataacctg tttgatcagg ccaagcactg     60

atggggacat cgggttatag agatgagaaa tcagctcgtt gccgcgatct accgccagag    120
```

```
tatactgggt tagatcgttt gtcccaatac taaagaagtc gacttctttc gccaggtggt    180

gagcgatgac cgccgcagcc ggtgtttcca ccatcacgcc cacttcgatg ctctcgtcaa    240

acgccttgcc ttcttcgcgc agctgcgcct tcagcgtctc gatttcgcct ttcagatcgc    300

gcacttcttc cacggagatg atcatcggga acatgatgcg cagtttaccg aacgccgagg    360

cgcgcaggat ggcgcgcagc tgggcgtgca ggatttcacg gcggtccatc gcgatgcgga    420

tggcgcgcca gccnaagaac ggattcattn tctta                               455
```

<210> SEQ ID NO 139
<211> LENGTH: 454
<212> TYPE: DNA
<213> ORGANISM: Salmonella enterica hadar
<220> FEATURE:
<221> NAME/KEY: misc_feature
<222> LOCATION: (444)..(444)
<223> OTHER INFORMATION: n is a, c, g, or t

<400> SEQUENCE: 139

```
ccgcacatgc cagtccattt accttctgca tgagaagcat caataacttg cttgatcaag     60

ttcagtacgg acggtgacat tggctggtaa aggtgtgaaa tcatatcatt accacggtca    120

actgccaggg tgtactgcgt taaatcattg gtgccgatac taaagaaatc aacttctttg    180

gctaaatgac gcgcaattgt cgccgcagcc ggtgtttcca ccatcacgcc aatctcaatg    240

ctttcgtcaa atgctttacc ttcgtcacgc agttcctgtt tgtagatttc aatctctttg    300

cgcagcgcgc gaacttcttc aacagagatg atcatcggga acataatgcg caatttaccg    360

aaagcggagg cacgcagaat cgcgcgaacc tggtcacgca ggatctcttt gcgatccatg    420

gcgatacgca cggcgcgcca gccnaagaac ggat                                454
```

<210> SEQ ID NO 140
<211> LENGTH: 454
<212> TYPE: DNA
<213> ORGANISM: Salmonella enteritidis
<220> FEATURE:
<221> NAME/KEY: misc_feature
<222> LOCATION: (444)..(444)
<223> OTHER INFORMATION: n is a, c, g, or t

<400> SEQUENCE: 140

```
ccgcacatgc cagtccattt accttctgca tgagaagcat caataacttg cttgatcaag     60

ttcagtacgg acggtgacat tggctggtaa aggtgtgaaa tcatatcatt accacggtca    120

actgccaggg tgtactgcgt taaatcattg gtgccgatac taaagaaatc aacttctttg    180

gctaaatgac gcgcaattgt cgccgcagcc ggtgtttcca ccatcacgcc aatctcaatg    240

ctttcgtcaa atgctttacc ttcgtcacgc agttcctgtt tgtagatttc aatctctttg    300

cgcagcgcgc gaacttcttc aacagagatg atcatcggga acataatgcg caatttaccg    360

aaagcggagg cacgcagaat cgcgcgaacc tggtcacgca ggatctcttt gcgatccatg    420

gcgatacgca cggcgcgcca gccnaagaac ggat                                454
```

<210> SEQ ID NO 141
<211> LENGTH: 454
<212> TYPE: DNA
<213> ORGANISM: Salmonella enterica Brandenburg
<220> FEATURE:
<221> NAME/KEY: misc_feature
<222> LOCATION: (444)..(444)
<223> OTHER INFORMATION: n is a, c, g, or t -continued

<400> SEQUENCE: 141
ccgcacatgc cagtccattt accttctgca tgagaagcat caataacttg cttgatcaag 60
ttcagtacgg acggtgacat tggctggtaa aggtgtgaaa tcatatcatt accacggtca 120
actgccaggg tgtactgcgt taaatcattg gtgccgatac taaagaaatc aacttctttg 180
gctaaatgac gcgcaattgt cgccgcagcc ggtgtttcca ccatcacgcc aatctcaatg 240
ctttcgtcaa atgctttacc ttcgtcacgc agttcctgtt tgtagatttc aatctctttg 300
cgcagcgcgc gaacttcttc aacagagatg atcatcggga acataatgcg caatttaccg 360
aaagcggagg cacgcagaat cgcgcgaacc tggtcacgca ggatctcttt gcgatccatg 420
gcgatacgca cggcgcgcca gccnaagaac ggat 454

<210> SEQ ID NO 142
<211> LENGTH: 454
<212> TYPE: DNA
<213> ORGANISM: Salmonella enterica derby
<220> FEATURE:
<221> NAME/KEY: misc_feature
<222> LOCATION: (444)..(444)
<223> OTHER INFORMATION: n is a, c, g, or t

<400> SEQUENCE: 142
ccgcacatgc cagtccattt accttctgca tgagaagcat caataacttg cttgatcaag 60
ttcagtacgg acggtgacat tggctggtaa aggtgtgaaa tcatatcatt accacggtca 120
actgccaggg tgtactgcgt taaatcattg gtgccgatac taaagaaatc aacttctttg 180
gctaaatgac gcgcaattgt cgccgcagcc ggtgtttcca ccatcacgcc aatctcaatg 240
ctttcgtcaa atgctttacc ttcgtcacgc agttcctgtt tgtagatttc aatctctttg 300
cgcagcgcgc gaacttcttc aacagagatg atcatcggga acataatgcg caatttaccg 360
aaagcggagg cacgcagaat cgcgcgaacc tggtcacgca ggatctcttt gcgatccatg 420
gcgatacgca cggcgcgcca gccnaagaac ggat 454

<210> SEQ ID NO 143
<211> LENGTH: 454
<212> TYPE: DNA
<213> ORGANISM: Salmonella enterica virschow
<220> FEATURE:
<221> NAME/KEY: misc_feature
<222> LOCATION: (444)..(444)
<223> OTHER INFORMATION: n is a, c, g, or t

<400> SEQUENCE: 143
ccgcacatgc cagtccattt accttctgca tgagaagcat caataacttg cttgatcaag 60
ttcagtacgg acggtgacat tggctggtaa aggtgtgaaa tcatatcatt accacggtca 120
actgccaggg tgtactgcgt taaatcattg gtgccgatac taaagaaatc aacttctttg 180
gctaaatgac gcgcaattgt cgccgcagcc ggtgtttcca ccatcacgcc aatctcaatg 240
ctttcgtcaa atgctttacc ttcgtcacgc agttcctgtt tgtagatttc aatctctttg 300
cgcagcgcgc gaacttcttc aacagagatg atcatcggga acataatgcg caatttaccg 360
aaagcggagg cacgcagaat cgcgcgaacc tggtcacgca ggatctcttt gcgatccatg 420
gcgatacgca cggcgcgcca gccnaagaac ggat 454

<210> SEQ ID NO 144
<211> LENGTH: 454
<212> TYPE: DNA
<213> ORGANISM: Salmonella enterica paratyphi B -continued
<220> FEATURE:
<221> NAME/KEY: misc_feature
<222> LOCATION: (444)..(444)
<223> OTHER INFORMATION: n is a, c, g, or t

<400> SEQUENCE: 144
ccgcacatgc cagtccattt accttctgca tgagaagcat caataacttg cttgatcaag 60
ttcagtacgg acggtgacat tggctggtaa aggtgtgaaa tcatatcatt accacggtca 120
actgccaggg tgtactgcgt taaatcattg gtgccgatac taaagaaatc aacttctttg 180
gctaaatgac gcgcaattgt cgccgcagcc ggtgtttcca ccatcacgcc aatctcaatg 240
ctttcgtcaa atgctttacc ttcgtcacgc agttcctgtt tgtagatttc aatctctttg 300
cgcagcgcgc gaacttcttc aacagagatg atcatcggga acataatgcg caatttaccg 360
aaagcggagg cacgcagaat cgcgcgaacc tggtcacgca ggatctcttt gcgatccatg 420
gcgatacgca cggcgcgcca gccnaagaac ggat 454

<210> SEQ ID NO 145
<211> LENGTH: 458
<212> TYPE: DNA
<213> ORGANISM: Streptococcus thermophilus

<400> SEQUENCE: 145
ccgctcatac cagcccattt accttcagcg tgagctgcct taataacgtt gttaatcaag 60
cgaaggattg atgggttata tggttggtaa aggtatgaaa cttgttcatt catacggtca 120
gcagccattg tgtattggat aaggtcgttt gtaccaattg agaagaaatc aacttcttta 180
gcaaattggt cagcaagcat tgctgcagct gggatttcaa tcatgatacc tacttcgatg 240
tcgtttgcaa cggcaacacc ttcagcaacc aatttagctt tttcttcttc aagaatacct 300
ttagcagtac ggaactcagt caacaaagca accattggga acatgatacg caatttaccg 360
tgaacagatg cacgaagcaa ggcacgtaat tgagtacgga acatttggtt accagtttca 420
gagatagaaa tacgtaatgc acggtaaccc aagaacgg 458

<210> SEQ ID NO 146
<211> LENGTH: 455
<212> TYPE: DNA
<213> ORGANISM: Streptococcus suis
<220> FEATURE:
<221> NAME/KEY: misc_feature
<222> LOCATION: (450)..(450)
<223> OTHER INFORMATION: n is a, c, g, or t

<400> SEQUENCE: 146
gcccacatac cagcccattt accttctgcg tgtgcagcct tgataacatt gttaatcaag 60
cgaaggattg atgggttata tggttggtag aggtatgaaa cttgttcatt catacggtct 120
gcagccattg tgtactggat aaggtcgttc gtaccgattg agaagaagtc aacttctttg 180
gcaaattggt ctgcaagcat tgctgctgca gggatttcaa tcatgatacc aacttggata 240
tcatccgcaa ctgctacacc ttcagccaac aagtttgctt tttcttcatc aaggattgct 300
tttgctgcac ggaattcagt caacaaggca accattggga acatgatacg aagtttacca 360
tgtactgatg aacgaagaag ggcacgcaac tgagtgcgga acatttggtt accagtctca 420
gagatagaga tacgaagggc acggaaaccn aagaa 455

<210> SEQ ID NO 147
<211> LENGTH: 449
<212> TYPE: DNA

-continued

<213> ORGANISM: Bacillus pseudomyco?es

<400> SEQUENCE: 147
ccgcacatac cagcccattt tccttcttta tgagcagcat cgataaccat ttttacaagg 60
cgtaaaatag atggattata cggttggtat aagtaagata cacgttcatt catacggtct 120
gcagccattg tgtattggat taggtcgttt gttccgatag agaagaaatc aacttctttt 180
gcaaactgat ctgctaatac tgcagaagcg ggaatttcta ccatcatacc tacctcaata 240
gcatcagaaa cagttgtacc agcttgaaca agtctttctt tctcttctaa taaaattgct 300
tttgcttgac ggaattcatc aagagttgca atcattggga acataatttt taaattacca 360
tatacgcttg cacgaagcaa tgcacgaagt tgtgtacgga acacatcttg ttcttcaagg 420
cataagcgaa tcgcacggta acccaagaa 449

<210> SEQ ID NO 148
<211> LENGTH: 450
<212> TYPE: DNA
<213> ORGANISM: Staphylococcus lugdunensis
<220> FEATURE:
<221> NAME/KEY: misc_feature
<222> LOCATION: (445)..(445)
<223> OTHER INFORMATION: n is a, c, g, or t

<400> SEQUENCE: 148
ccgcacatac cagtccattt accttcttta tgagaagctt caatcacttg tttcactaga 60
cgtaaaatag ctggattata tggttgataa aggtatgata cacgttctga catgcggtca 120
gcagccattg tgtattgaat caaatcatta gtaccgatac tgaagaaatc aacttcttta 180
gcaaagatat cagctaatgc agctgttgat gggatttcta ccattattcc gagctcgata 240
tcatctgaca cgtcatgtcc ttcatttttt agattttctt tttcttctaa aagaagcgct 300
ttggcatctc taaactcatt aatagtagca accattggga acataatatt taatttttcc 360
atatgctgaa gcacgcaaaa gagcgcgcaa ctgtggtctg aaaatatcag gttgatctaa 420
gcacaatcga atcgcacggt aaccnaagaa 450

<210> SEQ ID NO 149
<211> LENGTH: 590
<212> TYPE: DNA
<213> ORGANISM: Cryptococcus neoformans

<400> SEQUENCE: 149
cgacagttat gaccgacccg gatcttctgt gatggatttg agtaagagca tatatgctgg 60
gacccgaaag atggtgaact atgcctgaat agggcgaagc caggggaaac tctggtggag 120
gctcgtagcg attctgacgt gcaaatcgat cgtcgaattt gggtataggg gcgaaagact 180
aatcgaacca tctagtagct ggttcctgcc gaagtttccc tcaggatagc agaaactcgc 240
atcagtttta tgaggtaaag cgaatgatta gaggccttgg ggacgaaacg tccttaacct 300
attctcaaac tttaaatgtg taagaagcac ttgtcactta attggacgag cgcatgcgaa 360
tgagagtttc tagtgggcca tttttggtaa gcagaactgg cgatgcggga tgaaccgatc 420
gcgaggttaa ggtgccggaa tacacgctca tcagacacca caaaaggtgt tagttcatct 480
agacagcagg acggtggcca tggaagtcgg aatccgctaa ggagtgtgta acaactcacc 540
tgccgaatga actagccctg aaaatggatg gcgctcaagc gtgttaccca 590

<210> SEQ ID NO 150
<211> LENGTH: 480

-continued

<212> TYPE: DNA
<213> ORGANISM: Streptococcus thermophilus
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 150
ttgnaacggc ttatgctgta gnacaagnac accgaagggg caagggataa gacccgaaac 60
tctcaggtaa aaggacagaa agcattgaat gtttttaact ttcagtaata gctttgtact 120
ttcagaggtc tggttaagcc aaacctcttt ttgatgtctc ggtctaagga gattttaaac 180
gcatgttaga ctttttcact tccattgatg actttgtatg gggacctccc cttcttgtcc 240
ttcttgtagg aactggtatc taccttacaa tccgtcttgg acttttgcaa atcattcgtc 300
tgcctaaagc ctttaaactt atctttgctg aagataaagg agagggtgat atttctagtt 360
ttgcagccct tgccacagca cttgctgcaa ctgttggtac tggtaacatt gttggtgttg 420
cgacagccat taagactggt gggcctggtg ctcttttctg gatgtggatt gctgctttct 480

<210> SEQ ID NO 151
<211> LENGTH: 457
<212> TYPE: DNA
<213> ORGANISM: Enterococcus villorum

<400> SEQUENCE: 151
ccgaaggggc aagggataag acccgaaact ctcaggtaaa aggacagaaa gcattgaatg 60
tttttaactt tcagtaatag ctttgtactt tcagaggtct ggttaagcca aacctctttt 120
tgatgtctcg gtctaaggag attttaaacg catgttagac tttttcactt ccattgatga 180
ctttgtatgg ggacctcccc ttcttgtcct tcttgtagga actggtatct accttacaat 240
ccgtcttgga cttttgcaaa tcattcgtct gcctaaagcc tttaaactta tctttgctga 300
agataaagga gagggtgata tttctagttt tgcagccctt gccacagcac ttgctgcaac 360
tgttggtact ggtaacattg ttggtgttgc gacagccatt aagactggtg ggcctggtgc 420
tcttttctgg atgtggattg ctgctttctt tggaatg 457

<210> SEQ ID NO 152
<211> LENGTH: 498
<212> TYPE: DNA
<213> ORGANISM: Streptococcus pyogenes
<220> FEATURE:
<221> NAME/KEY: misc_feature
<222> LOCATION: (4)..(4)
<223> OTHER INFORMATION: n is a, c, g, or t

<400> SEQUENCE: 152
ttanaggcgc cgaggggcaa ggcatactgc tcaatctctc aggcaaaagg acagaaggta 60
aaatacaaac accattaaga acagtcttag tctttttgt gtttgctgtt ttatcattgc 120
ttcagaagtt gtctcaaaga aagagatagc ttttttcttt tggcgtcttc gatgactttt 180
aggagagaaa gatgatagca ctcgttaaat taattgataa ccttgtttgg ggaccgcccc 240
tcttaatttt attggttggg acggggattt accttaccag tcatttagga ttaattcaaa 300

-continued

```
tcttaaaact accaagagcc tttaaactca ttttttcaga tgacgaagga catggagata    360

tttcatcctt tgctgctctt gcaactgccc ttgccgctac tgtcggaact ggtaacattg    420

ttggggttgc cactgctatc aagtctggtg gtcctggagc gctcttttgg atgtgggttg    480

ccgctttttt tggaatgg                                                  498
```

<210> SEQ ID NO 153
<211> LENGTH: 476
<212> TYPE: DNA
<213> ORGANISM: Streptococcus mutans

<400> SEQUENCE: 153

```
gcgccgaggg gcaaggctgt ttgctcaaac tctcaggcaa aaggacagaa aagaaaaaaa     60

gaatttttaa tgttgaaaca attcttatct tctaactcta gaggtatcgt caagtattga    120

caacctcttt tttgatttcc atttcggttt atgaggagaa aagtttatat gttaacattt    180

tttaaagctc tagacagctt tgtctggggt gttcccctat tagttctttt agtcggtact    240

ggaatttatt tgagtactcg cttaagatta ttgcaggtat tgaaactccc tttagccttt    300

aaactcatct ttgccgagga caaaggggaa ggtgatattt cgagttttgc ggctttagct    360

actgctcttg ctgccactgt tggaactgga aatatcgttg gtgttgccac tgcaatcaaa    420

gctggcggtc cgggagcact cttttggatg tggatagcag ctttttttgg aatggc        476
```

<210> SEQ ID NO 154
<211> LENGTH: 576
<212> TYPE: DNA
<213> ORGANISM: Streptococcus agalactiae
<220> FEATURE:
<221> NAME/KEY: misc_feature
<222> LOCATION: (31)..(31)
<223> OTHER INFORMATION: n is a, c, g, or t

<400> SEQUENCE: 154

```
aagtagcaac atctttgtat tgacaccaag natgtgctct aggcgccgaa ggggcaagaa     60

gagtaaaaca actcctccaa tctctcaggc aaaaggacag aagctaaaag ccaatattaa    120

taatgagtag taagcttatt aagtttacta ctacctttat ttgtgcgctt tttagctagc    180

atctttcaga agttatctct tttagagata actttttttcg tttcattaca gaatccatag    240

gtatgtcatg tatcaaagga gaacatatgc taacactttt tactcatatc aatagcttcg    300

tttggggtcc acctttactt gctttattag tcggaacagg tatttaccta tcatttcgct    360

taggttttgt tcaattgaga caactttcta gagctttcaa attgattttc cgagaagata    420

acggacaagg ggatatttca agttatgctg ctcttgcaac tgctcttgct gcaacggtag    480

ggacaggtaa tatcgttggt gtggctacgg ctattaaatc tggaggacca ggagctttgt    540

tttggatgtg ggtagccgcc ttttttggaa tggccc                              576
```

<210> SEQ ID NO 155
<211> LENGTH: 440
<212> TYPE: DNA
<213> ORGANISM: Streptococcus sanguis
<220> FEATURE:
<221> NAME/KEY: misc_feature
<222> LOCATION: (237)..(237)
<223> OTHER INFORMATION: n is a, c, g, or t

<400> SEQUENCE: 155

```
tagaaccgct caaactctca ggtaaaagga cagagcgaag aggcagggat ttccctactc     60

cagcacatcc aggagtacat gttttgcatg tgctctttct ttttctcggt gtgaaaagga    120
```

-continued

```
gcttatatca tgttggaaat attgaatcgt ctggattctt ttgtttgggg tccgcccctg    180

ctcattttgc tggttggtac tggtatctat ctcagtctgc gtctgggctt gctgcanatt    240

tttcgacttc ctcgtgcctt tcggctaatc tttgtatcgg acgaggagca tcagggcgat    300

gtctctagct ttgcggctct ctgtacggct ctagccgcga ctgtgggaac gggaaatatc    360

atcggagtgg caactgccat taaaaccggt ggaccggggg cgctcttctg gatgtgggtg    420

gctgctttct ttggaatggc                                                440
```

```
<210> SEQ ID NO 156
<211> LENGTH: 450
<212> TYPE: DNA
<213> ORGANISM: Streptococcus oralis

<400> SEQUENCE: 156

gggcaaggca ggtaactgct caaactctca ggtaaaagga cagagctagg atagaccgct     60

ttttggcatt tatctaagca ttccagagta catgtatctt gcatgtactc tttcttttgg    120

ggttgaaaga taggagaagg acatgttaga attgcttaaa gcgcttgatg cttttgcttg    180

ggggcctccc ctcttgatct tattggtcgg aacgggtatc tatttgacca tccgactggg    240

ccttttgcag gttactcgtc tccctaaggc ctttcagttg atctttacca aggacaaggg    300

gcacggcgat gtgtcgagct ttgctgctct ctgtacggct ctagcagcca cagttggtac    360

gggaaatatc atcggggtag cgacagccat taaggttgga ggaccagggg ccctcttttg    420

gatgtggatg gcggccttct ttggaatggc                                     450
```

```
<210> SEQ ID NO 157
<211> LENGTH: 498
<212> TYPE: DNA
<213> ORGANISM: Streptococcus suis
<220> FEATURE:
<221> NAME/KEY: misc_feature
<222> LOCATION: (12)..(12)
<223> OTHER INFORMATION: n is a, c, g, or t

<400> SEQUENCE: 157

ttttggcccg angggcaagg tagtcctgct tggaaaagta gagctactga aactctcagg     60

taaaaggaca gagcgttgaa aaataggctt tttctgtatt tttcacgttg attctagagg    120

ttgaagtgtt cagcctcttt ttgtttttcc ggcagcttta tcgggttaga aacgcttagg    180

aggaactatg ttagaactat ttaaggctat caacaatctt gtttggggac cgcccctctt    240

gttactattg gtcggaacgg gtgtctattt taccctacgg ttgggagtat ttcagattgg    300

caaattgccg acggcttttc gtctgatttt ctccagtgac cagtctggtc agggagatgt    360

gtccagtttt gcggctctgt gtacggcttt agcagcgaca gttggtacag gaaatatcgt    420

cggagttgcg acagctatta ctacaggtgg tcctggggct cttttctgga tgtgggttgc    480

ggcctttttt ggaatggc                                                  498
```

```
<210> SEQ ID NO 158
<211> LENGTH: 469
<212> TYPE: DNA
<213> ORGANISM: Staphylococcus simulans

<400> SEQUENCE: 158

atccggcttt gagtttaaag ctattgatgc tttaattacg aacttccatc tgccgaagtc     60

cacacttgtc atgttagttt cagcattcag ttcaaaacaa tatattttaa atgcatacca    120
```

-continued

```
aacagctgtc gaaatgaaat atcgattctt cagctttggt gatgcaatgt taattattta    180

agggagtcgt gaaaaagtta tgcctgcagt aacttatgaa catatcaaaa catgtaaaca    240

atccggtgca aggttaggaa tcgtgcatac accgcacggt tcgtttgaaa cacctatgtt    300

tatgccagta ggaactcaag ctaccgttaa aactatgagt cctgaagaac taagggaaat    360

taatgcacaa atcattttag gcaacacata ccatttatgg ttgcaacccg gcaatgacat    420

tattaaacgc gcgggtggtt tgcataaatt tatgatttgg aatggccac                469
```

<210> SEQ ID NO 159
<211> LENGTH: 467
<212> TYPE: DNA
<213> ORGANISM: Enterococcus faecalis

<400> SEQUENCE: 159

```
gtaaaggcac cgaaggggca aggcaggtaa ctgctcaaac tctcaggtaa aaggacagag     60

ctaggataga ccgctttttg gcatttatct aagcattcca gagtacatgt atcttgcatg    120

tactctttct tttggggttg aaagatagga gaaggacatg ttagaattgc ttaaagcgct    180

tgatgctttt gcttgggggc ctcccctctt gatcttattg gtcggaacgg gtatctattt    240

gaccatccga ctgggccttt tgcaggttac tcgtctccct aaggcctttc agttgatctt    300

taccaaggac aaggggcacg gcgatgtgtc gagctttgct gctctctgta cggctctagc    360

agccacagtt ggtacgggaa atatcatcgg ggtagcgaca gccattaagg ttggaggacc    420

aggggccctc ttttggatgt ggatggcggc cttctttgga atggccc                  467
```

<210> SEQ ID NO 160
<211> LENGTH: 468
<212> TYPE: DNA
<213> ORGANISM: Streptococcus pneumoniae

<400> SEQUENCE: 160

```
gtaaaggcac cgaaggggca aggcaggcaa ctgctcaaac tctcaggtaa aaggacagag     60

ctaggataga ccgcttttta gcatttatct aagcattcca gagtacatgt atcttgcatg    120

tgctctttct tttggggttg aaacgatagg agaaggaaat gttagaattg cttaaatcaa    180

tcgatgcttt tgcttgggga ccgcccctct tgattttatt ggtcggaaca gggatttacc    240

taaccatgcg gctaggactc ttgcaggttt tgcgtctgcc caaggccttt cagcttattt    300

ttatccagga taagggacat ggtgatgtat ccagttttac agctctgtgt acagccttgg    360

catcaactgt tggaacagga aatatcatag gagttgcgac ggctatcaag gttggtggac    420

caggagctct attttggatg tggatggcgg ttttctttgg aatggccc                 468
```

<210> SEQ ID NO 161
<211> LENGTH: 463
<212> TYPE: DNA
<213> ORGANISM: Enterococcus durans
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 161

-continued

```
ngnccgaggg gcaaggtcag nacaactgct caaactctca ggtaaaagga cagagctagg     60

atagaccgct ttttagcatt tatctaagca ttccagagta catgtatctt gcatgtgctc    120

tttcttttgg ggttgaaacg ataggagaag gaaatgttag aattgcttaa atcaatcgat    180

gcttttgctt ggggaccgcc cctcttgatt ttattggtcg gaacagggat ttacctaacc    240

atgcggctag gactcttgca ggttttgcgt ctgcccaagg cctttcagct tatttttatc    300

caggataagg gacatggtga tgtatccagt tttacagctc tgtgtacagc cttggcatca    360

actgttggaa caggaaatat cataggagtt gcgacggcta tcaaggttgg tggaccagga    420

gctctatttt ggatgtggat ggcggttttc tttggaatgg ccc                      463
```

<210> SEQ ID NO 162
<211> LENGTH: 517
<212> TYPE: DNA
<213> ORGANISM: Bacillus anthracis
<220> FEATURE:
<221> NAME/KEY: misc_feature
<222> LOCATION: (1)..(1)
<223> OTHER INFORMATION: n is a, c, g, or t

<400> SEQUENCE: 162

```
ngaggaaaac gagcaccgaa ggagcaaatc cgctactata gcggataatc tctcaggtaa     60

aaggacagag acaagcgaaa gaaaatgccg atttgtatcg gtttattttt ctatcccttg    120

tttctccaga gaccatttca tttacttgaa gtggttttta ttttttctaa aaaaggagaa    180

taaagatgga gacagtaagt aaagtattag aacaaatcaa tcactatgtg tggggattac    240

caacgttatt gttactcgtt ggtactggta ttattctcac agtgcgttta aaaggtttac    300

agtttagtaa actattatac gctcacaaac tagcttttaa aaaatcagaa gatacatctt    360

cctctggaga tattagccac ttccaagcgc ttatgacagc tatggcggca acgattggta    420

tgggaaatat agctggtgtt gcaactgctg tgacgatcgg tggacctggt gcaatctttt    480

ggatgtggat tactgctttg tttggaatgg cccaaaa                             517
```

<210> SEQ ID NO 163
<211> LENGTH: 539
<212> TYPE: DNA
<213> ORGANISM: Bacillus anthracis Sterne
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 163

```
tncncgcttt aaatagcgta gnaggcaaaa cgagcaccga aggagcaaat ccgctactat     60

agcggataat ctctcaggta aaaggacaga gacaagcgaa agaaaatgcc gatttgtatc    120

ggtttatttt tctatccctt gtttctccag agaccatttc atttacttga agtggttttt    180

attttttcta aaaaaggaga ataaagatgg agacagtaag taaagtatta gaacaaatca    240

atcactatgt gtggggatta ccaacgttat tgttactcgt tggtactggt attattctca    300

cagtgcgttt aaaaggttta cagtttagta aactattata cgctcacaaa ctagctttta    360
```

-continued

```
aaaaatcaga agatacatct tcctctggag atattagcca cttccaagcg cttatgacag    420

ctatggcggc aacgattggt atgggaaata tagctggtgt tgcaactgct gtgacgatcg    480

gtggacctgg tgcaatcttt tggatgtgga ttactgcttt gtttggaatg gcccaaaaa     539
```

<210> SEQ ID NO 164
<211> LENGTH: 539
<212> TYPE: DNA
<213> ORGANISM: Bacillus anthracis Butare
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 164

```
nncncncgct ntaaatagcg tagaggcaaa acgagcaccg aaggagcaaa tccgctacta     60

tagcggataa tctctcaggt aaaaggacag agacaagcga aagaaaatgc cgatttgtat    120

cggtttattt ttctatccct tgtttctcca gagaccattt catttacttg aagtggtttt    180

tattttttct aaaaaaggag aataaagatg gagacagtaa gtaaagtatt agaacaaatc    240

aatcactatg tgtggggatt accaacgtta ttgttactcg ttggtactgg tattattctc    300

acagtgcgtt taaaaggttt acagtttagt aaactattat acgctcacaa actagctttt    360

aaaaaatcag aagatacatc ttcctctgga gatattagcc acttccaagc gcttatgaca    420

gctatggcgg caacgattgg tatgggaaat atagctggtg ttgcaactgc tgtgacgatc    480

ggtggacctg gtgcaatctt ttggatgtgg attactgctt tgtttggaat ggcccaaaa     539
```

<210> SEQ ID NO 165
<211> LENGTH: 538
<212> TYPE: DNA
<213> ORGANISM: Bacillus anthracis
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 165

```
tntntcgctt tnatagcgta gtaggcaaaa cgagcaccga aggagcaaat ccgctactat     60

agcggataat ctctcaggta aaaggacaga gacaagcgaa agaaaatgcc gatttgtatc    120

ggtttatttt tctatccctt gtttctccag agaccatttc atttacttga agtggttttt    180

atttttttcta aaaaaggaga ataaagatgg agacagtaag taaagtatta gaacaaatca    240

atcactatgt gtggggatta ccaacgttat tgttactcgt tggtactggt attattctca    300

cagtgcgttt aaaaggttta cagtttagta aactattata cgctcacaaa ctagctttta    360
```

-continued

```
aaaaatcaga agatacatct tcctctggag atattagcca cttccaagcg cttatgacag    420

ctatggcggc aacgattggt atgggaaata tagctggtgt tgcaactgct gtgacgatcg    480

gtggacctgg tgcaatcttt tggatgtgga ttactgcttt gtttggaatg gcccaaaa      538


<210> SEQ ID NO 166
<211> LENGTH: 541
<212> TYPE: DNA
<213> ORGANISM: Bacillus anthracis Coda-Cerva
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t

<400> SEQUENCE: 166

ctntncncgc tttaaatagc gtagaggcaa aacgagcacc gaaggagcaa atccgctact     60

atagcggata atctctcagg taaaaggaca gagacaagcg aaagaaaatg ccgatttgta    120

tcggtttatt tttctatccc ttgtttctcc agagaccatt tcatttactt gaagtggttt    180

ttattttttc taaaaaagga gaataaagat ggagacagta agtaaagtat tagaacaaat    240

caatcactat gtgtggggat taccaacgtt attgttactc gttggtactg gtattattct    300

cacagtgcgt ttaaaaggtt tacagtttag taaactatta tacgctcaca aactagcttt    360

taaaaaatca gaagatacat cttcctctgg agatattagc cacttccaag cgcttatgac    420

agctatggcg gcaacgattg gtatgggaaa tatagctggt gttgcaactg ctgtgacgat    480

cggtggacct ggtgcaatct tttggatgtg gattactgct ttgtttggaa tggcccaaaa    540

a                                                                     541


<210> SEQ ID NO 167
<211> LENGTH: 537
<212> TYPE: DNA
<213> ORGANISM: Bacillus anthracis
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (533)..(533)
<223> OTHER INFORMATION: n is a, c, g, or t

<400> SEQUENCE: 167

tncncgcttt naatagcgta gaggcaaaac gagcaccgaa ggagcaaatc cgctactata     60

gcggataatc tctcaggtaa aaggacagag acaagcgaaa gaaaatgccg atttgtatcg    120

gtttattttt ctatcccttg tttctccaga gaccatttca tttacttgaa gtggttttta    180

tttttctaa aaaaggagaa taaagatgga gacagtaagt aaagtattag aacaaatcaa     240
```

-continued

```
tcactatgtg tggggattac caacgttatt gttactcgtt ggtactggta ttattctcac    300

agtgcgttta aaaggtttac agtttagtaa actattatac gctcacaaac tagcttttaa    360

aaaatcagaa gatacatctt cctctggaga tattagccac ttccaagcgc ttatgacagc    420

tatggcggca acgattggta tgggaaatat agctggtgtt gcaactgctg tgacgatcgg    480

tggacctggt gcaatctttt ggatgtggat tactgctttg tttggaatgg ccnaaaa       537
```

<210> SEQ ID NO 168
<211> LENGTH: 531
<212> TYPE: DNA
<213> ORGANISM: Bacillus cereus

<400> SEQUENCE: 168

```
tgcttgctag agcgcggagg aaaacgagca ccgaaggagc aaatccgcta ctttagcgga     60

taatctctca ggtaaaagga cagagacaag cgaaagaaaa agccgattgt atcggtttat    120

ttttctatcc cttgtttctc cagagaccat ttcatttact tgaagtggtt tttatttttt    180

ctaaaaaagg agaataaaga tggagacagt aagtaaagta ttagaacaac tgaatcaata    240

cgtgtgggga ttaccaactt tgttgctact cgttggaaca ggtatcattc tcacagtgcg    300

tttaaaaggt ttacagttta gtaaactatt atacgctcac aaactagcat ttaaaaaatc    360

agaagatgcc tcttcttctg gagatattag tcacttccaa gcacttatga cagctatggc    420

cgcaacgatt ggtatgggaa atatagccgg tgttgcaaca gctgttacaa ttggtggtcc    480

tggtgcaata ttttggatgt ggattaccgc tttatttgga atggcccaaa a             531
```

<210> SEQ ID NO 169
<211> LENGTH: 527
<212> TYPE: DNA
<213> ORGANISM: Bacillus cereus

<400> SEQUENCE: 169

```
tagcagtcgc ggcggaaaaa cgagcaccga aggagcaaat ccgctacttt agcggataat     60

ctctcaggta aaaggacaga gacaagcgaa agaaaaagcc gattgtatcg gtttattttt    120

ctatcccttg tttctccaga gaccatttca tttacttgaa gtggttttta tttttttctaa    180

aaaaggagaa taaagatgga gacagtaagt aaagtattag aacaactaaa tcaatacgtg    240

tggggattac caactttgtt gctactcgtt ggaacaggta tcattctcac agtgcgtttg    300

aaaggtttac agtttagtaa actattatac gctcacaaac tagcgtttaa aaaatcagaa    360

gatacttctt cttctggaga tattagtcac ttccaagcac tcatgacagc tatggccgca    420

acgattggta tgggtaatat agccggtgtt gcaacagcgg ttacaattgg tggtcctggt    480

gcaatatttt ggatgtggat taccgcttta tttggaatgg cccaaaa                  527
```

<210> SEQ ID NO 170
<211> LENGTH: 519
<212> TYPE: DNA
<213> ORGANISM: Bacillus thuringiensis serovar israelensis

<400> SEQUENCE: 170

```
tatagcgcag aggaaaacga gcaccgaagg agcaaatccg ctactatagc ggataatctc     60

tcaggtaaaa ggacagagac aagcgaaaga aaatgccgat ttgtatcggt ttatttttct    120

atcccttgtt tctccagaga ccatttcatt tacttgaagt ggtttttatt tttttctaaa    180

aaaggagaat acagatggag acagtaagta aagtgttaga acaaatcaat cactatgtgt    240

ggggactacc aacgttgttg ttactcgttg gtactggtat cattctcaca gtgcgtttaa    300
```

-continued

```
aaggtttaca gtttagtaaa ctattatacg ctcacaaact agcttttaaa aaatcagaag    360

atacatcttc ttctggagat attagccact tccaagcgct tatgacagct atggcggcaa    420

cgattggtat gggaaatatc gctggtgttg caacagctgt gacaatcggt ggtcccggtg    480

caatcttttg gatgtggatt actgctttgt ttggaatgg                           519
```

<210> SEQ ID NO 171
<211> LENGTH: 522
<212> TYPE: DNA
<213> ORGANISM: Bacillus myco?es serovar

<400> SEQUENCE: 171

```
gtggaggaaa gagagcaccg aaggagcaaa tccgctagct agtatagcgg ataatctctc     60

aggtaaaagg acagagacaa gcgaaagaaa atgccgattt ggatcggttt atttttctat    120

cacttgtttc tccagagacc atttcatttt gtgaagtggt tttttatttt ttctaaaaag    180

gagaataaag atggagacag taagtaaagt actagaacaa atcaatcatt acgtatgggg    240

attaccaacc ttgttcctac tcgttggaac tggaatcatt cttacagtgc gtctaaaagg    300

tttacagttt agtaaactat tatacgctca caaactagct tttaaaaaat cagaagacac    360

atcttctact ggagatatta gtcattttca agcacttatg accgctatgg cagcaacaat    420

tggaatggga aatatagctg gtgtcgcaac cgctgttaca attggtggtc ccggtgcaat    480

attttggatg tggattaccg ccctgtttgg aatggcccaa aa                       522
```

<210> SEQ ID NO 172
<211> LENGTH: 530
<212> TYPE: DNA
<213> ORGANISM: Bacillus myco?es serovar
<220> FEATURE:
<221> NAME/KEY: misc_feature
<222> LOCATION: (458)..(458)
<223> OTHER INFORMATION: n is a, c, g, or t

<400> SEQUENCE: 172

```
cgcttctata gcgcggagga aaacgagcac cgaaggagca aatccgctaa tctagcggat     60

aatctctcag gtaaaaggac agagacaagc gaaagaaaat gccgatttgt atcggtttat    120

ttttctatcc cttgtttctc cagagaccat ttcatttcct tgaagtggtt tttatttttt    180

ctaaaaaagg agaatacaga tggagacagt aagtaaagta ttagaacaaa ttaatcagta    240

tgtgtggggg ttgccaactt tattgctact cgttggaact ggtatcattc tcacagtgcg    300

cttaaaaggt ttacagttta gtaaactaat atacgctcac aaacttgctt ttaaaaaatc    360

agaggataca tcatcttctg gagatattag tcacttccaa gcactgatga cggctatggc    420

tgcaacgatt ggtatgggaa atatagcagg tgtcgcanct gctgtgacga tcggtggacc    480

cggtgcgatc ttctggatgt ggattaccgc gttgtttgga atggcccaaa               530
```

<210> SEQ ID NO 173
<211> LENGTH: 515
<212> TYPE: DNA
<213> ORGANISM: Bacillus thuringiensis serovar Kurstaki

<400> SEQUENCE: 173

```
gaggaaacag agcaccgaag gagcaaatcc gcttatatta gcggataatc tctcaggtaa     60

aaggacagag acaagcgaaa gaaaacgccg atttgtatcg gtttattttt ctattccttg    120

tttctccaga gaccatttca tttatgtgaa gtggtttttt attttttcta aaaggagaat    180
```

-continued

```
aaagatggag acagtaagta aagtattaga acaaatcaat cactacgtat ggggattacc    240

gaccttattc cttctaatcg gaactggaat cattctcaca gtgcgcctaa aaggtttaca    300

gtttagtaga ctattatacg ctcacaaact agcatttcga aaatcagaag acacatcttc    360

tttgggagat attagtcatt tccaagcact catgacagca atggccgcaa ctattgggat    420

gggaaatata gccggtgtcg caacagctgt tacaatcggt gggccagggg caatattttg    480

gatgtggatc actgccttgt ttggaatggc ccaaa                               515
```

<210> SEQ ID NO 174
<211> LENGTH: 533
<212> TYPE: DNA
<213> ORGANISM: Enterococcus faecium

<400> SEQUENCE: 174

```
gacggaattc tggagagacc ttattaggcg ccgaaggggc aaggcatact gctcaatctc     60

tcaggcaaaa ggacagaagg tagaatacaa acaccattaa gaacagtctt agtctttttt    120

gtgtttgctg ttttatcatt gcttcagaag ttgtctcaaa gaaagagata gctttttttct    180

tttggcgtct tcgatgactt ttaggagaga aagatgatag cactcgttaa attaattgat    240

aaccttgttt ggggaccgcc cctcttaatt ttattggttg ggacggggat ttaccttacc    300

agtcatttag gattaattca aatcttaaaa ctaccaagag cctttaaact catttttttca    360

gatgacgaag gacatggaga tatttcatcc tttgctgctc ttgcaactgc ccttgccgct    420

actgtcggaa ctggtaacat tgttggggtt gccactgcta tcaagtctgg tagtcctgga    480

gcgctctttt ggatgtgggt tgccgctttt tttggaatgg caacaaaata cgc           533
```

<210> SEQ ID NO 175
<211> LENGTH: 536
<212> TYPE: DNA
<213> ORGANISM: Enterococcus casseliflavus
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t

<400> SEQUENCE: 175

```
gnaccggaat tctgagagac cttattaggg cgccggaagg ggcaaggcat actgctcaat     60

ctctcaggcn aaaggncaga aggtaaaata caaacaccat taagaacagt cttagtcttt    120

tttgtgtttg ctgttttatc attgcttcag aagttgtctc aaagaaagag atagcttttt    180

tcttttggcg tcttcgatga cttttaggag agaaagatga tagcactcgt taaattaatt    240

gataaccttg tttggggacc gcccctctta attttattgg ttgggacggg gatttacctt    300

accagtcatt taggattaat tcaaatctta aaactaccaa gagcctttaa actcattttt    360

tcagatgacg aaggacatgg agatatttca tcctttgctg ctcttgcaac tgcccttgcc    420

gctactgtcg gaactggtaa cattgttggg gttgccactg ctatcaagtc tggtggtcct    480

ggagcgctct tttggatgtg ggttgccgct ttttttggaa tggccacaaa atacgc        536
```

<210> SEQ ID NO 176
<211> LENGTH: 508

-continued

<212> TYPE: DNA
<213> ORGANISM: Enterococcus flavescens

<400> SEQUENCE: 176
aggcgccgaa ggggcaaggc atactgctca atctctcagg caaaaggaca gaaggtaaaa 60
tacaaacacc attaagaaca gtcttagtct tttttgtgtt tgctgtttta tcattgcttc 120
agaagttgtc tcaaagaaag agatagcttt tttcttttgg cgtcttcgat gacttttagg 180
agagaaagat gatagcactc gttaaattaa ttgataacct tgtttgggga ccgcccctct 240
taattttatt ggttgggacg gggatttacc ttaccagtca tttaggatta attcaaatct 300
taaaactacc aagagccttt aaactcattt tttcagatga cgaaggacat ggagatattt 360
catcctttgc tgctcttgca actgcccttg ccgctactgt cggaactggt aacattgttg 420
gggttgccac tgctatcaag tctggtggtc ctggagcgct cttttggatg tgggttgccg 480
ctttttttgg tatggccaca aaatacgc 508

<210> SEQ ID NO 177
<211> LENGTH: 498
<212> TYPE: DNA
<213> ORGANISM: Enterococcus gallinarum

<400> SEQUENCE: 177
gaacggaatt ctggagagac cgtaaaggca ccgaaggggc aaggcaggta actgctcaaa 60
ctctcaggta aaaggacaga gctaggatag accgcttttt ggcatttatc taagcattcc 120
agagtacatg tatcttgcat gtactctttc ttttggggtt gaaagatagg agaaggacat 180
gttagaattg cttaaagcgc ttgatgcttt tgcttggggg cctcccctct tgatcttatt 240
ggtcggaacg ggtatctatt tgaccatccg actgggcctt ttgcaggtta ctcgtctccc 300
taaggccttt cagttgatct ttaccaagga caaggggcac ggcgatgtgt cgagctttgc 360
tgctctctgt acggctctag cagccacagt tggtacggga aatatcatcg ggtagcgac 420 agccattaag gttggaggac caggggccct cttttggatg tggatggcgg ccttctttgg 480
aatggcaact aaatacgc 498

<210> SEQ ID NO 178
<211> LENGTH: 497
<212> TYPE: DNA
<213> ORGANISM: Enterococcus raffinosus

<400> SEQUENCE: 178
gacggaattc tggagagacc gtaaaggcac cgaaggggca aggcaggtaa ctgctcaaac 60
tctcaggtaa aaggacagag ctaggataga ccgctttttg gcatttatct aagcattcca 120
gagtacatgt atcttgcatg tactctttct tttggggttg aaagatagga gaaggacatg 180
ttagaattgc ttaaagcgct tgatgctttt gcttgggggc ctcccctctt gatcttattg 240
gtcggaacgg gtatctattt gaccatccga ctgggccttt tgcaggttac tcgtctccct 300
aaggcctttc agttgatctt taccaaggac aaggggcacg gcgatgtgtc gagctttgct 360
gctctctgta cggctctagc agccacagtt ggtacgggaa atatcatcgg ggtagcgaca 420
gccattaagg ttggaggacc aggggccctc ttttggatgt ggatggcggc cttctttgga 480
atggccacca aatacgc 497

<210> SEQ ID NO 179
<211> LENGTH: 480
<212> TYPE: DNA

-continued

<213> ORGANISM: Streptococcus mitis
<220> FEATURE:
<221> NAME/KEY: misc_feature
<222> LOCATION: (3)..(3)
<223> OTHER INFORMATION: n is a, c, g, or t

<400> SEQUENCE: 179
atnttaaggc acccaagggc aaggtcaggc aactgctcaa actctcaggt aaaaggacag 60
agctaggata gaccgctttt tagcatttat ctaagcattc cagagtacat gtatcttgca 120
tgtgctcttt cttttggggt tgaaaagata ggagaaggaa atgttagaat tgcttaaatc 180
aattgatgct tttgcttggg gtccacccct cttgattcta ttggtcggga cagggattta 240
cctaactgct cgtctaggcc tcttgcaggt tttgcgtttg cctaaggcct ttcagcttat 300
ttttactaag gacaaggggc atggcgatgt atccagcttt gcggccttgt gtacagccct 360
agcagcgaca gttggtacgg gaaatattat cggggtggcg acggctatca aggtcggtgg 420
cccaggagcc ctcttttgga tgtggatggc cgctttcttt ggaatggccc aaaataccgc 480

<210> SEQ ID NO 180
<211> LENGTH: 598
<212> TYPE: DNA
<213> ORGANISM: Streptococcus canis
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 180
ntagtncttt ttaatgacac tagtgacctt tcgttagtat gtttttaagg actgagtatt 60
gtaatactaa catgaaagaa ctagacaggc gccgaagggg caaggctaga cacacagcta 120
gctcaaactc tcaggcaaaa ggacagaaga taagaatcga ttaacaggta aggtgtatta 180
tctttgtcag tcttcttatc acttttcagg agttatcact acgataactc cttttttcta 240
ttctaactgt catcatagga cgctatgttt tattaggaga cttattcgta tatgctaaac 300
ttttttacaa tgctagatga tatggtctgg ggtgccccac tgcttattct gttggtggga 360
acagggattt atttaactgt tcggcttggc ttactccagg ttttaaaatt acctaaagcc 420
tttaaattaa ttttcgcaga cgataaaggt caaggggata tttctagttt tgccgctctt 480
gctactgctc ttgcagcaac agtaggtact ggtaacatcg ttggtgtagc aacagctatc 540
aaagctggtg gtcctggagc cctattttgg atgtggattg ctgctttctt tggaatgg 598

<210> SEQ ID NO 181
<211> LENGTH: 1680
<212> TYPE: DNA
<213> ORGANISM: Listeria monocytogenes

<400> SEQUENCE: 181
gttagaaaaa ggaagttcta ttgtagcatc gccaaaaatc catcaaacct tattagataa 60
ctacctgcct taaagaaagc gctcaacata aaaaaacttg ttttcagaaa ataaaaatcg 120
tgccaaatcg gctcagctat gctataatag gtaagttgat ttaaacgaga cgatagcgac 180
ggaggaaaat aaatctattt tcctctttct tttggctaat cttcacgata aatgtttgga 240
tttttaattt aggaggaaac aagattgaat ttaagaaatg atattcgtaa tgtagcaatt 300
attgcccacg ttgaccatgg taaaacaact ctagtagacc aattattacg ccagtcaggc 360

-continued

```
acattccgcg acaatgaaac agttgcagaa cgcgcaatgg acaacaatga tttagaaaga    420
gaacgcggta ttacaatttt agcgaaaaat acagcgatta agtatgaaga tacacgtgta    480
aacatcatgg atacacctgg acacgccgat ttcggtggag aagtagaacg tatcatgaaa    540
atggttgatg gtgttctttt agtagtggac gcgtatgaag gtacgatgcc tcaaacacgt    600
tttgtactaa aaaaagcact agaacaaaac ctaactccaa tcgtagtagt aaacaaaatt    660
gaccgtgact ttgctcgccc agaagaagtt gttgatgaag tattagaatt attcatcgaa    720
ctaggcgcaa acgacgatca attagaattc ccagttgttt atgcttctgc aatcaacgga    780
acttcaagct atgattccga tccagcagaa caaaaagaaa caatgaaacc acttttagac    840
acaattatcg aacatatccc ggctccagtt gataatagcg acgaaccatt acaattccaa    900
gtatcattac ttgattataa tgactatgtt ggtcgtatcg gtattggccg cgtattccgt    960
ggaacaatgc acgtgggaca aacagttgct ttaattaaac ttgatggcac agtaaaacaa   1020
ttccgtgtaa cgaaaatgtt cggtttcttc ggactaaaac gtgacgaaat taaagaagca   1080
aaagctggtg atttagtagc attagcaggt atggaagaca tcttcgttgg tgaaacagta   1140
acaccatttg accaccaaga agcacttccg ttattacgta ttgatgagcc aaccttgcaa   1200
atgactttcg taacaaataa cagtcctttc gctggtcgtg aaggtaaaca cgtaacaagc   1260
cgtaaaattg aagaacgttt acttgcagag cttcaaacgg acgtatcttt acgcgtagag   1320
ccaacagctt cccctgacgc ttgggtagtt tctggtcgtg gtgagcttca tttatccatt   1380
ttgatcgaaa caatgcgtcg cgaaggttat gaattacaag tttctaaacc agaagtaatc   1440
atccgtgaaa ttgatggcgt gaaatgtgaa ccagtagaag atgttcaaat tgatactcca   1500
gaagaattca tgggttccgt tattgaatct atcagccaac gtaaaggcga aatgaaaaac   1560
atgattaacg atggcaacgg acaagttcgt ttacaattca tggttccagc tcgtggctta   1620
atcggttata caactgattt cctttcaatg actcgtggtt atggtattat caaccacaca   1680
```

<210> SEQ ID NO 182
<211> LENGTH: 1620
<212> TYPE: DNA
<213> ORGANISM: Listeria innocua

<400> SEQUENCE: 182

```
ataaaaaaac tcattttcag aaaataaaaa tagtgctaaa tccgcttagc tatgctataa     60
taggtaagtt gatttaaacg agacgatagc gacggaggaa aataaatcta ttttcctctt    120
tcttttggct aatcttcacg ataaatgttt ggatttttaa tttaggagga aacaagattg    180
aatttaagaa acgatattcg taatgtagca attattgccc acgttgacca tggtaaaact    240
acactagtag accaattact acgccaatca ggtactttcc gcgacaatga aacagttgca    300
gaacgtgcaa tggacaacaa tgatttagaa agagaacgcg gtattacaat tttagcgaaa    360
aatacagcaa ttaagtatga agatacacgc gtaaacatca tggatacacc tggacacgcc    420
gattttggtg gagaagtaga acgtatcatg aaaatggttg atggtgttct tttagtagtg    480
gacgcgtatg aaggtactat gcctcaaaca cgttttgtac taaaaaaagc actagaacaa    540
aacctaactc caatcgtagt agtaaacaaa attgaccgtg actttgctcg cccagaagaa    600
gttgttgatg aagtactaga attattcatc gaactaggtg cgaacgacga tcaattagaa    660
ttcccagttg tttatgcttc tgcaattaac ggaacttcaa gctttgaatc cgacccagca    720
gaacaaaaag aaacaatgaa accactttta gacactatta ttgaacatat tccagctcca    780
```

-continued

```
gttgataaca gcgacgagcc attacaattc caagtttctt tacttgatta taatgactat    840

gttggtcgta ttggtattgg ccgcgttttc cgtggaacaa tgcacgtagg acaaacagtt    900

gccttaatta aactagacgg cacagtaaaa caattccgtg taacgaaaat gttcggtttc    960

ttcggactaa aacgtgacga aattaaagaa gcaaaagcgg gtgacttagt agcacttgca   1020

ggaatggaag acatcttcgt cggtgaaaca gtaacaccat ttgaccacca agaagcactt   1080

ccacttttac gtattgatga gccaaccttg caaatgactt ttgtaacaaa taacagtcct   1140

ttcgcaggcc gtgaaggtaa acacgtaaca agccgtaaaa ttgaagaacg cttacttgca   1200

gaacttcaaa cggatgtatc tttacgcgtt gaaccaacag cttctccaga cgcatgggta   1260

gtatctggtc gtggtgagct tcacttgtct atcttaattg aaacgatgcg tcgtgaaggt   1320

tatgagttac aagtttctaa accagaagta atcatccgtg aaatcgatgg cgtgaaatgt   1380

gaaccagtag aagacgttca aattgatact ccagaagaat tcatgggttc agttattgaa   1440

tctatcagcc aacgtaaagg cgaaatgaaa aacatgatta acgacggcaa tggccaagtt   1500

cgtttacaat tcatggttcc agctcgtgga ttaatcggtt atacaactga tttcctttca   1560

atgacacgtg gttatggtat tatcaaccat acattcgata gctaccaacc aatccaaaaa   1620
```

<210> SEQ ID NO 183
<211> LENGTH: 1380
<212> TYPE: DNA
<213> ORGANISM: Bacillus cereus

<400> SEQUENCE: 183

```
ttactttcac aaaagtaaga atacaactat attttcattc ttgcttttat tttaattgct     60

attgtatccc cttcgctctt ataatagaga aggattaaaa agacattagg agttggacat    120

gttgaaaaaa cgacaagatt tacgtaatat agcaattatt gcccacgttg accatggtaa    180

aacaacactt gttgaccagt tattacgtca agcggggact ttccgtgcga acgaacacgt    240

tgaagaacgc gcaatggatt caaatgatct agaaagagaa cgcggtatta caattttagc    300

gaaaaataca gcgattcact atgaagataa aagaattaac attttagata cacctggtca    360

cgctgacttc ggtggagaag tagaacgtat catgaaaatg gttgatggtg ttttacttgt    420

tgttgatgca tatgaaggtt gtatgccaca aacacgattt gttttaaaga aagctcttga    480

gcaaaactta actccaatcg tagttgtaaa caaaattgac cgtgacttcg ctcgtccaga    540

tgaagtagtt gatgaagtaa tcgacttatt cattgagctt ggtgcaaacg aagatcaatt    600

agagttccca gttgtatttg catcagcaat gaacggaaca gcaagcttag attcaaatcc    660

agcaaatcaa gaagagaata tgaaatcatt attcgataca attatcgaac atattccagc    720

accaattgat aacagcgaag agccacttca attccaagta gcacttcttg attacaacga    780

ctacgttgga cgtattggag ttggtcgcgt attccgcggt acaatgaagg ttggacaaca    840

agttgcttta atgaaagtag acggaagcgt gaagcaattc cgcgtaacga aattattcgg    900

ttacatggga ttaaaacgtc aagaaattga agaagcaaaa gcaggggact tagtagccgt    960

ttctggtatg gaagacatta acgtaggtga aacagtatgt ccagttgaac atcaagatgc   1020

gttaccatta ttacgtattg atgagccaac actacaaatg acgttccttg taaataacag   1080

cccatttgca ggtcgtgaag gtaaatacat tacatctcgt aaaattgaag agcgtcttcg   1140

ttcacaatta gaaacagatg taagtttacg tgtagataat acagattctc ctgatgcgtg   1200

gatcgtatct ggacgtgggg aactacattt atctatctta attgaaaaca tgcgtcgtga   1260

aggttatgaa ttacaagtat ctaagccaga agtaatcatt aaagaagttg atggcgtaag   1320
```

-continued

```
atgtgagcct gtagagcgcg tacaaatcga tgtacctgaa gaatacactg gttctattat   1380
```

<210> SEQ ID NO 184
<211> LENGTH: 1680
<212> TYPE: DNA
<213> ORGANISM: Bacillus anthracis

<400> SEQUENCE: 184

```
ctatattttc attcttgatt ttattttaat tgctattgta tccccttcgc tcttataata     60
gagaaggatt aaaaagacat taggagttgg acatgttgaa aaaacgacaa gatttacgta    120
atatagcaat tattgcccac gttgaccatg gtaaaacaac acttgttgac cagttattac    180
gtcaagcggg gactttccgt gcgaacgaac acgttgaaga acgcgcaatg gattcaaatg    240
atctagaaag agaacgcggt attacaattt tagcgaaaaa tactgcgatt cactatgaag    300
ataaaagaat taacatttta gatacaccag gtcacgctga cttcggtgga gaagtagaac    360
gtattatgaa aatggttgat ggtgtattac ttgttgttga tgcatatgaa ggttgtatgc    420
cacaaacacg atttgtttta aagaaagctc ttgagcaaaa cttaactcca atcgtagttg    480
taaataaaat tgaccgtgac ttcgctcgtc ctgatgaagt agttgatgaa gtaatcgact    540
tattcatcga acttggtgca aacgaagatc aattagagtt cccagttgta tttgcatcag    600
caatgaacgg aacagcaagc ttagattcaa acccagcaaa tcaagaagag aatatgaaat    660
cattatttga tacaattatt gaacatattc ctgcaccaat tgataacagc gaagagccac    720
ttcaattcca agtagcactt cttgattaca acgactatgt tggacgtatc ggggttggac    780
gcgtattccg cggtacaatg aaggttggac aacaagttgc tttaatgaaa gtagacggaa    840
gtgtaaaaca attccgcgta acgaaactat ttggttatat gggattaaaa cgtcaagaaa    900
ttgaagaagc aaaagctgga gacttagtag ctgtttctgg tatggaagac attaacgtag    960
gtgaaacagt atgtccagtt gaacatcaag atgcgttacc attattacgt attgatgagc   1020
caacactaca aatgacattc cttgtaaata acagcccatt tgcaggtcgt gaaggtaaat   1080
acattacatc tcgtaaaatt gaagagcgtc ttcgttcaca attagaaaca gatgtaagtt   1140
tacgcgtaga taatacagaa tctcctgatg cgtggatcgt atctggacgt ggggaactac   1200
atttatctat cttaatcgaa aacatgcgtc gtgaaggtta tgaactacaa gtatctaaac   1260
cagaagtaat cattaaagaa gttgatggcg taagatgtga gcctgtagag cgtgtgcaaa   1320
ttgatgtacc tgaagaatac actggttcta ttatggaatc tatgggtgca cgtaaaggtg   1380
aaatgttaga tatggtgaat aacggaaacg gtcaagttcg ccttactttc atggttccag   1440
cacgtggttt aattggttac acaacagaat tcttaacatt aactcgtggt tacggtattt   1500
taaaccatac attcgattgc taccaaccag tacacgctgg acaagttggt ggacgtcgtc   1560
aaggtgttct agtttcactt gaaacaggaa aagcatcaca atacggtatt atgcaagttg   1620
aagaccgtgg tgtaatcttc gttgaaccag gtacagaagt atatgctggt atgattgttg   1680
```

<210> SEQ ID NO 185
<211> LENGTH: 1270
<212> TYPE: DNA
<213> ORGANISM: Staphylococcus aureus

<400> SEQUENCE: 185

```
tcaattatat gatataataa aaaagttgta attaaaagtg ggattttact taagaaagaa     60
ggaaactatt tatatgacta ataaaagaga agatgtccgc aatatagcaa ttattgctca    120
```

-continued

```
cgttgaccat ggtaaaacaa ctttagtaga tgagttgtta aaacaatctg gtatattcag    180
agaaaatgaa catgtcgatg aacgtgcaat ggactctaac gatatcgaaa gagagcgtgg    240
aattacgatt ctagccaaaa atacggctgt tgattataaa ggtacacgta ttaatatttt    300
ggatacacca ggacatgcag actttggtgg agaagtagaa cgtattatga aaatggttga    360
tggggttgtc ttagtagtag atgcgtatga aggtacaatg cctcaaacac gttttgtact    420
taaaaaagcg ctagaacaaa acctgaaacc tgttgttgtt gttaataaaa ttgataaacc    480
atcagcacgt ccagagggtg ttgtagatga agttttagat ttatttattg aattagaagc    540
aaacgatgaa caattagaat tccctgttgt ttatgcttca gcagtaaatg gaacagctag    600
cttagatcct gaaaaacaag atgataattt acaatcatta tatgaaacaa ttattgatta    660
tgtaccagct ccaattgata acagtgatga gccattacaa ttccaagtag cattgttgga    720
ctacaatgat tatgttggac gtattggtat tggtcgtgta ttcagaggta aaatgcgtgt    780
cggagataat gtatcactaa ttaaattaga cggtacagtg aaaaacttcc gtgtaactaa    840
aatctttggt tactttggat taaaacgttt agaaattgaa gaagcacaag ctggagattt    900
aattgctgtt tcaggtatgg aagacattaa tgttggtgaa actgtaacac cacatgacca    960
tcaagaagca ttgccagttc tacgtattga tgagcctact cttgaaatga catttaaagt   1020
taacaattct ccatttgctg gccgtgaagg tgactttgta acagcacgtc aaattcaaga   1080
acgtttaaat caacaattag aaacagatgt atctttgaaa gtttctaaca cagattctcc   1140
agatacatgg gtagttgctg gtcgcggtga attgcattta tcaatcctta ttgaaaatat   1200
gcgtcgtgaa ggttatgaat tacaagtttc aaaaccacaa gtaattatta aagaaataga   1260
tggtgtaatg                                                          1270
```

```
<210> SEQ ID NO 186
<211> LENGTH: 1320
<212> TYPE: DNA
<213> ORGANISM: Staphylococcus epidermidis

<400> SEQUENCE: 186
```

```
accccacctt ttacttatct tttcaataat atatgatata ataaaacagt tgcaattaaa     60
agtgggagta tacacaagaa aggaatttat aaaatgacta atttaagaga agatgttcgt    120
aatatagcga ttattgcgca tgtcgaccat ggtaaaacaa cattagtaga ccagttgctt    180
aaacaatcag gtatatttcg tgaaaacgaa catgtcgacg agcgtgcaat ggactctaat    240
gatttagaaa gagaacgtgg tattacgatt cttgctaaga atacagcgat agattataaa    300
ggaacgcgta tcaatatatt agacacacct ggccacgccg attttggtgg tgaagttgaa    360
cgtatcatga aaatggttga cggtgtcgta ctagtggttg acgcatatga aggtacaatg    420
cctcaaactc gttttgttct taaaaaagct ttagaacaaa acttaaaacc ggttgtagtt    480
gtgaataaaa ttgataaacc agctgctaga cctgagggag ttgtagatga agtattagac    540
ttattcattg aattggaagc gaatgatgag caattagact tcccagttgt ttatgcttca    600
gctgtgaatg gaacagcaag tttagactct gaaaagcaag acgaaaatat gcaatcccta    660
tacgagacga ttattgacta tgtaccggca ccagtagata attcagatga accattacaa    720
ttccaaattg ctttactaga ttataatgat tatgtaggtc gtataggcgt tggacgtgtg    780
ttcagaggta aaatgcgtgt aggtgataat gtatcactaa ttaaattaga tggtacagtt    840
aagaactttc gtgtgacgaa aatatttggt tactttggtc ttaaacgtga agaaattgaa    900
gaagcacaag caggagactt aatagctgtt tcaggtatgg aagatattaa cgttggtgaa    960
```

-continued acagttacac cacatgatca tcgtgaccca ttaccggtgt tacgtattga tgaaccaacc 1020
ctagaaatga cttttaaagt aaataactct ccgtttgctg gacgtgaagg tgattatgta 1080
acagctcgac aaattcaaga aagattagat caacaacttg aaacagatgt ttctttaaaa 1140
gttacaccta ctgatcaacc agattcatgg gttgttgctg gtcgtggtga actacacttg 1200
tctattctta ttgaaaacat gagacgtgaa ggctttgaat tacaggtttc taaacctcaa 1260
gttattttaa gagaaatcga tggtgtgtta agtgaaccat ttgagcgtgt acaatgtgaa 1320

<210> SEQ ID NO 187
<211> LENGTH: 1320
<212> TYPE: DNA
<213> ORGANISM: Bacillus subtilis

<400> SEQUENCE: 187
gaaaaacgtg acgcttttaa agaggatgtg tgatataata tgaaagttat ctaatttttt 60
taggagatga aaaagtgaaa cttcgaaatg atcttcgcaa catcgcgatt attgcccacg 120
ttgaccatgg gaaaacgact ctagtcgatc agcttttaca tcaggctggt acgttccgtg 180
ccaacgaaca ggttgctgaa cgcgcaatgg actctaatga tcttgaacgc gaacgcggca 240
ttacaatatt ggcgaaaaat actgcgatta actataaaga tacacgtatc aatattttgg 300
acacccctgg acatgcagac tttgggggag aagtagaacg gattatgaaa atggttgacg 360
gcgtagtgct tgtcgttgac gcatatgaag gctgtatgcc tcaaactcgt tttgttctga 420
aaaaagctct tgagcaaaac ctgaaccctg ttgttgttgt aaacaaaatt gaccgtgact 480
ttgctcgtcc agaggaagtt atcgatgaag ttctggatct gttcattgag cttgatgcca 540
atgaagagca gctcgagttc ccagtggtat atgcttccgc gattaatgga acagcgagtc 600
ttgatccgaa acaacaggat gaaaacatgg aagctttata tgaaaccatt attaagcatg 660
ttccggcacc tgttgataat gcagaggagc cgcttcaatt ccaagttgcc cttcttgact 720
acaacgacta tgtaggccgt atcggaatcg gacgcgtatt ccgcggcaca atgaaagtcg 780
gacagcaggt ttctcttatg aagcttgacg gaacggcaaa gtcattccgt gttacaaaga 840
tttttggttt ccaaggctta aagcgtgtgg aaattgaaga agcaaaagcg ggagacctcg 900
ttgcggtttc cgggatggaa gatatcaacg ttggtgaaac ggtatgtcct gtagaccatc 960
aagatccgct tccggtcctt cgcattgatg agccgacact tcaaatgaca tttgtcgtga 1020
ataacagtcc gtttgcaggc cgtgaaggca aatatgtaac ggcccgcaaa atcgaagagc 1080
gtcttcaatc acagcttcag acggatgtga gcttgcgtgt tgagccaaca gcttctcctg 1140
atgcttgggt tgtttcagga cgcggtgagc tgcacttgtc aattttaatt gaaaatatgc 1200
gtcgtgaggg ctatgagctt caagtgtcaa aacctgaagt tattatcaaa gaaatcgacg 1260
gcgtacgctg tgagcctgtt gaacgtgtgc aaattgatgt tcctgaagag catactggct 1320

<210> SEQ ID NO 188
<211> LENGTH: 1560
<212> TYPE: DNA
<213> ORGANISM: Streptococcus mutans

<400> SEQUENCE: 188
ggaatggaaa agtaaaagag aagaattagt tctttttga gataatgaca gggattagta 60
tgagctgttg tcttttgttt ttgcaatact ggttgattga ggacttattt tataaaattt 120
ggagatacca agactgcgac tttgctatct tggtttttct tttatatttt aaaacattta 180

-continued

```
catatctctc ctgagttttt ccctaatttt tatggtataa tagataagtt gaaataaatt    240

aatgtaaaat gtaagaggaa ttatgacaaa ttttagagaa gatattagaa atgttgctat    300

cattgcccac gttgaccatg ggaaaacaac ccttgttgat gagctcttaa aacaatcgca    360

tacacttgat gagcataaaa aattagaaga acgtgcgatg gactctaatg atcttgaaaa    420

agagcgtggg attactattc ttgcaaaaaa tactgctgtt gcctacaatg gtgtacgtat    480

taacattatg gacacaccag gacatgcgga ttttggtgga gaagtagagc gtatcatgaa    540

aatggttgat ggggttgttc ttgttgttga tgcttatgaa ggtaccatgc cgcaaacacg    600

ttttgttttg aaaaaagctt tggaacaaaa cctggttcca atcgtggtgg tgaataagat    660

tgacaagcca tcagctcgtc cggcagaagt tgttgatgaa gttcttgaac ttttcattga    720

acttggagca gatgatgacc agttagagtt tccagtcgtt tacgcttcgg cgattaatgg    780

aacttcttca ttatcagatg aaccagcgga tcaagaacat acaatggcac ccgtttttga    840

tactattatt gagcatattc cagcaccgat cgataattca gatcagccac ttcaatttca    900

agtgtctctc cttgattata acgactttgt tggacgtatc ggtattgggc gagtcttccg    960

tggttctgtt aaagtcgggg atcaagtgac actttctaaa cttgatggta caacaaagaa   1020

ttttcgtgtt acaaaacttt tcggtttctt cggtttggaa cgtcgtgaga ttaaggaagc   1080

taaggctggc gatttgattg ctgtttcagg tatggaagat atctttgttg gtgaaacgat   1140

tacaccaact gatgctgtag aaccacttcc tattcttcac attgatgagc caactctgca   1200

aatgaccttt ttagctaaca attccccttt tgcaggccgt gaaggtaaat ttgtaacctc   1260

gcgtaaggta gaagagcgtt tgttggcaga attgcaaaca gatgtttccc ttcgtgtaga   1320

agccactgac tcaccagata aatggacggt ttcaggtcgt ggggagttac atctgtcaat   1380

ccttattgaa accatgcgcc gtgaaggata tgagctgcaa gtatcgcgtc cagaagttat   1440

tatcaaagaa attgatggca tcaaatgtga gccatttgaa cgcgtgcaaa ttgacacacc   1500

ggaagaatac caaggtgctg ttatccagtc cctttcagaa cgtaaaggtg aaatgcttga   1560
```

<210> SEQ ID NO 189
<211> LENGTH: 1259
<212> TYPE: DNA
<213> ORGANISM: Streptococcus pneumoniae

<400> SEQUENCE: 189

```
aagcggagtg aaaacattta cacttgcttg agttatgtta tttatttgaa attatggtat     60

aatcgttcag ttagaaaata aattttgaat attatagagg aaatcatgac aaaattaaga    120

gaagatatcc gtaacattgc gattatcgcc cacgttgacc acggtaaaac aaccctggtt    180

gacgaattat tgaaacaatc agaaacgctt gatgcacgta ctgaattggc agagcgtgct    240

atggactcaa acgatatcga aaaagagcgt ggaatcacca tccttgctaa aaatactgcc    300

gttgcttaca acggaactcg tatcaacatt atggacacac caggacacgc ggacttcggt    360

ggagaagttg agcgtatcat gaaaatggtt gacggtgttg tcttggtcgt agatgcctat    420

gaaggaacca tgccacaaac tcgtttcgta ttgaaaaaag ccttggaaca agaccttgtc    480

ccaatcgtgg ttgttaacaa aatcgataag ccatcagctc gtccagcaga agtagtggat    540

gaagtcttgg aacttttcat cgagcttggt gcagatgacg accagcttga tttcccagtg    600

gtttatgctt cagcgatcaa cggaacttct tcattgtcag atgatccagc tgaccaagaa    660

gcgactatgg caccaatctt tgacacgatt atcgaccata tcccagctcc agtagataac    720

tcagatgagc ctttgcagtt ccaagtgtca cttttggact acaatgactt cgttggacgt    780
```

-continued

```
atcggtatcg gtcgtgtctt ccgtggtaca gttaaggttg gggaccaagt taccctttct    840
aaacttgacg gtacaactaa aaacttccgt gttacaaaac tcttcggttt ctttggtttg    900
gaacgtcgtg aaatccaaga agccaaagcg ggtgacttga ttgccgtttc aggtatggaa    960
gacatctttg tcggtgaaac catcactccg acagatgcag tagaagctct tccaatccta   1020
cacatcgatg agccaactct tcaaatgact ttcttggtca acaactcacc atttgctggt   1080
aaagaaggta aatgggtaac ttctcgtaag gtggaagaac gcttgcaggc agaattgcaa   1140
acagacgttt cccttcgtgt tgacccaact gattcaccag ataaatggac tgtttcagga   1200
cgtggagaat tgcacttgtc aatccttatc gaaacaatgc gtcgtgaggg ctatgaact    1259
```

```
<210> SEQ ID NO 190
<211> LENGTH: 1860
<212> TYPE: DNA
<213> ORGANISM: Streptococcus agalactiae

<400> SEQUENCE: 190
```

```
agaaatgaat taaattgaaa aaagtagaaa ataaatggca taaataatga aatgatgaaa     60
agttttctta tcacaaatag gcagttaata tgaaaacatt tacacttgtg taaattctgt    120
tttttaagaa aaattgtgtt ataattcata agttaacaga attacattat aaaatagagg    180
aaaacatgac aaatttaaga acagatatcc gtaacgttgc gatcattgcc cacgttgacc    240
acggtaaaac aactctcgtt gatgaattat taaaacaatc acatactctt gatgagcgta    300
aagagcttga agaacgtgca atggattcaa atgatatcga aaaagaacgt ggtatcacca    360
ttcttgcaaa aaatacagcc gtagcataca acgatgttcg tatcaatatt atggacacac    420
ctggtcacgc ggactttggt ggtgaagttg agcgtattat gaaaatggtt gatggtgttg    480
ttttagtcgt tgatgcctac gaaggaacaa tgccacaaac acgttttgtt ttgaagaaag    540
ctcttgaaca aaacttaatt ccaatcgttg ttgtaaataa aattgataag ccgtcagctc    600
gtccatcaga ggttgttgat gaagttcttg aactatttat tgagctcggt gctgatgatg    660
atcaactaga tttccctgtt gtttatgctt cagctatcaa tggaacatct tcaatgtcag    720
atgatccttc agatcaagaa aaaacaatgg caccgatttt tgatactatc attgatcaca    780
ttccagcccc agttgacaac tcggaagaac cacttcaatt ccaagtttct cttcttgatt    840
acaatgattt tgtaggacgt attggtattg gacgtgtttt ccgcgggact gtcaaagttg    900
gagatcaagt tactctttca aaacttgatg gtacaactaa aaacttccgc gtaacaaaac    960
tttttggttt ctttggactt gaacgtaaag aaatccaaga ggctaaagcg ggtgatttaa   1020
tcgctgtttc tggtatggaa gatatcttcg ttggtgagac agtaactccg acagatgcta   1080
ttgaaccact accagtttta cgtattgacg agccaacact tcaaatgact ttcttggtga   1140
ataattcacc atttgcaggt cgcgaaggta aatggattac gtcacgtaag gttgaagaac   1200
gtcttttagc agaattacaa acagacgttt ctttacgtgt tgacccaaca gattcgccag   1260
ataaatggac ggtttcaggg cgtggagaat tacatttatc tatccttatt gaaacaatgc   1320
gtcgtgaggg atatgaactt caagtatcac gtccagaagt tatcatcaaa gaaattgatg   1380
gtgttcaatg cgagccgttt gagcgtgttc aaattgatac tccagaagaa tatcagggtg   1440
ctattatcca aagtttgtca gagcgtaaag gtgatatgct tgatatgcag atggttggta   1500
atggtcaaac gcgtttgatt ttcttgattc ctgcacgtgg tttgattggt tattcaacag   1560
agtttctttc aatgacacgt ggatatggta tcatgaatca tacttttgac cagtatctac   1620
```

-continued

```
cggttgttca aggagaaatt ggtggtcgtc atcgtggtgc cttggtttct attgaaaatg   1680

gtaaagcaac tacatattca attatgcgta ttgaagaacg tgggactatc tttgtaaatc   1740

caggtataga agtttatgaa ggaatgattg ttggtgagaa ttctcgtgat aatgacctcg   1800

gagtcaatat tacaactgct aaacaaatga caaatgtccg ttcagcaact aaagatcaaa   1860
```

<210> SEQ ID NO 191
<211> LENGTH: 1500
<212> TYPE: DNA
<213> ORGANISM: Streptococcus pyogenes

<400> SEQUENCE: 191

```
gtcttaaaag acggtattga ttattgggat ggcaaagtta aacaaacaac ctagttaaga     60

gtaacgtgga gttaagggga ataaaggcag tcactgtctc aaaaaacctta attccttttt   120

ttgctgtatc cagacttgct gaaagtctga aaatatttac aattgattaa aaccagtttt    180

ttaaaacatt ttgtgttata cttatctagt taaaatatat ttacttagag gaacaaatga    240

ctaacttaag aaacgatatc cgtaacgtag cgattattgc ccacgttgac cacggaaaaa    300

caacacttgt agatgaatta ttaaaacaat cccatactct tgatgagcgt aaagagcttc    360

aagagcgtgc catggattcc aatgaccttg aaaaagaacg tgggattaca atccttgcga    420

aaaatacggc agtagcctat aacgatgttc gtattaacat catggatacc ccaggacacg    480

cggacttcgg tggtgaagtt gaacgtatca tgaaaatggt tgacggggtt gttcttgttg    540

tggatgccta cgaaggaaca atgccccaga cgcgtttcgt attgaaaaaa gcacttgagc    600

aaaaccttat cccgatcgtt gtggtgaaca agattgacaa accttcagct cgtccagcag    660

aagttgtaga tgaagtgctt gaattattca tcgaacttgg tgccgatgat gagcaattgg    720

aattcccagt tgtttacgca tcagctatta atggaacatc atcattatca gatgaccctg    780

ctgaccaaga gcatactatg gcaccgatct ttgatacgat tattgatcat attccagcgc    840

cagttgataa ttcagatgag cctttgcaat tccaagtgtc acttttggac tacaacgatt    900

tcgtaggtcg tatcggtatc ggtcgtgttt tccgtggtac tgttaaagtg ggtgaccaag    960

taactctttc aaaacttgat ggtaccacta aaaacttccg tgttacaaaa ctgtttggtt   1020

tcttcggttt ggaacgtcgt gaaattcaag aagctaaagc aggtgacttg attgctgttt   1080

caggtatgga agatatcttt gttggagaaa ccattacacc aactgactgt gtggaagctc   1140

tgccaattct tcgtattgat gagccaacac ttcagatgac tttcttggtc aataactctc   1200

cttttgcagg tcgtgaaggt aaatggatca cgtcacgtaa ggttgaagaa cgtcttttag   1260

cagaattgca aacagacgtg tcacttcgtg ttgacccaac agattcgcca gataaatgga   1320

cggtttcagg gcgtggagaa ttgcatttat ctatcctcat tgaaaccatg cgccgtgaag   1380

gctatgaact tcaagtatca cgtccagaag ttatcatcaa agaaattgat ggtgtcaaat   1440

gtgaaccgtt tgagcgtgtt caaattgata caccagaaga atatcagggt gcaatcatcc   1500
```

<210> SEQ ID NO 192
<211> LENGTH: 1740
<212> TYPE: DNA
<213> ORGANISM: Enterococcus faecalis

<400> SEQUENCE: 192

```
catcacgcaa cggaaatcgg acaagcaagc atgggcgtgc gtattagcgg ttgtgcaggt     60

ttggaaatta ttgctatgtt aaaaggcaac catcatggct atttatctaa tctaagtcct    120

tgggattatg cagcaggctt agtacttttg gaagaatttg ggtttaaata ctctggtatt    180
```

-continued

```
acaggaaaac cattaacttt tgcgggtcgt gaatacttta ttgcagcaac tcctgaaacc    240

tatgatgaag tatttacccg atatttaaat gaatcggaat aatcaaagaa gagcgttgct    300

gaaaggtaag gctcttcctc ttttaaaaga gaaaaatttg taaaaaaatg tccttgtttt    360

cagaaaaagc cgaataattt ctaaaacttt cattattttt gcaggcgaaa gccttttttt    420

aatgaaaaaa gtttgctata ataagcagtc ggcttttatg gacttaagta acataagcgt    480

atatagataa ggagcaatta aattgaaata cagagatgat attcgtaacg tggcaattat    540

cgcccacgtt gaccatggta aaacaacctt agtagatgaa cttttaaaac aatctgacac    600

tttagatgga cacacacaat tacaagaacg tgcaatggat tccaatgcac ttgaaagtga    660

acgtggaatt actatcttag caaaaaatac agccgtagat tataacggta cacgtatcaa    720

cattctagat acaccaggac acgcggactt cggtggtgaa gtagaacgta tcatgaaaat    780

ggtagacggt gttgttttag ttgtcgatgc gtatgaagga acaatgcctc aaacacgttt    840

cgtattgaaa aaagcattag aacaaaaagt aacaccaatc gtggttgtta acaaaattga    900

caaaccttct gctcgtcctg aacacgtagt agatgaagtt ttagagttat tcatcgaatt    960

aggtgcagac gacgatcaat tagatttccc agttgtttat gcttctgctt taaacggaac   1020

ttcaagtgaa tcagatgatc cagcagatca agagccaaca atggccccaa tttttgataa   1080

aattattgaa catgtgccag ctccagttga caattcagac gaaccacttc aattccaagt   1140

ctcattacta gactacaacg attacgttgg acgtattggg attggccgtg tgttccgtgg   1200

cacaatgaaa gtcggcgacc aagttgcgtt gatgaaatta gatggcagcg tgaaaaattt   1260

ccgtgtaacg aaaattttag gtttctttgg cttacaacgt gtggaaattg atgaagcaaa   1320

agcgggcgat ttaattgccg tttctggaat ggaagacatt ttcgttgggg aaacagttgt   1380

agatgttcac aatcaagaag cattaccaat tctacacatt gatgagccaa ccttacaaat   1440

gactttctta gttaacaatt ctccatttgc gggacgtgaa ggaaaataca tcaccgctcg   1500

taaaatcgaa gaacgtttaa tggctgagtt acaaacagac gtatctttac gtgttgatcc   1560

aattggccca gattcttgga ctgtatcagg tcgtggcgaa ttgcatttat caattttaat   1620

tgaaaacatg cgtcgtgaag gctatgaatt acaagtttct cgtccagaag ttattgaacg   1680

tgaaattgat ggagttaaat gtgaaccatt tgaacgtgtt caaattgaca cacctgaaga   1740
```

<210> SEQ ID NO 193
<211> LENGTH: 1620
<212> TYPE: DNA
<213> ORGANISM: Lactococcus lactis

<400> SEQUENCE: 193

```
cgaaaaagca agttaaatat gttgtaaata atggtgttac attagataat actagtggtg     60

ggcctaattt ggctgcacct gtgacggtgg atagtcaggt aatttcgaac gataaaggta    120

cgattatggg tgtaaggacc tatacagcag atttaagcca agcagaagta gttaaaaaag    180

tgggtaattt gaatgcaatg tcctttggag aattttgggg tacaaaagtt tttgctgcca    240

gccaaaatca gacaaattca gataagactt attctgttac gtttaaactg aatataaatt    300

ggatagtatc taatggctat gcttcgctaa caaaagtaac aggtggctat ggttcttgca    360

ttgaccatgt ttatgttgct aattctagtg ttactactgc aacgaatggt cagattaaag    420

gttcaagtgg ttatactcaa caagttgatg acaaatcaga agggaatagt ttatcgtggt    480

caattacgcg aaactataaa cctgtaaaag ttccagcaag tggggcaaat gtaggagcta    540
```

-continued

```
cgtattttgc cacacttaaa cggggaaata gtacatggaa attccaaaca acaaatagag    600

cttattaagt gggaggaagt ggaatgaata taaaaggcat aaaaatttgg caagtatttc    660

ttgcattcat catttggata ggaaccatgt ttcttcctgc aacggtaaat caggctaaat    720

tgaatacgaa ttttgactat aaaaaaagtc gagaaaattt cttttatttt ctttttcatc    780

aagtcccttt ttatagtttc attttgggat tggtgttgct tatatcactt tttctcattt    840

ataggaaaat aaattttagt gtctattttt cttttgctag tcttattttt tacattagtt    900

tcttagttat agcttttccg tctatgatta tttttaatca tagtttatct gggaatactt    960

ttggggctga actttctatc tttctaacct tttatggagc tggatatatt attgctgttc   1020

tatttggttt agttgctttt cttttactct ttctctacag tttaagaata aaagaatgtt   1080

aacaacataa tcatttttac tgattttatt aattataaaa aaataaagaa ctccttagaa   1140

atttttcttt ggggttttca ttttggaagt aaaaaaatct ttgttaggct tgtaaacgtg   1200

tgcatttaca gcttttagaa aagtgtgcta taatgggtta gatatatacg aaagtaaggt   1260

atgataaaat tgactaaatt acgcgaagat attagaaacg tcgctgttat tgcccacgtt   1320

gaccatggta aaactacatt ggttgacgaa ctcttaaaac aatctcaaac gttggatgct   1380

cgtaaagaat tagctgaacg tgcgatggac tcaaatgcac ttgagcaaga acgtgggatt   1440

actatccttg ccaaaaatac agcagttgaa tataacggaa ctcgtatcaa catcttggac   1500

acaccaggtc acgcggactt cggtggagaa gttgaacgta ttatgaaaat ggttgatggg   1560

gttgtcctcg ttgtcgatgc ttatgaagga acaatgcctc aaacacgttt tgttttgaaa   1620
```

```
<210> SEQ ID NO 194
<211> LENGTH: 468
<212> TYPE: DNA
<213> ORGANISM: Neisseria meningitidis groupe B
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 194

tttnnggcgg ntgttaccta catcgagccg attatgtggc agacggtgga gaagattatc     60

gccaaagagc ggcccgatgc gattctgccc acgatgggcg gccagaccgc gctgaactgt    120

gcgctggatt tggcgcgcaa cggcgtgctg gcgaaataca acgtcgagtt aatcggcgcg    180

acagaagacg cgattgacaa ggcggaagac cgtggccgct ttaaagaagc gatggaaaaa    240

atcggtttgt cttgcccgaa atcttttgtc tgccacacga tgaacgaagc cttggcggcg    300

caagaacagg tcggcttccc gacgctgatt cgtccgtctt tcacgatggg cggttcgggc    360

ggcggcattg cctacaataa agacgagttt ttggcgattt gcgaacgcgg tttcgatgcg    420

tcgcccacgc acgagctgct gattgagcag tccgtcctcg gctggaaa                 468
```

```
<210> SEQ ID NO 195
<211> LENGTH: 459
<212> TYPE: DNA
<213> ORGANISM: Neisseria meningitidis groupe C

<400> SEQUENCE: 195

gttacctaca tcgagccaat tatgtggcag acggtggaga agattatcgc caaggagcgt     60

cctgatgcga ttctgcccac gatgggcggt cagaccgcgc tgaactgtgc gctggatttg    120
```

-continued gcgcgcaacg gcgtgctggc gaaatacaat gtcgagctga tcggcgcgac ggaagacgcg 180
attgacaagg cggaagaccg cggtcgtttt aaagaagcga tggaaaaaat cggcctctcc 240
tgcccgaaat cttttgtctg ccacacgatg aacgaagctt tggcagcgca agaacaggtc 300
ggcttcccta ccctgattcg tccgtctttc acgatgggcg gttcgggcgg cggcattgcc 360
tacaataaag atgagttttt ggcgatttgc gaacgcggtt tcgatgcgtc gcctacgcac 420
gagctgctga ttgagcagtc tgttcctcgg ctggaaaga 459

<210> SEQ ID NO 196
<211> LENGTH: 458
<212> TYPE: DNA
<213> ORGANISM: Enterobacter cloaceae

<400> SEQUENCE: 196
gcaacctaca tcgagccaat tcactgggaa gtggtacgta aaatcatcga gaaagagcgt 60
ccggatgcgg ttctgccgac catgggtggc cagactgcgc tgaactgtgc gctggagctg 120
gagcgtcagg gcgtgctgga agagttcggc gtgaccatga ttggtgcgac cgccgacgcg 180
attgataaag cagaagaccg tcgtcgcttc gacgtggcga tgaaaaaaat cggcctcgac 240
accgcgcgtt ccggtatcgc tcacaacatg gaagaggcgc tggccgttgc ggctgaagtg 300
ggttatccgt gcatcatccg tccttccttc accatgggcg gcaccggcgg cggtatcgcc 360
tacaaccgcg aagagtttga agagatttgc gagcgcggcc tggatctctc cccaaccaaa 420
gagctgctga ttgatgaatc gctgattggc tggaaaga 458

<210> SEQ ID NO 197
<211> LENGTH: 453
<212> TYPE: DNA
<213> ORGANISM: Klebsiella pneumoniae

<400> SEQUENCE: 197
ctacatcgag ccgattcact gggaagtggt gcgtaaaatc atcgaaaaag agcgcccgga 60
tgcggtgctg ccgaccatgg gcggccagac ggcgctgaac tgcgcgctcg agctggagcg 120
tcagggggtc ctggctgaat tcggcgtgac catgattggt gccaccgccg atgcgattga 180
taaagccgaa gaccgtcgcc gtttcgatat cgcaatgaaa aaaatcggcc tcgacaccgc 240
gcgctctggt atcgcccaca cgatggaaga ggcgctggcg gttgccgccg acgttggttt 300
cccgtgcatc atccgtccgt ccttcaccat gggcggcacc ggcggcggta tcgcctataa 360
ccgcgaagag ttcgaagaaa tctgcgaacg cggcctggat ctctctccga ccaacgaact 420
gctgatcgat gaatcgctga tcggctggaa aga 453

<210> SEQ ID NO 198
<211> LENGTH: 458
<212> TYPE: DNA
<213> ORGANISM: Shigella sonnei

<400> SEQUENCE: 198
gcgacctaca tcgagccgat tcactgggaa gtagtacgca agattattga aaaagagcgc 60
ccggacgcgg tgctgccaac gatgggcggt cagacggcgc tgaactgcgc gctggagctg 120
gagcgtcagg gcgtgttgga agagttcggc gtgactatga ttggtgcgac cgccgatgcg 180
attgataaag cagaagaccg ccgtcgtttc gacgtagcga tgaagaaaat tggtctggaa 240
accgcgcgtt ccggtatcgc acacacgatg gaagaagcgc tggcggttgc cgctgacgtg 300

-continued ggcttcccgt gcattattcg cccatccttt accatgggcg gtagcggcgg cggtatcgct 360
tataaccgcg aagagtttga agaaatttgc gcccgcggtc tggatctctc cccaaccaaa 420
gagctgctga ttgatgagtc gctgatcggc tggaaaga 458

<210> SEQ ID NO 199
<211> LENGTH: 458
<212> TYPE: DNA
<213> ORGANISM: Escherichia coli

<400> SEQUENCE: 199
gcaacctaca tcgagccgat tcactgggaa gttgtacgca agattattga aaaagagcgc 60
ccggacgcgg tgctgccaac gatgggcggt cagacggcgc tgaactgcgc gctggagctg 120
gaacgtcagg gcgtgttgga agagttcggt gtcaccatga ttggtgccac tgccgatgcg 180
attgataaag cagaagaccg ccgtcgtttc gacgtagcga tgaagaaaat tggtctggaa 240
accgcgcgtt ccggtatcgc acacacgatg gaagaagcgc tggcggttgc cgctgacgtg 300
ggcttcccgt gcattattcg cccatccttt accatgggcg gtagcggcgg cggtatcgct 360
tataaccgtg aagagtttga agaaatttgc gcccgcggtc tggatctctc tccgaccaaa 420
gagttgctga ttgatgagtc gctgatcggc tggaaaga 458

<210> SEQ ID NO 200
<211> LENGTH: 453
<212> TYPE: DNA
<213> ORGANISM: Pseudomonas aeruginosa

<400> SEQUENCE: 200
ctacatcgag ccgatcaagt gggccaccgt ggccaagatc atcgagaagg aacgccccga 60
cgcgctgctg ccgaccatgg gcggccagac cgcgctgaac tgcgccctgg acctggagcg 120
ccacggcgtg ctggagaagt tcggcgtgga gatgatcggc gccaatgccg ataccatcga 180
caaggccgag gaccgctcgc gcttcgacaa ggcgatgaag gatatcggcc tggcctgtcc 240
gcgctcgggc atcgcccaca gcatggagga ggcctacggc gtgctcgagc aggtcggctt 300
cccctgcatc atccgtccgt ccttcaccat gggcggcacc ggcggcggta tcgcctacaa 360
ccgtgaagag ttcgaagaga tctgcgcccg tggcctcgac ctgtcgccga ccaacgagct 420
gttgatcgac gagtcgctga tcggctggaa aga 453

<210> SEQ ID NO 201
<211> LENGTH: 458
<212> TYPE: DNA
<213> ORGANISM: Escherichia coli

<400> SEQUENCE: 201
gcgacctaca tcgagccgat tcactgggaa gtggtacgta agattattga aaaagagcgc 60
ccggacgcgg tgctgccaac catgggcggt cagacggcgc tgaactgcgc gctggagctg 120
gaacgtcagg gcgtgttgga agagttcggc gtcaccatga ttggtgccac tgccgatgcg 180
attgataaag cagaagaccg ccgtcgtttc gacgtagcga tgaagaaaat tggtctggaa 240
accgcgcgtt ccggtatcgc acatacgatg gaagaagcgc tggcggttgc cgctgacgtg 300
ggcttcccgt gcattattcg cccatccttt accatgggcg gtagcggcgg cggtatcgct 360
tataaccgcg aagagtttga agaaatttgc gcccgcggtc tggatctctc tccgaccaaa 420
gagttgctga ttgatgagtc gctgatcggc tggaaaga 458

-continued

<210> SEQ ID NO 202
<211> LENGTH: 454
<212> TYPE: DNA
<213> ORGANISM: Salmonella typhimurium

<400> SEQUENCE: 202
cctacatcga gccgattcac tgggaagtgg tgcgcaaaat cattgaaaaa gagcgtccgg 60
atgcggtgct gccgaccatg ggcggccaga ccgcgctgaa ctgcgcgctg gagctggagc 120
ggcagggcgt gctggaagag ttcggcgtca ccatgattgg tgcgaccgcc gacgccattg 180
ataaagccga agaccgtcgt cgcttcgata tcgcgatgaa gaaaattggt ctcgacaccg 240
cgcgttccgg tatcgcgcac actatggaag aagcgctggc ggttgccgct gacgtgggct 300
tcccgtgcat catccggcct agctttacca tgggcggcac cggcggcggt atcgcttaca 360
accgtgaaga gttcgaagaa atctgcgaac gcggtctgga cctctcgcca accaacgagc 420
tgctgattga tgaatcgctg atcggctgga aaga 454

<210> SEQ ID NO 203
<211> LENGTH: 461
<212> TYPE: DNA
<213> ORGANISM: Salmonella enterica hadar
<220> FEATURE:
<221> NAME/KEY: misc_feature
<222> LOCATION: (7)..(7)
<223> OTHER INFORMATION: n is a, c, g, or t

<400> SEQUENCE: 203
tgatgcncct acatcgagcc gattcactgg gaagtggtac gcaaaatcat cgaaaaagag 60
cgtccggatg cggtgctgcc gaccatgggc ggccagacgg cgctgaactg cgcgctggag 120
ctggagcggc agggcgtgct ggaagagttc ggcgtcacca tgattggcgc caccgccgac 180
gccattgata aagccgaaga ccgtcgtcgc ttcgatatcg cgatgaagaa aattggtctc 240
gacaccgcgc gttccggtat cgcgcacact atggaagaag cgctggcggt tgccgctgac 300
gtgggcttcc cgtgcatcat ccgtccgtcc tttaccatgg gcggcaccgg cggcggtatc 360
gcttacaacc gtgaagagtt cgaagaaatc tgcgaacgcg gtctggacct ctcgccaacc 420
aacgagctgc tgattgatga atcgctgatc ggctggaaag a 461

<210> SEQ ID NO 204
<211> LENGTH: 464
<212> TYPE: DNA
<213> ORGANISM: Salmonella enteritidis

<400> SEQUENCE: 204
ggctgatgcc cctacatcga gccgattcac tgggaagtgg tacgcaaaat catcgaaaaa 60
gagcgtccgg atgcggtgct gccgaccatg ggcggccaga cggcgctgaa ctgcgcgctg 120
gagctggagc ggcagggcgt gctggaagag ttcggcgtca ccatgattgg cgccaccgcc 180
gacgccattg ataaagccga agaccgtcgt cgcttcgata tcgcgatgaa gaaaattggt 240
ctcgacaccg cgcgttccgg tatcgcgcac actatggaag aagcgctggc ggttgccgct 300
gacgtgggct tcccgtgcat catccgtccg tcctttacca tgggcggcac cggcggcggt 360
atcgcttaca accgtgaaga gttcgaagaa atctgcgaac gcggtctgga cctctcgcca 420
accaacgagc tgctgattga tgaatcgctg atcggctgga aaga 464

<210> SEQ ID NO 205
<211> LENGTH: 452
<212> TYPE: DNA

-continued

<213> ORGANISM: Salmonella enterica Brandenburg

<400> SEQUENCE: 205
tacatcgagc cgattcactg ggaagtggtg cgcaaaatca ttgaaaaaga gcgtccggat 60
gcggtgctgc cgaccatggg cggccagacg gcgctgaact gcgcgctgga gctggagcgg 120
cagggcgtgc tcgaagagtt cggcgtcacc atgattggcg ccaccgccga cgccattgat 180
aaagccgaag accgtcgtcg cttcgatatc gcgatgaaga aaattggtct cgacaccgcg 240
cgttccggta tcgcgcacac tatggaagaa gcgctggcgg ttgccgctga tgtgggcttc 300
ccgtgcatca tccgtccgtc ctttaccatg ggcggcaccg gtggcggtat cgcttacaac 360
cgtgaagagt tcgaagaaat ctgcgaacgc ggtctggacc tctcgccaac caacgagctg 420
ctgattgatg aatcgctgat cggctggaaa ga 452

<210> SEQ ID NO 206
<211> LENGTH: 453
<212> TYPE: DNA
<213> ORGANISM: Salmonella enterica derby

<400> SEQUENCE: 206
ctacatcgag ccgattcact gggaagtggt gcgcaaaatc atcgaaaaag agcgtccgga 60
tgcggtgctg ccgaccatgg gcggccagac cgcgctgaac tgcgcgctgg agctggagcg 120
gcagggcgtg ctcgaagagt tcggcgtcac catgattggc gccaccgccg acgccattga 180
taaagccgaa gaccgtcgtc gcttcgatat cgcgatgaag aaaatcggtc tcgacaccgc 240
gcgttccggt atcgcgcaca ctatggaaga agcgctggcg gttgccgctg acgtgggctt 300
cccgtgcatc atccgtccgt cctttaccat gggcggcacc ggcggcggta tcgcttacaa 360
ccgtgaagag ttcgaagaaa tctgcgaacg cggtctggac ctctcgccaa ccaacgagct 420
gctgattgat gaatcgctga tcggctggaa aga 453

<210> SEQ ID NO 207
<211> LENGTH: 453
<212> TYPE: DNA
<213> ORGANISM: Salmonella enterica virschow

<400> SEQUENCE: 207
ctacatcgag ccgattcact gggaagtggt gcgcaaaatc attgaaaaag agcgtccgga 60
tgcagtgctg ccgaccatgg gcggccagac ggcgctgaac tgtgcgctgg agctggagcg 120
gcagggcgtg ctggaagagt tcggcgtcac catgattggc gccaccgccg acgccattga 180
taaagccgaa gaccgtcgtc gcttcgatat cgcgatgaag aaaattggtc tcgacaccgc 240
gcgttccggt atcgcgcaca ctatggaaga agcgctggcg gttgccgctg acgtgggctt 300
cccgtgcatc atccgtccgt cctttaccat gggcggcacc ggcggcggta tcgcttacaa 360
ccgtgaagag ttcgaagaaa tctgcgaacg cggtctggac ctctcgccaa ccaacgagct 420
gctgattgat gaatcgctga tcggctggaa aga 453

<210> SEQ ID NO 208
<211> LENGTH: 453
<212> TYPE: DNA
<213> ORGANISM: Salmonella paratyphi B

<400> SEQUENCE: 208
ctacatcgag ccgattcact gggaagtggt gcgcaaaatc attgaaaaag agcgtccgga 60
tgcagtgctg ccgaccatgg gcggccagac cgcgctgaac tgcgcgctgg agctggagcg 120

-continued

```
gcagggcgtg ctcgaagagt tcggcgtcac catgattggc gccaccgccg acgccattga    180

taaagccgaa gaccgtcgtc gcttcgatat cgcgatgaag aaaattggtc tcgacaccgc    240

gcgttccggt atcgcgcaca ctatggaaga agcgctggcg gttgccgctg acgtgggctt    300

cccgtgcatc atccggccta gctttaccat gggcggcacc ggcggcggta tcgcttacaa    360

ccgtgaagag ttcgaagaaa tctgcgaacg cggtctggac ctctcgccaa ccaacgagct    420

gctgattgat gaatcgctga tcggctggaa aga                                 453
```

<210> SEQ ID NO 209
<211> LENGTH: 503
<212> TYPE: DNA
<213> ORGANISM: Proteus vulgaris

<400> SEQUENCE: 209

```
cgacagtcat gaccgaccct gaaatggcgg atgccaccta catcgagcct attcattggc     60

aagtcgtcag aaaaattatt gaaaaagagc gccctgatgc gattttgcca acaatggggg    120

ggcaaacggc attaaattgc gcattagaat tagaacgtca aggtgtgtta gctgaattcg    180

gtgtgaccat gattggtgct acggctgatg ctatcgataa agcagaagat agacaacgct    240

ttgataaagc aatgaaaaaa atcggcttag gcacagctcg ctcaggtatt gctcataatc    300

tagaagaagc ttttgccgtc gctgaagatg tcggattccc ttgcatcatt cgtccttcat    360

ttactatggg cggcacgggg ggcggtatcg cttataaccg tgaagaattt gaagaaattt    420

gtactcgtgg attagattta tcaccgacta acgagttatt gattgatgaa tcacttattg    480

gttggaaaga gtacgagatg gaa                                            503
```

<210> SEQ ID NO 210
<211> LENGTH: 503
<212> TYPE: DNA
<213> ORGANISM: Enterobacter aerogenes

<400> SEQUENCE: 210

```
cgacactcat gaccgacccg gaaatggccg atgcgaccta tatcgagccg attcactggg     60

aagtggtgcg taaaattatc gaaaaagagc gtccggacgc ggtgctgccg accatgggcg    120

gccagaccgc gctgaactgc gcgctggagc tggagcgtca gggcgtgctg gcagagttcg    180

gcgtgaccat gattggtgcg accgccgatg cgatcgataa agcggaagac cgccgtcgct    240

tcgacgtggc gatgaagaaa atcggtctcg acaccgcgcg ttccggcatt gcgcacacca    300

tggaagaagc gctggcggtg gccgctgaag ttggcttccc atgcatcatc cgtccgtcct    360

ttactatggg cggcaccggc ggcggtatcg cctataaccg cgaagagttc gaagaaatct    420

gcgaacgcgg cctggatctc tctccgacca acgaactgct gattgatgaa tcgctgatcg    480

gctggaagga atacgaaatg gaa                                            503
```

<210> SEQ ID NO 211
<211> LENGTH: 453
<212> TYPE: DNA
<213> ORGANISM: Burkholderia cepacia

<400> SEQUENCE: 211

```
cgacagtcat gaccgatccg gaccgcgaca tcacagcgac agtgatgcgt gaacgaacta     60

ggctagtgaa atttatccgg cgccggatac gcgacccgga cgatgccgag gacatcctgc    120

aggatgtgtt tcacgagttc gtacaagcgt atcgacttcc agcgcccatt gaacaggtga    180
```

-continued

```
gcgcgtggct tttccgtgcc gcgcgcaacc gaatcgtcga ccgttttcgc aagaagaagg    240

agcagccgct ggccgacctg tcggaggtcg acgatgacgc gaacagcgag tatcgcctcg    300

acctcgcgct accggcgcat gatgccggcc ccgaagcact ctacgctcgc acgctcgtgc    360

tcaaggcctt gcaggatgcg ctcgacgagt tgccgacgaa tcagcgtgac gtctttatcg    420

cacacgagct ggagggtcag tcataaatgt cga                                 453
```

<210> SEQ ID NO 212
<211> LENGTH: 616
<212> TYPE: DNA
<213> ORGANISM: Burkholderia mallei

<400> SEQUENCE: 212

```
ggcgttgcgt gaggagggct acaaggtcat cctcgtcaac agcaacccgg cgacgatcat     60

gaccgatccg aacacggcgg acgtcacgta catcgagccg atcacgtggg aagtcgtcga    120

gcgcatcatc gcgaaggagc gccccgacgc gatcctgccg acgatgggcg gccagaccgc    180

gctgaactgc gcgctcgacc tgttccacca cggcgtgctc gagaagtacg gcgtcgagct    240

gatcggcgcg tcgccggagg cgatcgacaa ggccgaagac cgccagaagt tcaaggacgc    300

gatgacgaag atcggcctcg gctcggcgaa gtccggcatc gcgcactcga tggaagaggc    360

gctgaaggtg cacgcggaca tcgcggcggc gacgggcggc agcggctacc cggtcgtgat    420

ccgcccgtcg ttcacgctcg gcggctcggg cggcggcatc gcgtacaacc gcgaggagtt    480

cgaggagatc tgcaagcgcg gcctcgatct gtcgccgacg cgcgagctgc tgatcgagga    540

atcgctgctc ggctggaagg agtacgagat ggaggtcgtg cgcgatcgcg ccgacaactg    600

catcatcgtc tgctcg                                                    616
```

<210> SEQ ID NO 213
<211> LENGTH: 616
<212> TYPE: DNA
<213> ORGANISM: Burkholderia pseudomallei

<400> SEQUENCE: 213

```
ggcgttgcgt gaggagggct acaaggtcat cctcgtcaac agcaacccgg cgacgatcat     60

gaccgatccg aacacggcgg acgtcacgta catcgagccg atcacgtggg aagtcgtcga    120

gcgcatcatc gcgaaggagc gccccgacgc gatcctgccg acgatgggcg gccaaaccgc    180

gctgaactgc gcgctcgacc tgttccacca cggcgtgctc gagaagtacg gcgtcgagct    240

gatcggcgcg tcgccggagg cgatcgacaa ggccgaagac cgccagaagt tcaaggacgc    300

gatgacgaag atcggcctcg gctcggcgaa gtccggcatc gcgcactcga tggaagaggc    360

gctgaaggtg cacgcggaca tcgcggcggc gacgggcggc agcggctacc cggtcgtgat    420

ccgcccgtcg ttcacgctcg gcggctcggg cggcggcatc gcgtacaacc gcgaggagtt    480

cgaggagatc tgcaagcgcg gcctcgatct gtcgccgacg cgcgagctgc tgatcgagga    540

atcgctgctc ggctggaagg agtacgagat ggaggtcgtg cgcgatcgcg ccgacaactg    600

catcatcgtc tgctcg                                                    616
```

<210> SEQ ID NO 214
<211> LENGTH: 502
<212> TYPE: DNA
<213> ORGANISM: Legionella pneumophila

<400> SEQUENCE: 214

```
cgacacttat gactgatcct gagcttgctg atgccaccta tatagagcct gttcaatgga     60
```

-continued aagaagtggc tcgtattatc gaaatagaga ggccagatgc tcttttaccg acgatgggag 120
gacaaacagc cttaaactgc gccttggact tggtaagaga aggggtatta gccaagtact 180
ctgttgaaat gataggagcg acgcgtgaag ccatagacag ggcggaagat agagaaaaat 240
ttcgccagct gatgattaaa atcggattgg atatgccaag gtcgacgatt gctcatagcc 300
tggaagaagc aattcaagta caagcccgtt taggctttcc tgccatcatc aggccttcat 360
ttaccatggg tggtagtgga ggcggtattg cctataatcg tgaagaattt gaagaaattt 420
gcattagagg attggagttg tcgccaactc acgagctttt gattgatgaa tcggttctgg 480
gttggaaaga atatgaaatg ga 502

<210> SEQ ID NO 215
<211> LENGTH: 502
<212> TYPE: DNA
<213> ORGANISM: Citrobacter freundii

<400> SEQUENCE: 215
cgacacttat gactgatccg gaaatggccg atgccaccta catcgagccg attcactggg 60
aagtggtacg caaaatcatt gagaaagagc gcccggatgc ggtgctgcca accatgggcg 120
gtcagacggc gctgaactgt gcgctggagc tggaacgcca gggcgtactg gctgaattcg 180
gcgtgaccat gattggcgca acggcggatg ccattgataa agcggaagac cgtcgtcgct 240
ttgatatcgc gatgaagaaa attggtctcg acaccgcgcg ctctggcatc gctcacacca 300
tggaagaagc gctggcggtt gctgctgacg tgggcttccc gtgcatcatc cgaccgagct 360
tcaccatggg cggcaccggc ggcggtatcg cttataaccg tgaagagttc gaagagattt 420
gtgaacgcgg tctggacctt tccccaacca acgagctgct gattgatgaa tcgctgattg 480
gctggaaaga gtacgaaatg ga 502

<210> SEQ ID NO 216
<211> LENGTH: 503
<212> TYPE: DNA
<213> ORGANISM: Acinetobacter baumanii

<400> SEQUENCE: 216
tccatttcgt actctttcca gccaattaaa gattcctcga tcaataattg gtgagtagga 60
gagaggtcga aaccacgttc acaaatctct aggaattctt cgcggttata tgcaatacca 120
ccgcctgaac cacccatagt gaatgacgga cggataatta ctgggaaacc aaagcgagat 180
tgaatttcca atgcttcttc cattgtttca gcaatggcag cttttggaca ttccaagccg 240
attttgcgca ttgcttcatc aaacaattta cggtcttcag ctttttcaat tgcttctttt 300
gttgcaccaa taagttctac gccgtatttt tctaatacac cattttcatc aagtgcaagt 360
gcgcagttaa gagcagtttg tccacccata gtagggagta ctgcatctgg gcgctctttt 420
tcaatgattt gagcaacagt ttgccaagta attggctcaa tataagttgc atcagccatt 480
gaagggtcag tcataagtgt cga 503

<210> SEQ ID NO 217
<211> LENGTH: 503
<212> TYPE: DNA
<213> ORGANISM: Serratia marcescens

<400> SEQUENCE: 217
cgacagttat gaccgacccg gagatggccg acgcgaccta tattgagccg atccactggg 60

-continued

```
aagtggtgcg caagatcatc gaaaaagagc gcccggatgc ggtgctgccg accatgggcg    120

gccagacggc gctgaactgc gcgctggagc tggagcgcca gggcgtgctg gccgagttcg    180

gcgttaccat gatcggcgcc accgccgatg cgattgacaa ggccgaagac cgtcgccgct    240

tcgatgtggc gatgaagaaa atcggtctgg ataccgcgcg ttccggcatc gcgcacacca    300

tggaagaagc gctggcggta gccgctgacg tcggcttccc gtgcatcatc cgcccttcct    360

ttaccatggg cggcaccggc ggcggcatcg cctacaaccg cgaagagttc gaagagatct    420

gcgaacgcgg tctggacctg tcgccgacca acgagctgct gatcgatgaa tcgctgatcg    480

gttggaaaga atacgagatg gaa                                            503
```

<210> SEQ ID NO 218
<211> LENGTH: 610
<212> TYPE: DNA
<213> ORGANISM: Pseudomonas putida

<400> SEQUENCE: 218

```
cgacactcat gaccgacccc ggatttgagt gaccaccatg ccaaaacgta cagacatcaa     60

aagcatcctg attctcggtg ccggcccgat cgtgatcggc caggcctgtg aattcgacta    120

ctccggcgcc caggcctgca aggccctgcg cgaggaaggt ttccgcgtca tcctggtgaa    180

ctccaaccca gccaccatca tgaccgaccc ggccatggcc gacgccacct acatcgagcc    240

gatcaagtgg cagtcggtgg ccaagatcat cgagaaagag cgcccggacg ccgttttgcc    300

gaccatgggt ggccagaccg ccctgaactg cgccctggac ctggagcgcc acggcgttct    360

ggagaagttt ggcgtagaga tgatcggtgc caacgccgat accatcgaca aggctgaaga    420

ccgctcgcgc ttcgacaagg ccatgaaaga catcggcctg gaatgcccgc gctcgggtat    480

cgcccacagc atggaagagg ccaatgcggt cctcgaaaag ctcggcttcc cgtgcatcat    540

tcgcccgtcg ttcaccatgg ggtggcaccg gcggtggtat cgcttacaac cgtgaagaat    600

tcgaagaaat                                                           610
```

<210> SEQ ID NO 219
<211> LENGTH: 466
<212> TYPE: DNA
<213> ORGANISM: Morganella morganii

<400> SEQUENCE: 219

```
cgaaaaagag cgcccggatg ccgttctgcc gaccatgggc ggacaaaccg cgctgaactg     60

tgcgctggat ctggaacgtc acggcgtgct ggcagagttc ggcgtcgaaa tgattggcgc    120

gacagcagat gcgattgata aagccgaaga tcgccgccgt ttcgatatcg cgatgaaaaa    180

aatcggtctg gatacagcgc gttccggtat cgcacacacc atggaagaag cgtttgcggt    240

cgccgatgat gtcggtttcc cgtgcattat ccgcccgtca ttcaccatgg gcggcaccgg    300

cggcggtatt gcgtataacc gtgaagaatt cgaggaaatc tgtacccgcg gcctggatct    360

ctccctgacc aacgaactgc tgattgatga atcactgatt ggctggaaag agtacgaaat    420

ggaaagggcg aattccagca cactggcggc cgttactagt ggatca                   466
```

<210> SEQ ID NO 220
<211> LENGTH: 503
<212> TYPE: DNA
<213> ORGANISM: Klebsiella oxytoca

<400> SEQUENCE: 220

```
cgacagttat gactgacccg gaaatggccg atgccaccta catcgagccg attcactggg     60
```

aagtggtgcg caagatcatt gagaaagagc gtccggatgc ggttctgccg accatgggcg 120
gccagacggc gctgaactgc gcgctggagc tggagcgtca gggcgtgctg gccgagttcg 180
gcgtgaccat gattggcgcg accgccgacg cgattgataa agccgaagac cgccgccgtt 240
tcgacgtggc gatgaagaaa atcggtctcg ataccgcgcg ttccggtatc gcgcatacca 300
tggaagaagc gctggcggtt gccgctgaag ttggcttccc gtgcatcatc cgtccgtcct 360
ttacgatggg cggcaccggc ggcggtatcg cctacaaccg cgaagagttc gaagagatct 420
gcgaacgcgg tctggatctc tcgccgacca acgagctgct gattgatgaa tcgctgatcg 480
gctggaaaga atacgaaatg gaa 503

<210> SEQ ID NO 221
<211> LENGTH: 502
<212> TYPE: DNA
<213> ORGANISM: Moraxella catarrhalis
<220> FEATURE:
<221> NAME/KEY: misc_feature
<222> LOCATION: (481)..(481)
<223> OTHER INFORMATION: n is a, c, g, or t
<220> FEATURE:
<221> NAME/KEY: misc_feature
<222> LOCATION: (493)..(493)
<223> OTHER INFORMATION: n is a, c, g, or t

<400> SEQUENCE: 221
ccacattatg actgacccgt ccatggctga tgccacttat attgaaccga ttacctggca 60
gacggtagag caaatcattg ccaaagagcg tcctgatgcc attttgccaa ccatgggtgg 120
acaaacggca cttaactgtg cgcttgacct tgacaaacat ggcgtgcttg ccaaatatgg 180
ctgtgagctg attggggcga ccaaagaagc cattgaaaaa gccgaagacc gtgaactgtt 240
tgataaagcc atgaaaaaaa tcggtctgga atgccccaaa gcagaaattg cacagagcat 300
ggatgatgct tttgccattc aagctaaggt tggttttccg tgcattatcc gcccatcatt 360
caccatgggg ggttctgggg gtggcattgc ttataaccgt gaggagttta ttgagatttg 420
tgagcgtggg tttgacttat cacccaccca ccagctgctc attgatgaga gtttaatcgg 480
ntggaaagag tangaaatgg aa 502

<210> SEQ ID NO 222
<211> LENGTH: 624
<212> TYPE: DNA
<213> ORGANISM: Brucella melitensis biovar 1

<400> SEQUENCE: 222
tcttcgatca gaacttcggt cgtcggcgaa gcgtcgaggc cgcgttcgat aatctcgaag 60
aattcctgac ggttataggc aatgccgccg ccggtgccgc cgagcgtgaa ggaggggcgg 120
atgatcgcgg gcaggccaac cacgtcgagc gcctgtgctg cctttgcaag cgcatggctc 180
atatagcgct gcttgcgctc cacttcgccg agctgccatt cggtttcaag cttgtcgagc 240
gccttgtcca gttcgtcgcc ggagaattgc gccttcacct ccgcgcgctt gacctcgtgg 300
cgcttgcggt cctcatcctt gatttcagtc gcattggcga acatcgagcc cggcgtgtcg 360
aggccgatct tcttcatggc ttcgcggaag agcgcgcggt cttcggcctt gtcgatagct 420
tcggccttgg cgccgatcat ctcgacgtta taacgttcaa gcacgcccat gcggcgcaag 480
gaaagcgcgg tgttgagcgc ggtctgtccg cccatcgtcg gcaggatcgc gtccgggcgc 540
tccttggcga tgatcttggc gacgacttcc ggcgtgatcg gctcgatata ggttgcatcc 600

-continued gccagatcgg gatcagtata aaat 624

<210> SEQ ID NO 223
<211> LENGTH: 618
<212> TYPE: DNA
<213> ORGANISM: Brucella melitensis biovar 2

<400> SEQUENCE: 223
ttcttcgatc agaacttcgg tcgtcggcga agcgtcgagg ccgcgttcga taatctcgaa 60
gaattcctga cggttatagg caatgccgcc gccggtgccg ccgagcgtga aggaggggcg 120
gatgatcgcg ggcaggccaa ccacgtcgag cgcctgtgct gcctttgcaa gcgcatggct 180
catatagcgc tgcttgcgct ccacttcgcc gagctgccat tcggtttcaa gcttgtcgag 240
cgccttgtcc agttcgtcgc cggagaattg cgccttcacc tccgcgcgct tgacctcgtg 300
gcgcttgcgg tcctcatcct tgatttcagt cgcattggcg aacatcgagc ccggcgtgtc 360
gaggccgatc ttcttcatgg cttcgcggaa gagcgcgcgg tcttcggcct tgtcgatagc 420
ttcggccttg gcgccgatca tctcgacgtt ataacgttca agcacgccca tgcggcgcaa 480
ggaaagcgcg gtgttgagcg cggtctgtcc gcccatcgtc ggcaggatcg cgtccgggcg 540
ctccttggcg atgatcttgg cgacgacttc cggcgtgatc ggctcgatat aggttgcatc 600
cgccagatcg ggatcagt 618

<210> SEQ ID NO 224
<211> LENGTH: 617
<212> TYPE: DNA
<213> ORGANISM: Brucella abortus biovar 1

<400> SEQUENCE: 224
tcttcgatca gtaacttcgg tcgtcggcga agcgtcgagg ccgcgttcga taatctcgaa 60
gaattcctga cggttatagg caatgccgcc gccggtgccg ccgagcgtga aggaggggcg 120
gatgatcgcg ggcaggccaa ccacgtcgag cgcctgtgct gcctttgcaa gcgcatggct 180
catatagcgc tgcttgcgct ccacttcgcc gagctgccat tcggtttcaa gcttgtcgag 240
cgccttgtcc agttcgtcgc cggagaattg cgccttcacc tccgcgcgct tgacctcttg 300
gcgcttgcgg tcctcatcct tgatttcagt cgcattggcg aacatcgagc ccggcgtgtc 360
gaggccgatc ttcttcatgg cttcgcggaa gagcgcgcgg tcttcggcct tgtcgatagc 420
ttcggccttg gcgccgatca tctcgacgtt ataacgttca agcacgccca tgcggcgcaa 480
ggaaagcgcg gtgttgagcg cggtctgtcc gcccatcgtc ggcaggatcg cgtccgggcg 540
ctccttggcg atgatcttgg cgacgacttc cggcgtgatc ggctcgatat aggttgcatc 600
cgccagatcg ggatcag 617

<210> SEQ ID NO 225
<211> LENGTH: 633
<212> TYPE: DNA
<213> ORGANISM: Brucella abortus biovar 2

<400> SEQUENCE: 225
cgcctcttcg atcagtaact tcggtcgtcc ggcgaagcgt cgaggccgcg ttcgataatc 60
tcgaagaatt cctgacggtt ataggcaatg ccgccgccgg tgccgccgag cgtgaaggag 120
gggcggatga tcgcgggcag gccaaccacg tcgagcgcct gtgctgcctt tgcaagcgca 180
tggctcatat agcgctgctt gcgctccact tcgccgagct gccattcggt ttcaagcttg 240
tcgagcgcct tgtccagttc gtcgccggag aattgcgcct tcacctccgc gcgcttgacc 300
tcttggcgct tgcggtcctc atccttgatt tcagtcgcat tggcgaacat cgagcccggc 360
gtgtcgaggc cgatcttctt catggcttcg cggaagagcg cgcggtcttc ggccttgtcg 420
atagcttcgg ccttggcgcc gatcatctcg acgttataac gttcaagcac gcccatgcgg 480
cgcaaggaaa gcgcggtgtt gagcgcggtc tgtccgccca tcgtcggcag gatcgcgtcc 540
gggcgctcct tggcgatgat cttggcgacg acttccggcg tgatcggctc gatataggtt 600
gcatccgcca gatcgggatc agtataaatt agt 633

<210> SEQ ID NO 226
<211> LENGTH: 632
<212> TYPE: DNA
<213> ORGANISM: Brucella suis biovar 1
<220> FEATURE:
<221> NAME/KEY: misc_feature
<222> LOCATION: (6)..(6)
<223> OTHER INFORMATION: n is a, c, g, or t

<400> SEQUENCE: 226
ttagancgcc tcttcgatca gaacttcggt cgtcggcgaa gcgtcgaggc cgcgttcgat 60
aatctcgaag aattcctgac ggttataggc aatgccgccg ccggtgccgc cgagcgtgaa 120
ggaggggcgg atgatcgcgg gcaggccaac cacgtcgagc gcctgcgctg cctttgcaag 180
cgcatggctc atatagcgct gcttgcgctc cacttcgccg agctgccatt cggtttcaag 240
cttgtcgagc gccttgtcca gttcgtcgcc ggagaattgc gccttcacct ccgcgcgctt 300
ggcctcgtgg cgcttgcggt cctcatcctt gatttcagtc gcattggcga gcatcgagcc 360
cggcgtgtcg aggccgatct tcttcatggc ttcgcggaag agcgcgcggt cttcggcctt 420
gtcgatagct tcggccttgg cgccgatcat ctcgacgtta taacgttcaa gcacgcccat 480
gcggcgcaag gaaagcgcgg tgttgagcgc ggtctgtccg cccatcgtcg gcaggatcgc 540
gtccgggcgc tccttggcga tgatcttggc gacgacttcc ggcgtgatcg gctcgatata 600
ggttgcatcc gccagatcgg gatcagtata aa 632

<210> SEQ ID NO 227
<211> LENGTH: 635
<212> TYPE: DNA
<213> ORGANISM: Brucella suis biovar 3

<400> SEQUENCE: 227
cccgcattct tcgatcagta acttcggtcg tcggcgaagc gtcgaggccg cgttcgataa 60
tctcgaagaa ttcctgacgg ttataggcaa tgccgccgcc ggtgccgccg agcgtgaagg 120
aggggcggat gatcgcgggc aggccaacca cgtcgagcgc ctgcgctgcc tttgcaagcg 180
catggctcat atagcgctgc ttgcgctcca cttcgccgag ctgccattcg gtttcaagct 240
tgtcgagcgc cttgtccagt tcgtcgccgg agaattgcgc cttcacctcc gcgcgcttgg 300
cctcgtggcg cttgcggtcc tcatccttga tttcagtcgc attggcgagc atcgagcccg 360
gcgtgtcgag gccgatcttc ttcatggctt cgcggaagag cgcgcggtct tcggccttgt 420
cgatagcttc ggccttggcg ccgatcatct cgacgttata acgttcaagc acgcccatgc 480
ggcgcaagga aagcgcggtg ttgagcgcgg tctgtccgcc catcgtcggc aggatcgcgt 540
ccgggcgctc cttggcgatg atcttggcga cgacttccgg cgtgatcggc tcgatatagg 600
ttgcatccgc cagatcggga tcagtataaa ttagt 635

<210> SEQ ID NO 228

-continued

<211> LENGTH: 624
<212> TYPE: DNA
<213> ORGANISM: Brucella canis

<400> SEQUENCE: 228
ttcttcgata gaacttcggt cgtcggcgaa gcgtcgaggc cgcgttcgat aatctcgaag 60
aattcctgac ggttataggc aatgccgccg ccggtgccgc cgagcgtgaa ggaggggcgg 120
atgatcgcgg gcaggccaac cacgtcgagc gcctgcgctg cctttgcaag cgcatggctc 180
atatagcgct gcttgcgctc cacttcgccg agctgccatt cggtttcaag cttgtcgagc 240
gccttgtcca gttcgtcgcc ggagaattgc gccttcacct ccgcgcgctt ggcctcgtgg 300
cgcttgcggt cctcatcctt gatttcagtc gcattggcga gcatcgagcc cggcgtgtcg 360
aggccgatct tcttcatggc ttcgcggaag agcgcgcggt cttcggcctt gtcgatagct 420
tcggccttgg cgccgatcat ctcgacgtta taacgttcaa gcacgcccat gcggcgcaag 480
gaaagcgcgg tgttgagcgc ggtctgtccg cccatcgtcg gcaggatcgc gtccgggcgc 540
tccttggcga tgatcttggc gacgacttcc ggcgtgatcg gctcgatata ggttgcatcc 600
gccagatcgg gatcagtata aaaa 624

<210> SEQ ID NO 229
<211> LENGTH: 632
<212> TYPE: DNA
<213> ORGANISM: Brucella ovis

<400> SEQUENCE: 229
accgcttctt cgatcagtaa cttcggtcgt cggcgaagcg tcgaggccgc gttcgataat 60
ctcgaagaat tcctgacggt tataggcaat gccgccgccg gtgccgccga gcgtgaagga 120
ggggcggatg atcgcgggca ggccaaccac gtcgagcgcc tgcgctgcct ttgcaagcgc 180
atggctcata tagcgctgct tgcgctccac ttcgccgagc tgccattcgg tttcaagctt 240
gtcgagcgcc ttgtccagtt cgtcgccgga gaattgcgcc ttcacctccg cgcgcttggc 300
ctcgtggcgc ttgcggtcct catccttgat ttcagtcgca ttggcgagca tcgagcccgg 360
cgtgtcgagg ccgatcttct tcatggcttc gcggaagagc gcgcggtctt cggccttgtc 420
gatagcttcg gccttggcgc cgatcatctc gacgttataa cgttcaagca cgcccatgcg 480
gcgcaaggaa agcgcggtgt tgagcgcggt ctgtccgccc atcgtcggca ggatcgcgtc 540
cgggcgctcc ttggcgatga tcttggcgac gacttccggc gtgatcggct cgatataggt 600
tgcatccgcc agatcgggat cagtataaaa tt 632

<210> SEQ ID NO 230
<211> LENGTH: 482
<212> TYPE: DNA
<213> ORGANISM: Francisella tularensis
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t

<400> SEQUENCE: 230
ccnactatta tgactgatcc ancaaccgca gataaaatct ttatcgagcc aattacggtt 60
gagagtgttg gtaaaattat cgctagagaa agaccagatg caatcttacc tacagtaggt 120
ggacaaactg cgcttaactg tgctttagca ttagacaaag ctggtatttt agaaaaatat 180
aatgtcgaaa tgcttggtgc aaaagctgac tctattgata aggcagaaaa tagagaaaga 240
tttaacaaag ccatggcaaa aattggctta gaggttccta gaaatgttgt agtgcaatcg 300
atggagcaag cttataaagc tctagaagat atcggactac cggctattat cagaccatca 360
tttacacttg gtggtagcgg tggtggtatc gcttatacaa aagaagagtt tgaaaaaatt 420
gtcaaaaatg gtctaagcct atcaccaaca aatgaagtac taatagagag gcaccctaan 480
at 482

<210> SEQ ID NO 231
<211> LENGTH: 480
<212> TYPE: DNA
<213> ORGANISM: Francisella tularensis
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (469)..(469)
<223> OTHER INFORMATION: n is a, c, g, or t
<220> FEATURE:
<221> NAME/KEY: misc_feature
<222> LOCATION: (472)..(472)
<223> OTHER INFORMATION: n is a, c, g, or t
<220> FEATURE:
<221> NAME/KEY: misc_feature
<222> LOCATION: (476)..(476)
<223> OTHER INFORMATION: n is a, c, g, or t
<220> FEATURE:
<221> NAME/KEY: misc_feature
<222> LOCATION: (479)..(479)
<223> OTHER INFORMATION: n is a, c, g, or t

<400> SEQUENCE: 231
acgaantaga ctgatccaac aaccgcagat aaaatcttta tcgagccaat tacggttgag 60
agtgttggta aaattatcgc tagagaaaga ccagatgcaa tcttacctac agtaggtgga 120
caaactgcgc ttaactgtgc tttagcatta gacaaagctg gtattttaga aaaatataat 180
gtcgaaatgc ttggtgcaaa agctgactct attgataagg cagaaaatag agaaaaattt 240
aacaaagcca tggcaaaaat tggcttagag gttcctagaa atgttgtagt gcaatcgatg 300
gagcaagctt ataaagctct agaagatatc ggactaccgg ctattatcag accatcattt 360
acacttggtg gtagcggtgg tggtatcgct tatacaaaag aagagtttga aaaaattgtc 420
aaaaatggtc taagcctatc accaacaaat gaagtactaa tagatgagnc ancctnaanc 480

<210> SEQ ID NO 232
<211> LENGTH: 503
<212> TYPE: DNA
<213> ORGANISM: Acinetobacter calcoaceticus

<400> SEQUENCE: 232
cgacagttat gactgatcct tcaatggctg atgcaactta tattgagccg attacttggc 60
aaacagttgc acagattatt gaaaaagaac gtccagatgc agtattgcca actatgggtg 120
gtcaaactgc attgaactgt gccctcgcac ttgatgagca cggcgttctt gctaaatata 180
atgttgaatt aattggtgca agcaaagaag cgattgagaa agccgaagat cgtaaactct 240
tcgatatcgc tatgcgcaaa attggcttgg aatgtccaaa agctgccatt gctgaaacaa 300

```
tggaagaagc tttaacaatc cagtcgcgct ttggttttcc tgtaattatt cgtccatcat    360

ttacaatggg tggttcgggc ggtggcattg catataaccg cgaagaattc cttgaaattt    420

gtgaacgtgg ttttgacctc tctcctactc accagttatt gatcgatgaa tctttaattg    480

gctggaaaga atacgagatg gaa                                             503
```

<210> SEQ ID NO 233
<211> LENGTH: 617
<212> TYPE: DNA
<213> ORGANISM: Mycobacterium tuberculosis

<400> SEQUENCE: 233

```
ggtgctgcgc gccgagggct tgcaggtcag cctggtgaac tctaatccgg ccaccatcat     60

gaccgacccg gagttcgccg accacaccta cgtagagccc atcaccccgg cgttcgtgga    120

gcgggttatc gcccaacagg ccgagcgggg caacaagatc gacgccctgc tggcgaccct    180

gggtgggcag accgcgctga acaccgcggt cgcgctgtac gagagcgggg tgctggaaaa    240

gtacggcgtg gaactcatcg gcgccgattt cgacgccatc cagcgcggcg aggaccggca    300

gcggttcaag gacatcgtcg ccaaggccgg tggcgaatcc gcccggagcc gagtgtgttt    360

caccatggcc gaagtgcgtg agacggtcgc cgagctcggc ctgccggtgg tggtgcggcc    420

gagcttcacc atgggcgggc tgggttcggg gatagcgtac tccaccgacg aggtcgaccg    480

gatggccggc gccgggctgg cggcctcgcc cagcgccaac gtgctcatcg aggaatcgat    540

ttacggctgg aaggaattcg aactcgagct gatgcgcgac ggccacgaca atgtggtggt    600

ggtgtgctcg atcgaaa                                                    617
```

<210> SEQ ID NO 234
<211> LENGTH: 617
<212> TYPE: DNA
<213> ORGANISM: Mycobacterium bovis subspecies bovis

<400> SEQUENCE: 234

```
ggtgctgcgc gccgagggct tgcaggtcag cctggtgaac tctaatccgg ccaccatcat     60

gaccgacccg gagttcgccg accacaccta cgtagagccc atcaccccgg cgttcgtgga    120

gcgggttatc gcccaacagg ccgagcgggg caacaagatc gacgccctgc tggcgaccct    180

gggtgggcag accgcgctga acaccgcggt cgcgctgtac gagagcgggg tgctggaaaa    240

gtacggcgtg gaactcatcg gcgccgattt cgacgccatc cagcgcggcg aggaccggca    300

gcggttcaag gacatcgtcg ccaaggccgg tggcgaatcc gcccggagcc gagtgtgttt    360

caccatggcc gaagtgcgtg agacggtcgc cgagctcggc ctgccggtgg tggtgcggcc    420

gagcttcacc atgggcgggc tgggttcggg gatagcgtac tccaccgacg aggtcgaccg    480

gatggccggc gccgggctgg cggcctcgcc cagcgccaac gtgctcatcg aggaatcgat    540

ttacggctgg aaggaattcg aactcgagct gatgcgcgac ggccacgaca acgtggtggt    600

ggtgtgctcg atcgaaa                                                    617
```

<210> SEQ ID NO 235
<211> LENGTH: 615
<212> TYPE: DNA
<213> ORGANISM: Mycobacterium avium subspecies paratuberculosis

<400> SEQUENCE: 235

```
ggtgctcaag gccgagggcc tgcaggtcag cctggtcaac tccaacccgg ccaccatcat     60

gaccgatccg gagtacgccg accacaccta cgtcgagccc atcacgccgg ccttcgtcga    120
```

-continued acgggtgatc gcgcagcagg ccgagcgggg caacaagatc gacgcgctgc tggccaccct 180
gggcgggcag accgcgctga acaccgccgt cgcgctgtac gagaacgggg cgctggaccg 240
ctacggggtg gaactgatcg gcgccgactt cgacgccatc cagcgcggcg aggaccggca 300
gcggttcaag gacatcgtcg ccaaggtcgg cggtgaatcc gcccgcagcc gagtgtgttt 360
caccatggac gaggtgcgcg agaccgtcgc cgaactgggc ctgccggtgg tggtgcggcc 420
cagcttcacc atgggcggcc tgggctcggg gatggcgcgc tccgtcgagg aggtcgaccg 480
gatggccggc gccgggctgg ccgaaagccc cagcgccaac gtgctgatcg aggaatccat 540
ctacggctgg aaggaattcg aactcgagct gatgcgcgac ggcaacgaca acgtcgtcgt 600
ggtgtgctcg atcga 615

<210> SEQ ID NO 236
<211> LENGTH: 600
<212> TYPE: DNA
<213> ORGANISM: Mycobacterium leprae

<400> SEQUENCE: 236
caagtgagtc tggtcaactc taacccggcc accatcatga ccgatccgga gttcgccgac 60
cacacctatg tcgagccgat tacgccggcc ttcgtggagc gggtgattgt tcagcaggcc 120
gagcgtggca acaggattga cgctttgcta gccaccttag gtgggcagac cgcgctcaac 180
acagcggtag cgctgtacga aaacggagtg ttggagcgct atggcgtcga gctcatcggt 240
gctgatttcg aggctatcca gcgtggtgag gaccggcagc gattcaaaga tctcgtcgct 300
aaggttggtg gtgaatccgc tcgcagtaaa gtgtgtttca ccatggatga ggtgcgtgaa 360
acagtcgagg atcttggcct tccggtggtg gtgcggccaa gtttcacgat gggcggattg 420
ggttcgggca tggctcactc cgacgaggag gttggccgga tggccggcgc cgggctggta 480
gcttcaccta gtgccaacgt gctgatcgag gaatcggtct atggttggaa ggaattcgaa 540
ctcgagctaa tgcgcgatgg acacgacagc gtcgtggtgg tgtgctcgat cgagaacgtt 600

<210> SEQ ID NO 237
<211> LENGTH: 618
<212> TYPE: DNA
<213> ORGANISM: Nocardia farcinica

<400> SEQUENCE: 237
ggtgctcaag tccgagggcc tgcgcgtgtc gctggtgaac tcgaacccgg ccacgatcat 60
gaccgatccc gagttcgccg acgccaccta cgtcgagccg atcacccccg aattcgtcga 120
gaaggtcatc gccaaggagc gccccgacgc gatcctggcg accctcggcg ggcagaccgc 180
gctcaacacc gcggtcgcgc tgcacgagcg cggcgtgctg gagaagtacg gcgtcgaact 240
gatcggcgcc gacttcgacg ccatccagcg cggtgaggac cggcagaagt tcaaggacat 300
cgtcgccaag gtcggcggtg agagcgcccg ctcgcgggtc tgcttcacca tggacgaggt 360
ccgcgagacc gtcgccgaac tgggcttccc ggtcgtcgtg cggccctcgt tcaccatggg 420
cgggctcggc tcgggcatgg cctacaacga cgaggacctg gaccggatcg ccggtggcgg 480
cctggccgcc tcgccgaccg ccaacgtcct gatcgaggag tccatcctcg gctggaagga 540
atacgagctc gagctcatgc gcgacggccg cgacaacgtc gtggtggtct gctccatcga 600
gaacgtcgac ccgatggg 618

<210> SEQ ID NO 238

-continued

<211> LENGTH: 525
<212> TYPE: DNA
<213> ORGANISM: Streptomyces coelicolor

<400> SEQUENCE: 238
ccggcgacga tcatgaccga cccggagatc gccgacgcca cctacgtcga gccgatcacc 60
cccgagttcg tcgagaagat catcgccaag gagcgccccg acgccctcct gcccacgctc 120
ggcggccaga cggccctgaa caccgcgatc tccctgcacg gcaacggcgt cctggagaag 180
tacggcgtcg aactgatcgg cgccaatgtg gaggccatca acaagggcga ggaccgcgac 240
ctgttcaagg aggtcgtcga ggaggtccgc aagaagatcg gccacggcga gtccgcccgg 300
tcctacatct gccactccat ggacgacgtc ctcaagggcg tcgacgcgct cggcggctac 360
cccgtcgtcg tccgcccctc cttcaccatg ggcggcgccg gctccggctt cgcccacgac 420
gaggacgaac tgcgccggat cgccggacag ggcctcaccc tctcgccgac caccgaggtg 480
ctcctggagg agtccatcct cggctggaag gagtacgagc tggag 525

<210> SEQ ID NO 239
<211> LENGTH: 618
<212> TYPE: DNA
<213> ORGANISM: Streptomyces avermitilis

<400> SEQUENCE: 239
atcctgcgcg ccgagggcct cagggtcatc ctggtcaact ccaacccggc gacgatcatg 60
accgacccgg agatcgccga cgccacctac gtcgagccga tcaccccgga gttcgtcgag 120
aagatcatcg ccaaggagcg gccggacgcg ctgctgccca ccctcggtgg tcagacggcc 180
ctgaacaccg ccatctccat gcacgagcag ggtgtgctgg agaagtacgg tgtcgagctg 240
atcggcgcca acgtcgaggc gatcaacaag ggcgaggacc gcgacctgtt caagggcgtc 300
gtcgaggccg tccgcgcgaa gatcgggcac ggcgaatccg cccgctcggt catctgccac 360
tccatggacg acgtgctcga gggcgtcgag accctcggcg gttaccccgt cgtcgtccgt 420
ccctccttca ccatgggcgg cgccggctcc ggcttcgcgc acgacgagga ggagctgcgc 480
cgcatcgcgg gtcagggcct gacgctctcc ccgaccaccg aggtgctcct ggaggagtcc 540
atcctcggct ggaaggagta cgagctggag ctgatgcgcg acaagaacga caacgtcgtg 600
gtcgtctgct ccatcgag 618

<210> SEQ ID NO 240
<211> LENGTH: 625
<212> TYPE: DNA
<213> ORGANISM: Corynebacterium efficiens

<400> SEQUENCE: 240
tgctcaagga ggagggcctg cgcgtcaccc tcatcaactc caacccggcc accatcatga 60
ccgaccccga gatggcggac cacacctacg tcgagccgat cgagcccgag tacatcgaga 120
agatcttcca gaaggagatc gaacagggcc acccgatcga caccgtcctg gcaaccctcg 180
gcggacaaac cgcccttaac gctgccatcc agctggaccg cctcggcatc ctggagaagt 240
acaacgtcga gctcatcggt gccgacatcg acgccatcga gcgtggtgag gaccgccaga 300
aattcaagga catcgtcgcc accatcggtg gtgaatcagc acgctccgcc gtctgccaca 360
acatggatga ggtctacgcc accgtcgagg agctcggtct cccggtcgtc gtgcgcccct 420
ccttcaccat gggtggtctg ggttccggtc tggcctacac catggaggac ctcgaccgca 480
tcgccggcgg tggcctcgcc gcctccccgg aggccaatgt cctgatcgag gagtccatcc 540

-continued tcggctggaa ggaatacgag ctggagctca tgcgcgacgg cgatgacaat gtggtggtca 600
tctgctccat cgagaacgtc gatgc 625

<210> SEQ ID NO 241
<211> LENGTH: 636
<212> TYPE: DNA
<213> ORGANISM: Corynebacterium glutamicum

<400> SEQUENCE: 241
ctgaaggaag agggactgcg cgtcaccctc atcaactcca acccagcaac gatcatgacc 60
gacccagaaa tggctgacca cacctacgtg gagccaatcg agccggaata catcgacaag 120
attttcgcta aggaaatcga gcagggccac ccaatcgacg ccgtcctggc aacccttggt 180
ggccagactg cacttaacgc agctatccag ctggatcgcc tcggcatcct ggaaaagtac 240
ggcgttgaac tcatcggtgc agacatcgat gccattgagc gcggcgaaga tcgccagaag 300
ttcaaggata ttgtcaccac catcggtggc gaatccgcgc gttcccgcgt ctgccacaac 360
atggaagaag tccacgagac tgtcgcagaa ctcggccttc cagtagtcgt gcgtccatcc 420
ttcactatgg gtggcctggg ctccggtctt gcatacaaca ccgaagacct tgagcgcatc 480
gctggtggcg gacttgctgc atctcctgaa gcaaacgtct tgatcgaaga atccatcctt 540
ggttggaagg aattcgagct cgagctcatg cgcgataccg cagacaacgt tgtggttatc 600
tgctccattg aaaacgtcga cgcactgggc gtgcac 636

<210> SEQ ID NO 242
<211> LENGTH: 525
<212> TYPE: DNA
<213> ORGANISM: Bordetella parapertussis

<400> SEQUENCE: 242
cccgccacca tcatgaccga ccccgaaacg gcggacgtca cctatatcga gcccatcacg 60
tggcaagcgg tcgagaagat catcgagcgc gagaagcccg atgcgctgct gcccaccatg 120
ggtggccaga ccgcgctgaa ctgcgcgctc gacctggccc accacggcgt gctgaaaaag 180
cacaacgtcg agctgatcgg cgccaacgag cacgccatcg agaaggccga agaccgccag 240
aagttcaagc aggccatgac cgacatcggc ctggaatcgg ccaagtcggg cgtggcccac 300
tcgatggacg aggcctggga agtgcagcgc cgcatcgcgg ccgacatcgg cacggcgggc 360
tttcccgtcg tcatccgccc cagcttcacg ctgggcggct cgggcggcgg catcgcctat 420
aacgccgagg aattcgaggt catctgccgc cgcggcctgg aagcctcgcc gaccaaggag 480
ctgctgatcg aggagtcgct gctcggctgg aaagagttcg agatg 525

<210> SEQ ID NO 243
<211> LENGTH: 617
<212> TYPE: DNA
<213> ORGANISM: Bordetella bronchiseptica

<400> SEQUENCE: 243
gcgctcaagg ccgagggtta ccggaccatc ctggtcaaca gcaaccccgc caccatcatg 60
accgaccccg aaacggcgga cgtcacctat atcgagccca tcacgtggca agcggtcgag 120
aagatcatcg agcgcgagaa gcccgatgcg ctgctgccca ccatgggcgg ccagaccgcg 180
ctgaactgcg cgctcgacct ggcccaccac ggcgtgctga aaaagcacaa cgtcgagctg 240
atcggcgcca acgagcacgc catcgagaag gccgaagacc gccagaagtt caagcaggcc 300

-continued atgaccgaca tcggcctgga atcggccaag tcgggcgtgg cccactcgat ggacgaggcc 360
tgggaagtgc agcgccgcat cgcggccgac atcggcacgg cgggctttcc cgtcgtcatc 420
cgccccagct tcacgctggg cggctcgggc ggcggcatcg cctataacgc cgaggaattc 480
gaggtcatct gccgccgcgg gctggaagcc tcgccgacca aggagctgct gatcgaggag 540
tcgctgctcg gctggaaaga gttcgagatg gaagtggtgc gcgacaaggc ggacaactgc 600
atcatcgtct gctcgat 617

<210> SEQ ID NO 244
<211> LENGTH: 617
<212> TYPE: DNA
<213> ORGANISM: Bordetella pertussis

<400> SEQUENCE: 244
gcgctcaagg ccgagggtta ccggaccatc ctggtcaaca gcaaccccgc caccatcatg 60
accgaccccg aaacggcgga cgtcacctat atcgagccca tcacgtggca agcggtcgag 120
aagatcatcg agcgcgagaa gcccgatgcg ctgctgccca ccatgggtgg ccagaccgcg 180
ctgaactgcg cgctcgacct ggcccaccac ggcgtgctga aaaagcacaa cgtcgagctg 240
atcggcgcca acgagcacgc catcgagaag gccgaagacc gccagaagtt caagcaggcc 300
atgaccgaca tcggcctgga atcggccaag tcgggcgtgg cccactcgat ggacgaggcc 360
tgggaagtgc agcgccgcat cgcggccgac atcggcacgg cgggctttcc cgtcgtcatc 420
cgccccagct tcacgctggg cggctcgggc ggcggcatcg cctataacgc cgaggaattc 480
gaagtcatct gccgccgcgg gctggaagcc tcgccgacca aggagctgct gatcgaggag 540
tcgctgctcg gctggaaaga gttcgagatg gaagtggtgc gcgacaaggc ggacaactgc 600
atcatcgtct gctcgat 617

<210> SEQ ID NO 245
<211> LENGTH: 616
<212> TYPE: DNA
<213> ORGANISM: Burkholderia mallei

<400> SEQUENCE: 245
ggcgttgcgt gaggagggct acaaggtcat cctcgtcaac agcaacccgg cgacgatcat 60
gaccgatccg aacacggcgg acgtcacgta catcgagccg atcacgtggg aagtcgtcga 120
gcgcatcatc gcgaaggagc gccccgacgc gatcctgccg acgatgggcg gccagaccgc 180
gctgaactgc gcgctcgacc tgttccacca cggcgtgctc gagaagtacg gcgtcgagct 240
gatcggcgcg tcgccggagg cgatcgacaa ggccgaagac cgccagaagt tcaaggacgc 300
gatgacgaag atcggcctcg gctcggcgaa gtccggcatc gcgcactcga tggaagaggc 360
gctgaaggtg cacgcggaca tcgcggcggc gacgggcggc agcggctacc cggtcgtgat 420
ccgcccgtcg ttcacgctcg gcggctcggg cggcggcatc gcgtacaacc gcgaggagtt 480
cgaggagatc tgcaagcgcg gcctcgatct gtcgccgacg cgcgagctgc tgatcgagga 540
atcgctgctc ggctggaagg agtacgagat ggaggtcgtg cgcgatcgcg ccgacaactg 600
catcatcgtc tgctcg 616

<210> SEQ ID NO 246
<211> LENGTH: 616
<212> TYPE: DNA
<213> ORGANISM: Burkholderia pseudomallei

<400> SEQUENCE: 246

-continued

```
ggcgttgcgt gaggagggct acaaggtcat cctcgtcaac agcaacccgg cgacgatcat     60
gaccgatccg aacacggcgg acgtcacgta catcgagccg atcacgtggg aagtcgtcga    120
gcgcatcatc gcgaaggagc gccccgacgc gatcctgccg acgatgggcg gccaaaccgc    180
gctgaactgc gcgctcgacc tgttccacca cggcgtgctc gagaagtacg gcgtcgagct    240
gatcggcgcg tcgccggagg cgatcgacaa ggccgaagac cgccagaagt tcaaggacgc    300
gatgacgaag atcggcctcg gctcggcgaa gtccggcatc gcgcactcga tggaagaggc    360
gctgaaggtg cacgcggaca tcgcggcggc gacgggcggc agcggctacc cggtcgtgat    420
ccgcccgtcg ttcacgctcg gcggctcggg cggcggcatc gcgtacaacc gcgaggagtt    480
cgaggagatc tgcaagcgcg gcctcgatct gtcgccgacg cgcgagctgc tgatcgagga    540
atcgctgctc ggctggaagg agtacgagat ggaggtcgtg cgcgatcgcg ccgacaactg    600
catcatcgtc tgctcg                                                    616
```

<210> SEQ ID NO 247
<211> LENGTH: 625
<212> TYPE: DNA
<213> ORGANISM: Pseudomonas putida

<400> SEQUENCE: 247

```
gcctgtaaag ccctgcgcga ggaaggtttc cgcgtcatcc tggtgaactc caacccagcc     60
accatcatga ccgacccggc catggctgac gccacctaca tcgagccgat caagtggcaa    120
tcggtggcca agatcatcga gaaagagcgc ccggacgccg tcctgccgac catgggtggc    180
cagaccgccc tgaactgcgc cctggacctg gagcgccacg gcgttctgga gaagttcggc    240
gtggagatga tcggtgccaa cgctgacacc atcgacaagg ccgaagaccg ttcgcgcttc    300
gacaaggcca tgaaggacat cggcctggag tgcccgcgct ccggtatcgc ccacagcatg    360
gaagaggcca atgcggtcct cgagaagctc ggcttcccgt gcatcattcg cccgtcgttc    420
accatgggcg gcaccggcgg cggtatcgct tacaaccgtg aagagttcga agaaatctgc    480
acccgtggtc tggacctgtc gccgaccaaa gagctgctga tcgacgaatc gctgatcggc    540
tggaaggaat acgagatgga ggtggtccgc gacaagaagg acaactgcat catcgtctgc    600
tcgatcgaga acttcgaccc gatgg                                          625
```

<210> SEQ ID NO 248
<211> LENGTH: 3234
<212> TYPE: DNA
<213> ORGANISM: Yersinia pseudotuberculosis

<400> SEQUENCE: 248

```
atgccaaaac gtacagatat aaaaagcatc ctgattctgg gcgcaggccc gattgttatc     60
ggccaggctt gtgagtttga ctactccggt gcccaagcgt gtaaagcact gcgcgaagag    120
ggttaccgtg tcattttggt gaactccaat ccggcgacta tcatgactga cccggaaatg    180
gccgatgcaa cttatatcga gccaattcat tgggaagtgg tgcgtaagat tatcgaaaaa    240
gagcgtccag atgctgtttt gcctacgatg ggtggccaaa ctgcactgaa ctgtgcattg    300
gaactggagc gtcagggtgt tctggcagaa tttggcgtca ccatgattgg tgcgaccgcc    360
gatgccatcg ataaagccga agaccgccgt cgctttgata tcgcgatgaa gaagattggt    420
ctggatacgg cccgctcagg tattgcgcat aacatggaag aagcactggc tgttgccgct    480
gatgtgggct tcccgtgcat tatccgccca tcctttacga tgggggcac tggtggcggt    540
```

-continued

```
atcgcttata accgtgaaga gttcgaagag atctgcgagc gcggtctgga tttgtcacca    600
accaaagagt tgttgattga cgaatcgctg attggctgga aagagtacga gatggaagtt    660
gtccgtgata aaaacgacaa ctgcatcatc gtttgctcca ttgaaaactt cgatgcgatg    720
gggattcaca ccggcgactc tatcactgtc gcaccggctc agaccctgac cgataaagaa    780
taccaaatca tgcgtaatgc ctcgatggcg gtactgcgtg aaatcggggt agaaaccggg    840
ggctctaacg tacagttctc cgtcaaccca aaaaatggtc gtttgattgt cattgagatg    900
aacccgcgtg tttctcgctc ttcagcactg gcctctaaag caaccggttt cccgattgcc    960
aagattgccg ccaaactggc ggtcggttac acactggatg agttgatgaa tgacatcacc   1020
ggtggccgta ctcctgcgtc ctttgagcct tctatcgact atgttgttac caagatccca   1080
cgctttaact ttgaaaaatt tgcgggtgcc aacgaccgtt tgaccacgca aatgaagtct   1140
gtgggtgaag tcatggccat tggccgcacg cagcaagaat cactgcaaaa agcactgcgc   1200
gggctggaag tgggcgcgac cggttttgac ccgaaagtga gcctggatga tcccgaagca   1260
ctgactaaaa ttcgtcgtga attgaaagaa gcgggtgcag aacgtatctg gtatatcgct   1320
gatgctttcc gtgcgggcat gtcggttgat ggtgtgttca atctgaccaa tgttgatcgc   1380
tggttcctgg tgcagattga agagctggtt cgtctggaag agagcgtggc agaactcggt   1440
atcaacggct tgactgctga atttatgcgt cacttgaaac gtaaaggttt cgccgatgct   1500
cgtttggcta aattggtcgg tgcagcagaa agtgaagtcc gtaaactgcg ttacaaatat   1560
ggtttacacc cggtttataa gcgtgttgat acctgcgcgg cagagttctc gacggatacg   1620
gcttacatgt actccaccta cgaggaagag tgcgaatcta acccaaccag cgatcgtccg   1680
aaagtgatgg tgctgggtgg cggcccgaac cgtatcggac aaggtattga gttcgactat   1740
tgctgcgtac acgcttcatt ggcactgcgt gaagacggtt acgaaaccat catggtgaac   1800
tgtaaccctg agacggtttc aaccgattat gacacctctg atcgtctcta cttcgagtca   1860
gtcacgctgg aagatgtgtt ggaaattgtc cgtattgaga aaccacaggg cgttatcgtg   1920
cagtacggtg gtcagacacc gctgaaatta gcccgcgagt tggaagcggc tggcgtcccc   1980
attattggga ccagtccgga tgccattgac cgtgccgaag accgtgagcg tttccagcag   2040
gcggtaaatc gtctgggcct gaaacagcca gcgaatgcca ccgtagcgac tatcgagcag   2100
gcggtggaaa aagccactgg tctgggctat ccactggtcg tacgcccttc ttatgttttg   2160
ggtggccgcg cgatggaaat tgtttatgac gagattgacc tgcgccgtta cttccagaat   2220
gccgtcagtg tatcgaatga tgcgccggta ttgcttgacc gcttccttga tgatgccgtc   2280
gaagtggatg tcgatgccat ttgtgatggt gaacgcgtgt tgatcggcgg cattatggaa   2340
catatagagc aagccggggt tcactctggt gactcagcct gttcattgcc tgcttacacc   2400
ctgagcaaag aaattcagga tgtgatgcgc caacaagtgg aaaaactggc ctttgaactc   2460
tgtgtccgcg gcctgatgaa tgtgcagttt gcggtgaaaa acaacgaagt ttacctgatt   2520
gaggttaacc cacgggcggc ccgtactgta cctttcgtgt ccaaagcgac cggtatgcca   2580
ctggcaaaaa ttgccgctcg tgtgatggtc ggccaatcgc tggctgagca gggcatgctg   2640
gaagaaatta ttccgcctta ctactcagtc aaggaagtgg tactgccgtt taataaattc   2700
cccggtgttg acccaatttt agggccagaa atgcgctcta ccggtgaagt catgggggtt   2760
ggccgtacct tcgctgaggc gttctctaaa gcgatgttgg gcagtcaatc tggcatgaaa   2820
aagagtggcc gtgcgctatt atccgtccgt gagggggata agcaccgggt ggtagacttg   2880
gcggcgaagc tgctaaaaca aggctttgaa ctggatgcaa cccacggaac ggcggtcgtg   2940
```

-continued ctgggcgagg cggggataaa cccacgtttg gttaacaagg tgcatgaagg ccgtccgcat 3000
attcaggacc gtattaagaa tggcgagtac acctatatcg tgaataccac agctgggcgt 3060
caggcgattg aagattctaa gctgatccgt cgcagtgctt tgcaatataa agtgcattac 3120
gatacgacct tgaacggtgg ttttgctacg gcgatggcgt taaatgcgga tccaaccgat 3180
caagtgattt cggtgcaaga gatgcatgcc aagattaaga atatgaaagc gtaa 3234

<210> SEQ ID NO 249
<211> LENGTH: 3234
<212> TYPE: DNA
<213> ORGANISM: Yersinia pestis

<400> SEQUENCE: 249
atgccaaaac gtacagatat aaaaagcatc ctgattctgg gcgcaggccc gattgttatc 60
ggccaggctt gtgagtttga ctactccggt gcccaagcgt gtaaagcact gcgcgaagag 120
ggttaccgtg tcattttggt gaactccaat ctggcgacta tcatgactga cccggaaatg 180
gccgatgcaa cttatatcga gccaattcat tgggaagtgg tgcgtaagat tatcgaaaaa 240
gagcgtccag atgctgtttt gcctacgatg ggtggccaaa ctgcactgaa ctgtgcattg 300
gaactggagc gtcagggtgt tctggcagaa tttggcgtca ccatgattgg tgcgaccgcc 360
gatgccatcg ataaagccga agaccgccgt cgctttgata tcgcgatgaa gaagattggt 420
ctggatacgg cccgctcagg tattgcgcat aacatggaag aagcactggc tgttgccgct 480
gatgtgggct tcccgtgcat tatccgccca tcctttacga tgggggcac tggtggcggt 540 atcgcttata accgtgaaga gttcgaagag atctgcgagc gcggtctgga tttgtctcca 600
accaaagagt tgttgattga cgaatcgctg attggctgga aagagtacga gatggaagtt 660
gtccgtgata aaaacgacaa ctgcatcatc gtttgctcca ttgaaaactt cgatgcgatg 720
gggattcaca ccggcgactc tatcactgtc gcaccggctc agaccctgac cgataaagaa 780
taccaaatca tgcgtaatgc ctcgatggcg gtactgcgtg aaatcggggt agaaaccggg 840
ggctctaacg tacagttctc cgtcaaccca aaaaatggtc gtttgattgt cattgagatg 900
aacccgcgtg tttctcgctc ttcagcactg gcctctaaag caaccggttt cccgattgcc 960
aagattgccg ccaaactggc ggtcggttac acactggatg agttgatgaa tgacatcacc 1020
ggtggccgta ctcctgcgtc ctttgagcct tctatcgact atgttgttac caagatccca 1080
cgctttaact ttgaaaaatt tgcgggtgcc aacgaccgtt tgaccacgca aatgaagtct 1140
gtgggtgaag tcatggccat tggccgcacg cagcaagaat cactgcaaaa agcactgcgc 1200
gggctggaag tgggcgcgac cggttttgac ccgaaagtga gcctggatga tcccgaagca 1260
ctgactaaaa ttcgtcgtga actgaaagaa gcgggtgcag aacgtatctg gtatatcgct 1320
gatgctttcc gtgcgggcat gtcggttgat ggtgtgttca atctgaccaa tgttgatcgc 1380
tggttcctgg tgcagattga agagctggtt cgtctggaag agagcgtggc agaactcggt 1440
atcaacggct tgactgctga atttatgcgt cacttgaaac gtaaaggttt cgccgatgct 1500
cgtttggcta aattggtcgg tgcagcagaa agtgaagtcc gtaaactgcg ttacaaatat 1560
ggtttacacc cggtttataa gcgtgttgat acctgcgcgg cagagttctc gacggatacg 1620
gcttacatgt actccaccta cgaggaagag tgcgaatcta acccaaccag cgatcgtccg 1680
aaagtgatgg tgctgggtgg cggcccgaac cgtatcggac aaggtattga gttcgactat 1740
tgctgcgtac acgcttcatt ggcactgcgt gaagacggtt acgaaaccat catggtgaac 1800

-continued

```
tgtaaccctg agacggtttc aaccgattat gacacctctg atcgtctcta cttcgagtca   1860

gtcacgctgg aagatgtgtt ggaaatcgtc cgtattgaga aaccacaggg cgttatcgtg   1920

cagtacggtg gtcagacacc gctgaaatta gcccgcgagt tggaagcggc tggcgtcccc   1980

attattggga ccagtccgga tgccattgac cgtgccgaag accgtgagcg tttccagcag   2040

gcggtaaatc gtctgggcct gaaacagcca gcgaatgcca ccgtagcgac tatcgagcag   2100

gcggtggaaa aagccactgg tctgggctat ccactggtcg tacgcccttc ttatgtgttg   2160

ggtggccgcg cgatggaaat cgtttatgac gagattgacc tgcgccgtta cttccagaat   2220

gccgtcagtg tatcgaatga tgcgccggta ttgcttgacc gcttccttga tgatgccgtc   2280

gaagtggatg tcgatgccat ttgtgatggt gaacgcgtgt tgatcggcgg cattatggaa   2340

catatagagc aagccggggt tcactctggt gactcagcct gttcattgcc tgcttacacc   2400

ctgagcaaag aaattcagga tgtgatgcgc caacaagtgg aaaaactggc ctttgaactc   2460

tgtgtccgcg gcctgatgaa tgtgcagttt gcggtgaaaa acaacgaagt ttacctgatt   2520

gaggttaacc cacgggcggc ccgtactgta cctttcgtgt ccaaagcgac cggtatgcca   2580

ctggcaaaaa ttgccgctcg tgtgatggtt ggccaatcgc tggctgagca gggcatgttg   2640

gaagaaatta ttccgcctta ctactcagtc aaagaagtgg tactgccgtt taataaattc   2700

cccggtgttg acccaatttt agggccagaa atgcgctcta ccggtgaagt catgggggtt   2760

ggccgtacct tcgctgaggc gttctctaaa gcgatgttgg gcagtcaatc tggcatgaaa   2820

aagagtggcc gtgcgctatt atccgtccgt gagggggata agcaccgggt ggtagacttg   2880

gcggcgaagc tgctaaaaca aggctttgaa ctggatgcaa cccacggaac ggcggtcgtg   2940

ctgggcgagg cggggataaa cccacgtttg gttaacaagg tgcatgaagg ccgtccgcat   3000

attcaggacc gtattaagaa tggcgagtac acctatatcg tgaataccac agctgggcgt   3060

caggcgattg aagattctaa gctgatccgt cgcagtgctt tgcaatataa agtgcattac   3120

gatacgacct tgaacggtgg ttttgctacg gcgatggcgt taaatgcgga tccaaccgat   3180

caagtgattt cggtgcaaga gatgcatgcc aagattaaga atatgaaagc gtaa         3234
```

```
<210> SEQ ID NO 250
<211> LENGTH: 3231
<212> TYPE: DNA
<213> ORGANISM: Vibrio cholerae

<400> SEQUENCE: 250

atgccaaaac gtactgacat tcaaagcatc cttatccttg gtgcgggtcc aattgttatc     60

ggtcaggctt gtgagtttga ctactcaggc gcgcaagcgt gtaaagccct gcgcgaagag    120

ggttaccgcg ttattctggt taactcaaac ccagcgacca tcatgactga cccagaaatg    180

gccgatgcga cttacatcga gcctatccac tgggaagtgg tgcgtaagat catcgaaaaa    240

gagcgcccag atgcgatttt gcccaccatg ggcggccaga ctgcgctgaa ctgtgcgctg    300

gcactcgaaa aacatggcgt attggctgag tttggcgttg agatgatcgg cgcaaccgcc    360

gatgcgattg ataaagcgga agaccgctca cgctttgata aagcgatgaa atcaatcggc    420

ctagagtgtc ctcgcgctga taccgcaaaa agcatggaag aagcgtacaa agtcctcgat    480

atggttggct tcccatgtat catccgtcct tctttcacca tgggcggcag cggtggtggt    540

atcgcttaca accgtgaaga gtttgaagaa atctgtactc gcggtctgga tctttcaccg    600

accaatgaac tgctgatcga tgaatcactg attggttgga aagagtacga gatggaagtg    660

gtgcgtgata agaacgataa ctgcatcatc gtctgtgcga ttgaaaactt cgacccaatg    720
```

-continued

```
ggcatccaca cgggtgactc gatcactgtc gctccagcgc aaacgctaac tgacaaagaa    780
taccaaatca tgcgtaacgc ctctttggcg gtactgcgtg aaatcggcgt agaaaccggc    840
ggttcaaacg ttcagtttgg tatcaacccg aaagatggcc gcatggtgat catcgagatg    900
aatccacgtg tatcgcgctc ttctgcgttg gcttcaaaag ccaccggttt cccaattgcg    960
aaagtggcgg ccaaactggc agtgggtttc actctggatg agttgatgaa cgacatcaca   1020
ggcggcgcaa caccagcctc gttcgaaccg accatcgact acgtggtcac taagatccct   1080
cgtttcaact tcgaaaaatt cgccggtgcc aatgaccgtc tgactacaca aatgaagtca   1140
gtaggtgagg tgatggcgat tggtcgtaac caacaagaat cactgcaaaa agcactgcgc   1200
ggcttggaag tgggtgcggc tggtctggat gagaaagtgg atctggacgc gccagacgct   1260
ctgaccaaaa ttcgttatga gctgaaagaa gcaggcgcag agcgtatttg gtacatcgcg   1320
gatgcattcc gtgccggtat gtcagtggat ggggtattta acctgaccaa catcgatcgc   1380
tggttcctag tgcaaattga agaactggtg aagctggaag ccgaagtgaa agccggtggc   1440
tttgcgggct tgaaccaaga cgtactgcgt aagatgaagc gcaaaggctt ctctgatgcg   1500
cgtttgtcaa aactgctcgg cgtgagcgaa aacgaaatcc gtcgtctgcg tgaccaatac   1560
aacatccacc cagtttacaa gcgtgtggat acctgcgcgg cagaatttaa gtcagatacg   1620
gcttacatgt actccacgta tgatgaagag tgtgaagcca atccgactga caaagacaag   1680
atcatggtgc tgggcggtgg tccaaaccgt atcggtcaag gtatcgagtt tgactactgc   1740
tgtgtacacg ccgcgcttgc actgcgtgaa gatggttacg aaaccatcat ggttaactgt   1800
aacccagaaa ccgtatcaac cgattacgac acctcagatc gcctctactt tgagcctgta   1860
actctagagg atgtgctggc tatcgtgcgt gttgagaagc caaaaggcgt gatcgtgcag   1920
tacggcggtc aaacaccact gaaactggcg cgagcgctgg aagcggctgg cgtacctgtg   1980
attggtacca gcccagatgc gattgaccgc gctgaagacc gtgaacgttt ccaacaagcg   2040
gtacagcgtt taggcctcaa acagccagac aacgcaaccg taaccgctat cgagcaagcg   2100
attgagaagt cgcgtgaaat cggtttccca ctcgtagttc gcccctctta tgttctgggt   2160
ggccgtgcga tggagattgt gtacgatgag caagatctgc gtcgttactt caacgaagcg   2220
gtgagcgtgt cgaatgaatc accagttctg ctggatcgct tccttgatga tgcaaccgaa   2280
gtggacgtgg atgcgatttg tgacggtgag cgcgtggtga ttggcggcat catggagcac   2340
attgaacaag cgggtgttca ctcaggtgac tcagcctgtt ctctgccggc ttacaccttg   2400
agccaagaaa tccaagacaa gatgcgtgag caagttgaga agttggcatt tgaactcggt   2460
gttcgtggcc tgatgaacat tcagtttgca gtcaaagaca acgaagttta cctgattgaa   2520
gtaaacccac gtgctgcgcg tactgtgccg tttgtttcta aagcaaccgg tgctccgctg   2580
gcgaaaatcg cggcgcgcgt gatggttgga caaactctgg agcaacaagg cttcaccaaa   2640
gagatcattc caccttacta ctcagttaaa gaagtggttc tgccgttcaa caagttcccg   2700
ggggttgacc cactgcttgg ccctgaaatg cgctcaaccg gtgaagtgat gggtgtgggt   2760
gccacgtttg ctgaagccta tgctaaagca gagttgggct gtggctcggt ttaccctgaa   2820
ggtggtcgtg cgctactttc ggtgcgtgaa ggtgacaaac agcgtgtagt ggatctggct   2880
tctaagctag tgaaactggg ttaccagttg gatgcgactc acggtactgc agtgattctg   2940
ggcgaagcgg gcatcaaccc acgtctggtt aacaaagtgc atgaaggtcg tccacacatt   3000
ctggatcgca tcaaaaacca cgagtacacc tacattgtga acacggcttc tggccgccaa   3060
```

-continued

```
gcaattgaag actcaaaagt actgcgccgt ggtgcattgg ctcacaaagt gaactacacc   3120

accacactga acgccgcctt cgcaacttgt atgtcacaca cggcggatgc caaagcatcc   3180

gtcacttcag tacaagagct gcatgcgcgt gtaaaagcga accaagctta a            3231
```

```
<210> SEQ ID NO 251
<211> LENGTH: 3234
<212> TYPE: DNA
<213> ORGANISM: Vibrio vulnificus

<400> SEQUENCE: 251

atgccaaaac gtactgacat tcaaagcatt cttatcctag gtgctggtcc aattgttatc     60

ggtcaggctt gtgagtttga ctactcaggc gcacaagcat gtaaagcgct acgtgaagaa    120

ggttaccgag ttatcctagt aaactcgaac ccagcgacca tcatgacaga cccagatatg    180

gcggatgcga cctacatcga gccaattcaa tgggaagtgg tacgcaagat tatcgaaaaa    240

gagcgtccag atgcggttct accaaccatg ggtggtcaga cggctctaaa ctgtgcgctt    300

gcgcttgaaa agcacggcgt gctagcggaa tttggcgtag aaatgatcgg tgcaactgct    360

gatgccatcg ataaagcgga agaccgttcg cgtttcgaca aagcgatgaa atctatcggc    420

ctagagtgtc ctcgtgctga tacggcgaag accatggaag aagcgtacaa agtgctcgat    480

atggttggct tcccatgtat catccgcccg tcattcacca tgggtggtac ggggggggggt    540

atcgcgtaca acaaagaaga gttcgaagaa atctgtcgcc gtggtcttga cctgtcgcca    600

accaatgaac tgcttatcga tgaatctttg atcggttgga aagagtacga aatggaagtg    660

gttcgcgaca aagcggacaa ctgtatcatc gtatgttcaa tcgaaaactt cgacccaatg    720

ggcatccaca ccggtgactc tatcaccgtg gcaccggctc aaacgctgac agataaagaa    780

taccaactga tgcgtaatgc gtcgctagcg gtacttcgtg aaatcggtgt agagacaggt    840

ggttcaaacg tgcagtttgg tatcaacccg aaagatggcc gtatggttat catcgagatg    900

aacccacgtg tatcgcgctc ttctgctcta gcgtcaaaag cgacaggttt ccctattgcg    960

aagattgcag cgaaactagc cgttggcttc acgcttgatg agctacaaaa tgacatcact   1020

ggtggtgcga cgccagcatc atttgaaccg accatcgact acgtagtgac taagattcct   1080

cgtttcaact tcgagaaatt tgccggtgct aacgaccgtt tgacgacgca aatgaagtca   1140

gttggtgaag tgatggccat tggccgtaac caacaagaat cactgcacaa agcgctgcgc   1200

ggtctagaag tgggcgcgac tggttttgat gagatggttg atcttgattc accagatgca   1260

ctgaccaaaa ttcgccacga gctgaaagaa gcgggcgctg agcgtatttg gtacattgcc   1320

gatgcattcc gtgcgggtat gtcagttgat ggtgtgttta acctaactaa catcgatcgc   1380

tggttcctgg ttcaaatcga agagattgtg aagctggaag agcaagtgaa agcgggtggt   1440

tttgctggtt taactcaaga tgtgcttcgt caaatgaagc gtaaaggttt ctccgacgct   1500

cgcctatcaa aactactcgg cgtggctgaa agtgaaatcc gtcgtctacg tgaccaattc   1560

gacatccacc ctgtatacaa gcgtgttgat acctgtgcgg cagaattctc atcggatacg   1620

gcttacatgt actcatctta tgatgatgag tgtgaagcga acccaaccga taaagaaaag   1680

atcatggttc tgggcggtgg tccaaaccgt atcggtcaag gtattgagtt tgactactgc   1740

tgtgtacacg cttcgctagc gctacgtgaa gatggttacg agaccatcat ggtgaactgt   1800

aacccagaaa ccgtatcaac cgactacgac acttcagacc gtctctactt tgaaccggtt   1860

actctagaag atgtgttggc gattgctcgt gttgaaaagc caaaaggcgt gatcgtgcag   1920

tacggtggtc aaactccact gaaactggcg cgtgcgctag aagcggcggg tgtaccaatt   1980
```

-continued

```
atcggtacta gccctgatgc catcgaccgt gcggaagacc gtgagcgttt ccaacaagcg   2040

gttgaccgct taggcctgct acagccagag aacgcaaccg taaccaccat ggagcaagcg   2100

gttgagaagt cgcgtgaaat tggcttccca ttggtcgttc gtccatctta cgtactgggt   2160

ggccgcgcta tggaaatcgt ttatgacgag caagacctac gccgctactt caacgaagcg   2220

gttagcgtgt cgaacgaatc accggttcta ctggatcgct tcctagacga tgcaattgaa   2280

gtcgatatcg acgctatctg tgacggtgag cgcgtggtga ttggcggtat catggagcac   2340

atcgagcaag cgggtgttca ctcaggtgac tcagcatgtt cactgcctgc ttacacgtta   2400

agccaagaaa tccaagacaa gatgcgtgag caagttgaaa agctggcatt tgagttgggc   2460

gttcgtggcc taatgaacac gcagtttgcc gtaaaagaca acgaagtgta cctcatcgaa   2520

gtgaaccctc gtgctgcacg taccgttcca ttcgtatcga aagcgaccgg tgcaccactt   2580

gcgaaaatcg cagcacgtgt tatggctggt cagtctctgg aatcgcaagg tttcaccaaa   2640

gagattattc ctccttacta ctcggtaaaa gaagtggttc tgccatttaa caagttccct   2700

ggcgttgacc cactattggg ccctgaaatg cgctcaacgg gtgaagtgat gggtgtaggt   2760

gcaacttttg ctgaagcgta tgcgaaagca gaactgggtt gtggcaatgt gtatcctgaa   2820

ggtggtcgtg cgctgctttc ggtacgcgaa ggcgacaagc aacgtgtggt tgacctagcg   2880

tctaaattac tgaaactagg gtacaagctg gatgcgacac acggtacggc agtgatctta   2940

ggtgaagcgg gcatcaaccc acgtctagta aacaaagtgc acgaaggtcg tcctcacatt   3000

cttgaccgca tcaagaacaa cgaatacacc tacatcgtga acacggcggc tggtcgtcaa   3060

gcgattgaag attcgaaagt tctacgccgt ggcgcacttg cagaaaaagt gaactacacc   3120

acgacactta acgcggcatt tgcgacctgt atgtctcata cggcggacgc gaaagcaagc   3180

gtgacgtcgg tacaggaact gcacgcgcaa gtgcaagcga gtttgaaagc gtaa         3234
```

<210> SEQ ID NO 252
<211> LENGTH: 3234
<212> TYPE: DNA
<213> ORGANISM: Vibrio parahaemolyticus

<400> SEQUENCE: 252

```
atgccaaaac gtactgacat tcaaagtatt ctaattcttg gtgctggtcc gattgttatc     60

ggtcaggcat gtgagtttga ctactctggc gcacaagcgt gtaaagctct tcgtgaagaa    120

ggctaccgag ttattctagt taactctaac ccagcaacca tcatgacaga ccctgaaatg    180

gcagatgcaa cttacatcga gccgattcaa tgggaagttg ttcgcaagat cattgagaaa    240

gaacgcccag atgcagtatt gccaacaatg ggtggtcaga cggcgcttaa ctgtgcgcta    300

gatctagaga agcacggcgt tcttgctgaa ttcggcgtag agatgattgg cgcaacggct    360

gacgcgattg ataaagcaga agaccgttct cgcttcgata aagcaatgaa gtctatcggc    420

cttgagtgtc ctcgtgctga taccgcgaag acgatggaag aagcttacaa agttttagac    480

atggttggct tcccttgtat catccgtcca tcgttcacca tgggtggtac gggtggcggt    540

atcgcgtaca acaaagaaga gtttgaagaa atctgtcgtc gtggtctgga tctttctccg    600

actaacgaac ttcttatcga tgaatcgcta atcggttgga aagagtacga aatggaagta    660

gttcgcgaca aagcggacaa ctgtatcatc gtatgttcaa tcgaaaactt cgacccaatg    720

ggcatccaca ccggtgactc aatcacggtt gctccagcgc aaactctgac tgacaaagaa    780

taccagctaa tgcgtaatgc atcgctagcg gttctgcgtg aaatcggtgt tgagacaggt    840
```

-continued

```
ggttcaaacg tacagtttgg tatcaacccg aaagatggcc gtatggttat catcgagatg    900
aacccacgtg tatctcgctc ttctgctctg gcatcaaaag caacaggttt cccaatcgct    960
aagattgcgg cgaaactggc tgttggcttt actctagacg agctgcaaaa cgacattaca   1020
ggtggtgcaa ctccggcatc attcgaacct actatcgact acgtagtgac caagattcct   1080
cgttttaact tcgagaaatt tgctggcgct aacgatcgac tgacgactca gatgaagtca   1140
gttggtgagg taatggcgat tggtcgtaac caacaagaat ctcttcacaa agcattacgt   1200
ggcctagagg ttggcgcgac tggctttgat gagatggttg acctagatgc acctgacgca   1260
ttaactaaga ttcgtcacga actaaaagaa gctggcgcag agcgtatctg gtatatcgca   1320
gatgcattcc gtgcgggcat gtcagtggat ggcgtgttta acctgacgaa cattgatcgc   1380
tggttcctag ttcaaattga agagctagtt aaactagaag agcaagtgaa agccggtggc   1440
tttgctggtc taacagaaga agttctacgc cagatgaaac gtaaaggttt ctctgatgct   1500
cgcctatcta aactgttagg tgtggcggaa agcgaaatcc gtcgtctacg tgaccagttt   1560
gacatccacc ctgtctacaa gcgagtggat acgtgtgcgg ctgagttctc ttctgatacg   1620
gcttacatgt actcatctta cgatgaagag tgtgaagcaa acccaacaga taaagacaag   1680
atcatggtac tgggcggtgg tccaaaccgt atcggtcaag gtatcgaatt cgactactgt   1740
tgtgtacatg catcactagc gcttcgtgaa gatggctacg aaaccattat ggtgaactgt   1800
aacccagaaa cagtatcgac agactacgat acatctgacc gtctttactt cgaaccagta   1860
actcttgaag atgtgttgtc tatcgcccgc gttgaaaagc caaaaggtgt gattgttcaa   1920
tacggtggtc aaacgccact taaactggct cgcgcactag aagctgcagg cgtgccaatc   1980
atcggtacaa gcccggatgc gattgaccgc gcagaagacc gtgagcgttt ccaggctgca   2040
gttgagcgtt taggtcttct acaaccacaa aacgcaacag taacggcgat ggagcaagcg   2100
gttgagaaat ctcgtgaaat cggcttccca ctcgttgttc gtccatctta cgttttgggt   2160
ggtcgtgcga tggaaatcgt ctacgatgaa caagacttgc gtcgttactt caacgaagca   2220
gtaagcgtat cgaatgaatc tccagttcta ctagaccgat tcctagatga tgcaacagaa   2280
gtggatatcg acgctatctg tgacggtgag cgcgtggtta tcggcggcat catggagcac   2340
attgagcaag cgggcgttca ctctggtgac tctgcatgtt cgcttcctgc ttatacacta   2400
agccaagaaa tccaagacaa gatgcgtgag caagttgaga agctggcgtt cgaacttggt   2460
gtacgtggcc tgatgaacac gcagtttgct gtaaaagaca acgaagttta cctaattgaa   2520
gtaaaccctc gtgctgcgcg tacggtacca ttcgtatcga aagcgacagg cgcaccacta   2580
gcgaaaatcg cggcacgtgt aatggcgggt caatctctgg aatcacaagg tttcactaaa   2640
gagattattc ctccttacta ctcagtcaaa gaagtcgttc tacctttcaa taagttccct   2700
ggcgttgacc ctctattagg tcctgaaatg cgctcaacag gtgaagtgat gggtgttggt   2760
gctacgtttg cagaagctta cgcaaaagca gagcttggct gtggcagtgt gtaccctgaa   2820
ggtggtcgtg cgctactttc tgttcgtgaa ggtgataagc agcgtgttgt tgaccttgcg   2880
tctaagctag taaaattggg ttaccaattg gatgcgactc acggtactgc tgtaatcctt   2940
ggtgaagcgg gtattaaccc tcgcctggta aacaaagtac atgaaggtcg tccacacatt   3000
cttgaccgca tcaagaacaa cgaatacacc tacattgtga acacggctgc aggtcgtcaa   3060
gctattgaag attcgaaagt tctacgccgc ggtgctctag cagaaaaagt gaactacaca   3120
acaacgctaa acgctgcgtt tgcaacgtgt atgtctcaca ctgctgatgc aaaagcgtca   3180
gtaacttctg ttcaggagct acacgctaaa gtaaaagcga gtctggaagc gtaa         3234
```

-continued

<210> SEQ ID NO 253
<211> LENGTH: 3231
<212> TYPE: DNA
<213> ORGANISM: Vibrio fischeri

<400> SEQUENCE: 253

```
atgccaaaac gtactgatat taaaagcgtt ctaattctag gtgccggtcc aattgtaatc     60
ggccaagcat gtgaatttga ctactctggt gcacaagcat gtaaagcact tcgtgaagaa    120
ggctaccgtg ttattcttgt gaactctaac ccagcaacaa tcatgactga cccagacatg    180
gctgatgcaa cgtacattga accaattcat tgggaagtgg ttcgtaacat catcgaaaaa    240
gagcgtccag atgcggtatt accaacaatg ggtggtcaaa cagcattaaa ctgtgcgctt    300
gatttagaaa agcacggtgt tcttgctgaa ttcggtgttg agatgattgg tgcaacagct    360
gatgcaattg ataaggcgga agaccgttct cgttttgata aagcgatgaa gtctattgga    420
cttgagtgtc cacgtgctga tacagcaaaa accatggaag aagcttacgg cgttctagat    480
atggttggtt tcccatgtat tattcgtcca tcatttacga tgggtggtac gggcggtggt    540
atcgcataca acaaagaaga gttcgaagaa atttgtcgtc gcggtttaga cctttcgcca    600
actaacgagc ttctaatcga tgaatcatta atcggttgga aagagtacga gatggaagtg    660
gttcgtgata agaacgataa ctgtatcatc gtatgtgcaa ttgaaaactt tgatgcgatg    720
ggtattcaca ctggtgactc aatcacggtt gcgccagcac aaacgctaac ggataaagaa    780
taccaactaa tgcgtaatgc atctctagct gtactgcgtg agattggtgt tgaaacgggt    840
ggctcaaacg tacagtttgg tattaacccg aaagatggtc gtatggttat catcgaaatg    900
aacccacgag tatctcgttc atctgcactt gcttctaaag caacaggttt ccctattgca    960
aaaattgcag cgaaattggc tattggcttt acgcttgacg agctaatgaa tgacattaca   1020
ggtggggcaa cgcctgcgtc atttgaacca acaatcgatt acgttgttac taagatccct   1080
cgttttaact tcgaaaaatt cgcaggggct aacgatcgcc taacaacaca gatgaaatca   1140
gttggtgaag tgatggctat cggccgtaac caacaagaat ctctacaaaa agcacttcgt   1200
ggcctagaag taggtgcgac tggttttgat gagatggttg atttagatgc tcctgatgca   1260
ttaacaaaaa ttcgtcatga actgaaagat gctggtgctg agcgtatttg gtacatcgct   1320
gatgcgttcc gtgcgggtat gtctgttgat ggtgtgttta atctaacgaa tgttgatcgt   1380
tggttcctag ttcaaattga agatttagta aaagaagaag aagcggttaa agcgggtggt   1440
tttgctaatt taaccgcaga tgcacttcgt aaacttaagc gtaaaggttt tgctgatgcg   1500
cgtctttcta aactattggg cgttggtgag agtgaaattc gtcgcctgcg tgaccagcat   1560
gatattcacc ctgtatacaa gcgtgtagat acgtgtgctg ctgagttctc atcagatacg   1620
gcttacatgt actcatctta tgatgaagag tgtgaagcaa atccaacaga caaagataag   1680
atcatgatct taggtggcgg tccaaaccgt atcggtcaag gtattgagtt tgattactgt   1740
tgtgtacacg catcattagc actacgagaa gatggctacg aaactatcat ggttaactgt   1800
aaccctgaga ctgtttctac ggattacgat acgtctgacc gtctatactt cgaaccagtt   1860
actctagaag atgtactagc aattgctcgt gttgagaaac caaaaggcgt gatagttcag   1920
tacggtggtc aaactccact taaactggct cgcgctcttg aagcagctgg tgttccaatc   1980
ataggtacaa gccctgatgc tatcgaccgt gcagaagacc gtgagcgttt ccaagttgct   2040
gtcgaccgtt tggagcttct tcaaccagaa aatgcaacgg ttactacaat ggagcaggcg   2100
```

-continued

```
attgataaat caaaagaaat cggcttccca ctcgtagtac gtccttctta tgttcttggt   2160

ggtcgtgcga tggaaatcgt atatgacgag caagacttac gtcgttactt caatgaagca   2220

gtaagcgtat caaatgaatc tccagtactt cttgatagct tccttgatga tgctgtagaa   2280

gtggatgttg atgcgatttg tgacggtgag caagtggtta tcggcggtat catggagcac   2340

atcgagcaag cgggtgttca ctctggtgac tcagcatgtt ctcttcctgc ttatacatta   2400

agcgaagaaa tccaagatgt aatgcgtgat caagtacgta agctggcatt cgagctaggt   2460

gttcgtggct taatgaatac acagtttgct gttaaagata acaaagtata cctaatcgaa   2520

gttaacccac gtgctgctcg tacggttcca ttcgtatcga aagcaactgg tgcaccatta   2580

gctaagattg cagcgcgtgt aatggcgggt caatctctag agtctcaagg ctttactaaa   2640

gagatcatcc caccatacta ctcagttaaa gaagtggtat taccgttcaa caaattccct   2700

ggtgttgacc cactgttagg cccagaaatg cgctcaacgg gtgaagttat gggtgttggt   2760

acaacgtttg ctgaagcatt tgctaaagct gaacttggct gtagcaaaga atacccagaa   2820

ggtggtcgtg cattactttc tgttcgtgaa ggtgataaga aacgtgttgt agatttagca   2880

aaacatcttg ttaaattggg ttaccaactg gatgcaactc acggtacagc agttattctt   2940

ggcgaagcgg gtattaaccc acgtctagta aacaaggtac atgaaggccg tcctcatatt   3000

cttgaccgta tcaagaatgg tgagtacacc tacatcgtta atactgcagc aggtcgtcaa   3060

gcgattgaag attctaaagt attacgtcgt ggtgcactag ctgagaaagt aaactacaca   3120

acaacgctaa atgcagcatt tgctagttgt ttagctcatg aagcggatga ccgtaaaacg   3180

gttaactctg ttcaagagct acacgctaaa gtggcagcta aatacgctta a            3231
```

<210> SEQ ID NO 254
<211> LENGTH: 3270
<212> TYPE: DNA
<213> ORGANISM: Campylobacter jejuni

<400> SEQUENCE: 254

```
atgccaaaac gaacagatat taaaagcatt ttacttatag gaagtggtcc tattgtgata     60

ggacaagctt gtgaatttga ttattctgga actcaagccg caaagacttt aaaagaatta    120

ggatatcgtg tagtattaat caactcaaat cctgcaacca tcatgacaga tcccgaattt    180

gcagatgcga cttatataga acccataaca aaagaaagta ttttaagtat tattaaaaaa    240

gaaaaaattg atgcaatttt gccaactatg ggtggacaag tagcgttaaa tgttgctatg    300

gaagtttatg aaagcggact tttaggagat gtgaaatttt taggcgcaaa tcctgaggcg    360

attaaaaaag gcgaagatcg tcaggttttt aaagaatgta tgaaaaaaat tggcatggat    420

ttgccaaaat cgatgtatgc gtataattat gacgaagctt taaaagccgt agatgaaatc    480

gactttcctt tgatgatccg tgcttcttat actttagggg gtgctggaag tggtgtggtt    540

tacaatatgg acgaatttaa agaacttacc aatactgctt tagctttatc acctattcat    600

gaaattttga ttgaagaaag tttgttaggt tggaaagaat atgaaatgga agttatacgc    660

gatagagcgg ataattgtat catagtttgt agcatagaaa atatcgatcc tatgggagtt    720

catacaggag atagtattac aatagctcca gcattaactt tgacagataa agaatatcaa    780

gttatgcgta atgcttcttt tgctattttg cgtgaaattg gtgtagatac aggcggaagt    840

aatgtgcaat ttgctatcaa cccaaaaaat ggaagaatga tagttataga aatgaatcca    900

agagtttcaa gatcaagtgc tttagcttct aaggcaacgg gttatcctat agcaaaggtt    960

gcgacacttt tggcagtagg ttttagctta gatgagatta aaaatgatat tacaggaact   1020
```

-continued

```
cctgcatctt tcgagcctgt gattgattat attgtaacaa aaattcctcg ctttaccttt   1080
gaaaaatttc caggagcaaa tacaacttta ggtacagcta tgaaaagtgt gggtgaggta   1140
atggctatag gacgcacttt taaagaaagt atacaaaaag cactttgttc gcttgagcgt   1200
tctttaagtg gttttgatag ggtaaaattt gaagatagaa atgatcttgt ttttaaaatt   1260
cgcaatgcca atgaaaagcg tttactttat gttgctcaag cttttaggga aggttttagc   1320
gtagaagaac tttatgagct ttgtaaaata gatccttggt ttttaacaca gattaaagaa   1380
attgtagatt ttgaagaaca aattgatatg gatattttaa acaataaggc tcttttgaga   1440
aaagcaaaaa ctatgggctt ttcagataaa atgatagcct tgcttgtaaa tttgaaagat   1500
aatttagaat taagccaaaa tgatatttat tatgtaagaa tgaagcaaaa aatcatcgca   1560
gaatttagtg aagtggatac ttgtgcgggt gaatttgaag ccttaactcc ttatctttat   1620
tcaagtatca atgtaagcga actcactcaa agtaaaaacg atgctaagga taaaaaagaa   1680
aaaaaagtga tgattatagg tggggggcca aaccgtatag gacaaggtat agaatttgac   1740
tatgcttgcg tacatgcttc ttttgcgctt aaagatatgg gtattaaaac tattatgtat   1800
aattgtaatc ctgaaaccgt ttcgactgac tatgatacaa gtgatatttt gtatttcgag   1860
cctattgatt tcgaacattt aagagcggtg attgagcgtg aaaaacctga tggagtgatt   1920
gtgcattttg gtggacaaac tcctttgaaa tttgctaagc gtttaagtgc ttttggagct   1980
aagattatag gtactagcgc aagagtaatt gatatggcag aagatagaaa gaaatttgcc   2040
gaatttatta caaagctagg tatcaatcag ccaaaaaatt ctactgcaac aagcgtagaa   2100
gaagcggttc ttaaggctag tgatataggg tatcctgtgc ttgtaagacc aagttatgtt   2160
ttaggtgggc gtgcgatgcg cgtggtaaat gatgaggctg aacttagact ctatatgcaa   2220
gaagctgtgg atgtaagcga taaaagccct gttttgatcg atcagttttt agacaatgct   2280
acagaaattg atgttgatgc gatttgtgat ggcaaagatg tttatgttgc aggaattatg   2340
gagcacatag aagaagcagg aattcattcg ggtgacagtg cttgttcttt gccgccttgc   2400
aatatcgatg aaaaaatgca agaatttatt gcacaaaaaa ccgcagatat tgctttaaat   2460
ttgggagttg taggactttt aaatatacaa tttgctttac ataataatga gctttatatg   2520
atagaggtaa atcctagagc tagtcgtacc ataccttttg ttagtaaagc tacgggtatt   2580
cctttagcaa aagtggcaac gcgtgtgatg tggcaaggaa atttaaaaga agctttaaaa   2640
ttttatgata cttttaaagt ggttaatttt gatactaaaa ttttacgccc taaaactcca   2700
aaatatatga gcgtgaaaga agcagtattt ccatttgcaa aacttagtgg aagtgattta   2760
gaattaggtc ctgaaatgcg ttcaacgggt gaagttatgg gtataagcaa ggattttgca   2820
aattcttatg cgaaaagtca aattgcatcg tttaatcatc ttccagagca aggcgtggta   2880
tttatctcct taaaagataa ggataaaaaa tataccaaaa aaatcgctgc agaatatgta   2940
aagcttggct ttaagcttat ggcaacaggg ggaacttgca aggaaatttt agaaagtggt   3000
tttgagtgcg aacttgtaca taaaatttca gaaggacgcc ccaatgttga agataaattg   3060
aaaaatggag aaattcactt agttatcaat acaagcgata gtcacagttt taaaggcgat   3120
acgaaaaaaa ttcgtgaaaa tattattcgt tttaaaatac cttattttac aaatttacga   3180
tcagctttag caggtgcaaa atcgattaaa gctatacaga gtaaatcttg cctagatgta   3240
aagagtttgc aagagtggct taaatcttga                                    3270
```

<210> SEQ ID NO 255

-continued

<211> LENGTH: 3357
<212> TYPE: DNA
<213> ORGANISM: Corynebacterium diphtheriae

<400> SEQUENCE: 255

```
atgccaaagc gcaatgacat caaacacgtc ctggttatcg gttccggtcc aatcgttatc     60
ggacaagcgt gtgagtttga ctattccgga acacaagcgt gccgagttct taaagaagaa    120
ggacttcgcg tcactttgat caactcgaat ccggcgacaa tcatgacgga tccagagttt    180
gctgatcata catatgttga gccgattgag ccggaatata ttgaaaagat ttttgaaaaa    240
gagatcgctg agggacaccc cgttgatgct gtcttggcaa cacttggtgg gcaaacggca    300
ttgaatgccg ctatcaaatt agatcgtcgc ggatctctcg aaaaatacaa cgtagaactc    360
atcggtgcag acatcgacgc cattgagcgc ggcgaggacc gccagaaatt caaagatatc    420
gttgcgaaaa ttggcggcga atcagcgcgt tcccgtgtat gccacaatat gcaagaggta    480
tatgacaccg ttgaagagct cggccttccg gtagttgtac gcccttcctt cactatgggc    540
ggtttggggt ccggacttgc cttcaatcaa gaggatctcg aacgaattgc cggcggtgga    600
ctcgcagcgt ctcccgaagc aaacgtgctt attgaagaat caattcttgg ctggaaagaa    660
tatgagcttg agctcatgcg tgatggtgct gataacgttg tggttatttg ttccattgaa    720
aatgttgatg cactaggcgt acacacaggt gattctgtta ctgtcgcacc tgctttgact    780
ctgactgatc gtgaatacca aaagatgcgt aatcaaggca tcgcgattat tcgtgaagta    840
ggggtcgaca ccggtggatg taacatccaa tttgcggtaa atccacgtga tggtcgtttg    900
atcaccattg agatgaatcc tcgtgtatct aggtcatccg cccttgcatc gaaagcaacg    960
ggattcccca tcgctaagat tgctgccaag ttggctatcg gatacacgct ggatgaaatt   1020
actaatgaca tcaccggtgt tacgccggcg gctttcgagc caacgctcga ttacgtagta   1080
gtcaagtctc cgcgctttgc gtttgagaag ttcacaggat ccgacgacac attgactaca   1140
acgatgaagt ccgttggtga ggcaatggct cttggccgta attacatcgc ggcgttgggt   1200
aaagtcatgc gttcgctaga aaacaagcaa gttggtttct ggacaacaag tgatgaattc   1260
tttgctgggg atcgcgctaa gaatcttgac gcagtgttag aagatctgaa acgcccgaca   1320
gaagggcgga tgtatgacgt ggagctggct cttcgccttg gcggctcaat tgaagaagta   1380
catcaagcgt ctgggcttga tccatggttc ttggcggagc ttcagtcatt aatagatttc   1440
cgagaatcct tgatgaaggc accggtgctg gatgagccgt tgcttcgaaa agccaaattc   1500
ttcggattgt ctgaccgcca aatcgcggcc cttcgtcccg aatttgcagg ggaagacggc   1560
gttcgtcgct tgcgatggtc attgggagta cggccagtat ttaagactgt agatacgtgc   1620
gctgcagaat ttgaagctac gactccatac cattattcag catatgaact cgatccagct   1680
gctgaatcgg aagtacgtcc tcaaactgaa aaagacaaga tcatcatttt gggatcaggt   1740
ccgaaccgaa ttggccaagg tattgagttt gactactcat gtgttcatgc tgcgctcgaa   1800
ctttcacgcg tggggtatga gacagttatg gttaactgca acccagaaac cgtgtcgaca   1860
gattatgaca ccgctgaccg tctgtatttc gagccactga catttgaaga tgttatggag   1920
gtctaccacg ccgaatcaga atctggacat gttgccggtg tgatcgttca gcttggcgga   1980
caaactccac ttggactagc cgaaaagctt cgtgatgcgg gtgtcccggt cattggtact   2040
actccagagg ctatcgatct agctgaagat cgaggagaat tcggtgaagt attgcgtaaa   2100
gcgcaattgc cagctccagc tttcggtacc gctacatcat ttgaggaagc taaaactgtt   2160
gccaataaca ttggttaccc agtattagtt cgtccatctt acgtcttggg cggccgtggc   2220
```

-continued

```
atggaaatcg tatacgacga aaattccttg cacgcgtaca tcgagcgagc taccgagatc   2280

acgagtgatc acccagtgct cgtggatcgc tttttagata atgcgattga aattgacgtt   2340

gatgcgcttt gtgatggcga aaatgtctac cttgctggtg ttatggaaca cattgaagaa   2400

gctggtattc actccggtga ctctgcttgt gcgctgccac ctatgacgct aggtgccgaa   2460

gatatcgaaa atgtccgtcg ctcaacagaa gcgttggcac atggtatcgg cgttaaagga   2520

ttgatgaatg ttcaatatgc cttgaaggat gacattcttt atgtgattga ggccaaccct   2580

cgtgcatctc gtacagtgcc ttttgtctcc aaagctacgg gtgtccactt agcaaaagca   2640

gcagcgcgaa tcatgactgg ggcaacgatt cctgagcttc aagcggaggg aatgattcca   2700

accggttacg atggtggttc tttgccagag aattcgccga ttgcggtgaa ggaagcagta   2760

cttccgttca atcgattccg tcgtcctgat ggcacaatgt tggatacttt gctaagtcct   2820

gagatgaaat caacgggcga agtcatgggg ctggctgata attttggtgc tgcatatgct   2880

aaggcagaac aggcggcttt tggtgcactt ccaactgaag gcactgtctt cgtatcagta   2940

gcaaaccgcg ataagcgtac tttgattttc ccaattcagc gcctagcttc acttggattc   3000

cgagtactgg caacatcagg cacagccgga atgctacgtc gcaatggtat tgaatgcgaa   3060

gttgtattga agcagaccca agtgcaggaa gcacgacaaa acggcactga ggggcagcgt   3120

tccgtagtgg atatgattaa agccggcgag gtggacctca ttcttaatac acctgcaggg   3180

tcttcaggag cgcgtcacga cggttaccag attcgcgcag cggcagtcaa cgttggcgtt   3240

cctctggtta ctaccgtgca aggtgttact gcggcagtac agggaatcga agcgcttagg   3300

gctggtgagc tcagcgttcg agcgctgcaa gagctagatc attcggtgac tcgatga      3357
```

<210> SEQ ID NO 256
<211> LENGTH: 462
<212> TYPE: DNA
<213> ORGANISM: Providencia stuartii
<220> FEATURE:
<221> NAME/KEY: misc_feature
<222> LOCATION: (7)..(8)
<223> OTHER INFORMATION: n is a, c, g, or t

<400> SEQUENCE: 256

```
tatggtnngc gattggccta tccattatct tgtaccgtgg gttatgacaa ttttgttcag     60

ctcctcgaag gggctcatgc aatggataag cactttaccc aaacggcttt tgaaaagaat    120

attcctgttc tccttggctt aattggcatt tggtataaca actttttga gtcggaaact    180

gaagcgattc tgccatatga tcaatatatg caccgttttg ccgcttattt ccaacaagga    240

aatatggagt caaatggtaa gtatattgac cgtaatggca acaaagtttc ttatcaaacg    300

gggccaatta tttggggtga accgggcacg aacggccaac atgcctttta tcaattgatc    360

catcaaggaa ctaaaatgat cccttgtgat tttattgcgc cagcagtaac gcataatcca    420

ctcggtgatc atcacgataa attactgtcg aacttcttcg cc                       462
```

<210> SEQ ID NO 257
<211> LENGTH: 466
<212> TYPE: DNA
<213> ORGANISM: Enterobacter cloaceae
<220> FEATURE:
<221> NAME/KEY: misc_feature
<222> LOCATION: (10)..(10)
<223> OTHER INFORMATION: n is a, c, g, or t

<400> SEQUENCE: 257

-continued

```
ctttgtggtn ctgcgatcgg cctgtctatc attctctccg tgggcttcga caactttgtt     60

gagctgctct ccggcgcgca cgcgatggac aaacacttct ccaccaccgc acctgagaaa    120

aacctgccgg tgctgctggc gctgatcggt atctggtaca acaacttctt cggcgcagag    180

accgaagcga tcctgccgta cgaccagtac atgcaccgct tcgcggctta cttccagcag    240

ggcaatatgg aatccaacgg taaatacgtt gaccgtaacg gcaacgcggt ggattaccag    300

actggcccaa tcatctgggg tgagccaggc accaacggtc agcacgcgtt ctaccagctg    360

attcaccagg ggaccaaaat ggtaccgtgc gatttcatcg ccccggctat cacccacaat    420

ccactgtctg atcaccatcc taaactgctg tctaacttct tcgccc                   466
```

<210> SEQ ID NO 258
<211> LENGTH: 464
<212> TYPE: DNA
<213> ORGANISM: Proteus mirabilis
<220> FEATURE:
<221> NAME/KEY: misc_feature
<222> LOCATION: (9)..(10)
<223> OTHER INFORMATION: n is a, c, g, or t

<400> SEQUENCE: 258

```
cttatggtnn gcaattggtt tatccattgt attatctatt ggttatgaca actttgagca     60

gttactgtcc ggtgctcatg ctatggataa tcactttaga accactgaag ctgaaaataa    120

tattccgatg atattggcgc ttattggcat ttggtataac aatttttttg gtaccgaaac    180

tgaagcgatt ctgccatacg atcaatatat gcaccgtttt gctgcttact tccaacaagg    240

taatatggaa tccaatggta aatatatcga ccgtgatgga aacaaagtca gttaccaaac    300

cggacctatt atttggggag agccggggac taatggtcag catgcgtttt atcaattaat    360

tcatcaagga accaaactga tcccttgtga ttttattgca ccagcgatca gccataatcc    420

attatctgat catcatgcaa aactaatgtc gaacttcttc gcaa                     464
```

<210> SEQ ID NO 259
<211> LENGTH: 462
<212> TYPE: DNA
<213> ORGANISM: Proteus vulgaris
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (461)..(461)
<223> OTHER INFORMATION: n is a, c, g, or t

<400> SEQUENCE: 259

```
ttatggtngc tattggtttg tctatcgctc tttccgttgg ttatgataat tttgagcaat     60

tattggaagg tgcccatgca atggataacc atttccaaac gacagctgct gaaaataacc    120

taccaatgat cctcgcgctg attggcattt ggtataacaa tttttttggt acagaaactg    180

aagcgattct gccctatgat caatacatgc atcgttttgc agcctatttc caacaaggca    240

atatggagtc aaatggtaag tatattgatc gcgatggtaa cgcagttaac tatcaaactg    300

gacctattat ttggggtgaa ccaggaacta atggtcagca tgcgttttac caattaattc    360

atcagggtac aaaaatgatc ccttgtgatt ttattgcgcc tgcaattagt cataatccat    420

taagtgatca ccatgctaag ttgatgtcta acttcttcgc na                       462
```

<210> SEQ ID NO 260
<211> LENGTH: 462

-continued

<212> TYPE: DNA
<213> ORGANISM: Enterobacter aerogenes

<400> SEQUENCE: 260
ctgtggtccg cctcggtctg tctatcattc tgtccgtcgg cttcgacaac ttcgttcagc 60
tgctgtccgg cgcccacgcc atggacaaac acttctctac cacgccggct gagaaaaacc 120
tgccggtact gctggcgctg attggtatct ggtacaacaa tttcttcggc gccgaaaccg 180
aagcaattct gccgtacgat cagtacatgc atcgctttgc cgcttacttc cagcagggca 240
acatggaatc caacggtaag tacgttgacc gtaacggcaa cgtcgtggat taccagactg 300
gccctatcat ctggggcgag ccggggacta acggtcagca cgcgttctat cagctgatcc 360
accagggcac caaaatggta ccgtgcgatt tcatcgcccc ggctatcacc cataacccgc 420
tgtctgacca ccatcagaaa ctgctgtcta acttcttcgc aa 462

<210> SEQ ID NO 261
<211> LENGTH: 464
<212> TYPE: DNA
<213> ORGANISM: Klebsiella pneumoniae
<220> FEATURE:
<221> NAME/KEY: misc_feature
<222> LOCATION: (462)..(462)
<223> OTHER INFORMATION: n is a, c, g, or t

<400> SEQUENCE: 261
ctgtggtcgg cgattggtct gtccatcatt ctctccgtgg gcttcgacaa cttcgttgag 60
ctgctgtccg gcgcgcatgc gatggataag cacttctcca ccactccggc ggagaaaaac 120
ctgccggtgc tgctggcgct gatcggcatc tggtacaaca acttcttcgg tgcggaaacc 180
gaagcgattc tgccgtacga ccagtacatg caccgctttg ccgcttactt ccagcagggc 240
aacatggagt ccaacggtaa gtatgttgac cgtaacggcc acgcggtaga ctaccagact 300
ggcccaatca tctggggtga gccgggcacc aacggtcagc acgcgttcta ccagctgatc 360
caccagggca ccaaaatggt accgtgcgat ttcatcgctc cggctatcac ccacaacccg 420
ctgtctgacc accatcagaa actgctgtct aacttcttcg cnaa 464

<210> SEQ ID NO 262
<211> LENGTH: 464
<212> TYPE: DNA
<213> ORGANISM: Escherichia coli
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t

<400> SEQUENCE: 262
tttgtggtng cgattggcct gtcgattgtt ctctccatcg gctttgataa cttcgttgaa 60
ctgctttctg gcgcacacgc gatggacaag catttctcca ccacgcctgc cgagaaaaac 120
ctgcctgtac tgttggcgct gattggcatc tggtacaaca atttctttgg tgcggaaact 180
gaagcgattc tgccgtatga ccagtatatg caccgtttcg cggcgtactt ccagcagggc 240
aatatggagt ccaacggtaa gtatgttgac cgtaacggta acgttgtgga ttaccagact 300
ggcccgatta tctggggtga accaggcact aacggtcagc acgcgttcta ccagctgatc 360
caccagggaa ccaaaatggt accgtgcgat ttcatcgctc cggctatcac ccataacccg 420

-continued

```
ctctctgatc accaccagaa actgctgtct aacttcttcg cnaa                 464
```

<210> SEQ ID NO 263
<211> LENGTH: 465
<212> TYPE: DNA
<213> ORGANISM: Escherichia coli
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (463)..(463)
<223> OTHER INFORMATION: n is a, c, g, or t

<400> SEQUENCE: 263

```
ctttgtggtn gcgattggcc tgtcgattgt tctctccatc ggctttgata acttcgttga     60

actgctttcc ggcgcacacg cgatggacaa gcatttctcc accacgcctg ccgagaaaaa    120

cctgcctgta ctgctggcgc tgattggcat ctggtacaac aatttctttg gtgcggaaac    180

tgaagcgatt ctgccgtatg accagtatat gcaccgtttc gcggcgtact tccagcaggg    240

caatatggag tccaacggta agtatgttga ccgtaacggt aacgttgtgg attaccagac    300

tggcccgatt atctggggtg aaccaggcac taacggtcag cacgcgttct accagctgat    360

ccaccaggga accaaaatgg taccgtgcga tttcatcgct ccggctatca cccataaccc    420

gctctctgat catcaccaga aactgctgtc taacttcttc gcnaa                465
```

<210> SEQ ID NO 264
<211> LENGTH: 463
<212> TYPE: DNA
<213> ORGANISM: Citrobacter freundii
<220> FEATURE:
<221> NAME/KEY: misc_feature
<222> LOCATION: (1)..(1)
<223> OTHER INFORMATION: n is a, c, g, or t

<400> SEQUENCE: 264

```
ntgtggtctg caatcggcct gtccatcatc ctgtccgtag gcttcgacaa ttttgttgag     60

ctgctctccg gcgcgcatgc gatggacaaa cacttctcca ccaccccggc tgagaaaaac    120

ctgccggtgc tgctggcgct gatcggtatc tggtacaaca acttcttcgg tgccgaaacc    180

gaagcgattc tgccgtatga ccagtatatg caccgtttcg cggcctactt ccagcagggc    240

aacatggaat ccaacggtaa atacgttgac cgtaacggca atgcggtgga ttaccagact    300

ggcccaatca tctggggtga gccgggtact aacggccagc atgcgttcta ccagctgatc    360

caccagggca ccaaaatggt gccgtgcgat ttcatcgcgc cggcaatcac ccacaacccg    420

ctgtcggatc accatccgaa actgctgtct aacttcttcg caa                  463
```

<210> SEQ ID NO 265
<211> LENGTH: 465
<212> TYPE: DNA
<213> ORGANISM: Haemophilus influenzae
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 265

```
cttnggtngc cttggtcttt caattgcgct atcaattggc tttgaaaact ttgaagcgtt     60
```

-continued

```
attaaatggc gcgcatgaaa tggatgaaca tttccgctct actccaatcg aacaaaatat    120

cccaaccact ttagcattag ttggtttatg gaataccaat tttcttggtg cgcaaacaga    180

agcgatctta ccttatgatc aatatttaca tcgcttcgca gcttattttc aacaaggtaa    240

tatggaatca aatggtaaat atgtggatcg tgatggcaat gtcattaaca attatcaaac    300

tggccctatc atttggggag aacctggtac aaacggacaa cacgcgttct atcaattaat    360

tcatcaaggc actactttaa ttccttgtga ttttatcgca cccgctcaaa gccataaccc    420

attggcagat catcacaata aattgctttc aaacttcttc gccaa                    465
```

<210> SEQ ID NO 266
<211> LENGTH: 462
<212> TYPE: DNA
<213> ORGANISM: Serratia marcescens
<220> FEATURE:
<221> NAME/KEY: misc_feature
<222> LOCATION: (418)..(418)
<223> OTHER INFORMATION: n is a, c, g, or t

<400> SEQUENCE: 266

```
tgtggtcggc gatcggtttg tcgattgcgc tgtccatcgg ttatgacaac ttcgagcagc     60

tgctgagcgg cgcgcacgcc atggacaagc acttcgccga aacgccggcg gagaaaaacc    120

tgccggtgtt gctggcgctg atcggtattt ggtacaacaa cttctttggc gccgaaaccg    180

aagccattct gccgtacgat cagtacatgc accgttttgc cgcttacttc cagcagggca    240

acatggaatc caacggcaag tacgtcgatc gcaacggcaa cccggtggat taccagaccg    300

gtcccatcat ttggggcgag ccgggcacca acggccagca tgcgttctat cagttgatcc    360

accagggcac caagctggtg ccgtgcgatt tcatcgcgcc ggccatcagc cataaccngc    420

tgggcgatca tcacgccaaa ctgctgtcca acttcttgcc aa                       462
```

<210> SEQ ID NO 267
<211> LENGTH: 462
<212> TYPE: DNA
<213> ORGANISM: Morganella morganii

<400> SEQUENCE: 267

```
gtggtcggcg attggtctgt ctatcgtgct ctctgtcggt tatgacaact tcacgcagtt     60

gctcgatggt gcgtatgcca tggacaagca cttcaccgaa actgaattct cacagaatat    120

tccggtgctg ctggcgctga ttggtctgtg gtacaacaat ttcttcggtg cggaaacaga    180

agcaattctg ccttatgatc agtacatgca ccgctttgcg gcctatttcc agcagggcaa    240

tatggagtcc aacgggaaat atgtggatcg taacggtaag gtggtttctc atcagaccgg    300

tccggttatc tggggtgagc ccggcaccaa cgggcagcat gcgttttatc agctgatcca    360

tcagggtacc aaactgatcc cgtgtgattt tatcgcaccg gctcagagcc ataatccgct    420

gggggatcat cacagtaaac tgctgtcgaa cttcttcgcc aa                       462
```

<210> SEQ ID NO 268
<211> LENGTH: 461
<212> TYPE: DNA
<213> ORGANISM: Klebsiella oxytoca

<400> SEQUENCE: 268

```
gtggtagcct cggcctgtcc atcatcctgt ccgtgggctt cgacaacttt gttgagctgc     60

tctccggcgc gcacgcgatg gataaacact tctccaccac cccggctgag aaaaacctgc    120
```

-continued

```
cggtgctgct ggcgctgatc ggtatctggt acaacaactt cttcggcgct gaaaccgaag    180

cgattctgcc gtacgaccag tatatgcacc gttttgccgc ttacttccag cagggcaaca    240

tggaatccaa cggtaaatac gttgaccgta acggcaacgc cgtggattac cagacgggcc    300

caatcatctg ggcgagccg gggaccaacg gtcagcacgc gttctaccag ctgattcacc     360

aggggaccaa aatggtgcct tgcgacttta tcgcgccggc gattacgcat aacccgctgt    420

ccgatcacca tccgaagctg ctgtctaact tcttcgccca a                        461
```

<210> SEQ ID NO 269
<211> LENGTH: 463
<212> TYPE: DNA
<213> ORGANISM: Shigella sonnei
<220> FEATURE:
<221> NAME/KEY: misc_feature
<222> LOCATION: (9)..(9)
<223> OTHER INFORMATION: n is a, c, g, or t

<400> SEQUENCE: 269

```
tttgtggtng cgattggcct gtcgattgtt ctctccatcg gctttgataa cttcgttgaa     60

ctgctttctg gcgcacacgc gatggacaag catttctcca ccacgcctgc cgagaaaaac    120

ctgcctgtcc tgctggcgct gattggcatc tggtacaata atttctttgg tgcggaaact    180

gaagcgattc tgccgtatga ccagtatatg caccgtttcg cggcgtactt ccagcagggc    240

aatatggagt ccaacggtaa gtatgttgac cgtaacggta acgttgtgga ttaccagact    300

ggcccgatta tctggggtga accaggcact aacggtcagc acgcgttcta ccagctgatc    360

caccagggaa ccaaaatggt accgtgcgat ttcatcgccc cggctatcac ccataacccg    420

ctctctgatc accaccagaa actgctgtct aacttcttcg caa                      463
```

<210> SEQ ID NO 270
<211> LENGTH: 463
<212> TYPE: DNA
<213> ORGANISM: Salmonella enteritidis
<220> FEATURE:
<221> NAME/KEY: misc_feature
<222> LOCATION: (13)..(13)
<223> OTHER INFORMATION: n is a, c, g, or t

<400> SEQUENCE: 270

```
gctgtggtct gcntcgggct gtccattatt ctgtccgtcg gtttcgacaa ctttgtcgag     60

ctgctttccg gcgcgcacgc gatggacaag catttctcca ccactccggc ggagaaaaac    120

ctacccattc tgctggcgtt gattggcatc tggtacaaca atttcttcgg cgcggaaacc    180

gaagccattc tgccgtacga ccagtatatg caccgtttcg ccgcctactt ccagcagggt    240

aacatggaat ccaacggtaa atacgttgac cgtagcggca acgccgtgga ttaccagaca    300

ggcccaatta tctggggcga accaggcacc aacggtcagc acgcgtttta tcaattgatt    360

caccagggta ctaaaatggt gccgtgtgat tttatcgccc cggctatcac ccataacccg    420

ctatccgatc atcatcagaa gctgctgtct aacttcttcg caa                      463
```

<210> SEQ ID NO 271
<211> LENGTH: 464
<212> TYPE: DNA
<213> ORGANISM: Salmonella enterica hadar
<220> FEATURE:
<221> NAME/KEY: misc_feature
<222> LOCATION: (14)..(14)
<223> OTHER INFORMATION: n is a, c, g, or t

<400> SEQUENCE: 271

-continued

```
cgctgtggtc tgcntcgggc tgtccattat tctgtccgtc ggtttcgaca actttgtcga     60
gctgctttcc ggcgcgcacg cgatggacaa gcatttctcc accactccgg cggagaaaaa    120
cctacccatt ctgctggcgt tgattggcat ctggtacaac aatttcttcg gcgcggaaac    180
cgaagccatt ctgccgtacg accagtatat gcaccgtttc gccgcctact tccagcaggg    240
taacatggaa tccaacggta aatacgttga ccgtagcggc aacgccgtgg attaccagac    300
aggcccaatt atctggggcg aaccaggcac caacggtcag cacgcgtttt atcaattgat    360
tcaccagggt actaaaatgg tgccgtgtga ttttatcgcc ccggctatca cccataaccc    420
gctatccgat catcatcaga agctgctgtc taacttcttc gcaa                      464
```

<210> SEQ ID NO 272
<211> LENGTH: 466
<212> TYPE: DNA
<213> ORGANISM: Salmonella enterica brandenburg
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (464)..(464)
<223> OTHER INFORMATION: n is a, c, g, or t

<400> SEQUENCE: 272

```
ncgctgtggt ctgcctcggg ctatccatta ttctgtccgt cggtttcgac aactttgtcg     60
agctgctttc cggcgcacac gcgatggaca agcatttctc caccactccg gcggagaaaa    120
acctacccgt tctgctggcg ttgattggca tctggtacaa caatttcttc ggcgcggaaa    180
ccgaagccat tctgccgtac gaccagtata tgcaccgttt cgccgcctac ttccagcagg    240
gcaacatgga atccaacggt aaatacgttg accgtaacgg caacgccgtg gattaccaga    300
caggcccaat tatctggggc gaaccaggca ccaacggtca gcacgcgttt tatcaattga    360
ttcaccaggg tactaaaatg gtgccgtgtg attttatcgc cccggctatc acccataacc    420
cgctatccga tcatcatcag aagctgctgt ctaacttctt cgcnaa                    466
```

<210> SEQ ID NO 273
<211> LENGTH: 464
<212> TYPE: DNA
<213> ORGANISM: Salmonella enterica derby
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t

<400> SEQUENCE: 273

```
gctgtggtct gcntcgggct gtccattatt ctgtccgtcg gtttcgacaa ctttgtcgag     60
ctgctttccg gcgcgcacgc gatggacaag catttctcca ccactccggc ggagaaaaac    120
ctacccattc tgctggcgtt gattggcatc tggtacaaca atttcttcgg cgcggaaacc    180
gaagccattc tgccgtacga ccagtatatg caccgtttcg ccgcctactt ccagcagggt    240
aacatggaat ccaacggtaa atacgttgac cgtaacggca acgccgtgga ttaccagaca    300
ggcccaatta tctggggcga accaggcacc aacggtcagc acgcgtttta tcaattgatt    360
caccagggta ctaaaatggt gccgtgtgat tttatcgccc cggctatcac ccataacccg    420
```

-continued ctatccgatc atcatcagaa gctgctgtct aacttcttcg cnaa 464

<210> SEQ ID NO 274
<211> LENGTH: 463
<212> TYPE: DNA
<213> ORGANISM: Salmonella enterica virschow

<400> SEQUENCE: 274
cgctgtggtc tgcctcgggc tgtccattat tctgtccgtc ggtttcgaca actttgtcga 60
gctgctttcc ggcgcgcacg cgatggacaa gcatttctcc accactccgg cggagaaaaa 120
cctacccatt ctgctggcgt tgattggcat ctggtacaac aatttcttcg gcgcggaaac 180
cgaagccatt ctgccgtacg accagtatat gcaccgtttc gccgcctact tccagcaggg 240
taacatggaa tccaacggta aatacgttga ccgtaacggc aacgccgtgg attaccagac 300
aggcccaatt atctggggcg aaccaggcac caacggtcag cacgcgtttt atcaattgat 360
tcaccagggt actaaaatgg tgccgtgtga ttttatcgcc ccggctatca cccataaccc 420
gctatccgat catcatcaga agctgctgtc taacttcttc caa 463

<210> SEQ ID NO 275
<211> LENGTH: 464
<212> TYPE: DNA
<213> ORGANISM: Salmonella enterica typhimurium
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t

<400> SEQUENCE: 275
gctgtggtct gcntcgggct gtccattatt ctgtccgtcg gtttcgacaa ctttgtcgag 60
ctgctttccg gcgcgcacgc gatggacaag catttctcca ccactccggc ggagaaaaac 120
ctacccattc tgctggcgtt gattggcatc tggtacaaca atttcttcgg cgcggaaacc 180
gaagccattc tgccgtatga ccagtatatg caccgtttcg ccgcctactt ccagcagggt 240
aacatggaat ccaacggtaa atacgttgac cgtaacggca acgccgtgga ttaccagaca 300
ggcccaatta tctggggcga accaggcacc aacggtcagc acgcgtttta tcaattgatt 360
caccagggta ctaaaatggt gccgtgtgat tttatcgccc cggctatcac ccataacccg 420
ctatccgatc atcatcagaa gctgctgtct aacttcttcg cnaa 464

<210> SEQ ID NO 276
<211> LENGTH: 464
<212> TYPE: DNA
<213> ORGANISM: Salmonella enterica paratyphi B
<220> FEATURE:
<221> NAME/KEY: misc_feature
<222> LOCATION: (14)..(14)
<223> OTHER INFORMATION: n is a, c, g, or t

<400> SEQUENCE: 276
cgctgtggtc tgcntcgggc tgtccattat tctgtccgtc ggtttcgaca actttgtcga 60
gctgctttcc ggcgcgcacg cgatggacaa gcatttctcc accactccgg cggagaaaaa 120
cctacccatt ctgctggcgt tgattggcat ctggtacaac aatttcttcg gcgcggaaac 180
cgaagccatt ctgccgtatg accagtatat gcaccgtttc gccgcctact tccagcaggg 240
taacatggaa tccaacggta aatacgttga ccgtaacggc aacgccgtgg attaccagac 300
aggcccaatt atctggggcg aaccaggcac caacggtcag cacgcgtttt atcaattgat 360
tcaccagggt actaaaatgg tgccgtgtga ttttatcgcc ccggctatca cccataaccc 420
gctatccgat catcatcaga agctgctgtc taacttcttc caaa 464

<210> SEQ ID NO 277
<211> LENGTH: 464
<212> TYPE: DNA
<213> ORGANISM: Serratia liquefasciens
<220> FEATURE:
<221> NAME/KEY: misc_feature
<222> LOCATION: (1)..(1)
<223> OTHER INFORMATION: n is a, c, g, or t

<400> SEQUENCE: 277
ntgtggtcgg cgattggcct gtctatcgcc ctgtcagtgg gttacgagaa ttttgaacag 60
ttgctgagcg gcgcgcacgc gatggacaaa cacttcgcgc aaacgccggc agagcaaaac 120
ctgccggtgc tgctggcgtt gatcggtatc tggtacaaca acttcttcgg tgcagaaacc 180
gaagctatcc tgccgtacga ccagtacatg caccgttttg ccgcttactt ccagcagggc 240
aacatggaat ccaacggtaa atatgtcgat cgcaacggca atccggtgga ctaccagacc 300
ggcccaatca tctggggcga gccgggcacc aacgggcagc acgcgtttta ccaactgatc 360
caccagggga ccaaactggt gccttgtgac tttatcgcgc cggccatcag ccataatccg 420
ctgagcgacc accatgcaaa actgctgtcg aacttcttcg ccaa 464

<210> SEQ ID NO 278
<211> LENGTH: 1860
<212> TYPE: DNA
<213> ORGANISM: Neisseria meningitidis serogroup A

<400> SEQUENCE: 278
acagaaaatc ctcgaagaca ccctgctgga acaatggcag tggctcaaac ctaaagaacc 60
gtaaacatcc tgcgtacaca aatgccgtct gaaacgcccc cacgcttcag acggcagacc 120
gtaaaaccta caaccccaat tcctcccaaa tctcatcaat cttagccgta accgcagggt 180 ctttttttaat cacccgtccc cattcgcggt cggtttcgcc cggccacttg ttggtcgcat 240
ccaaacccat tttgccgcca agtccgctga cggggctggc gaagtcgagg tagtcgatgg 300
gcgtgttttc catcaaaacg gtatcgcgca cggggtccat gcgcgtggtt accgcccaga 360
tgacttcttt ccagtcgcgc acatccacat cgtcatccac cacaatgatg aatttggtgt 420
acataaactg gcgcaggaac gaccagcagc ccatcatcac gcgcttggcg tgtccggcgt 480
actgtttttt catgctcacc accgccatgc ggtaggagca gccttcgggc ggcaggtaaa 540
aatcggtgat ttcggggaac tgcttttgca aaagcggtac gaacacttcg ttcaacgcca 600
cgcccaaaac ggcgggttca tcgggcggtt tgcctgtgta ggtagagtgg taaatcgggt 660
tttcgcgcat ggtgatgcgt tcgaccgtaa acacggggaa atggtcctgc tcgttgtaat 720
agcccgtgtg gtcgccgtat ggaccttcca acgcggtttc gtttggatgg atgacgcctt 780
ccaacacgat ttctgcgcgg gcaggcactt gcaaatcgtt gccgatacat ttcaccagtt 840
ccgtccgcga accgcgcagc agtccggcaa actggtattc gctcaaggta tcgggaacgg 900
gcgttaccgc gcccaaaatg gtggcagggt cgcagccgag cacgacggcg acgggatacg 960
gcgtatcggg attgagtttg cggaattcct gataatccag cgcgccgccg cgatgcgaca 1020
gccagcgcat aatcagcttg tttatgccga ttaattgttg gcggtaaatg ccgagatttt 1080

-continued ggcgtttttt gtgcggcccg cgcgtgacgg tcaagcccca cgttaccagc ggcgcaacgt 1140
cttccggcca gcaatgctga atcggaagtt gatacaaatc aacgtcttcg ccttcccata 1200
cgatttcctg acacggcgca tttttcacca cgttcggcgc catgctccaa atgtctttca 1260
agagcggcag tttggaaaac gcgtctttaa tgcctttggg cggttcgggt tctttcaaat 1320
acgccagcgt ctgcccgatt tcgcgcagct tggacacgct gtccgcgccc atgcccatcg 1380
ccacacgttc gggcgtgccg aacaggtttg ccaacacggg ataatcatag cgcgtaccgt 1440
cgggcttaac tgggtgttca aacaacaacg ccggcccttc ggcgcgcagc acgcggtcgg 1500
cgatttcggt catttccaaa tgcggggaaa cggggtgcgc gatgcgtttg agtttgccct 1560
gctgctcgag catggcgatg aagtcgcgca ggtctttgta tttcatattc atccttttttg 1620 tccttttatc ctgagcaatc cgattcggat accgccccta tccttgcctg cgcttcggca 1680
tattctatgc cgtgataaaa gtcgcgtacc agcggatgtt cgctgccttg atggagttgc 1740
aacaaaggac gttgaccatc gggttgggta acgacattgc aatgcaaacc gaaggtgtcg 1800
gattcgtaag gggcagccg gttgcagatc atgccgaaat aaacggcgtt ttcagggttg 1860

<210> SEQ ID NO 279
<211> LENGTH: 588
<212> TYPE: DNA
<213> ORGANISM: Klebsiella oxytoca

<400> SEQUENCE: 279
acgaccagac gcccatcatg acgcgtttcg cgtgaccggc gtactgcttc ttcatcgtga 60
cgaccgccag gcgataggaa cagccttcag gcggcaaata gaaatccacg atttcaggaa 120
actgcttttg cagaatgggg acgaacactt cgttcagcgc aacgcccagt accgccggct 180
catccggcgg gcgcccggta taggtcgagt gatagatggc atcttcacgc tgagtaatgt 240
gggtaacggt aaagaccggg aagttatcca cttcattgta gtagccagta tggtcgccat 300
aggggccttc cggcgccatt tctccggctt caatataccc ttccagcacg atctccgcgc 360
tggcgggcac ctcaagatcg ttagagatgc acttcacgac ttcggttttg gtgccgcgca 420
gtagcccggc aaaagcgtat tcggaaagag tatccggaac cggagtcacc gccccgagaa 480
tggttgccgg atcggcgccc agcgcgacgg agaccgggaa acgctcgcca ggacgcgccg 540
cgcaccactc ctggaagtcc agcgcgccgc cgcgatgcga tagccaac 588

<210> SEQ ID NO 280
<211> LENGTH: 1479
<212> TYPE: DNA
<213> ORGANISM: Salmonella enterica subsp. enterica serovar

<400> SEQUENCE: 280
atggacgcca tgaaatatca cgatttacgc gacttcctga cgctacttga gcaacagggg 60
gaactaaaac gcatcacgct acctgtggat cctcatctgg aaattacgga aatcgctgac 120
cgcacgctgc gtgccggtgg accggcgttg ctgtttgaaa gtcctaaagg ttacgccatg 180
ccggtgctgt gcaacctttt tggcacgcca aaacgcgtgg cgatgggcat ggggcaggat 240
gatgtttccg ccttacggga agtgggtaaa ttattagcgt ttctgaaaga acctgagccg 300
ccgaaaggct ttcgcgatct gtttgacaag ctgccgcagt ttaagcaagt gctgaatatg 360
ccgacgaaac ggttacgcgg cgcgccttgc cagcagaaaa tcgcgtctgg cgatgatgtc 420
gatttaacgc gtcttcctgt catgacctgt tggccggacg acgccgcgcc gctgattacc 480
tggggactga cggtaacgcg tggcccgcac aaagaacggc aaaacctggg catttatcgt 540

-continued

```
cagcagttga taggtaaaaa taagctgatt atgcgctggc tgtctcaccg cggcggcgcg    600

ttggattttc aggagtggtt agccgcgcgt ccgggtgaac gtttcccggt ctccgtcgca    660

ttgggcgccg atccggcgac gatacttggc gccgtgactc ctgttcccga tactctgtcg    720

gagtatgcct ttgcgggcct gctgcgcggc acgaaaactg aagtggttaa atgcctttct    780

aacgatctgg aagtgcctgc cagcgccgag attatccttg aaggttacat tgagccggga    840

gagatggcgc cggaaggacc gtatggcgat catacgggct attataatga agtggataac    900

tttccggtct ttaccgtcac gcatattacg cagcgtgagg atgccatcta tcactccacc    960

tataccgggc gtccgcccga tgagcctgcg gtattagggg tggcgctcaa tgaagtcttc   1020

gtgcctattc tgcaaaaaca gtttccggaa atcgtcgact tttatctgcc gccggaaggg   1080

tgttcttacc gcctggcggt agtgacgatg aaaaagcagt acgctggtca tgcgaaacgc   1140

gtcatgatgg gcgtctggtc gtttttgcgc cagtttatgt atacgaaatt tgttatcgtt   1200

tgcgatgatg acgttaacgc acgcgactgg aatgatgtga tctgggcgat taccacccgt   1260

atggaccctg cgcgggatac ggtgctggtt gaaaatacgc cgattgatta cctggatttt   1320

gcctcgccgg tctccgggct gggttcaaaa atggggctgg atgccacaaa caaatggccg   1380

ggcgaaaccc aacgcgagtg ggtcgtcct attgttaaag atcctgaagt taccgcacgt   1440

attgatgcga tttgggatga gctggctatc tttaaataa                          1479
```

```
<210> SEQ ID NO 281
<211> LENGTH: 1488
<212> TYPE: DNA
<213> ORGANISM: Salmonella typhimurium

<400> SEQUENCE: 281

gaggctacaa tggacgccat gaaatatcac gatttacgcg acttcctgac gctacttgag     60

cagcaggggg aactaaaacg catcacgcta cctgtggatc ctcatctgga aatcacggaa    120

atcgctgacc gcacgctgcg tgccggtgga ccggcgttgc tgtttgaaaa tcctaaaggt    180

tacgccatgc cggtgctgtg caaccttttt ggcacgccaa aacgcgtggc gatgggcatg    240

gggcaggatg atgtttccgc cttacgggaa gtgggtaaat tattagcgtt tcttaaagaa    300

cctgagccgc cgaaaggctt tcgcgatctg tttgacaagc tgccgcagtt taagcaagtg    360

ctgaatatgc cgacgaaacg gttacgcggc gcgccttgcc agcagaaaat cgcgtctggc    420

gatgatgtcg atttaacgcg tcttcctgtc atgacctgtt ggccggacga cgccgcgccg    480

ctgattacct ggggactgac ggtaacgcgt ggtccgcaca aagagcggca aaacctgggc    540

atttatcgtc agcagttgat aggtaaaaat aagctgatta tgcgctggct gtctcaccgc    600

ggcggcgcgc tggattttca ggagtggtta gccgcgcgtc cgggtgaacg tttcccggtc    660

tccgtcgcat tgggcgccga tccggcgacg atacttggcg ccgtgactcc tgttcccgat    720

actctgtcgg agtatgcctt tgcgggcctg ctgcgcggca cgaaaactga agtggttaaa    780

tgcctttcta acgatctgga agtgcctgcc agcgccgaga ttatccttga aggttacatt    840

gagccgggag agatggcgcc ggaaggaccg tatggcgatc atacgggcta ttataatgaa    900

gtggatagct ttccggtctt taccgtcacg catattacac agcgtgagga tgccatctat    960

cactccacct ataccgggcg tccgcccgat gagcctgcgg tattaggggt ggcgctcaat   1020

gaagtcttcg tgcctattct gcaaaaacag tttccggaaa tcgtcgactt ttatctgccg   1080

ccggaagggt gttcttaccg cctggcggta gtgacgatga aaaagcagta cgctggtcat   1140
```

-continued

```
gcgaaacgcg tcatgatggg cgtctggtcg tttttgcgcc agtttatgta tacgaaattt   1200

gttatcgttt gcgatgatga cgttaacgca cgcgactgga atgatgtgat ctgggcgatt   1260

accacccgta tggaccctgc acgggatacg gtgctggttg aaaatacgcc gattgattac   1320

ctggattttg cctcgccggt ctccgggctg ggttcaaaaa tggggctgga tgccacaaac   1380

aaatggccgg gcgaaaccca acgcgagtgg ggtcgtccta ttgttaaaga tcctgaagtt   1440

accgcgcgta ttgatgcgat ttgggatgag ctggctatct ttaaataa                1488
```

<210> SEQ ID NO 282
<211> LENGTH: 1494
<212> TYPE: DNA
<213> ORGANISM: Escherichia coli

<400> SEQUENCE: 282

```
atggacgcca tgaaatataa cgatttacgc gacttcttga cgctgcttga acagcagggt     60

gagctaaaac gtatcacgct cccggtggat ccgcacctgg aaatcactga aattgctgac    120

cgcactttgc gtgccggtgg gcctgcgctg ttgttcgaaa accctaaagg ctactcaatg    180

ccggtgctgt gcaacctgtt cggtacgcca aagcgcgtgg cgatgggcat ggggcaggaa    240

gatgtttcgg cgctgcgtga agttggtaaa ttattggcgt ttctgaaaga gccggagccg    300

ccaaaaggtt tccgcgacct gtttgataaa ctgccgcagt ttaagcaagt attgaacatg    360

ccgacaaagc gactgcgtgg tgcaccctgc caacaaaaaa tcgtctctgg cgatgacgtc    420

gatctcaatc gcattcccat tatgacctgc tggccggaag atgccgcgcc gctgattacc    480

tgggggctca ccgtaacgcg cggcccgcat aaagagcggc agaatctggg catttatcgc    540

cagcagctaa ttggtaaaaa caaactgatt atgcgctggc tgtcgcatcg cggcggcgcg    600

ttggattatc aggagtggtg tgcggcgcat ccgggcgaac gtttcccggt ttctgtggcg    660

ctgggtgccg atcctgccac gattctcggt gcagtcaccc ccgttccgga tacgctttca    720

gagtatgcgt ttgccggatt gctgcgcggt accaagaccg aagtggtgaa gtgtatctcc    780

aatgaccttg aagtgcccgc cagtgcggag attgtgctgg aagggtatat cgaacaaggc    840

gaaactgcgc cggaagggcc gtatggcgac cacaccggtt actataacga agtcgatagt    900

tttccggtat ttaccgtgac gcatattacc cagcgtgaag atgcgattta tcattccacc    960

tataccgggc gtccgccaga tgaacctgcg gtactgggtg tagcactgaa cgaagtgttc   1020

gtgccgattc tgcaaaaaca gttcccggaa attgtcgatt tttatctgcc gccggaaggc   1080

tgttcttatc gtctggcggt agtgacgatc aaaaaacagt acgccggaca cgcgaagcgc   1140

gtcatgatgg gcgtctggtc gttcttacgc cagtttatgt acactaaatt tgtgatcgtt   1200

tgcgatgatg acgtcaacgc ccgcgactgg aacgatgtga tttgggcgat taccacccgt   1260

atggacccgg cgcgggatac tgttctggta gaaaatacgc ctattgatta tctggatttt   1320

gcctcgcctg tctccgggct gggttcaaaa atggggctgg atgccacgaa taaatggccg   1380

ggtgaaaccc agcgtgaatg ggacgtcccc atcaaaaaag atccagatgt tgtcgcgcat   1440

attgacgcca tttgggatga actggctatt tttaacaacg gtaaaagcgc ctga         1494
```

<210> SEQ ID NO 283
<211> LENGTH: 1494
<212> TYPE: DNA
<213> ORGANISM: Escherichia coli

<400> SEQUENCE: 283

```
atggacgcca tgaaatataa cgatttacgc gacttcttga cgctgcttga acagcagggt     60
```

-continued

```
gagctaaaac gtatcacgct cccggtggat ccgcatctgg aaatcactga aattgctgac    120
cgcactttgc gtgccggtgg gcctgcgctg ttgttcgaaa accctaaagg ctactcaatg    180
ccggtgctgt gcaacctgtt cggtacgcca aagcgcgtgg cgatgggcat ggggcaggaa    240
gatgtttcgg cgctgcgtga agttggtaaa ttattggcgt ttctgaaaga gccggagccg    300
ccaaaaggtt tccgcgacct gtttgataaa ctgccgcagt ttaagcaagt attgaacatg    360
ccgacaaagc ggctgcgtgg tgcgccctgc caacaaaaaa tcgtctctgg cgatgacgtc    420
gatctcaatc gcattcccat tatgacctgc tggccggaag atgccgcgcc gctgattacc    480
tgggggctga cagtgacgcg cggcccacat aaagagcggc agaatctggg catttatcgc    540
cagcagctga ttggtaaaaa caaactgatt atgcgctggc tgtcgcatcg cggcggcgcg    600
ctggattatc aggagtggtg tgcggcgcat ccgggcgaac gtttcccggt ttctgtggcg    660
ctgggtgccg atcccgccac gattctcggt gcagtcactc ccgttccgga tacgctttca    720
gagtatgcgt ttgccggatt gctacgtggc accaagaccg aagtggtgaa gtgtatctcc    780
aatgatcttg aagtgcccgc cagtgcggag attgtgctgg aagggtatat cgaacaaggc    840
gaaactgcgc cggaagggcc gtatggcgac cacaccggtt actataatga agtcgatagt    900
ttcccggtat ttaccgtgac gcatattacc cagcgtgaag atgcgattta ccattccacc    960
tataccgggc gtccgccaga tgagcccgcg gtgctgggtg tcgcactgaa cgaagtgttt   1020
gtgccgattc tgcaaaaaca gttcccggaa attgtcgatt tttacctgcc gccggaaggc   1080
tgctcttatc gcctggcggt agtgacaatc aaaaaacagt acgccggaca cgcgaagcgc   1140
gtcatgatgg gcgtctggtc gttcttacgc cagtttatgt acactaaatt tgtgatcgtt   1200
tgcgatgatg acgttaacgc acgcgactgg aacgatgtga tttgggcgat taccacccgt   1260
atggacccgg cgcgggatac tgttctggta gaaaatacgc ctattgatta tctggatttt   1320
gcctcgcctg tctccgggct gggttcaaaa atggggctgg atgccacgaa taaatggccg   1380
ggggaaaccc agcgtgaatg ggacgtcccc atcaaaaaag atccagatgt tgtcgcgcat   1440
attgacgcca tctgggatga actggctatt tttaacaacg gtaaaagcgc ctga         1494
```

<210> SEQ ID NO 284
<211> LENGTH: 1479
<212> TYPE: DNA
<213> ORGANISM: Salmonella enterica subsp. enterica serovar Typhi

<400> SEQUENCE: 284

```
atggacgcca tgaaatatca cgatttacgc gacttcctga cgctacttga gcagcagggg     60
gaactaaaac gcatcacgct acctgtggat cctcatctgg aaatcacgga aatcgctgac    120
cgcacgctgc gtgccggtgg accggcgttg ctgtttgaaa atcctaaagg ttacgccatg    180
ccggtgctgt gcaacctttt tggcacgcca aaacgcgtgg cgatgggcat ggggcaggat    240
gatgtttccg ccttacggga agtgggtaaa ttattagcgt ttctgaaaga acctgagccg    300
ccgaaaggct ttcgcgatct gtttgacaag ctgccgcagt ttaagcaagt gctgaatatg    360
ccgacgaaac ggttacgcgg cgcgccttgc cagcagaaaa tcgcgtctgg cgatgatgtc    420
gatttaacgc gtcttcctgt catgacctgt tggccggacg acgccgcgcc gctgattacc    480
tggggactga cggtaacgcg tggcccgcac aaagaacggc aaaacctggg catttatcgt    540
cagcagttga taggtaaaaa taagctgatt atgcgctggc tgtctcaccg cggcggcgcg    600
ttggattttc aggagtggtt agccgcgcgt ccgggtgaac gtttcccggt ctccgtcgca    660
```

-continued

```
ttgggcgccg atccggcgac gatacttggc gccgtgactc ctgttcccga tactctgtcg    720

gagtatgcct ttgcgggcct gctgcgcggc acgaaaactg aagtggttaa atgcctttct    780

aacgatctgg aagtgcctgc cagcgccgag attatccttg aaggttacat tgagccggga    840

gagatggcgc cggaaggacc gtatggcgat catacgggct attataatga agtggataac    900

tttccggtct ttaccgtcac gcatattacg cagcgtgagg atgccatcta tcactccacc    960

tataccgggc gtccgcccga tgagcctgcg gtattagggg tggcgctcaa tgaagtcttc   1020

gtgcctattc tgcaaaaaca gtttccggaa atcgtcgact tttatctgcc gccggaaggg   1080

tgttcttacc gcctggcggt agtgacgatg aaaaagcagt acgctggtca tgcgaaacgc   1140

gtcatgatgg gtgtctggtc gtttttgcgc cagtttatgt atacgaaatt tgttatcgtt   1200

tgcgatgatg acgttaacgc acgcgactgg aatgatgtga tctgggcgat taccacccgt   1260

atggaccctg cgcgggatac ggtgctggtt gaaaatacgc cgattgacta cctggatttt   1320

gcctcgccgg tctccgggct gggttcaaaa atggggctgg atgccacaaa caaatggccg   1380

ggcgaaaccc aacgcgagtg ggtcgtcct attgttaaag atcctgaagt taccgcgcgt   1440

attgatgcga tttgggatga gctggctatc tttaaataa                          1479
```

<210> SEQ ID NO 285
<211> LENGTH: 1494
<212> TYPE: DNA
<213> ORGANISM: Escherichia coli

<400> SEQUENCE: 285

```
atggacgcca tgaaatataa cgatttacgc gacttcttga cgttgcttga acagcagggt     60

gagctaaaac gtatcacgct cccggtggac ccgcatctgg aaatcactga aattgctgac    120

cgcacgctgc gtgctggtgg gcctgcgctg ttgtttgaaa accctaaagg gtactcaatg    180

ccggtgctgt gcaacttgtt cggtacgcca aagcgcgtag cgatgggtat gggccaggaa    240

gatgtttcag cactgcgtga agtcggtaaa ttattagcat ttctgaaaga accagagccg    300

ccaaaaggtt ttcgcgatct gtttgataag ctgccgcagt ttaagcaggt gttaaacatg    360

ccgacaaagc gactgcgcgg tgcaccctgc caacaaaaaa tcgtctctgg cgatgacgtc    420

gatctcaacc gtattcccat tatgacctgt tggccggaag atgccgcgcc gctgattaca    480

tgggggctaa ccgttacacg tggccctcat aaagagcgac agaatctggg catttatcgc    540

cagcaactga ttggtaaaaa caagctgatt atgcgttggc tgtcgcatcg cggcggcgcg    600

ctggattatc aggagtggtg tgcggcgcat ccaggtgaac gtttcccgat ctctgtggcg    660

ttgggcgctg atccggcaac cattctcggt gcagtcacac cagtaccaga tactttgtcg    720

gaatacgcct ttgccggatt gctacgtggc accaaaaccg aagtagtgaa gtgtatttcc    780

aatgatctcg aagtgcccgc cagtgcggag attgtgctgg aagggtatat cgaacaaggc    840

gaaatggcgc cagaaggacc gtatggtgac cacactggtt actataacga agtcgatagt    900

ttcccggtat ttaccgtgac gcatattacc cagcgtgaag atgcgattta ccattccacc    960

tataccgggc gtccgccaga tgaacccgcg gtactgggag tggcgttgaa cgaagtattt   1020

gttcccattc tgcaaaagca gttcccggaa attgtcgatt tttacctgcc gccggaaggc   1080

tgctcttatc gcctggcggt agtgacaatc aaaaaacagt acgccggaca cgcgaagcgc   1140

gtcatgatgg gcgtctggtc gttcttacgc cagtttatgt acactaaatt tgtgatcgtt   1200

tgcgatgatg acgttaacgc acgcgactgg aacgatgtga tttgggcgat taccacccgt   1260

atggacccag cgcgggatac tgttctggta gaaaatacgc ctattgatta tctggatttt   1320
```

-continued

```
gcctcgcctg tctccgggct gggttcaaaa atggggctgg atgccacgaa taaatggccg   1380

ggggaaaccc agcgtgaatg gggacgtccc atcaaaaaag atccagatgt tgtcgcacat   1440

attgacgcca tctgggatga actggctatt tttaacaacg gtaaaagcgc ctga         1494
```

<210> SEQ ID NO 286
<211> LENGTH: 1494
<212> TYPE: DNA
<213> ORGANISM: Shigella flexneri

<400> SEQUENCE: 286

```
atggacgcca tgaaatataa cgatttacgc gacttcctga cgctgcttga acagcagggt     60

gagctaaaac gtatcacgct cccggtggat ccgcatctgg aaatcactga aattgctgac    120

cgcactctgc gtgctggtgg gcctgcgctg ttgttcgaaa accctaaagg ctactcaatg    180

ccggtgctgt gcaacctgtt cggtacgcca aagcgcgtgg cgatgggcat ggggcaggaa    240

gatgtttcga cgctgcgtga agttggtaaa ttattggcgt ttctgaaaga gccggagccg    300

ccaaaaggtt tccgcgacct gtttgataaa ctgccgcagt ttaagcaggt gttaaacatg    360

ccgacaaagc gactgcgtgg tgcgccctgc caacaaaaaa tcgtctctgg cgatgacgtc    420

gatctcaatc gcattcccat tatgacctgc tggccggaag atgccgcgcc gctgattacc    480

tgggggctga ccgtaacgcg cggcccgcat aaagagcggc agaatctggg catttatcgc    540

cagcagctga ttggtaaaaa caaactgatt atgcgctggc tgtcgcatcg cggcggcgcg    600

ctggattatc aggagtggtg tgcggcgcat ccgggcgaac gtttcccggt ttctgtggcg    660

ctgggtgccg atcctgccac gattctcggt gcagtcaccc ccgttccgga tacgctttca    720

gagtatgcgt ttgccggatt gctacgcggc accaaaaccg aagtagtaaa gtgtatttcc    780

aatgacctcg aagtgccagc cagtgccgaa atcgtcctgg aagggtatat cgatcctggt    840

gagatggcgc cggaagggcc gtatggtgac cacacaggtt actataatga agtcgataat    900

ttcccggtgt ttaccgtgac gcatattacc cagcgtgaag atgcgattta ccattccacc    960

tataccgggc gtccgccaga tgagcccgcg gtactgggcg tggcgttgaa cgaagtgttt   1020

gtaccgattc tgcaaaaaca gttcccggaa attgtcgatt tttacctgcc gccggaaggc   1080

tgttcttatc gtctggcggt agtgacgatc aaaaaacagt acgccggaca cgcgaagcgc   1140

gtcatgatgg gcgtctggtc gttcttacgc cagtttatgt acactaaatt tgtgatcgtt   1200

tgcgatgatg acgtcaacgc acgcgactgg aacgatgtga tttgggcgat taccacccgt   1260

atggacccgg cgcgggatac tgttctggta gaaaatacgc ctattgatta tctggatttt   1320

gcctcgcctg tctctgggct gggttcaaaa atggggctgg atgccacgaa taaatggccg   1380

ggggaaaccc agcgtgaatg gggacgtccc atcaaaaaag atccagatgt tgtcgcgcat   1440

attgacgcca tctgggatga actggctatt tttaacaacg gtaaaagcgc ctga         1494
```

<210> SEQ ID NO 287
<211> LENGTH: 1467
<212> TYPE: DNA
<213> ORGANISM: Pseudomonas aeruginosa

<400> SEQUENCE: 287

```
atgacgttca aggatctccg cgatttcatc gcccagctgg agcagcgcgg tgcgttgaag     60

cgcatccagg tgccgatttc ccccgtgctc gagatgaccg aggtgtgcga ccgcacgttg    120

cgcgccaagg gcccggcatt gctgttcgaa aagccgaccg gcttcgacat gccggtgctc    180
```

-continued

```
ggcaacctgt tcggtacgcc ggagcgcgtg gcgctgggca tgggcgccga ggacgtcggc    240
gcactgcgcg agatcggcaa gctgctggcg caactcaagg agcccgagcc gccgaagggc    300
ctcaaggacg cctgggccaa gctgccgatg tacaggaagg tcctgtccat ggcgccgaag    360
gtgctcaagg acgccccctg ccaggaagtg gtcgaggagg gcgaggacgt cgacctcggc    420
cggctgccgg tccagacctg ctggccgggc gatgtcgggc cgctgatcac ctggggcctg    480
accgttaccc gcgggccgaa caaggaacgg cagaacctgg gcatctaccg ccagcaggtg    540
atcggccgca acaaggtgat catgcgctgg ctcagccatc gcggcggcgc actggactac    600
cgcgagtggt gccagaagca tccgggccag ccctatccgg tagccgtggc gctgggcgcc    660
gatccggcga ccatcctcgg tgcggtgacg ccggtgccgg acaccctttc cgaatacgct    720
ttcgccggcc tgttgcgcgg gcatcgtacc gagctggtca agtgtcgcgg gagcgacttg    780
caggtgccgg ccagcgccga gatcgtcctc gaaggggtga tccaccccgg cgagatggcc    840
gacgaaggcc cctatggcga tcacaccggc tactacaacg aggtcgatcg cttcccggtg    900
ttcaccgtcg agcgcgtcac ccgccggcag aaaccgatct accacagcac ctacaccggg    960
cgtccgccgg acgagccggc gatcctcggg gtggcgctga acgaagtgtt cgtgccgatc   1020
ctgcagaagc agttcccgga aatcgtcgat ttctacctgc cgccggaagg ttgttcctac   1080
cggatggcgg tggtgaccat gaagaagcag tacccagggc acgccaagcg cgtgatgctc   1140
ggggtctggt cgttcctgcg gcagttcatg tacaccaagt tcgtcatcgt caccgacgat   1200
gacatcgatg cgcgcgactg gaacgatgtg atctgggcca tcaccacgcg gatggacccc   1260
aagcgcgaca cggtgatgat cgacaacacg cccatcgact acctcgactt cgcctcgccg   1320
gtttccggcc tcggctcgaa gatggggctt gatgccaccc acaagtggcc gggcgagacc   1380
agccgcgaat gggggcgcgc catcgtcaag gacgaagcgg tgacacggcg catcgacgcc   1440
ctctggtcga gcctcgggat cgactga                                        1467
```

<210> SEQ ID NO 288
<211> LENGTH: 1467
<212> TYPE: DNA
<213> ORGANISM: Pseudomonas syringae pv. tomato

<400> SEQUENCE: 288

```
atgaaattca aagatctaag ggatttcgtg cagcagttgg agcagcgcgg agagttgaaa     60
cgcattcaga tgccgatctc gcctgtgctg gaaatgactg aaatctgtga ccgtaccttg    120
cgcgccaaag gcccggccct gctgtttgaa aacccggttg gctttgatat tccggtgctg    180
ggcaacctgt tcggcacgcc ggagcgcgtg gccatgggca tgggcgcgga agccgtcacc    240
gagctgcgcg aaatcggcaa gttgcttgcg tttctcaagg agcccgagcc gcccaaaggc    300
ctgaaagatg cctggtccaa gctgcccatc ttccgcaaag tcatcgccat ggcgcccaag    360
gtcgtcaagg atgcaccctg ccaggagatc gtcatcgagg gtgatgacgt cgatctcggc    420
atgttgccgg tgcagacctg ctggccgggc gatgtcgcgc cgctgatcac ctggggcctg    480
accgtgacca aaggcccgaa caaggagcgg cagaacctcg gtatttatcg ccagcaggtc    540
atcggccgca acaagatcat catgcgctgg ctcagccatc gcggtggcgc gcttgacttc    600
cgcgactggt gcgtcaagca tcctggcgag ccttatccgg tggccgtcgc actgggcgcg    660
gacccggcga ccattctcgg tgccgtgacg ccggtgcccg acagcctgtc cgaatacgcc    720
ttcgccgggc tactgcgtgg ctcgcgcacc gagctgatca agtgccgtgg cagcaacctg    780
caagtgccag ccagtgccga aatcgtgctt gagggcgtga ttcatccggg cgagatggcc    840
```

-continued

```
aacgaaggcc cctacggcga tcacaccggt tattacaacg aagtcgacag ctttccggtg    900
ctcaccgtcg agcgcatcac ccaccgcatc aagccgatct accacagcac ctacaccggg    960
cgtccaccgg acgagccggc tatcctgggt gtggcgctga acgaagtgtt cgtgccgatt   1020
ctgcagaagc agtttccgga aatcgtcgat ttctacctgc cgcccgaggg gtgctcttac   1080
cgcatggcgg tggtgactat caagaaacag taccccggcc atgccaagcg cgtgatgctg   1140
ggcgtctggt cgttcctgcg ccagtttatg tacaccaaat ttgtgatcgt caccgatgac   1200
gacatcaatg cgcgtgactg gaatgacgtg atctgggcca tcaccacccg catggacccc   1260
aagcgcgaca cggtcatgat cgacaacacg cccatcgatt acctcgattt tgcctctccg   1320
gtgtctggat tgggatcaaa aatgggcctg gatgccacta acaaatggcc aggggaaacc   1380
acccgcgaat ggggcagggc gatcgtcaag gacgaagcca ccacgcgccg ggtggacgag   1440
atctggactc agttgggaat agactga                                       1467
```

<210> SEQ ID NO 289
<211> LENGTH: 1497
<212> TYPE: DNA
<213> ORGANISM: Yersinia pseudotuberculosis

<400> SEQUENCE: 289

```
atgatcagca tgaaataccg tgacttacgt gacttcctct cattactgga acagaggggg     60
gaacttaaac gcattagcca gcccattgat ccttatttgg aaatgacaga aattgccgat    120
cgcacgttac gtgctggtgg gcctgcgtta ctttttgaga accctaaagg ttacagcatg    180
cccgtgttgt gtaatctgtt tggcaccgct aagcgagtcg ccatggggat ggggcaagaa    240
gatgtcagcg ccctgcgaga tgttggtaaa ttattggcct tcctgaaaga acccgatccc    300
ccaaaaggtt tccgtgactt atttgataag ctgccaaaat ttaagcaggt attgaatatg    360
ccaacgaaac gcttgaactc ggccccgtgt caggagcaag tttggcaagg tgaggatgtt    420
gatttaagtc gcatccctgt gatgcactgc tggccagaag atgccgcacc actagtctct    480
tggggggttga ctattacacg tggtccccac aaagaacggc agaatctagg catctatcgc    540
cagcaggtat tgggtaaaaa caaattaatt atgcgttggc tatcgcatcg tggtggtgcg    600
ctggattatc aggagtggtg tgaggcacac cctggtgaac gttttccggt cgctgtcgcc    660
ttgggagcag accctgctac gatcttagcc gcagtgaccc cggtaccaga cacgctgtct    720
gaatatgcct ttgccggctt gttacgcggc cataaaacgg aagtggtgaa gtgtctttcc    780
aatgaccttg aagttcctgc aagtgcagaa attgtattgg aaggatatat cgaacaaggt    840
gatatggctc cggaaggtcc ttatggtgat catacgggct attacaatga aatagataat    900
ttccccgtgt ttaccgtcac gcatattaca cagcgccaag acgcaattta tcattcaacc    960
tatacgggcc gaccaccgga tgaacctgcg gtaatggggg tggcactgaa cgaagtcttt   1020
gtacctattt tgcaaaagca attcccggaa attgttgatt tctacttgcc accagaaggg   1080
tgctcatacc ggttggcggt ggtaaccatc aagaaacaat atgcaggcca tgccaaacgc   1140
gtgatgatgg gagtatggtc gtttttacgc cagtttatgt ataccaagtt tgttattgtt   1200
tgtgatgacg atattaatgc tcgtgattgg aatgatgtaa tttgggcgat caccacccgg   1260
atggacccat cccgcgatac ggtgttaatt gaaaatacac cgatagatta tttggatttc   1320
gcctcaccgg tttccggttt gggatcgaaa atggggctgg atgccaccaa caaatggcca   1380
gcagagactc cgcgtgaatg gggcgtccaa attaagatgg acgaagacgt ccgtgcccgt   1440
```

-continued attgatgctc tgtgggatga gctggccatt ttcagtgaca aagacgcgaa acgctaa 1497

<210> SEQ ID NO 290
<211> LENGTH: 1485
<212> TYPE: DNA
<213> ORGANISM: Neisseria meningitidis serogroup B

<400> SEQUENCE: 290
atgaatatga aatacaaaga cctgcgcgac ttcatcgcca tgctcgagca gcagggcaaa 60
ctcaagcgcg tcgcacaccc catttccccg tatttggaaa tgaccgaaat cgccgaccgc 120
gtgctgcgtg ccgaagggcc ggcgttgctg tttgaaaacc cgattaagcc cgacggtacg 180
cgctacggtt atcccgtgtt ggcaaacctg ttcggcacgc ccgaacgtgt ggcgatgggc 240
atgggcgcgg acagcgtgtc caagctgcgt gaaattgggc agacgctggc gtatttgaaa 300
gaacccgaac cgcccaaagg catcaaagat gcgttttcca aactgccgct gctgaaagac 360
atttggagca tggcgccgaa cgtggtgaaa aacgcgccgt gtcaggaaat cgtgtgggaa 420
ggcgaagacg ttgatttgta tcaacttccg attcagcatt gctggccgga agacgttgcg 480
ccgctggtaa cgtggggctt gaccgtcacg cgcgggccgc acaaaaaacg ccaaaatctc 540
ggcatttacc gccaacaact catcggcaaa aacaagctga ttatgcgttg gctgtcgcat 600
cgcggcggcg cgttggatta tcaggagttc cgcaaactca atcccgatac gccgtatccc 660
gtcgccgtcg tactcggctg cgacccgcc accattttgg gcgcggtaac gcctgttccc 720
gataccttga gcgaatacca gtttgccgga ctgctgcgcg gttcgcggac ggagctggtg 780
aaatgtatcg gcaacgattt gcaagtgcct gcccgcgcag aaatcgtgtt ggaaggcgtc 840
atccatccga acgaaaccgc gttggaaggc ccgtacggcg accacaccgg ctattacaac 900
gagcaggatt atttccctgt gtttacggtc gaacgcatca ccatgcgcga aaacccgatt 960
taccattcga cctacacggg caaaccgccc gatgaacccg ccgttttggg cgtggcgttg 1020
aacgaagtgt tcgtaccgct tttgcaaaag cagttccccg aaatcaccga tttctacctg 1080
ccgcccgaag gctgctccta ccgcatggcg gtggtgagca tgaaaaaaca gtacgccgga 1140
cacgccaagc gcgtgatgat gggctgctgg tcgttcctgc gccagtttat gtataccaaa 1200
ttcatcatcg tggtggatga cgatgtgaac gtgcgcgact ggaaagaagt catctgggcg 1260
gtcaccacgc gcatggaccc cgtgcgcgac actgttttgg tagaaaacac gcccatcgat 1320
tatctcgact tcgccagccc cgtcagcgga ctcggcggca aaatgggttt ggatgcgacc 1380
aacaaatggc cgggagaaac cgaccgcgaa tggggacgcg tcatcaaaaa agaccctgcg 1440
gttacggcta agattgatgg gatttgggag gaattggggt tgtag 1485

<210> SEQ ID NO 291
<211> LENGTH: 1479
<212> TYPE: DNA
<213> ORGANISM: Neisseria gonorrhoeae

<400> SEQUENCE: 291
atgaaataca aagacctgcg cgacttcatc gctatgctcg agcagcaggg caagctcaag 60
cgcgtcgccc accccgtttc cccgcatttg gaaatgaccg aaattgccga ccgcgtgttg 120
cgcgccgaag ggccggcgtt gttgtttgaa aacccggtta agcccgacgg tacgcgctat 180
gattatcccg tgttggcgaa cctgttcggc acccccgaac gtgtggcgat gggcatgggc 240
gcggacagcg tgtccaagct gcgcgaaatc gggcagacgc tggcgtattt gaaagaaccc 300
gaaccgccca aaggcatcaa agacgcgttt tccaaactgc cgctgttgaa agatatttgg 360

```
agcatggcgc cgaacgtggt gaaaaacgcg ccgtgtcagg aaatcgtgtg ggaaggagaa    420

gacgttgatt tgtatcagct tccgattcaa cattgctggc cggaagacgt tgcgccgctg    480

gtaacgtggg gcttgaccgt cacgcgcggg ccgcacaaaa aacgccaaaa tctcggcatt    540

taccgtcaac aactcatcgg caaaaacaag ctggttatgc gctggctgtc gcatcgcggc    600

ggcgcgttgg attatcagga attccgcaaa ctcaatcccg atacgccgta tcccgtcgcc    660

gtcgtactcg gttgcgaccc ctccaccatt ttgggcgcgg taacgcccgt tcccgatact    720

ttgagcgaat accagtttgc cggactgctg cgcggttcgc ggacggagct ggtgaaatgt    780

atcggcagcg atttgcaagt gcctgcccgt gctgaaattg tattggaagg cgtgattcat    840

ccaaacgaaa ccgcgttgga aggcccatac ggcgaccaca cgggctatta caacgagcag    900

ggccatttcc ctgtgtttac ggtcgaacgc atcaccatgc gcgaaaaccc gatttaccac    960

tctacctaca caggcaaacc gcccgacgaa cctgccgttt tgggcgtggc gttgaacgaa   1020

gtgttcgtac cgcttttgca aaagcagttc tccgaaatca ccgatttcta cctgccgccc   1080

gaaggctgtt cctaccgcat ggcggtggtc agcatgaaaa aacagtacgc cggacacgcc   1140

aagcgcgtga tgacgggctg ctggtcgttc ctgcgccagt ttatgtacac caaattcatc   1200

atcgtggtgg atgacgatgt aaacgtgcgc gactggaaag aagtcatctg ggcggtaacc   1260

acgcgcatgg accccgtccg cgacaccgtt ttggtggaaa acacgcccat cgactacctc   1320

gacttcgcca gccccgtcag cggactcggc ggcaaaatgg gtttggatgc gaccagcaaa   1380

tggccgggag aaaccgaccg cgaatgggga cgggtaatca aaaaagaccc tgcggttacg   1440

gttaaaattg atgggatttg ggggaaattg gggttgtag                          1479
```

<210> SEQ ID NO 292
<211> LENGTH: 1497
<212> TYPE: DNA
<213> ORGANISM: Yersinia pestis

<400> SEQUENCE: 292

```
atgatcagca tgaaataccg tgacttacgt gacttcctct cattactgga acagaggggg     60

gaacttaaac gcattagcca gcccattgat ccttatttgg aaatgacaga aattgccgat    120

cgcacgttac gtgctggtgg gcctgcgtta ctttttgaga accctaaagg ttacagcatg    180

cccgtgttgt gtaatctgtt tggcaccgct aagcgagtcg ccatggggat ggggcaagaa    240

gatgtcagcg ccctgcgaga tgttggtaaa ttattggcct tcctgaaaga acccgatccc    300

ccaaaaggtt tccgtgactt atttgataag ctgccaaaat ttaagcaggt attgaatatg    360

ccaacgaaac gcttgaactc ggccccgtgt caggagcaag tttggcaagg tgaggatgtt    420

gatttaagtc gcatccctgt gatgcactgc tggccagaag atgccgcacc actagtctct    480

tgggggttga ctattacacg tggtccccac aaagaacggc agaatctagg catctatcgc    540

cagcaggtat tgggtaaaaa caaattaatt atgcgttggc tatcgcatcg tggtggtgcg    600

ctggattatc aggagtggtg tgaggcacac cctggtgaac gttttccggt cgctgtcgcc    660

ttgggagcag accctgctac gatcttagcc gcagtgaccc cggtaccaga cacgctgtct    720

gaatatgcct ttgccggctt gttacgcggc cataaaacgg aagtggtgaa gtgtctttcc    780

aatgaccttg aagttcctgc aagtgcagaa attgtattgg aaggatatat cgaacaaggt    840

gatatggctc cggaaggtcc ttatggtgat catacgggct attacaatga aatagataat    900

ttccccgtgt ttaccgtcac gcatattaca cagcgccaag acgcaattta tcattcaacc    960
```

-continued

```
tatacgggcc gaccaccgga tgaacctgcg gtaatggggg tggcactgaa cgaagtcttt   1020

gtacctattt tgcaaaagca attcccggaa attgttgatt tctacttgcc accagaaggg   1080

tgctcatacc ggttggcggt ggtaaccatc aagaaacaat atgcaggcca tgccaaacgc   1140

gtgatgatgg gaatatggtc gtttttacgc cagtttatgt ataccaagtt tgttattgtt   1200

tgtgatgacg atattaatgc tcgtgattgg aatgatgtaa tttgggcgat caccacccgg   1260

atggacccat cccgcgatac ggtgttaatt gaaaatacac cgatagatta tttggatttc   1320

gcctcaccgg tttccggttt gggatcgaaa atggggctgg atgccaccaa caaatggcca   1380

gcagagactc cgcgtgaatg gggcgtcca attaagatgg acgaagacgt ccgtgcccgt    1440

attgatgctc tgtgggatga gctggccatt ttcagtgaca aagacgcgaa acgctaa      1497
```

<210> SEQ ID NO 293
<211> LENGTH: 1653
<212> TYPE: DNA
<213> ORGANISM: Pseudomonas putida

<400> SEQUENCE: 293

```
ttgattgggg ccgccttgcg gcccttcgcg ggcaagcccg ctcctgcaca ggtcattgcg     60

gcccttgtag gagcgggctt ccgcgaaggg atgcaaagcg gccccaatgc attttcaccc    120

ccaaacaagg cccgaacggc gctacactct gcaccccgac cgatacggcc aacacgaggc    180

tcctgcatgc agtatcgcga cttgcgcgac ttcattcgtg gcctggaaca gcgcggcgag    240

ctcaagcgca tccaggtacc gatctccccc gtcctggaaa tgaccgaggt ctgcgaccgc    300

accctgcgcg ccaagggccc ggcattgttg ttcgaaaagc ccaccggctt cgacatccca    360

gtgctgggca acctgttcgg taccccggag cgggtggcca tgggcatggg cgccgagtcg    420

gtcagcgaac tgcgggaaat cggcaagctg ctggccttcc tcaaggagcc tgagccgccc    480

aagggcctga aggacgcctg gtcgaagctg ccgatcttca agaaggtcgt gtcgatggcg    540

ccaaaagtgg tcaaggacgc ggtgtgccag gaagtggtgg tcgagggtga cgatgtcgac    600

cttggcacgc tgccgattca gcactgctgg cctggcgacg tggcgccgct gattacctgg    660

ggcctcaccg tgacccgtgg cccgaacaag gaccgccaga acctgggcat ctaccgccag    720

caggtgatcg gccgcaacaa ggtgatcatg cgctggctca gccatcgtgg cggcgccctc    780

gattaccgag agtggtgcga gaagaacccc ggccagccgt ttccggtcgc cgtggccctg    840

ggcgctgacc cagcgaccat tctcggcgcg gtgaccccgg tcccggacac cctttccgag    900

tacgccttcg ccggcctgct gcgaggcaat cgcaccgagc tggtcaagtg ccgtggcagc    960

aacctgcagg taccggcaac cgccgagatc attctggaag ggtgatcca cccaggcgaa    1020

atggccccgg aaggccctta cggcgatcac acgggctact acaacgaagt ggacagtttc   1080

ccggtgttca ccgttgagcg catcacccac cggcaaaaac cgatctacca cagcacctac   1140

accggccggc cgccagatga gccggccatt ctcggcgtgg cgctgaacga agtgttcgtg   1200

ccgatcctgc agaagcagtt cccggaaatc accgacttct acctgccgcc ggaaggctgc   1260

tcgtaccgca tggcggtggt gaccatgaag aaacagtacc caggccacgc caagcgcgta   1320

atgctgggtg tgtggtcgtt cctgcgacag ttcatgtaca ccaagttcgt tattgtcacc   1380

gatgacgata tcaacgctcg tgactggaac gatgtgatct gggccattac cacgcgcatg   1440

gaccccaagc gtgatacggt aatgattgac aataccccga tcgactacct ggactttgcg   1500

tcaccggtgt cggggctggg ttcgaagatg ggcctggacg ctacgcacaa gtggccgggc   1560

gagactacac gcgaatgggg ccgggtcatc gtcaaggatg aggccgtcac ccgccgtatc   1620
```

-continued gatgagctgt gggatcagtt gggaatagat tga 1653

<210> SEQ ID NO 294
<211> LENGTH: 587
<212> TYPE: DNA
<213> ORGANISM: Serratia marcescens

<400> SEQUENCE: 294
cagacgccca tcatcacgcg tttcgcatgg ccggcgtact gttttttcat ggtcactacc 60
gccaggcggt aagagcaccc ttccggcggc agatagaaat cgacgatttc cgggaactgc 120
ttttgcagga tcggtacgaa cacttcattc agcgccacgc ccaggatcgc cggctcatcc 180
ggcgggcggc cggtgtaggt cgagtggtag atcgcgttgc ggcgctgggt gatgtgagta 240
acggtgaaca ccgggaactg gtcgatttca ttgtagtaac cggtgtggtc gccgtagggg 300
ccttccggcg ccatttcacc cggctcgata tagccttcaa gcacgatttc ggcgctggcg 360
ggcacttcca gatcgttgga aaggcacttg accacttcgg ttttgttgcc gcgcagcaac 420
ccggcaaagg cgtattcgga caaggtatca ggcaccggcg tgaccgcacc gaggatggta 480
gcaggatcgg cgcccagcgc caccgcaacc gggaaacgct cgcccgggtg cgcctggcac 540
cactcctgat aatccagcgc gccgccgcga tgcgacagcc aacgcat 587

<210> SEQ ID NO 295
<211> LENGTH: 1560
<212> TYPE: DNA
<213> ORGANISM: Burkholderia mallei

<400> SEQUENCE: 295
atgaaataca gagatttacg cgatttcatc catggcctcg agcagcgcgg cgagttgcgg 60
cgcgtcaccc agcccgtatc gcccgtcctc gaaatgaccg aactctgcga ccgcgtgctg 120
cgcgcgggcg gccccgcact cctgttcgac gcgccggccg gccaccggtt tccggtgctc 180
ggcaatctgt tcggcacgcc gcggcgcgtc gcgctcggca tgggcgtcga cgccgacgac 240
gaagcggcgc tcgcgtcgct gcgcgacatc ggccgcctgc tgtccgcgct caaggagccg 300
gacccgccga agcgcctgaa agacgcgggc aagttgctgt cgctcgcgaa ggccgtgtgg 360
gacatgggcc cgaagacggt ctccgcgccg ccgtgccagg agatcgtctg ggaaggcgac 420
gacgtcgatc tgcacaagct gccgatccag acctgctggc cgggcgacgc cgggccgctg 480
ctcacgtggg gcctgaccgt cacgcgcggg ccgaacaaga cgcgccagaa tctgggcatc 540
taccggcagc aactgatcgg acgcaacaaa ctgatcatgc gctggctcgc gcatcgcggc 600
ggcgcgctcg atttccgcga attcgcgctg aagcatccgg gccagcccta tcccgtcgcc 660
gtcgtgctcg gcgccgatcc ggcgacgatg ctcggggccg tcacgcccgt gcccgattcg 720
ctgtccgaat accagttcgc gggcctgctg cgcggcgcgc gcaccgagct cgcgaaatgc 780
gtgacgcccg gcgtcgacgc gctgcaggtg ccggcgcgcg cggaaatcgt gctcgaaggc 840
ttcatccacc cgcagcaagg cgcgcccgcg ccggcgcccg aaggcgcgcc gccgcggccg 900
gccgcgggcg cggcggccgg ctacgagcat gcgctcgagg gcccgtacgg cgatcacacc 960
ggctactaca acgagcagga atggtttccg gtcttcacgg tcgagcggat cacgatgcgc 1020
cgcgatgcga tctaccactc gacgtacacc ggcaagccgc ccgacgagcc ggccgtgctc 1080
ggcgtcgcgc tgaacgaagt gttcgtgccg ctgctgcaga agcagttcgc cgagatcacc 1140
gatttctatc tgccgcccga gggttgcagc taccggatgg cgatcgtcca gatgaagaag 1200

-continued

```
agttacgcgg gacacgcgaa gcgggtgatg ttcggcgtct ggagcttcct gcggcagttc   1260

atgtatacga agttcatcgt ggtcgtcgac gaggacgtga acgtgcgcga ctggaaggaa   1320

gtgatctggg cgatcacgac gcgcgtcgat ccggcgcgcg acacggtgct cgtcgagaac   1380

acgccgatcg actatctcga cttcgcgtcg cccgtcgccg gcctcggctc gaagatgggg   1440

ctcgatgcga ccaacaagtg gccgggcgaa acccagcgcg aatggggccg gccgatcgag   1500

atggacgccg ccgtgaaggc gcgcgtcgat cgtctgtgga cggagatcgg cctatcgtga   1560
```

<210> SEQ ID NO 296
<211> LENGTH: 1560
<212> TYPE: DNA
<213> ORGANISM: Burkholderia pseudomallei

<400> SEQUENCE: 296

```
atgaaataca aagatttacg cgatttcatc catggcctcg agcagcgcgg cgagttgcgg     60

cgcgtcaccc agcccgtatc gcccgtcctc gaaatgaccg aactctgcga ccgcgtgctg    120

cgcgcgggcg gccccgcgct cctgttcgac gcgccggccg gccaccggtt tccggtgctc    180

ggcaatctgt tcggcacgcc gcggcgcgtc gcgctcggca tgggcgtcga cgccgacgac    240

gaagcggcgc tcgcgtcgct gcgcgacatc ggccgcctgc tgtccgcgct caaggagccg    300

gacccgccga agcgcctgaa ggacgcgggc aagttgctgt cgctcgcgaa ggccgtgtgg    360

gacatgagcc cgaagacggt ctccgcgccg ccgtgccagg agatcgtctg ggaaggcgac    420

gacgtcgatc tgcacaagct gccgatccag acctgctggc cgggcgacgc cgggccgctg    480

ctcacgtggg gcctgaccgt cacgcgcggg ccgaacaaga cgcgccagaa tctgggcatc    540

taccggcagc aactgatcgg acgcaacaaa ctgatcatgc gctggctcgc gcatcgcggc    600

ggcgcgctcg atttccgcga attcgcgctg aagcatccgg gccagcccta tcccgtcgcc    660

gtcgtgctcg gcgccgatcc ggcgacgatg ctcggggccg tcacgcccgt gcccgattcg    720

ctgtccgaat accagttcgc gggcctgctg cgcggcgcgc gcaccgaact cgcgaaatgc    780

gtgacgcccg gcgtcgacgc gctgcaggtg ccggcgcgcg cggaaatcgt gctcgaaggc    840

ttcatccacc cgcagcaagg cgcgcccgcg ccggcgcccg aaggcgcgcc gccgcggccg    900

gccgcgggcg cggcggccgg ctacgagcat gcgctcgagg gcccgtacgg cgatcacacc    960

ggctactaca acgagcagga atggtttccg gtcttcacgg tcgagcggat cacgatgcgc   1020

cgcgatgcga tctaccactc gacgtacacc ggcaagccgc ccgacgagcc ggccgtgctc   1080

ggcgtcgcgc tgaacgaagt gttcgtgccg ctgctgcaga agcagttcgc cgagatcacc   1140

gatttctatc tgccgcccga gggttgcagc taccggatgg cgatcgtcca gatgaagaag   1200

agttacgcgg gacacgcgaa gcgggtgatg ttcggcgtct ggagcttcct gcggcagttc   1260

atgtatacga agttcatcgt ggtcgtcgac gaggacgtga acgtgcgcga ctggaaggaa   1320

gtgatctggg cgatcacgac gcgcgtcgat ccggcgcgcg acacggtgct cgtcgagaac   1380

acgccgatcg actatctcga cttcgcttcg cccgtcgccg gcctcggctc gaagatgggg   1440

ctcgatgcga ccaacaagtg gccgggcgaa acccagcgcg aatggggccg gccgatcgag   1500

atggacgccg ccgtgaaggc gcgcgtcgat cgtctgtgga cggagatcgg cctgtcgtga   1560
```

<210> SEQ ID NO 297
<211> LENGTH: 1545
<212> TYPE: DNA
<213> ORGANISM: Bordetella parapertussis

<400> SEQUENCE: 297

-continued

```
ttgaagtatc gcgacctccg agattttctt gcccagcttg aacgccaggg cgaactcaaa     60
cgcatcaccg cgccggtctc gacgcggctg gaaatgaccg agattgccga ccgggtgctg    120
cgcgccggcg gcccggccct gctgttcgag aacgcccgcc acaacgacgc gccggccgac    180
atgccggtgc tggccaacct gttcggcacg ccgcggcggg tcgcctgggg catgggggcc    240
gacgacgtcg gcgccctgcg cgaaaccggc gaactgctgg cctccctgcg cgagcccgaa    300
gcgcccaagg gcctgcgcga cgcgctggcc aaggtgtcca tgctgaaagc cgccctgtgg    360
gacatgagcc ccaagaccgt gcgcagcgcc gcctgccagg aaatcgtctg ggaaggcgcc    420
gacgtcgacc tgggccgcct gcccatccag acctgctggc cgggcgatgt ggcgcccctg    480
ctcgcctggg gcctggtgat cacgcgcggg ccgaacgccc ggcggcagaa cctgggtatc    540
taccgccagc agccgctggg gccgaacaag ctgatcatgc gctggctgtc gcaccgcggc    600
ggcgcgctgg acttccgcga ccacgcccag gcccacccgg gcaagtcgtt tcccatcgcc    660
gtggcgctgg gtgccgaccc ggccaccatc ctggacgcgg tcacgccggt gccggacacg    720
ctgtccgaat accagttcgc cgggctgctg cgcggctcgc gcaccgaggt cgtcaaggcg    780
ctgggcagcg acctgtcggt gccggcctcg gccgagatcg tgctcgaggg ccacctgctg    840
ccggccgacg atccgcgcgc cgtcgctgcc gcggtgcccg agggcgccaa cccgcccccg    900
gccaccggct acgaaatggc cctcgaaggc ccctatggcg accataccgg ctactacaac    960
gagcaggact ggttcccggt gttcacggtg gaccgcatca ccatgcggcg caaccccatc   1020
taccactcca cctataccgg caagccgccc gacgagccgg ccgtgctggg cgtggcgctg   1080
aacgaggtat tcgtgccgct gctgcgccgc cagctgcccg aaatcgtcga tttctacctg   1140
cccccggaag gctgcagcta ccgcctggcg gtggtgtcga tccgcaagca gtacgccggc   1200
cacgccaagc gcgtgatgtt cggcctgtgg agcgtgctgc ggcagttcat gtacaccaag   1260
ttcatcgtgg tggtcgacga agacatcgac ccgcgcgact ggaccgaagt ggtctgggcc   1320
atgaccacgc gcatggaccc cgtgcgcgac acggtgctgg tcgagaacac gccgatcgat   1380
tacctcgatt tcgcctcgcc ggtgtccggc ctgggcggca agatggggct ggacgccacc   1440
aacaagtggc cgggcgaaac cagccgcgaa tggggcacgc ccatacacat ggacgaggcg   1500
gtcaagcgcc gggtggatgc catgtgggac acgctgggac tgtag                   1545
```

<210> SEQ ID NO 298
<211> LENGTH: 1545
<212> TYPE: DNA
<213> ORGANISM: Bordetella bronchiseptica

<400> SEQUENCE: 298

```
ttgaagtatc gcgacctccg agattttctt gcccagcttg aacgccaggg cgaactcaaa     60
cgcatcaccg cgccggtctc gacgcggctg gaaatgaccg agattgccga ccgggtgctg    120
cgcgccggcg gcccggccct gctgttcgag aacgcccgcc acaacgacgc gccggccgac    180
atgccggtgc tggccaacct gttcggcacg ccgcggcggg tcgcctgggg catgggggcc    240
gacgacgtcg gcgccctgcg cgaaaccggc gaactgctgg cctccctgcg cgagcccgaa    300
gcgcccaagg gcctgcgcga cgcgctggcc aaggtgtcca tgctgaaagc cgccctgtgg    360
gacatgagcc ccaagaccgt gcgcagcgcc gcctgccagg aaatcgtctg ggaaggcgcc    420
gacgtcgacc tgggccgcct gcccatccag acctgctggc cgggcgatgt ggcgcccctg    480
ctcgcctggg gcctggtgat cacgcgcggg ccgaacgccc ggcggcagaa cctgggtatc    540
```

-continued

```
taccgccagc agccgctggg gccgaacaag ctgatcatgc gctggctgtc gcaccgcggc    600

ggcgcgctgg acttccgcga ccacgcccag gcccacccgg gcaagccgtt tcccatcgcc    660

gtggcgctgg gtgccgaccc ggccaccatc ctgggcgcgg tcacgccggt gccggacacg    720

ctgtccgaat accagttcgc cgggctgctg cgcggctcgc gcaccgaggt cgtcaaggcg    780

ctgggcagcg acctgtcggt gccggcctcg gccgagatcg tgctcgaggg ccacctgctg    840

ccggccgacg atccgcgcgc cgtcgctgcc gcggtgcccg agggcgccaa cccgcccccg    900

gccaccggct acgaaatggc cctcgaaggc ccctatggcg accataccgg ctactacaac    960

gagcaggact ggttcccggt gttcacggtg gaccgcatca ccatgcggcg caaccccatc   1020

taccactcca cctataccgg caagccgccc gacgagccgg ccgtgctggg cgtggcgctg   1080

aacgaggtat tcgtgccgct gctgcgccgc cagctgcccg aaatcgtcga tttctacctg   1140

cccccggaag gctgcagcta ccgcctggcg gtggtgtcga tccgcaagca gtacgccggc   1200

cacgccaagc gcgtgatgtt cggcctgtgg agcgtgctgc ggcagttcat gtacaccaag   1260

ttcatcgtgg tggtcgacga agacatcgac ccgcgcgact ggaccgaagt ggtctgggcc   1320

atgaccacgc gcatggaccc cgtgcgcgac acggtgctgg tcgagaacac gccgatcgat   1380

tacctcgatt tcgcctcgcc ggtgtccggc ctgggcggca agatggggct ggacgccacc   1440

aacaagtggc cgggcgaaac cagccgcgaa tggggcacgc ccatacacat ggacgaggcg   1500

gtcaagcgcc gggtggatgc catgtgggac acgctgggac tgtag                   1545
```

<210> SEQ ID NO 299
<211> LENGTH: 1560
<212> TYPE: DNA
<213> ORGANISM: Bordetella pertussis Tohama

<400> SEQUENCE: 299

```
ttgccgggat ctgccttgaa gtaccgcgac ctccgagatt ttcttgccca gctcgaacgc     60

cagggcgaac tcaaacgcat caccgcgccg gtctcgacgc ggctggaaat gaccgagatt    120

gccgaccggg tgctgcgcgc cggcggcccg gccctgctgt tcgagaacgc ccgccacaac    180

gacgcgccgg ccgacatgcc ggtgctggcc aacctgttcg gcacgccgcg gcgggtcgcc    240

tggggcatgg gggccgacga cgtcggcgcc ctgcgcgaaa ccggcgaact gctggcctcc    300

ctgcgcgagc ccgaagcgcc caagggcctg cgcgacgcgc tggccaaggt gtccatgctg    360

aaagccgccc tgtgggacat gagccccaag accgtgcgca gcgccgcctg ccaggaaatc    420

gtctgggaag gcgccgacgt cgagctgagc cgcctgccca tccagacctg ctggccgggc    480

gacgtggcgc ccctgctcgc ctggggcctg gtgatcacgc gcgggccgaa cgcccggcgg    540

cagaacctgg gcatctaccg ccagcagccg ctggggccga acaagctgat catgcgctgg    600

ctgtcgcacc ggggcggcgc gctggacttc cgcgaccacg cccaggccca cccgggcaag    660

ccgtttccca tcaccgtggc gctgggcgcc gacccggcca ccatcctggg cgcggtcacg    720

ccggtgccgg acacgctgtc cgaataccag ttcgccgggc tgctgcgcgg ctcgcgcacc    780

gaggtcgtca aggcgctggg cagcgacctg tcggtgccgg cctcggccga gatcgtgctc    840

gagggccacc tgctgccggc cgacgatccg cgcgccgtcg ctgccgtggt gcccgagggc    900

gccaacccgc ccccggccac cggctacgaa atggcgctcg aaggccccta tggcgaccat    960

accggctact acaacgagca ggactggttc ccggtgttca cggtggaccg catcaccatg   1020

cggcgcaacc ccatctacca ctccacctat accggcaagc cgcccgacga gccggccgtg   1080

ctgggcgtgg cgctgaacga ggtattcgtg ccgctgctgc gccgccagct gcccgagatc   1140
```

-continued

```
gtcgatttct acctgccccc ggaaggctgc agctaccgcc tggcggtggt gtcgatccgc   1200

aagcagtacg ccggccacgc caagcgcgtg atgttcggcc tgtggagcgt gctgcggcag   1260

ttcatgtaca ccaagttcat cgtggtggtc gacgaagaca tcgacccgcg cgactggacc   1320

gaagtggtct gggccatgac cacgcgcatg gaccccgtgc gcgacacggt gctggtcgag   1380

aacgcgccta tcgattacct ggatttcgcc tcgccggtgt ccggcctggg cggcaagatg   1440

gggctggacg ccaccaacaa gtggccgggc gaaaccagcc gcgaatgggg cacgcccata   1500

cacatggacg aagcggtcaa gcgccgggtg gatgccatgt gggacacgct gggactgtag   1560
```

<210> SEQ ID NO 300
<211> LENGTH: 1467
<212> TYPE: DNA
<213> ORGANISM: Legionella pneumophila subsp. pneumophila str.
      Philadelphia

<400> SEQUENCE: 300

```
atgaagtatt cagatctgag agatttcata gcccaacttg aatcacgtga attattaaaa     60

cgtattgatt atcctgtatc acctcatctt gagatgaccc tagtcagcga taaagtgttg    120

cgctcaggag ggccagccct tctgtttacc aatacccccca attacaacat gcctgtactg    180

accaatcttt ttggtacggt agagcgcgtg gctttgggaa tgggtgagga atcaatagtg    240

gctttgaggg agattggaaa attattggct gctttaaagg agcccgatcc tcccaaaggc    300

ttcaaagacg cttttagcaa gttgccctta ttgaaacaag cgctgaatat ggcacccaaa    360

tatgtcagtg gagccgagtg ccagactcat gtgtgggaaa aggatgaagt ggatttaacc    420

ttattgccca tccaaacgtg ttggcccgga gatgttgctc ctctaattac ctggggtttg    480

gttactactc gtggcccaca ccagtccaga gaaaacatgg gcatctatcg ccagcaacta    540

ttaagtaaaa acaaattgat catgcgctgg ttatctcacc gcggaggtgc tttggattac    600

caggcctggc aacaagaata tcccaaagag cgtttccctg ttgcggtgac tttaggcgct    660

gatccagcca ccatactggc agcagttact cccgttcctg atactttgtc tgaatacgct    720

tttgcgggct tgcttagagg acaacgaact cggttgactc gatgcattgg caatgatttg    780

catgttccag ccagcgcaga aattgttttg gaaggttatc tggagccagg aaatgaggcg    840

cccgaagggc cttatggcga tcacaccggt tattataatg aagtccaatc ttttcctgtt    900

tttacggtag agcgtattac tcatcgcgat aaacctattt accacagtac ttataccgga    960

agaccgccag atgagccagc cattttggga gttgccttaa atgaagtgtt cattcccttg   1020

ttacaaaaac aattcccaga gattgtggat ttttatttgc cgccagaagg atgctcttat   1080

cgtttggctg tagtcactat aaaaaagcaa tatccaggac atgctaaacg tattatgatg   1140

gctgtttggt ctttcttgcg ccagtttatg tataccaagt tcgtcattgt ttgtgatgat   1200

gatgtggacg cgcgcaattg gcaagatgtc atatgggcaa tgaccacacg catggatccg   1260

tcccgcgata cagtcatggt agaaaataca cccattgatt atctggactt cgcttcccca   1320

gtttcaggat tgggttccaa gatgggtatg gatgctacca gtaaatggcc aggagaaaca   1380

caaagagaat ggggtaaacc aattacgatg gatgaagatg tgcttaatag agtaaatggt   1440

tattggtcct tattaggatt aaaataa                                        1467
```

<210> SEQ ID NO 301
<211> LENGTH: 598
<212> TYPE: DNA
<213> ORGANISM: Klebsiella pneumoniae -continued

<400> SEQUENCE: 301

```
aatggcgcag gaacgaccag acgcccatca ttacgcgctt ggcatgtccc gcgtactgtt     60
ttttcatggt caccaccgcc aggcgatagg agcacccttc cggcggcaga tagaaatcaa    120
cgatttccgg gaactgcttt tgcaggatcg gcacaaagac ttcattcagc gccacgccca    180
gcaccgctgg ctcatcgggc ggtcggccgg tataggtaga atgataaatc gcgtcttcac    240
gctgggtaat atgggttacc gtaaataccg ggaagctgtc cacttcatta tagtaaccgg    300
tgtgatcgcc atacgggcct tccggcgcca tttcaccggc ctcaatgtag ccttcaagca    360
caatttccgc gctggccggc acttcaaggt cattggaaac gcacttaacc acttcggtct    420
tggtgccgcg cagcaggcct gcgaaagcat attccgacag ggtatcgggc accggcgtca    480
ccgcgccaag aatggttgcc ggatcggcgc caagcgccac ggaaaccggg aagcgttcgc    540
ccggacgcgc cgcgcaccac tcctggaaat ccagcgcgcc gccgcgatga gacagcca      598
```

<210> SEQ ID NO 302
<211> LENGTH: 578
<212> TYPE: DNA
<213> ORGANISM: Serratia liquefasciens

<400> SEQUENCE: 302

```
cccatcatta cgcgtttagc atgaccagca tactgtttct tgatggtcac caccgccaga     60
cgataagaac agccttcggg cggcagatag aaatcgacaa tttccgggaa ctgcttttgc    120
agaatgggaa cgaagacttc gttcagcgcc acgcccagca ccgcaggctc atccggcgga    180
cggccggtgt aggtcgagtg gtaaatggca tcgcgacgct gggtgatgtg agtgatggta    240
aataccggga agtggtcgat ctcgttgtag taaccggtgt gatcgccata cgggccttcc    300
ggtgccattt cacccggttc aatgtagcct tccaacacga tttccgcgct ggccggcact    360
tccaaatcgc aggagaggca cttgaccact tcggttttgt tgccacgcag cagcccggca    420
aaagcatatt cagacagggt atccggtacc ggcgtcaccg cgccgaggat agtggcggga    480
tccgccccta atgccaccgc aaccgggaaa cgctcaccag ggtgcgcctg acaccattcc    540
tgataatcca acgcgccgcc acggtgggac agccaact                            578
```

<210> SEQ ID NO 303
<211> LENGTH: 1320
<212> TYPE: DNA
<213> ORGANISM: Brucella melitensis

<400> SEQUENCE: 303

```
cccgaagcac ccgaaacacc gatgacgatc cgcttcatat ccgtttgtcc ctgtcgaggc     60
cgagttcatc ccagatcgcg tccacacggg cgatggtttc ttcattcatg gccagaacct    120
tgccccattc gcggtccgtt tcaggaccga tcttgttggt ggcgtcaaga ccgagctttc    180
cgccaaggcc ggagcgtggc gaggcgaaat ccagataatc gaccggcgtg tcggaaagtg    240
tcaccacgtc gcggcttgca tcaaagcggg tggcaagcgc ccacatcaca tcgtcccagt    300
tgtgtacatc gatatcggga tcgacggcga taatgagctt ggtatagctg aactgcggca    360
gcatggacca aagccccatc atcacgcgcc gcgcctgccc cggataacgc ttgtcgatgg    420
aaaccaccat ggcgcggtag gaacaggcgg caggcggcag ccagagatcg gctatctcgg    480
gaaactgctt gcgcacgaca ggcacgaaaa gctggttcat cacctcgcca agccgcgaag    540
gctcgtccgg cgggcgctcc gtataggtgg aaagatagac cggcttcttg cgcatggtga    600
```

-continued

```
tcgccgtcac ctgcatgacg ggaaacgcct ccacgctgtt ataatagccg gtatggtccc    660

cataaggccc ttcgggcgcg gtttgtgtag cggaaacccg accttcaaga acgatttctg    720

cattggcggg caccatcagc ggcaccgtgc gcccctgcgt gacacacggc ctgcgcccgc    780

ccagaaggcc ggaaaatgca agctcgctca tgccttccgg cagcggcata actgcggcca    840

gaatggtcgc cgggtcaacg ccgatggcaa ttgcaaccgg catgtcctca ccgcgctttt    900

gccacatgcg atggtggcgc gcgccgccgc gatgcgcgag ccagcgcatg ataagccggt    960

tctctcccag tttctgcatc cggtaaatgc cgacattgac atcggaggga tcgtccggcg   1020

cgcgtgtgat aacgagcggc caggtgatga gcggcgcagg ctcgcccggc cagcaccatt   1080

ggatcggcag cgtgtcgaga ttgaccgatg cgccttccat cacaaggcca tgaaccggcg   1140

cccggctcac ctggcgcggg cgcatgttga gggctgcctt ggccatcggc agcttttccc   1200

atatttcacc ggccgaacgc ggcggcttcg gcgcacgcaa ttcggccagc atttcagcca   1260

gaagcggcaa ttcctccggc agacgcccaa gcccccaggc gatacgccgc tcggacccga   1320
```

<210> SEQ ID NO 304
<211> LENGTH: 1425
<212> TYPE: DNA
<213> ORGANISM: Haemophilus influenzae

<400> SEQUENCE: 304

```
ttagccgtga taacgcccta cgcctaattc atcttcttta cgtgtgcgat tcatcacttc     60

ttgtggagat tgcgcaatac gtaatcccat ttcatcttca gtacgcacca cttcgccacg    120

taacgaatta gtataaacat cagtgatttt cacatccaca aacttaccga tcatttctgg    180

agaaccttgg aaattaacaa tacgattcgt ttcagtacgt cccgtcaatt ccataatatc    240

tttcttcgat gggccttcaa ctaacacgcg ctgctctgtg ccaagcatac gacggctaaa    300

ttgtgccgct tgttgattaa tacgctcttg tagcacataa agacgctgtt tcttttcatc    360

ttccgtgaca tcatctggca tatctgctgc tggcgtacct ggtcgggctg agtacacaaa    420

actgaagctc atatcaaagt ttacttgtgc aatcaaattc atagtttgct caaaatcttc    480

cgccgtttca ccagggaaac caacaataaa gtcagagctg atttgaatat ctgggcgcac    540

agcacgaagt ttacgaataa tggatttata ttctaatgcg gtatgagcac gtttcatcat    600

tgttaataca cggtcagaac ctgcttgcac tggaagatgt aagaaactca ctaattcagg    660

cgtatcacga tacacatcaa taatatcatc ggtaaattct attggatgac tggttgtgaa    720

acgtaaacgg tcaataccat caattgatgc gacaagacga agcaactcag caaagctgca    780

aatttgacca tcatgcgttg gcccacgata agcatttaca ttttgaccaa gtagattgac    840

ctcacgcaca ccttgttccg caagttgcgc aatttcaaat agcacatcat ctacaggacg    900

gctaacttct tctccacgag tataaggcac aacacaaaaa gtacagtatt tattacagcc    960

ttccataatg gaaacaaatg ccgttgggcc ttctgcgcga ggttctggta agcggtcaaa   1020

tttctcaatt tcagggaaac ttacgtctac gacggaactt tttccaccac gaatttgatt   1080

aatcatttca ggcaagcgat gcaaagtttg cgggccaaaa ataatatcca cataaggcgc   1140

acgatggcga atatgttccc cttcttgaga ggctacacag ccgcccacac caatcactaa   1200

atttggatta tttttcttta attctttcca acgcccaagt tggtggaaca ctttttcttg   1260

tgctttttca cgaatagaac aggtatttaa taataatacg tctgcttctt caggtgcttc   1320

cgtgagttct aatccgtggg tgcttaataa aagatcagcc attttagatg aatcatattc   1380

attcatctgg cagccccaag ttttaatatg taatttttga gtcat                   1425
```

-continued

<210> SEQ ID NO 305
<211> LENGTH: 1425
<212> TYPE: DNA
<213> ORGANISM: Pasteurella multocida

<400> SEQUENCE: 305
ctacgcgtga taacgtccca cgccgagttc atcttcttta cgagtacgat taatcaccat 60
ttgtggcgat tgaacaacgc gaagtcccat ttgttcttca gttctaacga cttcaccacg 120
cagtgagtta gtaaacacat ccgtgatctt gatatcaaca aacttcccaa tcatatcagg 180
cgtgcccaca aaattgacga tacgattagt ttctgtacgc cctgtgagtt ccattaaatc 240
ttttttcgag ggtccttcca ctaacacgcg ctgttctgtg cctaacattg ctcgactaaa 300
ttgcgcggct tgattgttaa tgcgttgttg caacacatat aaacgttgtt tcttctcttc 360
ttctgtcaca tcatcaggca tatctgctgc tggcgtgcct ggacgtgctg aataaatgaa 420
gctgaaactc atatcaaaat ttacttgtgc aattaaattc atggtttgct cgaaatcttc 480
tgctgtttcg cccgggaaac cgacaataaa atctgagcta atttgaatct ctggacgcac 540
cgctcttaac ttccgaataa tcgatttata ttctaatgcc gtatgattgc gtttcatcat 600
agataacaca cgatcagaac cactttgtac aggtaagtgt aagaaactca ccaactctgg 660
cgtatcacgg tacacatcaa taatgtcatc agtgaactca attgggtgac tggtggtaaa 720
acgtaaacgg tcaataccat caatagcggc tactaaacgt aacaattccg caaaagtaca 780
aataccgtca tcatgagttg caccacgata agcgttcacg ttttgtccta ataaattcac 840
ttcacgcacg ccttgctctg ccaactgtgc aatttcaaat aatacatcat ccactggacg 900
actgacttct tcaccacgcg tataaggcac gacacagaat gagcaatatt tattacagcc 960
ttccataatg gatacgaaag cagttggacc ttctgcacgc ggttctggta aacggtcgaa 1020
tttttcaatt tctggaaaac tgacatcgac tactgagctt ttaccacctc tgatctgatt 1080
gatcatttca ggtaaacgat gtaaggtttg tggtccaaaa ataatatcga cataaggagc 1140
acgagtacga atgtgttctc cttcttgtga ggcaacacag cccccaacac cgataacgag 1200
tcccggctta tgtttcttta attctttcca acgtcctaat tgatggaaaa ctttttcttg 1260
tgctttttca cgaattgagc aagtgtttaa caataacaca tccgcttctt ccggaatttc 1320
tgttaactct aagccgtgag tactgtttaa gagatctgcc attttagatg aatcatattc 1380
attcatctga caaccccacg ttttaatatg taatttttgc gtcat 1425

<210> SEQ ID NO 306
<211> LENGTH: 1428
<212> TYPE: DNA
<213> ORGANISM: Haemophilus ducrei

<400> SEQUENCE: 306
ttacagattt actgcgtatt tgcctacacc taaatcatct tccttacggg tccgtgcaat 60
gacacttgat gctgattcaa caatacgtaa acccatttga tcttctgttc tgatcacttc 120
accgcgtaat gagtttgagt aaacatcggt gattttaata tctacgaatt tgccgatcat 180
atttggtgtg ccgatgaaat taactacacg attggtttct gtacgacccg ttaattccat 240
aatatctttt ttagatgggc cttcaaccaa aattcgttgt tcagtgccaa gcattaagcg 300
actaaattgc atcgcttgat ggttaattcg ttgttgtaag tgtgctaagc ggtctttttt 360
ctcattttca gacacatcat caggtaagtc tgatgcaggc gtacctggac gcgcagagta 420

-continued

```
gataaagcta aagctcatat caaaattgac ttgttcaata attttcattg tttgttcaaa    480

gtcttccgct gtttcgccag gaaagccaac aatgaaatct gagctaattt ggatatttgg    540

acgaaccgca cgtaatttac gaataatggc tttgtattct aatgcggtgt ggttacgttt    600

catcatggtt aaaacacgat cggcgccact ttggataggt aaatgcaaga agctgaccaa    660

ttctggagta tcacgataca cttcaataat gtcgtcggtg aattcaatgg ggtggcttgt    720

ggtataacgt aagcggtcaa taccatcaat ggcggcaact aaacgtaata attctgcaaa    780

agtgcaaatg ccaccatcaa aggtttcacc acggtaagca ttaacgtttt gacccagcaa    840

gttaacttca cgaacgcctt gctctgctaa ttgtgcgatt tcgaataaga catcatcaac    900

agggcgggaa acttcttcac cacgggtata aggcactaca cagaatgagc agtatttatt    960

acagccttcc ataattgata cgaaagcagt tggaccttct gctttgggtt ctggtaagcg   1020

gtcgaatttt tcaatttctg ggaaggagat atcgactact gcacgatcgc ctgatcggat   1080

ctggttgatc atttctggta agcggtgcaa tgtttgtggc ccaaatacta tatcaacaaa   1140

aggggcacgt tcacggatat gttcaccttc ttgtgaagca acacagccac caacgccaat   1200

aattaaatcg ggtttgtcct ttttccagtt tttccaacga ccaagttgtg aaaagacttt   1260

ttcttgtgct ttttcacgaa ttgagcaagt attcaataat aaaatatccg cttcttcagg   1320

tttatcggtt aattctaatc cgtgtgttga gtttaagaga tctgccattt ttgatgagtc   1380

atactcattc atttggcaac cccaagttgt gatatgtaat tttgccat                1428
```

```
<210> SEQ ID NO 307
<211> LENGTH: 1425
<212> TYPE: DNA
<213> ORGANISM: Vibrio parahaemolyticus

<400> SEQUENCE: 307
```

```
ttatggcgta aaagtagcta cacctagctc atcttcgcga cgtgttttcg ccatcatttg     60

tgttggagaa atcacactac gaaggtccat gtctttttct gtacgtacta gctcaccacg    120

tagcgagttt gcaaatacgt ccgtaatctt cacgtcaacg aactgaccaa ttaggtctgc    180

gctaccttca aagtttacta cacggttgtt ttctgtacga gcgcgcagtt ccattaggtt    240

tttcttagaa gggccttcaa ccagtacacg ctgctcagta gcaagcatta ggcgtgagta    300

acgcattgct tgtgcattga tggtttgttg cagctcgtat agacgctctt tcttcacttg    360

ctctggtata tcacaagggt aatctgccgc aggtgtacct ggacgaggtg agaagataaa    420

gctgaagctc atgtcaaagt ctacgtcttt gattagcttc attgtgtctt ggaagtcttt    480

gtctgtttca ccagggaaac caacaataaa gtcagaactg atttggatat caggacgcgc    540

tttacgtagt ttacggatga tcgacttgta ctcgatagct gtgtgaggac gcttcatcat    600

cgttagaata cggtcactac cactttgtac tggcaggtgt aggaaactca caagctccgg    660

ggtatcttcg taaaccgcga tgatgtcgtc tgtaaactct agcgggtggc tagtcgtgaa    720

acgaatacgg tcgataccat cgatagatgc aacgagacga agcagttcag caaaagagca    780

gatctcgccg tcgtgcatag ggccacggta tgcgtttacg ttttgaccta gtaggttaac    840

ttcacgtaca ccttgttccg ctagctgtgc aatctcgaat aacacgtcat ccattggacg    900

actaacttct tcaccacgag tgtatggtac aacgcagtaa gtgcagtatt ttgaacagcc    960

ttccatgata gaaacaaacg ccgtcgcacc ttctgcacgt ggctcaggta ggcggtcgaa   1020

cttttcaatc tctgggaacg aaatgtccat taccggtgca tcgtcagttt gagattgttt   1080

gatcatctca ggtaggcggt gcagagtttg agggccaaag atcacgtcaa cgtatggtgc   1140
```

-continued acgctcacgg atgtggtcac cttcttgtgt tgctacacaa ccacctacac cgataactac 1200
gccaggtttt ttatctttta gtgttttcca acggcctagc tggtggaaaa ctttctcttg 1260
cgctttttca cggatcgaac aggtgttaag tagaagtacg tctgcttcct ctggctcttc 1320
cgtcagctca tagccgtttg cagcattaag caggtcggcc atttttgatg aatcgtattc 1380
gttcatctgg cagccccagg ttttaattag cagtttctta ctcat 1425

<210> SEQ ID NO 308
<211> LENGTH: 1473
<212> TYPE: DNA
<213> ORGANISM: Yersinia pestis

<400> SEQUENCE: 308
gaatttacca atcatgtcgg gtgaaccctc aaagttcacg acgcggttgt tttccgtacg 60
cccggccagt tccatgacat ttttgcgaga ggtaccctcc accaaaacac gctgtactgt 120
ccctaccatc ttacggctaa tttccatcgc ctgttggcta atgcgttgtt gcaggatatg 180
tagccgctgt tttttctcct cttcggacac attgttgggt aaatcagccg ctggtgtgcc 240
gggacgcggg gagtaaataa agctgtagct ggtatcaaaa tgaatatctg cgaccagttt 300
catggtctgt tcaaaatcct gctgggtttc accagggaag ccgacaataa aatcagaact 360
tatctggata tcagggcgtg cttgacgcag tttgcggatg atggctttgt attccaaggc 420
ggtatgggca cgcttcatca tggtcaaaat acggtcagaa ccgctttgta ccggcaaatg 480
caggaagctc accaattcag gcgtatcgcg ataaacatca atgatatcgt cagtaaactc 540
aatggggtgg ctggtggtaa atcgtaccct atcgatacca tcaatcgccg caaccaaacg 600
caacagctcg gcaaaactac agatatcgcc atcgtaggtt gccccgcggt aggcgttaac 660
attctggccg agtaagttga cttcacgtac gccttgagcg gctaactggg cgatttcaaa 720
aagaatgtca tcgcttggac ggctgacttc ctcgcctcgg gtgtagggta cgacacagaa 780
tgtacaatat ttattgcagc cttccatgat cgaaacaaac gcagttgggc cttcagcccg 840
tggttctggc aaacggtcaa atttttcaat ttcgggaaaa ctgatatcca cgacagggct 900
attcgttcct tgcacgtggt taatcatttc cggtaaacga tgcagcgttt gtggcccgaa 960
gatgacatcg acacaggggg cgcgctggcg caattgttca ccttcctgtg acgccacgca 1020
accaccgacc ccaataatca actgcgggtt tttctctttc aataatttcc attgccctag 1080
caggctgaat actttttcct gtgctttttc ccggatagaa caggtattta gcagcagtaa 1140
atccgcttct tccgggatgg tggttaactg gtagccatgg gtactggcca agagatctgc 1200
cattttagat gaatcgtatt cattcatctg gcaaccccag gttttgatat gcagtttttt 1260
agtcatcggg ttattcatca tcaaaatcac ctcgttccgt gcggtactcc gttgtggtag 1320
ataatctccg ttgtagtaga gagtcgcaaa ggcttcgtcg ttagggagca ttgtagtcat 1380
ttgcctctgc gatgaccacc gcagaaccgt tgagttattc tgttgagtga taaaaaatcc 1440
gttacactgc ggttagacaa aaccttgcta atg 1473

<210> SEQ ID NO 309
<211> LENGTH: 1216
<212> TYPE: DNA
<213> ORGANISM: Vibrio cholerae

<400> SEQUENCE: 309
tcttcacttc ttccgacaga tcgcaaggat agtcagcggc gggtgtgcct ggacgaggtg 60

-continued

```
agaaaataaa gctaaagctc atgtcgaaat cgacatcgcg gatcagcttc atggtgtctt    120

ggaaatcttt gtcggtttcc cctgggaagc caacgataaa atcagagctg atttgaatat    180

ctgggcgtgc tttacgtagc ttacggatga tggatttgta ctcaatcgcc gtatgtggac    240

gcttcatcat agtcagaatg cgatcgctcc cactttgtac tggcaagtgc aggaagctca    300

ccagctcagg cgtgtcttcg tacactgcaa taatgtcatc ggtaaattcg agtgggtggc    360

tagtggtaaa gcggatacga tcgatgccgt caatggtggc gaccaaacgc agtaattcag    420

cgaaagagca aatgccgcca tcgtgagtgg caccacggta agcgttgacg ttttgaccca    480

gcaggttaac ttcacgcacc ccttgctcgg caagctgagc gatctcgaac aggacatcgt    540

ccataggacg gctgacttct tcaccgcgtg tgtaaggcac tacgcagtaa gtacagtatt    600

ttgagcagcc ttccatgata gaaacgaacg ccgttgggcc ttccgcacgt ggctcaggca    660

ggcggtcgaa tttttcaatc tcagggaaag agatatccat cacgggcgcg tcgctggttt    720

gcgattgttt aatcatttct ggcagacgat gcagcgtctg tgggccgaag atgacatcca    780

cataaggcgc acgatcgcga atcgagtcac cttcttgagt agcaacacag ccaccgacac    840

cgatcacgac acctggcttc ttgtctttca gggttttcca acgaccgagt tggtggaaga    900

ctttttcctg cgccttttca cgaatcgaac aggtgtttag gagtaaaacg tcagcttcct    960

cgggtatttc tgtcagctca tagccgtttg cagcattaag caggtcagcc attttcgatg   1020

aatcgtactc gttcatctgg cagccccaag ttttaattag cagtttctta ctcatctcac   1080

tttcgctcgt tcaatagttc ttcaatcatt tgagctgtag ctcacattct agccgccctc   1140

tcggcggtaa gcggcgtatt gtactgcttt aaaaaccgac tgactagtaa ttggcggaat   1200

tctcttgtaa cccttg                                                   1216
```

<210> SEQ ID NO 310
<211> LENGTH: 1424
<212> TYPE: DNA
<213> ORGANISM: Escherichia coli

<400> SEQUENCE: 310

```
ttacggctga taataaccca cgccaaggtc gttttctttg cgggtacggg caatcactga     60

ttccggtgtt tctgccacgc gcagacccat ttcatcttca gtacgcacca ctttaccgcg    120

cagagagttc gggtagacgt cggtaatttc tacatcgacg aatttaccga tcatatccgg    180

cgtgccttcg aagttgacca cgcggttatt ttccgtacgc ccggaaagct ccatgatgct    240

cttacgcgat gtaccttcta ccagaatacg ctgggtggtg ccgagcatcc ggcggctcca    300

cgccatcgct tgctgattaa tgcgctcttg cagaatatac agacgctgct tcttctcttc    360

ttccggaaca tcatcaacca tatcggcggc tggtgtaccc ggacgtgcag agaagataaa    420

gctgtagctc atgtcgaaat tgacgtcggc aatcagcttc atcgttttct cgaagtcttc    480

ggtggtttcg ccagggaagc caacgatgaa atcagaactg atctgaatat ctggacgcgc    540

cgcacgcagt ttacggatga tcgctttgta ctccagcgcc gtatgggtac ggcccatcag    600

gttcagaatg cgatcggaac cgctctgtac cggcagatgc aggaagctca ccagctccgg    660

cgtgtcgcga tacacttcga tgatacgtcg gtgaattcga tcggatggct ggtggtaaag    720

cgaatacgat cgatcccgtc gatcgcagca accagacgca gcagatcggc aaacgatccg    780

gtggtgccgt cgtagttttc accacgccag gcgttcacgt tctgaccgag caggttgact    840

tcacgcacgc cctgagccgc aagctgggca atctcaaaca gaatatcgtc ggacggacgg    900

cttacctctt caccacgggt gtaaggcacc acgcagtagg tgcaatattt attgcagcct    960
```

-continued

```
tccatgatgg agacaaacgc ggtcggccct tcggcgcgcg gttccggtag acggtcaaac   1020

ttctcgattt ccgggaagct gatatctaca accgggctgc ggtcgccacg cacggagttg   1080

atcatctccg gcagacggtg cagcgtttgc ggcccaaaaa taatatcgac atagtgggcg   1140

cgctggcgaa tgtgctcgcc ttcttgcgat gccacgcagc caccgacgcc gataatcagg   1200

tctggattct tctcttttaa cagtttccag cgacccaact gatggaagac tttttcctga   1260

gccttctcgc ggattgagca ggtgttcagc agcagcacat ccgcttcttc cgccacgtcg   1320

gtcagttgat agccgtgggt ggcatccagc agatcggcca tcttcgatga atcgtactcg   1380

ttcatctgac agccccaggt tttaatatgg agttttttgg tcat                    1424
```

<210> SEQ ID NO 311
<211> LENGTH: 1425
<212> TYPE: DNA
<213> ORGANISM: Escherichia coli

<400> SEQUENCE: 311

```
ttacggctga taataaccca cgccaaggtc gttttctttg cgagtacggg caatcaccga     60

ttctggtgtt tctgccacgc gcagacccat ttcatcttca gtacgcacca ctttaccgcg    120

cagagagttc gggtagacgt cggtaatttc tacatcgacg aatttaccga tcatatccgg    180

cgtgccttcg aagttgacca cgcggttatt ttccgtacgc ccggaaagct ccatgatgct    240

cttacgcgat gtaccttcta ccagaatacg ctgggtggtg ccgagcatcc ggcggytcca    300

cgccatcgct tgctgattga tacgttcttg cagaatatac agacgctgct tcttctcttc    360

ttccggaaca tcatcaacca tatcggcggc tggtgtaccc ggacgtgcag agaagataaa    420

gctgtagctc atgtcgaaat tgacgtcggc aatcagcttc atcgttttct cgaagtcttc    480

ggtggtttcg ccagggaagc cgacgatgaa gtcagaactg atctgaatat ctggacgcgc    540

cgcacgcagt ttacggatga tcgctttgta ctccagcgcc gtatgggtac gtcccatcag    600

gttcagaatg cgatcggaac cgctctgtac cggcagatgc aggaagctca ccagctccgg    660

cgtgtcgcga tacacttcga tgatatcgtc ggtgaattcg atcggatggc tggtggtaaa    720

gcgaatacga tcgatcccgt cgatcgcagc aaccagacgc aacagatcgg caaacgatcc    780

ggtggtgccg tcgtagtttt caccacgcca ggcgttcacg ttctgaccga gcaggttgac    840

ttcacgcacg ccctgagccg caagctgggc aatctcaaac agaatatcgt cagacggacg    900

gcttacctct tcaccacggg tgtaaggcac cacgcagtag gtgcaatatt tattgcagcc    960

ttccatgatg gagacaaacg cggtcggccc ttcggcgcgc ggttccggta gacggtcaaa   1020

cttctcgatt tccgggaagc tgatatctac aaccgggctg cggtcgccgc gcacggagtt   1080

gatcatctcc ggcagacggt gcagcgtttg cggcccaaaa ataatatcga catagtgggc   1140

gcgctggcga atgtgctcgc cttcttgcga tgccacgcag ccaccgacgc cgataatcag   1200

gtctggattc ttctctttta acagtttcca gcgacccaac tgatggaaga ctttttcctg   1260

agccttctcg cggattgagc aggtgttcag cagcagcaca tccgcttctt ccgccacgtc   1320

ggtcagttga tagccgtggg tggcatccag cagatcggcc atcttcgatg aatcgtactc   1380

gttcatctga cagccccagg ttttaatatg gagttttttg gtcat                   1425
```

<210> SEQ ID NO 312
<211> LENGTH: 1560
<212> TYPE: DNA
<213> ORGANISM: Pseudomonas aeruginosa -continued

<400> SEQUENCE: 312
ccgccgtacg gtcgtcggcc tcaatgcagg gtgctgtcga tcagggtacc gcgcagcgag 60
tgcggcagcg cgtcgtcgat gtgcacctgg gcgaactggc cgatcaggcg tggattgtcg 120
cagcggaagt tgacgatccg gttgttctcg gtgcgcccct ggagcatgcc tgggtccttc 180
ttcgagaagt cggtgaccag gatccgctgg gtgctgccga ccatgcgccg gctgatctcg 240
tagccttgct ggtggatgcg gctctggagg atctgcaggc gctgtttctt cacttcttcc 300
ggcaggtcgt cggcgaggtc ggcggcgggc gtgccgggcc gcgcgctgta gatgaaggag 360
aaggagaagt cgaagccgac gtcctccacc agcttcatgg tctgctcgaa gtccttctcg 420
gtttcgccgg ggaaaccgac gatgaagtcg gagctgatgc agatgtccgg taccgcggcc 480
ttcagcttgc ggatacgcga cttgtattcc agcacggtat ggttgcgctt catcgccgcc 540
agcacgcggt cggagcccga ctgcaccggc aggtggatga atttcaccag ctccggcacc 600
tcggcgtggg cctggatcag cgcgtcggag aattccagcg ggtgcgaggt ggtatagcgg 660
atgcgctcga taccgtcgac ggcggcgacc acccgcagca gttcggcgaa gtcggccagg 720
cggccatcgt gggtcaggcc gcggaagccg ttgacgttct gtcccagcag ggtgacttcg 780
cggacgccgt tctcggccag gtggatcact tcggcgatca cgtcgtcgaa tggtcggctg 840
acttcctcgc cgcgggtgta gggcaccacg cagaagctgc agtacttgct gcagccttcc 900
atcaccgaga cgaaggcggt ggggccatcg acccgcggtt ccggcaggcg gtcgaatttc 960
tcgatttccg ggaaggacac gtcgacctgc ggcttgcgcg tgctgcgcgc ggcgtcgatc 1020
atttccggca ggcggtgcag ggtctgcggg ccgaagacca cgtcgacata gggcgcgcgc 1080
tcacggatcg cggcgccttc ctggctggcc acgcagccgc cgacgccgat caccaggtcg 1140
ggattctgct gcttcagctc gcgccacatg ccgagcttgg aaaacacctt ttcctgggcc 1200
ttctcgcgga tcgagcaggt attgagcagg atgacgtcgg cctcggcggc gttttcggtc 1260
acctcgaggg cttggtgttc accgagcagg tccgccattc gcgacgagtc gtactcgttc 1320
atctggcagc cgtgggtttc gatgaaaagc ttcttggcca tgcgcttcgt cggacagttc 1380
gaaaaggacc gcgcattata gagggcgggg cccccggttc ctagcgttgc tggccgaaag 1440
gctgtgctat gattcgcgcc cttcattttc cggcattgct ttccccgcca tgaacaagcg 1500
cgaaaacccc atctacaagg tgattttcct caaccagggc caggtcttcg agatgtatgc 1560

<210> SEQ ID NO 313
<211> LENGTH: 1344
<212> TYPE: DNA
<213> ORGANISM: Bordetella pertussis

<400> SEQUENCE: 313
tcattcggct ccggatgtgt cgcgttcgat gccggcgaca cggccgcgca gcgagttggt 60
gtgggcgtgg gtgacgacga cgtcgaccat gtggccgatc aggcgcggca cgccgggaaa 120
gttgacgata cggttgttct cggtacggcc catcagctcg ttggggtcgc gccgcgaagg 180
gccttcgacc agcacgcgct ggcgggtgcc gatcatgccc tgggcgatgg ccgcggcctg 240
ctggttgatg agcgcctgca actgctgcag gcggcgcagc ttgacgtcct gcggcgtgtc 300
atcgtgcagg tcggcggccg gcgtgccggg ccggcgcgaa tacacgaacg agaacgaggt 360
gtcgaagccg acgtcctcga tcagcttcat ggtcttctgg aagtcctcct cggtctcgcc 420
cgggaaacca acgatgaagt ccgaggacag cgtcaggctg gggcgcgcag cgcgcaggcg 480
gcgcaccacg gacttgaact ccagcgcggt gtagccgcgc ttcatggccg ccagcacccg 540

-continued gtcgctgccg gcctgcaccg gcaggtgcag gaacgacacc agcttgggca gccgtgcgta 600
ggcgtcgacc atgcgctggg tcatttcctt cggatgcgag gtggtgtagc ggatccgttc 660
gataccggga atctcgtgca cgtattccag cagcatggcg aaatcggcga tttcgccgct 720
gtcgcccatg gcgccgcggt aggcgttgac gttctggccc agcagcgtga cttccttgac 780
gccctggtcg gccaggtcgg cgacctcgag caggacgtcg tcgaaggggc gcgacacttc 840
ttcgccgcgc gtgtagggca ccacgcagaa gctgcaatac ttgctgcagc cttccatgat 900
ggacacgaac gcggtggcgc cgtcgacgcg cggcgggggc agggcgtcga acttctcgat 960
ctcggggaag ctgatgtcga cctgcgacac gccctgggcg cggcggcgct tgatcaggtc 1020
gggcagccgg tgcagggtct gcgggccgaa caccacgtcg acatagggcg cgcgcttgac 1080
gatggcctcg ccttcctggc tggccacgca gccgcccacg ccgatcacca ggttggggtt 1140
ctgcttcttg aggtgctgta cccggcccag gtcggagaac accttctcct gcgccttctc 1200
gcgcacggaa caggtgttga acaggatgac atcggcatcc tcggggttgt cggtcagctc 1260
caggccctgg tcggcgcgca gcacgtcggc catcttgtcc gagtcgtact cgttcatctg 1320
gcagccgaag gtgcggatat acaa 1344

<210> SEQ ID NO 314
<211> LENGTH: 1428
<212> TYPE: DNA
<213> ORGANISM: Bordetella parapertussis

<400> SEQUENCE: 314
tcattcggct ccggatgtgt cgcgttcgat gccggcgaca cggccgcgca gcgagttggt 60
gtgggcgtgg gtgacgacga cgtcgaccat gtggccgatc aggcgcggca cgccgggaaa 120
gttgacgata cggttgttct cggtacggcc catcagctcg ttggggtcgc gccgcgaagg 180
gccttcgacc agcacgcgct ggcgggtgcc gatcatgccc tgggcgatgg ccgcggcctg 240
ctggttgatg agcgcctgca actgctgcag gcggcgcagc ttgacgtcct gcggcgtgtc 300
atcgtgcagg tcggcggccg gcgtgccggg ccggcgcgaa tacacgaacg agaacgaggt 360
gtcgaagccg acgtcctcga tcagcttcat ggtcttctgg aagtcctcct cggtctcgcc 420
cgggaaaccg acgatgaagt ccgaggacag cgtcaggctg gggcgcgcag cgcgcaggcg 480
gcgcaccacg gacttgaact ccagcgcggt gtagccgcgc ttcatggccg ccagcacccg 540
gtcgctgccg gcctgcaccg gcaggtgcag gaacgacacc agcttgggca gccgtgcgta 600
ggcgtcgacc atgcgctggg tcatttcctt cggatgcgag gtcgtgtagc ggatccgttc 660
gataccggga atctcgtgca cgtattccag cagcatggcg aaatcggcga tttcgccgct 720
gtcgcccatg gcgccgcggt aggcgttgac gttctggccc agcagcgtga cttccttgac 780
gccctggtcg gccaggtcgg cgatctcgag caggacgtcg tcgaagggcc gcgacacttc 840
ttcgccgcgc gtgtagggca ccacgcagaa gctgcaatac ttgctgcagc cttccatgat 900
ggacacgaac gcggtggcgc cgtcgacgcg cggcgggggc agggcgtcga acttctcgat 960
ctcgggaaag ctgatgtcga cctgggacac gccctgggcg cggcggcgct tgatcaggtc 1020
gggcagccgg tgcagggtct gcgggccgaa caccacgtcg acatagggcg cgcgcttgac 1080
gatggcctcg ccctcctggc tggccacgca gccgcccacg ccgatcacca ggttggggtt 1140
ctgcttcttg aggtgctgta cccggcccag gtcggagaac accttctcct gcgccttctc 1200
gcgcacggaa caggtgttga acaggatgac atcggcatcc tcggggttgt cggtcagctc 1260

-continued

```
caggccctgg tcggcgcgca gcacgtcggc catcttgtcc gagtcgtact cgttcatctg   1320

gcagccgaag gtgcggatat acaatttgcc caggccctgg gcggtggtgg ccggcgtgcc   1380

ggcatcggac gggctggcgc cgtcgcgttt gacagtggtt tcttgcat                1428
```

<210> SEQ ID NO 315
<211> LENGTH: 1374
<212> TYPE: DNA
<213> ORGANISM: Burkholderia pseudomallei

<400> SEQUENCE: 315

```
tcagtgcgtg gcggcgctcg cgtcgccgtg cgcgagcacg agctcgccgc gcagcgagtg     60

gggatacgcg tgattgatct tcacgtcgat catctggccg atcaggcgcg ggtgcgcggc    120

gctcggcgcg ggaaaattca cgacccggtt gttctcggtg cggcccgcga gctcgttcgg    180

atccttgcgc gacggcccct cgacgaggat tcgctcgacc ttgccgagca tcgactggct    240

gatcctcgcg acgttctcct cgatcgtcgc ctgcagatgt tgcaggcgct tgagcttgag    300

ctcgcgcggc gtgtcgtcgg cgagattcgc ggccggcgtg ccgggccgcg ggctgtagat    360

gaacgagaag ctcgtgtcgt agctcatctc gtgaacgagc gccatcgtct tgtcgaagtc    420

ggcgtcggtc tcgccgggga aacccacgat gatgtccgtg gacagcgaca gattcgggcg    480

gatcgcgcgc agcttgcgga tcaccgattt gtattcgagc acggtgtagc cgcgcttcat    540

cgccatcagg atgcggtccg agccgtgctg gacgggcagg tgcagatggt cgacgagctt    600

cggcaccttc gcgtagacgt cgagcaggcg ctgcgtgaac tccttcggat gcgatgtcgt    660

gtagcggatc cgctcgatgc cggggatgtc ggcgacatat tcgatcagcg tcgcgaaatc    720

ggcgatctcg gccgagccgg ccgcgatcgc gccgcggtag gcgttcacgt tctggccgag    780

cagcgtgact tcgcgcacgc cctggtcggc gaggcccgcg acctcggtca agacgtcgtc    840

gagcgggcgc gacacttcat cgccgcgcgt gtacggcacg acgcagtagc tgcagtactt    900

cgagcagcct tccatgatcg acacgaacgc gctcggccct tcgacgcgag cgggcggcag    960

atggtcgaac ttctcgattt cggggaacgt gatgtcgacc tgcgcgcggc cgctttcgcg   1020

gcgcgcgtcg atcatctgcg gcaggcggtg cagcgtttgc gggccgaaca cgagatcgac   1080

gtacggcgcg cgcgcgacga tcgacgcgcc ttcctggctc gccacgcagc cgccgacgcc   1140

gatcagcagg tccggcttcg cttccttcag ctcgcgcacg cggccgagat cggagaacac   1200

cttctcctgc gccttttctc gcaccgagca ggtgttgaac aggatgatgt ccgcgtcttc   1260

cggggtgtcg gttttctcga ggccctcggc cgcattgagc acgtcgacca tcttgtcgga   1320

gtcgtactcg ttcatctggc agccgaaggt ttttacgtaa actttcttgg tcat         1374
```

<210> SEQ ID NO 316
<211> LENGTH: 1425
<212> TYPE: DNA
<213> ORGANISM: Vibrio vulnificus

<400> SEQUENCE: 316

```
ttatggcgta aatgtcgcta cacctagctc atcttcgcgg cgtgttttgg ccatcatttg     60

tgttggcgaa atcacgctac gtaggtccat atctttttca gtacgtacaa tctcaccacg    120

cagtgagttc gcaaatacat cggtaatttt cacatcaacg aactgaccaa tcagatctgc    180

gctaccttca aagtttacta cacggttgtt ttctgtacga gcacgtagct ccatcaagtt    240

cttcttagaa gggccttcaa ccagtacacg ctgctctgtg cctagcatga ggcgagagta    300

acgcatggct tgtgcgttga tttgttgttg cagttcgtac aagcgctctt tcttcgtctc    360
```

-continued ttctgaaaga tcacatgggt aatctgccgc aggagtacca gggcgaggag agaagatgaa 420
gctgaagctc atgtcaaagt cgacatcttt gatcagcttc atggtgtctt ggaaatcttt 480
gtcgctttca cctgggaagc caacaataaa gtcagaactg atttggatat caggacgcgc 540
tttacgcagt ttacgaatga tcgacttgta ttcgatgcca gtgtgaggac gcttcatcat 600
cgtcagaatg cgatcgctac cactttgtac tggtagatga aggaagctca ccagctctgg 660
cgtatcttcg tagacagcga tgatatcatc ggtgaactca agtgggtggc tggtggtaaa 720
gcgaatacgg tcgataccat cgatagacgc aacaaggcga agcagttctg caaaagaaca 780
gatttcacca tcgtgcgttg ggccacggta tgcgtttacg ttttggccta gcaggttgac 840
ttcgcgaaca ccttgctcgg caagttgcgc gatttcgtaa agcacatcgt ccattgggcg 900
gctgacttct tcaccacgag tgtaaggcac tacgcagtaa gtacagtact tagaacagcc 960
ttccatgata gaaacgaatg cggttgcgcc ttctgcacgt ggttctggca gactgtcaaa 1020
cttctcgatt tctgggaatg aaatgtccat cactggtgca tcttcacttt gtgattgttt 1080
gatcatttca ggaagacggt gcaaggtttg cgggccaaag ataacgtcaa caaaaggtgc 1140
acgttcacga atgtgatcgc cttcctgtgt tgctacacaa ccaccaacac cgatcacgac 1200
gcctggcttt ttatctttga gtgttttcca acggccaagc tggtggaaca ctttttcttg 1260
cgccttttca cggatcgaac aggtgttaag taatagaaca tctgcttctt ctggttcttc 1320
tgtcaattcg tagccatttg ctgcgttcag cagatccgcc attttcgatg aatcgtattc 1380
gttcatctgg caaccccagg ttttaattag cagtttctta ctcat 1425

<210> SEQ ID NO 317
<211> LENGTH: 1425
<212> TYPE: DNA
<213> ORGANISM: Vibrio fischeri

<400> SEQUENCE: 317
ctatggcgta aaagtaccta caccaagatc atcttcacga cgtgtctttt ccatcatttc 60
tgctggagtc ataacaacac gtaaacccat gtctttttct gtacgaacta gttcaccacg 120
cagtgagttc gcaaatacat ctgtgatttt aacatcaaca aattgaccaa taagatccgc 180
tgaaccttca aagtttacaa cacggttgtt ttcagtacga gcacgaagtt ccatcaggtt 240
tttcttcgat gggccttcaa ctaatacacg ttgctcagtg tctagcatta gacgagagta 300
gcgcattgct tggctgttta cttgctgttg cagttcagct aggcgatctt tcttctcttg 360
ttcagggata tcacatggat aatcagcagc aggtgttcct ggacgcgcag agaagatgaa 420
actaaagctc atgtcgaagt cgacatcttt aatcagtttc attgtatctt ggaagtcttt 480
cgccgtttca ccagggaagc caacaataaa gtcagaactg atttgaatat caggacgagc 540
cttacgtaat ttacgaatga ttgatttgta ttcaatcgct gtgtgagggc gcttcatcat 600
agttagaata cgatcagaac cactttgaac aggtaagtgt aagaaactta ctagctctgg 660
cgtatcttcg tatacagcga tgatgtcatc accaaactct aatgggtggc ttgttgtaaa 720
gcgtaaacgg tcgataccat cgatagatgc aaccatacgt aataattcag caaatgtgca 780
gatatcaccg tcgtgcattg gaccacggta cgcgttaacg ttttgaccca ataggtttac 840
ttcacgtacg ccttgctctg caagctgtgc aatttcaaat aatacgtcat caagaggacg 900
gcttacttct tcaccacgag tgtatggaac aacacagtaa gtacagtact tagaacaccc 960
ttccataata gaaacgaacg ctgttgcacc ttctgctttt ggttcaggaa ggttatcgaa 1020

-continued cttttcgatc tctgggaatg aaatatccat tactggtttt tcatttgatt gagattggcg 1080
gatcatttca ggtaaacggt gtaaagtttg tggaccaaaa attacgtcaa cgtatggagc 1140
tcgttggcga atatgatcac cttcttgagt tgcaacacaa ccaccaacac cgatcactag 1200
atctggtttt ttatctttta ggtttttcca gcggcctaat tggtgaaaca ctttctcttg 1260
tgctttttca cgaatagagc aggtatttaa tagtagaacg tcagcttctg ttggttcttc 1320
tgttaattca taaccatttg cggcacctaa aaggtcggcc attttagatg aatcgtattc 1380
gttcatctga cagccccagg ttttgatcag cagtttctta gtcat 1425

<210> SEQ ID NO 318
<211> LENGTH: 1425
<212> TYPE: DNA
<213> ORGANISM: Yersinia pseudotuberculosis

<400> SEQUENCE: 318
ttaaggctga taaataccta caccaatttc attttcttta cgggtgcgag caatcaccga 60
ttgcggtgac tcgtgggttc gcaggtccat ctgatcttct gtacgcagta aaatgccgcg 120
cagtgaactg gcataaacgt taacaatttc gacatcaacg aatttaccaa tcatgtcggg 180
tgaaccctca aagttcacga cgcggttgtt ttccgtacgc ccggccagtt ccatgacatt 240
tttgcgagag gtcccctcca ccaaaacacg ctgtactgtc cctaccatct tacggctaat 300
ttccatcgcc tgttggctaa tgcgttgttg caggatatgt agccgctgtt ttttctcctc 360
ttcggacaca ttgtcgggta aatcagccgc tggtgtgccg ggacgcgggg agtaaataaa 420
gctgtagctg gtatcaaaat gaatatctgc gaccagtttc atggtctgtt caaaatcctg 480
ctgggtttca ccagggaagc cgacaataaa atcagaactt atctggatat cagggcgcgc 540
ctgacgcagt ttgcggatga tggctttgta ttccagggcg gtatgggcac gcttcatcat 600
ggtcaaaata cggtcagaac cgctttgtac cggcaaatgc aggaagctca ccaattcagg 660
cgtatcgcga taaacatcaa tgatatcgtc agtaaactca atggggtggc tggtggtaaa 720
tcgtatccta tcgataccat caatggccgc aaccaaacgc aacagctcgg caaaactaca 780
gatatcgcca tcgtaggttg ccccgcggta ggcgttaaca ttctggccga gtaagttgac 840
ttcacgtacg ccttgagcgg ctaactgggc gatttcaaaa agaatgtcat cgcttggacg 900
gctgacttcc tcgcctcggg tgtagggtac gacacagaat gtacaatatt tattgcagcc 960
ttccatgatc gaaacaaacg cagttgggcc ttcagcccgt ggttctggca aacggtcaaa 1020
tttttcaatt tcgggaaaac tgatatccac gacagggcta ttcgttcctt gcacgtggtt 1080
aatcatttcc ggtaaacgat gcagcgtttg tggcccgaag atgacatcga cacagggggc 1140
gcgctggcgc aattgttcac cttcctgtga cgccacgcaa ccaccgaccc caataatcaa 1200
ctgcgggttt ttctctttca ataatttcca ttgccctagc aggctgaata ctttttcctg 1260
tgctttttcc cggatagaac aggtatttag cagcagtaaa tccgcttctt ccgggatggt 1320
ggttaactgg tagccatggg tactggccaa gagatctgcc attttagatg aatcgtattc 1380
attcatctgg caaccccagg ttttgatatg cagtttttta gtcat 1425

<210> SEQ ID NO 319
<211> LENGTH: 1467
<212> TYPE: DNA
<213> ORGANISM: Salmonella enterica subspecies paratyphi A

<400> SEQUENCE: 319
ttaaggctgg tagaatccta cgcccagctc attttcttta cgggtacggg caatgacgga 60

```
ctccggcgtt tcggcgacgc gcagccccat ttcatcttcg gtacgcacca cttttccgcg    120
cagggagttc ggatagacgt cagtaatttc cacatcgaca aacttaccaa tcatctccgg    180
cgtgccttca aagttcacca cccgattgtt ttcggtacgg ccagacagtt ccataatgtt    240
tttacgtgac gtgccttcca ccagaatgcg ctgtgtcgtg ccgagcatac ggcggctcca    300
tgccatcgcc tgctgattga tacgctcttg cagaatatac agacgctgct tttctcttc     360
ttccggtacg tcatcaacca tatcggcagc cggcgttccc ggacgcgcag agaagataaa    420
gctgtagctc atatcaaagt tgacgtcagc gataagcttc atggtttttt cgaaatcatc    480
ggtagtttcg ccagggaatc cgacgataaa gtcagagctt atctgaatgt ccggccgcgc    540
cgcgcgcagt ttacggatga ttgctttata ttccagcgca gtgtgggtgc gccccatcag    600
attcaacacg cgatcggaac cgctctgtac cggcagatgc aggaaactga ccagctccgg    660
cgtatcgcgg tacacctcga taatatcgtc ggtgaactca atcggatggc tggtggtaaa    720
gcgaatacgg tcaatgccgt cgatggcggc aaccagacgc agcagatcgg caaaggtgcc    780
agtggtgccg tcgtagtttt ctccgcgcca ggcgttaacg ttctggccca acaggttgac    840
ctcacgcacg ccctgcgccg ctaactgggc gatttcgaac aggatatcgt ctgagggacg    900
gctgacttct tcaccgcggg tatacggcac cacgcagtaa gtacaatatt tattgcagcc    960
ttccatgata gaaacgaaag cggtcgggcc ttctgcgcgc ggttccggca aacggtcgaa   1020
cttctcgatt tccgggaagc tgatatcgac caccgggctg cggtcgccac gcacggagtt   1080
aatcatctcc ggcaggcggt gtgaggtttg cggaccaaaa ataatgtcga cgtaatgggc   1140
gcgttgacga atgtgctcgc cttcctggga agccacgcag ccgccgacgc cgataatcag   1200
atcgggattt ttctctttta acagtctcca gcgacctaat tgatggaaga ctttttcctg   1260
agccttctcg cggattgagc aggtattcaa cagcagcaca tccgcctctt ccgccacgtc   1320
ggtcagttga tagccgtggg tggcgtccag cagatcggcc atcttcgatg aatcgtactc   1380
gttcatctga cagccccagg ttttaatatg gagtttttta gtcatcgact tgctcttgcg   1440
aaatagtggc tgaaaagcag ggcgcat                                      1467
```

<210> SEQ ID NO 320
<211> LENGTH: 1425
<212> TYPE: DNA
<213> ORGANISM: Salmonella typhimurium

<400> SEQUENCE: 320

```
ttaaggctgg tagaatccta cgcccagctc attttcttta cgggtacggg caatgacgga     60
ctccggcgtt tcggcgacgc gcagccccat ttcatcttcg gtacgcacca cttttccgcg    120
cagggagttc ggatagacgt cagtaatttc cacatcgaca aacttaccaa tcatctccgg    180
cgtgccttca aagttcacca cccgattgtt ttcggtacgg ccagacagtt ccataatgtt    240
tttacgcgac gtgccttcca ccagaatgcg ctgtgtcgtg ccgagcatac ggcggctcca    300
tgccatcgcc tgctgattga tacgctcttg cagaatatac agacgctgct tcttctcttc    360
ttccggcacg tcatcaacca tatcggcagc cggcgttccc ggacgcgcag agaagataaa    420
gctgtagctc atatcaaagt tgacgtcagc gataagcttc atggtttttt cgaaatcatc    480
ggtagtttcg ccagggaatc cgacgataaa gtcagagctt atctgaatgt ccggccgcgc    540
cgcgcgcagt ttacggatga ttgctttata ttccagcgca gtgtgggtgc gccccatcag    600
attcaacacg cgatcggaac cgctctgtac cggcagatgc aggaaactga ccagttccgg    660
```

-continued

```
cgtatcgcgg tatacctcga taatatcgtc ggtgaactca atcggatggc tggtggtaaa     720

gcgaatacgg tcaatgccgt cgatggcggc aaccagacgc agcagatcgg caaaggtacc     780

ggtggtgccg tcgtagtttt ctccgcgcca ggcgttaacg ttctggccca gcaggttgac     840

ctcacgcacg ccctgcgccg ctaactgggc gatttcgaac aggatatcgt ctgagggacg     900

gctgacttct tcaccgcggg tatacggtac cacacagtaa gtacaatatt tattgcagcc     960

ttccatgata gaaacgaaag cggtcgggcc ttctgcgcgc ggttccggca aacggtcgaa    1020

cttctcgatt tccgggaagc tgatatcgac caccgggctg cggtcgccac gcacggagtt    1080

aatcatctcc ggtaggcggt gtaaggtttg cgggccaaaa ataatgtcga cgtaatgggc    1140

gcgttgacga atgtgctcgc cttcctggga agccacgcag ccgccgacgc cgataatcag    1200

atcgggattt ttctctttta acagtctcca gcgacctaat tgatggaaga ctttttcctg    1260

agccttctcg cggattgagc aggtattcaa cagcagcaca tccgcctctt ccgccacgtc    1320

ggtcagttga tagccgtggg tggcgtccag cagatcggcc atcttcgatg aatcgtactc    1380

gttcatctga cagccccagg ttttaatatg gagtttttta gtcat                    1425
```

<210> SEQ ID NO 321
<211> LENGTH: 1425
<212> TYPE: DNA
<213> ORGANISM: Shigella flexneri

<400> SEQUENCE: 321

```
ttacggctga taataaccca cgccaaggtc gttttctttg cgggtgcggg caatcaccga      60

ctccggtgtt tctgccatgc gcagacccat ttcatcttca gttcgcacca ctttaccgcg     120

cagagagttc gggtagacgt cggtaatttc tacatcgacg aatttaccga tcatatccgg     180

tgtgccctcg aagttgacca cgcggttatt ttcggtacgc ccggaaagct ccatgatgct     240

cttacgcgaa gtcccttcta ccagaatacg ctgggtggtg ccgagcatcc gacggctcca     300

tgccatcgct tgctgattga tacgttcttg cagaatatac agacgctgct tcttctcttc     360

ttccggaaca tcatcaacca tatcggcggc aggcgttcct ggacgtgcag agaagataaa     420

gctgtagctc atgtcgaaat tgacgtcggc aatcagcttc atcgttttct cgaagtcttc     480

ggtggtttcg ccagggaagc caacaatgaa gtcagaactg atctgaatat ccggacgcgc     540

cgcacgcagt ttacggatga tcgctttgta ctccagcgcc gtatgggtac gtcccatcag     600

gttcagaatg cgatcggaac cgctctgtac cggcagatgc aggaagctca ccagctcagg     660

cgtgtcgcgg tacacttcga tgatatcgtc ggtgaattcg atcggatggc tggtggtaaa     720

gcgaatacga tcgatcccgt cgatcgcagc aaccagacgc aacagatcgg caaacgatcc     780

ggtggtgccg tcgtagttct caccacgcca ggcattcaca ttctgaccga gcaggttgac     840

ttcacgcacg ccctgagccg caagctgggc aatctcaaac agaatatcgt cagacggacg     900

gcttacctct tcaccacggg tgtaaggcac cacgcagtag gtgcaatatt tattgcagcc     960

ttccatgatg gagacaaacg cggtcggccc ttcggcgcgc ggttccggca gacggtcaaa    1020

cttctcgatt tccgggaagc tgatatctac aaccgggctg cggtcgccgc gcacggagtt    1080

gatcatctcc ggcagacggt gcagcgtttg cggcccaaaa ataatatcga catagtgggc    1140

gcgctggcga atgtgctcgc cttcttgcga tgccacgcag ccaccgacgc cgataatcag    1200

gtctggattc ttctctttta acagtttcca gcgacccaac tgatggaaga ctttttcctg    1260

agccttctcg cggattgagc aggtgttcag cagtagcaca tccgcttctt ccgccacgtc    1320

ggtcagttga tagccgtggg tggcatccag cagatcggcc atcttcgatg aatcgtactc    1380
```

gttcatctga cagccccagg ttttaatatg gagtttttttg gtcat 1425

<210> SEQ ID NO 322
<211> LENGTH: 1329
<212> TYPE: DNA
<213> ORGANISM: Pseudomonas syringae

<400> SEQUENCE: 322
ttactgtagc agcgagccac gcaacgagtg gggctgcgca tcatcaatgt gtacgtcggc 60
aaactgcccg atcaggcggg gattgtcgca gcgaaaattg acaatccggt tgttctcggt 120
gcgaccttgc agttcgccgg ggtctttctt tgagtaatct gtaaccagaa tacgctggat 180
gctgccaacc atctgtcggc tgatctcgaa accctgttgg ttcaggcgat gttgcaacgc 240
ggccagtcgc tctttttca gcgcttccgg cgtgtcgtct ttcaggtcag cggccggtgt 300
gccggggcgc gggctgtaaa tgaacgagaa cgagaagtcg aaaccggcgt cttcgatcag 360
cttcatggtg ttgtcgaaat ccttttcggt ttcaccgggg aagccaacga tgaagtcgga 420
actgatgctg atacccggca ctgccgcccg aagcttgcgt agcctggact tgtattccag 480
cgtggtgtgg ttgcgtttca tggccgccag aatgcggtcc gaacctgact gcaccggcaa 540
atgcaggtgc ttgaccagtt ccggcacgtc ggcgtgcgcc tgaatcaggc tgtcggaaaa 600
ctcgagcggg tgcgaggttg tgtaacgaat gcggtcgatg ccatcgacga cggcaactgc 660
ccgaatcaga tcagccaagt cggcgactcg cccgtcatgg gtggtgccgc gataaccgtt 720
gacgttctgc cccagcagtg tgacttcgcg cacgccgtgt tcggccaggt gagtgacctc 780
ggtcagcacg tcatcgaacg gtcggctgac ttcttcgccg cgcgtgtagg gcaccacgca 840
gaaggtgcag tacttgctgc agccttccat caccgacacg taagcactcg ggccatccac 900
gcgcggctcg ggcaagtggt cgaatttttc gatctcgggg aatgaaacat cgacctgcgg 960
caagcgggtg atgcgcgctg cgtcgatcat ttccggcagg cggtgcaatg tttgcgggcc 1020
gaacaccacg tccacgtagg gcgcgcggtc gcggatggcc gcgccttcct ggctggcaac 1080
acagccgccg acggcaatca ccatctcggg gttggccagt ttcagctcac gccagcggcc 1140
gagctgcgaa tagacccggt cttgcgcacg ctcgcgaatc gagcaggtgt tgagcaggat 1200
cacgtcggcg tcttccgcgc gagcggtgac ttccagagcc tgatgttcgc ccagcagatc 1260
gaccatgcgc gagctgtcgt actcgttcat ctggcaaccg tgggtttcga tgtaaagctt 1320
cttggccat 1329

<210> SEQ ID NO 323
<211> LENGTH: 1374
<212> TYPE: DNA
<213> ORGANISM: Burkholderia mallei

<400> SEQUENCE: 323
tcagtgcgtg gcggcgctcg cgtcgccgtg cgcgagcacg agctcgccgc gcagcgagtg 60
cggatacgcg tgattgatct tcacgtcgat catctggccg atcaggcgcg ggtgcgcggc 120
gctcggcgcg ggaaaattca cgacccggtt gttctcggtg cggcccgcga gctcgttcgg 180
atccttgcgc gacggcccct cgacgaggat tcgctcgacc ttgccgagca tcgactggct 240
gatcctcgcg acgttctcct cgatcgtcgc ctgcagatgt tgcaggcgct tgagcttgag 300
ctcgcgcggc gtgtcgtcgg cgagattcgc ggccggcgtg ccgggccgcg ggctgtagat 360
gaacgagaag ctcgtgtcgt agctcatctc gtgaacgagc gccatcgtct tgtcgaagtc 420

-continued

```
ggcgtcggtc tcgccgggga aacccacgat gatgtccgtg gacagcgaca gattcgggcg    480

gatcgcgcgc agcttgcgga tcaccgattt gtattcgagc acggtgtagc cgcgcttcat    540

cgccatcagg atgcggtccg agccgtgctg gacgggcagg tgcagatggt cgacgagctt    600

cggcaccttc gcgtagacgt cgagcaggcg ctgcgtgaac tctttcggat gcgatgtcgt    660

gtagcggatc cgctcgatgc cggggatgtc ggcgacatat tcgatcagcg tcgcgaaatc    720

ggcgatctcg gccgagccgg ccgcgatcgc gccgcggtag gcgttcacgt tctggccgag    780

cagcgtgact tcgcgcacgc cctggtcggc gaggcccgcc acctcggtca agacgtcgtc    840

gagcgggcgc gacacttcat cgccgcgcgt gtacggcacg acgcagtagc tgcagtactt    900

cgagcagcct tccatgatcg acacgaacgc gctcggccct tcgacgcgag cgggcggcag    960

atggtcgaac ttctcgattt cggggaacgt gatgtcgacc tgcgcgcggc cgctttcgcg   1020

gcgcgcgtcg atcatctgcg gcaggcggtg cagcgtttgc gggccgaaca cgagatcgac   1080

gtacggcgcg cgcgcgacga tcgacgcgcc ttcctggctc gccacgcagc cgccgacgcc   1140

gatcagcagg tccggcttcg cttccttcag ctcgcgcacg cggccgagat cggagaacac   1200

cttctcctgc gccttttctc gcaccgagca ggtgttgaac aggatgatgt ccgcgtcttc   1260

cggggtgtcg gttttctcga ggccctcggc cgcattgagc acgtcgacca tcttgtcgga   1320

gtcgtactcg ttcatctggc agccgaaggt ttttacgtaa actttcttgg tcat         1374
```

<210> SEQ ID NO 324
<211> LENGTH: 1344
<212> TYPE: DNA
<213> ORGANISM: Legionella pneumophila

<400> SEQUENCE: 324

```
ttaggctggc tgcatctcct tttcaagcag ccttcctcgc aatgaattag gtagtgcgtc     60

actaatttgg acatctataa attgtccaat taaatgaggt ggtccatcaa aattaactac    120

acggttacat tcagtacgac cagataattg ctgtgaactt ttcttggaaa atccggtaac    180

cagaattttt tgcttgctgc ctatcattga ttcactgtaa cgagctgcat tcattaataa    240

tctgttttgt aaaatctgta aacgttgctt tttgatctcc ataggcgtgt catcaggtaa    300

atttgctgca ggagttcctg gtcttgggct gtatataaag ctgaaagagg tatcaaaacc    360

gatttcatgc acaagatcca tagtgtcctg gaaatctttg tctgtctctc cgggaaagcc    420

tacaataatg tcagtagata agcgaatgtc tggtcgaatt ttccttaatt tacgaatttt    480

ggatttaaat tccaaagcag tgtaccctcg tttcattaac gataaaatgc gatcggatcc    540

gctttgtacc ggaaggtgta aatgattggc aagctctgga acctcagcgt aggcattaat    600

caaattttca gaaaatgcca agggatgtga tgttgtgaaa cgtattcttc ctattccatc    660

gatagcggca atataatgaa ttaacagggc aagatcggct atatccccat tgtccataat    720

acctctgtaa tcgttcacat tttggcctag taaattaatc tctctgacgc cttgactggc    780

taattgataa cactcagcca atacatcatc aaatggtctg ctgatttctt cgccacgggt    840

gtagggcacc acacagaagc tgcaatattt actacagcct tccattatag atacaaaagc    900

tgtagggcct tctgctcttg gtgcgggtaa atgatcaaat ttctctattt ctggaaagct    960

gatatcaaca acagatttat ttttctcaag cctttcattg agcagggcag ggagcctgtg   1020

taatgtctgt ggcccaaata cgatatcaac aaacggtgct ctttttatga tgtctgagcc   1080

ttcctggctc gctacgcatc ctcccactcc aatgagcaca tgagggtttt tggctttata   1140

ttctcgccat tgacccagtt gagaaaaaac tttttcctgt gctttttctc gaattgagca   1200
```

-continued tgtgtttaat aaaataacat cggcatcctc gacttgatca gttttgacca aaccatggga 1260
agcgtaaagt acttctgcca ttttagaaga atcgtattca ttcatttggc agccatttgt 1320
tttaatatat aattttttaa ccat 1344

<210> SEQ ID NO 325
<211> LENGTH: 1428
<212> TYPE: DNA
<213> ORGANISM: Bordetella bronchiseptica

<400> SEQUENCE: 325
tcattcggct ccggatgtgt cgcgttcgat gccggcgaca cggccgcgca gcgagttggt 60
gtgggcgtgg gtgacgacga cgtcgaccat gtggccgatc aggcgcggca cgccgggaaa 120
gttgacgata cggttgttct cggtacggcc catcagctcg ttggggtcgc gccgcgaagg 180
gccttcgacc agcacgcgct ggcgggtgcc gatcatgccc tgggcgatgg ccgcggcctg 240
ctggttgatg agcgcctgca actgctgcag gcggcgcagc ttgacgtcct gcggcgtgtc 300
atcgtgcagg tcggcggccg gcgtgccggg ccggcgcgaa tacacgaacg agaacgaggt 360
gtcgaagccg acgtcctcga tcagcttcat ggtcttctgg aagtcctcct cggtctcgcc 420
cgggaaaccg acgatgaagt ccgaggacag cgtcaggctg gggcgcgcag cgcgcaggcg 480
gcgcaccacg gacttgaact ccagcgcggt gtagccgcgc ttcatggccg ccagcacccg 540
gtcgctgccg gcctgcaccg gcaggtgcag gaacgacacc agcttgggca gccgtgcgta 600
ggcgtcgacc atgcgctggg tcatttcctt cggatgcgag gtcgtgtagc ggatccgttc 660
gataccggga atctcgtgca cgtattccag cagcatggcg aaatcggcga tttcgccgct 720
gtcgcccatg gcgccgcggt aggcgttgac gttctggccc agcagcgtga cttccttgac 780
gccctggtcg gccaggtcgg cgacctcgag caggacgtcg tcgaagggcc gcgacacttc 840
ttcgccgcgc gtgtagggca ccacgcagaa gctgcaatac ttgctgcagc cttccatgat 900
ggacacgaac gcggtggcgc cgtcgacgcg cggcgggggc agggcgtcga acttctcgat 960
ctcgggaaag ctgatgtcga cctgcgacac gccctgggcg cggcggcgct tgatcaggtc 1020
gggcagccgg tgcagggtct gcgggccgaa caccacgtcg acatagggcg cgcgcttgac 1080
gatggcctcg ccctcctggc tggccacgca gccgcccacg ccgatcacca ggttggggtt 1140
ctgcttcttg aggtgctgta cccggcccag gtcggagaac accttctcct gcgccttctc 1200
gcgcacggaa caggtgttga acaggatgac atcggcatcc tcggggttgt cggtcagctc 1260
caggccctgg tcggcgcgca gcacgtcggc catcttgtcc gagtcgtact cgttcatctg 1320
gcagccgaag gtgcggatat acaatttgcc caggccctgg gcggtggtgg ccggcgtgcc 1380
ggcatcggac gggctggcgc cgtcgcgttt gacagtggtt tcttgcat 1428

<210> SEQ ID NO 326
<211> LENGTH: 597
<212> TYPE: DNA
<213> ORGANISM: Enterococcus faecalis

<400> SEQUENCE: 326
ctatttgaag ggcgcaaggt gtcatgttgg atatcgatca aggaacctat ccatttgtta 60
cttcctctaa tccagtagct ggtggcgtaa ctatcggtag tggcgttggt ccatcaaaaa 120
ttaataaagt ggttggtgtc tgcaaagcgt acacttcacg tgtcggtgac ggcccattcc 180
caacagaatt atttgatgaa acaggagaaa ccattcgtcg tgtcggtaaa gaatacggaa 240

-continued

```
caacaacagg acgtccgcgt cgtgtcggtt ggtttgattc agtagtcatg cgtcattcaa    300

aacgtgtatc agggattaca aacttgtcat taaactcgat tgacgtgtta agtggtttag    360

aaacggtgaa aatttgtaca gcttatgaac ttgatggtga attaatttat cattatccag    420

caagcttgaa agaattaagc cgctgtaaac cagtttatga agaattacca ggttggtctg    480

aagatatcac tggttgcaaa actttagccg atttaccagc taatgctcgt aactatgtgc    540

atcggatttc agaattagtt ggtgtgcgca tttcaacatt ctcagtaggg ccagacc       597
```

<210> SEQ ID NO 327
<211> LENGTH: 597
<212> TYPE: DNA
<213> ORGANISM: Enterococcus gallinarum

<400> SEQUENCE: 327

```
ctcttcgagg tgcgcaagga gttatgctag atattgatca aggaacatat ccgttcgtaa     60

catcctcaaa tccagtagct ggtggagtaa ccattggtag tggagtgggt ccttctaaaa    120

tcaataaagt agttggtgtt tgtaaagcat atacttcaag agttggtgac ggcccattcc    180

caacagaact tttgatgaa acaggcaatc aaattcgtga agttggccgt gaatatggta    240

cgacaactgg tcgtccacgt cgtgttggtt ggtttgactc tgttgtcatg cgtcattcaa    300

aacgtgtttc tggtatcacg aatctgtctt taaattcaat tgatgttttg agcggcttgg    360

aaactgtaaa aatttgtact gcttatgaat tagatggaga attgatttat cattatcctg    420

caagtctaaa agaattgaat cgttgtaaac cagtctatga agagttacca ggctggtcag    480

aagatattac tggatgcaaa acattagctg atcttcctga aaatgcacgt aactatgtac    540

atcgtatctc tgaattagtt ggggttcgta tctcaacatt ctcagtaggt cctgacc       597
```

<210> SEQ ID NO 328
<211> LENGTH: 598
<212> TYPE: DNA
<213> ORGANISM: Enterococcus flavescens
<220> FEATURE:
<221> NAME/KEY: misc_feature
<222> LOCATION: (594)..(594)
<223> OTHER INFORMATION: n is a, c, g, or t

<400> SEQUENCE: 328

```
ctttttgaag gtgctcaagg cgtgatgctg gatatcgacc aaggaaccta tcctttcgtg     60

acatcatcca accccgttgc tgggggagtc actattggta gtggtgtggg tccttcaaaa    120

atcaacaaag tcgttggtgt ctgcaaagct tacacctctc gggtaggaga tggtcctttc    180

ccaacggaac tgtttgatga aacaggtgaa caaatccgta agatcggtcg tgaatacgga    240

acaacgacag gacgtcctcg ccgtgtgggc tggtttgata ccgtcgtgat gcgccattca    300

aaacgtgttt cagggattac aaacctatcc cttaactcga tcgatgtctt gagcggctta    360

gaaaccgtga agatctgtac ggcttatgaa ctagacggcg aattgatcta tcattaccca    420

gcaagcttga aagagttgaa ccgctgcaaa ccagtctacg aagaacttcc tggctggtct    480

gaagacatta ctggctgcaa aacattagca gatctgccag aaaatgcacg caattacgtt    540

caccgcatct ctgaattagt cggtgtccgc atttcgacct tctcagtagg gccngacc      598
```

<210> SEQ ID NO 329
<211> LENGTH: 598
<212> TYPE: DNA
<213> ORGANISM: Streptococcus agalactiae
<220> FEATURE:
<221> NAME/KEY: misc_feature -continued
<222> LOCATION: (581)..(581)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t

<400> SEQUENCE: 329
ctctttgaag ggcgcaagga gttatgctcg acattgatca aggaacatac ccatttgtaa 60
catcttccaa tccagtagca ggtggtgtca caattggttc gggagttgga ccaagtaaaa 120
ttaataaagt agtaggtgta tgtaaagctt acactagccg tgttggtgat ggaccattcc 180
caacagaact ttttgatgag gttggtgacc gtattcgtga gattggtaaa gagtatggta 240
caacgaccgg tcgtcctcgt cgcgttggat ggtttgattc tgttgttatg cgtcacagcc 300
gtcgagtatc aggtattact aacctctctc tgaattcaat tgatgttctt tcagggcttg 360
atacggtgaa aatttgtgtg gcttatgacc ttgatgggaa acgtattgac tattacccag 420
caagccttga acagctaaaa cgttgtaaac caatctatga agaattaccg ggctggtctg 480
aagatattac agcttgtcgt agcttagatg atcttccaga aaatgcacgt aattacgttc 540
gccgtgttgg cgaattggtt ggtgttcgta tttctacttt nctcagtagg nccaggtc 598

<210> SEQ ID NO 330
<211> LENGTH: 599
<212> TYPE: DNA
<213> ORGANISM: Streptococcus sanguis

<400> SEQUENCE: 330
ctttttgaag gggctcaagg agttatgctc gacattgatc aaggaacata cccatttgta 60
acatcttcca atccagtagc aggtggtgtc acaattggtt cgggagttgg accaagtaaa 120
attaataaag tagtaggtgt atgtaaagct tacactagcc gtgttggtga tggaccattc 180
ccaacagaac tttttgatga ggttggtgac cgtattcgtg agattggtaa agagtatggt 240
acaacgaccg gtcgtcctcg tcgcgttgga tggtttgatt ctgttgttat gcgtcacagc 300
cgtcgagtat caggtattac taacctctct ctgaattcaa ttgatgttct ttcagggctt 360
gatacggtga aaatttgtgt ggcttatgac cttgatggga aacgtattga ctattaccca 420
gcaagccttg aacagctaaa acgttgtaaa ccaatctatg aagaattacc gggctggtct 480
gaagatatta cagcttgtcg tagcttagat gatcttccag aaaatgcacg taattacgtt 540
cgccgtgttg gcgaattggt tggtgttcgt atttctactt tctcagttgg gtccagacc 599

<210> SEQ ID NO 331
<211> LENGTH: 598
<212> TYPE: DNA
<213> ORGANISM: Enterococcus faecium
<220> FEATURE:
<221> NAME/KEY: misc_feature
<222> LOCATION: (581)..(581)
<223> OTHER INFORMATION: n is a, c, g, or t

<400> SEQUENCE: 331
ttcttcgaag gggcgcaagg ggttatgctg gatattgacc aagggactta tccatttgta 60
acttcttcta atccagttgc aggggagtca ccatcggttc cggtgttggt ccgagcaaaa 120
ttgacaaggt agttggtgtc tgcaaggcct acaccagtcg ggtcggagat ggaccattcc 180
caacagagct ttttgatgaa gttggtgacc gcattcgtga tatcggccac gaatatggca 240
ctaccactgg tcgcccacgt cgggtaggtt ggtttgactc ggttgttatg cgccatagcc 300

-continued

```
gccgtgtatc agggattacc aatctttcgc ttaactccat cgatgtcttg agtggtctgg    360

atacagtgaa aatctgtgta gcttatgact tggatggcca aagaatcgac cactacccag    420

ctagtctgga acagctcaag cgctgcaagc cgatttacga agagctgcca ggctggtcag    480

aggacatcac tggagtccgc agtctggaag acttgccaga aaatgcccgt aactatgttc    540

gccgagtgag tgagctggtt ggcgttcgca tttctacctt nctcagtagg gccagacc      598
```

<210> SEQ ID NO 332
<211> LENGTH: 598
<212> TYPE: DNA
<213> ORGANISM: Enterococcus durans

<400> SEQUENCE: 332

```
ctctttgaag gggcacaagg tgtgatgttg gatatcgatc aaggaacgta tccatttgtg     60

acttcttcta atccggtagc tggtggtgta acgatcggta gtggcgttgg cccttcaaag    120

atcaataaag tcgttggtgt atgtaaagct tatacttctc gtgtaggaga tggcccattc    180

ccaacagaac tatttgacga aacaggtcaa caaatccgtg aagtcggtcg tgaatatggt    240

acgacaacag gtcgacctcg tcgtgtcggt tggtttgata cagtcgtggt gcgccattca    300

aaacgtgtat caggaatcac taacctatca ttgaattcaa tcgatgtatt aagcggacta    360

gaaacagtaa aaatctgtac agcgtatgaa ttagatggag aattgatcta tcattaccca    420

gcaagcctga aagaattgaa acgttgcaaa ccagtatacg aagaacttcc tggttggtct    480

gaagatatta cagcatgtaa aacacttgct gaactaccag aaaacgcccg taactatgtt    540

agacgtatct cagagcctgt aggagtccgt atttcaacat tctcagtagg tccagacc      598
```

<210> SEQ ID NO 333
<211> LENGTH: 597
<212> TYPE: DNA
<213> ORGANISM: Streptococcus pyogenes

<400> SEQUENCE: 333

```
ctatttgaag gggcacaagg ggttatgctt gatattgacc aggaacgtac ccatttgtaa     60

cgtcttcaaa cccagttgct ggtggtgtaa ccattggttc tggtgttggc ccaaataaaa    120

tcaacaaagt agttggtgtc tgtaaagcct acacaagccg tgtcggtgat gggccattcc    180

ctacagaact ctttgatgaa gtgggtgagc gcattcgtga agtgggtcat gagtacggga    240

caacgaccgg ccgtccacgt cgtgtcggtt ggtttgattc ggttgtcatg cgccacagtc    300

gtcgtgtatc aggtattact aacctctctc tgaattcaat tgatgttctt tcagggcttg    360

atacggttaa gatttgtgtg gcttatgacc ttgatgggaa acgtattgac tattacccag    420

caaaccttga acaactcaaa cgttgcaaac caatctatga agaattacca ggctggcaag    480

aggacatcac aggtgttcgt agccttgatg agcttcctga aaatgcccgc aactacgttc    540

gtcgtgttgg agaattggtt ggcgttcgca tttcaacctt ctcagttggg ccagacc       597
```

<210> SEQ ID NO 334
<211> LENGTH: 599
<212> TYPE: DNA
<213> ORGANISM: Streptococcus pneumoniae

<400> SEQUENCE: 334

```
ctatttgaag gggctcaagg tgttatgcta gatatcgacc aaggtactta tccatttgtt     60

acgtcatcaa accctgtagc tggtggtgtg acaattggtt ctggtgtcgg tccaagcaag    120

attgacaagg ttgtaggtgt atgtaaagct tatacgagtc gtgtaggaga tggtcctttc    180
```

```
ccaactgagt tgtttgatga agtgggagaa cgtatccgtg aagtgggtca tgaatatggt    240

acaacaactg gtcgtccacg tcgtgtaggt tggtttgact cagttgtgat gcgtcatagc    300

cgtcgtgttt ctggtattac taacctttct ttgaactcta ttgatgtttt gagcggtttg    360

gatactgtga aaatctgtgt ggcctatgat cttgacggtc aacgtattga ctactatcca    420

gctagtcttg agcaattgaa acgttgcaag cctatctatg aagagttgcc aggttggtca    480

gaagatatta ccggagttcg caatttggaa gatcttcctg agaatgcgcg taactatgtt    540

cgtcgtgtga gtgaattggt tggcgttcgt atttctactt ttctcagtag gtccaggcc     599
```

<210> SEQ ID NO 335
<211> LENGTH: 598
<212> TYPE: DNA
<213> ORGANISM: Streptococcus oralis

<400> SEQUENCE: 335

```
cttttcgaag gtgcgcaagg tgtcatgttg gacattgatc aagggactta tccatttgtt     60

acttcttcaa accctgtcgc tggtggtgtg acgattgggt ctggtgttgg tccaagtaag    120

attgacaagg ttgtaggtgt ctgtaaagcc tacacaagtc gtgtaggaga tggaccgttc    180

ccaactgaat tatttgatga agtgggagat cgcatccgtg aagtaggtca tgaatatggt    240

acaacaactg gtcgtccacg tcgtgtgggt tggtttgact cagttgtgat gcgtcacagc    300

cgccgtgtat ctgggattac caatctttca ttgaactcta tagatgtttt gagtggtttg    360

gatactgtga aaatctgtgt cgcctatgat cttgatggtc aacgtattga ttactatcct    420

gctagtcttg agcagttgaa acgttgtaag ccaatctacg aggaattgcc aggttggtca    480

gaagacatca ctggagtccg taatttggaa gaccttcctg agaatgcacg caactatgtt    540

cgtcgtgtaa gcgagttggt tggtgttcgt atctcaactt tctcagttgg gccagatc      598
```

<210> SEQ ID NO 336
<211> LENGTH: 598
<212> TYPE: DNA
<213> ORGANISM: Staphylococcus hominis

<400> SEQUENCE: 336

```
ctctttgaag gagcgcaagg agttatgtta gatatcgacc atggtacata tccttttgta     60

acgtcaagta atcctgtggc aggtaatgtg acagtaggaa ctggcgtggg tccaaccttc    120

gtatctaaag tgattggggt atgtaaatcc tatacatctc gtgtaggtga cggcccattc    180

cctactgaat tattcgacga agatggtcat catattagag aagtaggtcg tgaatatgga    240

acgacaacag gacgtcctcg tcgtgtaggt tggttcgact cagttgtatt acgtcactct    300

cgtcgtgtaa gtggtattac agacttatct attaactcaa ttgacgtttt aacaggttta    360

gatacggtta aaatttgtac agcttatgag ttagatggtg aaacaatcac agaatatcca    420

gcaaacttag accaattacg tcgttgtaaa ccaattttcg aagagttacc tggttggacg    480

gaagacatta caggttgtcg tacattagaa gaattacctg aaaacgcacg taaatactta    540

gaacgtattt ctgaattatg tggcgttcat atttcaatct tctcagtagg tccaggcc      598
```

<210> SEQ ID NO 337
<211> LENGTH: 598
<212> TYPE: DNA
<213> ORGANISM: Bacillus anthracis

<400> SEQUENCE: 337

-continued

```
ctatttgaag gtgctcaagg tgttatgctt gatatcgacc acggtacgta cccgttcgtt     60

acatcttcta acccaattgc tggtggtgta acagttggaa ctggagttgg tcctgcgaaa    120

gttactcgcg ttgtaggtgt atgtaaagca tatacaagcc gcgttggtga tggtccattc    180

cctactgagc ttcatgacga aattggtcat caaattcgtg aagttggtcg tgagtatgga    240

acgacaactg gtcgtccacg ccgcgtaggt tggttcgata gcgttgttgt aagacatgca    300

cgtcgtgtta gtggtttaac agatttatca ttaaactcta tcgacgttct aactggtatt    360

ccaacactta aaatttgtgt tgcttacaaa tgcgatggga aagttatcga tgaagttcca    420

gcaaacttaa acattttagc gaaatgtgag cctgtatacg aagagcttcc aggttggaca    480

gaagatatta ctggtgtaag atcattagat gagcttcctg aaaatgctcg aaaatacgta    540

gaacgtgttt ctgagttaac aggagttcaa ttatctatgt tctcagtagg gccagacc      598
```

<210> SEQ ID NO 338
<211> LENGTH: 562
<212> TYPE: DNA
<213> ORGANISM: Bacillus cereus
<220> FEATURE:
<221> NAME/KEY: misc_feature
<222> LOCATION: (4)..(4)
<223> OTHER INFORMATION: n is a, c, g, or t

<400> SEQUENCE: 338

```
gacncggtac gtacccgttc gttacatctt ctaacccaat tgctggtggt gtaacagttg     60

gaactggagt tggtcctgcg aaagttactc gcgttgtagg tgtatgtaaa gcatatacaa    120

gccgcgttgg tgatggtcca ttccctactg agcttcatga tgaaattggt catcaaattc    180

gtgaagttgg tcgcgagtat ggaacgacaa ctggtcgtcc acgccgcgta ggttggttcg    240

atagcgttgt tgtaagacat gcacgtcgtg ttagtggttt aacggatcta tcattaaatt    300

ctatcgacgt tttaacaggt attccaactc ttaaaatttg tgtagcttac aaatacaatg    360

gcgaagttat tgatgaagtt ccagctaact taaacatttt agcgaaatgt gagcctgtat    420

atgaagagct tccaggttgg gaagaagata ttactggtgt aaaatcatta gatgaacttc    480

ctgaaaatgc acgaaaatac gtagaacgtg tttctgagtt aacaggaatt caaatatcta    540

tgttctcagt aggtccccac ca                                             562
```

<210> SEQ ID NO 339
<211> LENGTH: 598
<212> TYPE: DNA
<213> ORGANISM: Bacillus megatherium

<400> SEQUENCE: 339

```
ctattcgaag gggcacaagg tgttatgtta gatatcgatc aaggaacata tccatttgtt     60

acatcttcaa acccagtagc gggtggagta acaattggtt ctggggtagg tccatctaaa    120

atcaaacacg ttgtaggtgt atcaaaagcg tatacaactc gtgttggtga cggccctttc    180

ccaactgaat taacaaacga aatcggtgat caaatccgtg aagtaggacg tgaatatggt    240

acaacaactg gtcgtcctcg ccgtgtaggt tggttcgaca gtgtagttgt acgtcatgct    300

cgtcgcgtta gtggaatcac agatctatct ttaaactcaa ttgatgtatt aacgggaatt    360

gagacattaa agatttgcgt agcttatcgt tataaagggg aagttatgga agaattccct    420

gctagcttaa aaacacttgc agagtgcgaa cctgtatatg aagagcttcc aggttggaca    480

gaagatatta cgggtgtgaa aacattagat gagttacctg ataacgctcg ccactactta    540

gagcgcgtgt ctcaattaac aggtattcct ttatctattt tctcagtagg tccaggcc      598
```

-continued

<210> SEQ ID NO 340
<211> LENGTH: 598
<212> TYPE: DNA
<213> ORGANISM: Enterococcus casseliflavus
<220> FEATURE:
<221> NAME/KEY: misc_feature
<222> LOCATION: (11)..(11)
<223> OTHER INFORMATION: n is a, c, g, or t

<400> SEQUENCE: 340
tattcgaagg nagctcaagg cgtgatgctg gatatcgacc aaggaaccta tcctttcgtg 60
acatcatcca accccgttgc tggaggtgtc accatcggta gtggtgtggg tccttcaaaa 120
atcaacaaag tcgttggtgt ctgcaaagct tacacctctc gggtaggaga tggtcctttc 180
ccaacggaac tgtttgatga aacaggtgaa caaattcgta agatcggtcg tgaatacgga 240
acaacgacag gacgtcctcg ccgtgtgggc tggtttgata ccgtcgtgat gcgccattca 300
aaacgggtct cagggatcac gaatctatcc cttaactcga tcgatgtctt gagcggctta 360
gaaaccgtga agatctgtac ggcttatgaa ctagacggcg aattgatcta tcattaccca 420
gcaagcttga aagagttgaa ccgctgcaaa ccagtctacg aagaacttcc tggctggtct 480
gaagacatta ctggctgcaa aacattagca gatctgccag aaaatgcacg caattacgtt 540
caccgcatct ctgaattagt cggtgtccgc atttcgacct tctcagtagg tccagacc 598

<210> SEQ ID NO 341
<211> LENGTH: 598
<212> TYPE: DNA
<213> ORGANISM: Enterococcus raffinosus

<400> SEQUENCE: 341
ctatttgaag gtgctcaagg cgttatgctg gatattgatc aaggaaccta tccatttgtt 60
acttcttcga acccagttgc cggtggggta actatcggta gtggtgtagg acctgctaaa 120
atcgacaaag ttgtcggtgt ttgtaaagcc tatacttcac gcgtaggtga tggacctttc 180
ccaactgaat tgtttgatga agttggagat cagattcgtg aagtcggtcg tgaatatgga 240
acgactactg gtcgtccacg tcgtgtgggc tggtttgact cggttgtgat gcgtcattca 300
aaacgtgttt ctgggattac gaatctttct ttaaactcga ttgatgtctt gagcggtctg 360
gatacagtga aaatttgtac agcgtatgag ctggacggag aactaattta ccattatcca 420
gcaagcctaa aagaattaaa tcgttgtaag cccgtttatg aagaactacc tggttggagc 480
gaagatatta caggctgccg tgatttagct gatctaccgg aaaatgcgcg taattatgta 540
cgtcgcgttt ctgaacttgt gggtgtgcgt atctcgacct tctcagttgg tcctggtc 598

<210> SEQ ID NO 342
<211> LENGTH: 598
<212> TYPE: DNA
<213> ORGANISM: Staphylococcus aureus

<400> SEQUENCE: 342
ctatttgaag gggcacaagg tgtaatgtta gatatcgacc atggtacata tccattcgtt 60
acatcaagta atccaattgc aggtaacgtt actgttggta caggtgtagg tcctacattc 120
gtttcaaagg taattggtgt atgtaaagct tatacatcac gtgttggtga tggtccattc 180
cctactgaat tattcgatga agatggacat catattagag aagttggtcg tgaatatggt 240
acaacaacag gacgtccacg tcgtgtaggt tggtttgatt cagttgtatt acgtcactct 300

-continued

```
cgtcgtgtaa gtggtattac agatttatct attaactcaa tcgatgtttt aacaggccta    360

gacacagtga aaatctgtac agcttatgaa ttagacggta aagaaattac tgagtaccca    420

gcaaacttag atcaattaaa acgttgtaaa ccaatctttg aagagttacc aggttggaca    480

gaagacgtaa caagtgtgcg tactttagaa gaattacctg aaaatgcacg taaatattta    540

gagcgtattt cagaattatg taatgtacaa atttctatct tctcagtagg tccaggcc      598
```

<210> SEQ ID NO 343
<211> LENGTH: 598
<212> TYPE: DNA
<213> ORGANISM: Staphylococcus epidermidis

<400> SEQUENCE: 343

```
ctcttcgaag gtgctcaagg tgtcatgtta gatatcgacc atggtacata tccattcgtt     60

acatctagta atccagttgc aggtaacgtt acagtaggta caggtgttgg ccctacatca    120

gtgtctaaag tgattggtgt atgtaaatca tatacatctc gtgtaggtga cggtccattc    180

ccaactgaac tttttgatga agatggccac catattagag aagtgggtcg tgaatatggt    240

acaactactg gacgtccacg tcgtgtaggt tggttcgact cagttgtatt acgtcattca    300

cgtcgtgtaa gtggtatcac agatctttca attaactcaa tcgacgtttt aacaggatta    360

gacacagtta aaatttgtac tgcttacgaa ttagatggtg aaaaaattac tgaataccca    420

gcaaacttag atcaattaag acgttgtaaa cctatcttcg aagagcttcc aggttggact    480

gaagacatta caggttgtcg tagtttagat gaacttcctg agaatgcacg taattactta    540

gagcgtattt cagaattatg cggtgtccat atttcaatct tctcagtagg tcctggtc      598
```

<210> SEQ ID NO 344
<211> LENGTH: 567
<212> TYPE: DNA
<213> ORGANISM: Stretpococcus mitis
<220> FEATURE:
<221> NAME/KEY: misc_feature
<222> LOCATION: (11)..(11)
<223> OTHER INFORMATION: n is a, c, g, or t

<400> SEQUENCE: 344

```
tatggctagc natagaccaa ggtacgtatc catttgttac gtcatcaaac cctgtggctg     60

gtggtgttac gattggttct ggtgttggtc caagtaagat tgacaaggtt gtaggtttat    120

gtaaagccta tacgagtcga gtaggagacg gtcctttccc aactgaattg tttgatgaag    180

tgggagaacg tatccgtgaa gttggtcatg aatatggtac aacaactggt cgtccacgtc    240

gtgtgggttg gtttgactca gttgtgatgc gtcatagtcg tcgtgtttct ggtattacta    300

atctttcatt gaactctatc gatgttttga gtggtttaga tacagtgaaa atctgtgtgg    360

cctatgatct tgatggtcaa cgtattgact actatccagc tagtcttgag caattgaaac    420

gttgcaagcc tatctatgaa gagttgccag gttggtcaga agatattact ggagttcgta    480

atttggaaga tcttcctgag aatgcgcgta actatgttcg tcgtgtgagt gaattggttg    540

gcgttcgtat ttctactttc tcagtag                                         567
```

<210> SEQ ID NO 345
<211> LENGTH: 572
<212> TYPE: DNA
<213> ORGANISM: Streptococcus species

<400> SEQUENCE: 345

```
atggcttgct attgaccaag ggtacatacc catttgtaac atcatctaac ccagtcgctg     60
```

-continued

```
gtggtgtaac aatcggttct ggtgttggtc caagtaaaat caacaaagtt gtcggtgtat    120

gtaaagccta cacaagccgt gttggtgacg gaccattccc aactgaactt ttagacgaag    180

ttggtgaccg catccgtgaa gtgggtcacg aatatgggac aacaactgga cgtccacgtc    240

gtgttggttg gtttgactca gttgttatgc gtcacagccg ccgcgtatca ggtatcacaa    300

acttgtcact taactcaatt gacgttcttt caggtcttga tacggtcaaa atctgtgtgg    360

catacgacct tgacggtcaa cgtatcgacc actacccagc aagccttgaa caattgaaac    420

gttgtaaacc aatctacgaa gaattgccag gttggtcaga agacatcaca ggttgccgta    480

gcctagatga acttcccgaa aatgctcgtg actacgttcg ccgtgttggt gaactcgttg    540

gtgttcgcat ttcaacattc tcagttggcc cc                                  572


<210> SEQ ID NO 346
<211> LENGTH: 571
<212> TYPE: DNA
<213> ORGANISM: Streptococcus canis
<220> FEATURE:
<221> NAME/KEY: misc_feature
<222> LOCATION: (9)..(9)
<223> OTHER INFORMATION: n is a, c, g, or t

<400> SEQUENCE: 346

tggcttgcna tcgaccaagg taacttaccc atttgttact tcttcaaacc cagttgctgg     60

tggggtaaca atcggttcag gtgttggtcc aagcaagatc aataaagttg tcggtgtatg    120

taaagcttac acaagccgtg ttggtgacgg tccgttccca acagaacttc tagatgaagt    180

tggagatcgt atccgtgaaa ttggtcacga atatggtaca acaactggac gtccacgtcg    240

tgttggttgg tttgactcag ttgttatgcg tcacagccgc cgcgtatcag gtatcacaaa    300

cttgtcactt aactcaatcg atgttctttc aggacttgat actgttaaaa tctgtgtggc    360

atacgacctt gacggtcaac gtatcgacca ctacccagca agtcttgaac aattgaaacg    420

ttgtaaacca atctacgaag aattgccagg ttggtcagaa gacatcacag gttgccgtag    480

cctagatgaa cttcccgaaa atgctcgtga ctacgttcgc cgtgttggtg aactcgttgg    540

tgttcgcatt tcaacattct cagttggccc c                                   571


<210> SEQ ID NO 347
<211> LENGTH: 573
<212> TYPE: DNA
<213> ORGANISM: Streptococcus mutans
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t

<400> SEQUENCE: 347

tatggcttgc nattgaccaa ggtaacctat ccatttgtaa cttcatcaaa tccagttgca     60

ggtggcgtta ccatcggatc tggtgttgga ccaagtaaaa tcaataaggt tgttggtgtc    120

tgcaaagcct ataccagccg tgtaggtgat ggtcctttcc ccacagaact ttttgaccaa    180

acgggagagc gcattcgtga agttgggcat gaatacggga caacaacagg gcgtccgcgt    240

cgagttggtt ggtttgactc agttgttatg cgtcacagcc gccgtgtatc aggcattacc    300

aatttatctc ttaactgtat tgatgtactt tcaggtcttg atatcgtaaa aatctgtgta    360
```

-continued gcctatgatt tggatggaaa acggattgat cactaccctg ccagtctcga acaactcaaa 420
cgctgtaaac ctatttatga agaattgccg ggctggtctg aagatattac aggggttcgc 480
agtttagaag atcttcctga aaatgctcgt aattatgtcc gccgtgtaag tgaattagtt 540
ggtgttcgta tttctacttt ctcagtngtc ccc 573

<210> SEQ ID NO 348
<211> LENGTH: 572
<212> TYPE: DNA
<213> ORGANISM: Streptococcus gordonii

<400> SEQUENCE: 348
taatgctagc aattgaccaa ggtacctatc catttgtaac ctcatctaat ccagttgctg 60
gtggtgtaac gatcggttct ggtgtgggtc ctagcaagat tgacaaagta gtgggtgttt 120
gtaaagccta tacaagtcgt gttggtgatg gtcctttccc aacagagctt ttcgatgaag 180
taggtgaccg cattcgtgag gttggtcatg agtatggtac aacaacagga cgtccgcgtc 240
gagttggttg gtttgactct gttgttatgc gccatagccg ccgtgtatct gggattacca 300
atctttcgct taactctatc gatgttttga gcggtctgga tacagtcaag atctgtgtag 360
cctatgattt ggatggccaa agaatcgacc actatccagc tagtttggaa cagcttaaac 420
gttgtaagcc gatttacgaa gagcttcctg gatggtctga agatattact ggcgttcgta 480
agttagaaga tcttccagaa aatgctcgca actatgttcg gcgagtaagc gagttggttg 540
gtgtacgtat ttccaccttc tcagttggcc cc 572

<210> SEQ ID NO 349
<211> LENGTH: 571
<212> TYPE: DNA
<213> ORGANISM: Bacillus species
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (565)..(565)
<223> OTHER INFORMATION: n is a, c, g, or t

<400> SEQUENCE: 349
tatggcttgc aattgacncg gtacgtaccc attcgttaca tcttctaacc cgattgcggg 60
tggtgtaaca gttggaactg gagttggtcc tgcgaaagtt actcgcgttg taggtgtatg 120
taaagcatat acaagccgtg ttggtgacgg tccattccct actgaactta atgatgaaat 180
tggtcatcaa attcgtgaag ttggtcgtga gtacggaaca acaactggtc gtccgcgccg 240
cgtaggttgg ttcgatagcg ttgttgtaag acatgcgcgt cgtgttagtg gtttaacgga 300
tctatcatta aattctatcg acgttttaac agatattccg actcttaaaa tttgtgttgc 360
ttacaaatac aatggcgaag ttatcgatga agttccagca aacttaaaca ttttagcaaa 420
atgtgagcct gtatatgaag agcttccagg ttggacagaa gatattactg gtgtaaaatc 480
attagacgag cttcctgaaa atgcacgaaa atacgtagaa cgtgtttctg agttaacagg 540
aattcaatta tctatgttct cagtngtccc c 571

<210> SEQ ID NO 350
<211> LENGTH: 574
<212> TYPE: DNA
<213> ORGANISM: Bacillus pumilus
<220> FEATURE:
<221> NAME/KEY: misc_feature -continued
<222> LOCATION: (570)..(570)
<223> OTHER INFORMATION: n is a, c, g, or t

<400> SEQUENCE: 350
gttatggctt gctattgatc aagggacata tccatttgtc acgtcatcta acccagtagc 60
tggaggagtg acgattggtt ctggcgtagg accaacaaaa attcaacatg tggtcggcgt 120
gtcaaaagcg tacacaacac gtgttggaga tggcccattc ccgacagaac tccatgatga 180
aattggcgat caaatccgtg aggttggccg tgaatacggt acaacaactg gacgtccgcg 240
ccgtgttggc tggtttgaca gtgtcgttgt ccgtcatgct cgacgtgtga gcgggattac 300
agatctatct cttaactcaa ttgatgtact gacagggatt gaaacattga aaatctgtgt 360
cgcttataaa ttgaacggag aaatcacaga ggaattccca gcaagtctaa atgaactagc 420
gaaatgtgag cctgtctacg aagaaatgcc aggatggaca gaggatatta caggcgtgaa 480
gaatttaagc gaactgcctg aaaatgcccg tcattattta gagcgcattt cacaattaac 540
aggtattcca ctttccattt tctcagttgn cccc 574

<210> SEQ ID NO 351
<211> LENGTH: 560
<212> TYPE: DNA
<213> ORGANISM: Enterococcus villorum
<220> FEATURE:
<221> NAME/KEY: misc_feature
<222> LOCATION: (557)..(557)
<223> OTHER INFORMATION: n is a, c, g, or t

<400> SEQUENCE: 351
tatcgaccag ggacatatcc atttgttact tcttccatcc agtagcaggt ggtgtaacaa 60
ttggtagtgg cgttggtcca tctaaaatta ataaagtcgt cggagtatgt aaagcttata 120
cttctcgtgt tggagatggc ccgttcccta cagaattatt tgatgaaaca gggcaacaaa 180
tacgtgaagt aggtcgtgaa tatggcacaa caacaggtcg tccacgacga gttggatggt 240
ttgatacggt tgttatgcgc cattcaaaac gtgtatcagg tattacaaat ttatctctta 300
attcgattga tgtattaagc ggattagaaa cagtaaaaat ttgtacggcc tatgaactag 360
atggtgagct gatttatcat tacccagcaa gtttgaaaga attgaaacgt tgtaaaccag 420
tatatgaaga actacctgga tggtctgaag atattacgaa atgcaagaca ctttctgaat 480
tgccagaaaa tgcacgtaac tatgtaagac gtatttctga gcttgtaggt gtacgcatct 540
ccacatttct cagtggnccc 560

<210> SEQ ID NO 352
<211> LENGTH: 563
<212> TYPE: DNA
<213> ORGANISM: Bacillus thuringensis
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t

<400> SEQUENCE: 352
cncggtacgt acccgttcgt tacatcttct aacccgattg cgggtggtgt aacagttgga 60
actggagttg gccctgcgaa agttactcgc gttgtaggtg tatgtaaagc atatacaagc 120
cgtgttggtg acggtccatt ccctactgaa cttaatgatg aaattggtca tcaaattcgt 180

-continued

```
gaagttggtc gtgagtacgg aacaacaact ggtcgtccgc gccgcgtagg ttggttcgat    240

agcgttgttg taagacatgc gcgtcgtgtt agtggtttaa cggatctatc attaaattct    300

atcgacgttc taacagatat tccaactctt aaaatttgtg ttgcttacaa atacaatggc    360

gaagttatcg atgaagttcc agcaaactta aacattttag cgaaatgtga gcctgtatat    420

gaagagcttc caggttggac agaagatatt actggtgtaa aatcattaga cgagcttcct    480

gaaaatgcaa gaaaatacgt agaacgtgtt tctgagttaa caggaattca attatctatg    540

ttctcagtgg ccccngggcc cca                                             563
```

<210> SEQ ID NO 353
<211> LENGTH: 555
<212> TYPE: DNA
<213> ORGANISM: Bacillus mycoides
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (548)..(548)
<223> OTHER INFORMATION: n is a, c, g, or t

<400> SEQUENCE: 353

```
ggtncgtacc cattcgttac atcttctaac ccgattgctg gtggtgtaac agttggaact     60

ggagttggtc ctgcgaaagt tactcgcgtt gtaggtgtat gtaaagcata tacaagccgt    120

gtaggtgatg gtccgttccc tactgagctt catgatgaaa ttggtcatca aattcgtgaa    180

gttggtcgtg aatacggaac aacaactggt cgtccacgcc gcgtaggttg gttcgatagc    240

gttgttgtaa gacatgcacg tcgtgttagt ggtttaacag atctatcatt aaattctatc    300

gacgttctaa caggtattcc aactcttaaa atttgtgttg cttacaaata caatggcgaa    360

gttatcgatg aagttccagc aaacttaaac attttagcga aatgtgagcc tgtatatgaa    420

gagcttccag gttggacaga agatattact ggtgtaagag cattagacga gcttcctgaa    480

aatgcacgaa aatacgtaga acgtgtttct gagttaacag gaattcaatt atctatgttc    540

tcagtggncc cccgg                                                      555
```

<210> SEQ ID NO 354
<211> LENGTH: 581
<212> TYPE: DNA
<213> ORGANISM: Bacillus weihennstephanensis
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (473)..(473)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (576)..(577)
<223> OTHER INFORMATION: n is a, c, g, or t

<400> SEQUENCE: 354

```
tttttttngg aagngcgcaa ggtgttatgc ttgatatcga ccacggtacg tacccgttcg     60
```

-continued

```
ttacatcttc taacccaatt gctggtggtg taacagttgg aactggagtt ggtcctgcga    120

aagttactcg cgttgtaggt gtatgtaaag catatacaag ccgtgttggt gatggtccat    180

tccctactga acttaatgat gaaatcggtc accaaattcg tgaagttggt cgtgaatacg    240

gaacaacaac gggtcgtcca cgccgtgtag gttggttcga tagcgttgtt gtaagacatg    300

cacgtcgtgt tagtggttta acagatttat cattaaactc tatcgatgta ttaacaggta    360

ttccaactgt taaaatttgt gttgcttaca aatgcaatgg cgaagttatc gatgaagttc    420

cagctaactt aaacatttta gcgaaatgtg agcctgtata tgaagagctt ccnggttgga    480

cagaagatgt tactgctgtg aaatcattgg atgagcttcc tgaaaatgca agaaaatacg    540

tagagcgtgt tttctgaatt aacnggaagc caattnncaa g                        581
```

<210> SEQ ID NO 355
<211> LENGTH: 572
<212> TYPE: DNA
<213> ORGANISM: Staphylococcus haemolyticus

<400> SEQUENCE: 355

```
caaggtgtca tgttagatat cgaccatggt acatatcctt tcgtaacttc aagtaaccct     60

gttgcaggta atgtaacagt tggtacaggt gtaggcccaa ctttcgtatc taaagtgatt    120

ggtgtatgta aagcatatac atctcgtgta ggcgatggtc cattccctac agaattattt    180

gatgaaaatg gacatcatat tagagaagtt ggtcgtgaat acggtacaac aacaggacgt    240

ccacgtcgtg taggttggtt tgactcagtt gtattacgtc actctcgtcg tgttagtggt    300

attacagact tatctattaa ctctatcgac gtacttacag gtcttgatac agtgaagatt    360

tgtactgctt acgaattaga tggagaagaa attacagaat atcctgctaa cttagatcaa    420

ttacgtcgtt gtaaaccaat ctttgaagag ttaccaggat gggaagaaga tatcactggt    480

tgccgtacat tagaagaatt accagataac gcacgtaaat acttagaacg catttctgaa    540

ttatgtaatg tacgtatttc aatcttctca gt                                  572
```

<210> SEQ ID NO 356
<211> LENGTH: 578
<212> TYPE: DNA
<213> ORGANISM: Staphylococcus saprophyticus

<400> SEQUENCE: 356

```
gcaaggtgtg atgttagata tcgaccatgg tacatatcca ttcgttcatc aagtaaccca     60

gttgcaggta atgtgactgt cggtggcggt gtaggtccaa cattcgtctc taaagttatc    120

ggtgtgtgta aagcctatac atcacgtgtc ggcgatggtc cattcccaac agaactattt    180

gacgaagatg ggcaccacat ccgtgaagta ggtcgtgaat acggtacaac aacaggacgt    240

ccacgtcgtg taggttggtt cgactcagtt gtattacgtc attctcgtcg tgcaagtggt    300

attacagatt tatctattaa ctcaattgat gtattaacag gccttaaaga agttaaaatc    360

tgtactgctt atgagttaga cggtaaagaa attacggaat acccagctaa cttgaaagac    420

ttacaacgtt gtaagccaat ttttgaaaca ttaccaggtt ggacagaaga tgtgacaggt    480

tgtcgttcat tagaagaatt acctaataat gcgcgtagat acttagaacg tatttctgaa    540

ttatgtgacg tgaagatttc aatcttctca gttggccc                            578
```

<210> SEQ ID NO 357
<211> LENGTH: 583
<212> TYPE: DNA

-continued

<213> ORGANISM: Bacillus subtilis
<220> FEATURE:
<221> NAME/KEY: misc_feature
<222> LOCATION: (542)..(542)
<223> OTHER INFORMATION: n is a, c, g, or t

<400> SEQUENCE: 357

```
ctcaaggggt tatgcttgat attgaccaag ggacataccc gtttgtcact tcatccaacc     60

cggtcgccgg aggggtgacg atcggttcag gcgtaggccc gacaaaaatc cagcacgtcg    120

tcggtgtatc taaagcgtac acaacccgtg tcggtgacgg tcctttcccg actgagctga    180

aagatgaaac cggggatcaa atccgtgaag tcggacgcga atacggcaca acgacaggcc    240

gtccgcgccg tgtcggctgg tttgacagcg ttgttgtccg ccatgcccgc cgcgtcagcg    300

gaatcacaga tctttctctg aactcaatcg atgtgctgac tggcattgaa acattgaaaa    360

tctgtgtcgc ttaccgctac aaaggtgaag tgattgaaga attcccggca agtctgaaag    420

ctctcgcaga gtgtgaaccg gtatatgaag aaatgcctgg ctggacggaa gatatcacag    480

gcgcaaaaac attaagcgat cttcctgaaa atgcgcgcca ttatctggaa cgcgtgtctc    540

anctgacagg tattccgctt tctattttct cagtaggtcc aga                      583
```

<210> SEQ ID NO 358
<211> LENGTH: 598
<212> TYPE: DNA
<213> ORGANISM: Listeria monocytogenes

<400> SEQUENCE: 358

```
tttggaaggg gcgcaagggg ttatgcttga tattgatcaa ggaacatatc catttgtaac     60

ttcaagtaac ccgattgctg gtggcgtaac tatcggtagt ggtgttggtc cttcaaaaat    120

caatcatgtt gttggtgtgg cgaaagctta tacaacacgt gttggtgatg gtcctttccc    180

aacagaatta tttgattcta ttggtgacac tattcgtgaa gtcggtcatg aatatggtac    240

aacgactggt cgtccgcgtc gtgtaggttg gtttgatagc gtagtggttc gtcatgcgcg    300

tcgtgttagt ggattaacag atttatcgtt aacactactt gatgttttga caggaattga    360

gacacttaaa atctgtgtag cttacaaatt agacggaaaa acaattacag agttcccagc    420

aagtttgaaa gatttagctc gttgcgaacc tgtttatgaa gaacttccag gctggacgga    480

agatattact ggagttacat cactagatga tcttccagtg aactgccgcc attacatgga    540

gcgtatcgcc caacttacgg gagtgcaagt ttctatgttc tcagtaggtc ccagacca      598
```

<210> SEQ ID NO 359
<211> LENGTH: 573
<212> TYPE: DNA
<213> ORGANISM: Lactococcus lactis
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t

<400> SEQUENCE: 359

```
tnatgcttga tattgacnag gaacataccc atttgtaact tctcaaaccc agtagctggt     60

ggggtaacga ttggctctgg tgtgggtcca tcaaaaattt caaaagttgt tggtgtttgt    120
```

-continued

```
aaagcctata cttcacgtgt gggtgatggt ccattcccaa cagaactttt tgatgaagtt    180

ggacatcaaa ttcgtgaagt aggacatgaa tatggaacaa caacaggacg tccacgtcgt    240

gttggttggt ttgactcagt cgtaatgcgt catgcaaaac gtgtttctgg cttgacaaat    300

cttagcttga attcaattga cgttctctca ggacttgaaa cagtaaaaat ttgtgttgct    360

tacgaacgta gtaatggtga acaaattact cattatccag catcacttaa ggaattagca    420

gattgcaaac caatctatga agaattgcca ggatggtctg aagatattac ttcatgccga    480

actttagaag agttaccaga agctgctcgt aactatgttc gtcgggttgg tgaactagtt    540

ggcgtacgta tctcgacttt ctcagtngtc ccc                                 573
```

<210> SEQ ID NO 360
<211> LENGTH: 419
<212> TYPE: DNA
<213> ORGANISM: Bacillus anthracis
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (407)..(407)
<223> OTHER INFORMATION: n is a, c, g, or t

<400> SEQUENCE: 360

```
accnntttta cagacgtaaa atagataggt tatatggttg gtataagtaa gatacttgtt     60

cgttcatacg gtctgcagcc attgtgtatt gaattaagtc atttgttccg atagagaaga    120

aatcaacttc ttttgcgaat tgatctgcta atactgctga agctgggatt tcaaccatca    180

taccaacttc aatagaatca gaaacagttg tacccacttc tacaagtttc gctttttctt    240

ctaataagat cgcttttgct tgacggaact catcaagagt tgcaatcatt gggaacataa    300

tttttaagtt accgtatacg ctagcacgaa gtaatgcacg aagttgtgta cggaacacat    360

cttgctcatc aagacataag cgaattgcac ggtagcccaa gaacggnttc attctctta     419
```

<210> SEQ ID NO 361
<211> LENGTH: 445
<212> TYPE: DNA
<213> ORGANISM: Bacillus cereus

<400> SEQUENCE: 361

```
gccttcttta tgagcagcat cgataaccat ttttacaaga cgtaaaatag atgggttata     60

tggttggtat aagtatgata cttgttcgtt catacggtct gcagccattg tgtattggat    120

taaatcattt gttccgatag agaagaagtc aacttctttc gcgaattgat ctgctaatac    180

tgctgaagct gggatttcaa ccatcatacc aacttcaata gaatcagaaa cagttgtacc    240

cgcttctaca agtttcgctt tctcttctaa taaaatcgct ttcgcttgac ggaactcatc    300

aagagttgca atcattggga acataatttt taagttaccg tatacgctag cacgaagtaa    360

tgcacgaagt tgtgtacgga acacatcttg ctcatcaaga cataagcgaa ttgcacggta    420

tcccaagaac ggatcattct cgtta                                          445
```

<210> SEQ ID NO 362
<211> LENGTH: 445
<212> TYPE: DNA
<213> ORGANISM: Listeria monocytogenes
<220> FEATURE:
<221> NAME/KEY: misc_feature
<222> LOCATION: (436)..(436)

-continued

<223> OTHER INFORMATION: n is a, c, g, or t

<400> SEQUENCE: 362
gccctcttta tgagaagcat caattaccat ttttactaaa cgtaagatgg atggattgta 60
tggttggtaa aggtaagaaa cgcgttcgtt catacggtcc gcagccattg tatactgaat 120
taagtcattt gttccgatag agaagaaatc aacttctttt gcaaattgat cagcaagaac 180
tgcagcggca ggaatttcaa tcataattcc aagttcgatg gaatcagata cttctgttcc 240
agcagctttt agttttgctt tctcatctag taaaatatca cgtgcttgac ggaattcatt 300
tactgttgca atcatcggga acataatttt taagttacca tatacacttg cgcgaagtaa 360
ggcgcgaagt tgcgtacgga ataattcttc attcgcaaaa caaagacgaa ttgcgcggaa 420
tcccaagaac ggatcnttct cctta 445

<210> SEQ ID NO 363
<211> LENGTH: 444
<212> TYPE: DNA
<213> ORGANISM: Streptococcus pneumoniae
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (425)..(425)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t

<400> SEQUENCE: 363
cgcgtgagct gctttgatcc attgttaatc aagcgtagga ttgatgggtt gtatggttgg 60
taaaggtatg aaacttgttc gttcatacgg tctgctgcca ttgtatattg gatcaagtca 120
tttgtaccaa ttgagaagaa gtcaacttct ttagcaaatt ggtctgcaag catagccgct 180
gcaggaatct cgatcatgat accaacttga atgttatccg caactgcaac accttcagca 240
agaaggtttg ctttttcttc atcaaagact gctttcgctg cacggaattc tttcaagagc 300
gcaaccattg ggaacatgat acgcaattga ccgtgaacag acgcacgaag aagagcacgg 360
atttgtgtgc ggaacatagc atctccagtc tcagagatag agatacgaag agcacggaat 420
ccnangaacg gatccttttt cnta 444

<210> SEQ ID NO 364
<211> LENGTH: 441
<212> TYPE: DNA
<213> ORGANISM: Streptococcus pyogenes
<220> FEATURE:
<221> NAME/KEY: misc_feature
<222> LOCATION: (419)..(419)
<223> OTHER INFORMATION: n is a, c, g, or t
<220> FEATURE:
<221> NAME/KEY: misc_feature
<222> LOCATION: (431)..(431)
<223> OTHER INFORMATION: n is a, c, g, or t
<220> FEATURE:
<221> NAME/KEY: misc_feature
<222> LOCATION: (436)..(436)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t

<400> SEQUENCE: 364

-continued tgcgctgctt tgatacattg ttgatcaaac gtaatattga tgggttgtat ggttggtaaa 60
ggtatgatac ttgttcgttc atacggtctg ctgccatagt gtattggata aggtcgtttg 120
ttccaattga gaagaaatca acttccttag caaattggtc tgcaagcata gcagctgcag 180
gaatctcaat catgatacca acttggatgt catcagcaac cgcaacgcct tctgcaagca 240
agtttgcttt ttcttcgtca aagactgctt ttgcagcacg gaattcttta agaagcgcaa 300
ccattgggaa cataatacga agttgtccgt gaacagaggc acgaagaagc gcacgcattt 360
gtgtgcggaa catggcatcc ccagtttcag agatggaaat acgaagagca cggaaaccna 420
agaacggatc nttttnccnt a 441

<210> SEQ ID NO 365
<211> LENGTH: 440
<212> TYPE: DNA
<213> ORGANISM: Streptococcus agalactiae
<220> FEATURE:
<221> NAME/KEY: misc_feature
<222> LOCATION: (431)..(431)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t

<400> SEQUENCE: 365
gagcagcttt gataacgttg ttaatcaaac gaaggattga tggattgtat ggttgataga 60
ggtatgaaac ttgctcattc atacggtccg cagccattgt gtattggata agatcattag 120
taccaattga gaagaaatca acttcttttg caaattggtc tgcaagcata gctgccgctg 180
ggatttcaat cataatacca acttcaatgc cttcagctac tgctacaccg tcagctaaca 240
agttcgcttt ctcttcttca aatatagctt tagcagcacg gaattcttta agcaaagcaa 300
ccattgggaa catgatgcgt agctgtccat gaactgaagc acgaagaagt gctcggattt 360
gtgtgcggaa cattgcatca ccagtttcag aaattgaaat acgcaatgca cggaatccca 420
agaacggatc ntttttcnta 440

<210> SEQ ID NO 366
<211> LENGTH: 439
<212> TYPE: DNA
<213> ORGANISM: Streptococcus mutans

<400> SEQUENCE: 366
tgagcagcct taacccatga tcaaccaagc gaagaatgga tggattataa ggttggtaga 60
ggtatgatac ttgttcattc atacggtcag cagccatggt gtattgaata aggtcatttg 120
taccgattga gaagaaatca acttccttag caaattggtc agccaacatt gcagctgcag 180
gaatttcaat catgatacca acttggatat catctgaaac agcaacgcct tcagctttaa 240
gattagcctt ttcttcttcc agaatacctt tagctttacg gaactcattg agcaaagcta 300
ccattgggaa catgatacgc aactgaccat gaacagaagc acgcaaaagg gcacgcaact 360
gtgtgcggaa catctgattg cctgtttctg agattgaaat acgaagtgca cgaaaaccaa 420
agaacggatc attctctta 439

<210> SEQ ID NO 367
<211> LENGTH: 445
<212> TYPE: DNA
<213> ORGANISM: Enterococcus flavescens
<220> FEATURE:

-continued

<221> NAME/KEY: misc_feature
<222> LOCATION: (436)..(436)
<223> OTHER INFORMATION: n is a, c, g, or t

<400> SEQUENCE: 367
cgtcgtgtgc tgcatcaatt acatttttaa ttaaacgtaa gattgatggg ttgtatggtt 60
ggtataagta agaaacgcgt tcgttcatac ggtctgccgc cattgtgtat tggattaagt 120
cgttggttcc aacactaaag aagtctactt ctttggcaaa tttatcagct aatacggcag 180
ctgctggaat ttcaatcata atacctactt ggatatcgtt tgaaacttca acaccttcgt 240
tgactaattt ttgtttttcg tcttcaaaga ttgctttcgc tgctctaaat tctttcaaag 300
tagcaaccat tgggaacatg atacgtaagt taccatgaac agacgcacgt aataatgcac 360
gcatttgtgt acggaacatg ccgtcaccta gttctgataa gctaatacgt aatgcacggt 420
aacccaagaa cggatnattc tcgta 445

<210> SEQ ID NO 368
<211> LENGTH: 448
<212> TYPE: DNA
<213> ORGANISM: Staphylococcus aureus
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t

<400> SEQUENCE: 368
nncccntctt atgtgacgct tcaataactt gtttaactaa acgtaagatt gaagggttat 60
atggttggta tagatatgat acacgctctg acatacggtc agcagctaat gtgtattgaa 120
ttaaatcatt tgtaccgata ctgaagaaat ctacttcttt agcaaagaca tcagctaatg 180
ctgctgttgc aggtatctct accatgattc ctaattctat atcatccgaa atgtcatgac 240
cttcattttt aaggtttcct ttttcttcta ataatatagc ttttgcttct ctaaattcgt 300
taattgttgc aaccattggg aacatgatat ttaacttacc ataaactgat gcacgtaata 360
atgcacgtag ctgtggtctg aaaatatctt gttgcgcaag gcataaacga atcgcacggt 420
aacccaagaa cggatccntt ntccttaa 448

<210> SEQ ID NO 369
<211> LENGTH: 443
<212> TYPE: DNA
<213> ORGANISM: Staphylococcus epidermidis
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t

<400> SEQUENCE: 369
cttctttatg agaagcttca ataacttgtt taactaatcg taaaattgaa ggattatatg 60

-continued gttgatataa gtatgaaact cgttcagaca tacggtcagc agctaatgtg tattgaatta 120
agtcattcgt tcctatacta aagaaatcta cttctttagc aaatacatca gcaagtgccg 180
cggtagctgg aatttcaacc ataataccta attcaatatc atctgaaact tcgtaacctt 240
cgcgaagaag attttctttc tcttcaagaa gcattgattt agcgtcacgg aattctttaa 300
ttgttgctac cattgggaac ataatattca atttcccata gactgaagca cgtagtaatg 360
cacgtaattg tggtctaaag atttccggct gtgctaaaca taaacgtatc gcacgataac 420
ccaagaacgg atcnttctnc gta 443

<210> SEQ ID NO 370
<211> LENGTH: 440
<212> TYPE: DNA
<213> ORGANISM: Bacillus thuringensis
<220> FEATURE:
<221> NAME/KEY: misc_feature
<222> LOCATION: (437)..(437)
<223> OTHER INFORMATION: n is a, c, g, or t

<400> SEQUENCE: 370
ctttatgagc agcatcgata accattttta caagacgtaa aatagatggg ttatatggtt 60
ggtataagta tgatacttgt tcgttcatac ggtctgcagc cattgtgtat tggattaaat 120
cattcgttcc gatagagaag aaatcaactt ctttcgcgaa ttgatctgct aatactgctg 180
aagctgggat ttcaaccatc ataccaactt caatagaatc agaaacagtt gtacccgctt 240
ctacaagttt cgctttctct tctaataaaa tcgctttcgc ttgacggaac tcatcaagag 300
ttgcaatcat tgggaacata atttttaagt tgccgtatac gctagcacga agtaatgcac 360
gaagttgtgt acggaacaca tcttgctcat caagacataa gcgaattgca cggtatccca 420
agaacggatc attctcntta 440

<210> SEQ ID NO 371
<211> LENGTH: 446
<212> TYPE: DNA
<213> ORGANISM: Staphylococcus hominis
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t

<400> SEQUENCE: 371
cnccnncctt atgaggaagc ttcaataacc tgtttaacta aacgtaaaat tgctggatta 60
tatggttgat ataaatatga aacacgttca gacatacgat cagctgccat agtatattga 120
attaagtcat tagttcctat actaaagaaa tctacttctt tagcaaagat atcagctaac 180
gcagcagtag aaggaatctc taccatgata cctacttcga tatcatcagc aacttcttgt 240

-continued

```
ccttcgctag ttaatttatc tttttcttct aaaagaatag ctttagcatc tctaaactct    300

ttaatagtag ctaccattgg gaacataata tttaatttac cataagcaga tgcgcgtaat    360

aacgcacgta attgtgttct gaagatgtct tgttgatcta agcacaaacg aattgcacga    420

taacccanga acggattcat ntcnta                                         446


<210> SEQ ID NO 372
<211> LENGTH: 445
<212> TYPE: DNA
<213> ORGANISM: Enterococcus faecium

<400> SEQUENCE: 372

cgcgtgtgct gcatcaatta catttttgat caaacgtaaa attgatgggt tatatggttg     60

gtacaagtaa gaaacgcgtt cgttcatacg gtctgctgcc attgtgtatt gaatcaaatc    120

gttcgtacct acagagaaga aatctacttc ttttgcaaac ttgtctgcta agactgctgc    180

tgctggaatc tcgatcatga tgccgacttg gatcgtatca gatacttcct tgccttcact    240

gatcaatttt tgtttttctt cttcaaagat cgcttttgct gcgcggaatt ctttgagtgt    300

agctaccata gggaacatga tacgtaagtt accatgaaca gatgcacgaa gcaatgcacg    360

catttgtgta cggaacattt cgtcgccttg ttcagataaa ctgatacgca atgcacgata    420

tcccaagaac ggatcattct cctta                                          445


<210> SEQ ID NO 373
<211> LENGTH: 445
<212> TYPE: DNA
<213> ORGANISM: Clostridium perfringens
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (434)..(435)
<223> OTHER INFORMATION: n is a, c, g, or t
<220> FEATURE:
<221> NAME/KEY: misc_feature
<222> LOCATION: (437)..(438)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t

<400> SEQUENCE: 373

cntgtttgtg agctccatct attgtcattt tgattaatct taatacagct ggatgcattg     60

gattgtaaag gtatgatacc ttttcactca ttctgtcagc agctaatgta tattgtatta    120

aatcgttagt tcctattgag aagaaatcaa catgcttagc taattcatca gcataaactg    180

ctgcagctgg gatttcaacc atgatacccc attgaattga atctgagtat gctatacctt    240

ctgcttttaa ctcagctttg cattcttcaa caaatgcttt agcttgttgg aattcttcta    300

atcctgaaat cattgggaac attactgcaa gatttccata aacagaagct cttaataaag    360

ctcttatttg aactctaaag atatcttttc tgtctaagca taatcttata gctctgtatc    420

ccaagaacgg atcnntnntc nttaa                                          445


<210> SEQ ID NO 374
<211> LENGTH: 440
<212> TYPE: DNA
<213> ORGANISM: Bacillus mycoides
<220> FEATURE:
<221> NAME/KEY: misc_feature
```

<222> LOCATION: (431)..(431)
<223> OTHER INFORMATION: n is a, c, g, or t
<220> FEATURE:
<221> NAME/KEY: misc_feature
<222> LOCATION: (437)..(437)
<223> OTHER INFORMATION: n is a, c, g, or t

<400> SEQUENCE: 374
ctttatgagc agcatcgatc accattttta caagacgtaa aattgatggg ttatatggtt 60
ggtataagta agatacacgt tcgttcatac ggtctgcagc cattgtgtat tggattaagt 120
catttgttcc gatagagaag aaatcgactt cttttgcgaa ttgatctgct aatactgctg 180
aagctggaat ttcaaccatc ataccaactt caatagaatc agaaacagtt gtacccgctt 240
ggacaagtct ttctttctct tctaataaaa tcgctttcgc ttgacggaat tcatcaagag 300
ttgcaatcat cgggaacata atttttaagt taccgtatac gctagcacga agtaatgcac 360
gaagttgtgt acggaacaca tcttgttctt caaggcataa gcgaattgca cggtatccca 420
agaacggatc nttctcntta 440

<210> SEQ ID NO 375
<211> LENGTH: 455
<212> TYPE: DNA
<213> ORGANISM: Streptococcus oralis
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t

<400> SEQUENCE: 375
cnntttccct tcgcgtgagc tgctttgata acgttgttga tcagcgtagg attgatgggt 60
tgtatggttg gtaaaggtat gaaacttgct cgttcatacg gtctgctgcc attgtgtatt 120
ggatcaagtc gtttgtacca attgagaaga agtcaacttc tttagcaaat tggtctgcaa 180
gcattgctgc tgcaggaatt tcgatcatga taccaacttg gatattatcc gcaactgcaa 240
caccttcagc aagaaggttt gctttttctt cgtcaaagac tgctttcgct gcacggaatt 300
ctttcaagag cgcaaccatt gggaacatga tacgtaattg accgtgaaca gacgcacgaa 360
gaagagcacg gatttgtgtg cggaacatag catctccagt ctcagagata gagatacgaa 420
gagcacggaa tccnaagaac ggatcntttc tctta 455

<210> SEQ ID NO 376
<211> LENGTH: 456
<212> TYPE: DNA
<213> ORGANISM: Enterococcus hirae
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t -continued

<400> SEQUENCE: 376
cnatttacct tcgcatgcgc tgcatcgatc acgtttttaa tcaaacgtag gattgatggg 60
ttgtaaggtt gatacaagta tgaaacacgt tcgttcatac ggtcagctgc catagtgtat 120
tggatcaagt cattcgttcc tactgagaag aagtcaactt ccttagcaaa cttgtcagct 180
aagacagctg ctgctggaat ttcgatcatg atgccgactt ggatcgtatc agatacttcc 240
acgccttcat tcaataattt ttgtttttcg tcttcaaaga ttgcttttgc agcacggaat 300
tctttaagag tcgctaccat tgggaacatg atacgtaagt ttccatgaac agatgcacgt 360
aataatgcgc gcatttgcgt acggaacatt tcgtcacctt gttctgacaa gctgattcgt 420
aatgcacgat agcccaagaa cggatcnttn tcctta 456

<210> SEQ ID NO 377
<211> LENGTH: 457
<212> TYPE: DNA
<213> ORGANISM: Enterococcus avium
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t

<400> SEQUENCE: 377
cnatttncct tcgcgtgcgc tgcatcaatc acgtttttga ttaagcgtag aattgatggg 60
ttatatggtt ggtaaaggta agaaacgcgt tcgttcatac ggtcagctgc catcgtgtat 120
tgaattaagt catttgttcc gatactgaag aaatcaactt ctttggcaaa cttgtcagct 180
agtacagctg cagctggaat ttcgatcatg attccgactt ggatcgtatc agaaacttcc 240
acgccttctt taaccaattt ttctttttct tcgttgaaca ttttcttcgc tgcacggaat 300
tcttttaatg tcgcaaccat tgggaacatg atgcgtaagt taccatgaac agaagcgcgc 360
aacaatgcac gtaattgtgt acggaacatg tcatcgccta gttcggatag actaatacgc 420
aatgcacgat aacccaagaa cggatcnttt ttcttaa 457

<210> SEQ ID NO 378
<211> LENGTH: 437
<212> TYPE: DNA
<213> ORGANISM: Staphylococcus saprophyticus

<400> SEQUENCE: 378
tcgtaagaag cttctattac ttgttttact aaacgtaata ttgaaggatt atatggttga 60
tacaagtaag aaacacgttc tgacattcta tcagcagcca ttgtatattg aattaaatca 120
ttcgttccta tactgaagaa atcaacttct ttagcaaata catctgccaa cgcagcagta 180
gaaggaattt ctaccataat accaagttcg atatcatcag aaacttcaat gccttcattt 240
gttaagttat ctttttcttc aagtaacaat gctttagcat cacggaactc ttggattgta 300
gctaccatag ggaacatgat attcaattta ccaaaagcag atgcacgtaa taatgcacgc 360
aactgtggtc tgaaaatatc aggttgatct aggcataaac ggatagcacg gtaacccaag 420
aacggatcat tctctta 437

-continued

```
<210> SEQ ID NO 379
<211> LENGTH: 430
<212> TYPE: DNA
<213> ORGANISM: Staphylococcus haemolyticus
<220> FEATURE:
<221> NAME/KEY: misc_feature
<222> LOCATION: (419)..(419)
<223> OTHER INFORMATION: n is a, c, g, or t
<220> FEATURE:
<221> NAME/KEY: misc_feature
<222> LOCATION: (422)..(422)
<223> OTHER INFORMATION: n is a, c, g, or t

<400> SEQUENCE: 379

gaagcttcat gacttgttta accaagcgta aaatagctgg gttataaggt tggtataagt     60

atgaaacgcg ttctgacata cggtcagctg ccatagtata ttgaattaaa tcattagtac    120

caatactgaa gaaatccatt tctttagcaa agatatcagc taaagcagct gtagatggaa    180

tctcaaccat gatacctaac tcaatttcat cagaaacgtc atgaccatca tttttaagat    240

tttctttttc ttctaacaga atggctttag catcacggaa ttcattgatt gtagctacca    300

ttgggaacat aatgtttaat ttaccgtaag ctgacgcgcg taataatgca cgtaattgtg    360

ttctgaaaat atcttgttga tctaagcata gacgaattgc tctgtaaccc aagaacggnt    420

cnttctctta                                                          430


<210> SEQ ID NO 380
<211> LENGTH: 444
<212> TYPE: DNA
<213> ORGANISM: Enterococcus flavescens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (438)..(439)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t

<400> SEQUENCE: 380

ngcatgcgct gagtcgatca cgtttttgat caaacgtaaa attgatgggt tgtatggttg     60

gtacaagtaa gacacgcgct cgttcatgcg gtctgcagcc attgtgtatt ggatcaagtc    120

attggtacca atactgaaga agtcaacttc cttcgcaaac ttgtctgcta agacagcagc    180

tgctggaatt tcgatcatga ttccgacttg gatctcgtta gaaacctcaa cgccttcgtc    240

aatcaatttt tgacgctctt cttcatacat tttcttcgca gtacggaact ctttcaatgt    300

tgccaccatt gggaacatga tacgtaagtt gccgtgagca gaagcacgta acaacgcacg    360

aagttgggta cggaacatgt catccccaag ttcagataag ctgatacgca atgcacgata    420

gcccaagaac ggatattnnt cnta                                          444


<210> SEQ ID NO 381
<211> LENGTH: 439
<212> TYPE: DNA
<213> ORGANISM: Enterococcus casseliflavus
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (434)..(434)
```

-continued

<223> OTHER INFORMATION: n is a, c, g, or t

<400> SEQUENCE: 381
gcgctgagtc gatacgtttt tgatcaaacg taaaattgat gggttgtatg gttggtacaa 60
gtaagacacg cgctcgttca tgcggtctgc agccatggtg tattggatca agtcattggt 120
accaatactg aagaagtcaa cttccttcgc aaacttgtct gctaagacag cagctgctgg 180
aatttcgatc atgattccga cttggatctc gttagaaacc tcaacgcctt cgtcaatcaa 240
tttttgacgc tcttcttcat acattttctt cgcagtacgg aactctttca atgttgccac 300
cattgggaac atgatacgta agttgccgtg agcagaagca cgtaacaacg cacgaagttg 360
ggtacggaac atgtcatccc caagttcaga taagctgata cgcaatgcac gatagcccaa 420
gaacggatna tttntctta 439

<210> SEQ ID NO 382
<211> LENGTH: 450
<212> TYPE: DNA
<213> ORGANISM: Enterococcus gallinarum
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (443)..(443)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t

<400> SEQUENCE: 382
accttngcat gtgctgaatc gattacgttt ttgatcaacg tagaatagat gggttatatg 60
gttggtaaag atatgaaact tgttcattca tacggtctgc agccattgtg tattggatca 120
agtcattggt accaatactg aagaagtcta cttccttggc aaatttgtca gctaagacag 180
ctgctgcagg aatttcgatc atgataccta cttgaatatc ttcagagacg gttacgcctt 240
catcgatcaa tttttgacgt tcttcttcgt acattttttt cgcagcacgg aactctttca 300
atgttgccac cattgggaac ataatccgca agtttccgtg agcagaagca cgtaacagcg 360
cacgaagttg tgtacggaac atgccgtcac ccaactcaga caaactgata cgcaatgcac 420
gatagcccaa gaacggatct ttntccntta 450

<210> SEQ ID NO 383
<211> LENGTH: 443
<212> TYPE: DNA
<213> ORGANISM: Enterococcus raffinosus
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (432)..(433)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t

<400> SEQUENCE: 383
ntgtgctgca tcaatgacgt ttttaatcaa acgtaagatt gatgggttat atggttgata 60
caggtatgaa acgcgttcgt tcatacggtc agcagccatt gtgtattgaa tcaagtcgtt 120

-continued tgttccgata ctaaagaagt caacttcttt tgcaaacttg tcagctagaa cagctgcggc 180
agggatctcg atcatgattc cgacttgaat cgtatcagaa accttcacgc cttcgttaac 240
aagcttttct ttttcttcgt tgaacatttt cttcgctgca cggaactctt ttaatgttgc 300
aaccattggg aacatgatgc gtaaattgcc atgaactgaa gcgcgtaaca atgcacgtaa 360
ctgtgtacgg aacatatcgt cgcctaattc agataaactg atacgcaatg cacgataacc 420
caagaacgga tnnttctncg taa 443

<210> SEQ ID NO 384
<211> LENGTH: 453
<212> TYPE: DNA
<213> ORGANISM: Enterococcus villorum
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (451)..(451)
<223> OTHER INFORMATION: n is a, c, g, or t

<400> SEQUENCE: 384
ggnctctcgt cgtnagctgc atcaatcacg tttttgatta aacgtaaaat tgatgggtta 60
taaggttggt ataagtatga aacgcgttcg ttcatacggt cagctgccat agtgtattga 120
atcaaatcat ttgttcctac tgagaagaag tcaacttcct tcgcaaactt gtcagctaaa 180
acagcagctg caggaatttc aatcataatg ccgacttgga tcgtatcaga tacttccacg 240
ccttcattca ataacttttg tttttcatct tcaaagattg cttttgcccc acggaattct 300
ttaagtgtcg ccaccattgg gaacatgata cgtaagttac cgtgaacgga tgcacgcaat 360
aacgcacgca tttgtgtacg gaacatttcg tctccttgtt cagaaagact gatacgtaat 420
gcacgatatc cnangaacgg nttatttttc nta 453

<210> SEQ ID NO 385
<211> LENGTH: 442
<212> TYPE: DNA
<213> ORGANISM: Clostridium difficile
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:

-continued

<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t

<400> SEQUENCE: 385
tttnnggang gcntctntcg tangcattgt ctatancagt ctttataagt cttaaaacag 60
ctggatnaaa ttgattgtaa agntaactta tcttttgatt cattctatca actgcacaag 120
tgtattgaat taaatcatta gttcctatag agaagaaatc tacgtgttta gccaatacat 180
cagatatcac agcagcagat ggaacttcta tcatcatacc aatttctaca tctttagcat 240
aagccacacc ttcagaatca agttctgcta aaacttcttt tacaacttct ttagcttgta 300
acaactcttc taaagatgaa atcattggga acatgattct taatcttcca tgaacactag 360
ctctatataa agctctcaat tgagtcttaa atatatcttt tctatctagg caaagtctta 420
ttgctctgta acccaagaac gg 442

<210> SEQ ID NO 386
<211> LENGTH: 444
<212> TYPE: DNA
<213> ORGANISM: Streptococcus mitis
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (424)..(424)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t

<400> SEQUENCE: 386
ngcgtgagct gccttgataa cgttgttgat caagcgaagg attgatgggt tatatggttg 60
gtaaaggtat gaaacttgct cgttcatacg gtctgctgcc attgagtatt ggatcaagtc 120
gtttgttcca attgacatga agtctacttc ttttgcaaat tggtctgcaa gcatcgctgc 180
tgcagggatt tcaatcatga taccaacttg gatatcatcc gcaactgcaa caccttcagc 240
aagaaggttt gccttttctt cttcataaac tgctttggct gcacggaatt ctttcaaaag 300
agcaaccatt gggaacatga tacgcaattg accatgaaca gaagcacgaa gaagagcacg 360
gatttgtgta cggaacattg catctccagt ttcagaaata gagatacgaa gggcacggaa 420
tccnaagaac ggatattttt cnta 444

<210> SEQ ID NO 387
<211> LENGTH: 446
<212> TYPE: DNA
<213> ORGANISM: Bacillus halodurans -continued
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (424)..(424)
<223> OTHER INFORMATION: n is a, c, g, or t
<220> FEATURE:
<221> NAME/KEY: misc_feature
<222> LOCATION: (435)..(436)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (443)..(443)
<223> OTHER INFORMATION: n is a, c, g, or t

<400> SEQUENCE: 387
nccttcgcta tgagctgctt taataaccat atcgacgagg cgtaaaatcg cagggtggta 60
tggctgatac aggtaggaga ctcgctcatt catgcggtca gcagccatcg tatattgaat 120
taagtcgttc gttccgatac tgaaaaagtc tacttctttt gcaaaaagat tagccgctac 180
cgccgtcgat gggatttcta ccatgattcc cacttcaatt gaatcggata cgtccactcc 240
ttcactaaga agcttgtctt tttcctcttg catgatcgct tttgcttggc gaagctcttc 300
aagggtggcg atcattggaa acatcacctt taagttaccg tatgtgcttg cgcgaagcaa 360
ggcacggagt tgggtccgga aaatatcttg tttttcaagg cacagacgaa tcgcccggaa 420
accnaagaac ggatnnttnt tcntaa 446

<210> SEQ ID NO 388
<211> LENGTH: 436
<212> TYPE: DNA
<213> ORGANISM: Bacillus weihenstephanensis
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (427)..(427)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t

<400> SEQUENCE: 388
ntgagcagca tcgataacca tttttacaag acgtaaaata gatgggttat atggttggta 60
taagtaagct acttgttcgt tcatacggtc tgcagccatt gtgtattgga ttaagtcatt 120
tgttccaata gagaagaaat caacttcttt tgcgaactga tcagctaata ctgctgaagc 180
tggaatttca accatcatac caacttcaat agaatcagaa acagttgtac ccgctttaac 240
aagtctttct ttctcttcta ataagattgc tttcgcttga cggaactcat caagagttgc 300
aatcattggg aacataattt ttaagttacc gtatacgcta gcacgaagta atgcacgaag 360
ttgtgtacgg aacacatctt gctcatcaag acataagcga attgcacggt atcccaagaa 420
cggatcnttc tcntta 436

<210> SEQ ID NO 389
<211> LENGTH: 458
<212> TYPE: DNA

-continued

<213> ORGANISM: Streptococcus species
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t

<400> SEQUENCE: 389
cnnanttncc ttcgcgtgag ctgctttgat aacgttgtta atcaacgaag gattgatggg 60
ttgtatggtt ggtaaaggta tgaaacttgt tcgttcatac ggtcagcagc cattgtgtat 120
tggataaggt cgtttgttcc gattgagaag aagtcaactt ctttcgcaaa ttggtcagca 180
agcatagctg cagctgggat ttcaatcatg ataccaactt ggatatcatc tgaaacggca 240
acaccttcag ctttaaggtt tgctttttct tcatcaaaga ttgctttagc agcacggaat 300
tctttaagaa gagcaaccat tgggaacatg atacgaagtt gtccgtgtac agatgcacga 360
agaagtgcac ggatttgtgt acggaacatt gcatttcctg tttctgagat agaaatacga 420
agtgcacgga atccnaagaa cggatccttt ttccttaa 458

<210> SEQ ID NO 390
<211> LENGTH: 446
<212> TYPE: DNA
<213> ORGANISM: Streptococcus gordonii
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (431)..(431)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t

<400> SEQUENCE: 390
ntgccttcgc atgagccgcc ttgataacat tgttgatcaa gcgaaggata gatgggttat 60
aaggttgata gaggtaagag acttgttcat tcatccggtc agctgccata gtgtactgga 120
tcaagtcgtt ggtaccaatt gagaagaagt caacttcctt ggcaaattga tccgccaaca 180
tagctgctgc tggaatttca atcatgatac ccacttgaat gttatccgct acagcaacac 240
cttcagcttg caatttcgct ttttcttctt cgtaaactgc tttagcctta cggaattctg 300
ttagaagggc taccattggg aacatgatac gtaattgtcc atgtacagac gcacgtaaga 360
gagcgcggat ttgtgtacgg aacatagcat taccagtttc agagatagag atacgcaaag 420
cacggaagcc naagaacggt cntttt 446

<210> SEQ ID NO 391
<211> LENGTH: 446
<212> TYPE: DNA
<213> ORGANISM: Streptococcus canis
<220> FEATURE:
<221> NAME/KEY: misc_feature -continued
<222> LOCATION: (2)..(2)
<223> OTHER INFORMATION: n is a, c, g, or t
<220> FEATURE:
<221> NAME/KEY: misc_feature
<222> LOCATION: (424)..(424)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t

<400> SEQUENCE: 391
cncgtgagct gctttgataa cgttgttaat caaacgaagg attgatgggt tgtatggttg 60
gtaaaggtat gaaacttgtt cgttcatacg gtcagcagcc attgtgtatt ggataaggtc 120
gtttgttccg attgagaaga agtcaacttc tttcgcaaat tggtcagcaa gcatagctgc 180
agctgggatt tcaatcatga taccaacttc gatatcatct gaaacggcaa caccttcagc 240
tttaaggttt gctttttctt catcaaagat tgctttagca gcacggaatt ctttaagaag 300
agcaaccatt gggaacatga tacgaagttg tccgtgtaca gatgcacgaa gaagtgcacg 360
gatttgtgta cggaacattg catttcctgt ttctgagata gaaatacgaa gtgcacggaa 420
tccnaagaac ggtcnttttt ctctaa 446

<210> SEQ ID NO 392
<211> LENGTH: 437
<212> TYPE: DNA
<213> ORGANISM: Bacillus pumilus
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (415)..(415)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t

<400> SEQUENCE: 392
cntacgctgc ttcataacaa gcgtaatcaa acgtaaaatc gctggattgt aaggctggta 60
aagataagac actcgttcgt tcattcgatc agcagccatt gtgtattgaa tcaaatcatt 120
tgttccaata ctgaagaaat caacttcttt tgcgaattgg tctgcgatga cagcggttga 180
tggaatttct accattatac cgatttcaat ggaatcggat acgtctgtac cagcggcaac 240
caatgcttct ttttcttcaa gtaaaatggc ttttgcttct ctaaattctg ataatgtcgc 300
gatcataggg aacatgattt tcaagtttcc atatgtactt gcacgaagta aggcgcgtag 360
ttgtgttctg aaaatctcct gttcttcgag gcaaaggcgg atcgctctaa agccnaagaa 420
cggatntttt tcnttaa 437

<210> SEQ ID NO 393
<211> LENGTH: 437
<212> TYPE: DNA
<213> ORGANISM: Bacillus species
<220> FEATURE:
<221> NAME/KEY: misc_feature
<222> LOCATION: (426)..(426)
<223> OTHER INFORMATION: n is a, c, g, or t
<220> FEATURE:

-continued

<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (431)..(431)
<223> OTHER INFORMATION: n is a, c, g, or t

<400> SEQUENCE: 393
tgagcgcatc gataaccatt tttacaagac gtaaaataga tgggttatat ggttggtata 60
agtatgatac ttgttcgttc atacggtctg cagccattgt gtattggatt aaatcatttg 120
ttccgataga gaagaagtca acttctttcg cgaattgatc tgctaatact gctgaagctg 180
ggatttcaac catcatacca acttcaatag aatcagaaac agttgtaccc gcttctacaa 240
gtttcgcttt ctcttctaat aaaattgctt ttgcttgacg gaactcatca agagttgcaa 300
tcattgggaa cataattttt aagttaccgt atacgctagc acgaagtaat gcacgaagtt 360
gtgtacggaa cacatcttgc tcatcaagac ataagcgaat tgcacggtat cccaagaacg 420
gatccnttnt nctttaa 437

<210> SEQ ID NO 394
<211> LENGTH: 443
<212> TYPE: DNA
<213> ORGANISM: Lactococcus lactis
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (422)..(422)
<223> OTHER INFORMATION: n is a, c, g, or t
<220> FEATURE:
<221> NAME/KEY: misc_feature
<222> LOCATION: (430)..(431)
<223> OTHER INFORMATION: n is a, c, g, or t
<220> FEATURE:
<221> NAME/KEY: misc_feature
<222> LOCATION: (437)..(437)
<223> OTHER INFORMATION: n is a, c, g, or t

<400> SEQUENCE: 394
gtgagctgct ttgatncatt gttaatcaaa cgaaggattg atggattgta aggttggtaa 60
aggtaagaaa cttgttcatt catacggtct gcagccattg tatattggat gaggtcgttt 120
gtaccaattg agaagaaatc aacttcctta gcaaattggt ctgcaagcat tgctgctgct 180
ggaatttcaa tcatgatacc tacttcgata ccatctgcaa ctggaacacc ttcagcaatc 240
aattttgctt tttcttcgtc ataaatcttc ttagctgcac ggaactcagt tacgagagca 300
accattggga acatgatacg aagttgtccg tgtacagaag cacgcaagag tgcacgcaat 360
tgtgtacgga acattccgtc accagctgtt gaaaggctga tacgaagtgc acgccatccc 420
angaacggtn ntttttnttt taa 443

<210> SEQ ID NO 395
<211> LENGTH: 454
<212> TYPE: DNA
<213> ORGANISM: Bacillus firmus
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t -continued
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (449)..(449)
<223> OTHER INFORMATION: n is a, c, g, or t

<400> SEQUENCE: 395
tccaggangg gttctntcnt angctgcgtc aattaccatt ttaactaaac gcaggattgc 60
aggattatac ggctggtaaa ggtaagaaac acgctcattc atgcggtctg cagccattgt 120
gtactgaatt agatcattag tgccaacact gaagaaatcg acttctttag caaactgatc 180
agccataaca gcagttgaag gaatttcaac cataattcca atttcaatgt tgtcggcaac 240
ctctgctcct tcgctcacaa gcttttgttt ttcttcttca aggattgctt tgccctgacg 300
gaattcttca agagtggcaa tcatagggaa catgatttta aggtttccat aggtgcttgc 360
tcttaataaa gcccttaatt gcgtcctgaa catatcctgt tcttccagac acagacgaat 420
cgcccggaag cccaagaacg gattcattnt ctta 454

<210> SEQ ID NO 396
<211> LENGTH: 434
<212> TYPE: DNA
<213> ORGANISM: Haemophilus influenzae
<220> FEATURE:
<221> NAME/KEY: misc_feature
<222> LOCATION: (425)..(426)
<223> OTHER INFORMATION: n is a, c, g, or t

<400> SEQUENCE: 396
tgagaggcat caatcacttg tttaattaaa ccaagcacag aggggtgcat cggattataa 60
agatgggaaa taaactcatt accgcgatct acagccaaag tatattgagt taaatcgtta 120
gtaccgatac taaagaaatc cacttctttt gctaaaaatt ttgcatttac tgcggcagag 180
ggggtttcga ccattacacc aacttggata ttattatcaa acagtctccc ctcttcacgt 240
aattccgctt ttaatgtttc aataaccgct tttaattccc gaatttcttc tacagaaata 300
atcatcggga acattaccgc caatttacca aaagctgaag cacgtaacac cgcgcgtaat 360
tgtgcattta aaatttcacg acgatctaat gcaatgcgaa tcgcacgcca tcccaagaac 420
ggatnntttt tctt 434

<210> SEQ ID NO 397
<211> LENGTH: 442
<212> TYPE: DNA
<213> ORGANISM: Streptococcus bovis
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t

<400> SEQUENCE: 397

-continued

```
tgagctgctt tgataacgtt gttaatcaaa cgaaggattg atgggttata tggttggtaa     60

aggtatgaaa cttgttcatt catacggtca gcagccattg tgtattggat aaggtcgttt    120

gttccgattg agaagaagtc aacttctttt gcaaattggt cagcaagcat agctgcagct    180

gggatttcaa tcatgatacc aacttggata tcatctgaaa cggcaacacc ttcagcttta    240

aggttagctt tttcttcatc aaagattgct ttagcagcac ggaattcttt aagaagtgca    300

accattggga acatgatacg aagttgtccg tgtacagatg cacgaagaag tgcacggatt    360

tgtgtacgga acattgcatt tcctgtttct gagatagaaa tacgaagtgc acggaatccn    420

aagaacggtc cntttttnct ta                                             442
```

<210> SEQ ID NO 398
<211> LENGTH: 443
<212> TYPE: DNA
<213> ORGANISM: Enterococcus durans
<220> FEATURE:
<221> NAME/KEY: misc_feature
<222> LOCATION: (431)..(432)
<223> OTHER INFORMATION: n is a, c, g, or t

<400> SEQUENCE: 398

```
tgtgctgcat caatcacgtt tttgatcaaa cgtaaaattg aagggttata aggttgatac     60

aagtaagata cacgttcgtt catgcggtca gctgccattg tgtattgaat caagtcattc    120

gtacctactg agaagaagtc aacttccttc gcaaacttat ctgctaagac agctgctgca    180

gggatttcaa tcatgatgcc gacttggatc gtatcagata cttccacgcc ttcgctcact    240

aatttttgtt tttcttcttc aaagattgct ttcgctgcac ggaattcttt aagagtcgct    300

accattggga acatgatgcg taagtttcca tgaacagatg cacgtaacaa tgcgcgcatt    360

tgtgtacgga acatttcgtc acctaattca gacaagctga tacgtagcgc acgatagccc    420

aagaacggat nnttttccct taa                                            443
```

<210> SEQ ID NO 399
<211> LENGTH: 450
<212> TYPE: DNA
<213> ORGANISM: Streptococcus sanguis
<220> FEATURE:
<221> NAME/KEY: misc_feature
<222> LOCATION: (434)..(435)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t

<400> SEQUENCE: 399

```
cgcatgagct gccttgataa cattgttaat caagcgaagg atagatggat tgtaaggttg     60

atagaggtaa gagacttgct cattcatccg gtcagccgcc atagtgtact gaatcaagtc    120

gttagtacca attgagaaga agtctacttc cttggcaaat tgatccgcca acatagctgc    180

tgctgggatt tcaatcatga tacccacttg gatattatct gctactgcaa cgccttcagc    240

ttgcagctta gctttttctt cgtcataaac cgctttagct ttgcggaatt ctgtcagaag    300

ggccaccatt gggaacatga tacgcaattg tccatgtaca gaagcacgca agagagcgcg    360

gatttgtgta cggaacatag catcgccagt ttcagagata gagatacgca aagcacggaa    420

accaaagaac ggtnnttttt ntctttaaaa                                     450
```

<210> SEQ ID NO 400
<211> LENGTH: 453

-continued

<212> TYPE: DNA
<213> ORGANISM: Escherichia coli
<220> FEATURE:
<221> NAME/KEY: misc_feature
<222> LOCATION: (440)..(441)
<223> OTHER INFORMATION: n is a, c, g, or t

<400> SEQUENCE: 400
tcctttacct tctgcatgag agcatcaata acttgcttga tcaagttcag tacggacggt 60
gacattggct ggtagagatg tgaaatcata tcattaccac ggtcaactgc cagggtgtac 120
tgcgttaaat cattggtgcc gatactaaag aaatcaactt ctttggctaa atgacgcgca 180
atggtcgcgg ctgctggtgt ttccaccatt acgccgatct caattgactc gtcaaatgct 240
ttaccttcgt cacgcaattc ctgtttgtag atctcgatct ctttcttcag tgcacgcact 300
tcttcaacag agatgatcat cgggaacata atgcgcagct taccgaaagc agaggcacgc 360
agaatcgcac gcacctggtc acgcaggatt tctttacgat ccatggcgat acgcactgca 420
cgccagccca agaacggatn nttttttctt taa 453

<210> SEQ ID NO 401
<211> LENGTH: 449
<212> TYPE: DNA
<213> ORGANISM: Serratia liquefasciens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (427)..(427)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (445)..(445)
<223> OTHER INFORMATION: n is a, c, g, or t

<400> SEQUENCE: 401
ntgncttctg catgagnatg catcaataac ctgtttgatc aggccaagca ctgatgggga 60
catcgggtta tagagatgag aaatcagctc attgccgcga tctaccgcca gagtatactg 120
ggttagatcg tttgtcccaa tactaaagaa gtcgacttct ttcgccaggt gatgagcaat 180
cactgccgcg gccggtgttt ccaccattac gcccacttca atggtctcgt caaaggcctt 240
ggattcttca cgcagctgcg ccttcagcgt ctcgatttca cctttcagat cgcggacttc 300
ttccacggaa atgatcatcg ggaacatgat gcgcagtttg ccgaacgcgg aagcgcgcag 360
gatggcgcgc agttgcgcgt gcaggatttc tctgcggtcc atggcgatac gaatcgcgcg 420
ccagccnaag aacgnttntt tttanttta 449

<210> SEQ ID NO 402

-continued

<211> LENGTH: 425
<212> TYPE: DNA
<213> ORGANISM: Proteus mirabilis

<400> SEQUENCE: 402
gtgtgatgca tcaatcacct gtttaatcag attaagtaca gcaggtgaca ttggattata 60
tagatgagat atcagctcat ttccacggtc tacagccaga gtatattgtg ttagatcgtt 120
agtcccaata ctgaaaaagt caacttcttt tgccatatgg cgagccataa cagccgctgc 180
tggcgtttca accataacac cgacttcgat agattcatca aaaggcttat tttcttcacg 240
aagctggctt ttcagtattt caagttccgc tttcaatgct cggatctctt caacagagat 300
aatcattgga aacataatac gtagtttacc aaaagcagac gctcttaaga tagcacgtaa 360
ttgtggatga aggatctctt tgcggtcaag acaaatacga attgcacgcc aacccaagaa 420
cggat 425

<210> SEQ ID NO 403
<211> LENGTH: 433
<212> TYPE: DNA
<213> ORGANISM: Proteus vulgaris

<400> SEQUENCE: 403
ccttctgcat gtgatgcatc aataacctgt tttatcaggt taagtactgc tggtgacatt 60
ggattataca gatgagatat cagctcattt ccacggtcta cagccagagt atattgtgtt 120
agatcgttag tcccaatact gaaaaagtca acttcttttg ccatgagacg tgccattacg 180
gccgccgcag ggtttcaac catgacaccg acttcgatag actcatcgaa agttttgttt 240
tctgcacgaa gctggctttt cagtatttca agttctgctt tcaatgcgcg aatctcttca 300
atagagataa tcattggaaa cataatgcgt agtttaccaa aagcagatgc tcttaagata 360
gcacgtaatt gcgaatgaag gatctcttta cggtcaagac aaatacgaat tgctctccaa 420
cccaagaacg gtc 433

<210> SEQ ID NO 404
<211> LENGTH: 503
<212> TYPE: DNA
<213> ORGANISM: Streptococcus pyogenes

<400> SEQUENCE: 404
ttattaggcg ccgaaggggc aaggcatact gctcaatctc tcaggcaaaa ggacagaagg 60
taaaatacaa acaccattaa gaacagtctt agtctttttt gtgtttgctg ttttatcatt 120
gcttcagaag ttgtctcaaa gaaagagata gctttttttct tttggcgtct tcgatgactt 180
ttaggagaga aagatgatag cactcgttaa attaattgat aaccttgttt ggggaccgcc 240
cctcttaatt ttattggttg ggacggggat ttaccttacc agtcatttag gattaattca 300
aatcttaaaa ctaccaagag cctttaaact cattttttca gatgacgaag gacatggaga 360
tatttcatcc tttgctgctc ttgcaactgc ccttgccgct actgtcggaa ctggtaacat 420
tgttggggtt gccactgcta tcaagtctgg tggtcctgga gcgctctttt ggatgtgggt 480
tgccgctttt tttggaatgg ccc 503

<210> SEQ ID NO 405
<211> LENGTH: 469
<212> TYPE: DNA
<213> ORGANISM: Streptococcus oralis

<400> SEQUENCE: 405

-continued

```
ccgtaaaggc accgaagggg caaggcaggt aactgctcaa actctcaggt aaaaggacag     60
agctaggata gaccgctttt tggcatttat ctaagcattc cagagtacat gtatcttgca    120
tgtactcttt cttttggggt tgaaagatag gagaaggaca tgttagaatt gcttaaagcg    180
cttgatgctt ttgcttgggg gcctcccctc ttgatcttat tggtcggaac gggtatctat    240
ttgaccatcc gactgggcct tttgcaggtt actcgtctcc ctaaggcctt tcagttgatc    300
tttaccaagg acaaggggca cggcgatgtg tcgagctttg ctgctctctg tacggctcta    360
gcagccacag ttggtacggg aaatatcatc ggggtagcga cagccattaa ggttggagga    420
ccaggggccc tcttttggat gtggatggcg gccttctttg gaatggccc                469
```

<210> SEQ ID NO 406
<211> LENGTH: 467
<212> TYPE: DNA
<213> ORGANISM: Streptococcus faecalis

<400> SEQUENCE: 406

```
gtaaaggcac cgaaggggca aggcaggtaa ctgctcaaac tctcaggtaa aaggacagag     60
ctaggataga ccgctttttg gcatttatct aagcattcca gagtacatgt atcttgcatg    120
tactctttct tttggggttg aaagatagga gaaggacatg ttagaattgc ttaaagcgct    180
tgatgctttt gcttgggggc ctcccctctt gatcttattg gtcggaacgg gtatctattt    240
gaccatccga ctgggccttt tgcaggttac tcgtctccct aaggcctttc agttgatctt    300
taccaaggac aaggggcacg gcgatgtgtc gagctttgct gctctctgta cggctctagc    360
agccacagtt ggtacgggaa atatcatcgg ggtagcgaca gccattaagg ttggaggacc    420
aggggccctc ttttggatgt ggatggcggc cttctttgga atggccc                  467
```

<210> SEQ ID NO 407
<211> LENGTH: 578
<212> TYPE: DNA
<213> ORGANISM: Streptococcus agalactiae

<400> SEQUENCE: 407

```
tataagtagc aacatctttg tattgacacc aagatgtgct ctaggcgccg aaggggcaag     60
aagagtaaaa caactcctcc aatctctcag gcaaaaggac agaagctaaa agccaatatt    120
aataatgagt agtaagctta ttaagtttac tactaccttt atttgtgcgc tttttagcta    180
gcatctttca gaagttatct cttttagaga taacttttt cgtttcatta cagaatccat    240
aggtatgtca tgtatcaaag gagaacatat gctaacactt tttactcata tcaatagctt    300
cgtttggggt ccacctttac ttgctttatt agtcggaaca ggtatttacc tatcatttcg    360
cttaggtttt gttcaattga gacaactttc tagagctttc aaattgattt tccgagaaga    420
taacggacaa ggggatattt caagttatgc tgctcttgca actgctcttg ctgcaacggt    480
agggacaggt aatatcgttg gtgtggctac ggctattaaa tctggaggac caggagcttt    540
gttttggatg tgggtagccg cctttttgg aatggccc                             578
```

<210> SEQ ID NO 408
<211> LENGTH: 468
<212> TYPE: DNA
<213> ORGANISM: Streptococcus pneumoniae

<400> SEQUENCE: 408

```
gtaaaggcac cgaaggggca aggcaggcaa ctgctcaaac tctcaggtaa aaggacagag     60
```

-continued

```
ctaggataga ccgcttttta gcatttatct aagcattcca gagtacatgt atcttgcatg    120

tgctctttct tttggggttg aaacgatagg agaaggaaat gttagaattg cttaaatcaa    180

tcgatgcttt tgcttgggga ccgcccctct tgattttatt ggtcggaaca gggatttacc    240

taaccatgcg gctaggactc ttgcaggttt tgcgtctgcc caaggccttt cagcttattt    300

ttatccagga taagggacat ggtgatgtat ccagttttac agctctgtgt acagccttgg    360

catcaactgt tggaacagga aatatcatag gagttgcgac ggctatcaag gttggtggac    420

caggagctct attttggatg tggatggcgg ttttctttgg aatggccc                  468
```

```
<210> SEQ ID NO 409
<211> LENGTH: 463
<212> TYPE: DNA
<213> ORGANISM: Enterococcus durans
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 409

ngnccgaggg gcaaggtcag nacaactgct caaactctca ggtaaaagga cagagctagg     60

atagaccgct ttttagcatt tatctaagca ttccagagta catgtatctt gcatgtgctc    120

tttcttttgg ggttgaaacg ataggagaag gaaatgttag aattgcttaa atcaatcgat    180

gcttttgctt ggggaccgcc cctcttgatt ttattggtcg gaacagggat ttacctaacc    240

atgcggctag gactcttgca ggttttgcgt ctgcccaagg cctttcagct tatttttatc    300

caggataagg gacatggtga tgtatccagt tttacagctc tgtgtacagc cttggcatca    360

actgttggaa caggaaatat cataggagtt gcgacggcta tcaaggttgg tggaccagga    420

gctctatttt ggatgtggat ggcggttttc tttggaatgg ccc                      463
```

```
<210> SEQ ID NO 410
<211> LENGTH: 536
<212> TYPE: DNA
<213> ORGANISM: Streptococcus anthracis

<400> SEQUENCE: 410

ccccctctcg ctttaaatag cgtagaggaa aacgagcacc gaaggagcaa atccgctact     60

atagcggata atctctcagg taaaaggaca gagacaagcg aaagaaaatg ccgatttgta    120

tcggtttatt tttctatccc ttgtttctcc agagaccatt tcatttactt gaagtggttt    180

ttattttttc taaaaaagga gaataaagat ggagacagta agtaaagtat tagaacaaat    240

caatcactat gtgtggggat taccaacgtt attgttactc gttggtactg gtattattct    300

cacagtgcgt ttaaaaggtt tacagtttag taaactatta tacgctcaca aactagcttt    360

taaaaaatca gaagatacat cttcctctgg agatattagc cacttccaag cgcttatgac    420

agctatggcg gcaacgattg gtatgggaaa tatagctggt gttgcaactg ctgtgacgat    480

cggtggacct ggtgcaatct tttggatgtg gattactgct ttgtttggaa tggccc        536
```

```
<210> SEQ ID NO 411
<211> LENGTH: 537
```

-continued

<212> TYPE: DNA
<213> ORGANISM: Bacillus cereus

<400> SEQUENCE: 411

```
ccccctcacg cctatcatat agtgcagagg aaacagagca ccgaaggagc aaatccgctg     60
tattagcgga taatctctca ggtaaaagga cagagacaag cgaaagaaaa cgccgatttg    120
tatcggttta tttttctatt ccttgtttct ccagagacca tttcatttat gtgaagtggt    180
tttttatttt ttctaaaagg agaataaaga tggagacagt aagtaaagta ttagaacaaa    240
tcaatcacta cgtatgggga ttaccaacct tattcctttt agtcgggact ggaatcattc    300
tcacagtgcg tctaaaaggt ttgcagttta gtaaactgtt atacgctcac aaactagcat    360
ttcgaaaatc agaagataca tcttctttgg gagatattag tcatttccaa gcactcatga    420
cagcaatggc cgccaccatc gggatgggaa atatagctgg tgtcgcaaca gctgttacaa    480
tcggtggacc gggggcaata ttttggatgt ggatcactgc cttgtttgga atggccc       537
```

<210> SEQ ID NO 412
<211> LENGTH: 561
<212> TYPE: DNA
<213> ORGANISM: Streptococcus mutans

<400> SEQUENCE: 412

```
actgataatt gacggacttc tggagagacc tactaggcgc cgaaggggca aggctgtttg     60
ctcaaactct caggcaaaag gacagaaaag aaaaaaagaa tttttaatgt tgaaacaatt    120
cttatcttct aactctagag gtatcgtcaa gtattgacaa cctctttttt gatttccatt    180
tcggtttatg aggagaaaag tttatatgtt aacatttttt aaagctctag acagccttgt    240
ctggggtgct cccctattag ttcttttagt cggtactgga atttatttga gtactcgctt    300
aagattattg caggtgttga aactcccttt agcctttaaa ctcatctttg ccgaggacaa    360
aggggaaggt gatatttcga gttttgcggc tttagctacc gctcttgctg ccactgttgg    420
aactggaaat atcgttggtg ttgccactgc aatcaaagct ggcggtccgg gagcactctt    480
ttggatgtgg atagcagctt tttttggtat ggcaactaaa tatgccgaag gtcttctggc    540
tataaaatac cgtactaagg a                                              561
```

<210> SEQ ID NO 413
<211> LENGTH: 1680
<212> TYPE: DNA
<213> ORGANISM: Listeria monocytogenes

<400> SEQUENCE: 413

```
gttagaaaaa ggaagttcta ttgtagcatc gccaaaaatc catcaaacct tattagataa     60
ctacctgcct taaagaaagc gctcaacata aaaaaacttg ttttcagaaa ataaaaatcg    120
tgccaaatcg gctcagctat gctataatag gtaagttgat ttaaacgaga cgatagcgac    180
ggaggaaaat aaatctattt tcctctttct tttggctaat cttcacgata aatgtttgga    240
tttttaattt aggaggaaac aagattgaat ttaagaaatg atattcgtaa tgtagcaatt    300
attgcccacg ttgaccatgg taaaacaact ctagtagacc aattattacg ccagtcaggc    360
acattccgcg acaatgaaac agttgcagaa cgcgcaatgg acaacaatga tttagaaaga    420
gaacgcggta ttacaatttt agcgaaaaat acagcgatta agtatgaaga tacacgtgta    480
aacatcatgg atacacctgg acacgccgat ttcggtggag aagtagaacg tatcatgaaa    540
atggttgatg gtgttctttt agtagtggac gcgtatgaag gtacgatgcc tcaaacacgt    600
```

-continued

```
tttgtactaa aaaaagcact agaacaaaac ctaactccaa tcgtagtagt aaacaaaatt    660

gaccgtgact ttgctcgccc agaagaagtt gttgatgaag tattagaatt attcatcgaa    720

ctaggcgcaa acgacgatca attagaattc ccagttgttt atgcttctgc aatcaacgga    780

acttcaagct atgattccga tccagcagaa caaaaagaaa caatgaaacc acttttagac    840

acaattatcg aacatatccc ggctccagtt gataatagcg acgaaccatt acaattccaa    900

gtatcattac ttgattataa tgactatgtt ggtcgtatcg gtattggccg cgtattccgt    960

ggaacaatgc acgtgggaca aacagttgct ttaattaaac ttgatggcac agtaaaacaa   1020

ttccgtgtaa cgaaaatgtt cggtttcttc ggactaaaac gtgacgaaat taaagaagca   1080

aaagctggtg atttagtagc attagcaggt atggaagaca tcttcgttgg tgaaacagta   1140

acaccatttg accaccaaga agcacttccg ttattacgta ttgatgagcc aaccttgcaa   1200

atgactttcg taacaaataa cagtcctttc gctggtcgtg aaggtaaaca cgtaacaagc   1260

cgtaaaattg aagaacgttt acttgcagag cttcaaacgg acgtatcttt acgcgtagag   1320

ccaacagctt cccctgacgc ttgggtagtt tctggtcgtg gtgagcttca tttatccatt   1380

ttgatcgaaa caatgcgtcg cgaaggttat gaattacaag tttctaaacc agaagtaatc   1440

atccgtgaaa ttgatggcgt gaaatgtgaa ccagtagaag atgttcaaat tgatactcca   1500

gaagaattca tgggttccgt tattgaatct atcagccaac gtaaaggcga aatgaaaaac   1560

atgattaacg atggcaacgg acaagttcgt ttacaattca tggttccagc tcgtggctta   1620

atcggttata caactgattt cctttcaatg actcgtggtt atggtattat caaccacaca   1680
```

<210> SEQ ID NO 414
<211> LENGTH: 1620
<212> TYPE: DNA
<213> ORGANISM: Listeria innocua

<400> SEQUENCE: 414

```
ataaaaaaac tcattttcag aaaataaaaa tagtgctaaa tccgcttagc tatgctataa     60

taggtaagtt gatttaaacg agacgatagc gacggaggaa aataaatcta ttttcctctt    120

tcttttggct aatcttcacg ataaatgttt ggatttttaa tttaggagga aacaagattg    180

aatttaagaa acgatattcg taatgtagca attattgccc acgttgacca tggtaaaact    240

acactagtag accaattact acgccaatca ggtactttcc gcgacaatga aacagttgca    300

gaacgtgcaa tggacaacaa tgatttagaa agagaacgcg gtattacaat tttagcgaaa    360

aatacagcaa ttaagtatga agatacacgc gtaaacatca tggatacacc tggacacgcc    420

gattttggtg gagaagtaga acgtatcatg aaaatggttg atggtgttct tttagtagtg    480

gacgcgtatg aaggtactat gcctcaaaca cgttttgtac taaaaaaagc actagaacaa    540

aacctaactc caatcgtagt agtaaacaaa attgaccgtg actttgctcg cccagaagaa    600

gttgttgatg aagtactaga attattcatc gaactaggtg cgaacgacga tcaattagaa    660

ttcccagttg tttatgcttc tgcaattaac ggaacttcaa gctttgaatc cgacccagca    720

gaacaaaaag aaacaatgaa accactttta gacactatta ttgaacatat tccagctcca    780

gttgataaca gcgacgagcc attacaattc caagtttctt tacttgatta taatgactat    840

gttggtcgta ttggtattgg ccgcgttttc cgtggaacaa tgcacgtagg acaaacagtt    900

gccttaatta aactagacgg cacagtaaaa caattccgtg taacgaaaat gttcggtttc    960

ttcggactaa aacgtgacga aattaaagaa gcaaaagcgg gtgacttagt agcacttgca   1020

ggaatggaag acatcttcgt cggtgaaaca gtaacaccat ttgaccacca agaagcactt   1080
```

ccacttttac gtattgatga gccaaccttg caaatgactt ttgtaacaaa taacagtcct 1140
ttcgcaggcc gtgaaggtaa acacgtaaca agccgtaaaa ttgaagaacg cttacttgca 1200
gaacttcaaa cggatgtatc tttacgcgtt gaaccaacag cttctccaga cgcatgggta 1260
gtatctggtc gtggtgagct tcacttgtct atcttaattg aaacgatgcg tcgtgaaggt 1320
tatgagttac aagtttctaa accagaagta atcatccgtg aaatcgatgg cgtgaaatgt 1380
gaaccagtag aagacgttca aattgatact ccagaagaat tcatgggttc agttattgaa 1440
tctatcagcc aacgtaaagg cgaaatgaaa aacatgatta acgacggcaa tggccaagtt 1500
cgtttacaat tcatggttcc agctcgtgga ttaatcggtt atacaactga tttcctttca 1560
atgacacgtg gttatggtat tatcaaccat acattcgata gctaccaacc aatccaaaaa 1620

<210> SEQ ID NO 415
<211> LENGTH: 1380
<212> TYPE: DNA
<213> ORGANISM: Bacillus cereus

<400> SEQUENCE: 415
ttactttcac aaaagtaaga atacaactat attttcattc ttgcttttat tttaattgct 60
attgtatccc cttcgctctt ataatagaga aggattaaaa agacattagg agttggacat 120
gttgaaaaaa cgacaagatt tacgtaatat agcaattatt gcccacgttg accatggtaa 180
aacaacactt gttgaccagt tattacgtca agcggggact ttccgtgcga acgaacacgt 240
tgaagaacgc gcaatggatt caaatgatct agaaagagaa cgcggtatta caattttagc 300
gaaaaataca gcgattcact atgaagataa aagaattaac attttagata cacctggtca 360
cgctgacttc ggtggagaag tagaacgtat catgaaaatg gttgatggtg ttttacttgt 420
tgttgatgca tatgaaggtt gtatgccaca aacacgattt gttttaaaga aagctcttga 480
gcaaaactta actccaatcg tagttgtaaa caaaattgac cgtgacttcg ctcgtccaga 540
tgaagtagtt gatgaagtaa tcgacttatt cattgagctt ggtgcaaacg aagatcaatt 600
agagttccca gttgtatttg catcagcaat gaacggaaca gcaagcttag attcaaatcc 660
agcaaatcaa gaagagaata tgaaatcatt attcgataca attatcgaac atattccagc 720
accaattgat aacagcgaag agccacttca attccaagta gcacttcttg attacaacga 780
ctacgttgga cgtattggag ttggtcgcgt attccgcggt acaatgaagg ttggacaaca 840
agttgcttta atgaaagtag acggaagcgt gaagcaattc cgcgtaacga aattattcgg 900
ttacatggga ttaaaacgtc aagaaattga agaagcaaaa gcaggggact tagtagccgt 960
ttctggtatg gaagacatta acgtaggtga aacagtatgt ccagttgaac atcaagatgc 1020
gttaccatta ttacgtattg atgagccaac actacaaatg acgttccttg taaataacag 1080
cccatttgca ggtcgtgaag gtaaatacat tacatctcgt aaaattgaag agcgtcttcg 1140
ttcacaatta gaaacagatg taagtttacg tgtagataat acagattctc ctgatgcgtg 1200
gatcgtatct ggacgtgggg aactacattt atctatctta attgaaaaca tgcgtcgtga 1260
aggttatgaa ttacaagtat ctaagccaga agtaatcatt aaagaagttg atggcgtaag 1320
atgtgagcct gtagagcgcg tacaaatcga tgtacctgaa gaatacactg gttctattat 1380

<210> SEQ ID NO 416
<211> LENGTH: 1680
<212> TYPE: DNA
<213> ORGANISM: Bacillus anthracis -continued

<400> SEQUENCE: 416
ctatattttc attcttgatt ttattttaat tgctattgta tccccttcgc tcttataata 60
gagaaggatt aaaaagacat taggagttgg acatgttgaa aaaacgacaa gatttacgta 120
atatagcaat tattgcccac gttgaccatg gtaaaacaac acttgttgac cagttattac 180
gtcaagcggg gactttccgt gcgaacgaac acgttgaaga acgcgcaatg gattcaaatg 240
atctagaaag agaacgcggt attacaattt tagcgaaaaa tactgcgatt cactatgaag 300
ataaaagaat taacatttta gatacaccag gtcacgctga cttcggtgga gaagtagaac 360
gtattatgaa aatggttgat ggtgtattac ttgttgttga tgcatatgaa ggttgtatgc 420
cacaaacacg atttgtttta aagaaagctc ttgagcaaaa cttaactcca atcgtagttg 480
taaataaaat tgaccgtgac ttcgctcgtc ctgatgaagt agttgatgaa gtaatcgact 540
tattcatcga acttggtgca aacgaagatc aattagagtt cccagttgta tttgcatcag 600
caatgaacgg aacagcaagc ttagattcaa acccagcaaa tcaagaagag aatatgaaat 660
cattatttga tacaattatt gaacatattc ctgcaccaat tgataacagc gaagagccac 720
ttcaattcca agtagcactt cttgattaca acgactatgt tggacgtatc ggggttggac 780
gcgtattccg cggtacaatg aaggttggac aacaagttgc tttaatgaaa gtagacggaa 840
gtgtaaaaca attccgcgta acgaaactat ttggttatat gggattaaaa cgtcaagaaa 900
ttgaagaagc aaaagctgga gacttagtag ctgtttctgg tatggaagac attaacgtag 960
gtgaaacagt atgtccagtt gaacatcaag atgcgttacc attattacgt attgatgagc 1020
caacactaca aatgacattc cttgtaaata acagcccatt tgcaggtcgt gaaggtaaat 1080
acattacatc tcgtaaaatt gaagagcgtc ttcgttcaca attagaaaca gatgtaagtt 1140
tacgcgtaga taatacagaa tctcctgatg cgtggatcgt atctggacgt ggggaactac 1200
atttatctat cttaatcgaa aacatgcgtc gtgaaggtta tgaactacaa gtatctaaac 1260
cagaagtaat cattaaagaa gttgatggcg taagatgtga gcctgtagag cgtgtgcaaa 1320
ttgatgtacc tgaagaatac actggttcta ttatggaatc tatgggtgca cgtaaaggtg 1380
aaatgttaga tatggtgaat aacggaaacg gtcaagttcg ccttactttc atggttccag 1440
cacgtggttt aattggttac acaacagaat tcttaacatt aactcgtggt tacggtattt 1500
taaaccatac attcgattgc taccaaccag tacacgctgg acaagttggt ggacgtcgtc 1560
aaggtgttct agtttcactt gaaacaggaa aagcatcaca atacggtatt atgcaagttg 1620
aagaccgtgg tgtaatcttc gttgaaccag gtacagaagt atatgctggt atgattgttg 1680

<210> SEQ ID NO 417
<211> LENGTH: 1270
<212> TYPE: DNA
<213> ORGANISM: Staphylococcus aureus

<400> SEQUENCE: 417
tcaattatat gatataataa aaaagttgta attaaaagtg ggattttact taagaaagaa 60
ggaaactatt tatatgacta ataaaagaga agatgtccgc aatatagcaa ttattgctca 120
cgttgaccat ggtaaaacaa ctttagtaga tgagttgtta aaacaatctg gtatattcag 180
agaaaatgaa catgtcgatg aacgtgcaat ggactctaac gatatcgaaa gagagcgtgg 240
aattacgatt ctagccaaaa atacggctgt tgattataaa ggtacacgta ttaatatttt 300
ggatacacca ggacatgcag actttggtgg agaagtagaa cgtattatga aaatggttga 360
tggggttgtc ttagtagtag atgcgtatga aggtacaatg cctcaaacac gttttgtact 420

-continued

```
taaaaaagcg ctagaacaaa acctgaaacc tgttgttgtt gttaataaaa ttgataaacc    480
atcagcacgt ccagagggtg ttgtagatga agttttagat ttatttattg aattagaagc    540
aaacgatgaa caattagaat tccctgttgt ttatgcttca gcagtaaatg gaacagctag    600
cttagatcct gaaaaacaag atgataattt acaatcatta tatgaaacaa ttattgatta    660
tgtaccagct ccaattgata acagtgatga gccattacaa ttccaagtag cattgttgga    720
ctacaatgat tatgttggac gtattggtat tggtcgtgta ttcagaggta aaatgcgtgt    780
cggagataat gtatcactaa ttaaattaga cggtacagtg aaaaacttcc gtgtaactaa    840
aatctttggt tactttggat taaaacgttt agaaattgaa gaagcacaag ctggagattt    900
aattgctgtt tcaggtatgg aagacattaa tgttggtgaa actgtaacac cacatgacca    960
tcaagaagca ttgccagttc tacgtattga tgagcctact cttgaaatga catttaaagt   1020
taacaattct ccatttgctg gccgtgaagg tgactttgta acagcacgtc aaattcaaga   1080
acgtttaaat caacaattag aaacagatgt atctttgaaa gtttctaaca cagattctcc   1140
agatacatgg gtagttgctg gtcgcggtga attgcattta tcaatcctta ttgaaaatat   1200
gcgtcgtgaa ggttatgaat tacaagtttc aaaaccacaa gtaattatta aagaaataga   1260
tggtgtaatg                                                          1270
```

<210> SEQ ID NO 418
<211> LENGTH: 1320
<212> TYPE: DNA
<213> ORGANISM: Staphylococcus epidermidis

<400> SEQUENCE: 418

```
accccacctt ttacttatct tttcaataat atatgatata ataaaacagt tgcaattaaa     60
agtgggagta tacacaagaa aggaatttat aaaatgacta atttaagaga agatgttcgt    120
aatatagcga ttattgcgca tgtcgaccat ggtaaaacaa cattagtaga ccagttgctt    180
aaacaatcag gtatatttcg tgaaaacgaa catgtcgacg agcgtgcaat ggactctaat    240
gatttagaaa gagaacgtgg tattacgatt cttgctaaga atacagcgat agattataaa    300
ggaacgcgta tcaatatatt agacacacct ggccacgccg attttggtgg tgaagttgaa    360
cgtatcatga aaatggttga cggtgtcgta ctagtggttg acgcatatga aggtacaatg    420
cctcaaactc gttttgttct taaaaaagct ttagaacaaa acttaaaacc ggttgtagtt    480
gtgaataaaa ttgataaacc agctgctaga cctgagggag ttgtagatga agtattagac    540
ttattcattg aattggaagc gaatgatgag caattagact tcccagttgt ttatgcttca    600
gctgtgaatg gaacagcaag tttagactct gaaaagcaag acgaaaatat gcaatcccta    660
tacgagacga ttattgacta tgtaccggca ccagtagata attcagatga accattacaa    720
ttccaaattg ctttactaga ttataatgat tatgtaggtc gtataggcgt tggacgtgtg    780
ttcagaggta aaatgcgtgt aggtgataat gtatcactaa ttaaattaga tggtacagtt    840
aagaactttc gtgtgacgaa aatatttggt tactttggtc ttaaacgtga agaaattgaa    900
gaagcacaag caggagactt aatagctgtt tcaggtatgg aagatattaa cgttggtgaa    960
acagttacac cacatgatca tcgtgaccca ttaccggtgt tacgtattga tgaaccaacc   1020
ctagaaatga cttttaaagt aaataactct ccgtttgctg gacgtgaagg tgattatgta   1080
acagctcgac aaattcaaga aagattagat caacaacttg aaacagatgt ttctttaaaa   1140
gttacaccta ctgatcaacc agattcatgg gttgttgctg gtcgtggtga actacacttg   1200
```

-continued tctattctta ttgaaaacat gagacgtgaa ggctttgaat tacaggtttc taaacctcaa 1260
gttattttaa gagaaatcga tggtgtgtta agtgaaccat ttgagcgtgt acaatgtgaa 1320

<210> SEQ ID NO 419
<211> LENGTH: 1320
<212> TYPE: DNA
<213> ORGANISM: Bacillus subtilis

<400> SEQUENCE: 419
gaaaaacgtg acgcttttaa agaggatgtg tgatataata tgaaagttat ctaatttttt 60
taggagatga aaaagtgaaa cttcgaaatg atcttcgcaa catcgcgatt attgcccacg 120
ttgaccatgg gaaaacgact ctagtcgatc agcttttaca tcaggctggt acgttccgtg 180
ccaacgaaca ggttgctgaa cgcgcaatgg actctaatga tcttgaacgc gaacgcggca 240
ttacaatatt ggcgaaaaat actgcgatta actataaaga tacacgtatc aatattttgg 300
acacccctgg acatgcagac tttgggggag aagtagaacg gattatgaaa atggttgacg 360
gcgtagtgct tgtcgttgac gcatatgaag gctgtatgcc tcaaactcgt tttgttctga 420
aaaaagctct tgagcaaaac ctgaaccctg ttgttgttgt aaacaaaatt gaccgtgact 480
ttgctcgtcc agaggaagtt atcgatgaag ttctggatct gttcattgag cttgatgcca 540
atgaagagca gctcgagttc ccagtggtat atgcttccgc gattaatgga acagcgagtc 600
ttgatccgaa acaacaggat gaaaacatgg aagctttata tgaaaccatt attaagcatg 660
ttccggcacc tgttgataat gcagaggagc cgcttcaatt ccaagttgcc cttcttgact 720
acaacgacta tgtaggccgt atcggaatcg gacgcgtatt ccgcggcaca atgaaagtcg 780
gacagcaggt ttctcttatg aagcttgacg gaacggcaaa gtcattccgt gttacaaaga 840
tttttggttt ccaaggctta aagcgtgtgg aaattgaaga agcaaaagcg ggagacctcg 900
ttgcggtttc cgggatggaa gatatcaacg ttggtgaaac ggtatgtcct gtagaccatc 960
aagatccgct tccggtcctt cgcattgatg agccgacact tcaaatgaca tttgtcgtga 1020
ataacagtcc gtttgcaggc cgtgaaggca aatatgtaac ggcccgcaaa atcgaagagc 1080
gtcttcaatc acagcttcag acggatgtga gcttgcgtgt tgagccaaca gcttctcctg 1140
atgcttgggt tgtttcagga cgcggtgagc tgcacttgtc aattttaatt gaaaatatgc 1200
gtcgtgaggg ctatgagctt caagtgtcaa aacctgaagt tattatcaaa gaaatcgacg 1260
gcgtacgctg tgagcctgtt gaacgtgtgc aaattgatgt tcctgaagag catactggct 1320

<210> SEQ ID NO 420
<211> LENGTH: 1560
<212> TYPE: DNA
<213> ORGANISM: Streptococcus mutans

<400> SEQUENCE: 420
ggaatggaaa agtaaaagag aagaattagt tctttttttga gataatgaca gggattagta 60
tgagctgttg tcttttgttt ttgcaatact ggttgattga ggacttattt tataaaattt 120
ggagatacca agactgcgac tttgctatct tggtttttct tttatatttt aaaacattta 180
catatctctc ctgagttttt ccctaatttt tatggtataa tagataagtt gaaataaatt 240
aatgtaaaat gtaagaggaa ttatgacaaa ttttagagaa gatattagaa atgttgctat 300
cattgcccac gttgaccatg ggaaaacaac ccttgttgat gagctcttaa aacaatcgca 360
tacacttgat gagcataaaa aattagaaga acgtgcgatg gactctaatg atcttgaaaa 420
agagcgtggg attactattc ttgcaaaaaa tactgctgtt gcctacaatg gtgtacgtat 480

-continued

```
taacattatg gacacaccag gacatgcgga ttttggtgga gaagtagagc gtatcatgaa    540
aatggttgat ggggttgttc ttgttgttga tgcttatgaa ggtaccatgc cgcaaacacg    600
ttttgttttg aaaaaagctt tggaacaaaa cctggttcca atcgtggtgg tgaataagat    660
tgacaagcca tcagctcgtc cggcagaagt tgttgatgaa gttcttgaac ttttcattga    720
acttggagca gatgatgacc agttagagtt tccagtcgtt tacgcttcgg cgattaatgg    780
aacttcttca ttatcagatg aaccagcgga tcaagaacat acaatggcac ccgtttttga    840
tactattatt gagcatattc cagcaccgat cgataattca gatcagccac ttcaatttca    900
agtgtctctc cttgattata acgactttgt tggacgtatc ggtattgggc gagtcttccg    960
tggttctgtt aaagtcgggg atcaagtgac actttctaaa cttgatggta caacaaagaa   1020
ttttcgtgtt acaaaacttt tcggtttctt cggtttggaa cgtcgtgaga ttaaggaagc   1080
taaggctggc gatttgattg ctgtttcagg tatggaagat atctttgttg gtgaaacgat   1140
tacaccaact gatgctgtag aaccacttcc tattcttcac attgatgagc caactctgca   1200
aatgaccttt ttagctaaca attccccttt tgcaggccgt gaaggtaaat ttgtaacctc   1260
gcgtaaggta gaagagcgtt tgttggcaga attgcaaaca gatgtttccc ttcgtgtaga   1320
agccactgac tcaccagata aatggacggt ttcaggtcgt ggggagttac atctgtcaat   1380
ccttattgaa accatgcgcc gtgaaggata tgagctgcaa gtatcgcgtc cagaagttat   1440
tatcaaagaa attgatggca tcaaatgtga gccatttgaa cgcgtgcaaa ttgacacacc   1500
ggaagaatac caaggtgctg ttatccagtc cctttcagaa cgtaaaggtg aaatgcttga   1560
```

<210> SEQ ID NO 421
<211> LENGTH: 1259
<212> TYPE: DNA
<213> ORGANISM: Streptococcus pneumoniae

<400> SEQUENCE: 421

```
aagcggagtg aaaacattta cacttgcttg agttatgtta tttatttgaa attatggtat     60
aatcgttcag ttagaaaata aattttgaat attatagagg aaatcatgac aaaattaaga    120
gaagatatcc gtaacattgc gattatcgcc cacgttgacc acggtaaaac aaccctggtt    180
gacgaattat tgaaacaatc agaaacgctt gatgcacgta ctgaattggc agagcgtgct    240
atggactcaa acgatatcga aaaagagcgt ggaatcacca tccttgctaa aaatactgcc    300
gttgcttaca acggaactcg tatcaacatt atggacacac caggacacgc ggacttcggt    360
ggagaagttg agcgtatcat gaaaatggtt gacggtgttg tcttggtcgt agatgcctat    420
gaaggaacca tgccacaaac tcgtttcgta ttgaaaaaag ccttggaaca agaccttgtc    480
ccaatcgtgg ttgttaacaa aatcgataag ccatcagctc gtccagcaga agtagtggat    540
gaagtcttgg aacttttcat cgagcttggt gcagatgacg accagcttga tttcccagtg    600
gtttatgctt cagcgatcaa cggaacttct tcattgtcag atgatccagc tgaccaagaa    660
gcgactatgg caccaatctt tgacacgatt atcgaccata tcccagctcc agtagataac    720
tcagatgagc ctttgcagtt ccaagtgtca cttttggact acaatgactt cgttggacgt    780
atcggtatcg gtcgtgtctt ccgtggtaca gttaaggttg gggaccaagt taccctttct    840
aaacttgacg gtacaactaa aaacttccgt gttacaaaac tcttcggttt ctttggtttg    900
gaacgtcgtg aaatccaaga agccaaagcg ggtgacttga ttgccgtttc aggtatggaa    960
gacatctttg tcggtgaaac catcactccg acagatgcag tagaagctct tccaatccta   1020
```

-continued cacatcgatg agccaactct tcaaatgact ttcttggtca acaactcacc atttgctggt 1080
aaagaaggta aatgggtaac ttctcgtaag gtggaagaac gcttgcaggc agaattgcaa 1140
acagacgttt cccttcgtgt tgacccaact gattcaccag ataaatggac tgtttcagga 1200
cgtggagaat tgcacttgtc aatccttatc gaaacaatgc gtcgtgaggg ctatgaact 1259

<210> SEQ ID NO 422
<211> LENGTH: 1860
<212> TYPE: DNA
<213> ORGANISM: Streptococcus agalactiae

<400> SEQUENCE: 422
agaaatgaat taaattgaaa aaagtagaaa ataaatggca taaataatga aatgatgaaa 60
agttttctta tcacaaatag gcagttaata tgaaaacatt tacacttgtg taaattctgt 120
tttttaagaa aaattgtgtt ataattcata agttaacaga attacattat aaaatagagg 180
aaaacatgac aaatttaaga acagatatcc gtaacgttgc gatcattgcc cacgttgacc 240
acggtaaaac aactctcgtt gatgaattat taaaacaatc acatactctt gatgagcgta 300
aagagcttga agaacgtgca atggattcaa atgatatcga aaaagaacgt ggtatcacca 360
ttcttgcaaa aaatacagcc gtagcataca acgatgttcg tatcaatatt atggacacac 420
ctggtcacgc ggactttggt ggtgaagttg agcgtattat gaaaatggtt gatggtgttg 480
ttttagtcgt tgatgcctac gaaggaacaa tgccacaaac acgttttgtt ttgaagaaag 540
ctcttgaaca aaacttaatt ccaatcgttg ttgtaaataa aattgataag ccgtcagctc 600
gtccatcaga ggttgttgat gaagttcttg aactatttat tgagctcggt gctgatgatg 660
atcaactaga tttccctgtt gtttatgctt cagctatcaa tggaacatct tcaatgtcag 720
atgatccttc agatcaagaa aaaacaatgg caccgatttt tgatactatc attgatcaca 780
ttccagcccc agttgacaac tcggaagaac cacttcaatt ccaagtttct cttcttgatt 840
acaatgattt tgtaggacgt attggtattg gacgtgtttt ccgcgggact gtcaaagttg 900
gagatcaagt tactctttca aaacttgatg gtacaactaa aaacttccgc gtaacaaaac 960
tttttggttt ctttggactt gaacgtaaag aaatccaaga ggctaaagcg ggtgatttaa 1020
tcgctgtttc tggtatggaa gatatcttcg ttggtgagac agtaactccg acagatgcta 1080
ttgaaccact accagtttta cgtattgacg agccaacact tcaaatgact ttcttggtga 1140
ataattcacc atttgcaggt cgcgaaggta aatggattac gtcacgtaag gttgaagaac 1200
gtcttttagc agaattacaa acagacgttt ctttacgtgt tgacccaaca gattcgccag 1260
ataaatggac ggtttcaggg cgtggagaat tacatttatc tatccttatt gaaacaatgc 1320
gtcgtgaggg atatgaactt caagtatcac gtccagaagt tatcatcaaa gaaattgatg 1380
gtgttcaatg cgagccgttt gagcgtgttc aaattgatac tccagaagaa tatcagggtg 1440
ctattatcca aagtttgtca gagcgtaaag gtgatatgct tgatatgcag atggttggta 1500
atggtcaaac gcgtttgatt ttcttgattc ctgcacgtgg tttgattggt tattcaacag 1560
agtttctttc aatgacacgt ggatatggta tcatgaatca tacttttgac cagtatctac 1620
cggttgttca aggagaaatt ggtggtcgtc atcgtggtgc cttggtttct attgaaaatg 1680
gtaaagcaac tacatattca attatgcgta ttgaagaacg tgggactatc tttgtaaatc 1740
caggtataga agtttatgaa ggaatgattg ttggtgagaa ttctcgtgat aatgacctcg 1800
gagtcaatat tacaactgct aaacaaatga caaatgtccg ttcagcaact aaagatcaaa 1860

<210> SEQ ID NO 423
<211> LENGTH: 1500
<212> TYPE: DNA
<213> ORGANISM: Streptococcus pyogenes

<400> SEQUENCE: 423
gtcttaaaag acggtattga ttattgggat ggcaaagtta aacaaacaac ctagttaaga 60
gtaacgtgga gttaagggga ataaaggcag tcactgtctc aaaaacctta attccttttt 120
ttgctgtatc cagacttgct gaaagtctga aaatatttac aattgattaa aaccagtttt 180
ttaaaacatt ttgtgttata cttatctagt taaaatatat ttacttagag gaacaaatga 240
ctaacttaag aaacgatatc cgtaacgtag cgattattgc ccacgttgac cacggaaaaa 300
caacacttgt agatgaatta ttaaaacaat cccatactct tgatgagcgt aaagagcttc 360
aagagcgtgc catggattcc aatgaccttg aaaaagaacg tgggattaca atccttgcga 420
aaaatacggc agtagcctat aacgatgttc gtattaacat catggatacc ccaggacacg 480
cggacttcgg tggtgaagtt gaacgtatca tgaaaatggt tgacggggtt gttcttgttg 540
tggatgccta cgaaggaaca atgccccaga cgcgtttcgt attgaaaaaa gcacttgagc 600
aaaaccttat cccgatcgtt gtggtgaaca agattgacaa accttcagct cgtccagcag 660
aagttgtaga tgaagtgctt gaattattca tcgaacttgg tgccgatgat gagcaattgg 720
aattcccagt tgtttacgca tcagctatta atggaacatc atcattatca gatgaccctg 780
ctgaccaaga gcatactatg gcaccgatct ttgatacgat tattgatcat attccagcgc 840
cagttgataa ttcagatgag cctttgcaat tccaagtgtc acttttggac tacaacgatt 900
tcgtaggtcg tatcggtatc ggtcgtgttt tccgtggtac tgttaaagtg ggtgaccaag 960
taactctttc aaaacttgat ggtaccacta aaaacttccg tgttacaaaa ctgtttggtt 1020
tcttcggttt ggaacgtcgt gaaattcaag aagctaaagc aggtgacttg attgctgttt 1080
caggtatgga agatatcttt gttggagaaa ccattacacc aactgactgt gtggaagctc 1140
tgccaattct tcgtattgat gagccaacac ttcagatgac tttcttggtc aataactctc 1200
cttttgcagg tcgtgaaggt aaatggatca cgtcacgtaa ggttgaagaa cgtcttttag 1260
cagaattgca aacagacgtg tcacttcgtg ttgacccaac agattcgcca gataaatgga 1320
cggtttcagg gcgtggagaa ttgcatttat ctatcctcat tgaaaccatg cgccgtgaag 1380
gctatgaact tcaagtatca cgtccagaag ttatcatcaa agaaattgat ggtgtcaaat 1440
gtgaaccgtt tgagcgtgtt caaattgata caccagaaga atatcagggt gcaatcatcc 1500

<210> SEQ ID NO 424
<211> LENGTH: 1740
<212> TYPE: DNA
<213> ORGANISM: Enterococcus faecalis

<400> SEQUENCE: 424
catcacgcaa cggaaatcgg acaagcaagc atgggcgtgc gtattagcgg ttgtgcaggt 60
ttggaaatta ttgctatgtt aaaaggcaac catcatggct atttatctaa tctaagtcct 120
tgggattatg cagcaggctt agtacttttg gaagaatttg ggtttaaata ctctggtatt 180
acaggaaaac cattaacttt tgcgggtcgt gaatacttta ttgcagcaac tcctgaaacc 240
tatgatgaag tatttacccg atatttaaat gaatcggaat aatcaaagaa gagcgttgct 300
gaaaggtaag gctcttcctc ttttaaaaga gaaaaatttg taaaaaaatg tccttgtttt 360
cagaaaaagc cgaataattt ctaaaacttt cattattttt gcaggcgaaa gccttttttt 420

-continued

```
aatgaaaaaa gtttgctata ataagcagtc ggcttttatg gacttaagta acataagcgt    480

atatagataa ggagcaatta aattgaaata cagagatgat attcgtaacg tggcaattat    540

cgcccacgtt gaccatggta aaacaacctt agtagatgaa cttttaaaac aatctgacac    600

tttagatgga cacacacaat tacaagaacg tgcaatggat tccaatgcac ttgaaagtga    660

acgtggaatt actatcttag caaaaaatac agccgtagat tataacggta cacgtatcaa    720

cattctagat acaccaggac acgcggactt cggtggtgaa gtagaacgta tcatgaaaat    780

ggtagacggt gttgttttag ttgtcgatgc gtatgaagga acaatgcctc aaacacgttt    840

cgtattgaaa aaagcattag aacaaaaagt aacaccaatc gtggttgtta acaaaattga    900

caaaccttct gctcgtcctg aacacgtagt agatgaagtt ttagagttat tcatcgaatt    960

aggtgcagac gacgatcaat tagatttccc agttgtttat gcttctgctt taaacggaac   1020

ttcaagtgaa tcagatgatc cagcagatca agagccaaca atggccccaa tttttgataa   1080

aattattgaa catgtgccag ctccagttga caattcagac gaaccacttc aattccaagt   1140

ctcattacta gactacaacg attacgttgg acgtattggg attggccgtg tgttccgtgg   1200

cacaatgaaa gtcggcgacc aagttgcgtt gatgaaatta gatggcagcg tgaaaaattt   1260

ccgtgtaacg aaaattttag gtttctttgg cttacaacgt gtggaaattg atgaagcaaa   1320

agcgggcgat ttaattgccg tttctggaat ggaagacatt ttcgttgggg aaacagttgt   1380

agatgttcac aatcaagaag cattaccaat tctacacatt gatgagccaa ccttacaaat   1440

gactttctta gttaacaatt ctccatttgc gggacgtgaa ggaaaataca tcaccgctcg   1500

taaaatcgaa gaacgtttaa tggctgagtt acaaacagac gtatctttac gtgttgatcc   1560

aattggccca gattcttgga ctgtatcagg tcgtggcgaa ttgcatttat caattttaat   1620

tgaaaacatg cgtcgtgaag gctatgaatt acaagtttct cgtccagaag ttattgaacg   1680

tgaaattgat ggagttaaat gtgaaccatt tgaacgtgtt caaattgaca cacctgaaga   1740
```

<210> SEQ ID NO 425
<211> LENGTH: 1620
<212> TYPE: DNA
<213> ORGANISM: Lactococcus lactis

<400> SEQUENCE: 425

```
cgaaaaagca agttaaatat gttgtaaata atggtgttac attagataat actagtggtg     60

ggcctaattt ggctgcacct gtgacggtgg atagtcaggt aatttcgaac gataaaggta    120

cgattatggg tgtaaggacc tatacagcag atttaagcca agcagaagta gttaaaaaag    180

tgggtaattt gaatgcaatg tcctttggag aattttgggg tacaaaagtt tttgctgcca    240

gccaaaatca gacaaattca gataagactt attctgttac gtttaaactg aatataaatt    300

ggatagtatc taatggctat gcttcgctaa caaaagtaac aggtggctat ggttcttgca    360

ttgaccatgt ttatgttgct aattctagtg ttactactgc aacgaatggt cagattaaag    420

gttcaagtgg ttatactcaa caagttgatg acaaatcaga agggaatagt ttatcgtggt    480

caattacgcg aaactataaa cctgtaaaag ttccagcaag tggggcaaat gtaggagcta    540

cgtattttgc cacacttaaa cggggaaata gtacatggaa attccaaaca acaaatagag    600

cttattaagt gggaggaagt ggaatgaata taaaaggcat aaaaatttgg caagtatttc    660

ttgcattcat catttggata ggaaccatgt ttcttcctgc aacggtaaat caggctaaat    720

tgaatacgaa ttttgactat aaaaaaagtc gagaaaattt cttttatttt ctttttcatc    780

aagtcccttt ttatagtttc attttgggat tggtgttgct tatatcactt tttctcattt    840
```

-continued

```
ataggaaaat aaattttagt gtctattttt cttttgctag tcttattttt tacattagtt    900

tcttagttat agcttttccg tctatgatta tttttaatca tagtttatct gggaatactt    960

ttggggctga actttctatc tttctaacct tttatggagc tggatatatt attgctgttc   1020

tatttggttt agttgctttt cttttactct ttctctacag tttaagaata aaagaatgtt   1080

aacaacataa tcatttttac tgattttatt aattataaaa aaataaagaa ctccttagaa   1140

atttttcttt ggggttttca ttttggaagt aaaaaaatct ttgttaggct tgtaaacgtg   1200

tgcatttaca gcttttagaa aagtgtgcta taatgggtta gatatatacg aaagtaaggt   1260

atgataaaat tgactaaatt acgcgaagat attagaaacg tcgctgttat tgcccacgtt   1320

gaccatggta aaactacatt ggttgacgaa ctcttaaaac aatctcaaac gttggatgct   1380

cgtaaagaat tagctgaacg tgcgatggac tcaaatgcac ttgagcaaga acgtgggatt   1440

actatccttg ccaaaaatac agcagttgaa tataacggaa ctcgtatcaa catcttggac   1500

acaccaggtc acgcggactt cggtggagaa gttgaacgta ttatgaaaat ggttgatggg   1560

gttgtcctcg ttgtcgatgc ttatgaagga acaatgcctc aaacacgttt tgttttgaaa   1620
```

<210> SEQ ID NO 426
<211> LENGTH: 670
<212> TYPE: DNA
<213> ORGANISM: Citrobacter freundii

<400> SEQUENCE: 426

```
atctggtaca acaatttctt cggtgctgaa accgaagcga ttctgccgta cgaccagtat     60

atgcaccgtt tcgcggccta cttccagcag ggcaatatgg aatccaatgg taaatacgtt    120

gaccgtaacg gcaatgcggt ggattaccag acaggcccaa tcatctgggg tgagccgggt    180

actaacggtc agcatgcgtt ctaccaactg attcatcagg gtaccaaaat ggttccgtgc    240

gatttcatcg ctccggcaat cacccacaac ccgctgtcgg atcaccatcc gaaactgctg    300

tctaacttct tcgctcagac cgaagcgctg gcttttggta aatcccgcga agtggttgag    360

caggaatacc gcgaccaggg taaagatccg gcaacgcttg accacgttgt gccgttcaaa    420

gtgttcgaag gtaaccgtcc aactaactcc atcctgctgc gcgaaatcac accgttcagc    480

ctgggtgcgc tgattgcgct gtacgagcac aaaatcttca ctcagggcgc gatcctgaat    540

atcttcacct ttgaccagtg gggcgttgag ctgggcaaac agctggcgaa tcgcattctg    600

ccagagctga atgatgataa agaaatcacc agccatgatt gctcaactaa cggtttgatt    660

aaccgctata                                                           670
```

<210> SEQ ID NO 427
<211> LENGTH: 670
<212> TYPE: DNA
<213> ORGANISM: Klebsiella pneumoniae

<400> SEQUENCE: 427

```
atctggtaca acaacttctt cggtgcggaa accgaagcga ttctgccgta cgaccagtac     60

atgcaccgct ttgccgctta cttccagcag ggcaacatgg agtccaacgg taagtatgtt    120

gaccgtaacg gccacgcggt agactaccag actggcccaa tcatctgggg tgagccgggc    180

accaacggtc agcacgcgtt ctaccagctg atccaccagg gcaccaaaat ggtaccgtgc    240

gatttcatcg ctccggctat cacccacaac ccgctgtctg accaccatca gaaactgctg    300

tctaacttct tcgcccagac cgaggccctg gcctttggta aatcccgcga agtggttgag    360
```

-continued caggaatatc gcgatcaggg taaagacccg gcgaccctgg agcacgtggt gccgttcaaa 420
gtgttcgaag gtaaccgccc gactaactcc atcctgctgc gcgagattac cccgttcagc 480
ctcggggcgc tgattgccct gtacgagcac aaaatcttca cccagggcgc gatcctcaac 540
atcttcacct ttgaccagtg gggcgttgag ctgggcaaac agctggctaa ccgcatcctg 600
ccggagctga aagacggcag cgaagttagc agccacgaca gctctactaa cggcctgatt 660
aaccgctata 670

<210> SEQ ID NO 428
<211> LENGTH: 670
<212> TYPE: DNA
<213> ORGANISM: Klebsiella oxytoca

<400> SEQUENCE: 428
atctggtaca acaacttctt cggcgctgaa accgaagcga ttctgccgta cgaccagtat 60
atgcaccgct ttgccgccta cttccagcag ggcaacatgg aatccaacgg taaatacgtt 120
gaccgtaacg gcaacgccgt ggattaccag acgggcccga tcatctgggg cgagccgggc 180
accaacggtc agcacgcgtt ctatcagctg attcaccagg ggaccaaaat ggtgccgtgc 240
gattttatcg ctccggcgat tacgcataac ccgctgtctg accatcatcc gaagctgctg 300
tctaacttct ttgcgcagac cgaagcgctg gcgtttggta aatcccgcga agtggttgaa 360
caggaatatc gcgatcaggg taaagatccc gcgacgctgg aacacgtggt gccgttcaaa 420
gtgtttgaag gcaaccgccc gactaactcc atcctgctgc gtgaaatcac gccgttcagt 480
ctgggcgcgc tgattgccct gtatgaacat aagattttca cccagggcgt gattatgaac 540
atcttcacct tcgaccagtg gggcgttgag ctgggcaaac agctggcgaa ccgcatcctg 600
ccggagctga aggatggttc tgaagtcagc agccacgaca gctccactaa cggcctgatt 660
aaccgctata 670

<210> SEQ ID NO 429
<211> LENGTH: 670
<212> TYPE: DNA
<213> ORGANISM: Escherichia coli

<400> SEQUENCE: 429
atctggtaca acaacttctt cggggctgaa accgaagcga ttctgccata cgaccagtac 60
atgcaccgtt ttgcggccta cttccagcag ggcaacatgg aatccaacgg taaatacgtt 120
gaccgtaacg gtaacgctgt ggattaccag actggcccaa tcatctgggg cgagccaggc 180
actaacggcc agcatgcgtt ctatcagctg atccaccagg gcaccaaaat ggttccgtgc 240
gatttcatcg ccccggccat tacccataac ccgctgtcag accaccatcc gaagctgctg 300
tctaacttct tcgcacagac tgaagcgctg gcgttcggta agtctcgtga cgtggttgag 360
caggaatacc gcgaccaggg taaagatccg gccacgctgg accacgttgt gccgttcaaa 420
gtgttcgaag gcaaccgtcc aaccaactcc atcctgctgc gcgaaattac gccgttcagc 480
ctgggtgcgc tgattgccct gtacgagcat aagatcttca ctcagggcgc tatcctgaac 540
atcttcacct ttgaccagtg gggcgttgag ctgggtaaac agctggcaaa ccgtatcctg 600
cctgaactgg gtgacgataa cgcgattaac agccacgaca gctccacaaa tggtctgatt 660
aaccgctata 670

<210> SEQ ID NO 430
<211> LENGTH: 501

-continued

<212> TYPE: DNA
<213> ORGANISM: Serratia marcescens

<400> SEQUENCE: 430
aagcactttg ccgaaacgcc ggcggagaaa aacctgccgg tgttgctggc gctgatcggt 60
atttggtaca acaacttctt tggcgccgaa accgaagcca ttctgccgta cgatcagtac 120
atgcaccgtt ttgccgctta cttccagcag ggcaagatgg aatccaacgg caagtacgtc 180
gatcgcaacg gcaacccggt ggattaccag accggtcccg tcatttgggg cgagccgggc 240
accaacggcc agcatgcgtt ctatcagttg atccaccagg gcaccaagct ggtgccgtgc 300
gatttcatcg cgccggccat cagccataac ccgctgggcg atcatcacgc caaactgctg 360
tccaacttct tcgctcagac cgaagcgctg gcgttcggca agtcgctgga agtggtggaa 420
gccgagttcg cggcgcaggg caaaactcct gagcaggtca agcacgtggc gccgttcaag 480
gtgtttgaag gcaaccggcc g 501

<210> SEQ ID NO 431
<211> LENGTH: 1103
<212> TYPE: DNA
<213> ORGANISM: Neisseria gonorrhoeae

<400> SEQUENCE: 431
ttcgcccttc gaccttatga ctgaccctga aatggcggat gttacctaca tcgaaccgat 60
tatgtggcag acggtggaga agattatcgc caaggagcgg cccgatgcga ttctgcccac 120
gatgggcggt cagaccgcgc tgaactgtgc gctggatttg gcgcgtaacg gcgtgctggc 180
gaaatacaat gtcgagttaa tcggcgcaac ggaagacgcg atcgacaagg cggaagaccg 240
cggccgcttt aaagaagcga tggaaaaaat cggcctctct tgcccgaaat cttttgtctg 300
ccacaccatg aacgaagcct tggcggcgca agaacaggtc ggctttccga cgctgattcg 360
tccgtctttc acgatgggcg gttcgggcgg cggcattgcc tacaataagg atgagttttt 420
ggcgatttgc gaacgcggtt tcgatgcgtc gcctacgcat gagctgctga ttgagcagtc 480
tgtgctcggc tggaaagagt acgagatgga agtggtgcgc gataaggcgg acaactgcat 540
catcatctgt tcgattgaaa acttcgaccc gatgggcgtt catacgggcg actcgattac 600
ggttgcgccg gcgcaaacgc tgacggacaa ggaataccaa atcatgcgca acgcttcgtt 660
ggcggtattg cgcgaaatcg gcgtggacac gggcggctcg aacgtgcagt ttgcggtgaa 720
ccctgaaaac ggcgagatga ttgtgatcga gatgaacccg cgcgtgagcc gttcgtccgc 780
gctggcttcc aaagcaacgg gcttcccgat tgcgaaggtg gcggcgaagc tggcggtcgg 840
ctttacgctg gacgagttgc gcaacgacat caccggcggc cgcacgcccg cgtcgttcga 900
gccttccatc gactatgtgg taaccaaaat cccgcgtttc gcgtttgaaa aattccccgc 960
cgcagacgac cgcctgacca cgcagatgaa atcagtaggc gaagtaaggg cgaattccag 1020
cacactggcg gccgttacta gtggatccga gctcggtacc aagcttgatg catagcttga 1080
gtattctaac gcgtcaccta aat 1103

<210> SEQ ID NO 432
<211> LENGTH: 1036
<212> TYPE: DNA
<213> ORGANISM: Serratia marcescens
<220> FEATURE:
<221> NAME/KEY: misc_feature
<222> LOCATION: (4)..(4)
<223> OTHER INFORMATION: n is a, c, g, or t
<220> FEATURE:

-continued

<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (994)..(994)
<223> OTHER INFORMATION: n is a, c, g, or t
<220> FEATURE:
<221> NAME/KEY: misc_feature
<222> LOCATION: (1025)..(1025)
<223> OTHER INFORMATION: n is a, c, g, or t
<220> FEATURE:
<221> NAME/KEY: misc_feature
<222> LOCATION: (1030)..(1030)
<223> OTHER INFORMATION: n is a, c, g, or t

<400> SEQUENCE: 432
tttngnattc gcccttcgac gattatgact gacccggcaa atggcggatg caacctacat 60
cgagccaatt cactgggaag tggtacgtaa aatcatcgag aaagagcgtc cggatgcggt 120
tctgccgacc atgggtggcc agactgcgct gaactgtgcg ctggagctgg agcgtcaggg 180
cgtgctggaa gagttcggcg tgaccatgat tggtgcgacc gccgacgcga ttgataaagc 240
agaagaccgt cgtcgcttcg acgtggcgat gaaaaaaatc ggcctcgaca cccgcgcgtt 300
ccggtatcgc tcacaacatg gaagaggcgc tggccgttgc ggctgaagtg ggttatccgt 360
gcatcatccg tccttccttc accatgggcg gcaccggcgg cggtatcgcc tacaaccgcg 420
aagagtttga agagatttgc gagcgcggcc tggatctctc cccaaccaaa gagctgctga 480
ttgatgaatc gctgattggc tggaaagagt acgagatgga agtggtgcgt gataaaaacg 540
acaactgcat catcgtctgc tccatcgaaa acttcgatgc gatgggtatc cacaccggcg 600
actccattac cgttgcgcca gcgcaaacgc tgaccgacaa agagtaccaa atcatgcgta 660
acgcatcgat ggcggtactg cgtgaaatcg gcgtcgaaac cggtggttct aacgtgcagt 720
tctcggtgaa cccgaaaacc ggccgtctga ttgttatcga aatgaacccg cgcgtgtccc 780
gctcctccgc gctggcttct aaagcgaccg gcttcccgat tgcgaaggtg gcggcgaaac 840
tggcggtcgg ttacaccctt gacgagctga tgaacgatat caccgggggc cgcacgcctg 900
cgtccttcga accgtctatc gactacgttg tgaccaaaat tccacgcttc aacttcgaga 960
aattcgctgg cgcgaacgac cgtctgacca cccngttgaa atcctgtaaa aagaagtaag 1020
gggtnactcn aaaaaa 1036

<210> SEQ ID NO 433
<211> LENGTH: 1111
<212> TYPE: DNA
<213> ORGANISM: Citrobacter freundii

<400> SEQUENCE: 433
tcgcccttcg actattatga ctgacccgga aatggccgat gccacctaca tcgagccgat 60
tcactgggaa gtggtacgca aaatcattga gaaagagcgc ccggatgcgg tgctgccaac 120
catgggcggt cagacggcgc tgaactgtgc gctggagctg gaacgccagg gcgtactggc 180
tgaattcggc gtgaccatga ttggcgcaac ggcggatgcc attgataaag cggaagaccg 240
tcgtcgcttt gatatcgcga tgaagaaaat tggtctcgac accgcgcgct ctggcatcgc 300
tcacaccatg gaagaagcgc tggcggttgc tgctgacgtg ggcttcccgt gcatcatccg 360
accgagcttc accatgggcg gcaccggcgg cggtatcgct tataaccgtg aagagttcga 420
agagatttgc gaacgcggtc tggacctttc cccaaccaac gagctgctga ttgatgaatc 480
gctgattggc tggaaagagt acgagatgga agtggtgcgt gataaaaacg acaactgcat 540

-continued catcgtctgc tccatcgaaa acttcgacgc gatgggcatc cataccggtg actccatcac 600
cgtagcacct gcccagacgc tgaccgacaa agaatatcaa atcatgcgta acgcctcgat 660
ggcggtactg cgtgaaatcg gcgtggaaac cggcggttct aacgtccagt ttgcggtaaa 720
cccgaaaaac ggtcgcctga ttgtcatcga gatgaacccg cgcgtatccc gctcctcggc 780
gctggcgtcc aaagctaccg gcttcccgat tgcgaaagtc gccgccaagc tggccgtagg 840
ttacaccctc gacgaactga tgaacgacac caccggcggc cgtactccgg cctcgtttga 900
gccgtccatc gactacgttg tgacgaaaat tccacgcttc aacttcgaga aattcgttgg 960
tgctaatgac cgtctgacca cgcagatgaa atcagtagga gaagtaaggg cgaattccag 1020
cacactggcg gccgttacta gtggatccga gctcggtacc aagcttgatg catagcttga 1080
gtattctaac gcgtcaccta aatagctggc g 1111

<210> SEQ ID NO 434
<211> LENGTH: 1125
<212> TYPE: DNA
<213> ORGANISM: Enterobacter aerogenes
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t
<220> FEATURE:
<221> NAME/KEY: misc_feature
<222> LOCATION: (1083)..(1083)
<223> OTHER INFORMATION: n is a, c, g, or t
<220> FEATURE:
<221> NAME/KEY: misc_feature
<222> LOCATION: (1124)..(1124)
<223> OTHER INFORMATION: n is a, c, g, or t

<400> SEQUENCE: 434
ttncgnattc gcccttcgac gattatgact gatccggaaa tggccgatgc gacctacatc 60
gagccgattc actgggaagt agtacgcaag attattgaaa aagagcgccc ggacgcggtg 120
ctgccaacga tgggcggtca gacggcgctg aactgcgcgc tggagctgga gcgtcagggc 180
gtgttggaag agttcggcgt gactatgatt ggtgcgaccg ccgatgcgat tgataaagca 240
gaagaccgcc gtcgtttcga cgtagcgatg aagaaaattg gtctggaaac cgcgcgttcc 300
ggtatcgcac acacgatgga agaagcgctg gcggttgccg ntgactgggc ttcccgtgca 360
ttattngncc catcctttac catgggcggt agcggcggcg gtatcgctta taaccgcgaa 420
gagttgaaga aatttgcgcc cgcggtcagg atctctcccc aaccaaagag ctgctgattg 480
atgagtcgct gatcggctgg aaagagtacg agatggaagt ggtgcgtgat aaaaacgaca 540
actgcatcat cgtctgctct atcgaaaact ttgatgcgat gggcatccat accggtgact 600
ccatcactgt cgcgccagcc caaacgctga ccgacaaaga atatcaaatc atgcgtaacg 660

-continued

```
cctcgatggc ggtgctgcgt gaaatcggcg ttgaaaccgg tggttccaat gtccagtttg    720

cggtgaaccc gaaaaacggt cgcctgattg ttatcgaaat gaacccacgc gtgtcccgtt    780

cttcggcgct ggcgtcgaaa gcgaccggtt tcccgattgc taaagtggcg gcgaaactgg    840

cggtgggtta catcctcgac gaactgatga acgacatcac tggcggacgt actccggcct    900

ccttcgagcc gtccatcgac tatgtggtta ctaaaattcc tcgcttcaac ttcgaaaaat    960

tcgctggtgc taacgaccgt ctgaccactc agatgaaatc cgtaggtgaa gtaagggcga   1020

attccagcac actggcggcc gttactagtg gatccgagct cggtaccaag cttgatgcat   1080

agncttgagt attctaacgc gtcacctaaa taggctggcg taanc                   1125
```

<210> SEQ ID NO 435
<211> LENGTH: 1118
<212> TYPE: DNA
<213> ORGANISM: Enterobacter cloacae
<220> FEATURE:
<221> NAME/KEY: misc_feature
<222> LOCATION: (1078)..(1078)
<223> OTHER INFORMATION: n is a, c, g, or t
<220> FEATURE:
<221> NAME/KEY: misc_feature
<222> LOCATION: (1089)..(1089)
<223> OTHER INFORMATION: n is a, c, g, or t
<220> FEATURE:
<221> NAME/KEY: misc_feature
<222> LOCATION: (1108)..(1108)
<223> OTHER INFORMATION: n is a, c, g, or t

<400> SEQUENCE: 435

```
attcgccctt cgacgattat gactgatccg gaaatggcgg atgcaaccta catcgagcca     60

attcactggg aagtggtacg taaaatcatc gagaaagagc gtccggatgc ggttctgccg    120

accatgggtg gccagactgc gctgaactgt gcgctggagc tggagcgtca gggcgtgctg    180

gaagagttcg gcgtgaccat gattggtgcg accgccgacg cgattgataa agcagaagac    240

cgtcgtcgct tcgacgtggc gatgaaaaaa atcggcctcg acaccgcgcg ttccggtatc    300

gctcacaaca tggaagaggc gctggccgtt gcggctgaag tgggttatcc gtgcatcatc    360

cgtccttcct tcaccatggg cggcaccggc ggcggtatcg cctacaaccg cgaagagttt    420

gaagagattt gcgagcgcgg cctggatctc tccccaacca aagagctgct gattgatgaa    480

tcgctgattg gctggaaaga gtacgagatg gaagtggtgc gtgataaaaa cgacaactgc    540

atcatcgtct gctccatcga aaacttcgat gcgatgggta tccacaccgg cgactccatt    600

accgttgcgc cagcgcaaac gctgaccgac aaagagtacc aaatcatgcg taacgcatcg    660

atggcggtac tgcgtgaaat cggcgtcgaa accggtggtt ctaacgtgca gttctcggtg    720

aacccgaaaa ccggccgtct gattgttatc gaaatgaacc cgcgcgtgtc ccgctcctcc    780

gcgctggctt ctaaagcgac cggcttcccg attgcgaagg tggcggcgaa actggcggtc    840

ggttacaccc ttgacgagct gatgaacgat atcaccgggg gccgcacgcc tgcgtccttc    900

gaaccgtcta tcgactacgt tgtgaccaaa attccacgct tcaacttcga gaaattcgct    960

ggcgcgaacg accgtctgac cacccagatg aaatcagtcg gcgaagtaag ggcgaattcc   1020

agcacactgg cggccgttac tagtggatcc gagctcggta ccaagcttga tgcatagnct   1080

tgagtattnc taacgcgtca cctaaatngt ctggcgaa                           1118
```

<210> SEQ ID NO 436
<211> LENGTH: 1110
<212> TYPE: DNA
<213> ORGANISM: Morganella morganii

<400> SEQUENCE: 436
ttggagtcgc ctcttcgacg attatgactg atccggcaaa tggcggatgc gacttacatc 60
gagccgattc actgggaagt ggtgcgcaaa atcatcgaaa aagagcgccc ggatgccgtt 120
ctgccgacca tgggcggaca aaccgcgctg aactgtgcgc tggatctgga acgtcacggc 180
gtgctggcag agttcggcgt cgaaatgatt ggcgcgacag cagatgcgat tgataaagcc 240
gaagatcgcc gccgtttcga tatcgcgatg aaaaaaatcg gtctggatac agcgcgttcc 300
ggtatcgcac acaccatgga agaagcgttt gcggtcgctg aagatgtcgg attccctgca 360
tcattcgtcc ttcatttact atgggcggca cggggggcgg tatcgcttat aaccgtgaag 420
aatttgaaga aatttgtact cgtggattag atttatcacc gactaacgag ttattgattg 480
atgaatcact tattggttgg aaagagtatg aaatggaggt ggtgcgcgat aaaaacgaca 540
actgcattat tgtctgctct atcgaaaact ttgatgcgat gggtatccat actggagatt 600
cgattacggt tgcaccagct caaacgttaa cggataaaga gtaccaaatt atgcgtaatg 660
cctcgatggc agtcttacgc gaaattggtg ttgaaacagg tggctctaac gttcagtttg 720
ctgttgaccc aaaaacagga cgcttaattg ttattgagat gaatccacgt gtttcacgtt 780
catcagcgct agcgtcaaaa gcgacaggat ttcctatcgc taaaatagcg gcaaaactgg 840
ctgtgggtta tacccttgat gagttaatga atgatatcac tggcggtaga acgcctgcct 900
cttttgagcc ttctatcgat tatgtggtaa caaaaattcc tcgatttaat tttgaaaaat 960
tcgcaggtac taatgacaga ttaaccacac aaatgaaatc cgtaggcgag taagggcgaa 1020
ttccagcaca ctggcggccg ttactagtgg atccgagctc ggtaccaagc ttgatgcata 1080
gcttgagtat tctaacgcgt cacctaaata 1110

<210> SEQ ID NO 437
<211> LENGTH: 1380
<212> TYPE: DNA
<213> ORGANISM: Escherichia coli

<400> SEQUENCE: 437
cacgacgccg cgccgttgtt cgaccacttt atcgagttaa ttgagcagta ccgtaaaacc 60
gctaagtaat caggagtaaa agagccatgc caaaacgtac agatataaaa agtatcctga 120
ttctgggtgc gggcccgatt gttatcggtc aggcgtgtga gtttgactac tctggcgcgc 180
aagcgtgtaa agccctgcgt gaagagggtt accgcgtcat tctggtgaac tccaacccgg 240
cgaccatcat gaccgacccg gaaatggctg atgcaaccta catcgagccg attcactggg 300
aagttgtacg caagattatt gaaaaagagc gcccggacgc ggtgctgcca acgatgggcg 360
gtcagacggc gctgaactgc gcgctggagc tggaacgtca gggcgtgttg gaagagttcg 420
gtgtcaccat gattggtgcc actgccgatg cgattgataa agcagaagac cgccgtcgtt 480
tcgacgtagc gatgaagaaa attggtctgg aaaccgcgcg ttccggtatc gcacacacga 540
tggaagaagc gctggcggtt gccgctgacg tgggcttccc gtgcattatt cgcccatcct 600
ttaccatggg cggtagcggc ggcggtatcg cttataaccg tgaagagttt gaagaaattt 660
gcgcccgcgg tctggatctc tctccgacca aagagttgct gattgatgag tcgctgatcg 720
gctggaaaga gtacgagatg gaagtggtgc gtgataaaaa cgacaactgc atcatcgtct 780
gctctatcga aaacttcgat gcgatgggca tccacaccgg tgactccatc actgtcgcgc 840
cagcccaaac gctgaccgac aaagaatatc aaatcatgcg taacgcctcg atggcggtgc 900

-continued

```
tgcgtgaaat cggcgttgaa accggtggtt ccaacgttca gtttgcggtg aacccgaaaa    960

acggtcgtct gattgttatc gaaatgaacc cacgcgtgtc ccgttcttcg gcgctggcgt   1020

cgaaagcgac cggtttcccg attgctaaag tggcggcgaa actggcggtg ggttacaccc   1080

tcgacgaact gatgaacgac atcactggcg gacgtactcc ggcctccttc gagccgtcca   1140

tcgactatgt ggttactaaa attcctcgct tcaacttcga aaaattcgcc ggtgctaacg   1200

accgtctgac cactcagatg aaatcggttg gcgaagtgat ggcgattggt cgcacgcagc   1260

aggaatccct gcaaaaagcg ctgcgcggcc tggaagtcgg tgcgactgga ttcgacccga   1320

aagtgagcct ggatgacccg gaagcgttaa ccaaaatccg tcgcgaactg aaagacgcag   1380
```

```
<210> SEQ ID NO 438
<211> LENGTH: 1120
<212> TYPE: DNA
<213> ORGANISM: Proteus mirabilis
<220> FEATURE:
<221> NAME/KEY: misc_feature
<222> LOCATION: (8)..(8)
<223> OTHER INFORMATION: n is a, c, g, or t

<400> SEQUENCE: 438

tctttcgnat tcgcccttcg actattatga ctgatcctga aatggcagat gccacttata     60

ttgagcctat tcattggcaa gtggtcagaa agattattga gaaagagcgc cctgatgcca    120

tattaccgac aatgggcgga caaacggcat taaactgtgc cttagaatta gagcgtcaag    180

gggtgttaac tgaatttggc gtaacaatga taggtgcaac ggctgatgct attgataaag    240

cggaagatag acaacgcttt gataaagcga tgaaaaaaat tggtctggat acggctcgtt    300

caggcatcgc tcatactatg gacgaagcat ttgcagtggc tgagcaagtg ggtttccctt    360

gtattattcg cccttcattt actatggggg gaacgggagg cgggatcgcc tataatcgtg    420

aggaatttga agaaatttgt actcgaggtt tagatttatc accgacaaat gaactattaa    480

ttgatgaatc attaattggc tggaaagagt atgaaatgga agtggtgcgc gataaaaatg    540

ataactgcat tatcgtttgc tccattgaaa actttgatgc gatggggatc cataccggtg    600

actctatcac ggttgctcca gcgcaaacgc taacagacaa agaatatcaa attatgcgta    660

atgcctcgat ggcagtatta cgcgagattg ggggttgaaac cggtggcccc aatgtgcaat    720

ttgccgttga tcctaaaaca gggcgtttaa ttgttattga aatgaaccct cgtgtttctc    780

gctcatcagc attagcgtca aaagcaacag gtttcccaat tgcaaaagtc gcggcaaaac    840

ttgcagtagg ttataccctc gatgagttga tgaatgatat cactggagga agaaccccag    900

cctcttttga accttctatt gattatgtag tgactaaaat ccctcgcttt aactttgaaa    960

aatttgccgg taccaatgac cgtttaacca cgcaaatgaa gtccgtaggc gaagtaaggg   1020

cgaattccag cacactggcg gccgttacta gtggatccga gctcggtacc aagcttgatg   1080

catagcttga gtattctaac gagtcaccta aatgctggcg                         1120
```

```
<210> SEQ ID NO 439
<211> LENGTH: 1112
<212> TYPE: DNA
<213> ORGANISM: Proteus vulgaris
<220> FEATURE:
<221> NAME/KEY: misc_feature
<222> LOCATION: (745)..(745)
<223> OTHER INFORMATION: n is a, c, g, or t
<220> FEATURE:
<221> NAME/KEY: misc_feature
<222> LOCATION: (761)..(761)
<223> OTHER INFORMATION: n is a, c, g, or t
```

<400> SEQUENCE: 439
attcgccctt cgacgattat gactgatcct gaaatggcgg atgccaccta catcgagcct 60
attcattggc aagtcgtcag aaaaattatt gaaaaagagc gccctgatgc gattttgcca 120
acaatggggg ggcaaacggc attaaattgc gcattagaat tagaacgtca aggtgtgtta 180
gctgaattcg gtgtgaccat gattggtgct acggccgatg ctatcgataa agcagaagat 240
agacaacgct ttgataaagc aatgaaaaaa atcggcttag gcacagctcg ctcaggtatt 300
gctcataatc tagaagaagc ttttgccgtc gctgaagatg tcggattccc ttgcatcatt 360
cgtccttcat ttactatggg cggcacgggg ggcggtatcg cttataaccg tgaagaattt 420
gaagaaattt gtactcgtgg attagattta tcaccgacta acgagttatt gattgatgaa 480
tcacttattg gttggaaaga gtatgaaatg gaggtggtgc gcgataaaaa cgacaactgc 540
attattgtct gctctatcga aaactttgat gcgatgggta tccatactgg agattcgatt 600
acggttgcac cagctcaaac gttaacggat aaagagtacc aaattatgcg taatgcctcg 660
atggcagtct tacgcgaaat tggtgttgaa acaggtggct ctaacgttca gtttgctgtt 720
gacccaaaac aggacgctta attgntattg agatgaatcc ncgtgtttca cgttcatcag 780
cgctagcgtc aaaagcgaca ggatttccta tcgctaaaat agcggcaaaa ctggctgtgg 840
gttataccct tgatgagtta atgaatgata tcactggcgg tagaacgcct gcctcttttg 900
agccttctat cgattatgtg gtaacaaaaa ttcctcgatt taattttgaa aaattcgcag 960
gtactaatga cagattagcc acacaaatga aatccgttgg cgaagtaagg gcgaattcca 1020
gcacactggc ggccgttact agtggatccg agctcggtac caagcttgat gcatagcttg 1080
agtattctaa cgcgtcacct aaatggctgg cg 1112

<210> SEQ ID NO 440
<211> LENGTH: 1260
<212> TYPE: DNA
<213> ORGANISM: Neisseria meningitides

<400> SEQUENCE: 440
ccaaacgtac cgacctaaaa tccatcctta tcatcggcgc cggccctatc gttatcggtc 60
aggcctgcga atttgactat tcgggcgcac aggcctgcaa ggctttgcgt gaagaaggct 120
ataaagtcat tttggtgaat tccaaccccg ccacgattat gaccgaccct gaaatggcgg 180
atgttaccta catcgagccg attatgtggc agacggtgga gaagattatc gccaaggagc 240
ggcctgatgc gattctgccc acgatgggcg gtcagaccgc gctgaactgt gcgctggatt 300
tggcacgcaa cggcgtgctg gcaaaataca atgtcgagct gattggcgcg acggaagacg 360
cgatcgacaa ggcggaagac cgcggccgct ttaaagaagc gatggaaaaa atcggtttgt 420
cttgcccgaa atcttttgtc tgccacacga tgaacgaagc tttggcggcg caggagcagg 480
tcggcttccc gacgctgatt cgtccttctt tcacgatggg cggttcgggc ggcggcattg 540
cctacaataa agacgagttt ttggcgattt gcgaacgcgg tttcgatgcg tcgcccacgc 600
acgagctgct gattgagcag tccgtcctcg gctggaaaga gtacgagatg gaggtggtgc 660
gcgataagaa cgataactgc atcatcattt gctcgattga aaacttcgac ccgatgggcg 720
tgcatacggg cgactcgatt acggttgcgc cggcgcaaac attgacagac aaagaatacc 780
aaatcatgcg taatgcttcg ttggcagtat tgcgcgaaat cggcgtggac acgggtggct 840
caaacgtgca gtttgcggtg aaccctgaaa acggcgagat gattgtgatt gagatgaacc 900

-continued

```
cgcgcgtgag ccgttcatcc gcgctggctt ccaaagcgac gggcttcccg attgcgaagg    960

tggcggcgaa actggcggtc ggctttacgc tggacgagtt gcgcaacgac atcaccggcg   1020

gtcgcacgcc cgcgtcgttc gagccttcga ttgattatgt ggtaaccaaa atcccgcgtt   1080

tcgcgtttga aaaattcccc gccgcagacg accgcctgac tacgcagatg aaatcggtgg   1140

gcgaagtgat ggcgatggga cgcacgattc aggaaagttt ccaaaaagcc ctgcgcggct   1200

tggaaacagg cttgtgcggc ttcaatccga gaagctccga caaagcggaa atccgccgcg   1260
```

<210> SEQ ID NO 441
<211> LENGTH: 1103
<212> TYPE: DNA
<213> ORGANISM: Klebsiella oxytoca

<400> SEQUENCE: 441

```
attcgccctt cgactattat gaccgacccg gaaatggccg atgccaccta catcgagccg     60

attcactggg aagtggtgcg caagatcatt gagaaagagc gtccggatgc ggttctgccg    120

accatgggcg gccagacggc gctgaactgc gcgctggagc tggagcgtca gggcgtgctg    180

gccgagttcg gcgtgaccat gattggcgcg accgccgacg cgattgataa agccgaagac    240

cgccgccgtt tcgacgtggc gatgaagaaa atcggtctcg ataccgcgcg ttccggtatc    300

gcgcatacca tggaagaagc gctggcggtt gccgctgaag ttggcttccc gtgcatcatc    360

cgtccgtcct ttacgatggg cggcaccggc ggcggtatcg cctacaaccg cgaagagttc    420

gaagagatct gcgaacgcgg tctggatctc tcgccgacca acgagctgct gattgatgaa    480

tcgctgatcg gctggaaaga gtacgagatg gaagtggtgc gtgataaaac gacaactgca    540

tcatcgtctg ctccatcgaa aacttcgacg cgatgggcgt ccacaccggc gactccatca    600

ccgtggcgcc ggcgcagacc ctgaccgaca aagagtacca aatcatgcgt aacgcctcga    660

tggcggtact gcgtgaaatc ggcgtagaga ccggcggttc caacgttcag ttctcggtga    720

acccgaaaga tggtcgcctg atcgttatcg aaatgaaccc gcgcgtctcc cgctcctcgg    780

cgctggcctc gaaagccacc ggcttcccga tcgctaaagt ggcggcgaag ctggcggttg    840

gttacaccct tgatgagctg atgaacgata tcaccggcgg ccgcaccccg gcgtcgtttg    900

agccgtccat cgactacgtc gtgaccaaaa tcccacgctt caactttgaa aaattcgtcg    960

gcgcgaacga ccgtctgacc acccagatga aatccgtcgg ggaagtaagg gcgaattcca   1020

gcacactggc ggccgttact agtggatccg agctcggtac caagcttgat gcatagcttg   1080

agtattctaa cgcgtcacct aaa                                           1103
```

<210> SEQ ID NO 442
<211> LENGTH: 1117
<212> TYPE: DNA
<213> ORGANISM: Legionella pneumophila
<220> FEATURE:
<221> NAME/KEY: misc_feature
<222> LOCATION: (1077)..(1077)
<223> OTHER INFORMATION: n is a, c, g, or t
<220> FEATURE:
<221> NAME/KEY: misc_feature
<222> LOCATION: (1088)..(1088)
<223> OTHER INFORMATION: n is a, c, g, or t

<400> SEQUENCE: 442

```
ttcgcccttc gactattatg actgatcctg agcttgctga tgccacctat atagagcctg     60

ttcaatggaa agaagtggct cgtattatcg aaatagagag gccagatgct cttttaccga    120

cgatgggagg acaaacagcc ttaaacagcg ccttggactt ggtaagagaa ggggtattag    180
```

-continued ccaagtactc tgttgaaatg ataggagcga cgcgtgaagc catagacagg gcggaagata 240
gagaaaaatt tcgccagctg atgattaaaa tcggattgga tatgccaagg tcggcgattg 300
ctcatagcct ggaagaagca attcaagtac aagcccgttt aggctttcct gccatcatca 360
ggccttcatt taccatgggt ggtagtggag gcggtattgc ctataatcgt gaagaatttg 420
aagaaatttg cattagagga ttggagttgt cgccaactca cgagcttttg attgatgaat 480
cggttctggg ttggaaagaa tatgaaatgg aagtcgtcag ggataaaaat gataattgca 540
ttattgtttg tactatagag aattttgacc ctatgggagt gcatactgga gattccatta 600
ccgttgctcc ggcacaaaca ttaactgata aagaatacca acggatgcgg gatgcggcga 660
ttaaagttct aagggcagtt ggtgtggata cgggaggttc caacgttcgg tttgctatta 720
atcctgaaga cgggcgcatg ctggttgtgg aaatgaaccc gcgtgtatct cgaagctcgg 780
ctttggcgtc aaaagcaacc ggttttccta ttgctaaggt cgcagctaaa ttggctgtgg 840
gctatacctt ggatgaattg aaaaacgaaa tcaccggagg taaaacacct gcgtcctttg 900
agcccagcat tgattacgtc gttaccaaag ttccacggtt taattttgat aaatttccac 960
aaactccaga tactcttacc acacagatga aatcagtcgg cgaagtaagg gcgaattcca 1020
gcacactggc ggccgttact agtggatccg agctcggtac caagcttgat gcatagnctt 1080
gagtattnct aacgcgtcac ctaaatagct ggcgaaa 1117

<210> SEQ ID NO 443
<211> LENGTH: 1800
<212> TYPE: DNA
<213> ORGANISM: Pseudomonas aeruginosa

<400> SEQUENCE: 443
tccaccagca gcgccgcgca gatatggcag ttgccgttgc ggcagctctg cggacagtcg 60
tagccaagcc gccgggcgcc atcgaggatg cgttcccccg gcagcagctc gaggcaggcg 120
ccggacggtt gcaggacgat acgcatcagt cgatcccgag gctcgaccag agggcgtcga 180
tgcgccgtgt caccgcttcg tccttgacga tggcgcgccc ccattcgcgg ctggtctcgc 240
ccggccactt gtgggtggca tcaagcccca tcttcgagcc gaggccggaa accggcgagg 300
cgaagtcgag gtagtcgatg ggcgtgttgt cgatcatcac cgtgtcgcgc ttggggtcca 360
tccgcgtggt gatggcccag atcacatcgt tccagtcgcg cgcatcgatg tcatcgtcgg 420
tgacgatgac gaacttggtg tacatgaact gccgcaggaa cgaccagacc ccgagcatca 480
cgcgcttggc gtgccctggg tactgcttct tcatggtcac caccgccatc cggtaggaac 540
aaccttccgg cggcaggtag aaatcgacga tttccgggaa ctgcttctgc aggatcggca 600
cgaacacttc gttcagcgcc accccgagga tcgccggctc gtccggcgga cgcccggtgt 660
aggtgctgtg gtagatcggt ttctgccggc gggtgacgcg ctcgacggtg aacaccggga 720
agcgatcgac ctcgttgtag tagccggtgt gatcgccata ggggccttcg tcggccatct 780
cgccggggtg gatcacccct tcgaggacga tctcggcgct ggccggcacc tgcaagtcgc 840
tcccgcgaca cttgaccagc tcggtacgat gcccgcgcaa caggccggcg aaagcgtatt 900
cggaaagggt gtccggcacc ggcgtcaccg caccgaggat ggtcgccgga tcggcgccca 960
gcgccacggc taccggatag ggctggcccg gatgcttctg gcaccactcg cggtagtcca 1020
gtgcgccgcc gcgatggctg agccagcgca tgatcacctt gttgcggccg atcacctgct 1080
ggcggtagat gcccaggttc tgccgttcct tgttcggccc gcgggtaacg gtcaggcccc 1140

-continued aggtgatcag cggcccgaca tcgcccggcc agcaggtctg gaccggcagc cggccgaggt 1200
cgacgtcctc gccctcctcg accacttcct ggcagggggc gtccttgagc accttcggcg 1260
ccatggacag gaccttcctg tacatcggca gcttggccca ggcgtccttg aggcccttcg 1320
gcggctcggg ctccttgagt tgcgccagca gcttgccgat ctcgcgcagt gcgccgacgt 1380
cctcggcgcc catgcccagc gccacgcgct ccggcgtacc gaacaggttg ccgagcaccg 1440
gcatgtcgaa gccggtcggc ttttcgaaca gcaatgccgg gcccttggcg cgcaacgtgc 1500
ggtcgcacac ctcggtcatc tcgagcacgg gggaaatcgg cacctggatg cgcttcaacg 1560
caccgcgctg ctccagctgg gcgatgaaat cgcggagatc cttgaacgtc attggcctaa 1620
ccattcactg caagacccca catcctacct gctcccggcc catccggcag caggcaaacg 1680
cggcattcgg tcactgctgg ctggcgatcc tcgagtcgtc gaggctctgt agcatcggct 1740
cgaacaaagg cccgagttca tgggccccct gggtcgaaag gtggttgtta tccatgtaca 1800

<210> SEQ ID NO 444
<211> LENGTH: 1800
<212> TYPE: DNA
<213> ORGANISM: Pseudomonas syringae

<400> SEQUENCE: 444
ccgagcagac atggcagtta ccgttgcgac agctttgcgg gcattcatgg cccagccgct 60
gtgcagcatc cagaatccgc tcgcccggca gggtttcgag taccgcaccc gagggctgca 120
aggttacacg catcagtcta ttcccaactg agtccagatc tcgtccaccc ggcgcgtggt 180
ggcttcgtcc ttgacgatcg ccctgcccca ttcgcgggtg gtttcccctg gccatttgtt 240
agtggcatcc aggcccattt ttgatcccaa tccagacacc ggagaggcaa aatcgaggta 300
atcgatgggc gtgttgtcga tcatgaccgt gtcgcgcttg gggtccatgc gggtggtgat 360
ggcccagatc acgtcattcc agtcacgcgc attgatgtcg tcatcggtga cgatcacaaa 420
tttggtgtac ataaactggc gcaggaacga ccagacgccc agcatcacgc gcttggcatg 480
gccggggtac tgtttcttga tagtcaccac cgccatgcgg taagagcacc cctcgggcgg 540
caggtagaaa tcgacgattt ccggaaactg cttctgcaga atcggcacga acacttcgtt 600
cagcgccaca cccaggatag ccggctcgtc cggtggacgc ccggtgtagg tgctgtggta 660
gatcggcttg atgcggtggg tgatgcgctc gacggtgagc accggaaagc tgtcgacttc 720
gttgtaataa ccggtgtgat cgccgtaggg gccttcgttg gccatctcgc ccggatgaat 780
cacgccctca agcacgattt cggcactggc tggcacttgc aggttgctgc cacggcactt 840
gatcagctcg gtgcgcgagc cacgcagtag cccggcgaag gcgtattcgg acaggctgtc 900
gggcaccggc gtcacggcac cgagaatggt cgccgggtcc gcgcccagtg cgacggccac 960
cggataaggc tcgccaggat gcttgacgca ccagtcgcgg aagtcaagcg cgccaccgcg 1020
atggctgagc cagcgcatga tgatcttgtt gcggccgatg acctgctggc gataaatacc 1080
gaggttctgc cgctccttgt tcgggccttt ggtcacggtc aggccccagg tgatcagcgg 1140
cgcgacatcg cccggccagc aggtctgcac cggcaacatg ccgagatcga cgtcatcacc 1200
ctcgatgacg atctcctggc agggtgcatc cttgacgacc ttgggcgcca tggcgatgac 1260
tttgcggaag atgggcagct tggaccaggc atctttcagg cctttgggcg gctcgggctc 1320
cttgagaaac gcaagcaact tgccgatttc gcgcagctcg gtgacggctt ccgcgcccat 1380
gcccatggcc acgcgctccg gcgtgccgaa caggttgccc agcaccggaa tatcaaagcc 1440
aaccgggttt tcaaacagca gggccgggcc tttggcgcgc aaggtacggt cacagatttc 1500

-continued

```
agtcatttcc agcacaggcg agatcggcat ctgaatgcgt ttcaactctc cgcgctgctc   1560

caactgctgc acgaaatccc ttagatcttt gaatttcatt aacccggcca tttatccaaa   1620

tagacgcaca tcgtacctgc tcccgccctc caaggcagca aatccacggc gcacaggcaa   1680

aaaaaatggt gccccgaagg acaccatttt ttgagccagc ctgtctgtta cttgcgtttc   1740

atggacagga agaactcgtc gttggtcttg gtctgcttga gcttgtcgat gaggaactcg   1800
```

<210> SEQ ID NO 445
<211> LENGTH: 1862
<212> TYPE: DNA
<213> ORGANISM: Bordetella parapertussis

<400> SEQUENCE: 445

```
aratggtgat ggggcgcggc gcccggcgct cgggcctgct caagctggcc ggcgtggcgc     60

tggtgggctg gcaggcatac cggatctggc agtccgcgcg cgaggagcgc caggccgatt    120

gagccaggcc ggcaggcggg cggccggcgc cgcccgcggc attgctacag tcccagcgtg    180

tcccacatgg catccacccg gcgcttgacc gcctcgtcca tgtgtatggg cgtgccccat    240

tcgcggctgg tttcgcccgg ccacttgttg gtggcgtcca gccccatctt gccgcccagg    300

ccggacaccg gcgaggcgaa atcgaggtaa tcgatcggcg tgttctcgac cagcaccgtg    360

tcgcgcacgg ggtccatgcg cgtggtcatg gcccagacca cttcggtcca gtcgcgcggg    420

tcgatgtctt cgtcgaccac cacgatgaac ttggtgtaca tgaactgccg cagcacgctc    480

cacaggccga acatcacgcg cttggcgtgg ccggcgtact gcttgcggat cgacaccacc    540

gccaggcggt agctgcagcc ttccgggggc aggtagaaat cgacgatttc gggcagctgg    600

cggcgcagca gcggcacgaa tacctcgttc agcgccacgc ccagcacggc cggctcgtcg    660

ggcggcttgc cggtataggt ggagtggtag atggggttgc gccgcatggt gatgcggtcc    720

accgtgaaca ccgggaacca gtcctgctcg ttgtagtagc cggtatggtc gccatagggg    780

ccttcgaggg ccatttcgta gccggtggcc gggggcgggt tggcgccctc gggcaccgcg    840

gcagcgacgg cgcgcggatc gtcggccggc agcaggtggc cctcgagcac gatctcggcc    900

gaggccggca ccgacaggtc gctgcccagc gccttgacga cctcggtgcg cgagccgcgc    960

agcagcccgg cgaactggta ttcggacagc gtgtccggca ccggcgtgac cgcgtccagg   1020

atggtggccg ggtcggcacc cagcgccacg gcgatgggaa acgacttgcc cgggtgggcc   1080

tgggcgtggt cgcggaagtc cagcgcgccg ccgcggtgcg acagccagcg catgatcagc   1140

ttgttcggcc ccagcggctg ctggcggtag atacccaggt tctgccgccg ggcgttcggc   1200

ccgcgcgtga tcaccaggcc ccaggcgagc aggggcgcca catcgcccgg ccagcaggtc   1260

tggatgggca ggcggcccag gtcgacgtcg gcgccttccc agacgatttc ctggcaggcg   1320

gcgctgcgca cggtcttggg gctcatgtcc cacagggcgg ctttcagcat ggacaccttg   1380

gccagcgcgt cgcgcaggcc cttgggcgct tcgggctcgc gcagggaggc cagcagttcg   1440

ccggtttcgc gcagggcgcc gacgtcgtcg gcccccatgc cccaggcgac ccgccgcggc   1500

gtgccgaaca ggttggccag caccggcatg tcggccggcg cgtcgttgtg gcgggcgttc   1560

tcgaacagca gggccgggcc gccggcgcgc agcacccggt cggcaatctc ggtcatttcc   1620

agccgcgtcg agaccggcgc ggtgatgcgt ttgagttcgc cctggcgttc aagctgggca   1680

agaaaatctc ggaggtcgcg atacttcaag gcagatcccg gcaaaatagt tacattcttg   1740

aggcaaaaca gaggttaaca tctgcctcct ctcattccac gcaggaggtc ccatgcccga   1800
```

-continued

```
tgcgtcagtg gccggcctgt tccgacagct ggcccaagga gtgcaccacc atctcgccga   1860

at                                                                  1862
```

<210> SEQ ID NO 446
<211> LENGTH: 1860
<212> TYPE: DNA
<213> ORGANISM: Neisseria meningitides

<400> SEQUENCE: 446

```
acagaaaatc ctcgaagaca ccctgctgga acaatggcag tggctcaaac ctaaagaacc     60

gtaaacatcc tgcgtacaca aatgccgtct gaaacgcccc cacgcttcag acggcagacc    120

gtaaaaccta caaccccaat tcctcccaaa tctcatcaat cttagccgta accgcagggt    180

ctttttaat cacccgtccc cattcgcggt cggtttcgcc cggccacttg ttggtcgcat     240

ccaaacccat tttgccgcca agtccgctga cggggctggc gaagtcgagg tagtcgatgg    300

gcgtgttttc catcaaaacg gtatcgcgca cggggtccat gcgcgtggtt accgcccaga    360

tgacttcttt ccagtcgcgc acatccacat cgtcatccac cacaatgatg aatttggtgt    420

acataaactg gcgcaggaac gaccagcagc ccatcatcac gcgcttggcg tgtccggcgt    480

actgtttttt catgctcacc accgccatgc ggtaggagca gccttcgggc ggcaggtaaa    540

aatcggtgat ttcggggaac tgcttttgca aaagcggtac gaacacttcg ttcaacgcca    600

cgcccaaaac ggcgggttca tcgggcggtt tgcctgtgta ggtagagtgg taaatcgggt    660

tttcgcgcat ggtgatgcgt tcgaccgtaa acacggggaa atggtcctgc tcgttgtaat    720

agcccgtgtg gtcgccgtat ggaccttcca acgcggtttc gtttggatgg atgacgcctt    780

ccaacacgat ttctgcgcgg gcaggcactt gcaaatcgtt gccgatacat ttcaccagtt    840

ccgtccgcga accgcgcagc agtccggcaa actggtattc gctcaaggta tcgggaacgg    900

gcgttaccgc gcccaaaatg gtggcagggt cgcagccgag cacgacggcg acgggatacg    960

gcgtatcggg attgagtttg cggaattcct gataatccag cgcgccgccg cgatgcgaca   1020

gccagcgcat aatcagcttg tttatgccga ttaattgttg gcggtaaatg ccgagatttt   1080

ggcgtttttt gtgcggcccg cgcgtgacgg tcaagcccca cgttaccagc ggcgcaacgt   1140

cttccggcca gcaatgctga atcggaagtt gatacaaatc aacgtcttcg ccttcccata   1200

cgatttcctg acacggcgca tttttcacca cgttcggcgc catgctccaa atgtctttca   1260

agagcggcag tttggaaaac gcgtctttaa tgcctttggg cggttcgggt tctttcaaat   1320

acgccagcgt ctgcccgatt tcgcgcagct tggacacgct gtccgcgccc atgcccatcg   1380

ccacacgttc gggcgtgccg aacaggtttg ccaacacggg ataatcatag cgcgtaccgt   1440

cgggcttaac tgggtgttca aacaacaacg ccggcccttc ggcgcgcagc acgcggtcgg   1500

cgatttcggt catttccaaa tgcggggaaa cggggtgcgc gatgcgtttg agtttgccct   1560

gctgctcgag catggcgatg aagtcgcgca ggtctttgta tttcatattc atccttttttg  1620

tccttttatc ctgagcaatc cgattcggat accgccccta tccttgcctg cgcttcggca   1680

tattctatgc cgtgataaaa gtcgcgtacc agcggatgtt cgctgccttg atggagttgc   1740

aacaaaggac gttgaccatc gggttgggta acgacattgc aatgcaaacc gaaggtgtcg   1800

gattcgtaag gggcagccg gttgcagatc atgccgaaat aaacggcgtt ttcagggttg    1860
```

<210> SEQ ID NO 447
<211> LENGTH: 1800
<212> TYPE: DNA
<213> ORGANISM: Shigella flexneri -continued

<400> SEQUENCE: 447

```
ctgaccagca cgaaaagaaa aggccgcgtc tggcacgatg cggacacgat atacggtatc     60
cgtgatagct gctaccgagg tcactttaca gcttaaggtt gtcatgcgct ttctctgtcg    120
gatcgataaa tagggcaaaa caaacgcgca tcaggcgctt ttaccgttgt taaaaatagc    180
cagttcatcc cagatggcgt caatatgcgc gacaacatct ggatcttttt tgatgggacg    240
tccccattca cgctgggttt cccccggcca tttattcgtg gcatccagcc ccatttttga    300
acccagccca gagacaggcg aggcaaaatc cagataatca ataggcgtat tttctaccag    360
aacagtatcc cgcgccgggt ccatacgggt ggtaatcgcc caaatcacat cgttccagtc    420
gcgtgcgttg acgtcatcat cgcaaacgat cacaaattta gtgtacataa actggcgtaa    480
gaacgaccag acgcccatca tgacgcgctt cgcgtgtccg gcgtactgtt ttttgatcgt    540
cactaccgcc agacgataag aacagccttc cggcggcagg taaaaatcga caatttccgg    600
gaactgtttt tgcagaatcg gtacaaacac ttcgttcaac gccacgccca gtaccgcggg    660
ctcatctggc ggacgcccgg tataggtgga atggtaaatc gcatcttcac gctgggtaat    720
atgcgtcacg gtaaacaccg ggaaattatc gacttcatta tagtaacctg tgtggtcacc    780
atacggccct tccggcgcca tctcaccagg atcgatatac ccttccagga cgatttcggc    840
actggctggc acttcgaggt cattggaaat acactttact acttcggttt tggtgccgcg    900
tagcaatccg gcaaacgcat actctgaaag cgtatccgga acgggggtga ctgcaccgag    960
aatcgtggca ggatcggcac ccagcgccac agaaaccggg aaacgttcgc ccggatgcgc   1020
cgcacaccac tcctgataat ccagcgcgcc gccgcgatgc gacagccagc gcataatcag   1080
tttgttttta ccaatcagct gctggcgata aatgcccaga ttctgccgct ctttatgcgg   1140
gccgcgcgtt acggtcagcc cccaggtaat cagcggcgcg gcatcttccg gccagcaggt   1200
cataatggga atgcgattga gatcgacgtc atcgccagag acgatttttt gttggcaggg   1260
cgcaccacgc agtcgctttg tcggcatgtt taacacctgc ttaaactgcg gcagtttatc   1320
aaacaggtcg cggaaacctt ttggcggctc cggctctttc agaaacgcca ataatttacc   1380
aacttcacgc agcgccgaaa catcttcctg ccccatgccc atcgccacgc gctttggcgt   1440
accgaacagg ttgcacagca ccggcattga gtagccttta gggttttcga acaacagcgc   1500
aggcccacca gcacgcagag tgcggtcagc aatttcagtg atttccagat gcggatccac   1560
cgggagcgtg atacgtttta gctcaccctg ctgttcaagc agcgtcagga agtcgcgtaa   1620
atcgttatat ttcatggcgt ccattgtagc ctcttaatct gcgcccatta tacggcgttc   1680
atctttgcaa tgctgtaaat ttgttaaatt agcgtgaact ctgacggtat aacgcaaacc   1740
ggggaatata attaacttag cgtaaagctt ttgctatcct tgcgccccga ttaaacggat   1800
```

<210> SEQ ID NO 448
<211> LENGTH: 1800
<212> TYPE: DNA
<213> ORGANISM: Escherichia coli K12

<400> SEQUENCE: 448

```
catgactgct ttcgcgtaaa ggttgatttc agaagcgcca atatgcagct cgataaaccc     60
tttttcatcc ggcgtcgaag ccattgagaa cggacgtttg tcgcgctcat ccatcactac    120
catcaaatac tgaccagcac gaaaagaaaa ggccgcgtct ggcacgatgc ggacacgata    180
tacggtatcc gtgatagctt ctaccgaggt cactttacag cttaaggttg tcatgcgctt    240
```

-continued

```
tctctgtcgg atcgataaat agggcaaaac aaacgcgcat caggcgcttt taccgttgtt    300
aaaaatagcc agttcatccc agatggcgtc aatatgcgcg acaacatctg gatctttttt    360
gatgggacgt ccccattcac gctgggtttc ccccggccat ttattcgtgg catccagccc    420
catttttgaa cccagcccgg agacaggcga ggcaaaatcc agataatcaa taggcgtatt    480
ttctaccaga acagtatccc gcgccgggtc catacgggtg gtaatcgccc aaatcacatc    540
gttccagtcg cgtgcgttaa cgtcatcatc gcaaacgatc acaaatttag tgtacataaa    600
ctggcgtaag aacgaccaga cgcccatcat gacgcgcttc gcgtgtccgg cgtactgttt    660
tttgattgtc actaccgcca ggcgataaga gcagccttcc ggcggcaggt aaaaatcgac    720
aatttccggg aactgttttt gcagaatcgg cacaaacact tcgttcagtg cgacacccag    780
caccgcgggc tcatctggcg gacgcccggt ataggtggaa tggtaaatcg catcttcacg    840
ctgggtaata tgcgtcacgg taaataccgg gaaactatcg acttcattat agtaaccggt    900
gtggtcgcca tacggccctt ccggcgcagt ttcgccttgt tcgatatacc cttccagcac    960
aatctccgca ctggcgggca cttcaagatc attggagata cacttcacca cttcggtctt   1020
ggtgccacgt agcaatccgg caaacgcata ctctgaaagc gtatccggaa cgggagtgac   1080
tgcaccgaga atcgtggcgg gatcggcacc cagcgccaca gaaaccggga aacgttcgcc   1140
cggatgcgcc gcacaccact cctgataatc cagcgcgccg ccgcgatgcg acagccagcg   1200
cataatcagt ttgtttttac caatcagctg ctggcgataa atgcccagat tctgccgctc   1260
tttatgtggg ccgcgcgtca ctgtcagccc ccaggtaatc agcggcgcgg catcttccgg   1320
ccagcaggtc ataatgggaa tgcgattgag atcgacgtca tcgccagaga cgattttttg   1380
ttggcagggc gcaccacgca gccgctttgt cggcatgttc aatacttgct taaactgcgg   1440
cagtttatca aacaggtcgc ggaaaccttt tggcggctcc ggctctttca gaaacgccaa   1500
taatttacca acttcacgca gcgccgaaac atcttcctgc cccatgccca tcgccacgcg   1560
ctttggcgta ccgaacaggt tgcacagcac cggcattgag tagcctttag ggttttcgaa   1620
caacagcgca ggcccaccgg cacgcaaagt gcggtcagca atttcagtga tttccagatg   1680
cggatccacc gggagcgtga tacgttttag ctcaccctgc tgttcaagca gcgtcaagaa   1740
gtcgcgtaaa tcgttatatt tcatggcgtc cattgtagcc tcttaatctg cgcccattat   1800
```

<210> SEQ ID NO 449
<211> LENGTH: 1800
<212> TYPE: DNA
<213> ORGANISM: Escherichia coli

<400> SEQUENCE: 449

```
agaagcgcca atatgcagct cgataaaccc tttttcatcc ggcgtcgagg ccattgagaa     60
cggacgtttg tcgcgctcat ccatcactac catcaaatac tgaccagcac gaaaagaaaa    120
ggccgcgtct ggcacgatgc ggacacgata tacggtatcc gtgatagctt ctaccgaggt    180
cactttacag cttaaggttg tcatgcgctt tctctgtcgg atcgataaat agggcaaaac    240
aaacgcgcat caggcgcttt taccgttgtt aaaaatagcc agttcatccc agatggcgtc    300
aatatgtgcg acaacatctg gatctttttt gatgggacgt ccccattcac gctgggtttc    360
ccccggccat ttattcgtgg catccagccc catttttgaa cccagcccgg agacaggcga    420
ggcaaaatcc agataatcaa taggcgtatt ttctaccaga acagtatccc gcgctgggtc    480
catacgggtg gtaatcgccc aaatcacatc gttccagtcg cgtgcgttaa cgtcatcatc    540
gcaaacgatc acaaatttag tgtacataaa ctggcgtaag aacgaccaga cgcccatcat    600
```

-continued gacgcgcttc gcgtgtccgg cgtactgttt tttgattgtc actaccgcca ggcgataaga 660
gcagccttcc ggcggcaggt aaaaatcgac aatttccggg aactgctttt gcagaatggg 720
aacaaatact tcgttcaacg ccactcccag taccgcgggt tcatctggcg gacgcccggt 780
ataggtggaa tggtaaatcg catcttcacg ctgggtaata tgcgtcacgg taaataccgg 840
gaaactatcg acttcgttat agtaaccagt gtggtcacca tacggtcctt ctggcgccat 900
ttcgccttgt tcgatatacc cttccagcac aatctccgca ctggcgggca cttcgagatc 960
attggaaata cacttcacta cttcggtttt ggtgccacgt agcaatccgg caaaggcgta 1020
ttccgacaaa gtatctggta ctggtgtgac tgcaccgaga atggttgccg gatcagcgcc 1080
caacgccaca gagatcggga aacgttcacc tggatgcgcc gcacaccact cctgataatc 1140
cagcgcgccg ccgcgatgcg acagccaacg cataatcagc ttgtttttac caatcagttg 1200
ctggcgataa atgcccagat tctgtcgctc tttatgaggg ccacgtgtaa cggttagccc 1260
ccatgtaatc agcggcgcgg catcttccgg ccaacaggtc ataatgggaa tacggttgag 1320
atcgacgtca tcgccagaga cgattttttg ttggcagggt gcaccgcgca gtcgctttgt 1380
cggcatgttt aacacctgct taaactgcgg cagcttatca aacagatcgc gaaaaccttt 1440
tggcggctct ggttctttca gaaatgctaa taatttaccg acttcacgca gtgctgaaac 1500
atcttcctgg cccataccca tcgctacgcg ctttggcgta ccgaacaagt tgcacagcac 1560
cggcattgag taccctttag ggttttcaaa caacagcgca ggcccaccag cacgcagcgt 1620
gcggtcagca atttcagtga tttccagatg cgggtccacc gggagcgtga tacgttttag 1680
ctcaccctgc tgttcaagca acgtcaagaa gtcgcgtaaa tcgttatatt tcatggcgtc 1740
cattgtagcc tcttaatctg cgcccattat acggcgttca tctttgcgat gctgtaaatt 1800

<210> SEQ ID NO 450
<211> LENGTH: 1500
<212> TYPE: DNA
<213> ORGANISM: Bordetella bronchiseptica

<400> SEQUENCE: 450
tcccacatgg catccacccg gcgcttgacc gcctcgtcca tgtgtatggg cgtgccccat 60
tcgcggctgg tttcgcccgg ccacttgttg gtggcgtcca gccccatctt gccgcccagg 120
ccggacaccg gcgaggcgaa atcgaggtaa tcgatcggcg tgttctcgac cagcaccgtg 180
tcgcgcacgg ggtccatgcg cgtggtcatg gcccagacca cttcggtcca gtcgcgcggg 240
tcgatgtctt cgtcgaccac cacgatgaac ttggtgtaca tgaactgccg cagcacgctc 300
cacaggccga acatcacgcg cttggcgtgg ccggcgtact gcttgcggat cgacaccacc 360
gccaggcggt agctgcagcc ttccgggggc aggtagaaat cgacgatttc gggcagctgg 420
cggcgcagca gcggcacgaa tacctcgttc agcgccacgc ccagcacggc cggctcgtcg 480
ggcggcttgc cggtataggt ggagtggtag atggggttgc gccgcatggt gatgcggtcc 540
accgtgaaca ccgggaacca gtcctgctcg ttgtagtagc cggtatggtc gccatagggg 600
ccttcgaggg ccatttcgta gccggtggcc gggggcgggt tggcgccctc gggcaccgcg 660
gcagcgacgg cgcgcggatc gtcggccggc agcaggtggc cctcgagcac gatctcggcc 720
gaggccggca ccgacaggtc gctgcccagc gccttgacga cctcggtgcg cgagccgcgc 780
agcagcccgg cgaactggta ttcggacagc gtgtccggca ccggcgtgac cgcgcccagg 840
atggtggccg ggtcggcacc cagcgccacg gcgatgggaa acggcttgcc cgggtgggcc 900

-continued tgggcgtggt cgcggaagtc cagcgcgccg ccgcggtgcg acagccagcg catgatcagc 960
ttgttcggcc ccagcggctg ctggcggtag atacccaggt tctgccgccg ggcgttcggc 1020
ccgcgcgtga tcaccaggcc ccaggcgagc aggggcgcca catcgcccgg ccagcaggtc 1080
tggatgggca ggcggcccag gtcgacgtcg gcgccttccc agacgatttc ctggcaggcg 1140
gcgctgcgca cggtcttggg gctcatgtcc cacagggcgg ctttcagcat ggacaccttg 1200
gccagcgcgt cgcgcaggcc cttgggcgct tcgggctcgc gcagggaggc cagcagttcg 1260
ccggtttcgc gcagggcgcc gacgtcgtcg gcccccatgc cccaggcgac ccgccgcggc 1320
gtgccgaaca ggttggccag caccggcatg tcggccggcg cgtcgttgtg gcgggcgttc 1380
tcgaacagca gggccgggcc gccggcgcgc agcacccggt cggcaatctc ggtcatttcc 1440
agccgcgtcg agaccggcgc ggtgatgcgt ttgagttcgc cctggcgttc aagctgggca 1500

<210> SEQ ID NO 451
<211> LENGTH: 1440
<212> TYPE: DNA
<213> ORGANISM: Bordetella pertussis

<400> SEQUENCE: 451
tgtatgggcg tgccccattc gcggctggtt tcgcccggcc acttgttggt ggcgtccagc 60
cccatcttgc cgcccaggcc ggacaccggc gaggcgaaat ccaggtaatc gataggcgcg 120
ttctcgacca gcaccgtgtc gcgcacgggg tccatgcgcg tggtcatggc ccagaccact 180
tcggtccagt cgcgcgggtc gatgtcttcg tcgaccacca cgatgaactt ggtgtacatg 240
aactgccgca gcacgctcca caggccgaac atcacgcgct tggcgtggcc ggcgtactgc 300
ttgcggatcg acaccaccgc caggcggtag ctgcagcctt ccgggggcag gtagaaatcg 360
acgatctcgg gcagctggcg gcgcagcagc ggcacgaata cctcgttcag cgccacgccc 420
agcacggccg gctcgtcggg cggcttgccg gtataggtgg agtggtagat ggggttgcgc 480
cgcatggtga tgcggtccac cgtgaacacc gggaaccagt cctgctcgtt gtagtagccg 540
gtatggtcgc catagggggcc ttcgagcgcc atttcgtagc cggtggccgg gggcgggttg 600
gcgccctcgg gcaccacggc agcgacggcg cgcggatcgt cggccggcag caggtggccc 660
tcgagcacga tctcggccga ggccggcacc gacaggtcgc tgcccagcgc cttgacgacc 720
tcggtgcgcg agccgcgcag cagcccggcg aactggtatt cggacagcgt gtccggcacc 780
ggcgtgaccg cgcccaggat ggtggccggg tcggcgccca gcgccacggt gatgggaaac 840
ggcttgcccg ggtgggcctg ggcgtggtcg cggaagtcca gcgcgccgcc ccggtgcgac 900
agccagcgca tgatcagctt gttcggcccc agcggctgct ggcggtagat gcccaggttc 960
tgccgccggg cgttcggccc gcgcgtgatc accaggcccc aggcgagcag gggcgccacg 1020
tcgcccggcc agcaggtctg gatgggcagg cggctcagct cgacgtcggc gccttcccag 1080
acgatttcct ggcaggcggc gctgcgcacg gtcttggggc tcatgtccca cagggcggct 1140
ttcagcatgg acaccttggc cagcgcgtcg cgcaggccct tgggcgcttc gggctcgcgc 1200
agggaggcca gcagttcgcc ggtttcgcgc agggcgccga cgtcgtcggc cccccatgccc 1260 caggcgaccc gccgcggcgt gccgaacagg ttggccagca ccggcatgtc ggccggcgcg 1320
tcgttgtggc gggcgttctc gaacagcagg gccgggccgc cggcgcgcag cacccggtcg 1380
gcaatctcgg tcatttccag ccgcgtcgag accggcgcgg tgatgcgttt gagttcgccc 1440

<210> SEQ ID NO 452
<211> LENGTH: 1050

-continued

<212> TYPE: DNA
<213> ORGANISM: Haemophilus influenzae

<400> SEQUENCE: 452
tatctgctgc tggcgtacct ggtcgggctg agtacacaaa actgaagctc atatcaaagt 60
ttacttgtgc aatcaaattc atagtttgct caaaatcttc cgccgtttca ccagggaaac 120
caacaataaa gtcagagctg atttgaatat ctgggcgcac agcacgaagt ttacgaataa 180
tggatttata ttctaatgcg gtatgagcac gtttcatcat tgttaataca cggtcagaac 240
ctgcttgcac tggaagatgt aagaaactca ctaattcagg cgtatcacga tacacatcaa 300
taatatcatc ggtaaattct attggatgac tggttgtgaa acgtaaacgg tcaataccat 360
caattgatgc gacaagacga agcaactcag caaagctgca aatttgacca tcatgcgttg 420
gcccacgata agcatttaca ttttgaccaa gtagattgac ctcacgcaca ccttgttccg 480
caagttgcgc aatttcaaat agcacatcat ctacaggacg gctaacttct tctccacgag 540
tataaggcac aacacaaaaa gtacagtatt tattacagcc ttccataatg gaaacaaatg 600
ccgttgggcc ttctgcgcga ggttctggta agcggtcaaa tttctcaatt tcagggaaac 660
ttacgtctac gacggaactt tttccaccac gaatttgatt aatcatttca ggcaagcgat 720
gcaaagtttg cgggccaaaa ataatatcca cataaggcgc acgatggcga atatgttccc 780
cttcttgaga ggctacacag ccgcccacac caatcactaa atttggatta tttttcttta 840
attctttcca acgcccaagt tggtggaaca ctttttcttg tgctttttca cgaatagaac 900
aggtatttaa taataatacg tctgcttctt caggtgcttc cgtgagttct aatccgtggg 960
tgcttaataa aagatcagcc attttagatg aatcatattc attcatctgg cagccccaag 1020
ttttaatatg taatttttga gtcattttct 1050

<210> SEQ ID NO 453
<211> LENGTH: 1425
<212> TYPE: DNA
<213> ORGANISM: Pasteurella multocida

<400> SEQUENCE: 453
ctacgcgtga taacgtccca cgccgagttc atcttcttta cgagtacgat taatcaccat 60
ttgtggcgat tgaacaacgc gaagtcccat ttgttcttca gttctaacga cttcaccacg 120
cagtgagtta gtaaacacat ccgtgatctt gatatcaaca aacttcccaa tcatatcagg 180
cgtgcccaca aaattgacga tacgattagt ttctgtacgc cctgtgagtt ccattaaatc 240 tttttcgag ggtccttcca ctaacacgcg ctgttctgtg cctaacattg ctcgactaaa 300
ttgcgcggct tgattgttaa tgcgttgttg caacacatat aaacgttgtt tcttctcttc 360
ttctgtcaca tcatcaggca tatctgctgc tggcgtgcct ggacgtgctg aataaatgaa 420
gctgaaactc atatcaaaat ttacttgtgc aattaaattc atggtttgct cgaaatcttc 480
tgctgtttcg cccgggaaac cgacaataaa atctgagcta atttgaatct ctggacgcac 540
cgctcttaac ttccgaataa tcgatttata ttctaatgcc gtatgattgc gtttcatcat 600
agataacaca cgatcagaac cactttgtac aggtaagtgt aagaaactca ccaactctgg 660
cgtatcacgg tacacatcaa taatgtcatc agtgaactca attgggtgac tggtggtaaa 720
acgtaaacgg tcaataccat caatagcggc tactaaacgt aacaattccg caaaagtaca 780
aataccgtca tcatgagttg caccacgata agcgttcacg ttttgtccta ataaattcac 840
ttcacgcacg ccttgctctg ccaactgtgc aatttcaaat aatacatcat ccactggacg 900

-continued

```
actgacttct tcaccacgcg tataaggcac gacacagaat gagcaatatt tattacagcc    960

ttccataatg gatacgaaag cagttggacc ttctgcacgc ggttctggta aacggtcgaa   1020

tttttcaatt tctggaaaac tgacatcgac tactgagctt ttaccacctc tgatctgatt   1080

gatcatttca ggtaaacgat gtaaggtttg tggtccaaaa ataatatcga cataaggagc   1140

acgagtacga atgtgttctc cttcttgtga ggcaacacag cccccaacac cgataacgag   1200

tcccggctta tgtttcttta attctttcca acgtcctaat tgatggaaaa ctttttcttg   1260

tgctttttca cgaattgagc aagtgtttaa caataacaca tccgcttctt ccggaatttc   1320

tgttaactct aagccgtgag tactgtttaa gagatctgcc atttagatg aatcatattc    1380

attcatctga caaccccacg ttttaatatg taatttttgc gtcat                   1425
```

<210> SEQ ID NO 454
<211> LENGTH: 1260
<212> TYPE: DNA
<213> ORGANISM: Haemophilus ducreyi

<400> SEQUENCE: 454

```
ggacgcgcag agtagataaa gctaaagctc atatcaaaat tgacttgttc aataattttc     60

attgtttgtt caaagtcttc cgctgtttcg ccaggaaagc caacaatgaa atctgagcta    120

atttggatat ttggacgaac cgcacgtaat ttacgaataa tggctttgta ttctaatgcg    180

gtgtggttac gtttcatcat ggttaaaaca cgatcggcgc cactttggat aggtaaatgc    240

aagaagctga ccaattctgg agtatcacga tacacttcaa taatgtcgtc ggtgaattca    300

atggggtggc ttgtggtata acgtaagcgg tcaataccat caatggcggc aactaaacgt    360

aataattctg caaaagtgca aatgccacca tcaaaggttt caccacggta agcattaacg    420

ttttgaccca gcaagttaac ttcacgaacg ccttgctctg ctaattgtgc gatttcgaat    480

aagacatcat caacagggcg ggaaacttct tcaccacggg tataaggcac tacacagaat    540

gagcagtatt tattacagcc ttccataatt gatacgaaag cagttggacc ttctgctttg    600

ggttctggta agcggtcgaa tttttcaatt tctgggaagg agatatcgac tactgcacga    660

tcgcctgatc ggatctggtt gatcatttct ggtaagcggt gcaatgtttg tggcccaaat    720

actatatcaa caaaaggggc acgttcacgg atatgttcac cttcttgtga agcaacacag    780

ccaccaacgc caataattaa atcgggtttg tcctttttcc agtttttcca acgaccaagt    840

tgtgaaaaga ctttttcttg tgctttttca cgaattgagc aagtattcaa taataaaata    900

tccgcttctt caggtttatc ggttaattct aatccgtgtg ttgagtttaa gagatctgcc    960

atttttgatg agtcatactc attcatttgg caaccccaag ttgtgatatg taattttgcc   1020

ataattttca aaaaataata aatatctcaa taagttaaaa taaaagcgta aagagacagt   1080

tccctttacg catctttaat cgtgctattc tacctgtttg cttatttttt cgctagagtt   1140

aatcgcttaa taagcaaaat gccacgatat tgctagcgtg acattttatc atgagaggat   1200

gttattgttt ggttaaggtc aatacaacac tttcaccggc aacaacattt ccaacttttt   1260
```

<210> SEQ ID NO 455
<211> LENGTH: 1080
<212> TYPE: DNA
<213> ORGANISM: Vibrio parahaemolyticus

<400> SEQUENCE: 455

```
aggacgcgct ttacgtagtt tacggatgat cgacttgtac tcgatagctg tgtgaggacg     60

cttcatcatc gttagaatac ggtcactacc actttgtact ggcaggtgta ggaaactcac    120
```

-continued

```
aagctccggg gtatcttcgt aaaccgcgat gatgtcgtct gtaaactcta gcgggtggct    180
agtcgtgaaa cgaatacggt cgataccatc gatagatgca acgagacgaa gcagttcagc    240
aaaagagcag atctcgccgt cgtgcatagg gccacggtat gcgtttacgt tttgacctag    300
taggttaact tcacgtacac cttgttccgc tagctgtgca atctcgaata acacgtcatc    360
cattggacga ctaacttctt caccacgagt gtatggtaca acgcagtaag tgcagtattt    420
tgaacagcct tccatgatag aaacaaacgc cgtcgcacct tctgcacgtg gctcaggtag    480
gcggtcgaac ttttcaatct ctgggaacga aatgtccatt accggtgcat cgtcagtttg    540
agattgtttg atcatctcag gtaggcggtg cagagtttga gggccaaaga tcacgtcaac    600
gtatggtgca cgctcacgga tgtggtcacc ttcttgtgtt gctacacaac cacctacacc    660
gataactacg ccaggttttt tatcttttag tgttttccaa cggcctagct ggtggaaaac    720
tttctcttgc gctttttcac ggatcgaaca ggtgttaagt agaagtacgt ctgcttcctc    780
tggctcttcc gtcagctcat agccgtttgc agcattaagc aggtcggcca tttttgatga    840
atcgtattcg ttcatctggc agccccaggt tttaattagc agtttcttac tcatctcact    900
ttcgctcgtt cagttgtact taaattggag agctattgct caaattatag ccgccatcac    960
ggcggtaagc ggcgtattgt actgctttaa aaagcacctg actagtgatc tgacgaattc   1020
tctgcaaacc ctgatgaaat ctagtttttt gccctatata cagcaaggtt ttttgttaaa   1080
```

<210> SEQ ID NO 456
<211> LENGTH: 1473
<212> TYPE: DNA
<213> ORGANISM: Yersinia pestis

<400> SEQUENCE: 456

```
gaatttacca atcatgtcgg gtgaaccctc aaagttcacg acgcggttgt tttccgtacg     60
cccggccagt tccatgacat ttttgcgaga ggtaccctcc accaaaacac gctgtactgt    120
ccctaccatc ttacggctaa tttccatcgc ctgttggcta atgcgttgtt gcaggatatg    180
tagccgctgt tttttctcct cttcggacac attgttgggt aaatcagccg ctggtgtgcc    240
gggacgcggg gagtaaataa agctgtagct ggtatcaaaa tgaatatctg cgaccagttt    300
catggtctgt tcaaaatcct gctgggtttc accagggaag ccgacaataa aatcagaact    360
tatctggata tcagggcgtg cttgacgcag tttgcggatg atggctttgt attccaaggc    420
ggtatgggca cgcttcatca tggtcaaaat acggtcagaa ccgctttgta ccggcaaatg    480
caggaagctc accaattcag gcgtatcgcg ataaacatca atgatatcgt cagtaaactc    540
aatggggtgg ctggtggtaa atcgtaccct atcgatacca tcaatcgccg caaccaaacg    600
caacagctcg gcaaaactac agatatcgcc atcgtaggtt gccccgcggt aggcgttaac    660
attctggccg agtaagttga cttcacgtac gccttgagcg gctaactggg cgatttcaaa    720
aagaatgtca tcgcttggac ggctgacttc ctcgcctcgg gtgtagggta cgacacagaa    780
tgtacaatat ttattgcagc cttccatgat cgaaacaaac gcagttgggc cttcagcccg    840
tggttctggc aaacggtcaa atttttcaat ttcgggaaaa ctgatatcca cgacagggct    900
attcgttcct tgcacgtggt taatcatttc cggtaaacga tgcagcgttt gtggcccgaa    960
gatgacatcg acacaggggg cgcgctggcg caattgttca ccttcctgtg acgccacgca   1020
accaccgacc ccaataatca actgcgggtt tttctctttc aataatttcc attgccctag   1080
caggctgaat actttttcct gtgctttttc ccggatagaa caggtattta gcagcagtaa   1140
```

-continued

```
atccgcttct tccgggatgg tggttaactg gtagccatgg gtactggcca agagatctgc   1200

cattttagat gaatcgtatt cattcatctg gcaaccccag gttttgatat gcagtttttt   1260

agtcatcggg ttattcatca tcaaaatcac ctcgttccgt gcggtactcc gttgtggtag   1320

ataatctccg ttgtagtaga gagtcgcaaa ggcttcgtcg ttagggagca ttgtagtcat   1380

ttgcctctgc gatgaccacc gcagaaccgt tgagttattc tgttgagtga taaaaaatcc   1440

gttacactgc ggttagacaa aaccttgcta atg                                1473
```

<210> SEQ ID NO 457
<211> LENGTH: 1440
<212> TYPE: DNA
<213> ORGANISM: Salmonella typhimurium

<400> SEQUENCE: 457

```
gccgagcata cggcggctcc atgccatcgc ctgctgattg atacgctctt gcagaatata     60

cagacgctgc ttcttctctt cttccggcac gtcatcaacc atatcggcag ccggcgttcc    120

cggacgcgca gagaagataa agctgtagct catatcaaag ttgacgtcag cgataagctt    180

catggttttt tcgaaatcat cggtagtttc gccagggaat ccgacgataa agtcagagct    240

tatctgaatg tccggccgcg ccgcgcgcag tttacggatg attgctttat attccagcgc    300

agtgtgggtg cgccccatca gattcaacac gcgatcggaa ccgctctgta ccggcagatg    360

caggaaactg accagttccg gcgtatcgcg gtatacctcg ataatatcgt cggtgaactc    420

aatcggatgg ctggtggtaa agcgaatacg gtcaatgccg tcgatggcgg caaccagacg    480

cagcagatcg gcaaaggtac cggtggtgcc gtcgtagttt tctccgcgcc aggcgttaac    540

gttctggccc agcaggttga cctcacgcac gccctgcgcc gctaactggg cgatttcgaa    600

caggatatcg tctgagggac ggctgacttc ttcaccgcgg gtatacggta ccacacagta    660

agtacaatat ttattgcagc cttccatgat agaaacgaaa gcggtcgggc cttctgcgcg    720

cggttccggc aaacggtcga acttctcgat ttccgggaag ctgatatcga ccaccgggct    780

gcggtcgcca cgcacggagt taatcatctc cggtaggcgg tgtaaggttt gcgggccaaa    840

aataatgtcg acgtaatggg cgcgttgacg aatgtgctcg ccttcctggg aagccacgca    900

gccgccgacg ccgataatca gatcgggatt tttctctttt aacagtctcc agcgacctaa    960

ttgatggaag actttttcct gagccttctc gcggattgag caggtattca acagcagcac   1020

atccgcctct tccgccacgt cggtcagttg atagccgtgg gtggcgtcca gcagatcggc   1080

catcttcgat gaatcgtact cgttcatctg acagccccag gttttaatat ggagtttttt   1140

agtcatcgac ttgctcttgc gaaatagtgg ctgaaaagca gggcgcatag tgtaatgctt   1200

tggcgcggtt gtgaccagta tgactgacgt cagccctaat gggtaaaaaa tcctgtaaac   1260

ttgtctaaaa cgtaacagga tgaatgacca tgacaaatca accaacggaa attgccattg   1320

tcggcggggg aatggtcggc ggcgcgctgg cgctgggtct ggcgcagcaa gggtttacgg   1380

tgatggtaat agaacatgcc gcgcctgcgc cgtttgtggc ggacagccag cctgacgtgc   1440
```

<210> SEQ ID NO 458
<211> LENGTH: 1216
<212> TYPE: DNA
<213> ORGANISM: Vibrio cholerae

<400> SEQUENCE: 458

```
tcttcacttc ttccgacaga tcgcaaggat agtcagcggc gggtgtgcct ggacgaggtg     60

agaaaataaa gctaaagctc atgtcgaaat cgacatcgcg gatcagcttc atggtgtctt    120
```

-continued

```
ggaaatcttt gtcggtttcc cctgggaagc caacgataaa atcagagctg atttgaatat    180
ctgggcgtgc tttacgtagc ttacggatga tggatttgta ctcaatcgcc gtatgtggac    240
gcttcatcat agtcagaatg cgatcgctcc cactttgtac tggcaagtgc aggaagctca    300
ccagctcagg cgtgtcttcg tacactgcaa taatgtcatc ggtaaattcg agtgggtggc    360
tagtggtaaa gcggatacga tcgatgccgt caatggtggc gaccaaacgc agtaattcag    420
cgaaagagca aatgccgcca tcgtgagtgg caccacggta agcgttgacg ttttgaccca    480
gcaggttaac ttcacgcacc ccttgctcgg caagctgagc gatctcgaac aggacatcgt    540
ccataggacg gctgacttct tcaccgcgtg tgtaaggcac tacgcagtaa gtacagtatt    600
ttgagcagcc ttccatgata gaaacgaacg ccgttgggcc ttccgcacgt ggctcaggca    660
ggcggtcgaa tttttcaatc tcagggaaag agatatccat cacgggcgcg tcgctggttt    720
gcgattgttt aatcatttct ggcagacgat gcagcgtctg tgggccgaag atgacatcca    780
cataaggcgc acgatcgcga atcgagtcac cttcttgagt agcaacacag ccaccgacac    840
cgatcacgac acctggcttc ttgtctttca gggttttcca acgaccgagt tggtggaaga    900
ctttttcctg cgcctttttca cgaatcgaac aggtgtttag gagtaaaacg tcagcttcct    960
cgggtatttc tgtcagctca tagccgtttg cagcattaag caggtcagcc attttcgatg   1020
aatcgtactc gttcatctgg cagccccaag ttttaattag cagtttctta ctcatctcac   1080
tttcgctcgt tcaatagttc ttcaatcatt tgagctgtag ctcacattct agccgccctc   1140
tcggcggtaa gcggcgtatt gtactgcttt aaaaaccgac tgactagtaa ttggcggaat   1200
tctcttgtaa cccttg                                                   1216
```

<210> SEQ ID NO 459
<211> LENGTH: 1080
<212> TYPE: DNA
<213> ORGANISM: Escherichia coli K12

<400> SEQUENCE: 459

```
tatacagacg ctgcttcttc tcttcttccg gaacatcatc aaccatatcg gcggctggtg     60
tacccggacg tgcagagaag ataaagctgt agctcatgtc gaaattgacg tcggcaatca    120
gcttcatcgt tttctcgaag tcttcggtgg tttcgccagg gaagccaacg atgaaatcag    180
aactgatctg aatatctgga cgcgccgcac gcagtttacg gatgatcgct ttgtactcca    240
gcgccgtatg ggtacggccc atcaggttca gaatgcgatc ggaaccgctc tgtaccggca    300
gatgcaggaa gctcaccagc tccggcgtgt cgcgatacac ttcgatgata cgtcggtgaa    360
ttcgatcgga tggctggtgg taaagcgaat acgatcgatc ccgtcgatcg cagcaaccag    420
acgcagcaga tcggcaaacg atccggtggt gccgtcgtag ttttcaccac gccaggcgtt    480
cacgttctga ccgagcaggt tgacttcacg cacgccctga gccgcaagct gggcaatctc    540
aaacagaata tcgtcggacg gacggcttac ctcttcacca cgggtgtaag gcaccacgca    600
gtaggtgcaa tatttattgc agccttccat gatggagaca aacgcggtcg gcccttcggc    660
gcgcggttcc ggtagacggt caaacttctc gatttccggg aagctgatat ctacaaccgg    720
gctgcggtcg ccacgcacgg agttgatcat ctccggcaga cggtgcagcg tttgcggccc    780
aaaaataata tcgacatagt gggcgcgctg gcgaatgtgc tcgccttctt gcgatgccac    840
gcagccaccg acgccgataa tcaggtctgg attcttctct tttaacagtt tccagcgacc    900
caactgatgg aagacttttt cctgagcctt ctcgcggatt gagcaggtgt tcagcagcag    960
```

-continued cacatccgct tcttccgcca cgtcggtcag ttgatagccg tgggtggcat ccagcagatc 1020
ggccatcttc gatgaatcgt actcgttcat ctgacagccc caggttttaa tatggagttt 1080

<210> SEQ ID NO 460
<211> LENGTH: 1140
<212> TYPE: DNA
<213> ORGANISM: Escherichia coli O157:H7

<400> SEQUENCE: 460
catcatcaac catatcggcg gctggtgtac ccggacgtgc agagaagata aagctgtagc 60
tcatgtcgaa attgacgtcg gcaatcagct tcatcgtttt ctcgaagtct tcggtggttt 120
cgccagggaa gccgacgatg aagtcagaac tgatctgaat atctggacgc gccgcacgca 180
gtttacggat gatcgctttg tactccagcg ccgtatgggt acgtcccatc aggttcagaa 240
tgcgatcgga accgctctgt accggcagat gcaggaagct caccagctcc ggcgtgtcgc 300
gatacacttc gatgatatcg tcggtgaatt cgatcggatg gctggtggta aagcgaatac 360
gatcgatccc gtcgatcgca gcaaccagac gcaacagatc ggcaaacgat ccggtggtgc 420
cgtcgtagtt ttcaccacgc caggcgttca cgttctgacc gagcaggttg acttcacgca 480
cgccctgagc cgcaagctgg gcaatctcaa acagaatatc gtcagacgga cggcttacct 540
cttcaccacg ggtgtaaggc accacgcagt aggtgcaata tttattgcag ccttccatga 600
tggagacaaa cgcggtcggc ccttcggcgc gcggttccgg tagacggtca aacttctcga 660
tttccgggaa gctgatatct acaaccgggc tgcggtcgcc gcgcacggag ttgatcatct 720
ccggcagacg gtgcagcgtt tgcggcccaa aaataatatc gacatagtgg gcgcgctggc 780
gaatgtgctc gccttcttgc gatgccacgc agccaccgac gccgataatc aggtctggat 840
tcttctcttt taacagtttc cagcgaccca actgatggaa gactttttcc tgagccttct 900
cgcggattga gcaggtgttc agcagcagca catccgcttc ttccgccacg tcggtcagtt 960
gatagccgtg ggtggcatcc agcagatcgg ccatcttcga tgaatcgtac tcgttcatct 1020
gacagcccca ggttttaata tggagttttt tggtcatcga cttgctcttg cgaaatagta 1080
gccaggaatg cagggcgcat agtgtaatgc tttgctgccg ttgtgaccag tatgagcgtt 1140

<210> SEQ ID NO 461
<211> LENGTH: 1560
<212> TYPE: DNA
<213> ORGANISM: Pseudomonas aeruginosa

<400> SEQUENCE: 461
ccgccgtacg gtcgtcggcc tcaatgcagg gtgctgtcga tcagggtacc gcgcagcgag 60
tgcggcagcg cgtcgtcgat gtgcacctgg gcgaactggc cgatcaggcg tggattgtcg 120
cagcggaagt tgacgatccg gttgttctcg gtgcgcccct ggagcatgcc tgggtccttc 180
ttcgagaagt cggtgaccag gatccgctgg gtgctgccga ccatgcgccg gctgatctcg 240
tagccttgct ggtggatgcg gctctggagg atctgcaggc gctgtttctt cacttcttcc 300
ggcaggtcgt cggcgaggtc ggcggcgggc gtgccgggcc gcgcgctgta gatgaaggag 360
aaggagaagt cgaagccgac gtcctccacc agcttcatgg tctgctcgaa gtccttctcg 420
gtttcgccgg ggaaaccgac gatgaagtcg gagctgatgc agatgtccgg taccgcggcc 480
ttcagcttgc ggatacgcga cttgtattcc agcacggtat ggttgcgctt catcgccgcc 540
agcacgcggt cggagcccga ctgcaccggc aggtggatga atttcaccag ctccggcacc 600
tcggcgtggg cctggatcag cgcgtcggag aattccagcg ggtgcgaggt ggtatagcgg 660

-continued

```
atgcgctcga taccgtcgac ggcggcgacc acccgcagca gttcggcgaa gtcggccagg    720

cggccatcgt gggtcaggcc gcggaagccg ttgacgttct gtcccagcag ggtgacttcg    780

cggacgccgt tctcggccag gtggatcact tcggcgatca cgtcgtcgaa tggtcggctg    840

acttcctcgc cgcgggtgta gggcaccacg cagaagctgc agtacttgct gcagccttcc    900

atcaccgaga cgaaggcggt ggggccatcg acccgcggtt ccggcaggcg gtcgaatttc    960

tcgatttccg ggaaggacac gtcgacctgc ggcttgcgcg tgctgcgcgc ggcgtcgatc   1020

atttccggca ggcggtgcag ggtctgcggg ccgaagacca cgtcgacata gggcgcgcgc   1080

tcacggatcg cggcgccttc ctggctggcc acgcagccgc cgacgccgat caccaggtcg   1140

ggattctgct gcttcagctc gcgccacatg ccgagcttgg aaaacacctt ttcctgggcc   1200

ttctcgcgga tcgagcaggt attgagcagg atgacgtcgg cctcggcggc gttttcggtc   1260

acctcgaggg cttggtgttc accgagcagg tccgccattc gcgacgagtc gtactcgttc   1320

atctggcagc cgtgggtttc gatgaaaagc ttcttggcca tgcgcttcgt cggacagttc   1380

gaaaaggacc gcgcattata gagggcgggg cccccggttc ctagcgttgc tggccgaaag   1440

gctgtgctat gattcgcgcc cttcattttc cggcattgct ttccccgcca tgaacaagcg   1500

cgaaaacccc atctacaagg tgattttcct caaccagggc caggtcttcg agatgtatgc   1560
```

<210> SEQ ID NO 462
<211> LENGTH: 20
<212> TYPE: DNA
<213> ORGANISM: Artificial Sequence
<220> FEATURE:
<223> OTHER INFORMATION: primer

<400> SEQUENCE: 462

```
ythttygaag gdgcdcaagg                                                  20
```

<210> SEQ ID NO 463
<211> LENGTH: 19
<212> TYPE: DNA
<213> ORGANISM: Artificial sequence
<220> FEATURE:
<223> OTHER INFORMATION: primer

<400> SEQUENCE: 463

```
grycwggmcc wactgagaa                                                   19
```

<210> SEQ ID NO 464
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: n is a, c, g, or t

<400> SEQUENCE: 464

```
ccngccatyt cwccrcacat                                                  20
```

<210> SEQ ID NO 465
<211> LENGTH: 22
<212> TYPE: DNA
<213> ORGANISM: Artificial Sequence
<220> FEATURE:
<223> OTHER INFORMATION: primer -continued

<400> SEQUENCE: 465
amgaratgaa yccrttcytd gg 22

<210> SEQ ID NO 466
<211> LENGTH: 20
<212> TYPE: DNA
<213> ORGANISM: Artificial Sequence
<220> FEATURE:
<223> OTHER INFORMATION: primer

<400> SEQUENCE: 466
gacggamytc tggagagacc 20

<210> SEQ ID NO 467
<211> LENGTH: 23
<212> TYPE: DNA
<213> ORGANISM: Artificial Sequence
<220> FEATURE:
<223> OTHER INFORMATION: primer

<400> SEQUENCE: 467
gcrtayttdg tdgccatwcc aaa 23

<210> SEQ ID NO 468
<211> LENGTH: 20
<212> TYPE: DNA
<213> ORGANISM: Artificial Sequence
<220> FEATURE:
<223> OTHER INFORMATION: primer

<400> SEQUENCE: 468
garcgtatya tgaaaatggt 20

<210> SEQ ID NO 469
<211> LENGTH: 17
<212> TYPE: DNA
<213> ORGANISM: Artificial Sequence
<220> FEATURE:
<223> OTHER INFORMATION: primer

<400> SEQUENCE: 469
catdccytca gdckcat 17

<210> SEQ ID NO 470
<211> LENGTH: 19
<212> TYPE: DNA
<213> ORGANISM: Artificial Sequence
<220> FEATURE:
<223> OTHER INFORMATION: primer

<400> SEQUENCE: 470
tgggtyggyg gycgttact 19

<210> SEQ ID NO 471
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (9)..(9)
<223> OTHER INFORMATION: n is a, c, g, or t

<400> SEQUENCE: 471
tcggtytgng craagaagtt 20

<210> SEQ ID NO 472
<211> LENGTH: 19
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (5)..(5)
<223> OTHER INFORMATION: n is a, c, g, or t

<400> SEQUENCE: 472
csacnatyat gacygaycc 19

<210> SEQ ID NO 473
<211> LENGTH: 20
<212> TYPE: DNA
<213> ORGANISM: Artificial sequence
<220> FEATURE:
<223> OTHER INFORMATION: primer

<400> SEQUENCE: 473
tccatytcrt aytcyttcca 20

<210> SEQ ID NO 474
<211> LENGTH: 20
<212> TYPE: DNA
<213> ORGANISM: Artificial Sequence
<220> FEATURE:
<223> OTHER INFORMATION: primer

<400> SEQUENCE: 474
aayttggtrt acatraactg 20

<210> SEQ ID NO 475
<211> LENGTH: 18
<212> TYPE: DNA
<213> ORGANISM: Artificial Sequence
<220> FEATURE:
<223> OTHER INFORMATION: primer

<400> SEQUENCE: 475
rvtgatyatg cgytggct 18

<210> SEQ ID NO 476
<211> LENGTH: 18
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 476
gccnggraad ccnacrat 18

<210> SEQ ID NO 477
<211> LENGTH: 20
<212> TYPE: DNA
<213> ORGANISM: Artificial Sequence
<220> FEATURE:

-continued

```
<223> OTHER INFORMATION: primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 477

gtntcnrtna tggaaggctg                                                20


<210> SEQ ID NO 478
<211> LENGTH: 22
<212> TYPE: DNA
<213> ORGANISM: Artificial Sequence
<220> FEATURE:
<223> OTHER INFORMATION: primer

<400> SEQUENCE: 478

gtgtaggtcc tacattcgtt tc                                             22


<210> SEQ ID NO 479
<211> LENGTH: 20
<212> TYPE: DNA
<213> ORGANISM: Artificial Sequence
<220> FEATURE:
<223> OTHER INFORMATION: primer

<400> SEQUENCE: 479

cattcgtttc aaaggtaatg                                                20
```

ASSAY FOR DETECTING AND IDENTIFYING MICRO-ORGANISMS

RELATED APPLICATIONS

This application is the U.S. National Phase under 35 U.S.C. §371 of International Application PCT/EP2005/002927, filed Mar. 18, 2005 which claims priority to BE 2004/0152, filed Mar. 19, 2004.

FIELD OF THE INVENTION

The present invention relates to an assay and a method for diagnosing and identifying micro-organisms, and in particular bacteria. The present invention also relates to an assay and a method for detecting micro-organisms, and in particular bacteria, in a sample, and for the discrimination thereof.

More in particular the present invention relates to an assay and a method for the molecular identification of bacteria according to Gram-, genus- species- and strain-specificity based on multigenotypic testing of bacterial DNA from human, animal or environmental samples.

BACKGROUND

In the medical and veterinary clinical setting, detection and species identification of harmful bacteria infecting biological fluids or tissues is a pre-requisite for appropriate and timely relevant antibiotherapy. Such identification is classically performed by conventional microbiological methods (culture on solid medium or in liquid phase). These conventional methods have however their own limitations.

Culture is always followed by phenotypic identification, which is based on the biochemical features of the bacteria. Usually, the whole process requires 48 to 72 hours to be completed. This period is unfortunately too long, considering the speed of bacterial growth in infected tissues and, for some bacteria, the pathological effects related the toxins that they produce. This time is also too long when bacteria are spread in the environment (aerosol, food or water contamination), where germs are able to infect humans or animals and spread rapidly on a epidemic way from an infected to a healthy body on a very short time. There is therefore a need for the rapid detection and identification of pathogenic bacterial agent(s) involved in human or animal infections or present in the environment.

A stream of studies carried out recently has confirmed that molecular identification is more efficient than phenotypic identification (Bosshard et al, 2003; Bosshard et al, 2004: Lecouvet et al, 2004) and genotypic definition of bacteria species has now become the gold standard (Clarridge, 2004). There is therefore an increasing need for identifying bacterial species with more reliable methods. While obvious in the hospital setting, it is also of interest of the post September 2001 era, where accuracy and speed in identification of deadly bacteria are priorities.

Aside of the time required for routine microbiologic detection, another limiting factor is sometimes the lack of bacterial growth, generating a false-negative microbiologic result. False-negative bacterial cultures are not unusual in the clinical practice, even when clinical and biological signs clearly suggest a florid and active infection (Lecouvet et al, 2004). This false-negativity may be due to a low organism burden, non-culturable or slowly growing micro-organisms or, most often, to prior antibiotic therapy (Trampuz et al, 2003; Tzanakaki et al, 2003). In this case, a false-negative result hampers correct etiological diagnosis regarding the bacterial origin of the infectious disease, and precludes the use of early targeted antibiotherapy. As delayed antibiotherapy may increase the risk of worse clinical outcome (Gutierrez et al, 1998; Yu et al, 2003, Lecouvet et al, 2004), this situation often prompts the use of empiric, broad spectrum and sometimes long-term therapy, and certainly when there is no microbiologic result.

The higher sensitivity, speed and accuracy of DNA amplification by PCR for identification of bacteria is expected to reduce the time to diagnosis, to improve the diagnostic rate, and to allow an early choice of specific antibiotic treatment. Over the last decade, this expectation has fuelled the development of numerous promising DNA assays for detecting and identifying bacteria at the species- or genera-level in human and environmental samples (Jonas et al, 2003; Palomares et al, 2003; Poyart et al, 2001; Xu et al, 2002).

These assays remain however restricted to single species and/or genera (Brakstad et al, 1992; Poyart et al, 2001; Vannuffel et al, 1998). Such restriction has various disadvantages. For instance, in the absence of any indication on the presence of bacterial agents in an environmental sample or in a biological tissue/fluid sample from human or animal origin suspected to be infected but showing no bacterial background due to the presence of a normal bacterial flora, molecular screening methods have to be applied which target the greatest as possible number of potentially pathogenic bacteria including the most feared bacteria (*Staphylococci, Streptococci, Bacillus anthracis, Enterobacteriacea, Neisseria*, etc. . . . ) that could be used by bioterrorists. In this case, the use of specific markers or well-defined genera requires multiple and/or repeated testing to confirm or exclude a bacterial diagnosis. Considering the cost of this strategy as well as the limited amount DNA usually available for one sample, this is practically impossible to be performed.

In another example, in samples from tissues showing a bacterial background due the presence of a normal flora, the identification of a well defined panel of pathogenic bacteria recognized as "prior key targets" in the clinical setting considered (e.g. community-acquired pneumonia) remains very difficult.

In view of the above, there is therefore a need for the rapid detection and identification of pathogenic bacterial agent(s) involved in human or animal infections or present in the environment.

There is also a need for identification and diagnostic tools, which allow screening for the presence of pathogenic bacterial agent(s), and to detect and identify these pathogenic bacteria within a bacterial background.

In particular, it is clear that there is a great need in the art for molecular screening/detection and identification assays and methods having a range of specificity that is as wide as possible in order to quickly detect the presence of bacteria (bacterial detection step), while allowing in parallel or subsequently, to identify the present bacterial species, genera and, optionally the strain (bacterial identification step).

In a first aspect, the present invention therefore aims to provide an improved assay for detecting micro-organisms, and in particular bacteria. It is further an aim of the invention to provide an improved assay for diagnosing bacterial infection of a sample and/or tissue.

In another aspect, the present invention also aims to provide an improved assay and method for the identification of micro-organisms. More in particular, the invention aims to identify and provide a series of specific, molecular markers for the detection and/or identification of micro-organisms, and preferably bacteria, in a Gram-, genus- species- and/or strain-specific way.

SUMMARY

The present invention relates to an assay for detecting and identifying one or more micro-organisms in a sample, characterized in that said assay comprises the use of at least two conserved molecular markers. Preferably said micro-organisms are bacteria. In a preferred embodiment, the assay of the present invention is characterized in that it comprises the use of at least one molecular marker that is conserved in Gram-positive bacteria and at least one molecular marker that is conserved in Gram-negative bacteria.

In the prior art, in order to detect the presence of bacteria in samples or tissues, extremely conserved molecular markers are generally used. The most commonly used sequences for detecting bacteria are the sequence of the gene coding for ribosomal DNA (16s rDNA gene) (Klaschik et al, 2002) and the 16S-23S intergenic region (Gurtler & Stanisich, 1996). However, ribosomal gene 16S rDNA does not always allow the distinction between species, as illustrated for the *Bacillus* species (La Scola et al, 2003). This is a major drawback in the 16S rDNA gene sequence identification method, because in some species, a sequence can be ambiguous since it does not distinguish between two closely related clinical species but disclosing however a distinct virulence phenotype (for instances, *Escherichia coli* K12 versus *Escherichia coli* O157:H7). This remark applies to the intergenic spacer 16S-23S rDNA as well (Gianinno et al, 2003). There is therefore a need to develop a molecular identification system which better discriminate bacteria than the 16S rDNA and the intergenic spacer 16S-23S rDNA.

In accordance with the present invention two series of conserved molecular markers were identified and characterized which are extremely suitable for permitting the detection and genotyping of micro-organisms, and in particular of bacteria, in a Gram-specific way. More in particular these molecular markers comprise on one hand markers preferentially conserved in Gram-positive bacteria and the other hand markers that are preferentially conserved in Gram-negative bacteria. The present invention now allows, by a combined use of these two types of conserved molecular marker sequences, to detect bacteria in a sample and to genotype these bacteria in a gram-specific way as well as in a genera-, species-, and even sometimes, strain-specific manner.

So far, in conventional microbiology, one distinguishes the bacteria according to the structure of their wall (the wall is present in all bacteria except mycoplasms). This structure conditions the color of bacteria after Gram staining (Gram is made of several successive steps including treatment with purple gentian, Lugol's solution, alcohol and fuchsine). The bacteria whose wall is permeable to alcohol lose their purple staining (violet gentian) and coloured in red (fuchsine), defining so what is considered as a Gram-negative bacteria. In Gram-positive bacteria, the wall is primarily made by peptidoglycane. In Gram-negative bacteria, the peptidoglycane layer is thin and the wall has a more complex structure. In the clinical practice, the choice of antibiotherapy relies primarily on Gram stain. Indeed, antibiotics targeting the bacterial wall are much more on Gram-positive bacteria. As already stated above, several clinical studies show that any delay with the initiation of antibiotherapy results in increased mortality and hospital morbidity. Practically, the microbiologic identification (culture) comes too late.

Such approach provides many advantageous compared to conventionally applied detection strategies, wherein no such gram-specificity is involved. The present invention now permits by the use two series of conserved molecular markers to rapidly determine the gram-phenotype of bacteria in a sample and as a consequence to rapidly determine the most suitable antibiotherapy to be applied. This can be substituted to the conventional Gram staining procedure which is far less sensitive.

In a preferred embodiment, the assay of the present invention is further characterized in that the molecular maker that is conserved in Gram-positive bacteria comprises PurA or Pstl. In a more preferred embodiment the molecular maker that is conserved in Gram-positive bacteria is selected from the group comprising the Spy0160 (marker I), Spy1372 (marker II), SpyM3_0902 & SpyM3_0903 (marker III) and Spy1527 (marker IV) marker sequences. In yet another more preferred embodiment, the molecular maker that is conserved in Gram-positive bacteria is selected from the group comprising the sequences with SEQ ID NOs 1-62, 64-107, 109-111, 117-129, 137, 145-148, 150-193, 233-237, 240-241, 255, 326-395, 397-399, 404-425.

Another preferred embodiment of the invention relates to an assay that is characterized in that the molecular maker that is conserved in Gram-negative bacteria is selected from the group comprising the Ecs0036 (marker V), HI1576 (marker VI), EG10839 and EG11396 (marker VII), and HI0019 (marker VIII) sequences.

In yet another preferred embodiment the molecular maker that is conserved in Gram-negative bacteria is selected from the group comprising the sequences with SEQ ID NOs 63, 108, 112-116, 130-136, 138-144, 194-232, 238-239, 242-254, 256-325, 396, 400-403, 426-461.

Table 1 summarizes sequences used in accordance with the present invention for the detection and identification of Gram-positive and Gram-negative bacteria.

TABLE 1

| | | | Gram-positive bacteria | | |
|---|---|---|---|---|---|
| Sequence | Gene | Marker | Sequences found in Gram-positive bacteria (SEQ ID NOs:) | Overlapping sequences found in Gram-negative bacteria (SEQ ID NOs:) | Sequences found in other organisms (SEQ ID NO:) |
| Spy0160 | PurA | I | 1-62; 326-359 | 63 | |
| Spy1372 | PstI | II | 64-107; 109-111; 117-129; 137; 145-148; 360-395; 397-399 | 108; 112-116; 130-136; 138-144; 396; 400-403 | 149 (*Cryptococcus neoformans*) |
| SpyM3_0902 & SpyM3_0903 | Hypothetical protein | III | 150-180; 404-412 | | |

TABLE 1-continued

| Spy1527 | Hypothetical protein | IV | 181-193; 413-425 | | |
|---|---|---|---|---|---|
| | | | Gram-negative bacteria | | |
| Sequence | Gene | Marker | Sequences found in Gram-negative bacteria | Overlapping sequences found in Gram-positive bacteria | Sequences found in other organisms |
| Ecs0036 | carB | V | 194-232; 238-239; 242-254; 431-442 | 233-237; 240-241; 255 | |
| HI1576 | pgi | VI | 256-277; 426-430 | | |
| EG10839 & EG11396 | sfrB & yigC | VII | 278-303; 443-451 | | |
| HI0019 | yleA | VIII | 304-325; 452-461 | | |

The present invention also relates to the use of an assay as defined herein for diagnosing bacterial infection of a sample.

The foregoing and other objects, features and advantages of the invention will become more readily apparent from the following detailed description of preferred embodiments.

DESCRIPTION OF THE FIGURES

FIG. 1 represents the amplification of a molecular marker I (Spy0160 or pur A) in Gram-positive bacteria.

FIG. 2 represents the amplification of a molecular marker II (Spy1372 or ptsl) in Gram-positive bacteria.

FIG. 3 represents the amplification of a molecular marker III (SpyM3__0902 & SpyM3__0903) in Gram-positive bacteria.

FIGS. 4A and 4B represent marker I (purA) sequences amplified from different Gram-positive bacteria (SEQ ID NOs 1-62), and from a Gram-negative bacterium (SEQ ID NO: 63).

FIGS. 5A-C represent marker II (pstl) sequences amplified from Gram-positive bacteria (SEQ ID NOs: 64-107; SEQ ID NOs: 109-111, SEQ ID NOs: 117-129, SEQ ID NO: 137, SEQ ID NOs 145-148), from some Gram-negative bacteria (SEQ ID NOs 108, 112-116, 130-136, 138-144) and from the fungi *Cryptococcus neoformans* (SEQ ID NO: 149).

FIG. 6 represents marker III (SpyM3__0902 & SpyM3__0903) sequences amplified from Gram-positive bacteria (SEQ ID NOs 150-180).

FIG. 7 represents marker IV (putative GTP-binding factor plus 160 nt downstream this ORF) sequences amplified from Gram-positive bacteria (SEQ ID NOs 181-193).

FIG. 8 represents the amplification of a molecular marker V (Ecs0036 or carB) in Gram-negative bacteria.

FIGS. 9A and B represent sequences amplified with molecular marker V (carB) from various Gram-negative bacteria (SEQ ID NOs 194-232, 238-239, 242-254) and from various Gram-positive bacteria (SEQ ID NOs 233-237, 240-241, 255).

FIG. 10 represents the amplification of a molecular marker VI (HI1576 or pgi) in Gram-negative bacteria.

FIG. 11 represents sequences amplified with molecular marker VI (HI1576 or pgi) from various Gram-negative bacteria (SEQ ID NOs 256-277).

FIG. 12 represents sequences amplified with molecular marker VII (EG10839 & EG11396or sfrB & yigC) in Gram-negative (SEQ ID NOs 278-303).

FIG. 13 represents sequences amplified with molecular marker VIII (HI0019 or hypothetic yleA protein) in Gram-negative bacteria (SEQ ID NOs 304-325).

FIG. 14 represents marker I (Spy0160 or purA) sequences amplified from different Gram-positive bacteria (SEQ ID NOs 326-359).

FIGS. 15A and B represent marker II (Spy1372 or pstl) sequences amplified from Gram-positive bacteria (SEQ ID NOs: 360-395; SEQ ID NOs: 397-399), and some Gram-negative bacteria (SEQ ID NOs 396, 400-403).

FIG. 16 represents marker III (SpyM__0902 & SpyM__0903) sequences amplified from Gram-positive bacteria (SEQ ID NOs 404-412).

FIG. 17 represents marker IV (Spy1527, a putative GTP-binding factor plus 160 nt downstream) sequences amplified from Gram-positive bacteria (SEQ ID NOs 413-425).

FIG. 18 represents sequences amplified with molecular marker VI (HI1576 or pgi) from various Gram-negative bacteria (SEQ ID NOs 426-430).

FIG. 19 represents sequences amplified with molecular marker V (Ecs0036 or carB) from various Gram-negative bacteria (SEQ ID NOs 431-442).

FIG. 20 represents sequences amplified with molecular marker VII ( EG10839 & EG11396 or sfrB & yigC) in Gram-negative (SEQ ID NOs 443-451).

FIG. 21 represents sequences amplified with molecular marker VIII (HI0019, hypothetic yleA protein) in Gram-negative bacteria (SEQ ID NOs 452-461).

DETAILED DESCRIPTION OF THE INVENTION

The following definitions serve to illustrate the terms and expressions used in the different embodiments of the present invention as set out below.

An "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated.

The term "probe" or "nucleic acid probe" refers to single stranded sequence-specific oligonucleotides which have a base sequence which is sufficiently complementary to hybridize to the target base sequence to be detected.

The term "primer" refers to a single stranded DNA oligonucleotide sequence capable of acting as a point of initiation for synthesis of a primer, extension product which is complementary to the nucleic acid strand to be copied. The length and the sequence of the primer must be such that they allow to prime the synthesis of the extension products. Preferably the primer is about 5-50 nucleotides long. Specific length and sequence will depend on the complexity of the required DNA or RNA targets, as well as on the conditions of primer use such as temperature and ionic strength.

The term "target" refers to nucleic acid molecules originating from a biological sample which have a base sequence complementary to the nucleic acid probe of the invention. The target nucleic acid can be single-or double-stranded DNA (if appropriate, obtained following amplification) and contains a sequence which has at least partial complementarity with at least one probe oligonucleotide.

The phrase "a (biological) sample" refers to a specimen such as a clinical sample (pus, sputum, blood, urine, etc. ) of human or animal, an environmental sample, bacterial colonies, contaminated or pure cultures, purified nucleic acid, etc. in which the target sequence of interest is sought.

The term "polynucleic acid" corresponds to either double-stranded or single-stranded cDNA or genomic DNA, containing at least 10, 20, 30, 40 or 50 contiguous nucleotides.

A polynucleic acid which is smaller than 100 nucleotides in length is often also referred to as an oligonucleotide. Single stranded polynucleic acid sequences are always represented in the present invention from the 5' end to the 3' end. By "oligonucleotide" is meant a nucleotide polymer generally about 10 to about 100 nucleotides in length, but which may be greater than 100 or shorter than 10 nucleotides in length.

The term "homologous" is synonymous for identical and means that polynucleic acids which are said to be e. g. 90% homologous show 90% identical base pairs in the same position upon alignment of the sequences.

"Hybridization" involves the annealing of a complementary sequence to the target nucleic acid (the sequence to be detected). The ability of two polymers of nucleic acid containing complementary sequences to find each other and anneal through base pairing interaction is a well-recognized phenomenon.

The term "stringency" indicates one used to describe the temperature and solvent composition existing during hybridization and the subsequent processing steps. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. Stringency is chosen to maximize the difference in stability between the hybrid formed with the target and the non-target nucleic acid.

By "complementary" is meant a property conferred by the base sequence of a single strand of DNA which may form a hybrid or double stranded DNA: DNA, through hydrogen bonding between Watson-Crick base pairs on the respective strands. Adenine (A) usually complements thymine (T), while guanine (G) usually complements cytosine (C).

By "hybrid" is meant the complex formed between two single stranded nucleic acid sequences by Watson-Crick base pairings or non-canonical base pairings between the complementary bases.

Molecular Marker sequences

In a first aspect, the present invention provides conserved molecular markers for the detection and/or identification of one or more micro-organisms, and preferably bacteria. More in particular, the present invention provides two series of conserved molecular markers which are extremely suitable for permitting the detection and genotyping of micro-organisms, and in particular of bacteria, in a Gram-specific way.

The term "molecular marker" and "molecular marker sequence" are used herein as synonyms. These terms refer to isolated and purified nucleic acid (DNA) molecules. The term "conserved molecular marker" as used herein refers to a coding or non coding DNA sequence, which can be found in the genome of various bacterial species, showing a sequence identity with an original sequence which is superior to or equal to 50%, and preferably superior to or equal to 65%, and more preferably superior to or equal to 80%.

According to the present invention, two series of conserved genetic markers were characterized: one preferentially conserved in Gram-positive bacteria and the other preferentially conserved in Gram-negative bacteria.

In a preferred embodiment, the molecular markers that are conserved in Gram-positive bacteria comprise Spy0160 (PurA) or Spy1372 (Pstl). More preferably the markers that are conserved in Gram-positive bacteria are selected from the group comprising Spy0160 Spy1372, SpyM3_0902 & SpyM3_0903, and Spy1527 marker sequences In another preferred embodiment, the molecular markers that are conserved in Gram-positive bacteria are any of the sequences with SEQ ID NOs 1-62, 64-107, 109-111, 117-129, 137, 145-148, 150-193, 233-237, 240-241, 255, 326-395, 397-399, 404-425.

In yet another preferred embodiment, the molecular markers that are conserved in Gram-negative bacteria are selected from the group comprising Ecs0036, HI1576, EG10839 & EG11396, and HI0019.

In another preferred embodiment, the molecular markers that are conserved in Gram-negative bacteria are any of the sequences with SEQ ID NOs 63, 108, 112-116, 130-136, 138-144, 194-232, 238-239, 242-254, 256-325, 396, 400-403, 426-461. However, it should be clear from the present invention that the present invention is not limited to the molecular marker sequences conserved in Gram-positive and in Gram-positive bacteria as described herein. Other conserved molecular marker sequences that can be characterized and identified for various other Gram-positive bacteria and other Gram-negative bacteria including according to the invention are considered to be included in the present application as well.

In another embodiment, the invention relates to the use of at least two conserved molecular markers for detecting bacteria in a sample.

In a preferred embodiment, the invention relates to the use of at least two conserved molecular markers for detecting and genotyping a bacterium on the basis of the Gram phenotype in a sample. Preferably, the invention relates to the use of at least one molecular marker that is conserved in Gram-positive bacteria and at least one molecular marker that is conserved in Gram-negative bacteria for detecting and genotyping a bacterium. In particularly preferred embodiment, the invention relates to the use of at least one molecular marker that is conserved in Gram-positive bacteria selected from the group comprising Spy0160, Spy1372, SpyM3_0902 & SpyM3_0903, Spy1527, or any of the sequences with SEQ ID NOs 1-62, 64-107, 109-111, 117-129, 137, 145-148, 150-193, 233-237, 240-241, 255, 326-395, 397-399, 404-425, and at least one molecular marker that is conserved in Gram-negative bacteria and that is selected from the group comprising Ecs0036, HI1576, EG10839 & EG11396, HI0019, or any of the sequences with SEQ ID NOs 63, 108, 112-116, 130-136, 138-144, 194-232, 238-239, 242-254, 256-325, 396, 400-403, 426-461.

The present invention thus provides for highly conserved molecular markers that can be used for detecting the molecular presence of micro-organisms, and in particular of bacteria, in samples and/or tissues, including in cultured samples which give a false-negative result using conventional detection techniques. The present conserved markers can also advantageously be used for detecting the molecular presence of micro-organisms, and in particular of bacteria, in samples from tissues showing bacterial background. In the latter case, the conserved molecular markers are preferably used in combination with specific primers or probes that directly target a pre-defined panel of bacteria of interest and that exclude the “background flora”. A suitable pre-defined panel of bacteria of interest may, for instance, include bacteria involved in community-acquired pneumonia, such as but is not limited to *Haemophilus influenzae, Legionella* species, *Staphylococcus aureus, Moraxella catarrhalis*, Gram-negative enteric bacteria.

It is further noted that the molecular identification of Gram phenotype is based on partially overlapping Gram-positive and Gram-negative markers. It must born in mind that, unlike in the present invention, another conserved marker (16S) shows an extensive overlap between Gram-positive and Gram-negative bacteria. In the present case, using concomitantly both series of partially overlapping markers in a combined way makes it possible to cover a much broader spectrum of bacterial pathogens while defining also precisely the Gram phenotype of those pathogens. The strategy relies upon the molecular detection of gene preferentially present in Gram-positive or Gram-negative bacterial. Each series of markers allows therefore improving overall detection in their respective group (either Gram-positive bacteria for preferentially Gram-positive markers, or Gram-negative bacteria for preferentially Gram-negative markers). Considering the somehow overlapping specificity for both groups, (overlap within the Gram-positive specificity for Gram-negative markers and overlap within the Gram-positive specificity for Gram-negative markers), the power of the molecular discrimination is even increased for some bacteria targeted by both groups of markers. This combined strategy overcomes the potential lack of specificity obtained when using one single marker towards some species, as is for instance the case when using a 16S marker.

In addition, the use of different markers which are mapped on different loci in the bacteria also improves the quality of the diagnosis in that it can more easily circumvent false positive reactions due to accidental PCR contamination hampering the use of one particular marker.

Primers and probes derived from conserved molecular markers

In another embodiment, the invention relates to a primer pair (forward and reverse primers) suitable for amplifying a molecular marker that is conserved in Gram-positive bacteria. More preferably, the invention relates to a primer pair suitable for amplifying any of the conserved molecular marker sequences that are conserved in Gram-positive bacteria as defined herein, and that are preferably selected from the group comprising Spy0160, Spy1372, SpyM3_0902 & SpyM3_0903, and Spy1527, or any of the sequences with SEQ ID NOs 1-62, 64-107, 109-111, 117-129, 137, 145-148, 150-193, 233-237, 240-241, 255, 326-395, 397-399, 404-425.

In another embodiment, the invention relates to a primer pair (forward and reverse primers) suitable for amplifying a molecular marker that is conserved in Gram-negative bacteria. More preferably, the invention relates to a primer pair suitable for amplifying any of the conserved molecular marker sequences that are conserved in Gram-negative bacteria as defined herein, and that are preferably selected from the group comprising Ecs0036, HI1576, EG10839 & EG11396 and HI0019, or any of the sequences with SEQ ID NOs 63, 108, 112-116, 130-136, 138-144, 194-232, 238-239, 242-254, 256-325, 396, 400-403, 426-461.

The primers of the present invention include at least 15-mer oligonucleotide and are preferably 70%, 80%, 90% or more than 95% homologous to the exact complement of the target sequence to be amplified. Those primers are about 15 to 50 nucleotides long, and preferably about 15 to 35 nucleotides long. Of course, primers consisting of more than 50 nucleotides can be used.

The present invention also relates to a nucleic acid probe capable of hybridizing to a molecular marker that is conserved in Gram-positive bacteria. More preferably, the invention relates to a nucleic acid probe capable of hybridizing any of the molecular marker sequences that are conserved in Gram-positive bacteria as defined herein, and that are preferably selected from the group comprising Spy0160 (PurA), Spy1372 (Pstl), SpyM3_0902 & SpyM3_0903, and Spy1527, or any of the sequences with SEQ ID NOs 1-62, 64-107, 109-111, 117-129,137, 145-148, 150-193, 233-237, 240-241, 255, 326-395, 397-399, 404-425.

In another embodiment, the present invention also relates to a nucleic acid probe capable of hybridizing to a molecular marker that is conserved in Gram-negative bacteria. More preferably, the invention relates to a nucleic acid probe capable of hybridizing any of the molecular marker sequences that are conserved in Gram-negative bacteria as defined herein, and that are preferably selected from the group comprising Ecs0036, HI1576, EG10839 & EG11396 and HI0019, or any of the sequences with SEQ ID NOs 63, 108, 112-116, 130-136, 138-144, 194-232, 238-239, 242-254, 256-325, 396, 400-403, 426-461.

The probe of the present invention preferably includes at least 15-mer oligonucleotide and are preferably 70%, 80%, 90% or more than 95% homologous to the exact complement of the target sequence to be detected. Those probes are preferably about 15 to 50 nucleotides long. The primers and probes of the invention can be used, for diagnostic purposes, in investigating the presence or the absence of a target nucleic acid in a biological sample, according to all the known hybridization techniques such as for instance dot blot, slot blot, hybridization on arrays including nanotools, real-time PCR, etc. . . .

The probes of the invention will preferably hybridize specifically to one or more of the above-mentioned molecular marker sequences.

The primers of the invention may amplify specifically one or more of the above-mentioned marker sequences. The design of specifically hybridising probes is within the skilled person’s knowledge. Also the design of primers which can specifically amplify certain sequences or molecular markers is within the skilled person’s knowledge.

The nucleic acid probes of this invention can be included in a composition or kit which can be used to rapidly determine the presence or absence of pathogenic species of interest (see below).

Compositions

In another embodiment, the invention relates to a composition. In a preferred embodiment, the invention relates to a composition comprising at least one primer pair (forward and reverse primers) suitable for amplifying a conserved molecular marker that is conserved in Gram-positive bacteria and at least one primer pair (forward and reverse primers) suitable for amplifying a conserved molecular marker that is conserved in Gram-negative bacteria.

Preferably, the composition comprises at least one primer pair suitable for amplifying any of the molecular marker sequences that are conserved in Gram-positive bacteria and that are selected from the group comprising Spy1060, Spy1372, SpyM3_0902 & $SpyM3_{13}$ 0903, and Spy1527, or any of the sequences with SEQ ID NOs 1-62, 64-107, 109-111, 117-129, 137, 145-148, 150-193, 233-237, 240-241, 255, 326-395, 397-399, 404-425, and at least one primer pair suitable for amplifying any of the molecular marker sequences that are conserved in Gram-negative bacteria and that are selected from the group comprising Ecs0036, HI1576, EG10839 & EG11396 and HI0019, or any of the sequences with SEQ ID NOs SEQ ID NOs 63, 108, 112-116, 130-136, 138-144, 194-232, 238-239, 242-254, 256-325, 396, 400-403, 426-461.

In yet another embodiment, the invention relates to a composition comprising at least one nucleic acid probe capable of hybridizing to a molecular marker that is conserved in Gram-positive bacteria, and at least one nucleic acid probe capable of hybridizing to a molecular marker that is conserved in Gram-negative bacteria. Preferably, the composition comprises at least one nucleic acid probe capable of hybridizing to a molecular marker that is conserved in Gram-positive bacteria selected from the group comprising Spy0160, Spy1372, SpyM3_0902 & SpyM3_0903, and Spy1527, or any of the sequences with SEQ ID NOs 1-62, 64-107, 109-111, 117-129, 137, 145-148, 150-193, 233-237, 240-241, 255, 326-395, 397-399, 404-425, and at least one at least one nucleic acid probe capable of hybridizing to a molecular marker that is conserved in Gram-negative bacteria selected from the group comprising Ecs0036, HI1576, EG10839 & EG11396 and HI0019, or any of the sequences with SEQ ID NOs 63, 108, 112-116, 130-136, 138-144, 194-232, 238-239, 242-254, 256-325, 396, 400-403, 426-461.

By "composition", it is meant that primers or probes complementary to bacterial DNA may be in a pure state or in combination with other primers or probes. In addition, the primers or probes may be in combination with salts or buffers, and may be in a dried state, in an alcohol solution as a precipitate, or in an aqueous solution.

Kits

In yet another embodiment, the invention relates to a kit for detecting and identifying one or more micro-organisms, preferably bacteria, in a sample, which comprises:

a) a composition comprising at least one primer pair (forward and reverse primers) suitable for amplifying a conserved molecular marker that is conserved in Gram-positive bacteria and at least one primer pair (forward and reverse primers) suitable for amplifying a conserved molecular marker that is conserved in Gram-negative bacteria; for amplifying polynucleic acids in said sample, b) a composition comprising at least one nucleic acid probe capable of hybridizing to a molecular marker that is conserved in Gram-positive bacteria, and at least one nucleic acid probe capable of hybridizing to a molecular marker that is conserved in Gram-negative bacteria, c) a buffer enabling hybridization reaction between the probes contained in said composition and the polynucleic acids present in said sample or amplified products therefrom or components necessary for producing the buffer, d) a solution for washing hybrids formed under the appropriate wash conditions or components necessary for producing the solution, and e) optionally a means for detection of said hybrids.

A kit according to the invention preferably includes all components necessary to assay for the presence of bacteria. In the universal concept, the kit includes a stable preparation of labeled probes, hybridization solution in either dry or liquid form for the hybridization of target and probe polynucleotides, as well as a solution for washing and removing undesireable and nonduplexed polynucleotides, a substrate for detecting the labeled duplex, and optionally an instrument for the detection of the label.

In a preferred embodiment, the present kit comprises a composition which comprises at least one primer pair suitable for amplifying any of the molecular marker sequences that are conserved in Gram-positive bacteria selected from the group comprising Spy0160, Spy1372, SpyM3_0902 & SpyM3_0903, and Spy1527, or any of the sequences with SEQ ID NOs 1-62, 64-107, 109-111, 117-129, 137, 145-148, 150-193, 233-237, 240-241, 255, 326-395, 397-399, 404-425, and at least one primer pair suitable for amplifying any of the molecular marker sequences that are conserved in Gram-negative bacteria selected from the group comprising Ecs0036, HI1576, EG10839 & EG11396 and HI0019, or any of the sequences with SEQ ID NOs 63, 108, 112-116, 130-136, 138-144, 194-232, 238-239, 242-254, 256-325, 396, 400-403, 426-461.

In yet another preferred embodiment, the present kit comprises a composition which comprises at least one nucleic acid probe capable of hybridizing to a molecular marker that is conserved in Gram-positive bacteria selected from the group comprising Spy0160, Spy1372, SpyM3_0902 & SpyM3_0903, and Spy1527, or any of the sequences with SEQ ID NOs 1-62, 64-107, 109-111, 117-129, 137, 145-148, 150-193, 233-237, 240-241, 255, 326-395, 397-399, 404-425, and at least one at least one nucleic acid probe capable of hybridising to a molecular marker that is conserved in Gram-negative bacteria selected from the group comprising Ecs0036, HI1576, EG10839 & EG11396 and HI0019, or any of the sequences with SEQ ID NOs 63, 108, 112-116, 130-136, 138-144, 194-232, 238-239, 242-254, 256-325, 396, 400-403, 426-461.

In yet another preferred embodiment, the kit according to the present invention further comprises one or more genus-, species and/or strain-specific nucleic acid probes capable of hybridizing to a genus-, species and/or strain-specific bacterial polynucleotide sequence.

DNA chip

In another preferred embodiment, the present invention provides a DNA chip in which nucleic acid probes are immobilized on a solid support. The invention relates to the manufacturing of a solid support (array-DNA chip) on which several sets of nucleic acid probes are covalently bound or directly synthesized.

In a preferred embodiment, the invention relates to a DNA chip in which at least one of nucleic acid probe capable of hybridizing to a molecular marker that is conserved in Gram-positive bacteria, and at least one nucleic acid probe capable of hybridizing to a molecular marker that is conserved in Gram-negative bacteria, is immobilized on a solid support.

Preferably, the DNA chip comprises at least one nucleic acid probe capable of hybridizing to a molecular marker that is conserved in Gram-positive bacteria selected from the group comprising Spy0160, Spy1372, SpyM3_0902 & SpyM3_0903, and Spy1527, or any of the sequences with SEQ ID NOs 1-62, 64-107, 109-111, 117-129, 137, 145-148, 150-193, 233-237, 240-241, 255, 326-395, 397-399, 404-425, and at least one nucleic acid probe capable of hybridizing to a molecular marker that is conserved in Gram-negative bacteria selected from the group comprising Ecs0036, HI1576, EG10839 & EG11396 and HI0019, or any of the sequences with SEQ ID NOs 63, 108, 112-116, 130-136, 138-144, 194-232, 238-239, 242-254, 256-325, 396, 400-403, 426-461 immobilized on a solid support.

In yet another preferred embodiment, the DNA chip according to the present invention further comprises one or more genus-, species and/or strain-specific nucleic acid probes capable of hybridizing to a genus-, species and/or strain-specific bacterial polynucleotide sequence.

The DNA chip which is formed by arranging DNA fragments of variety of base sequences on the surface of a narrow substrate in high density is used in finding out the information on DNA of an unknown sample by hybridization between an immobilized DNA and unknown DNA sample complementary thereto. Examples of the solid carrier on which the probe oligonucleotides are fixed include inorganic materials such as glass and silicon and polymeric materials such as acryl, polyethylene terephtalate (PET), polystyrene, polycarbonate and polypropylene. The surface of the solid substrate can be flat or have a multiple of hole. The probes are immobilized on the substrate by covalent bond of either 3' end or 5' end. The immobilization can be achieved by conventional techniques, for example, using electrostatic force, binding between aldehyde coated slide and amine group attached on synthetic oligomeric phase or spotting on amine coated slide, L-lysine coated slide or nitrocellulose coated slide. The immobilization and the arrangement of various probes onto the solid substrate are carried out by pin microarray, inkjet, photolithography, electric array, etc.

The term "DNA chip" as used herein, is to be understood in its broadest sense, i.e. including nanochips or nanotools that are designed to recognize a specific pattern of nucleic acids through hybridization.

Assay

In another embodiment, the invention relates to an assay for detecting and identifying one or more micro-organisms, preferably bacteria, in a sample, characterized in that said assay comprises the use of at least two conserved molecular markers, and preferably comprises the use of at least one molecular marker that is conserved in Gram-positive bacteria and at least one molecular marker that is conserved in Gram-negative bacteria.

In the prior art, ultimate molecular species identification results classically from sequence analysis of an amplification product and the comparison of this sequence with those which are available in public DNA database (for instance, GeneBank . . .). The sequence analysis requires nearly 24 hours to complete the various analytical steps: amplicon purification, cycle sequencing, reading and interpretation of the results.

The present invention provides a strategy which permits to significantly reduce the time requested for genera, species, and optionally strain, identification of bacteria in a sample compared to classical identification strategies as described above. More in particular, the present strategy preferably consists in amplifying a set of conserved genetic markers and either to hybridize produced amplicons on specific capture probes covalently bound on an array or, alternatively, to hybridize a specific probe during the amplification step (e.g. real-time PCR with Taqman or molecular Beacon probes). The result of the identification will include information regarding the Gram phenotype of bacteria present in the sample of interest (or a combination of both Gram phenotype in case of mixed infections with Gram-positive and Gram-negative), as well as information on genera and species to which they belong. The final results will integrate all the hybridization signals generated by the selected markers.

In a preferred embodiment, the method for detecting and identifying one or more micro-organisms, preferably bacteria, in a sample may comprise the following steps:

a) If appropriate isolating and/or concentrating the DNA present in said sample;
b) amplifying said DNA with
   - at least one pair of (forward and reverse) primers suitable for amplifying a molecular marker that is conserved in Gram-positive bacteria, and
   - at least one pair of (forward and reverse) primers suitable for amplifying a molecular marker that is conserved in Gram-negative bacteria,
c) hybridizing the amplified DNA fragments obtained in step b) with genus-, and/or species-, and/or strain-specific primers or nucleic acid probes
d) detecting the hybrids formed in step c) and
e) identifying micro-organisms in said sample from the differential hybridization signals obtained in step d)

The present invention allows to detect the presence of bacteria in human, animal and/or environmental samples, and, at the same time, to identify those bacteria, including, highly pathogenic ones. Such detection and identification system is based on the pattern of hybridization of several combined DNA fragments. Identification relies upon concomitant signals generated by a panel of unrelated markers. The system provides discrimination based on the Gram-phenotype as well as genus- and species-specificity.

To provide nucleic acid substrates for use in the detection and identification of micro-organisms in clinical samples using the present assay, nucleic acid, preferably DNA, is extracted from the sample. The nucleic acid may be extracted from a variety of clinical samples, or environmental samples, using a variety of standard techniques or commercially available kits.

A second step is an amplification of the desired DNA region of the target DNA by PCR. Examples of the PCR include most typical PCR using the same amounts of forward and reverse primers, multiplex PCR in which a multiple of target DNAs can be amplified at once by adding various primers simultaneously, ligase chain reaction (LCR) in which target DNA is amplified using specific 4 primers and ligase and the amount of fluorescence is measured by ELISA (Enzyme Linked Immunosorbent Assay), and the other PCR such as Hot Start PCR, Nest-PCR, DOP-PCR (degenerate oligonucleotide primer PCR), RT-PCR (reverse transcription PCR), Semi-quantitative RT-PCR, Real time PCR, RACE (rapid amplification of cDNA ends), Competitive PCR, STR (short tandem repeats), SSCP (single strand conformation polymorphism), DDRT-PCR (differential display reverse transcriptase), etc.

A further step comprises the hybridization of the amplified DNA fragments obtained in step b) with specific primers or nucleic acid probes. The choice of the applied hybridization technique should not be considered as limitative for the present invention. Nanotools can also be designed to recognize a specific nucleic acid pattern with or without PCR amplification.

In one embodiment, step c) may include an identification by contacting the amplified DNA fragments obtained in step b) with a composition comprising at least one nucleic acid probe capable of hybridizing to a molecular marker that is conserved in Gram-positive bacteria, and at least one nucleic acid probe capable of hybridizing to a molecular marker that is conserved in Gram-negative bacteria. In such case, steps b) and c) of the above described method are performed subsequently. For instance, identification may be performed using a reverse hybridization procedure (dot blot, slot blot, hybridization on micro-, macro- or nano-arrays, etc. . . . ) In such case, hybridization of marked amplicons is performed on Gram-, genera- and species-specific nucleic acid probes bound covalently on the array (e.g. micro- or macro-arrays). While the result is visual, the reading can also be automated, facilitating therefore the use in the clinical practice.

In another embodiment, step c) may include the use of real-time PCR with specific probes (multiplex approach) which allows to have a specific result in a couple of hours. Simplex or multiplex PCR techniques in real-time include the use of specific acid probes on a DNA target during the PCR step (e.g. Taqman probes, molecular beacons or MGB (Minor Groove Binding) probes, etc. . . ). In such case, steps b) and c) of the above described method are performed simultaneously. A significant advantage of using a real-time PCR technique is the increased speed, e.g. only a couple of hours are required for obtained final results. This is mainly due to the reduced cycle times, removal of separate post-PCR detection procedures, and the use of sensitive fluorescence detection equipment, allowing earlier amplicon detection. Another advantage of a real-time PCR technique is that it is a single tube procedure with the reading during the PCR and no manipulation required at the end of the procedure. This single tube procedure prevents therefore the risk of molecular contamination existing with other PCR procedures, including micro- and macro-array techniques. Preferably a nested real-time PCR strategy is used to increase the sensitivity of the method with a detection limit of one DNA copy in tissue samples.

The formed hybrids can be quantified by labeling the target with a fluorescence or radioactive isotope in accordance to conventional methods. The labeling may be carried out by the use of labeled primers or the use of labeled nucleotides incorporated during the polymerase step of the amplification.

According to a preferred embodiment of the present invention, the primers suitable for amplifying a molecular marker that is conserved in Gram-positive bacteria used in step b) of the above mentioned method preferably comprise primers suitable for amplifying a molecular marker selected from the group comprising Spy0160, Spy1372, SpyM3_0902 & SpyM3_0903, Spy1527, or any of the sequences with SEQ ID NOs 1-62, 64-107, 109-111, 117-129, 137, 145-148, 150-193, 233-237, 240-241, 255, 326-395, 397-399, 404-425.

According to another preferred embodiment of the present invention, the primers suitable for amplifying a molecular marker that is conserved in Gram-negative bacteria used in step b) of the above mentioned method preferably comprise primers suitable for amplifying a molecular marker selected from the group comprising Ecs0036, HI1576, EG10839 & EG11396 and HI0019, or any of the sequences with SEQ ID NOs 63, 108, 112-116, 130-136, 138-144, 194-232, 238-239, 242-254, 256-325, 396, 400-403, 426-461.

The following examples are meant to illustrate the present invention. Examples 1-3 present and describe molecular marker sequences that have been characterized on a wide panel of clinical and reference bacterial genera species and bacterial strains and that allow the discrimination between Gram-positive and Gram-negative bacteria as well as genera and species identification. Example 4 illustrates the use of molecular markers according to the present invention for the detection and identification of *Bacillus* bacteria and for the discrimination between various *Bacillus* strains of the same species. Example 5 illustrates nucleic acid probes according to the present invention.

EXAMPLES

Example 1

Characterization of Molecular Markers of Genes Enabling the Identification of Gram-Positive Bacteria The present example aims to test the Gram-positive specificity of several markers. The list of Gram-positive bacteria used in the present example (study of markers specificity) is given in table 2A.

TABLE 2A

| Gram-positive bacteria | | |
|---|---|---|
| genus | species | strain reference |
| *Bacillus* | *anthracis* | 1978 |
| *Bacillus* | *anthracis* | STERNE |
| *Bacillus* | *anthracis* | BUTARE |
| *Bacillus* | *anthracis* | 1655H85 |
| *Bacillus* | *anthracis* | CODA-CERVA |
| *Bacillus* | *anthracis* | 2054H82 |
| *Bacillus* | *cereus* | ATCC10987 |
| *Bacillus* | *cereus* | ATCC 14579 |
| *Bacillus* | *pumilus* | Clinical |
| *Bacillus* | species | Clinical |
| *Bacillus* | *thuringiensis kurstaki* | T03A016 HD_1 |
| *Bacillus* | *thuringiensis israelensi* | 4Q2_72 |
| *Bacillus* | *mycoides* | MYC003 |
| *Bacillus* | *mycoides* | NRS306 |
| *Bacillus* | *weihenstephanensis* | WSBC10204 |
| *Bacillus* | *halodurans* | DSMZ 497 |
| *Bacillus* | *firmus* | DSMZ 12643 |
| *Bacillus* | *megatherium* | DSMZ 1324 |
| *Bacillus* | *pseudomycoides* | DSMZ 12442 |
| *Clostridium* | *difficile* | DSMZ 1296 |
| *Clostridium* | *perfingens* | DSMZ 756 |
| *Enterococcus* | *faecium* | DSMZ 6177 |
| *Enterococcus* | *faecalis* | DSMZ 2570 |
| *Enterococcus* | *flavescens* | DSMZ 7370 |
| *Enterococcus* | *durans* | DSMZ 20633 |
| *Enterococcus* | *casseliflavus* | DSMZ 20680 |
| *Enterococcus* | *gallinarum* | DSMZ 20628 |
| *Enterococcus* | *hirae* | DSMZ 20160 |
| *Enterococcus* | *raffinosus* | DSMZ 75633 |
| *Enterococcus* | *avium* | DSMZ 20679 |
| *Enterococcus* | *villorum* | CODA-CERVA |
| *Lactococcus* | *lactis* | DSMZ 20481 |
| *Listeria* | *monocytogenes* | DSMZ 20600 |
| *Listeria* | *innocua* | DSMZ 20649 |
| *Staphylococcus* | *aureus* | ATCC 35884 |
| *Staphylococcus* | *epidermidis* | ATCC 14990 |
| *Staphylococcus* | *hominis* | ATCC 27844 |
| *Staphylococcus* | *haemolyticus* | ATCC 29970 |
| *Staphylococcus* | *saprophyticus* | ATCC 15305 |
| *Staphylococcus* | *xylosus* | ATCC 35663 |
| *Staphylococcus* | *simulans* | ATCC 27848 |
| *Staphylococcus* | *cohnii cohni,* | ATCC 35662 |
| *Staphylococcus* | *capitis capitis* | ATCC 27840 |
| *Staphylococcus* | *sciuri* | ATCC 29062 |
| *Staphylococcus* | *warneri* | ATCC 27836 |
| *Staphylococcus* | *lugdunensis* | ATCC 43809 |
| *Staphylococcus* | *gallinarum* | ATCC C3572 |

TABLE 2A-continued

| Gram-positive bacteria | | |
|---|---|---|
| genus | species | strain reference |
| *Staphylococcus* | *schleiferi schleiferi* | ATCC 43808 |
| *Staphylococcus* | *capitis ureolyticus* | ATCC 49326 |
| *Staphylococcus* | *cohnii urealyticum* | ATCC 49330 |
| *Staphylococcus* | *auricularis* | ATCC 33753 |
| *Staphylococcus* | *caseolyticus* | ATCC 13548 |
| *Staphylococcus* | *intermedius* | ATCC 29663 |
| *Streptococcus* | *pyogenes* | DSMZ 20565 |
| *Streptococcus* | *agalactiae* | DSMZ 2134 |
| *Streptococcus* | *pneumoniae* | DSMZ 20566 |
| *Streptococcus* | *oralis* | DSMZ 20627 |
| *Streptococcus* | *sanguinis* | DSMZ 20567 |
| *Streptococcus* | *mitis* | DSMZ 12643 |
| *Streptococcus* | *gordonii* | DSMZ 6777 |
| *Streptococcus* | *canis* | DSMZ 20386 |
| *Streptococcus* | *mutans* | DSMZ 20523 |
| *Streptococcus* | subspecies | Clinical |
| *Streptococcus* | *bovis* | DSMZ 20480 |
| *Streptococcus* | *thermophilus* | DSMZ 20617 |
| *Streptococcus* | *suis* | DSMZ 9682 |

The following sequences have been characterized and used for multigenotypic identification of Gram-positive bacteria.

The Spy0160 sequence (marker I) from *Streptococcus pyogenes* (accession number: AE006485.1; position 3201 to 4030) is part of an open reading frame homologous for the gene purA. The purA protein plays an important role in the novo bacterial synthesis of purines. It catalyses the synthesis of adenylosuccinate starting from inosine monophosphate (IMP) and of aspartate, and using energy provided by the GTP. The first nucleotides alignments performed suggested the existence of conserved sequences similar to the Spy0160 sequence in a few Gram-positive bacteria. These findings have been extended to a wide panel of bacteria that were available in our DNA bank and confirmed that this marker was present in almost all Gram-positive bacteria and was very helpful in discrimination of closely related Gram-positive species and in many cases could allow discrimination between strains of the same species A second marker is the Spy1372 sequence (Marker II) from *Streptococcus pyogenes* (accession n° AE004092, position 1139277 to 1141010). The corresponding gene probably encodes an enzyme involved in the transport of sugar in bacteria. Indeed, this gene is homologous to gene ptsl of *Staphylococcus aureus* coding for a phosphoenol pyruvate phosphatase (accession n° NC_002758, from position 1137273 to 1138991). This gene is part of PTS operon (phosphotransferase system) including several genes coding for proteins involved in importation of sugar by bacteria (Plumbridge et al, 2002). The product of ptsl gene is a protein called Enzyme I, which may be phosphorylated by phosphoenol pyruvate. Phosphorylated Enzyme I can give its phosphate group to another protein of the PTS group through a cascade which leads to the entry of glucose in the bacterial periplasm (Stentz et al, 1997).

A third marker is the SpyM3_0902-SpyM3_0903 sequence (Marker III) from *Streptococcus pyogenes* MGAS315 (accession n° AE014154, from position 40670 to 41160). This sequence is located downstream the gene encoding alpha-helicase and corresponds to the open reading frame of a hypothetical protein.

A fourth marker is the Spy1527 sequence (Marker IV) from *Streptococcus pyogenes* from position 1201 to 2464, including nucleotides 2465 to 2625 (accession n° AE006586). The Spy1527 sequence corresponds to the gene typA, coding for a putative GTP-binding protein (GTP-BP). The fragment from position 2465 to 2625 does not correspond to an open reading frame, but is a non-coding sequence.

A first analysis of some available complete bacterial genomes suggests that homologous sequences were present in most of those bacteria.

A further analysis has been performed on reference strains and on several hundreds clinical strains provided by Belgian hospitals. The conservation of targets of interest (purA and ptsl (i.e. Marker I and II) has been confirmed in the genome of all these reference and clinical strains. This analysis confirmed the very little genomic variability of these sequences within a species of interest: This feature is crucial to allow the use of these marker sequences in a strategy of multigenotypic identification of Gram-positive bacteria.

Example 2

Characterization of Molecular Markers of Genes Enabling the Identification of Gram-Negative Bacteria The present example aims to test the Gram-negative specificity of several markers. The list of Gram-positive bacteria used in the present example (study of markers specificity) is given in table 2B.

TABLE 2B

| Gram-negative bacteria | | |
|---|---|---|
| genus | species | strain reference |
| *Acinetobacter* | *baumanii* | ATCC 19606 |
| *Acinetobacter* | *calcoaceticus* | DSMZ 1139D |
| *Bordetella* | *parapertussis* | Clinical |
| *Bordetella* | *bronchiseptica* | Clinical |
| *Bordetella* | *pertusis* | Clinical |
| *Brucella* | *melitensis* biovar | 16M |
| *Brucella* | *melitensis* biovar 2 | 63/9 |
| *Brucella* | *abortus* biovar 1 | 544 |
| *Brucella* | *abortus* biovar 2 | 86/8/59 |
| *Brucella* | *canis* | RM6/66 |
| *Brucella* | *ovis* | 63/290 |
| *Brucella* | *suis* biovar 1 | 1330 |
| *Brucella* | *suis* biovar 2 | 686 |
| *Burkholderia* | *cepacia* | ATCC 17770 |
| *Citrobacter* | *freundii* | DSMZ 30039 |
| *Cryptococcus* | *neoformans* | DSMZ 70219 |
| *Enterobacter* | *cloaceae* | ATCC 13047 |
| *Enterobacter* | *aerogenes* | DSMZ 13048 |
| *Escherishia* | *coli* O157:H7 | DSMZ 8579 |
| *Escherishia* | *coli* K12 | DSMZ 6367 |
| *Francisella* | *tularensis* | SVA/T7 |
| *Haemophilus* | *influenzae* | DSMZ 9999 |
| *Haemophilus* | *ducrei* | — |
| *Klebsiella* | *pneumoniae* | ATCC 13883 |
| *Klebsiella* | *oxytica* | ATCC 43863 |
| *Legionella* | *pneumophilia* | DSMZ 7513 |
| *Moraxella* | *catarrhalis* | DSMZ 11994 |
| *Morganella* | *morganii* | ATCC 25830 |
| *Neisseria* | *meningitidis* groupe C | ISP ??? |
| *Neisseria* | *meningitidis* groupe B | clinical |
| *Pasteurella* | *multocida* | — |
| *Proteus* | *mirabilis* | ATCC 29906 |
| *Proteus* | *vulgaris* | ATCC 13315 |
| *Providencia* | *stuartii* | ATCC 29914 |
| *Pseudomonas* | *aeruginosa* | DSMZ 50071 |
| *Pseudomonas* | *putida* | ATCC 12633 |
| *Pseudomonas* | *syringae* | ATCC 39254 |
| *Salmonella* | *enteritidis* | Clinical |
| *Salmonella* | *enterica hadar* | Clinical |
| *Salmonella* | *enterica brandenburg* | Clinical |
| *Salmonella* | *enterica derby* | Clinical |
| *Salmonella* | *enterica virchow* | Clinical |

TABLE 2B-continued

| Gram-negative bacteria | | |
|---|---|---|
| genus | species | strain reference |
| *Salmonella* | *enterica typhimurium* | Clinical |
| *Salmonella* | *enterica* paratyphi B | Clinical |
| *Serratia* | *liquefasciens* | ATCC 27592 |
| *Serratia* | *marcescens* | ATCC 13880 |
| *Shigella* | *sonnei* | Clinical |
| *Shigella* | *flexneri* | — |
| *Vibrio* | *parahaemolyticus* | — |
| *Vibrio* | *cholerae* | — |
| *Yersinia* | *pestis* | — |

The following sequences have been characterized and used for multigenotypic identification of Gram-negative bacteria.

The HI1576 sequence (marker VI) from *Haemophilus influenzae* corresponds to the gene coding for phosphoglucose isomerase (accession n° U32831, from position 12660 to 13991) an enzyme playing a role in glucidic metabolism especially for glycolysis (Morris et al, 2001).

Another sequence is the Ecs0036 sequence (marker V) from *Escherichia coli* O157:H7 (accession n° AP002550; from position 35200 to 36200). It is believed that this sequence encodes the large carbamoyl-synthetase unit, an enzyme which catalysis the synthesis of carbamoyl phosphate, from glutamine, bicarbonate and two ATP molecules through a mechanism which requires several successive steps (Raushel et al, 2001). The synthesized carbamoyl-phosphate contributes to de novo synthesis of pyrimidic bases in bacteria (Minic et al, 2001).

Another sequence is the EG10839 & EG11396 (sfrB & yigC) sequence (=marker VII) from *Escherichia coli* K12 (accession n° NC_000913; from position 4022578 to 4024071). The corresponding protein is not yet known. When considering the sequence of the gene, it is a putative flavoprotein reductase. A search in DNA databases allowed us to find homologous sequences in some bacteria.

The HI0019 (=marker VII) sequence from *Haemophilus influenzae* (accession n° U32687, from position 7501 to 8550). This sequence shares all the characteristics of a coding sequence. However, the product of this coding sequence does not match any known protein. This sequence is homologous to the gene coding for the hypothetical protein yleA from *Pasteurella multocida* (accession n° AF23940) whose function is totally unknown.

Example 3

Additional Molecular Marker Sequences

This example illustrates the determination of marker sequences homologous to the sequences Spy0160, Spy1372, SpyM3-0902 & SpyM3-0903, Spy1527, Ecs0036, HI1576, and EG10839 & EG11396 as defined above in other Gram-positive or Gram-negative bacteria. These marker sequences were obtained using sets of degenerated primers, which have been identified based on theoretical alignments of the above-defined marker sequence (see examples 1-2) with sequences available in DNA databases.

Table 3A-H represents some degenerated primer sequences that have been used to amplify homologous marker sequences present in other Gram-positive or Gram-negative bacteria. PCR amplification was done using the identified degenerated primers on bacterial DNA isolated from various other Gram-positive or Gram-negative bacteria. Amplification was done under conditions of low stringency. In table 3A-H, the conditions the PCR programs and applied temperatures are indicated.

TABLE 3A

Target sequence: Homologs of Spy0160 (purA gene or Marker I) in Gram-positive bacteria

| Primers | Sequence | Tm | Annealing temperature during the PCR | Amplicon size |
|---|---|---|---|---|
| GRP1-S | 5'-YTHTTYGAAGGDGCDCAAGG-3' (SEQ ID NO: 462) | 61° C. | 50° C. | 585 bp |
| GRP1-AS | 5'-GRYCWGGMCCWACTGAGAA-3' (SEQ ID NO: 463) | 59° C. | | |

TABLE 3B

Target sequence: Homologs of Spy1372 (pstI gene or Marker II) in Gram-positive bacteria

| Primers | Sequence | Tm | Annealing temperature during the PCR | Amplicon size |
|---|---|---|---|---|
| GRP2-S | 5'-CCNGCCATYTCWCCRCACAT-3' (SEQ ID NO: 464) | 63° C. | 50° C. | 443 bp |
| GRP2-AS | 5'-AMGARATGAAYCCRTTCYTDGG-3' (SEQ ID NO: 465) | 64° C. | | |

TABLE 3C

Target sequence: Homologs of SpyM3_0902 & SpyM3_0903 (Marker III) in Gram-positive bacteria

| Primers | Sequence | Tm | Annealing temperature during the PCR | Amplicon size |
|---|---|---|---|---|
| GRP3-S | 5'-GACGGAMYTCTGGAGAGACC-3' (SEQ ID NO: 466) | 57° C. | 48° C. | around 600 bp |
| GRP3-AS | 5'-GCRTAYTTDGTDGCCATWCCAAA-3' (SEQ ID NO: 467) | 59° C. | | |

TABLE 3D

Target sequence: Homologs of Spy1527 (typA gene-Marker IV) in Gram-positive bacteria

| Primers | Sequence | Tm | Annealing temperature during the PCR | Amplicon size |
|---|---|---|---|---|
| GRP4-S | 5'-GARCGTATYATGAAAATGGT-3' (SEQ ID NO: 468) | 57° C. | 45° C. | 885 bp |
| GRP4-AS | 5'-CATDCCYTCAGDCKCAT-3' (SEQ ID NO: 469) | 59° C. | | |

TABLE 3E

Target sequence: Homologs of HI1576 (glucose-6-phosphate isomerase gene-marker VI) in Gram-negative bacteria

| Primers | Sequence | Tm | Annealing temperature during the PCR | Amplicon size |
|---|---|---|---|---|
| GN-1-S | 5'-TGGGTYGGYGGYCGTTACT-3' (SEQ ID NO: 470) | 63° C. | 50° C. | around 500 bp |
| GN-1-AS | 5'-TCGGTYTGNGCRAAGAAGTT-3' (SEQ ID NO: 471) | 64° C. | | |

TABLE 3F

Target sequence: Homologs of Ecs0036 (Carb-P, large subunit gene- or Marker V) in Gram-negative bacteria

| Primers | Sequence | Tm | Annealing temperature during the PCR | Amplicon size |
|---|---|---|---|---|
| GN-2-S | 5'-CSACNATYATGACYGAYCC-3' (SEQ ID NO: 472) | 63° C. | 50° C. | 500-650 bp |
| GN-2-AS | 5'-TCCATYTCRTAYTCYTTCCA-3' (SEQ ID NO: 473) | 64° C. | | |

TABLE 3G

| Target sequence: Homologs of EG10839 & EG11396 (sfrB & yigC or Marker VII) in Gram-negative bacteria | | | | |
|---|---|---|---|---|
| Primers | Sequence | Tm | Annealing temperature during the PCR | Amplicon size |
| GN-3-S | 5'-AAYTTGGTRTACATRAACTG-3' (SEQ ID NO: 474) | 63° C. | 50° C. | Around 600 bp |
| GN-3-AS | 5'-RVTGATYATGCGYTGGCT-3' (SEQ ID NO: 475) | 64° C. | | |

TABLE 3H

| Target sequence: Homologs of HI0019 (yleA or Marker VIII) in Gram-negative bacteria | | | | |
|---|---|---|---|---|
| Primers | Sequence | Tm | Annealing temperature during the PCR | Amplicon size |
| GN-4-S | 5'-GCCNGGRAADCCNACRAT-3' (SEQ ID NO: 476) | 63° C. | 60° C. | Around 500 bp |
| GN-4-AS | 5'-GTNTCNRTNATGGAAGGCTG-3' (SEQ ID NO: 477) | 64° C. | | |

An example of a PCR amplification used to obtain marker sequences from bacteria is as follows: 10 ng of genomic DNA from each bacterial strain tested is added to a mixture containing 10 mM Tris HCl pH 9, 2.5 mM MgCl2, 50 mM KCl, 0.1% Triton X-100 (v/v), 300 nM of each primer (forward and reverse; see table 3 for primers used), 0.25 mM desoxynucleotides triphosphates (Roche Diagnostics, Mannheim, Germany), 2.5 U de Taq Polymerase Expand High Fidelity (Roche Diagnostics, Mannheim, Germany) in a final volume of 50 μl. Amplifications were carried out in a Mastercycler gradient (Applied Biosystem 2400, USA). An initial activation step of Expand High Fidelity (94° C. for 3 min) is followed by 35 cycles (94° C. for 40 s, annealing temperature equal to Tm −5 or −10° C. for 50 s, 72° C. for 1 min) and a final extension for 10 min.

Amplified DNA fragments were run on a 2% agarose gel stained with ethidium-bromide and visualized on a UV transilluminator.

FIGS. 1-3 illustrate the amplification in some Gram-positive bacteria of molecular markers which are homologous to markers I to III respectively. FIGS. 8 and 10 illustrate the amplification in some Gram-negative bacteria of molecular markers homologous to markers V (Ecs0036) and VI (HI1576) respectively. FIGS. 4-7, 9 and 11-21 illustrate molecular marker sequences from different Gram-positive bacteria or Gram-negative bacteria.

Example 4

Use of an Assay According to the Invention for Molecular Identification of Various *Bacillus* Species and Strains The present example illustrates the use of an assay according to the invention for the molecular identification of various *Bacillus* species, including *Bacillus anthracis*, species that cannot be discriminated with ribosomal 16S rDNA gene (La Scola et al, 2003). Table 4 summarizes the results obtained for the various *Bacillus* species with the current genotyping assay. The analyses were performed using the markers I, II and III. Marker I corresponds to the Spy0160 sequence, Marker II corresponds to the Spy1372 sequence, Makrer III corresponds to the SpyM3_0902 & Spy M3_0903 sequence.

Primers where designed for these markers and with these primers DNA of *Bacillus* was amplified. Then, the obtained amplified sequences were sequenced and compared by alignment. Table 4 indicates the number of modified nucleotides in the amplified marker sequences of these different *Bacillus* species and strains. The 16S ribosomal marker is not relevant in this context and cannot be used for identifying *Bacillus* species because the amplicons corresponding to each *Bacillus* species will give comparable nucleic acid sequences, with variations not exceeding 1% on the whole gene.

TABLE 4

Use of different molecular markers for the identification of *Bacillus* species

| | Molecular marker | *B. cereus* 10987 | *B. cereus* 14579 | *B. thuringiensis* 4Q2-72 *israelensis* | *B. anthracis* 1978 |
|---|---|---|---|---|---|
| *B. cereus* | Marker III (SEQ ID NO: 168) | | 8 | 29 | 29 |
| | Marker I (SEQ ID NO: 18) | | 1 | 23 | 21 |

TABLE 4-continued

Use of different molecular markers for the identification of *Bacillus* species

| | Molecular marker | *B. cereus* 10987 | *B. cereus* 14579 | *B. thuringiensis* 4Q2-72 *israelensis* | *B. anthracis* 1978 |
|---|---|---|---|---|---|
| | Marker II (SEQ ID NO: 70) | | 2 | 3 | 11 |
| | 16S | | 0 | 0 | ND |
| *B. cereus* 14579 | Marker III (SEQ ID NO: 169) | 8 | | 32 | 31 |
| | Marker I (SEQ ID NO: 19) | 1 | | 22 | 20 |
| | Marker II (SEQ ID NO: 71) | 2 | | 5 | 13 |
| | 16S | 0 | | 0 | ND |
| *B. thuringiensis* 4Q2-72 *israelensis* | Marker III (SEQ ID NO: 170) | 29 | 32 | | 12 |
| | Marker I (SEQ ID NO: 33) | 23 | 22 | | 30 |
| | Marker II (SEQ ID NO: 80) | 3 | 5 | | 12 |
| | 16S | 0 | 0 | | ND |
| *B. anthracis* 1978 | Marker III (SEQ ID NO: 162) | 29 | 31 | 12 | |
| | Marker I (SEQ ID NO: 12) | 21 | 20 | 30 | |
| | Marker II (SEQ ID NO: 64) | 11 | 13 | 12 | |
| | 16S | ND | ND | ND | |

ND = not determined

This example shows unambiguously that the combined use of several unrelated molecular markers markedly improves bacterial species identification, as well as, to some extent, characterization of a well-determined strain within a particular species. The present method is so specific that it can go beyond the species identification and discriminate strains of the same species.

Example 5

Nucleic Acid Probes According to the Present Invention

This example illustrates an oligonucleotide (nucleic acid probe) that has been designed from marker I of *Staphylococcus aureus* (SEQ ID NO: 23) 5'-gtgtaggtcctacattcgtttc-3' (SEQ ID NO: 478). This oligonucleotide is specific for *S. aureus* species and can therefore allow discrimination of this species with other bacteria whereas another nucleic acid probe, the oligonucleotide 5'-cattcgtttcaaaggtaatg-3' (SEQ ID NO:479) which is located on the same marker allows discrimination of different strains of *S. aureus* (i.e. strains MRSA MW2 and MRSA COL versus strains Mu-50 and N315). These multi-resistant strains carry different methicillin resistance cassette chromosome and their resistance patterns to antimicrobials agents are different.

The illustrated nucleic acid probes can for instance advantageously be used in an assay according to the present invention, on a DNA chip according to the present invention. The two oligonucleotides provided above can be considered as specific probes which can be bound on a biochip and therefore allow discrimination between various amplicons obtained from MRSA strains amplified with the primers of table 3.

Conclusion

The present invention demonstrates that multigenotypic molecular analyses according to Gram-, genus- species- and strain-specificity can be achieved by using concomitantly or sequentially a panel of distinct conserved molecular markers, either by conventional polymerase chain reaction PCR (with exploitation of single nucleotide specific polymorphism or SNP), real-time PCR (with/without specific Taqman probes), or post-PCR reverse hybridization on solid support (micro-, macro- or nano-array). The analyses allow a fast and specific detection of bacterial DNA and a wide bacterial genotyping in human, animal or environmental samples.

The combined use of the herein described molecular markers allows rapid and specific molecular identification of a wide panel of bacteria in samples and/or tissues, even in samples showing a background bacterial flora. To the applicant's knowledge, there is no such diagnostic tool that is based on the use of a panel of various highly conserved bacterial moleculer markers for detecting and identifying bacteria according to Gram-, genus-, species-, and to some extent also strain-classification. Compared to the existing typing systems, we believe that this is a major improvement, in view of the increased need for rapid and multigenotypic bacterial diagnoses, especially when considering nosocomial infections and epidemic bacterial diseases occurring in a natural, accidental or criminal setting. To this respect, molecular typing of bacteria according to the Gram phenotype is of particular interest when appropriate antibiotherapy has to be rapidly started.

REFERENCES

Bosshard P P, Abels S, Altwegg M, Bottger E C, Zbinden R. Comparison of conventional and molecular methods for identification of aerobic catalase-negative gram-positive cocci in the clinical laboratory. J Clin Microbiol 2004;42: 2065-2073.

Bosshard P P, Abels S, Zbinden R, Bottger E C, Altwegg M. Ribosomal DNA sequencing for identification of aerobic gram-positive rods in the clinical laboratory (an 18-month evaluation). J Clin Microbiol 2003;41:4134-3140.

Brakstad O G, Aasbakk K, and Maeland J A. Detection of *Staphylococcus aureus* by polymerase chain amplification of the nuc gene J Clin Microbiol. 1992;32:1768-1772.

Clarridge J E 3rd. Impact of 16S rRNA gene sequence analysis for identification of bacteria on clinical microbiology and infectious diseases. Clin Microbiol Rev 2004;17:840-862.

Giannino V, Santagati M, Guardo G. Cascone C, Rappazzo G, Stefani S. Conservation of the mosaic structure of the four internal transcribed spacers and localisation of the rrn operons on the *Streptococcus pneumoniae* genome. FEMS Microbiol Lett 2003;223:245-252.

Gurtler V and Stanisich V A. New approaches to typing and identification of bacteria using the 16S-23S rDNA spacer region. Microbiology 1996;142:3-16.

Gutierrez A, Ramos M A, Sanz J C, Bernal A, Agirrezabal J, Casado Y, Martinez M. Bacterial meningitis in emergency medicine. Factors associated with delay of antimicrobial therapy. Enferm lnfecc Microbiol Clin 1998;16:302-306.

Jonas D, Spitzmuller B, Weist K, Ruden H, Daschner F D. Comparison of PCR-based methods for typing *Escherichia coli*. Clin Microbiol Infect 2003;9:823-831.

Klaschik S, Lehmann L E, Raadts A, Book M, Hoeft A, Stuber F. Real-time PCR for detection and differentiation of gram-positive and gram-negative bacteria. J Clin Microbiol 2002; 40:4304-4307.

La Scola B, Zeaiter Z, Khamis A, Raoult D. Gene-sequence-based criteria for species definition in bacteriology: the Bartonella paradigm. Trends Microbiol 2003;11:318-321.

Lecouvet F, L. M. Irenge, B. Vandercam, A. Nzeusseu, S. Hamels, J. L. Gala. The etiologic diagnosis of infectious discitis is improved by amplification-based DNA analysis. Arthritis & Rheumatism 2004;9:2985-2994.

Palomares C, Torres M J, Torres A, Aznar J, Palomares J C. Rapid detection and identification of *Staphylococcus aureus* from blood culture specimens using real-time fluorescence PCR. Diagn Microbiol Infect Dis 2003;45:183-189.

Poyart C, Quesne G, Boumaila C, and Trieu-Cuot P. Rapid and accurate species-level identification of coagulase-negative *Staphylococci* by using the soda gene as a target. J Clin Microbiol 2001;39:4296-4301.

Trampuz A, Steckelberg J M, Osmon D R, Cockerill F R, Hanssen A D, Patel R. Advances in the laboratory diagnosis of prosthetic joint infection. Reviews in Medical Microbiology Reviews in medical Microbiology 2003;14:1-14.

Tzanakaki G, Tsolia M, Vlachou V, Theodoridou M, Pangalis A, Foustoukou M, Karpathios T, Blackwell C C, Kremastinou J. Evaluation of non-culture diagnosis of invasive *meningococcal* disease by polymerase chain reaction (PCR). FEMS Immunology and Medical Microbiology 2003;39:31-36.

Xu J, Rao J R, Millar B C, Elborn J S, Evans J, Barr J G, Moore J E. Improved molecular identification of *Thermoactinomyces* spp. associated with mushroom worker's lung by 16S rDNA sequence typing. J Med Microbiol 2002;51:1117-1127.

Yu D T, Black E, Sands K E, Schwartz J S, Hibberd P L, Graman P S, Lanken P N, Kahn K L, Snydman D R, Parsonnet J, Moore R, Platt R, Bates D W. Severe sepsis: variation in resource and therapeutic modality use among academic centers. Crit Care. 2003;7:R24-R34.

---

What is claimed is:

1. An assay for detecting and identifying one or more bacteria in a sample, wherein said assay comprises detecting the presence or absence of at least two conserved molecular markers in the sample, thereby identifying one or more bacteria, wherein at least one molecular marker is conserved in Gram-positive bacteria and consists of SEQ ID NO: 14, and at least one molecular marker is conserved in Gram-negative bacteria and consists of SEQ ID NO: 230.

2. A method for diagnosing bacterial infection of a sample comprising screening the sample for the presence of at least two conserved molecular markers and diagnosing bacterial infection based on the presence of the at least two conserved molecular markers, wherein at least one molecular marker is conserved in Gram-positive bacteria and consists of SEQ ID NO: 14, and at least one molecular marker is conserved in Gram-negative bacteria and consists of SEQ ID NO: 230.

3. An assay for detecting and identifying Bacillus anthracis in a sample, wherein said assay comprises detecting the presence or absence of a conserved molecular marker in the sample, thereby identifying *Bacillus anthracis*, wherein said molecular marker consists of SEQ ID NO 14.

4. An assay for detecting and identifying *Francisella tularensis* in a sample, wherein said assay comprises detecting the presence or absence of a conserved molecular marker in the sample, thereby identifying *Francisella tularensis*, wherein said molecular marker consists of SEQ ID NO 230.

5. The method of claim 1, wherein the method further comprises detecting an additional molecular marker that is conserved in Gram-positive bacteria and which is selected from the group consisting of the sequences of SEQ ID NOs: 1-13, 15-62, and 326-359, and/or detecting an additional molecular marker that is conserved in Gram-negative bacteria and which is selected from the group consisting of SEQ ID NOs: 194-229, 231-232, 238-239, 242-254 and 431-442.

6. The method of claim 2, wherein the method further comprises detecting an additional molecular marker that is conserved in Gram-positive bacteria and which is selected from the group consisting of the sequences of SEQ ID NOs: 1-13, 15-62, and 326-359, and/or detecting an additional molecular marker that is conserved in Gram-negative bacteria and which is selected from the group consisting of SEQ ID NOs: 194-229, 231-232, 238-239, 242-254 and 431-442.

* * * * *

UNITED STATES PATENT AND TRADEMARK OFFICE

CERTIFICATE OF CORRECTION

PATENT NO. : 7,785,780 B2
APPLICATION NO. : 10/591791
DATED : August 31, 2010
INVENTOR(S) : Gala et al.

It is certified that error appears in the above-identified patent and that said Letters Patent is hereby corrected as shown below:

Figure 1, Line 5, "3. *Streptococcus penumoniae*" should be changed to --3. *Streptococcus pneumoniae*--

Figure 2, Line 5, "3. *Listeria moniocytogenes*" should be changed to --3. *Listeria monocytogenes*--

Figure 2, Line 7, "5. *Streptococcus peneumoniae*" should be changed to --5. *Streptococcus pneumoniae*--

Figure 2, Line 14, "12. *Bacillus thuringensis*" should be changed to --12. *Bacillus thuringiensis*--

Figure 2, Line 16, "14. *Enteococcus faecium*" should be changed to --14. *Enterococcus faecium*--

Figure 5B, Line 22, "112. *Enterobacter cloaceae*" should be changed to --112. *Enterobacter cloacae*--

Figure 5B, Line 35, "125. *Staphylococcus capitis uralyticus*" should be changed to --125. *Staphylococcus capitis ureolyticus*--

Figure 5C, Line 8, "131. *Salmonella typhymurium*" should be changed to --131. *Salmonella typhimurium*--

Figure 5C, Line 20, "143. *Salmonella enterica virschow*" should be changed to --143. *Salmonella enterica virchow*--

Figure 9A, Line 4, "194. *Neissaria meningitidis groupe B*" should be changed to --194. *Neissaria meningitidis group B*--

Figure 9A, Line 5, "195. *Neisseria meningitidis groupe C*" should be changed to --195. *Neisseria meningitidis group C*--

Figure 9A, Line 6, "196. *Enterobacter cloaceae*" should be changed to --196. *Enterobacter cloacae*--

Figure 9A, Line 17, "207. *Salmonella enterica virschow*" should be changed to --207. *Salmonella enterica virchow*--

Figure 10, Line 18, "17. Leigonella pneumophila" should be changed to --17. Legionella pneumophila--

Signed and Sealed this
First Day of March, 2011

David J. Kappos
*Director of the United States Patent and Trademark Office*

Figure 11, Line 4, "257. *Enterobacter cloaceae*" should be changed to --257. *Enterobacter cloacae*--

Figure 11, Line 21, "274. *Salmonella enterica virschow*" should be changed to --274. *Salmonella enterica virchow*--

Figure 13, Line 5, "306. *Haemophilus ducrei*" should be changed to --306. *Haemophilus ducreyi*--

Figure 14, Line 21, "344 *Stretpococcus mitis*" should be changed to --344 *Streptococcus mitis*--

Figure 14, Line 29, "352 *Bacillus thuringensis*" should be changed to --352 *Bacillus thuringiensis*--

Figure 14, Line 31, "354 *Bacillus weihennstephanensis*" should be changed to --354 *Bacillus weihenstephanensis*--

Figure 15A, Line 14, *"SEQ ID NO. 370 Bacillus thuringensis*" should be changed to --*SEQ ID NO. 370 Bacillus thuringiensis*--

Column 8, Line 21, "marker sequences" should be changed to --marker sequences.--

Column 11, Line 13, "comprising Spy1060," should be changed to --comprising Spy0160,--

Column 14, Line 27, "acid probes" should be changed to --acid probes.--

Column 14, Line 30, "in step d)" should be changed to --in step d).--

Column 16, TABLE 2A, Line 39, "*thuringiensis israelensi*" should be changed to --*thuringiensis israelensis*--

Column 16, TABLE 2A, Line 63, "*cohni cohni,*" should be changed to --*cohni cohnii*--

Column 17, Line 40, "of the same species" should be changed to --of the same species.--

Column 18, TABLE 2B, Line 37, "*pertusis*" should be changed to --*pertussis*--

Column 18, TABLE 2B, Line 38, "*melitensis* biovar" should be changed to --*melitensis* biovar 1--

Column 18, TABLE 2B, Line 46, "*cloaceae*" should be changed to --*cloacae*--

Column 18, TABLE 2B, Line 48, "*Escherishia*" should be changed to --*Escherichia*--

Column 18, TABLE 2B, Line 49, "*Escherishia*" should be changed to --*Escherichia*--

Column 18, TABLE 2B, Line 51, "*ducrei*" should be changed to --*ducreyi*--

Column 18, TABLE 2B, Line 56, "*meningitidis* groupe C" should be changed to --*meningitidis* group C--

Column 18, TABLE 2B, Line 57, "*meningitidis* groupe B" should be changed to --*meningitidis* group B--

Column 20, Line 5, "(=marker VII)" should be changed to --(=marker VIII)--

Column 24, Line 44, "Makrer III" should be changed to --Marker III--

Columns 23-24, TABLE 4, Line 61, "*B. cereus*" should be changed to --*B. cereus* 10987--

Column 26, Line 46, "bacterial moleculer" should be changed to --bacterial molecular--

Column 27, Line 21, "of the rrn" should be changed to --of the rRNA--

Column 28, Lines 15-16, “infection. Reviews in Medical Microbiology” should be changed to --infection.--

Columns 121-122, Line 28, “<213> ORGANISM: Enterobacter cloaceae” should be changed to --<213> ORGANISM: Enterobacter cloacae--

Columns 131-132, Line 16, “<213> ORGANISM: Staphylococcus capitis uralyticus” should be changed to --<213> ORGANISM: Staphylococcus capitis ureolyticus--

Columns 135-136, Line 16, “<213> ORGANISM: Salmonella typhymurium” should be changed to --<213> ORGANISM: Salmonella typhimurium--

Columns 143-144, Line 30, “<213> ORGANISM: Salmonella enterica virschow” should be changed to --<213> ORGANISM: Salmonella enterica virchow--

Columns 191-192, Line 22, “<213> ORGANISM: Neisseria meningitidis groupe B” should be changed to --<213> ORGANISM: Neisseria meningitidis group B--

Columns 191-192, Line 43, “<213> ORGANISM: Neisseria meningitidis groupe C” should be changed to --<213> ORGANISM: Neisseria meningitidis group C--

Columns 193-194, “Line 10, “<213> ORGANISM: Enterobacter cloaceae” should be changed to --<213> ORGANISM: Enterobacter cloacae--

Columns 199-200, Line 27, “<213> ORGANISM: Salmonella enterica virschow” should be changed to --<213> ORGANISM: Salmonella enterica virchow--

Columns 253-254, “Line 40, “<213> ORGANISM: Enterobacter cloaceae” should be changed to --<213> ORGANISM: Enterobacter cloacae--

Columns 267-268, Line 5, “<213> ORGANISM: Salmonella enterica virschow” should be changed to --<213> ORGANISM: Salmonella enterica virchow--

Columns 307-308, Line 33, “<213> ORGANISM: Haemophilus ducrei” should be changed to --<213> ORGANISM: Haemophilus ducreyi--

Columns 349-350, “<213> ORGANISM: Stretpococcus mitis” should be changed to --<213> ORGANISM: Streptococcus mitis--

Columns 355-356, Line 36, “<213> ORGANISM: Bacillus thuringensis” should be changed to --<213> ORGANISM: Bacillus thuringiensis--

Columns 357-358, Line 34, “<213> ORGANISM: Bacillus weihennstephanensis” should be changed to --<213> ORGANISM: Bacillus weihenstephanensis--

Columns 371-372, Line 11, “<213> ORGANISM: Bacillus thuringensis” should be changed to --<213> ORGANISM: Bacillus thuringiensis--